(12) United States Patent
Burgdorf et al.

(10) Patent No.: US 9,006,440 B2
(45) Date of Patent: Apr. 14, 2015

(54) FUROPYRIDINE DERIVATIVES

(75) Inventors: Lars Burgdorf, Frankfurt am Main (DE); Melanie Schultz, Darmstadt (DE); Tatjana Ross, Eschborn (DE); Brian Hodous, Cambridge, MA (US); Justin Potnick, Acton, MA (US); Amanda E. Sutton, Hingham, MA (US); Bayard R. Huck, Sudbury, MA (US)

(73) Assignee: Merck Patent GmbH, Darmstadt (DE)

(*) Notice: Subject to any disclaimer, the term of this patent is extended or adjusted under 35 U.S.C. 154(b) by 75 days.

(21) Appl. No.: 13/819,166

(22) PCT Filed: Jul. 29, 2011

(86) PCT No.: PCT/EP2011/003831
§ 371 (c)(1),
(2), (4) Date: Feb. 26, 2013

(87) PCT Pub. No.: WO2012/025187
PCT Pub. Date: Mar. 1, 2012

(65) Prior Publication Data
US 2013/0225569 A1 Aug. 29, 2013

(30) Foreign Application Priority Data
Aug. 27, 2010 (EP) .................................. 10008928

(51) Int. Cl.
| C07D 491/048 | (2006.01) |
| A61K 31/4355 | (2006.01) |
| C07D 491/04 | (2006.01) |
| C07D 519/00 | (2006.01) |
| A61K 31/4709 | (2006.01) |
| A61K 31/496 | (2006.01) |
| A61K 31/506 | (2006.01) |
| A61K 31/5377 | (2006.01) |
| A61K 31/5383 | (2006.01) |
| A61K 45/06 | (2006.01) |

(52) U.S. Cl.
CPC .......... *C07D 491/048* (2013.01); *C07D 491/04* (2013.01); *C07D 519/00* (2013.01); *A61K 31/4355* (2013.01); *A61K 31/4709* (2013.01); *A61K 31/496* (2013.01); *A61K 31/506* (2013.01); *A61K 31/5377* (2013.01); *A61K 31/5383* (2013.01); *A61K 45/06* (2013.01)

(58) Field of Classification Search
CPC ........................ C07D 491/048; A61K 31/4355
USPC .................... 546/115, 116; 514/302
See application file for complete search history.

(56) References Cited

U.S. PATENT DOCUMENTS

| 6,187,777 | B1 | 2/2001 | Norman et al. |
| 6,583,154 | B1 | 6/2003 | Norman et al. |
| 2002/0004511 | A1 | 1/2002 | Luzzio et al. |
| 2011/0098293 | A1* | 4/2011 | Mannion et al. ........... 514/233.8 |

FOREIGN PATENT DOCUMENTS

WO 99/40091 A1 8/1999

OTHER PUBLICATIONS

Patani et. al. "Bioisosterism: A Rational Approach in Drug Design" Chemical Reviews 1996, 96, 3147-3176.*
Miyazki et. al. "Design and effective synthesis of novel templates, 3,7-diphenyl-4-amino-thieno and furo-[3,2-c]pyridines as protein kinase inhibitorsand in vitro evaluation targeting angiogenetic kinases." Bioorganic & Medicinal Chemistry Letters 2007, 17, 250-254.*
Michelotti et. al. "Two classes of p38a MAP kinase inhibitors having a common diphenylether core but exhibiting divergent binding modes" Bioorganic & Medicinal Chemistry Letters 2005, 15, 5274-5279.*
Jiang et. al. "3,5-Disubstituted quinolines as novel c-Jun N-terminal kinase inhibitors." Bioorganic & Medicinal Chemistry Letters 2007, 17, 6378-6382.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*
Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*
Trisha Gura "Cancer Models: Systems for Identifying New Drugs Are Often Faulty" Science Nov. 7, 1997: vol. 278. No. 5340, pp. 1041-1042.*
Weinblatt "Effects of Fostamatinib (R788), an Oral Spleen Tyrosine Kinase Inhibitor, on Health-related Quality of Life in Patients with Active Rheumatoid Arthritis: Analyses of Patient-reported Outcomes from a Randomized, Double-blind, Placebo-controlled Trial." The Journal of Rheumatology 2013, 40:4, 369.*
Nijjar "Inhibition of spleen tyrosine kinase in the treatment of rheumatoid arthritis." Rheumatology 2013;52:1556-1562.*
Simone, Oncology: Introduction, Cecil Textbook of Medicine, 20th Edition, 1996 vol. 1, pp. 1004-1010.*
International Search Report for PCT/EP2011/003831 (Apr. 5, 2012).

* cited by examiner

*Primary Examiner* — David K O Dell
(74) *Attorney, Agent, or Firm* — Millen, White, Zelano, Branigan, P.C.

(57) ABSTRACT

Compounds of the formula I

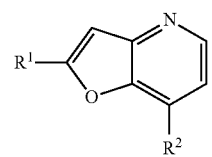

in which $R^1$ and $R^2$ have the meanings indicated in Claim 1, are inhibitors of Syk, and can be employed, inter alia, for the treatment of rheumatoid arthritis and/or systemic lupus.

23 Claims, No Drawings

FUROPYRIDINE DERIVATIVES

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular tyrosine kinases, furthermore to pharmaceutical compositions which comprise these compounds, and to the use of the compounds for the treatment of kinase-induced diseases.

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

One of the key events in the signaling pathway following the activation of mast cells is activation of the tyrosine kinase Syk. Mast cells play a critical role in asthma and allergic disorders by releasing pro-inflammatory mediators and cytokines. Antigen-mediated aggregation of FcεRJ, the high-affinity receptor for IgE, results in activation of mast cells. This triggers a series of signaling events resulting in the release of mediators, including histamine, proteases, leukotrienes and cytokines. These mediators cause increased vascular permeability, mucus production, bronchoconstriction, tissue degradation and inflammation, thus playing key roles in the etiology and symptoms of asthma and allergic disorders. Syk kinase acts as a central initiator of all subsequent signaling leading to mediator release. The critical role of Syk kinase in the signaling path was demonstrated by the complete inhibition of mediator release by a protein containing the SH2 domains of Syk kinase that functioned as an inhibitor of Syk kinase (J. A. Taylor et al, Molec. and Cell Biol, 15: 4149-4157 (1995)).

Syk (Spleen-Tyrosine-Kinase) is a 72 kDa non-receptor tyrosine kinase belonging to the subfamily of intracellular tyrosine kinases that comprises ZAP70, Pyk2, Abl, Tie2, KDR and HER, among others. Syk is a major regulator of FcR (FcγRI, II, III, FcεRI, FcαR) and BCR signaling and is expressed throughout hematopoietic lineage, as well as in fibroblasts, osteoclasts, hepatocytes, epithelial and neuronal cells. In addition to the C terminal kinase domain, SYK exhibits two SH2 domains and over 10 autophosphorylation sites[1].

By means of both its SH2 domains SYK is specifically recruited to phosphorylated ITAMs (Immunoreceptor Tyrosine-based Activation Motifs present in immunoreceptors such as FcγRI, IIA, IIIA, FcαR, FcεRI and BCR, expressed by monocytes, macrophages, mast cells, neutrophils and B cells) and specifically mediates immunoreceptor signaling triggered by activation of those receptors in mast cells, B cells, macrophages, monocytes, neutrophils, eosinophils, NK cells, DC cells platelets and osteoclasts[1,2].

Upon BCR cross linking, tyrosine residues at the ITAM motifs of the cytosolic tail of the Igα/Igβ are phosphorylated by the Src-family kinase Lyn, generating docking sites for SYK that is thus recruited to the BCR immunocomplex. SYK is then phosphorylated and activated by the Src-family kinase Lyn. Upon activation, SYK will phosphorylate the adaptor protein BLNK allowing its interaction with both BTK and PLCγ$_2$ via their respective SH2 domains. SYK phosphorylated—and thus activated—BTK will in turn phosphorylate and activate PLCγ$_2$ leading to IP$_3$ formation, Ca$^{2+}$ mobilization, PKC and MAPK activation and consequent NFAT, AP-1 and NFκB transcription factor activation, resulting in activation and surface marker expression, cytokine release, survival and proliferation of B cells[3]. In mast cells, allergen activated FcεRI is phosphorylated by LYN and FYN and recruits SYK which is in turn phosphorylated by LYN and further autophosphorylated, becoming fully activated. Activated SYK phosphorylates the two adaptor molecules NTAL and LAT creating more docking sites for SH2 containing proteins such as PLCγ$_1$, vav, and the p85 regulatory subunit of PI3K, resulting in mast cell degranulation and cytokine production[4]. Syk's critical role in signal transduction of mast cells is confirmed by reproducible observation that the 10-15% of basophils (circulating mast cells) from human donors that cannot degranulate have reduced amounts of Syk protein[5,6]. In addition, SYK is required for the bone resorption activity of osteoclasts. Upon stimulation of osteoclasts by αvβ3 integrin, SYK becomes phosphorylated, most likely by c-Src, in a DAP-12/FcγRII dependent mechanism, leading to SPL-76 and Vav3 phosphorylation and subsequent cytoskeletal reorganisation. SYK deficient osteoclasts are inactive and show defective cytoskeletal reorganisation. In correlation with this, SYK deficient embryos show defective skeletal mass[7,8].

BCR-mediated activation of B-cells in the lymph nodes, as well as FcR-mediated activation of dendritic cells, monocytes, macrophages, neutrophils and mast cells in the joints, are essential components of the cellular patho-physiological mechanisms taking place during rheumatoid arthritis (RA). Moreover, activation of osteoclasts leads to the bone and cartilage destruction which are hallmarks of this pathology[9]. SYK signaling should therefore play a pivotal role during the development of arthritis, both at the periphery and on the site of inflammation[10]. Indeed, an orally available Syk inhibitor R406—developed by Rigel—induced a significant improvement of clinical scores and significantly reduced serum cytokine concentrations, as well as bone erosion, in a murine model of RA[11,12]. Moreover, this inhibitor has shown efficacy (ACR scores improvement) and good tolerability in RA Phase II studies in humans[13,14,15].

In SLE B cells contribute essentially towards pathogenesis via production of autoantibodies resulting in immune complex formation, stimulation of Fc receptors and finally in an excessive and chronic activation of inflammation. In a murine model of SLE treatment with a Syk inhibitor resulted in a reduction of numbers of class-switched germinal center, marginal zone, newly formed and follicular B cells and therefore in disease mitigating effects[18].

Although TCR signals are transmitted by the intracellular tyrosine kinase ZAP-70 in thymocytes and naïve T cells, several studies indicate that differentiated effector T cells, such as those involved in the pathophysiology of Multiple sclerosis (MS) or systemic lupus erythematosus (SLE), show a down regulation of the TCRzeta chain and a concomitant upregulation of the TCR/CD3 chain and its interaction with FcRγ. Those studies show that the TCR/CD3/FcRgamma complex in effector cells recruits and activates Syk, instead of ZAP-70, tyrosine kinase. This physiologic switch in TCR signaling occurs exclusively in effector, and not naive or memory T cells[16,17,18]. Not surprisingly then, SYK inhibitors have been shown to delay disease progression and to improve survival in murine models of SLE[17,18,19,20,21].

SYK inhibitors may also find a use in asthma, allergy, multiple sclerosis and other diseases such as thrombocytopenia purpura and T or B cell lymphomas[1,10,14,22-35]. Treatment of prediseased NZB/W mice with a Syk inhibitor prevented the development of renal disease demonstrated by reduced glomerular sclerosis, tubular damage, proteinuria and BUN levels[18].

REFERENCES

1. Turner, M., Schweighoffer, E., Colucci, F., Di Santo, J. P. & Tybulewicz, V. L. Tyrosine kinase SYK: essential functions for immunoreceptor signalling. *Immunol Today* 21, 148-154 (2000).
2. Ghosh, D. & Tsokos, G. C. Spleen tyrosine kinase: an Src family of non-receptor kinase has multiple functions and represents a valuable therapeutic target in the treatment of autoimmune and inflammatory diseases. *Autoimmunity* 43, 48-55.
3. Lindvall, J. M., et al. Bruton's tyrosine kinase: cell biology, sequence conservation, mutation spectrum, siRNA modifications, and expression profiling. *Immunol Rev* 203, 200-215 (2005).
4. Gilfillan, A. M. & Tkaczyk, C. Integrated signalling pathways for mast-cell activation. *Nat Rev Immunol* 6, 218-230 (2006).
5. Gomez, G., Schwartz, L. & Kepley, C. Syk deficiency in human nonreleaser lung mast cells. *Clin Immunol* 125, 112-115 (2007).
6. Kepley, C. L., Youssef, L., Andrews, R. P., Wilson, B. S. & Oliver, J. M. Syk deficiency in nonreleaser basophils. *J Allergy Clin Immunol* 104, 279-284 (1999).
7. Zou, W., et al. Syk, c-Src, the alphavbeta3 integrin, and ITAM immunoreceptors, in concert, regulate osteoclastic bone resorption. *J Cell Biol* 176, 877-888 (2007).
8. Reeve, J. L., et al. SLP-76 couples Syk to the osteoclast cytoskeleton. *J Immunol* 183, 1804-1812 (2009).
9. Klareskog, L., Catrina, A. I. & Paget, S. Rheumatoid arthritis. *Lancet* 373, 659-672 (2009).
10. Wong, B. R., Grossbard, E. B., Payan, D. G. & Masuda, E. S. Targeting Syk as a treatment for allergic and autoimmune disorders. *Expert Opin Investig Drugs* 13, 743-762 (2004).
11. Braselmann, S., et al. R406, an orally available spleen tyrosine kinase inhibitor blocks fc receptor signaling and reduces immune complex-mediated inflammation. *J Pharmacol Exp Ther* 319, 998-1008 (2006).
12. Pine, P. R., et al. Inflammation and bone erosion are suppressed in models of rheumatoid arthritis following treatment with a novel Syk inhibitor. *Clin Immunol* 124, 244-257 (2007).
13. Tomillero, A. & Moral, M. A. Gateways to clinical trials. *Methods Find Exp Clin Pharmacol* 31, 47-57 (2009).
14. Bajpai, M. Fostamatinib, a Syk inhibitor prodrug for the treatment of inflammatory diseases. *IDrugs* 12, 174-185 (2009).
15. Weinblatt, M. E., et al. Treatment of rheumatoid arthritis with a Syk kinase inhibitor: a twelve-week, randomized, placebo-controlled trial. *Arthritis Rheum* 58, 3309-3318 (2008).
16. Krishnan, S., Warke, V. G., Nambiar, M. P., Tsokos, G. C. & Farber, D. L. The FcR gamma subunit and Syk kinase replace the CD3 zeta-chain and ZAP-70 kinase in the TCR signaling complex of human effector CD4 T cells. *J Immunol* 170, 4189-4195 (2003).
17. Krishnan, S., et al. Differential expression and molecular associations of Syk in systemic lupus erythematosus T cells. *J Immunol* 181, 8145-8152 (2008).
18. Bahjat, F. R., et al. An orally bioavailable spleen tyrosine kinase inhibitor delays disease progression and prolongs survival in murine lupus. *Arthritis Rheum* 58, 1433-1444 (2008).
19. Smith, J., et al. A Spleen Tyrosine Kinase Inhibitor Reduces the Severity of Established Glomerulonephritis. *J Am Soc Nephrol* (2009).
20. Enyedy, E. J., et al. Fc epsilon receptor type I gamma chain replaces the deficient T cell receptor zeta chain in T cells of patients with systemic lupus erythematosus. *Arthritis Rheum* 44, 1114-1121 (2001).
21. Perl, A. Systems biology of lupus: mapping the impact of genomic and environmental factors on gene expression signatures, cellular signaling, metabolic pathways, hormonal and cytokine imbalance, and selecting targets for treatment. *Autoimmunity* 43, 32-47.
22. Smith, J., et al. A spleen tyrosine kinase inhibitor reduces the severity of established glomerulonephritis. *J Am Soc Nephrol* 21, 231-236.
23. Sanderson, M. P., Gelling, S. J., Rippmann, J. F. & Schnapp, A. Comparison of the anti-allergic activity of Syk inhibitors with optimized Syk siRNAs in FcepsilonRI-activated RBL-2H3 basophilic cells. *Cell Immunol* 262, 28-34.
24. Podolanczuk, A., Lazarus, A. H., Crow, A. R., Grossbard, E. & Bussel, J. B. Of mice and men: an open-label pilot study for treatment of immune thrombocytopenic purpura by an inhibitor of Syk. *Blood* 113, 3154-3160 (2009).
25. Bajpai, M., Chopra, P., Dastidar, S. G. & Ray, A. Spleen tyrosine kinase: a novel target for therapeutic intervention of rheumatoid arthritis. *Expert Opin Investig Drugs* 17, 641-659 (2008).
26. Friedberg, J. W., et al. Inhibition of Syk with fostamatinib disodium has significant clinical activity in non-Hodgkin lymphoma and chronic lymphocytic leukemia. *Blood* 115, 2578-2585.
27. Gao, C., et al. Eptifibatide-induced thrombocytopenia and thrombosis in humans require FcgammaRIIa and the integrin beta3 cytoplasmic domain. *J Clin Invest* 119, 504-511 (2009).
28. Marjon, K. D., Marnell, L. L., Mold, C. & Du Clos, T. W. Macrophages activated by C-reactive protein through Fc gamma RI transfer suppression of immune thrombocytopenia. *J Immunol* 182, 1397-1403 (2009).
29. Chen, L., et al. SYK-dependent tonic B-cell receptor signaling is a rational treatment target in diffuse large B-cell lymphoma. *Blood* 111, 2230-2237 (2008).
30. Ponzoni, M., et al. Syk expression patterns differ among B-cell lymphomas. *Leuk Res* (2010).
31. Pechloff, K., et al. The fusion kinase ITK-SYK mimics a T cell receptor signal and drives oncogenesis in conditional mouse models of peripheral T cell lymphoma. *J Exp Med* 207, 1031-1044 (2009).
32. Uckun, F. M., Ek, R. O., Jan, S. T., Chen, C. L. & Qazi, S. Targeting SYK kinase-dependent anti-apoptotic resistance pathway in B-lineage acute lymphoblastic leukaemia (ALL) cells with a potent SYK inhibitory pentapeptide mimic. *Br J Haematol* 149, 508-517 (2010).
33. Wilcox, R. A., et al. Inhibition of Syk protein tyrosine kinase induces apoptosis and blocks proliferation in T-cell non-Hodgkin's lymphoma cell lines. *Leukemia* 24, 229-232 (2009).
34. Feldman, A. L., et al. Overexpression of Syk tyrosine kinase in peripheral T-cell lymphomas. *Leukemia* 22, 1139-1143 (2008).

35. Wang, L., et al. Alternative splicing disrupts a nuclear localization signal in spleen tyrosine kinase that is required for invasion suppression in breast cancer. *Cancer Res* 63, 4724-4730 (2003).

In addition to mast cells, Syk is expressed in other hematopoietic cells including B cells, where it is thought to play an essential role in transducing signals required for the transition of immature B cells into mature recirculating B cells (M. Turner et al, Immunology Today, 21: 148 (2000)). B cells are reported to play an important role in some inflammatory conditions such as lupus (O. T. Chan et al., Immunological Rev, 169: 107-121 (1999)) and rheumatoid arthritis (A. Cause et al, Biodrugs, 15(2): 73-79 (2001)).

Syk was also reported to be an element of the signaling cascade in beta-amyloid and prion fibrils leading to production of neurotoxic products (C. K. Combs et al., J. Neuroscl, 19: 928-939 (1999)). Furthermore, an inhibitor of Syk blocked the production of these neurotoxic products. Thus furopyridine derivatives would potentially be useful in the treatment of Alzheimer's disease and related neuroinflammatory diseases. Another report (Y. Kuno et al., Blood, 97, 1050-1055 (2001)) demonstrates that Syk plays an important role in malignant progression. A TEL-Syk fusion protein was found to transform hematopoietic cells suggesting a role in the pathogenesis of hematopoietic malignancies. Therefore furopyridine derivatives may be useful in the treatment of certain types of cancers.

Other protein tyrosine kinases involved in hematologic malignancies include ABL (ABLI), ARG (ABL2), PDGFβR, PDGFaR, JAK2, TRKC, FGFRI, FGFR3, FLT3, and FRK.

The Janus kinases (JAK) are a family of tyrosine kinases consisting of JAKI, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas (for a review of the pharmaceutical intervention of the JAK/STAT pathway see Frank, Mol. Med. 5, 432:456 (1999), and Seidel et al, Oncogene 19, 2645-2656 (2000)). JAK2 is a well validated target with strong potential in the treatment of myeloproliferative disorders (MPDS), which include polycythemia vera (PV), essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

Fms-like tyrosine kinase 3 (FLT3), which is also known as FLK-2 (fetal liver kinase 2) and STK-I (stem cell kinase 1), plays an important role in the proliferation and differentiation of hematopoietic stem cells. FLT3 receptor kinase is expressed in normal hematopoietic cells, placenta, gonads, and brain. However, this enzyme is expressed at very high levels on the cells of more than 80% of myelogenous patients and of a fraction of acute lymphoblastic leukemia cells. Furthermore, the enzyme can also be found on cells from patients with chronic myelogenous leukemia in lymphoid blast crisis. It has been reported that FLT3 kinase is mutated in 30% of acute myeloid leukemia (AML) and in a subset of acute lymphoblastic leukemia (ALL) as well (Gilliland et al, Blood 100, 1532-1542 (2002); Stirewalt et al, Nat. Rev. Cancer, 3, 650-665 (2003)). The most common activating mutations in FLT3 are internal tandem duplications within the juxtamembrane region, while point mutations, insertions, or deletions in the kinase domain are less common. Some of these mutant FLT3 kinases are constitutively active. FLT3 mutations have been associated with a poor prognosis (Malempati et al., Blood, 104, 11 (2004)). More than a dozen known FLT3 inhibitors are being developed and some have shown promising clinical effects against AML (Levis et al Int. J. Hematol, 52, 100-107 (2005)).

It has been reported that some of small-molecule FLT3 inhibitors are effective in inducing apoptosis in cell lines with FLT3-activating mutations and prolonging survival of mice that express mutant FLT3 in their bone marrow cells (Levis et al, Blood, 99, 3885-3891 (2002); Kelly et al, Cancer Cell, 1, 421-432 (2002); Weisberg et al, Cancer Cell, 1, 433-443 (2002); Yee et al, Blood, 100, 2941-2949 (2002)).

BTK, a member of the Tec family of non-receptor tyrosine kinases, is a signaling enzyme expressed in all hematopoietic cells types except T lymphocytes and natural killer cells. BTK plays a well documented role in the B-cell signaling pathway linking cell surface B-cell receptor stimulation to downstream intracellular responses. BTK is also a regulator of B-cell development, activation, signaling, and survival (Kurosaki, Curr Op Imm, 2000, 276-281; Schaeffer and Schwartzberg, Curr Op Imm 2000, 282-288). In addition, BTK exerts a physiological effect through other hematopoetic cell signaling pathways, e.g., Toll like receptor (TLR) and cytokine receptor-mediated TNF-a production in macrophages, IgE receptor (FcepsilonRI) signaling in Mast cells, inhibition of Fas/APO-1 apoptotic signaling in B-lineage lymphoid cells, and collagen-stimulated platelet aggregation.

In particular, the present invention relates to compounds and to the use of compounds in which the inhibition, regulation and/or modulation of signal transduction by Syk plays a role.

The synthesis of small compounds which specifically inhibit, regulate and/or modulate signal transduction by tyrosine kinases in particular Syk, is therefore desirable and an aim of the present invention.

Moreover, aim of this invention is the synthesis of new compounds for the prevention and treatment of rheumatoid arthritis, systemic lupus, asthma, allergic rhinitis, ITP, multiple sclerosis, leukemia, breast cancer and maligna melanoma. Surprisingly we have identified furopyridines that inhibit selectively SYK, BTK, KDR, Src, Zap70, Fak, Pyk2, Flt3 or Jak or inhibit a selection of these kinases.

It has been found that the compounds according to the invention and salts thereof have very valuable pharmacological properties while being well tolerated.

The present invention specifically relates to compounds of the formula I which inhibit, regulate and/or modulate signal transduction by Syk, to compositions which comprise these compounds, and to processes for the use thereof for the treatment of Syk-induced diseases and complaints.

The compounds of the formula I can furthermore be used for the isolation and investigation of the activity or expression of Syk. In addition, they are particularly suitable for use in diagnostic methods for diseases in connection with unregulated or disturbed Syk activity.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed are assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-anti-bodies (phospho-ABs). The phospho-AB binds only the phosphorylated substrate. This binding can be detected by chemiluminescence using a second peroxidase-conjugated anti-sheep antibody (Ross et al., 2002, Biochem. J.).

PRIOR ART

Other heterocyclic Syk inhibitors are described in WO2008/118823, WO2009/136995, WO 2010/027500.

SUMMARY OF THE INVENTION

The invention relates to compounds of the formula I

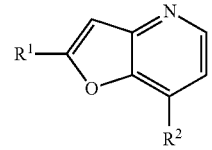

in which
$R^1$ denotes $Ar^1$ or $Het^1$,
$R^2$ denotes $Ar^2$, $Het^2$, $NH(CH_2)_nAr^2$, $O(CH_2)_nAr^2$ or $NH(CH_2)_nHet^2$,
$Ar^1$ denotes phenyl, naphthyl or biphenyl, each of which is unsubstituted or mono-, di- or trisubstituted by Hal, A, $O(CH_2)_pCyc$, Alk, $(CH_2)_nOH$, $(CH_2)_nOA$, $(CH_2)_nCOOH$, $(CH_2)_nCOOA$, $S(O)_mA$, phenoxy, benzyloxy, $(CH_2)_nNH_2$, $(CH_2)_nNHA$, $(CH_2)_nNA_2$, $[C(R^3)_2]_nCN$, $NO_2$, $(CH_2)_nCONH_2$, $(CH_2)_nCONHA$, $(CH_2)_nCONA_2$, $SO_2NH_2$, $SO_2NHA$, $SO_2NA_2$, $NHCONH_2$, $(CH_2)_nNHCOA$, $(CH_2)_nNHCOAlk$, $NHCOCH=CH(CH_2)_pNA_2$, CHO, COA, $SO_3H$, $O(CH_2)_pNH_2$, $O(CH_2)_pNHCOOA$, $O(CH_2)_pNHA$, $O(CH_2)_pNA_2$, $NH(CH_2)_pNH_2$, $NH(CH_2)_pNHCOOA$, $NH(CH_2)_pNHA$, $NH(CH_2)_pNA_2$, $NHCOHet^3$, $COHet^3$, $(CH_2)_nHet^3$, $O(CH_2)_nHet^3$ and/or $O(CH_2)_nCH(OH)(CH_2)Het^3$,
$Ar^2$ denotes phenyl, naphthyl or biphenyl, each of which is unsubstituted or mono-, di- or trisubstituted by Hal, A, $(CH_2)_nOH$, $(CH_2)_nOA$, $O(CH_2)_pCyc$, $OAr^3$, benzyloxy, $(CH_2)_nCOOH$, $(CH_2)_nCOOA$, $S(O)_mA$, $(CH_2)_nNH_2$, $(CH_2)_nNHA$, $(CH_2)_nNA_2$, $[C(R^3)_2]_nCN$, $NO_2$, $CONH(CH_2)_pNH_2$, $CONH(CH_2)_pNHA$, $CONH(CH_2)_pNA_2$, $CONH(CH_2)_pOA$, $CONH(CH_2)_pOH$, $(CH_2)_nCONH_2$, $(CH_2)_nCONHA$, $(CH_2)_nCONA_2$, $SO_2NH_2$, $SO_2NHA$, $SO_2NA_2$, $NHCONH_2$, CHO, COA, $SO_3H$, $O(CH_2)_pNH_2$, $O(CH_2)_pNHA$, $O(CH_2)_pNA_2$, $(CH_2)_nNHCOA$, $(CH_2)_nNHCOAlk$, $CONHAr^3$, $NHCOAr^3$, $CONH(CH_2)_nHet^3$, $NHCOHet^3$, $COHet^3$, $(CH_2)_nHet^3$, $S(CH_2)_nHet^3$ and/or $O(CH_2)_nHet^3$,
$Het^1$ denotes a mono- or bicyclic aromatic heterocycle having 1 to 4 N, O and/or S atoms, which may be unsubstituted or mono- or disubstituted by $Het^4$, A, benzyl, OH and/or OA,
$Het^2$ denotes a mono- or bicyclic saturated, unsaturated or aromatic heterocycle having 1 to 4 N, O and/or S atoms, which may be unsubstituted or mono-, di-, tri- or tetrasubstituted by Hal, $(CH_2)_nHet^4$, $NH(CH_2)_nHet^4$, $OHet^4$, A, $(CH_2)_nCOOH$, $(CH_2)_nCOOA$, phenyl, benzyl, CHO, COA, $(CH_2)_nNH_2$, $(CH_2)_nNHA$, $(CH_2)_nNA_2$, CN, $(CH_2)_nOH$, $(CH_2)_nOA$, $(CH_2)_pCH(OH)(CH_2)_pOH$, $(CH_2)_pCH(OH)(CH_2)_pOA$, $NH(CH_2)_pNH_2$, $NHSO_2A$, $NASO_2A$, $SO_2A$ and/or =O,
$Het^3$ denotes a mono- or bicyclic saturated, unsaturated or aromatic heterocycle having 1 to 4 N, O and/or S atoms, which may be unsubstituted or mono-, di-, tri- or tetrasubstituted by A, Hal, $(CH_2)_nNH_2$, $(CH_2)_nNHA$, $(CH_2)_nNA_2$, $(CH_2)_nOH$, $(CH_2)_nOA$, COOA, $Ar^3$ and/or =O,
$Het^4$ denotes a monocyclic saturated, unsaturated or aromatic heterocycle having 1 to 4 N, O and/or S atoms, which may be unsubstituted or mono-, di- or trisubstituted by A,
$R^3$ denotes H or alkyl having 1, 2, 3 or 4 C-atoms,
A denotes unbranched or branched alkyl having 1-10 C atoms, in which 1-7H atoms may be replaced by F and/or Cl and/or in which one or two non-adjacent $CH_2$ groups may be replaced by O, NH, S, SO, $SO_2$ and/or by CH=CH groups, or cyclic alkyl having 3-7 C atoms, which may be unsubstituted or monosubstituted by OH, NHCOOA or $NH_2$, Cyc denotes cyclic alkyl having 3-7 C atoms, Alk denotes alkenyl or alkinyl having 2, 3, 4, 5 or 6 C-atoms, $Ar^3$ denotes phenyl, which is unsubstituted or mono-, di- or trisubstituted by Hal and/or A, Hal denotes F, Cl, Br or I, m denotes 0, 1 or 2, n denotes 0, 1, 2, 3 or 4, P denotes 1, 2, 3 or 4, and pharmaceutically usable solvates, salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides.

It is understood, that the invention also relates to the solvates of the salts. The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically usable salts, solvates, tautomers and stereoisomers thereof, characterised in that a) the compound of the formula IIa

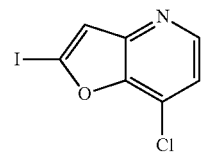

IIa is reacted with a compound of the formula IIIa $R^1$-L　　　　　　　　　　　　　　　　　　　　　　IIIa in which $R^1$ has the meaning indicated in claim 1, and L denotes a boronic acid or a boronic acid ester group, in a Suzuki-type coupling to give a compound of the formula IVa

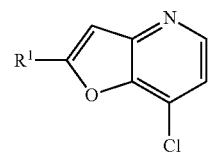

IVa in which $R^1$ has the meaning indicated in claim 1, which subsequently is reacted with a compound of the formula Va $R^2$-L　　　　　　　　　　　　　　　　　　　　　　Va in which $R^2$ has the meaning indicated in claim 1, and L denotes a boronic acid or a boronic acid ester group, in a Suzuki-type coupling, or b) the compound of the formula IIb

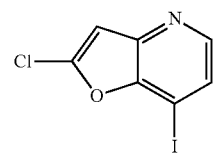

IIb is reacted with a compound of the formula Va $R^2$-L　　　　　　　　　　　　　　　　　　　　　　Va in which R² has the meaning indicated in claim 1,
and L denotes a boronic acid or a boronic acid ester group,
in a Suzuki-type coupling
to give a compound of the formula IVb

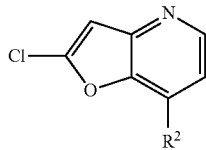

in which R² has the meaning indicated in claim 1,
which subsequently is reacted with a compound of the formula IIIa $$R^1-L \qquad \qquad \text{IIIa}$$

in which R¹ has the meaning indicated in claim 1,
and L denotes a boronic acid or a boronic acid ester group,
in a Suzuki-type coupling,
or c) it is liberated from one of its functional derivatives by treatment with a solvolysing or hydrogenolysing agent,
and/or
a base or acid of the formula I is converted into one of its salts.

Above and below, the radicals R¹ and R² have the meanings indicated for the formula I, unless expressly stated otherwise.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoro-ethyl.

Moreover, A denotes preferably $CH_2OCH_3$, $CH_2CH_2OH$, $CH_2NHCH_2$ or $NHCH_2CH_3$.

Cyclic alkyl (cycloalkyl) preferably denotes cyclopropyl, cyclobutyl, cyclopentyl, cyclohexyl or cycloheptyl.

Cyc denotes cyclic alkyl having 3-7 C atoms, preferably denotes cyclopropyl, cyclobutyl, cyclopentyl, cyclohexyl or cycloheptyl.

Alk denotes unbranched or branched alkenyl or alkinyl having 2, 3, 4, 5 or 6 C-atoms, preferably denotes isopropenyl, prop-2-inyl, vinyl oder allyl.

Ar¹ denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)-phenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino) phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)-phenyl, o-, m- or p-(methylsulfonyl)phenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-[2-(morpholin-4-yl)ethoxy]phenyl, o-, m- or p-[3-(N,N-diethylamino)propoxy]phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4, 6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar¹ furthermore preferably denotes phenyl, naphthyl or biphenyl, each of which is unsubstituted or mono-, di- or trisubstituted by Hal, A, $O(CH_2)_p$Cyc, COA, Alk, $[C(R^3)_2]_n$ CN, $(CH_2)_n$OH, $(CH_2)_n$OA, $(CH_2)_n$NH_2, $(CH_2)_n$NHA, $(CH_2)_n$NA_2, $(CH_2)_n$COOH, $(CH_2)_n$COOA, $S(O)_m$A, phenoxy, benzyloxy, $(CH_2)_n$NHCOA, $(CH_2)_n$NHCOAlk, NHCOCH=CH$(CH_2)_p$NA_2, $O(CH_2)_p$NH_2, $O(CH_2)_p$NH-COOA, $O(CH_2)_p$NHA, $O(CH_2)_p$NA_2, $NH(CH_2)_p$NH_2, $NH(CH_2)_p$NHCOOA, $NH(CH_2)_p$NHA, $NH(CH_2)_p$NA_2, NHCOHet³, COHet³, $(CH_2)_n$Het³, $O(CH_2)_n$Het³ and/or $O(CH_2)_n$CH(OH)$(CH_2)$Het³.

Ar² denotes, for example, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N,N-methylaminocarbonyl)-phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)-phenyl, o-, m- or p-(piperidinylcarbonyl)phenyl, o-, m- or p-[2-(morpholin-4-yl)ethoxy]phenyl, o-, m- or p-[3-(N,N-diethylamino)propoxy]phenyl, o-, m- or p-[3-(3-diethylaminopropyl)ureido]phenyl, o-, m- or p-(3-diethylamino-propoxycarbonylamino)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4- methoxyphenyl, 3-amino-6-methylphenyl, 3-chloro-4-acetamidophenyl or 2,5-dimethyl-4-chlorophenyl.

$Ar^2$ furthermore preferably denotes phenyl, naphthyl or biphenyl, each of which is unsubstituted or mono-, di- or trisubstituted by Hal, A, COA, $(CH_2)_nOH$, $(CH_2)_nOA$, $O(CH_2)_pCyc$, $OAr^3$, $(CH_2)_nNH_2$, $(CH_2)_nNHA$, $(CH_2)_nNA_2$, benzyloxy, $(CH_2)_nCOOH$, $(CH_2)_nCOOA$, $S(O)_mA$, $SO_2NH_2$, $SO_2NHA$, $SO_2NA_2$, $O(CH_2)_pNH_2$, $O(CH_2)_pNHA$, $O(CH_2)_pNA_2$, $[C(R^3)_2]_nCN$, $NO_2$, $CONH(CH_2)_pNH_2$, $CONH(CH_2)_pNHA$, $CONH(CH_2)_pNA_2$, $CONH(CH_2)_pOA$, $CONH(CH_2)_pOH$, $(CH_2)_nCONH_2$, $(CH_2)_nCONHA$, $(CH_2)_nCONA_2$, $(CH_2)_nNHCOA$, $(CH_2)_nNHCOAlk$, $CONHAr^3$, $NHCOAr^3$, $CONH(CH_2)_nHet^3$, $NHCOHet^3$, $COHet^3$, $(CH_2)_nHet^3$, $Het^3$, $S(CH_2)_nHet^3$ and/or $O(CH_2)_nHet^3$.

Irrespective of further substitutions, $Het^1$ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or 5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo[3.2.1]octyl or dibenzofuranyl.

$Het^1$ preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzotriazolyl, indolyl, benzo-1,3-dioxolyl, 2,3-dihydro-benzo[1,4]dioxinyl, indazolyl or benzothiadiazolyl, each of which is unsubstituted or mono-, di- or trisubstituted by $Het^4$, A, benzyl, $(CH_2)_nOH$ and/or $(CH_2)_nOA$.

Irrespective of further substitutions, $Het^2$ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo[3.2.1]octyl or dibenzofuranyl.

The heterocyclic radicals may also be partially or fully hydrogenated. Irrespective of further substitutions, $Het^2$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

$Het^2$ preferably denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzothiophenyl, benzotriazolyl, indolyl, indolinyl, benzo-1,3-dioxolyl, 2,3-dihydro-benzo[1,4]dioxinyl, 1,3-dihydro-indolyl, 1,3-dihydro-benzimidazolyl, dihydropyranyl, 3,4-dihydro-2H-pyrano[2,3-b]pyridinyl, 1,2,3,4-tetrahydro-[1,8]naphthyridinyl, furopyridinyl, indazolyl, benzo[1,4]oxazinyl, pyrido[3,2-b][1,4]oxazinyl or benzothiadiazolyl, each of which is unsubstituted or mono-, di- or trisubstituted by Hal, $(CH_2)_nHet^4$, $NH(CH_2)_nHet^4$, $OHet^4$, A, $(CH_2)_nOH$, $(CH_2)_nOA$, $(CH_2)_pCH(OH)(CH_2)_pOH$, $(CH_2)_pCH(OH)(CH_2)_pOA$, $(CH_2)_nCOOA$, phenyl, benzyl, CHO, COA, $(CH_2)_nNH_2$, $(CH_2)_nNHA$, $(CH_2)_nNA_2$, $NH(CH_2)_pNH_2$, CN, $NHSO_2A$, $NASO_2A$, $SO_2A$ and/or $=O$.

Irrespective of further substitutions, $Het^3$ denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo[3.2.1]octyl or dibenzofuranyl.

The heterocyclic radicals may also be partially or fully hydrogenated. Irrespective of further substitutions, $Het^3$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3- dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

$Het^3$ preferably denotes piperidinyl, piperazinyl, pyrrolidinyl, morpholinyl, 2,3-dihydro-pyrazolyl, 1,2-dihydro-pyridyl, furyl, thienyl, pyrrolyl, imidazolyl, pyrazolyl, oxazolyl, isoxazolyl, thiazolyl, isothiazolyl, pyridyl, pyrimidinyl, triazolyl, 4,5-dihydro-1H-[1,2,4]triazolyl, tetrazolyl, oxadiazolyl, thiadiazolyl, tetrahydro-benzothiophenyl, pyridazinyl or pyrazinyl, each of which is unsubstituted or mono-, di-, tri- or tetrasubstituted by A, Hal, $(CH_2)_nNH_2$, $(CH_2)_nNHA$, $(CH_2)_nNA_2$, $(CH_2)_nOH$, $(CH_2)_nOA$, COOA, $Ar^3$ and/or =O. Furthermore, $Het^3$ denotes 1,3-oxazinanyl, 1,4-dihydropyridinyl, 1,2,3,4-tetrahydro-6-pyridinyl, tetrahydropyranyl, 1,4-dioxanyl, 1,3-dioxanyl, hexahydropyridazinyl or hexahydropyrimidinyl.

$Het^4$ preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, piperidinyl, piperazinyl, tetrahydro-pyranyl, pyrrolidinyl or morpholinyl, each of which is unsubstituted or mono-, di- or trisubstituted by A.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ig, which conform to the formula I and in which the radicals not designated in greater detail have the meaning indicated for the formula I, but in which in Ia $Het^1$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzotriazolyl, indolyl, benzo-1,3-dioxolyl, 2,3-dihydro-benzo[1,4]dioxinyl, indazolyl or benzothiadiazolyl, each of which is unsubstituted or mono-, di- or trisubstituted by $Het^4$, A, benzyl, $(CH_2)_nOH$ and/or $(CH_2)_nOA$;

in Ib $Het^2$ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzothiophenyl, benzotriazolyl, indolyl, indolinyl, benzo-1,3-dioxolyl, 2,3-dihydro-benzo[1,4]dioxinyl, 1,3-dihydro-indolyl, 1,3-dihydro-benzimidazolyl, dihydropyranyl, 3,4-dihydro-2H-pyrano[2,3-b]pyridinyl, 3,4-dihydro-2H-pyrano[2,3-b]pyridinyl, 1,2,3,4-tetrahydro-[1,8]naphthyridinyl, furopyridinyl, indazolyl, benzo[1,4]oxazinyl, pyrido[3,2-b][1,4]oxazinyl or benzothiadiazolyl, each of which is unsubstituted or mono-, di- or trisubstituted by Hal, $(CH_2)_nHet^4$, $NH(CH_2)_nHet^4$, $OHet^4$, A, $(CH_2)_nOH$, $(CH_2)_nOA$, $(CH_2)_pCH(OH)(CH_2)_pOH$, $(CH_2)_pCH(OH)(CH_2)_pOA$, $(CH_2)_nCOOA$, phenyl, benzyl, CHO, COA, $(CH_2)_nNH_2$, $(CH_2)_nNHA$, $(CH_2)_nNA_2$, $NH(CH_2)_pNH_2$, CN, $NHSO_2A$, $NASO_2A$, $SO_2A$ and/or =O;

in Ic $Het^3$ denotes piperidinyl, piperazinyl, pyrrolidinyl, morpholinyl, 2,3-dihydro-pyrazolyl, 1,2-dihydro-pyridyl, furyl, thienyl, pyrrolyl, imidazolyl, pyrazolyl, oxazolyl, isoxazolyl, thiazolyl, isothiazolyl, pyridyl, pyrimidinyl, triazolyl, 4,5-dihydro-1H-[1,2,4]triazolyl, tetrazolyl, oxadiazolyl, thiadiazolyl, tetrahydro-benzothiophenyl, pyridazinyl or pyrazinyl, each of which is unsubstituted or mono-, di-, tri- or tetrasubstituted by A, Hal, $(CH_2)_nNH_2$, $(CH_2)_nNHA$, $(CH_2)_nNA_2$, $(CH_2)_nOH$, $(CH_2)_nOA$, COOA, $Ar^3$ and/or =O;

in Id A denotes unbranched or branched alkyl having 1-10 C atoms, in which 1-7H atoms may be replaced by F and/or Cl and/or in which one or two non-adjacent $CH_2$ groups may be replaced by O and/or NH, or cyclic alkyl having 3-7 C atoms, which may be unsubstituted or monosubstituted by OH, NHCOOA or $NH_2$;

in Ie $Ar^1$ denotes phenyl, naphthyl or biphenyl, each of which is unsubstituted or mono-, di- or trisubstituted by Hal, A, $O(CH_2)_pCyc$, COA, Alk, $[C(R^3)_2]_nCN$, $(CH_2)_nOH$, $(CH_2)_nOA$, $(CH_2)_nNH_2$, $(CH_2)_nNHA$, $(CH_2)_nNA_2$, $(CH_2)_nCOOH$, $(CH_2)_nCOOA$, $S(O)_mA$, phenoxy, benzyloxy, $(CH_2)_nNHCOA$, $(CH_2)_nNHCOAlk$, $NHCOCH=CH(CH_2)_pNA_2$, $O(CH_2)_pNH_2$, $O(CH_2)_pNHCOOA$, $O(CH_2)_pNHA$, $O(CH_2)_pNA_2$, $NH(CH_2)_pNH_2$, $NH(CH_2)_pNHCOOA$, $NH(CH_2)_pNHA$, $NH(CH_2)_pNA_2$, $NHCOHet^3$, $COHet^3$, $(CH_2)_nHet^3$, $O(CH_2)_nHet^3$ and/or $O(CH_2)_pCH(OH)(CH_2)Het^3$;

in If $Ar^2$ denotes phenyl, naphthyl or biphenyl, each of which is unsubstituted or mono-, di- or trisubstituted by Hal, A, COA, $(CH_2)_nOH$, $(CH_2)_nOA$, $O(CH_2)_pCyc$, $OAr^3$, $(CH_2)_nNH_2$, $(CH_2)_nNHA$, $(CH_2)_nNA_2$, benzyloxy, $(CH_2)_nCOOH$, $(CH_2)_nCOOA$, $S(O)_mA$, $SO_2NH_2$, $SO_2NHA$, $SO_2NA_2$, $O(CH_2)_pNH_2$, $O(CH_2)_pNHA$, $O(CH_2)_pNA_2$, $[C(R^3)_2]_nCN$, $NO_2$, $CONH(CH_2)_pNH_2$, $CONH(CH_2)_pNHA$, $CONH(CH_2)_pNA_2$, $(CH_2)_nCONH_2$, $(CH_2)_nCONHA$, $(CH_2)_nCONA_2$, $CONH(CH_2)_pOA$, $CONH(CH_2)_pOH$, $(CH_2)_nNHCOA$, $(CH_2)_nNHCOAlk$, $CONHAr^3$, $NHCOAr^3$, $CONH(CH_2)_nHet^3$, $NHCOHet^3$, $COHet^3$, $(CH_2)_nHet^3$, $S(CH_2)_nHet^3$ and/or $O(CH_2)_nHet^3$;

in Ig R' denotes $Ar^1$ or $Het^1$, $R^2$ denotes $Ar^2$, $Het^2$, $NH(CH_2)_nAr^2$, $O(CH_2)_nAr^2$ or $NH(CH_2)_nHet^2$, $Ar^1$ denotes phenyl, naphthyl or biphenyl, each of which is unsubstituted or mono-, di- or trisubstituted by Hal, A, $O(CH_2)_pCyc$, COA, Alk, $[C(R^3)_2]_nCN$, $(CH_2)_nOH$, $(CH_2)_nOA$, $(CH_2)_nNH_2$, $(CH_2)_nNHA$, $(CH_2)_nNA_2$, $(CH_2)_nCOOH$, $(CH_2)_nCOOA$, $S(O)_mA$, phenoxy, benzyloxy, $(CH_2)_nNHCOA$, $(CH_2)_nNHCOAlk$, $NHCOCH=CH(CH_2)_pNA_2$, $O(CH_2)_pNH_2$, $O(CH_2)_p$ NHCOOA, O(CH$_2$)$_p$NHA, O(CH$_2$)$_p$NA$_2$, NH(CH$_2$)$_p$NH$_2$, NH(CH$_2$)$_p$NHCOOA, NH(CH$_2$)$_p$NHA, NH(CH$_2$)$_p$ NA$_2$, NHCOHet$^3$, COHet$^3$, (CH$_2$)$_n$Het$^3$, O(CH$_2$)$_n$Het$^3$ and/or O(CH$_2$)$_n$CH(OH)(CH$_2$)Het$^3$, Ar$^2$ denotes phenyl, naphthyl or biphenyl, each of which is unsubstituted or mono-, di- or trisubstituted by Hal, A, COA, (CH$_2$)$_n$OH, (CH$_2$)$_n$OA, O(CH$_2$)$_p$Cyc, OAr$^3$, (CH$_2$)$_n$NH$_2$, (CH$_2$)$_n$NHA, (CH$_2$)$_n$NA$_2$, benzyloxy, (CH$_2$)$_n$COOH, (CH$_2$)$_n$COOA, S(O)$_m$A, SO$_2$NH$_2$, SO$_2$NHA, SO$_2$NA$_2$, O(CH$_2$)$_p$NH$_2$, O(CH$_2$)$_p$NHA, O(CH$_2$)$_p$NA$_2$, [C(R$^3$)$_2$]$_n$CN, NO$_2$, CONH(CH$_2$)$_p$NH$_2$, CONH(CH$_2$)$_p$NHA, CONH(CH$_2$)$_p$NA$_2$, CONH(CH$_2$)$_p$OA, CONH(CH$_2$)$_p$OH, (CH$_2$)$_n$CONH$_2$, (CH$_2$)$_n$CONHA, (CH$_2$)$_n$CONA$_2$, (CH$_2$)$_n$NHCOA, (CH$_2$)$_n$NHCOAlk, CONHAr$^3$, NHCOAr$^3$, CONH(CH$_2$)$_n$Het$^3$, NHCOHet$^3$, COHet$^3$, (CH$_2$)$_n$Het$^3$, S(CH$_2$)$_n$Het$^3$ and/or O(CH$_2$)$_n$Het$^3$, Het$^1$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzotriazolyl, indolyl, benzo-1,3-dioxolyl, 2,3-dihydro-benzo[1,4]dioxinyl, indazolyl or benzothiadiazolyl, each of which is unsubstituted or mono-, di- or trisubstituted by Het$^4$, A, benzyl, (CH$_2$)$_n$OH and/or (CH$_2$)$_n$OA, Het$^2$ denotes piperidinyl, piperazinyl, pyrrolidinyl, morpholinyl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzothiophenyl, benzotriazolyl, indolyl, indolinyl, benzo-1,3-dioxolyl, 2,3-dihydro-benzo[1,4]dioxinyl, 1,3-dihydro-indolyl, 1,3-dihydro-benzimidazolyl, dihydropyranyl, 1,2,3,4-tetrahydro-[1,8]naphthyridinyl, furopyridinyl, indazolyl, benzo[1,4]oxazinyl, pyrido[3,2-b][1,4]oxazinyl or benzothiadiazolyl, each of which is unsubstituted or mono-, di- or trisubstituted by Hal, (CH$_2$)$_n$Het$^4$, NH(CH$_2$)$_n$Het$^4$, OHet$^4$, A, (CH$_2$)$_n$OH, (CH$_2$)$_n$OA, (CH$_2$)$_p$CH(OH)(CH$_2$)$_p$OH, (CH$_2$)$_p$CH(OH)(CH$_2$)$_p$OA, (CH$_2$)$_n$COOA, phenyl, benzyl, CHO, COA, (CH$_2$)$_n$NH$_2$, (CH$_2$)$_n$NHA, (CH$_2$)$_n$NA$_2$, NH(CH$_2$)$_p$ NH$_2$, CN, NHSO$_2$A, NASO$_2$A, SO$_2$A and/or =O, Het$^3$ denotes piperidinyl, piperazinyl, pyrrolidinyl, morpholinyl, 2,3-dihydro-pyrazolyl, 1,2-dihydro-pyridyl, furyl, thienyl, pyrrolyl, imidazolyl, pyrazolyl, oxazolyl, isoxazolyl, thiazolyl, isothiazolyl, pyridyl, pyrimidinyl, triazolyl, 4,5-dihydro-1H-[1,2,4]triazolyl, tetrazolyl, oxadiazolyl, thiadiazolyl, tetrahydro-benzothiophenyl, pyridazinyl or pyrazinyl, each of which is unsubstituted or mono-, di-, tri- or tetrasubstituted by A, Hal, (CH$_2$)$_n$NH$_2$, (CH$_2$)$_n$NHA, (CH$_2$)$_n$NA$_2$, (CH$_2$)$_n$OH, (CH$_2$)$_n$OA, COOA, Ar$^3$ and/or =O, Het$^4$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, piperidinyl, piperazinyl, tetrahydro-pyranyl, pyrrolidinyl or morpholinyl, each of which is unsubstituted or mono-, di- or trisubstituted by A, R$^3$ H or alkyl having 1, 2, 3 or 4 C-atoms, A denotes unbranched or branched alkyl having 1-10 C atoms, in which 1-7 H atoms may be replaced by F and/or Cl and/or in which one or two non-adjacent CH$_2$ groups may be replaced by O and/or NH, or cyclic alkyl having 3-7 C atoms, which may be unsubstituted or monosubstituted by OH, NHCOOA or NH$_2$, Cyc denotes cyclic alkyl having 3-7 C atoms, Alk alkenyl having 2, 3, 4, 5 or 6 C-atoms, Ar$^3$ denotes phenyl, which is unsubstituted or mono-, di- or trisubstituted by Hal and/or A, m denotes 0, 1 or 2, n denotes 0, 1, 2, 3 or 4, p denotes 1, 2, 3 or 4;

and pharmaceutically usable salts, solvates, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formulae II and III are generally known. If they are novel, however, they can be prepared by methods known per se. The pyridazinones of the formula II used are, if not commercially available, generally prepared by the method of W. J. Coates, A. McKillop, Synthesis, 1993, 334-342.

Compounds of the formula I can preferably be obtained by reacting in a first step the compound of the formula IIa with a compound of the formula IIIa to give a compound of formula IVa.

In the compounds of the formula IIIa, L preferably denotes

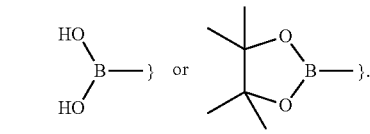

The reaction is generally carried out under conditions of a Suzuki-type coupling.

Depending on the conditions used, the reaction time is between a few minutes and 14 days, the reaction temperature is between about −30° and 140°, normally between 0° and 100°, in particular between about 60° and about 90°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to ethanole, toluene, dimethoxyethane, 1,4-dioxane and/or water.

In a second step the compound of the formula IVa is reacted with a compound of the formula Va.

In the compounds of the formula Va, L preferably denotes

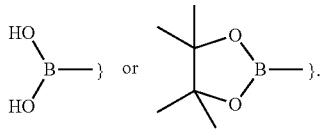

The reaction is generally carried out under conditions of a Suzuki-type coupling as given above.

Alternatively, compounds of the formula I can preferably be obtained by reacting in a first step the compound of the formula IIb with a compound of the formula Va to give a compound of formula IVb, which subsequently is reacted with a compound of the formula IIIa.

Both reaction steps are generally carried out under conditions of a Suzuki-type coupling as given above.

It is furthermore possible to convert a compound of the formula I into another compound of the formula I, for example by reducing nitro groups to amino groups (for example by hydrogenation on Raney nickel or Pd/carbon in an inert solvent, such as methanol or ethanol).

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an aminoprotecting group instead of an H atom bonded to an N atom, for example those which conform to the formula I, but contain an NHR' group (in which R' is an aminoprotecting group, for example BOC or CBZ) instead of an NH₂ group.

Preference is furthermore given to starting materials which carry a hydroxyl-protecting group instead of the H atom of a hydroxyl group, for example those which conform to the formula I, but contain an R"O-phenyl group (in which R" is a hydroxylprotecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "aminoprotecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the aminoprotecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred aminoprotecting groups are BOC and Mtr, furthermore CBZ, Fmoc, benzyl and acetyl.

The term "hydroxylprotecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxylprotecting groups are not crucial since they are removed again after the desired chemical reaction or reaction sequence; preference is given to groups having 1-20, in particular 1-10, carbon atoms. Examples of hydroxylprotecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

The trityl group is employed to protect the amino acids histidine, asparagine, glutamine and cysteine. They are cleaved off, depending on the desired end product, using TFA/10% thiophenol, with the trityl group being cleaved off from all the said amino acids; on use of TFA/anisole or TFA/thioanisole, only the trityl group of His, Asn and Gln is cleaved off, whereas it remains on the Cys side chain.

The Pbf (pentamethylbenzofuranyl) group is employed to protect Arg. It is cleaved off using, for example, TFA in dichloromethane.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Moreover, the invention relates to the compounds of the formula IVa

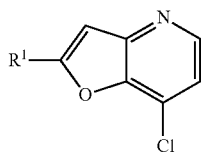

IVa in which
R¹ denotes Ar¹ or Het¹,
Ar¹ denotes phenyl, naphthyl or biphenyl, each of which is unsubstituted or mono-, di- or trisubstituted by Hal, A, O(CH$_2$)$_p$Cyc, COA, Alk, [C(R³)$_2$]$_n$CN, (CH$_2$)$_n$OH, (CH$_2$)$_n$OA, (CH$_2$)$_n$NH$_2$, (CH$_2$)$_n$NHA, (CH$_2$)$_n$NA$_2$, (CH$_2$)$_n$COOH, (CH$_2$)$_n$COOA, S(O)$_m$A, phenoxy, benzyloxy, (CH$_2$)$_n$NHCOA, (CH$_2$)$_n$NHCOAlk, NHCOCH=CH(CH$_2$)$_p$NA$_2$, O(CH$_2$)$_p$NH$_2$, O(CH$_2$)$_p$NHCOOA, O(CH$_2$)$_p$NHA, O(CH$_2$)$_p$NA$_2$, NH(CH$_2$)$_p$NH$_2$, NH(CH$_2$)$_p$NHCOOA, NH(CH$_2$)$_p$NHA, NH(CH$_2$)$_p$NA$_2$, NHCOHet³, COHet³, (CH$_2$)$_n$Het³, O(CH$_2$)$_n$Het³ and/or O(CH$_2$)$_n$CH(OH)(CH$_2$)Het³,
Het¹ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, quinolyl, isoquinolyl, benzimidazolyl, benzotriazolyl, indolyl, benzo-1,3-dioxolyl, 2,3-dihydro-benzo[1,4]dioxinyl, indazolyl or benzothiadiazolyl, each of which is unsubstituted or mono-, di- or trisubstituted by Het⁴, A, benzyl, (CH$_2$)$_n$OH and/or (CH$_2$)$_n$OA,
Het³ denotes piperidinyl, piperazinyl, pyrrolidinyl, morpholinyl, 2,3-dihydro-pyrazolyl, 1,2-dihydro-pyridyl, furyl, thienyl, pyrrolyl, imidazolyl, pyrazolyl, oxazolyl, isoxazolyl, thiazolyl, isothiazolyl, pyridyl, pyrimidinyl, triazolyl, 4,5-dihydro-1H-[1,2,4]triazolyl, tetrazolyl, oxadiazolyl, thiadiazolyl, tetrahydro-benzothiophenyl, pyridazinyl or pyrazinyl, each of which is unsubstituted or mono-, di-, tri- or tetrasubstituted by A, Hal, (CH$_2$)$_n$NH$_2$, (CH$_2$)$_n$NHA, (CH$_2$)$_n$NA$_2$, (CH$_2$)$_n$OH, (CH$_2$)$_n$OA, COOA, Ar³ and/or =O,
R³ denotes H or alkyl having 1, 2, 3 or 4 C-atoms,
A denotes unbranched or branched alkyl having 1-10 C atoms, in which 1-7H atoms may be replaced by F and/or in which one or two non-adjacent CH$_2$ groups may be replaced by O and/or NH,
or
cyclic alkyl having 3-7 C atoms
Alk denotes alkenyl or alkinyl having 2, 3, 4, 5 or 6 C-atoms,
Ar³ denotes phenyl, which is unsubstituted or mono-, di- or trisubstituted by Hal and/or A,
n denotes 0, 1, 2, 3 or 4,
p denotes 1, 2, 3 or 4, and pharmaceutically acceptable solvates, salts, tautomers and stereoisomers thereof, including mixtures thereof in all ratios.

Preferred meanings of the radicals are the same as described for compounds of the formula I.

Compounds of formula Ia are useful intermediates for the preparation of compounds of formula I.

Moreover, compounds of formula Iva show Syk inhibitory activity and hence, can be used as medicaments.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methyl-glutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethyl-piperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)methylamine(tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically acceptable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal anti-bodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The disclosed compounds of the formula I can be administered in combination with other known therapeutic agents including agents for the treatment of RA (rheumatoid arthritis). As used here, the term "agents for the treatment of RA" relates to any agent which is administered to a patient with RA for the purposes of treating the RA.

The medicaments below are preferably, but not exclusively, combined with the compounds of the formula I:
1. NSAIDs (non-steroidal anti-inflammatory drugs) and analgesics
2. Glucocorticoids (low oral doses)
3. Conventional disease-modifying antirheumatic drugs (DMARDs)
   Methotrexate
   Leflunomide
   Sulfasalazine
   Hydroxycloroquine
   Azathioprine
   Ciclosporin
   Minocycline
   Gold
4. Biologic response modifiers (BRMs)—>target molecules/immune cells involved in the inflammatory process, and include the following agents:
   TNF inhibitors
      etanercept (Enbrel)
      infliximab (Remicade)
      adalimumab (Humira)
   B-cell-directed therapy
      rituximab (Rituxan)
   T-cell/B-cell coactivation signal inhibitor
      abatacept (Orencia)
   IL-1 receptor antagonist
      anakinra (Kineret)

| | MECHANISM OF ACTION |
|---|---|
| Golimumab | Fully humanized monoclonal antibody to TNF |
| Certolizumab pegol | Anti-TNF agent with just the Fab portion attached to the polyethylene glycol |
| Tocilizumab | Humanized monoclonal anti-IL-6 antibody that binds to the soluble and membrane-expresses IL-6 receptor |
| Ocrelizumab | Humanized-second generation anti-CD20 antibody that depletes B cells |
| Ofatumumab | Human monoclonal anti-CD20 IgG1 antibody |
| Denosumab | Fully humanized monoclonal antibody that binds to and inhibits the receptor activator for nuclear factor-kB ligand |
| TRU-015 | New class of CD20-directed protein therapeutics |
| Oral small molecules (JAK, Syk, MAP kinase inhibitors) | Cytoplasmic targets |
| Tolerogens (dnaJP1) | Immunotherapy based on T-cell tolerization |

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, solvates and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically acceptable salts, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, solvates and stereoisomers thereof, including mixtures thereof in all ratios,
and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer, metabolic conditions or conditions treatable or preventable by inhibition of a kinase or a kinase pathway, in one embodiment, the Syk, FLT-3, JAKI and/or JAK2 pathway. In one embodiment an effective amount of a compound of formula (I) is an amount that inhibits a kinase in a cell, such as, for example, in vitro or in vivo. In some embodiments, the effective amount of the compound of formula (I) inhibits the kinase in a cell by 10%, 20%, 30%, 40%, 50%, 60%, 70%, 80%, 90% or 99%, compared to the activity of the kinase in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans, in the treatment of tyrosine kinase-induced diseases.

The present invention encompasses the use of the compounds of the formula I and/or physiologically acceptable salts and solvates thereof for the preparation of a medicament for the treatment or prevention of rheumatoid arthritis, systemic lupus, asthma, allergic rhinitis, ITP, multiple sclerosis, leukemia, breast cancer and maligna melanoma.

Examples of inflammatory diseases include rheumatoid arthritis, psoriasis, contact dermatitis, delayed hypersensitivity reaction and the like.

Also encompassed is the use of the compounds of the formula I and/or physiologically acceptable salts and solvates thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The present invention specifically relates to compounds of the formula I and pharmaceutically acceptable salts, solvates, tautomers and stereoisomers thereof, including mixtures thereof in all ratios, for the use for the treatment of diseases in which the inhibition, regulation and/or modulation inhibition of Syk plays a role.

The present invention specifically relates to compounds of the formula I and pharmaceutically acceptable salts, solvates, tautomers and stereoisomers thereof, including mixtures thereof in all ratios, for the use for the inhibition of Syk.

The present invention specifically relates to compounds of the formula I and pharmaceutically acceptable salts, solvates, tautomers and stereoisomers thereof, including mixtures thereof in all ratios, for the use for the treatment of rheumatoid arthritis, systemic lupus, asthma, allergic rhinitis, ITP, multiple sclerosis, leukemia, breast cancer, maligna melanoma.

The present invention specifically relates to methods for treating or preventing an inflammatory condition, immunological condition, autoimmune condition, allergic condition, rheumatic condition, thrombotic condition, cancer, infection, neurodegenerative disease, neuroinflammatory disease, cardiovascular disease or metabolic condition, comprising administering to a subject in need thereof an effective amount of a compound of formula I or a pharmaceutically acceptable salt, tautomer, stereoisomer or solvate thereof.

In another aspect provided herein are methods of inhibiting a kinase in a cell expressing said kinase, comprising contacting said cell with an effective amount of a compound of formula I or a pharmaceutically acceptable salt, tautomer, stereoisomer or solvate thereof. In one embodiment the kinase is Syk, FLT3, JAK1 or JAK2 or JAK3 or BTK, or mutants or isoforms thereof, or combinations of two or more thereof.

Representative immunological conditions that compounds of formula I are useful for treating or preventing include, but are not limited to, Behcet's syndrome, non-allergy mast cell diseases (e.g., mastocytosis and treatment of anaphylaxis), ankylosing spondylitis, osteoarthritis, rheumatoid arthritis (RA), multiple sclerosis, lupus, inflammatory bowel disease, ulcerative colitis, Crohn's disease, myasthenia gravis, Grave's disease, transplant rejection, humoral transplant rejection, non-humoral transplant rejection, cellular transplant rejection, immune thrombocytopenic purpura (ITP), idiopathic thrombocytopenic purpura, diabetes, immunological response to bacterial, parasitic, helminth infestation or viral infection, eczema, dermatitis, graft versus host disease, Goodpasture's disease, hemolytic disease of the newborn, autoimmune hemolytic anemia, anti-phospholipid syndrome, ANCA-associated vasculitis, Churg-Strauss syndrome, Wegeners granulomatosus, pemphigus vulgaris, serum sickness, mixed cryoglobulinemia, peripheral neuropathy associated with IgM antibody, microscopic polyangiitis, Hashimoto's thyroiditis, Sjogrens syndrome, fibrosing conditions (such as those dependent on the innate or adaptive immune systems or local mesenchyma cells) or primary biliary cirrhosis.

Representative autoimmune conditions that compounds of formula I are useful for treating or preventing include, but are not limited to, autoimmune hemolytic anemia (A1HA), Behcet's syndrome, Crohn's disease, type I diabetes, Goodpasture's disease, Grave's disease, Hashimoto's thyroiditis, idiopathic thrombocytopenic purpura, lupus, multiple sclerosis, amyotrophic lateral sclerosis, myasthenia gravis, pemphigus vulgaris, primary biliary cirrhosis, rheumatoid arthritis, scleroderma, Sjogren's syndrome, ulcerative colitis, or Wegeners granulomatosus.

Representative allergic conditions that compounds of formula I are useful for treating or preventing include, but are not limited to, anaphylaxis, hay fever, allergic conjunctivitis, allergic rhinitis, allergic asthma, atopic dermatitis, eczema, urticaria, mucosal disorders, tissue disorders and certain gastrointestinal disorders.

Representative rheumatic conditions that compounds of formula I are useful for treating or preventing include, but are not limited to, rheumatoid arthritis, gout, ankylosing spondylitis, or osteoarthritis.

Representative inflammatory conditions that compounds of formula I are useful for treating or preventing include, but are not limited to, non-ANCA (anti-neutrophil cytoplasmic autoantibody) vasculitis (e.g., wherein Syk function is associated with neutrophil adhesion, diapedesis and/or activation), psoriasis, asthma, allergic rhinitis, allergic conjunctivitis, chronic urticaria, hives, anaphylaxis, bronchitis, chronic obstructive pulmonary disease, cystic fibrosis, inflammatory bowel disease, irritable bowel syndrome, gout, Crohn's disease, mucous colitis, ulcerative colitis, allergy to intestinal antigens (such as gluten enteropathy), diabetes (e.g., Type I diabetes and Type II diabetes) and obesity. In some embodiments, the inflammatory condition is a dermatologic condition, such as, for example, psoriasis, urticaria, hives, eczema, scleroderma, or dermatitis. In other embodiments, the inflammatory condition is an inflammatory pulmonary condition, such as, for example, asthma, bronchitis, chronic obstructive pulmonary disease (COPD), or adult/acute respiratory distress syndrome (ARDS). In other embodiments, the inflammatory condition is a gastrointestinal condition, such as, for example, inflammatory bowel disease, ulcerative colitis, Crohn's disease, idiopathic inflammatory bowel disease, irritable bowel syndrome, or spastic colon.

Representative infections that compounds of formula I are useful for treating or preventing include, but are not limited to, bacterial, parasitic, prion, viral infections or helminth infestation.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Representative cardiovascular diseases that compounds of formula I are useful for treating or preventing include, but are not limited to, restenosis, atherosclerosis and its consequences such as stroke, myocardial infarction, ischemic damage to the heart, lung, gut, kidney, liver, pancreas, spleen or brain.

Representative metabolic conditions that compounds of formula I are useful for treating or preventing include, but are not limited to, obesity and diabetes (e.g., Type I and II diabetes). In a particular embodiment, provided herein are methods for the treatment or prevention of insulin resistance. In certain embodiments, provided herein are methods for the treatment or prevention of insulin resistance that leads to diabetes (e.g., Type II diabetes). In another embodiment, provided herein are methods for the treatment or prevention of syndrome X or metabolic syndrome. In another embodiment, provided herein are methods for the treatment or prevention of Type II diabetes, Type I diabetes, slow-onset Type I diabetes, diabetes insipidus (e.g., neurogenic diabetes insipidus, nephrogenic diabetes insipidus, dipsogenic diabetes insipidus, or gestagenic diabetes insipidus), diabetes mellitus, gestational diabetes mellitus, polycystic ovarian syndrome, maturity-onset diabetes, juvenile diabetes, insulin-dependant diabetes, non-insulin dependant diabetes, malnutrition-related diabetes, ketosis-prone diabetes, pre-diabetes (e.g., impaired glucose metabolism), cystic fibrosis related diabetes, hemochromatosis and ketosis-resistant diabetes.

Representative neurodegenerative and neuroinflammatory diseases that compounds of formula I are useful for treating or preventing include, but are not limited to, Huntington's disease, Alzheimer's disease, viral (e.g., HIV) or bacterial-associated encephalitis and damage.

In another embodiment, provided herein are methods for the treatment or prevention of fibrotic diseases and disorders. In a particular embodiment, provided herein are methods for the treatment or prevention of idiopathic pulmonary fibrosis, myelofibrosis, hepatic fibrosis, steatofibrosis and steatohepatitis.

In another embodiment, provided herein are methods for the treatment or prevention of diseases associated with thrombotic events such as but not limited to atherosclerosis, myocardial infarction and ischemic stroke.

The following abbreviations refer respectively to the definitions below: aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), CDCl$_3$ (deuterated chloroform), CD$_3$OD (deuterated methanol), CH$_3$CN (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-d$_6$ (deuterated dimethylsulfoxide), EDC (1-(3-dimethyl-aminopropyl)-3-ethylcarbodiimide), ESI (Electro-spray ionization), EtOAc (ethyl acetate), Et$_2$O (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), K$_2$CO$_3$ (potassium carbonate), LC (Liquid Chromatography), MeOH (methanol), MgSO$_4$ (magnesium sulfate), MS (mass spectrometry), MTBE (Methyl tert-butyl ether), NaHCO$_3$ (sodium bicarbonate), NaBH$_4$ (sodium borohydride), NMM (N-methyl morpholine), NMR (Nuclear Magnetic Resonance), PyBOP (benzotriazole-1-yloxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Description of the In Vitro Assays
SYK Flash Plate Assay

The kinase assay is performed either as 384-well Flashplate assay (for e.g. Topcount measurement) or as 384-well Image-Flashplate assay (for LEADseeker measurement).

2.5 nM SYK, 400 nM Biotin-Aha-Aha-KEDPDYEWP-SAKK and 10 μM ATP (spiked with 0.3 μCi 33P-ATP/well) are incubated in a total volume of 50 μl (60 mM Hepes, 10 mM MgCl$_2$, 1.2 mM Dithiothreitol, 0.02% Brij35, 0.1% BSA, pH 7.5) with or without test compound for 1 hours at 30° C. The reaction is stopped with 25 μl 200 mM EDTA. After 30 Min at 30° C. the liquid is removed and each well washed thrice with 100 μl 0.9% sodium chloride solution. Non-specific reaction is determined in presence of 0.1 μM Staurosporine. Radioactivity is measured with Topcount (when using Flashplates) or with LEADseeker (when using Image-Flashplates) respectively. Results (e.g. IC50-values) are calculated with program tools provided by the IT-department (e.g. Symyx Assay Explorer, Genedata Screener).

Enzymatic Assays Using the Caliper LifeSciences Technology

The assays described here are performed on the Caliper Life Sciences LC3000 system This technology provides data on enzyme activity via measurement of the relative amounts of phosphorylated or unphosphorylated fluorescently labelled substrate peptide at the end of an enzymatic reaction. These different states of peptide are resolved by applying a potential difference across the sample. The presence of the charged phosphate group on the product (as opposed to the substrate) causes a different peptide mobility between the two peptides. This is visualized by excitation of the fluorescent label on the substrate and product peptides and represented as peaks within the analysis software.

In order to measure inhibitor activity of kinase inhibitors on this technology, a TTP Mosquito liquid handling instrument is used to place 0.25 ul of the appropriate concentration of inhibitor in 100% DMSO (for a dose response curve calculation) into each well of a 384-well plate. To this reaction components are added to a final volume of 25 ul. The table below indicates the sequences and concentrations for the assays described in this report. Standard components are 1 mM DTT (Sigma, D0632), 1 mM MgCl2 (Sigma, M1028), 100 mM HEPES pH 7.5 (Calbiochem, 391338), 0.015% Brij-35 (Sigma, B4184).

| Enzyme | Enzyme Concentration (ng/ul) | ATP Concentration (uM) | Peptide Sequence (@ 1 uM) |
|---|---|---|---|
| Syk (BPS Bioscience, CA, USA) | 0.06 | 5 | FITC-AHA-KEDPDYEWPSAKKK-NH2 |
| KDR (BPS Bioscience, CA, USA) | 3.3 | 160 | FITC-AHA-EEPLYWSFPAKKK-NH2 |
| Src (Carna Bioscience, Kobe, Japan) | 0.1 | 36 | FITC-AHA-EEPLYWSFPAKKK-NH2 |
| ZAP-70 (BPS Bioscience, CA, USA) | 0.5 | 5 | FITC-AHA-EDPIYEFLPAKKK-NH2 |
| FAK (Carna Bioscience, Kobe, Japan) | 3 | 100 | FITC-AHA-KKSRGDYMTMQIG-NH2 |
| PYK2 (Carna Bioscience, Kobe, Japan) | 0.25 | 50 | FITC-AHA-SIESDIYAEIPDETLRR-NH2 |
| FLT3 (BPS Bioscience, CA, USA) | 5.7 | 350 | FITC-AHA-EAIYAAPFAKKK-NH2 |
| JAK2 (Carna Bioscience, Kobe, Japan) | 0.025 | 13 | FITC-AHA-gpkgtgyiktelisys |
| BTK (Carna Bioscience, Kobe, Japan) | 0.2 | 75 | FITC-AHA-EEPLYWSFPAKKK-NH2 |
| Lyn (Carna Bioscience, Kobe, Japan) | 0.1 | 15 | FITC-AHA-EEPLYWSFPAKKK-NH2 |
| Fyn (Carna Bioscience, Kobe, Japan) | 0.0075 | 50 | FITC-AHA-EEPLYWSFPAKKK-NH2 |

The reaction is incubated for 90 min at 25 C, and then stopped by the addition of 70 ul of Stop buffer (100 mM HEPES pH 7.5, 0.015% Brij-35, 10 mM EDTA (Sigma, E7889)).

The plate is read on a Caliper LC 3000 in an Off-Chip mobility shift assay format, on a 12-sipper chip. Unphosphorylated substrate and phosphorylated product peptide resolve as separate peaks allowing direct measurement of percentage of conversion of substrate to product. The percent conversion can be plotted against concentration of inhibitor to produce a sigmoidal dose response curve, from which an IC50 can be calculated using GeneData Condoseo or a similar product.

Cellular Activity Assays

1. BCR Crosslinking-Induced BLNK Phosphorylation

Ramos cells incubated overnight in IMDM medium containing 5% FCS were resuspended in IMDM medium without serum ($3.3 \times 10^6$ cells/ml). 90 µl of cell suspension (300'000 cells) were incubated with 10 µl of SYK inhibitors (in 3% DMSO) for 20 minutes at 37° C., in 96 well plates. After preincubation with inhibitors, cells were activated with 10 µg/ml of goat antihuman anti-IgM for 10 minutes at 37° C. After stimulation, cells were fixed by addition of 80 µl of 4% paraformaldehyde followed by a 10 minutes incubation at RT and fixed in 0.1% Triton X-100 in PBS. BLNK phosphorylation was detected by flow cytometry after staining of the cells with anti-BLNK-pY84-PE antibodies from BD pharmingen, for 45 minutes at RT.

BLNK phosphorylation in $CD19^+$ peripheral blood mononuclear cells (PBMC) isolated from buffy coats of healthy volunteers was performed using the same protocol and staining the cells with a mixture of anti-BLNK-pY84-PE, anti CD-19 PerCp and Anti-IgM APC antibodies from BD Pharmingen.

2. BCR Crosslinking-Induced CD69 Up-Regulation

To quantify anti-IgM-induced CD69 up-regulation in peripheral blood mononuclear cells, 90 µl of PBMC cell suspension (containing $1 \times 10^6$ cells) were preincubated with 10 µl of SYK inhibitors (in 3% DMSO) for 1 h at 37° C./5% $CO_2$. After preincubation with inhibitors cells were stimulated with 10 µg/ml of goat antihuman anti-IgM during 18 hours at 37° C./5% $CO_2$. After stimulation cells were stained with a cocktail containing goat IgG (1:200 dilution), CD19-PerCpCy5.5 (5 µl) and CD69-APC (3 µl) antibodies in PBS containing 4% FCS. CD69 expression in $CD19^+$ cells was quantified by flow cytometry.

In Vivo Assays

CIA

For induction of collagen-induced arthritis (CIA) male DBA/1 mice are injected with 500 µl pristane i.p. on day −21. On day 0 mice are immunized with 100 µg chicken collagen type II (CII) in Complete Freund's Adjuvant (CFA) intradermally, distributed over pinnae and one site on the back on day 0. On day 21, mice will receive an i.p. booster immunization (100 µg) with soluble CII in PBS. Dosing of Syk inhibitor will be prophylactic: starting day 0 and continued until day 10 and before boost starting on day 20 and continued until day 30. Compounds will be administered orally twice a day at doses of 3, 10 and 30 mg/kg.

Body weight and clinical score will be recorded on a daily basis. Arthritis severity is graded using a clinical scoring system based on the assessment of inflammation in individual paws. The scale for this clinical score ranges from 0-4 for each individual paw.

GIA

For induction of Glucose-6-phosphate isomerase-induced arthritis (GIA) female DBA/1 mice are immunized with 100 µg G6PI in Complete Freund's Adjuvant (CFA) intradermally, distributed over pinnae and one site on the back on day 0. Dosing of Syk inhibitor will be prophylactic starting day 0 and continued until day 14. Compounds will be administered orally twice a day at doses of 3, 10 and 30 mg/kg.

Body weight and clinical score will be recorded on a daily basis. Arthritis severity is graded using a clinical scoring system based on the assessment of inflammation in individual paws. The scale for this clinical score ranges from 0-4 for each individual paw.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

Mass spectrometry (MS): EI (electron impact ionisation) M+
    FAB (fast atom bombardment) (M+H)+
    ESI (electrospray ionisation) (M+H)+
APCI-MS (atmospheric pressure chemical ionisation-mass spectrometry) (M+H)+.

Mass spectrometry (MS): EI (electron impact ionisation) M+
    FAB (fast atom bombardment) (M+H)+
    ESI (electrospray ionisation) (M+H)+
APCI-MS (atmospheric pressure chemical ionisation-mass spectrometry) (M+H)+.

m.p.=melting point

HPLC data provided in the examples described below (retention time given) were obtained as followed:
method A:
1 min 99% A,
in 2.5 min from 99% A to 100% B,
followed by 1.5 min 100% B and 1 min 99% A.
Column: Chromolith SpeedRod RP-18e; 50-4.6 mm;
detection 220 nM (solvent A: H$_2$0 (0.1% TFA),
solvent B: ACN (0.1% TFA);
method F: In 8 min from 98% A to 100% B,
within 0.1 min to 98% A,
during 1.9 min 98% A (solvent A H$_2$0 (0.1% TFA), solvent B: ACN (0.1% TFA));
column: Xbridge C8 5 µM, 4.6×50 mm; flow rate: 2 mL/min.
Method H: 0.2 min 99% A; within 2.6 min from 1% B to 100% B, followed by 0.6 min 100% B and within 0.1 min to 99% A. Column Chromolith
Performance RP18e 100-3 mm, flow rate 2 ml/min, detection 220 nM; Solvent A: H2O (0.05% HCOOH), Solvent B: ACN (0.04% HCOOH)

LCMS data provided in the examples are given with retention time, purity and/or mass in m/z. The results were obtained as followed: mass spectrum: LC/MS Waters ZMD (ESI) or Hewlett Packard System of the HP 1100 series (ion source: electrospray (positive mode); scan: 100-1000 m/z; fragmentation-voltage: 60 V; gas-temperature: 300° C., DAD: 220 nm; flow rate: 2.4 ml/min. The used splitter reduced the flow rate after the DAD for the MS to 0.75 ml/min; column: Chromolith Speed ROD RP-18e 50-4.6; solvent: LiChrosolv-quality from the company Merck KGaA or as mentioned in the method;

method B: A—0.1% HCOOH, B—MeOH: flow-1.0 ml/min.; column: Atlantis C8 (50×4.6 mm 5 Um, +ve mode);

method C: A—10 mM, B—MeOH: flow 1.0 ml/min, column: XBridge C8 (30×2.1 mm 3.5 Um, +ve mode);

method D: A—0.1% TFA in H$_2$O, B—0.1% TFA in ACN: flow-2.0 ml/min; column: XBridge C8 (50×4.6 mm 3.5 Um, +ve mode;

method E: within 2.8 min from 96% C to 100% D, followed by 0.5 min 100% D and within 0.1 min to 96% C; column Chromolith SpeedRod RP-18e; 50-4.6 mm; detection 220 nM; solvent C: H$_2$O (0.05% HCOOH), solvent D: ACN (0.05% HCOOH).

Method G: Within 2.8 min from 96% C to 100% D, followed by 0.5 min 100% D and within 0.1 min to 96% C. Column Chromolith SpeedRod RP-18e; 50-4.6 mm; detection 220 nM; Solvent C: H2O (0.1% TFA), Solvent D: ACN (0.1% TFA)

Preparative HPLC was performed on a Agilent 1200; column: Chromolith prep RP 18e Merck KGaA; mobile phase: 0.1% formic acid in water/0.1% formic acid in acetonitrile.

$^1$H NMR was recorded on Bruker DPX-300, DRX-400 or AVII-400 spectrometer, using residual signal of deuterated solvent as internal reference. Chemical shifts (δ) are reported in ppm relative to the residual solvent signal (δ=2.49 ppm for $^1$H NMR in DMSO-d$_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

The microwave chemistry is performed on a single mode microwave reactor Emrys™ Optimiser from Personal Chemistry.

Preparation of Reactants 2-(Trimethylsilyl)furo(3,2-b)pyridine

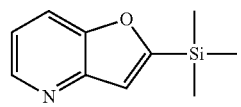

Ethynyltrimethylsilane (32.5 ml, 0.2298 mol), copper(I) iodide (2.2 g, 0.0114 mol) and bis(triphenylphospine)palladium(II)chloride (4.1 g, 0.0057 mol) are added to a degassed solution of 2-Bromopyridine-3-ol (20 g, 0.1149 mol) in dioxane (20 ml). The mixture is stirred for 5 min under nitrogen and then triethyl amine (80 ml, 0.574 7 mol) is added. The mixture is heated to 500° C. for 18 h, cooled to RT, filtered through celite and the filtrate is concentrated under reduced pressure. The crude material is purified by column chromatography by using petrolether and ethyl acetate (90:10) as an eluent to afford (22 g, 56%) of the title compound as a brown liquid. TLC: hexane/ethyl acetate: (9/1): R$_f$=0.50; LCMS (method B): 4.875 min (purity 98.4%); M+H$^+$ 192.1; $^1$H NMR (DMSO-d$_6$, 400 MHz) δ [ppm] 8.50-8.48 (1H, dd, J$_1$=1

Hz, J$_2$=4.6 Hz), 8.015-7.9923 (1H, dd, J$_1$=1 Hz, J$_2$=8.32 Hz), 7.352-7.350 (1H, d, J$_1$=0.8 Hz), 7.314-7.280 (1H, m), 0.372-0.355 (9H, s).

2-(Trimethylsilyl)furo(3,2-b)pyridine N-oxide

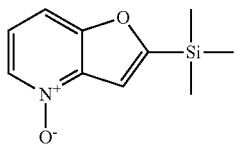

A solution of m-CPBA (17 g, 0.098 mmol) in DCM (80 ml) is added to a solution of 2-(Trimethylsilyl)furo(3,2-b)pyridine (7.5 g, 0.0392 mol) in dry DCM (50 ml) at 0° C. The reaction mixture is stirred at RT for 4 h and then diluted with DCM (100 ml), washed with saturated sodium bicarbonate (2×100 ml) and saturated brine (50 ml), dried over sodium sulphate and evaporated to afford the title compound as (6 g, 73.5%) light brown oil. TLC: chloroform/methanol (9/1): R$_f$=0.8; $^1$H NMR (DMSO-d$_6$, 400 MHz) δ [ppm] 8.21-8.19 (1H, d, J$_1$=6.4 Hz), 7.693-7.671 (1H, d, J$_1$=8.52 Hz), 7.465-7.163 (1H, d, J$_1$=1 Hz), 7.333-7.296 (1H, dd, J$_1$=6.36 Hz, J$_2$=8.48 Hz), 0.372-0.355 (9H, s).

7-Chloro-2-(trimethylsilyl)furo(3,2-b)pyridine

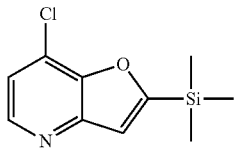

A solution of 2-(trimethylsilyl)furo(3,2-b)pyridine N-oxide (32 g, 0.153 mol) in POCl$_3$ (150 ml) is heated to 100° C. for 2 h in a sealed pressure tube. The reaction mixture is cooled to RT, concentrated under vacuum, the residue is dissolved in DCM (500 ml), washed with saturated sodium bicarbonate (100 ml×2), water (50 ml×2) and with sat brine (50 ml), dried over sodium sulphate and concentrated under vacuum. The crude material is purified by column chromatography by using petrolether/ethyl acetate (9:1) as an eluent to afford the title compound as (18 g, 52%) light brown oil. TLC: hexane/ethyl acetate: (8/2): R$_f$=0.80; $^1$H NMR (DMSO-d$_6$, 400 MHz) δ [ppm] 8.461-8.448 (1H, d, J=5.2 Hz), 7.502-7.477 (2H, m), 0.372-0.355 (9H, s); LCMS (method C): 3.29 min (purity 95.8%), M+H$^+$ 226.0.

7-Chloro-2-iodofuro[3,2-b]pyridine

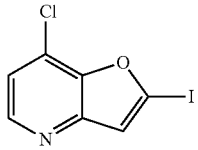 [SMILES: Clc1ccnc2cc(I)oc12]

N-Iodo succinimide (110 g, 0.486 mol) and potassium fluoride (3.2 g, 0.053 mol) are added to a stirred solution of 7-Chloro-2-(trimethylsilyl)furo[3,2-b]pyridine (11 g, 0.0486 mol) in dry acetonitrile (65 ml) at RT. The reaction mixture is heated at 50° C. for 2 h under nitrogen, cooled to RT and evaporate under reduced pressure. The residue is dissolved in ethyl acetate (500 ml), washed with saturated sodium thiosulfate (100 ml×2), water (100 ml×2) and saturated brine (100 ml), dried over sodium sulphate and concentrated under reduced pressure to afford the title compound (10.5 g, 77.3%) as an off white solid. TLC: hexane/ethyl acetate: (8/2): R$_f$=0.60; LCMS (method D): 3.49 min (purity 97.7%), M+H$^+$ 279.8; $^1$H NMR (DMSO-d$_6$, 400 MHz) δ [ppm] 8.41-8.405 (1H, d, J=5.3 Hz), 7.545 (1H, s), 7.448-7.435 (1H, d, J=5.2 Hz).

EXAMPLE 1

7-Chloro-2-(3,4,5-trimethoxy-phenyl)-furo[3,2-b]pyridine ("A1")

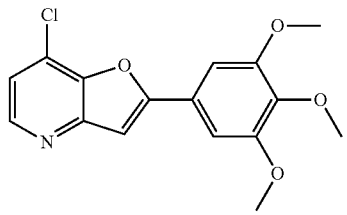 [SMILES: COc1cc(-c2cc3nccc(Cl)c3o2)cc(OC)c1OC]

7-Chloro-2-iodo-furo[3,2-b]pyridine (1.467 mmol), 3,4,5-trimethoxybenzene boronic acid (1.539 mmol), palladium (II)-acetate (0.076 mmol), 2-dicyclohexylphosphino-2',6'-dimethoxybiphenyl (0.146 mmol) and K$_2$CO$_3$ (4.399 mmol) are suspended in 1,4-dioxane (11 ml) and water (1.00 ml) is added. The suspension is heated over 45 min at 150° C. in the microwave. The solvent is removed in vacuo. The product is purified over column chromatography (SiO$_2$, heptane, ethyl acetate). The product is isolated as yellow powder (yield 57%); LCMS (method E): 2.43 min (purity 100%), M+H$^+$ 320.0; $^1$H NMR (500 MHz, DMSO-d$_6$) δ [ppm] 8.45 (d, J=5.3, 1H), 7.79 (s, 1H), 7.49 (d, J=5.2, 1H), 7.29 (s, 2H), 3.91 (s, 6H), 3.75 (s, 3H).

Analogous reaction gives the following compounds:

| Compound no. | |
|---|---|
| "A2" | 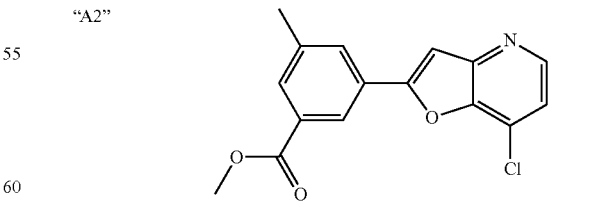 |

3-(7-Chloro-furo[3,2-b]pyridin-2-yl)-5-methyl-benzoic acid methyl ester
HPLC (method A): Rt 2.8 min (purity 99.3%); LCMS (ESI$^+$) (method E): Rt 2.763 min, M + H$^+$ 302 m/z

| Compound no. | |
|---|---|
| "A3" | 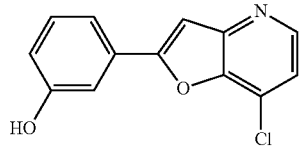 [SMILES: Oc1cccc(-c2cc3nccc(Cl)c3o2)c1] |

3-(7-chlorofuro[3,2-b]pyridin-2-yl)phenol
HPLC (method A): Rt 2.67 min (purity 92%); LCMS (ESI+)
(method E): Rt 1.8 min, M + H+ 246.1 m/z

| "A4" | 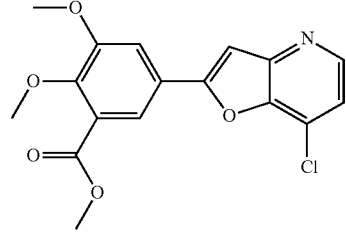 [SMILES: COC(=O)c1cc(-c2cc3nccc(Cl)c3o2)cc(OC)c1OC] |
|---|---|

5-(7-Chloro-furo[3,2-b]pyridin-2-yl)-2,3-dimethoxy-
benzoic acid methyl ester
HPLC (method A): Rt 2.69 min (purity 95%); LCMS (ESI+)
(method E): Rt 2.47 min, M + H+ 348.0 m/z

EXAMPLE 2

7-Phenyl-2-(3,4,5-trimethoxy-phenyl)-furo[3,2-b]pyridine ("A5")

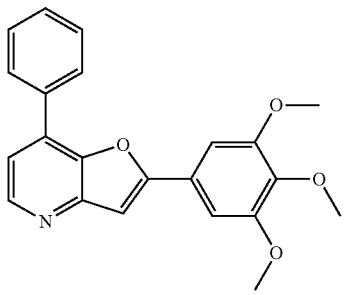 [SMILES: COc1cc(-c2cc3nccc(-c4ccccc4)c3o2)cc(OC)c1OC]

7-Chloro-2-(3,4,5-trimethoxy-phenyl)-furo[3,2-b]pyridine (0.061 mmol), phenyl boronic acid (0.064 mmol), palladium(II)-acetate (0.004 mmol), 2-dicyclohexylphosphino-2',6'-dimethoxybiphenyl (0.006 mmol) and $K_2CO_3$ (0.181 mmol) are suspended in 1,4-dioxane (1.00 ml) and water (100.00 µl). The suspension is heated to 150° C. in the microwave for 45 min. The solvent is removed in vacuo and the product purified over column chromatography ($SiO_2$, heptan, ethyl acetate). The product is isolated as yellow solid (yield 32%); HPLC (method A): Rt 2.6 min (purity 93.2%); LCMS (ESI+) (method E): Rt 2.416 min, M+H+ 362.1 m/z; $^1$H NMR (500 MHz, DMSO-$d_6$) δ [ppm] 8.57 (d, J=5.1, 1H), 8.16-8.10 (m, 2H), 7.74 (s, 1H), 7.65 (t, J=7.7, 2H), 7.60 (d, J=5.1, 1H), 7.56 (t, J=7.4, 1H), 7.31 (s, 2H), 3.91 (s, 6H), 3.74 (s, 3H).

Analogous reaction gives the following compounds:

| Compound no. | |
|---|---|
| "A6" | 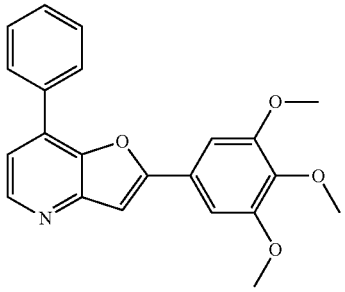 [SMILES: COc1cc(-c2cc3nccc(-c4ccccc4)c3o2)cc(OC)c1OC] |

7-Phenyl-2-(3,4,5-trimethoxy-phenyl)-furo[3,2-b]pyridine
HPLC (method A): Rt 2.6 min (purity 93.2%); LCMS (ESI+)
(method E): Rt 2.416 min, M + H+ 362.1 m/z; $^1$H NMR (500 MHz, DMSO-$d_6$) δ [ppm] 8.57 (d, J = 5.1, 1H), 8.16-8.10 (m, 2H), 7.74 (s, 1H), 7.65 (t, J = 7.7, 2H), 7.60 (d, J = 5.1, 1H), 7.56 (t, J = 7.4, 1H), 7.31 (s, 2H), 3.91 (s, 6H), 3.74 (s, 3H)

| "A7" | 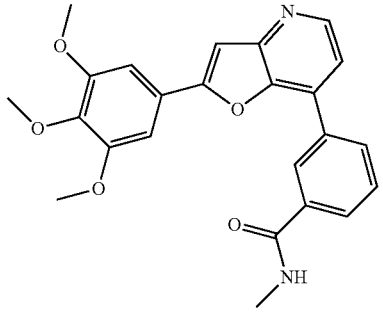 [SMILES: CNC(=O)c1cccc(-c2ccnc3cc(-c4cc(OC)c(OC)c(OC)c4)oc23)c1] |
|---|---|

N-Methyl-3-[2-(3,4,5-trimethoxy-phenyl)-furo[3,2-b]pyridin-7-yl]-benzamide
HPLC (method A): Rt 2.52 min (purity 100%); LCMS (ESI+) (method E): Rt 1.938 min, M + H+ 419.1 m/z; $^1$H NMR (500 MHz, DMSO-$d_6$) δ [ppm] 8.82 (s, 1H), 8.63 (dd, J = 8.9, 4.9, 2H), 8.27 (d, J = 7.8, 1H), 8.01 (d, J = 7.8, 1H), 7.78 (s, 1H), 7.73 (dd, J = 14.5, 6.5, 2H), 7.38 (s, 2H), 3.93 (s, 6H), 3.75 (s, 3H), 2.83 (d, J = 4.5, 3H)

| "A8" | 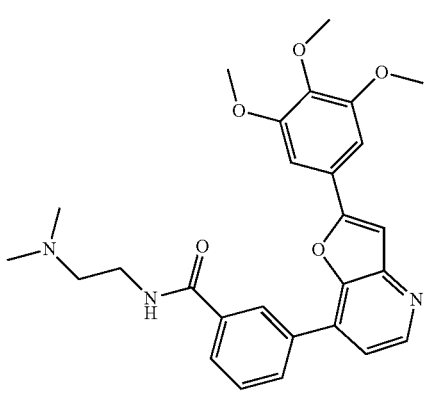 |
|---|---|

N-(2-Dimethylamino-ethyl)-3-[2-(3,4,5-trimethoxy-phenyl)-furo[3,2-b]pyridin-7-yl]-benzamide
HPLC (method A): Rt 2.43 min (purity 100%); LCMS (ESI+) (method E): Rt 1.609 min, M + H+ 476.2 m/z; $^1$H NMR (500 MHz, DMSO-$d_6$) δ [ppm] 8.85 (d, J = 12.2, 1H), 8.70 (s, 1H), 8.59 (t, J = 7.9, 1H), 8.30 (t, J = 9.9, 1H), 8.02 (d, J = 7.7, 1H), 7.82-7.77 (m, 1H), 7.76-7.69 (m, 2H), 7.38 (s, 2H), 4.00-3.89 (m, 6H), 3.76 (d, J = 22.0, 3H), 3.46 (s, 2H), 2.72-2.56 (m, 2H), 2.45-2.29 (m, 6H); m.p. 125° C.

| Compound no. | |
|---|---|
| "A9" | 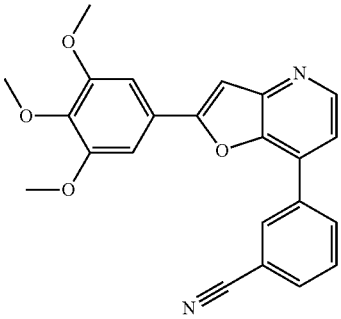 [SMILES: COc1cc(-c2cc3nccc(-c4cccc(C#N)c4)c3o2)cc(OC)c1OC] |

3-[2-(3,4,5-Trimethoxy-phenyl)-furo[3,2-b]pyridin-7-yl]-benzonitrile
HPLC (method A): Rt 2.63 min (purity 99.9%); LCMS (ESI+) (method E): Rt 2.421 min, M + H+ 387.1 m/z; $^1$H NMR (400 MHz, DMSO-$d_6$) δ [ppm] 8.67 (t, J = 1.5, 1H), 8.61 (d, J = 5.1, 1H), 8.51-8.44 (m, 1H), 8.06-7.97 (m, 1H), 7.85 (t, J = 7.9, 1H), 7.76 (s, 1H), 7.72 (d, J = 5.1, 1H), 7.33 (s, 2H), 3.92 (s, 6H), 3.75 (s, 3H)

| "A10" | 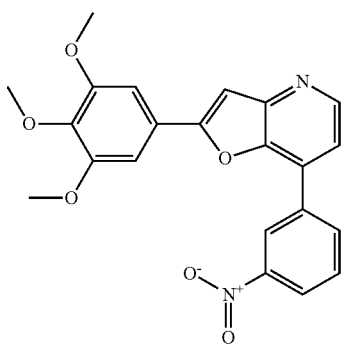 [SMILES: COc1cc(-c2cc3nccc(-c4cccc([N+](=O)[O-])c4)c3o2)cc(OC)c1OC] |
|---|---|

7-(3-Nitro-phenyl)-2-(3,4,5-trimethoxy-phenyl)-furo[3,2-b]pyridine
HPLC (method A): Rt 2.69 min (purity 98.2%); LCMS (ESI+) (method E): Rt 2.585 min, M + H+ 407.1 m/z

| "A11" | 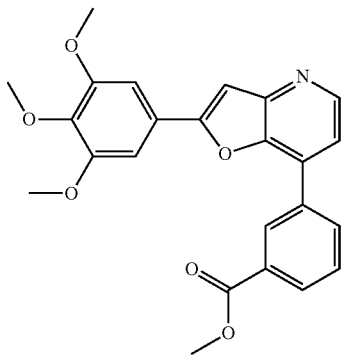 [SMILES: COC(=O)c1cccc(-c2ccnc3cc(-c4cc(OC)c(OC)c(OC)c4)oc23)c1] |
|---|---|

3-[2-(3,4,5-Trimethoxy-phenyl)-furo[3,2-b]pyridin-7-yl]-benzoic acid methyl ester
HPLC (method A): Rt 2.73 min (purity 99.6%); LCMS (ESI+) (method E): Rt 2.56 min, M + H+ 420.1 m/z; $^1$H NMR (400 MHz, DMSO-$d_6$) δ [ppm] 8.91 (t, J = 1.7, 1H), 8.60 (d, J = 5.1, 1H), 8.38 (dd, J = 7.9, 1.8, 1H), 8.13 (dd, J = 6.5, 1.4, 1H), 7.84-7.75 (m, 2H), 7.71 (d, J = 5.1, 1H), 7.33 (d, J = 18.1, 2H), 3.99-3.88 (m, 9H), 3.75 (s, 3H)

| Compound no. | |
|---|---|
| "A12" | 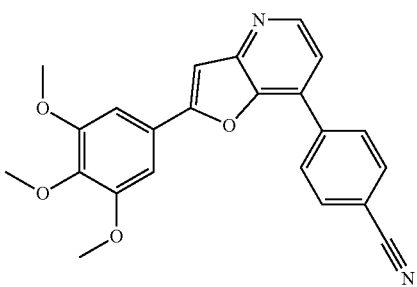 [SMILES: COc1cc(-c2cc3nccc(-c4ccc(C#N)cc4)c3o2)cc(OC)c1OC] |

4-[2-(3,4,5-Trimethoxy-phenyl)-furo[3,2-b]pyridin-7-yl]-benzonitrile
HPLC (method A): Rt 2.69 min (purity 98.7%); LCMS (ESI+) (method E): Rt 2.445 min, M + H+ 387.1 m/z; $^1$H NMR (400 MHz, DMSO-$d_6$) δ [ppm] 8.62 (d, J = 5.1, 1H), 8.40-8.29 (m, 2H), 8.17-8.09 (m, 2H), 7.79 (s, 1H), 7.68 (d, J = 5.1, 1H), 7.31 (s, 2H), 3.92 (s, 6H), 3.74 (s, 3H)

| "A13" | 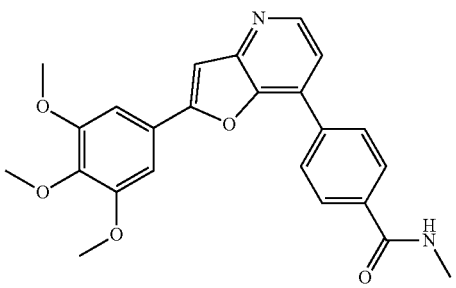 |
|---|---|

N-Methyl-4-[2-(3,4,5-trimethoxy-phenyl)-furo[3,2-b]pyridin-7-yl]-benzamide
HPLC (method A): Rt 2.49 min (purity 100%); LCMS (ESI+) (method E): Rt 1.913 min, M + H+ 419.1 m/z; $^1$H NMR (400 MHz, DMSO-$d_6$) δ [ppm] 8.62 (d, J = 5.2, 1H), 8.58 (d, J = 4.4, 1H), 8.24 (d, J = 8.6, 2H), 8.12-8.06 (m, 2H), 7.78 (s, 1H), 7.71 (d, J = 5.2, 1H), 7.33 (s, 2H), 3.92 (s, 6H), 3.75 (s, 3H), 2.84 (d, J = 4.5, 3H); m.p. 137° C.

| "A14" | 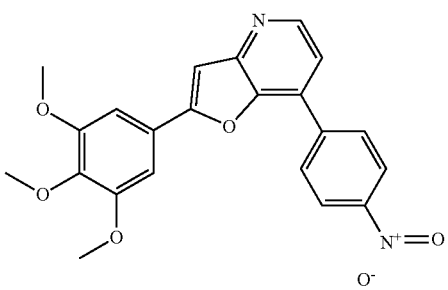 |
|---|---|

7-(4-Nitro-phenyl)-2-(3,4,5-trimethoxy-phenyl)-furo[3,2-b]pyridine
HPLC (method A): Rt 2.68 min (purity 100%); LCMS (ESI+) (method E): Rt 2.576 min, M + H+ 407.1 m/z

| Compound no. | |
|---|---|
| "A15" | 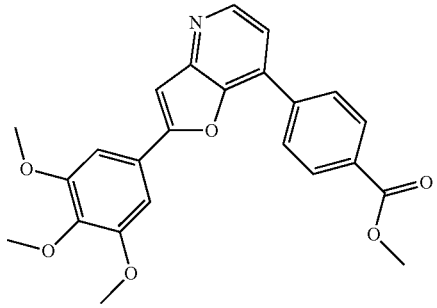 [SMILES: COC(=O)c1ccc(-c2ccnc3cc(-c4cc(OC)c(OC)c(OC)c4)oc23)cc1] |

4-[2-(3,4,5-Trimethoxy-phenyl)-furo[3,2-b]pyridin-7-yl]-benzoic acid methyl ester
HPLC (method A): Rt 2.64 min (purity 100%); LCMS (ESI$^+$) (method E): Rt 2.55 min, M + H$^+$ 420.1 m/z

| "A16" | 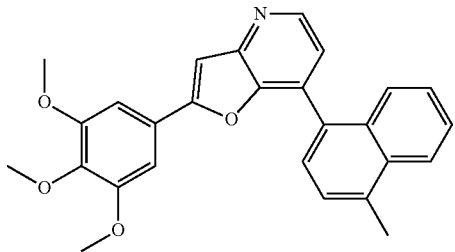 [SMILES: COc1cc(-c2cc3nccc(-c4ccc(C)c5ccccc45)c3o2)cc(OC)c1OC] |
|---|---|

7-(4-Methyl-naphthalen-1-yl)-2-(3,4,5-trimethoxy-phenyl)-furo[3,2-b]pyridine
HPLC (method A): Rt 2.72 min (purity 97.9%); LCMS (ESI$^+$) (method E): Rt 2.813 min, M + H$^+$ 426.1 m/z; m.p. 136.5° C.

| "A17" | 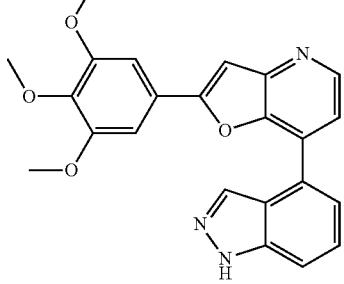 |
|---|---|

7-(1H-Indazol-4-yl)-2-(3,4,5-trimethoxy-phenyl)-furo[3,2-b]pyridine
HPLC (method A): Rt 2.51 min (purity 96.9%); LCMS (ESI$^+$) (method E): Rt 1.984 min, M + H$^+$ 402.1 m/z; $^1$H NMR(500 MHz, DMSO-d$_6$) δ [ppm] 13.40 (s, 1H), 8.79-8.50 (m, 1H), 8.26 (d, J = 14.7, 1H), 7.80 (s, 1H), 7.76 (d, J = 8.3, 1H), 7.68 (dd, J = 13.9, 7.0, 2H), 7.63-7.57 (m, 1H), 7.27 (d, J = 16.3, 2H), 3.86 (d, J = 10.8, 6H), 3.73 (d, J = 5.3, 3H)

| "A18" | 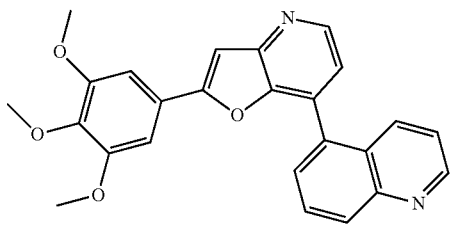 [SMILES: COc1cc(-c2cc3nccc(-c4cccc5ncccc45)c3o2)cc(OC)c1OC] |
|---|---|

5-[2-(3,4,5-Trimethoxy-phenyl)-furo[3,2-b]pyridin-7-yl]-quinoline

| Compound no. | |
|---|---|

HPLC (method A): Rt 2.43 min (purity 98.4%); LCMS (ESI$^+$) (method E): Rt 2.058 min, M + H$^+$ 413.1 m/z; m.p. 222° C.

| "A19" | 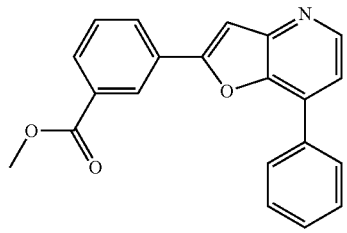 [SMILES: COC(=O)c1cccc(-c2cc3nccc(-c4ccccc4)c3o2)c1] |
|---|---|

3-(7-Phenyl-furo[3,2-b]pyridin-2-yl)-benzoic acid methyl ester
HPLC (method A): Rt 2.64 min (purity 99%); LCMS (ESI$^+$) (method E): Rt 2.673 min, M + H$^+$ 330.1 m/z; $^1$H NMR (400 MHz, DMSO-d$_6$) δ [ppm] 8.63 (d, J = 5.1, 1H), 8.54 (t, J = 1.6, 1H), 8.36-8.29 (m, 1H), 8.12 (dd, J = 5.2, 3.3, 2H), 8.09-8.04 (m, 1H), 7.90 (s, 1H), 7.74 (t, J = 7.8, 1H), 7.71-7.63 (m, 3H), 7.59 (ddd, J = 7.3, 3.8, 1.2, 1H), 3.91 (d, J = 12.7, 3H)

| "A20" | 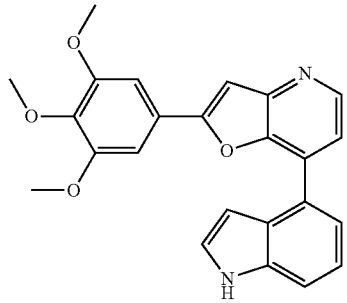 [SMILES: COc1cc(-c2cc3nccc(-c4cccc5[nH]ccc45)c3o2)cc(OC)c1OC] |
|---|---|

7-(1H-Indol-4-yl)-2-(3,4,5-trimethoxy-phenyl)-furo[3,2-b]pyridine
HPLC (method A): Rt 2.57 min (purity 100%); LCMS (ESI$^+$) (method E): Rt 2.03 min, M + H$^+$ 401.1 m/z; $^1$H NMR (400 MHz, DMSO-d$_6$) δ [ppm] 11.43 (s, 1H), 8.63 (d, J = 5.2, 1H), 7.78 (s, 1H), 7.64 (dd, J = 13.6, 6.7, 2H), 7.57-7.50 (m, 2H), 7.40-7.31 (m, 1H), 7.26 (s, 2H), 6.61 (s, 1H), 3.84 (s, 6H), 3.73 (s, 3H)

| "A21" | 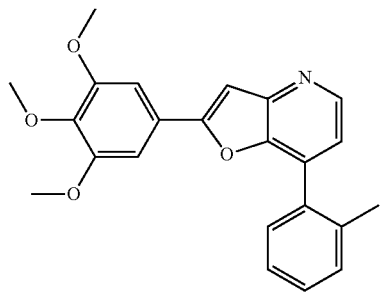 |
|---|---|

7-o-Tolyl-2-(3,4,5-trimethoxy-phenyl)-furo[3,2-b]pyridine
HPLC (method A): Rt 2.59 min (purity 100%); LCMS (ESI$^+$) (method E): Rt 2.477 min, M + H$^+$ 376.1 m/z; $^1$H NMR (400 MHz, DMSO-d$_6$) δ [ppm] 8.58 (d, J = 5.0, 1H), 7.76 (s, 1H), 7.47 (dt, J = 5.4, 4.3, 3H), 7.40 (dt, J = 8.6, 5.3, 1H), 7.32 (d, J = 5.0, 1H), 7.18 (s, 2H), 3.85 (s, 6H), 3.72 (s, 3H), 2.29 (s, 3H)

| Compound no. | |
|---|---|
| "A22" | 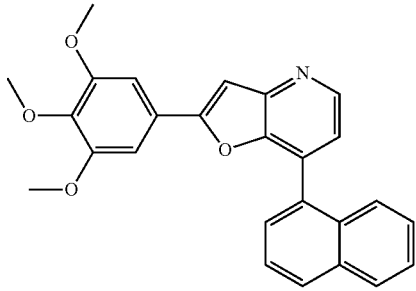 [SMILES: COc1cc(-c2cc3nccc(-c4cccc5ccccc45)c3o2)cc(OC)c1OC] |

7-Naphthalene-1-yl-2-(3,4,5-trimethoxy-phenyl)-furo[3,2-b]pyridine
HPLC (method A): Rt 2.65 min (purity 100%); LCMS (ESI+) (method E): Rt 2.656 min, M + H+ 412.1 m/z

| | |
|---|---|
| "A23" | 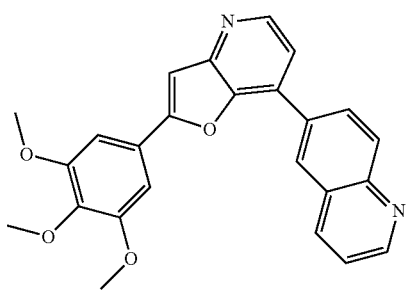 [SMILES: COc1cc(-c2cc3nccc(-c4ccc5ncccc5c4)c3o2)cc(OC)c1OC] |

6-[2-(3,4,5-Trimethoxy-phenyl)-furo[3,2-b]pyridin-7-yl]-quinoline
HPLC (method A): Rt 2.48 min (purity 100%); LCMS (ESI+) (method E): Rt 2.15 min, M + H+ 413.1 m/z

| | |
|---|---|
| "A24" | 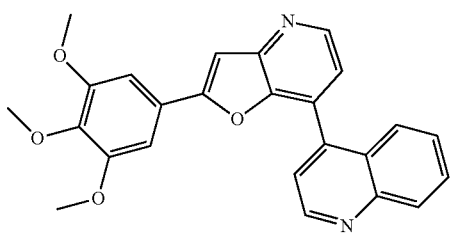 [SMILES: COc1cc(-c2cc3nccc(-c4ccnc5ccccc45)c3o2)cc(OC)c1OC] |

4-[2-(3,4,5-Trimethoxy-phenyl)-furo[3,2-b]pyridin-7-yl]-quinoline
HPLC (method A): Rt 2.52 min (purity 100%); LCMS (ESI+) (method E): Rt 2.19 min, M + H+ 413.1 m/z

| | |
|---|---|
| "A25" | 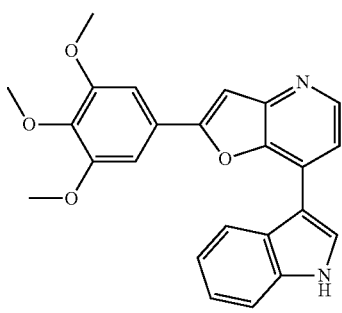 [SMILES: COc1cc(-c2cc3nccc(-c4c[nH]c5ccccc45)c3o2)cc(OC)c1OC] |

7-(1H-Indol-3-yl)-2-(3,4,5-trimethoxy-phenyl)-furo[3,2-b]pyridine
HPLC (method A): Rt 2.68 min (purity 100%); LCMS (ESI+) (method E): Rt 2.592 min, M + H+ 401.1 m/z

| Compound no. | |
|---|---|
| "A26" | 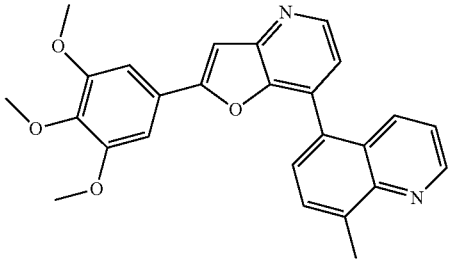 [SMILES: COc1cc(-c2cc3nccc(-c4ccc(C)c5ncccc45)c3o2)cc(OC)c1OC] |

8-Methyl-5-[2-(3,4,5-trimethoxy-phenyl)-furo[3,2-b]pyridin-7-yl]-quinoline
HPLC (method A): Rt 2.49 min (purity 99.7%); LCMS (ESI+) (method E): Rt 2.328 min, M + H+ 427.1 m/z

| | |
|---|---|
| "A27" | 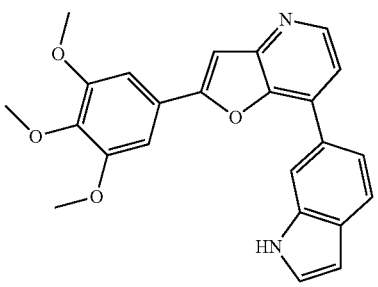 [SMILES: COc1cc(-c2cc3nccc(-c4ccc5cc[nH]c5c4)c3o2)cc(OC)c1OC] |

7-(1H-Indol-6-yl)-2-(3,4,5-trimethoxy-phenyl)-furo[3,2-b]pyridine
HPLC (method A): Rt 2.61 min (purity 95.9%); LCMS (ESI+) (method E): Rt 2.11 min, M + H+ 401.1 m/z; 1H NMR (500 MHz, DMSO-d6) δ [ppm] 11.42 (s, 1H), 8.53 (d, J = 5.1, 1H), 8.31 (d, J = 36.6, 1H), 7.81-7.69 (m, 3H), 7.62 (t, J = 5.7, 1H), 7.53 (dd, J = 8.3, 5.5, 1H), 7.37-7.32 (m, 2H), 6.59-6.50 (m, 1H), 3.95 (d, J = 22.7, 6H), 3.74 (s, 3H)

| | |
|---|---|
| "A28" | 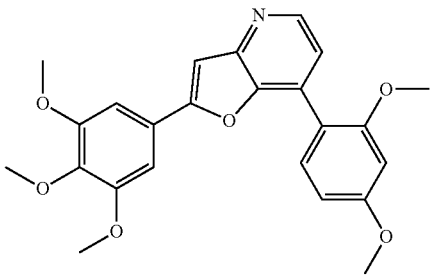 |

7-(2,4-Dimethoxy-phenyl)-2-(3,4,5-trimethoxy-phenyl)-furo[3,2-b]pyridine
HPLC (method A): Rt 2.61 min (purity 97.1%); LCMS (ESI+) (method E): Rt 2.153 min, M + H+ 422.1 m/z; 1H NMR (500 MHz, DMSO-d6) δ [ppm] 8.75-8.26 (m, 1H), 7.72-7.64 (m, 1H), 7.61-7.49 (m, 1H), 7.37-7.27 (m, 1H), 7.22 (d, J = 9.5, 2H), 6.81 (d, J = 2.3, 1H), 6.74 (dd, J = 8.5, 2.4, 1H), 3.89-3.85 (m, 12H), 3.73 (d, J = 10.1, 3H)

| | |
|---|---|
| "A29" | 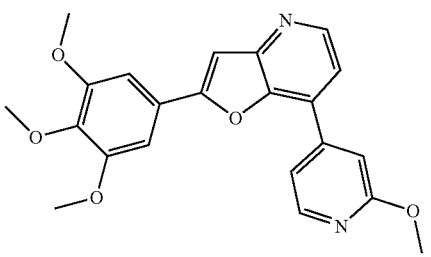 |

-continued

| Compound no. | |
|---|---|
| | 7-(2-Methoxy-pyridin-4-yl)-2-(3,4,5-trimethoxy-phenyl)-furo[3,2-b]pyridine<br>HPLC (method A): Rt 2.61 min (purity 100%); LCMS (ESI+) (method E): Rt 2.451 min, M + H+ 393.1 m/z; 1H NMR (500 MHz, DMSO-d6) δ [ppm] 8.60 (d, J = 5.1, 1H), 8.41 (d, J = 5.3, 1H), 7.76 (s, 1H), 7.73-7.66 (m, 2H), 7.53 (t, J = 10.5, 1H), 7.33 (d, J = 28.4, 2H), 3.96 (s, 3H), 3.91 (s, 6H), 3.77-3.70 (m, 3H) |
| "A30" | 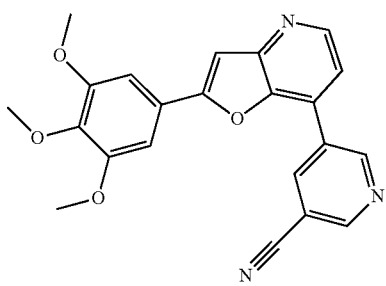 [SMILES: COc1cc(-c2cc3nccc(-c4cncc(C#N)c4)c3o2)cc(OC)c1OC]<br>5[2-(3,4,5-Trimethoxy-phenyl)-furo[3,2-b]pyridin-7-yl]-nicotinonitrile<br>HPLC (method A): Rt 2.63 min (purity 99.6%); LCMS (ESI+) (method E): Rt 2.204 min, M + H+ 388.1 m/z; 1H NMR (400 MHz, DMSO-d6) δ [ppm] 9.60 (d, J = 2.2, 1H), 9.18 (d, J = 1.9, 1H), 9.10 (t, J = 2.1, 1H), 8.64 (d, J = 5.1, 1H), 7.86-7.73 (m, 2H), 7.34 (s, 2H), 3.92 (s, 6H), 3.75 (s, 3H) |
| "A31" | 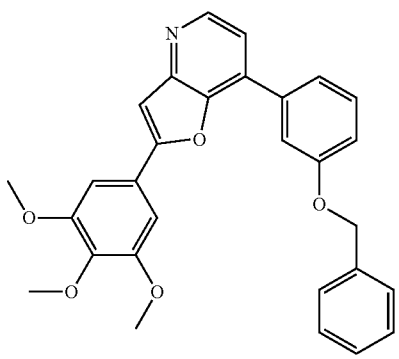 [SMILES: COc1cc(-c2cc3nccc(-c4cccc(OCc5ccccc5)c4)c3o2)cc(OC)c1OC]<br>7-(3-Benzyloxy-phenyl)-2-(3,4,5-trimethoxy-phenyl)-furo[3,2-b]pyridine<br>HPLC (method A): Rt 2.83 min (purity 98.5%); LCMS (ESI+) (method E): Rt 2.889 min, M + H+ 468.1 m/z; 1H NMR (500 MHz, DMSO-d6) δ [ppm] 8.56 (d, J = 5.1, 1H), 7.88-7.84 (m, 1H), 7.76 (s, 1H), 7.72 (d, J = 7.9, 1H), 7.64 (d, J = 5.1, 1H), 7.56 (t, J = 8.0, 1H), 7.50 (d, J = 7.1, 2H), 7.43 (dd, J = 10.1, 4.7, 2H), 7.36 (dd, J = 8.4, 6.2, 1H), 7.32 (s, 2H), 7.21 (dd, J = 8.2, 2.3, 1H), 5.24 (s, 2H), 3.86 (d, J = 9.0, 6H), 3.73 (d, J = 9.0, 3H); m.p. 138° C. |
| "A32" | 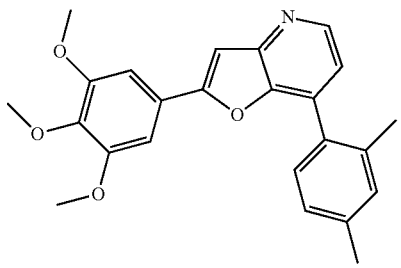<br>7-(2,4-Dimethyl-phenyl)-2-(3,4,5-trimethoxy-phenyl)-furo[3,2-b]pyridine<br>HPLC (method A): Rt 2.69 min (purity 100%); LCMS (ESI+) (method E): Rt 2.64 min, M + H+ 390.1 m/z; 1H NMR (400 |

-continued

| Compound no. | |
|---|---|
| | MHz, DMSO-d6) δ [ppm] 8.56 (d, J = 5.1, 1H), 7.80 (d, J = 15.9, 1H), 7.38 (d, J = 7.8, 1H), 7.30 (d, J = 5.1, 1H), 7.27 (s, 1H), 7.20 (d, J = 9.8, 3H), 3.84 (s, 6H), 3.71 (s, 3H), 2.37 (s, 3H), 2.26 (s, 3H); m.p. 178° C. |
| "A33" | 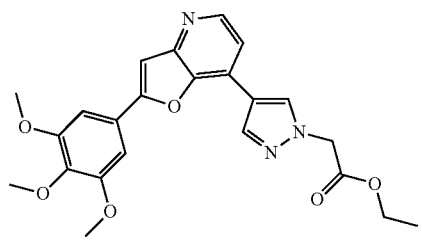 [SMILES: CCOC(=O)Cn1cc(-c2ccnc3cc(-c4cc(OC)c(OC)c(OC)c4)oc23)cn1]<br>{4-[2-(3,4,5-Trimethoxy-phenyl)-furo[3,2-b]pyridin-7-yl]-pyrazol-1-yl}-acetic acid ethyl ester<br>HPLC (method A): Rt 2.56 min (purity 100%); LCMS (ESI+) (method E): Rt 1.90 min, M + H+ 438.1 m/z; 1H NMR (500 MHz, DMSO-d6) δ [ppm] 8.82 (s, 1H), 8.55 (d, J = 5.4, 1H), 8.45 (s, 1H), 7.79 (s, 1H), 7.76 (d, J = 5.2, 1H), 7.41 (s, 2H), 5.26 (s, 2H), 4.19 (q, J = 7.1, 2H), 3.96 (s, 6H), 3.76 (s, 3H), 1.29-1.20 (m, 3H) |
| "A34" | 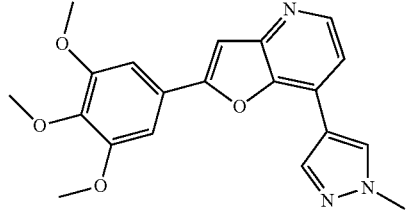<br>7-(1-Methyl-1H-pyrazol-4-yl)-2-(3,4,5-trimethoxy-phenyl)-furo[3,2-b]pyridine<br>HPLC (method A): Rt 2.84 min (purity 100%); LCMS (ESI+) (method E): Rt 1.72 min, M + H+ 366.1 m/z; 1H NMR (400 MHz, DMSO-d6) δ [ppm] 8.75 (s, 1H), 8.55 (d, J = 5.6, 1H), 8.40 (s, 1H), 7.79 (s, 1H), 7.76 (d, J = 5.6, 1H), 7.42 (s, 2H), 4.01 (s, 3H), 3.96 (s, 6H), 3.76 (s, 3H) |
| "A35" | 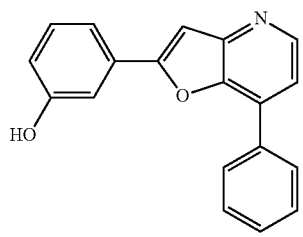 [SMILES: Oc1cccc(-c2cc3nccc(-c4ccccc4)c3o2)c1]<br>3-(7-Phenyl-furo[3,2-b]pyridin-2-yl)-phenol<br>HPLC (method A): Rt 2.67 min (purity 100%); LCMS (ESI+) (method E): Rt 1.78 min, M + H+ 288.1 m/z; 1H NMR (500 MHz, DMSO-d6) δ [ppm] 9.79 (s, 1H), 8.60 (d, J = 5.2, 1H), 8.12 (dd, J = 5.2, 3.3, 2H), 7.69-7.64 (m, 4H), 7.62-7.55 (m, 1H), 7.48 (d, J = 8.0, 1H), 7.42-7.39 (m, 1H), 7.36 (t, J = 7.9, 1H), 6.90 (ddd, J = 8.1, 2.4, 0.7, 1H) |

EXAMPLE 3

3-[2-(3,4,5-Trimethoxy-phenyl)-furo[3,2-b]pyridin-7-yl]-phenol ("A36")

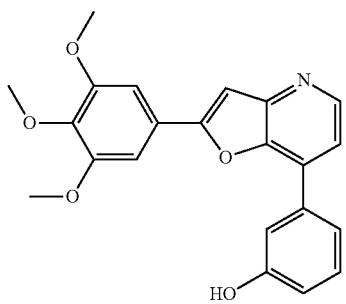 [SMILES: COc1cc(-c2cc3nccc(-c4cccc(O)c4)c3o2)cc(OC)c1OC]

7-(3-Benzyloxy-phenyl)-2-(3,4,5-trimethoxy-phenyl)-furo[3,2-b]pyridine (0.137 mmol) is dissolved in THF (10 ml) and Pd—C 5% (0.2 g) is added, and the compound is hydrogenated 2 days at room temperature. The reaction solution is filtered and the filtrate removed in vacuo. The precipitate is suspended in diethylether and filtrated. The product is obtained after drying at 40° C. for 4 h as yellow solid (23 mg, 44%); HPLC (method A): Rt 2.55 min (purity 99.2%); LCMS (ESI$^+$) (method E): Rt 1.995 min, M+H$^+$ 378.1 m/z; $^1$H NMR (400 MHz, DMSO-d$_6$) δ [ppm] 9.73 (s, 1H), 8.54 (d, J=5.1, 1H), 7.72 (s, 1H), 7.60-7.55 (m, 1H), 7.55-7.48 (m, 2H), 7.42 (t, J=7.9, 1H), 7.32 (s, 2H), 6.96-6.91 (m, 1H), 3.91 (s, 6H), 3.74 (s, 3H).

2-{3-[2-(3,4,5-Trimethoxy-phenyl)-furo[3,2-b]pyridin-7-yl]-phenoxy}-ethyl)-carbamic acid tert.-butyl ester ("A37"

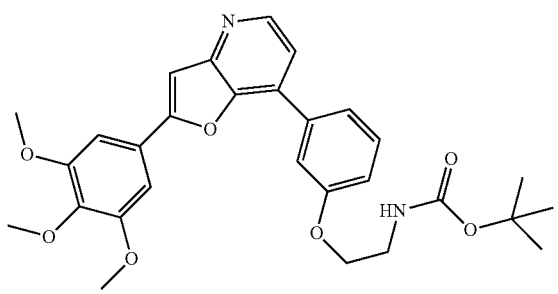 [SMILES: COc1cc(-c2cc3nccc(-c4cccc(OCCNC(=O)OC(C)(C)C)c4)c3o2)cc(OC)c1OC]

3-[2-(3,4,5-Trimethoxy-phenyl)-furo[3,2-b]pyridin-7-yl]-phenol (0.047 mmol) is dissolved in ACN (1.00 ml) and K$_2$CO$_3$ (0.478 mmol) and 2-(Boc-amino) ethyl bromide (0.058 mmol) is added. The mixture is stirred 23 h at 70° C. 2-(Boc-amino) ethyl bromide (0.036 mmol) is added and the mixture is stirred 24 h at 70° C. The reaction solution is allowed to cool to RT and water is added. The solution is extracted with ethylacetate, the combined organic layers dried over MgSO$_4$ and the solvent is removed in vacuo. The product is isolated as yellow solid in quantitative yields. LCMS (ESI$^+$) (method E): Rt 2.56 min, M+H$^+$ 521.2 m/z.

2-{3-[2-(3,4,5-Trimethoxy-phenyl)-furo[3,2-b]pyridin-7-yl]-phenoxy}-ethylamine ("A38")

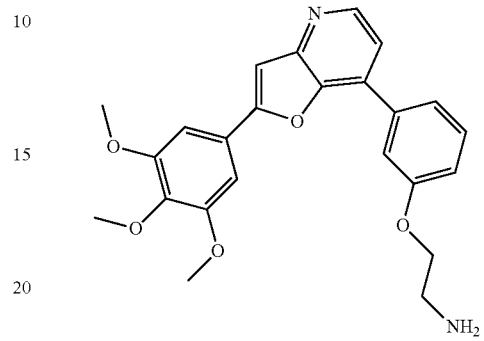

(2-{3-[2-(3,4,5-Trimethoxy-phenyl)-furo[3,2-b]pyridin-7-yl]-phenoxy}-ethyl)-carbamic acid tert-butyl ester (0.046 mmol) is dissolved in 4M HCl in Dioxan (1 ml, 4.000 mmol) and stirred 5 h at RT. The solvent is removed in vacuo and the precipitate suspended in diethylether. The precipitate is filtered and dried in vacuo at 40° C. The product is isolated as yellow solid (82% yield). HPLC (method A): Rt 2.44 min (purity 97.1%); LCMS (ESI$^+$) (method E): Rt 1.588 min, M+H$^+$ 421.1 m/z; HCl salt: $^1$H NMR (400 MHz, DMSO-d$_6$) δ [ppm] 8.61 (d, J=5.2, 1H), 8.10 (s, 3H), 7.77 (dd, J=11.5, 4.4, 3H), 7.67 (d, J=5.2, 1H), 7.61 (t, J=8.1, 1H), 7.33 (s, 2H), 7.25-7.17 (m, 1H), 4.33 (t, J=5.1, 2H), 3.92 (s, 6H), 3.75 (s, 3H), 3.26 (dd, J=10.3, 5.3, 2H).

EXAMPLE 4

3-Methyl-5-(7-phenyl-furo[3,2-b]pyridin-2-yl)-benzoic acid ("A39")

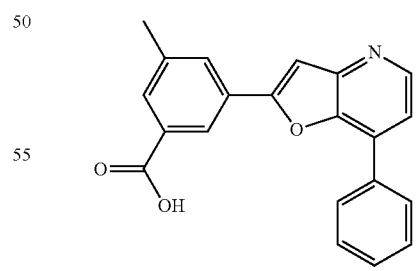

3-Methyl-5-(7-phenyl-furo[3,2-b]pyridin-2-yl)-benzoic acid methyl ester (61.321 μmol) is dissolved in THF (300.00 μl) and LiOH 1M (122,600 μmol) is added. The reaction solution is stirred 26 h at RT and diluted with H$_2$O (10 ml) and 1M HCl (122.6 μl) is added. The precipitate is filtered and washed with water and dried in vacuo. The product is obtained as colorless solid in quantitative yield; LCMS (ESI⁺) (method E): Rt 2.25 min, M+H⁺ 330.1 m/z.

2,3-dimethoxy-5-(7-phenylfuro[3,2-b]pyridin-2-yl)benzoic acid ("A40")

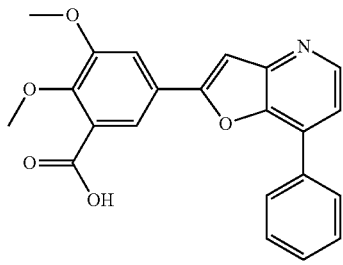 [SMILES: COc1cc(-c2cc3nccc(-c4ccccc4)c3o2)cc(C(=O)O)c1OC]

Starting from methyl 2,3-dimethoxy-5-(7-phenylfuro[3,2-b]pyridin-2-yl)benzoate (119 µmol) the product is prepared as described as above as yellow solid in a yield of 70%; LCMS (ESI⁺) (method E): Rt 1.81 min, M+H⁺ 376.1 m/z.

3-[2-(3,4,5-Trimethoxy-phenyl)-furo[3,2-b]pyridin-7-yl]-benzoic acid ("A41")

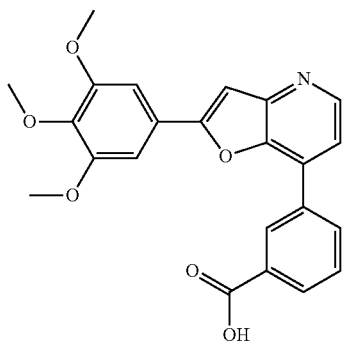 [SMILES: COc1cc(-c2cc3nccc(-c4cccc(C(=O)O)c4)c3o2)cc(OC)c1OC]

Starting from 3-[2-(3,4,5-trimethoxy-phenyl)-furo[3,2-b]pyridin-7-yl]-benzoic acid methyl ester (0.114 mmol), the product is prepared as above and obtained as a yellow solid in a yield of 95%. HPLC (method A): Rt 2.51 min (purity 99.4%); LCMS (ESI⁺) (method E): Rt 2.075 min, M+H⁺ 406.1 m/z; ¹H NMR (400 MHz, DMSO-d₆) δ [ppm] 13.30 (s, 1H), 9.01 (t, J=1.6, 1H), 8.63 (d, J=5.2, 1H), 8.37 (dd, J=6.4, 1.5, 1H), 8.17-8.08 (m, 1H), 7.85-7.73 (m, 3H), 7.38 (s, 2H), 3.91 (d, J=12.6, 6H), 3.75 (s, 3H).

4-[2-(3,4,5-Trimethoxy-phenyl)-furo[3,2-b]pyridin-7-yl]-benzoic acid ("A42")

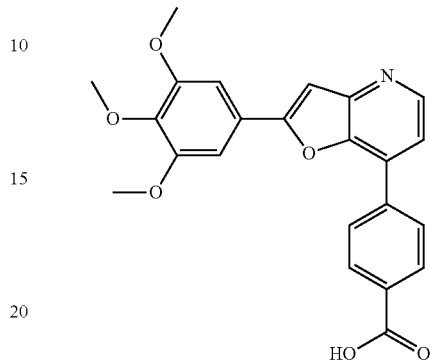

Starting from 4-[2-(3,4,5-trimethoxy-phenyl)-furo[3,2-b]pyridin-7-yl]-benzoic acid methyl ester (0.072 mmol), the product is prepared as above as and obtained as orange solid in a yield of 65%. HPLC (method A): Rt 2.53 min (purity 99.8%); LCMS (ESI⁺) (method E): Rt 2.111 min, M+H⁺ 406.1 m/z; ¹H NMR (400 MHz, DMSO-d₆) δ [ppm] 8.64 (d, J=5.2, 1H), 8.32-8.26 (m, 2H), 8.23-8.17 (m, 2H), 7.80 (s, 1H), 7.72 (d, J=5.2, 1H), 7.34 (s, 2H), 3.92 (s, 6H), 3.75 (s, 3H), 3.68 (s, 1H).

EXAMPLE 5

N-(2-Hydroxy-1,1-dimethyl-ethyl)-3-methyl-5-(7-phenyl-furo[3,2-b]pyridin-2-yl)-benzamide ("A43")

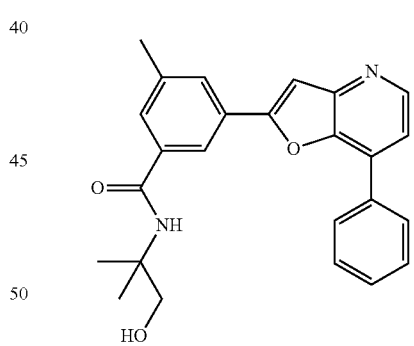

3-Methyl-5-(7-phenyl-furo[3,2-b]pyridin-2-yl)-benzoic acid (79 µmol) and N-(3-dimethylaminopropyl)-N'-ethylcarbodiimidhydrochlorid (86,592 µmol) are dissolved in N,N-dimethylformamid (300.00 µl) and 4-methylmorpholin (157.354 µmol) and 1-hydroxybenzotriazolhydrat (86.849 µmol) are added and stirred 5 min at RT. A solution of 2-amino-2-methyl-propan-1-ol (80,000 µmol) in N,N-dimethylformamid (100.00 µl) is added. The mixture is stirred 4.5 h at RT. The reaction solution is poured into water and extracted with ethylacetate. The combined organic layers are dried over MgSO₄ and the solvent is removed in vacuo. The product is isolated after reversed phase column chromatography as yellow solid (33 µmol, 42% yield). HPLC (method A): Rt 2.55 min (purity 98.5%); LCMS (ESI⁺) (method E): Rt 2.199 min, M+H⁺ 401.1 m/z; ¹H NMR (500 MHz, DMSO-d₆) δ [ppm] 8.60 (d, J=5.1, 1H), 8.18 (s, 1H), 8.16-8.10 (m, 2H), 7.96 (s, 1H), 7.77 (s, 1H), 7.70 (d, J=8.9, 2H), 7.65 (dd, J=14.7, 6.4, 3H), 7.58 (d, J=7.4, 1H), 4.16 (br, 1H), 3.54 (s, 2H), 2.47 (s, 3H), 1.35 (s, 6H).

N-(2-hydroxy-1,1-dimethyl-ethyl)-2,3-dimethoxy-5-(7-phenylfuro[3,2-b]pyridin-2-yl)benzamide ("A44")

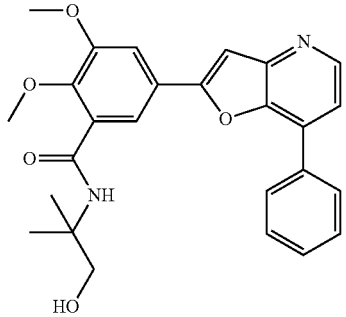 [SMILES: COc1cc(-c2cc3nccc(-c4ccccc4)c3o2)cc(C(=O)NC(C)(C)CO)c1OC]

Starting from 2,3-dimethoxy-5-(7-phenylfuro[3,2-b]pyridin-2-yl)benzoic acid (120 µmol) and 2-Amino-2-methylpropan-1-ol (123 µmol) the product is prepared analogously to "A43" and obtained as a yellow solid in a yield of 28%. HPLC (method A): Rt 2.64 min (purity 93.5%); LCMS (ESI⁺) (method E): Rt 1.9 min, M+H⁺ 447.2 m/z; ¹H NMR (500 MHz, DMSO-d₆) δ [ppm] 8.61 (d, J=5.2, 1H), 8.21 (s, 1H), 8.13-8.08 (m, 2H), 7.89 (d, J=2.1, 1H), 7.82 (s, 1H), 7.78 (d, J=2.1, 1H), 7.70-7.63 (m, 3H), 7.61-7.55 (m, 1H), 3.98 (s, 3H), 3.90 (s, br, 1H), 3.86 (s, 3H), 3.46 (s, 2H), 1.35 (s, 6H).

N-(2-Amino-cyclohexyl)-3-[2-(3,4,5-trimethoxy-phenyl)-furo[3,2-b]pyridin-7-yl]-benzamide ("A45")

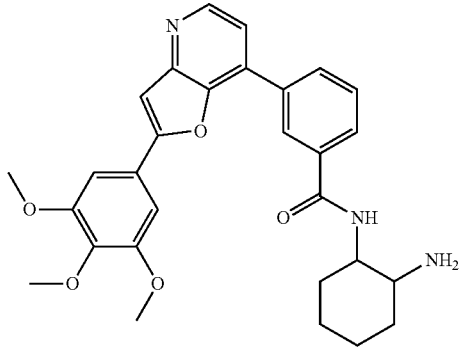 [SMILES: COc1cc(-c2cc3nccc(-c4cccc(C(=O)NC5CCCCC5N)c4)c3o2)cc(OC)c1OC]

3-[2-(3,4,5-Trimethoxy-phenyl)-furo[3,2-b]pyridin-7-yl]-benzoic acid (0.049 mmol) is dissolved in N,N-dimethylformamid (1.00 ml) and N-(3-dimethyl-aminopropyl)-N'-ethyl-carbodiimidhydrochloride (0.110 mmol), 1-hydroxybenzotriazolhydrat (0.111 mmol), 4-Methylmorpholin (0.146 mmol) and 1,2-Diaminocyclohexane (0.049 mmol) are added. The reaction solution is stirred 2 d at RT. Water is added and the solvent removed in vacuo. The product is isolated after column reversed phase column chromatography as yellow solid in a yield of 27%. HPLC (method A): Rt 2.47 min (purity 100%); LCMS (ESI⁺) (method E): Rt 1.69 min, M+H⁺ 502.2 m/z.

1-{3-[2-(3,4,5-Trimethoxy-phenyl)-furo[3,2-b]pyridin-7-yl]-benzoyl}-pyrrolidin-3-yl)-carbamic acid tert-butyl ester ("A46")

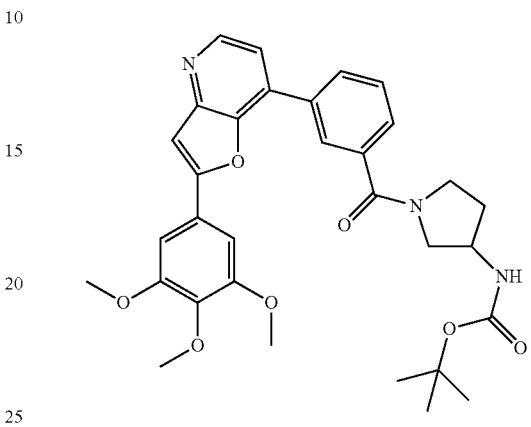

Starting from 3-[2-(3,4,5-trimethoxyphenyl)furo[3,2-b]pyridin-7-yl]benzoic acid (0.099 mmol) and 3-(tert-Butoxycarbonylamino)pyrrolidine (0.102 mmol) the product is prepared analogously to "A43" and obtained as yellow solid in a yield of 70%. HPLC (method A): Rt 2.64 min (purity 95%); LCMS (ESI⁺) (method E): Rt 1.99 min, M+H⁺ 574.31 m/z; ¹H NMR (500 MHz, DMSO-d₆) δ [ppm] 8.61 (d, J=5.2, 1H), 8.42 (s, 1H), 8.27-8.16 (m, 1H), 7.79 (s, 1H), 7.70 (ddd, J=21.6, 13.1, 6.5, 3H), 7.35 (d, J=6.4, 2H), 7.23 (dd, J=34.4, 6.1, 1H), 4.13-4.07 (m, 1H), 3.93 (s, 3H), 3.92 (s, 3H), 3.74 (s, 3H), 3.70-3.47 (m, 3H), 3.36-3.27 (m, 1H), 2.10-1.95 (m, 1H), 1.92-1.68 (m, 1H), 1.40 (s, 4H), 1.30 (s, 5H).

tert.-Butyl 3-[[3-[2-(3,4,5-trimethoxyphenyl)furo[3,2-b]pyridin-7-yl]benzoyl]amino]pyrrolidine-1-carboxylate ("A47")

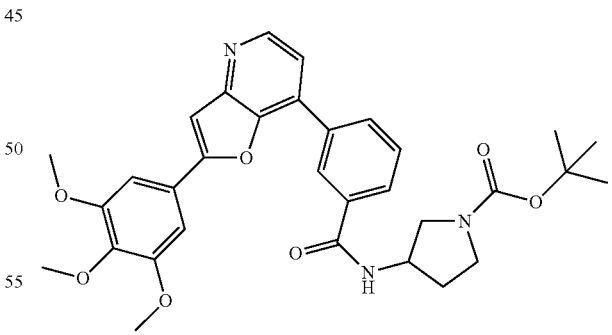

Starting from 3-[2-(3,4,5-trimethoxyphenyl)furo[3,2-b]pyridin-7-yl]benzoic acid (0.099 mmol) and (+/−)-3-amino-1-N—BOC-pyrrolidine (0.102 mmol) the product is prepared analogously to "A43" and obtained as yellow solid in a yield of 64%. HPLC (method A): Rt 2.68 min (purity 99.3%); LCMS (ESI⁺) (method E): Rt 2.11 min, M+H⁺ 574.3 m/z; ¹H NMR (500 MHz, DMSO-d₆) δ[ppm] 8.82 (s, 1H), 8.71 (d, J=6.3, 1H), 8.62 (d, J=5.2, 1H), 8.28 (d, J=8.0, 1H), 8.06 (d, J=7.9, 1H), 7.79 (s, 1H), 7.74 (dd, J=13.0, 6.4, 2H), 7.37 (s, 2H), 4.46 (s, 1H), 3.93 (s, 6H), 3.75 (s, 3H), 3.48-3.39 (m, 1H), 3.34 (d, J=7.0, 2H), 3.22 (d, J=4.2, 1H), 2.19-2.09 (m, 1H), 1.99-1.86 (m, 1H), 1.41 (s, 9H).

N-(2-methoxyethyl)-3-[2-(3,4,5-trimethoxyphenyl)furo[3,2-b]pyridin-7-yl]benzamide ("A48")

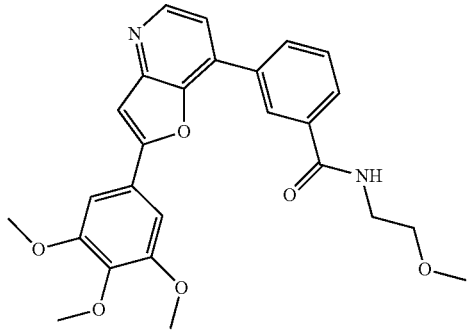

Starting from 3-[2-(3,4,5-trimethoxyphenyl)furo[3,2-b]pyridin-7-yl]benzoic acid (0.062 mmol) and 2-methoxyethylamin (0.069 mmol) the product is prepared analogously to "A43" and obtained as colorless solid in a yield of 62%. HPLC (method A): Rt 2.53 min (purity 98.8%); LCMS (ESI$^+$) (method E): Rt 1.78 min, M+H$^+$ 463.2 m/z; $^1$H NMR (500 MHz, DMSO-d$_6$) δ [ppm] 8.84 (s, 1H), 8.79-8.72 (m, 1H), 8.60 (d, J=5.1, 1H), 8.28 (d, J=8.3, 1H), 8.03 (d, J=7.9, 1H), 7.78 (s, 1H), 7.75-7.70 (m, 2H), 7.35 (d, J=16.3, 2H), 3.93 (s, 6H), 3.74 (s, 3H), 3.54-3.43 (m, 4H), 3.28 (s, 3H).

N-(3-dimethylaminopropyl)-3-[2-(3,4,5-trimethoxyphenyl)furo[3,2-b]pyridin-7-yl]benzamide ("A49")

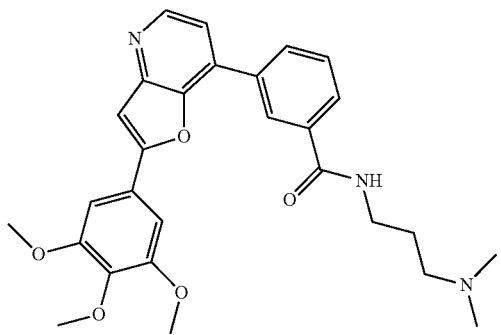

Starting from 3-[2-(3,4,5-trimethoxyphenyl)furo[3,2-b]pyridin-7-yl]benzoic acid (0.062 mmol) and N,N-dimethyltrimethylendiamin (0.064 mmol) the product is prepared analogously to "A43" and obtained as yellow solid in a yield of 33%. HPLC (method A): Rt 2.45 min (purity 99.3%); LCMS (ESI$^+$) (method E): Rt 1.56 min, M+H$^+$ 490.3 m/z; $^1$H NMR (500 MHz, DMSO-d$_6$) δ [ppm] 8.82 (s, 1H), 8.77-8.68 (m, 1H), 8.60 (d, J=5.1, 1H), 8.27 (d, J=7.8, 1H), 8.01 (d, J=7.8, 1H), 7.78 (s, 1H), 7.77-7.69 (m, 2H), 7.37 (s, 2H), 3.93 (s, 6H), 3.74 (s, 3H), 3.49-3.18 (m, 2H), 2.45-2.10 (m, 8H), 1.78-1.63 (m, 2H).

Morpholino-[3-[2-(3,4,5-trimethoxyphenyl)furo[3,2-b]pyridin-7-yl]phenyl]methanone ("A50")

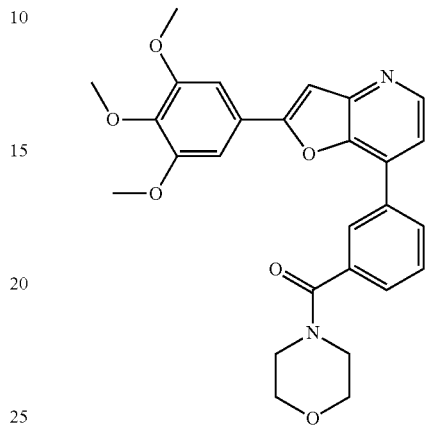

Starting from 3-[2-(3,4,5-trimethoxyphenyl)furo[3,2-b]pyridin-7-yl]benzoic acid (0.062 mmol) and 4-methylmorpholin (0.182 mmol) the product is prepared analogously to "A43" and obtained as colorless solid in a yield of 70%. HPLC (method A): Rt 2.59 min (purity 98.1%); LCMS (ESI$^+$) (method E): Rt 1.76 min, M+H$^+$ 475.2 m/z; $^1$H NMR (500 MHz, DMSO-d$_6$) δ [ppm] 8.58 (d, J=5.1, 1H), 8.29 (t, J=1.5, 1H), 8.19 (d, J=8.0, 1H), 7.76 (s, 1H), 7.74-7.65 (m, 2H), 7.58 (d, J=7.6, 1H), 7.33 (s, 2H), 3.91 (d, J=11.4, 6H), 3.74 (s, 3H), 3.69-3.37 (m, 8H).

EXAMPLE 6

3-[2-(3,4,5-Trimethoxy-phenyl)-furo[3,2-b]pyridin-7-yl]-benzylamine ("A51")

3-[2-(3,4,5-Trimethoxy-phenyl)-furo[3,2-b]pyridin-7-yl]-benzonitrile (0.067 mmol) is dissolved in methanol/NH$_3$ (10%, 10 ml) and sponge nickel catalyst (70%, 0.1 g) is added. The mixture is hydrogenated at 5.6 bar at 50° C. for 15 h. The suspension is filtrated and the solvent removed in vacuo. The precipitate is suspended in diethylether and filtrated. The product is obtained after drying in vacuo as slight green solid (67% yield). HPLC (method A): Rt 2.41 min (purity 97.3%); LCMS (ESI$^+$) (method E): Rt 1.527 min, M+H$^+$ 391.1 m/z; $^1$H NMR (400 MHz, DMSO-d$_6$) δ [ppm] 8.56 (d, J=4.8, 1H), 8.25 (s, 1H), 7.93 (d, J=7.1, 1H), 7.74 (s, 1H), 7.65-7.45 (m, 3H), 7.34 (s, 2H), 3.92 (s, 6H), 3.88 (s, 2H), 3.81-3.68 (m, 5H).

N-[[3-[2-(3,4,5-trimethoxyphenyl)furo[3,2-b]pyridin-7-yl]phenyl]methyl]-acetamide ("A52")

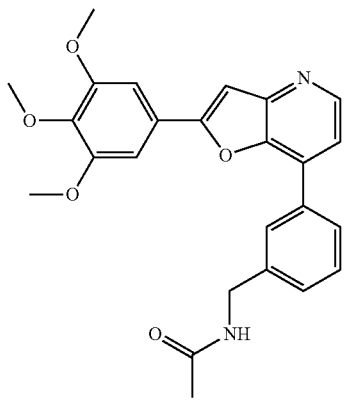 [SMILES: COc1cc(-c2cc3nccc(-c4cccc(CNC(C)=O)c4)c3o2)cc(OC)c1OC]

3-[2-(3,4,5-Trimethoxy-phenyl)-furo[3,2-b]pyridin-7-yl]-benzylamine (0.036 mmol) is dissolved in acetic acid (1.00 ml) and acetic acid anhydride (0.159 mmol) is added. The reaction solution is stirred 4 d at RT. Water is added and extracted with ethyl acetate. The combined organic layers are washed with brine and dried over MgSO$_4$. The product is isolated after removal of the solvent in vacuo as yellow solid (45% yield). HPLC (method A): Rt 2.52 min (purity 99.4%); LCMS (ESI$^+$) (method E): Rt 1.87 min, M+H$^+$ 433.1 m/z; $^1$H NMR (500 MHz, DMSO-d$_6$) δ [ppm] 8.57 (d, J=5.1, 1H), 8.44 (t, J=5.7, 1H), 8.09 (d, J=12.1, 1H), 7.97 (d, J=7.8, 1H), 7.76 (d, J=2.8, 1H), 7.69-7.56 (m, 2H), 7.44 (t, J=9.5, 1H), 7.33 (d, J=7.8, 2H), 4.39 (d, J=5.9, 2H), 3.91 (d, J=11.1, 6H), 3.78-3.70 (m, 3H), 1.91-1.77 (m, 3H).

4-[2-(3,4,5-Trimethoxy-phenyl)-furo[3,2-b]pyridin-7-yl]-benzylamine ("A53")

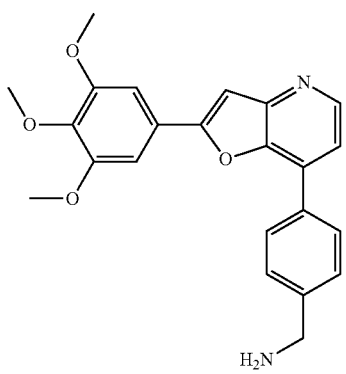 [SMILES: COc1cc(-c2cc3nccc(-c4ccc(CN)cc4)c3o2)cc(OC)c1OC]

Starting from 4-[2-(3,4,5-Trimethoxy-phenyl)-furo[3,2-b]pyridin-7-yl]-benzonitrile the product is prepared analogously to "A51" and obtained as a yellow solid (21 mg, 73% yield). HPLC (method A): Rt 2.41 min (purity 99.1%); LCMS (ESI$^+$) (method E): Rt 1.511 min, M+H$^+$ 391.2 m/z; $^1$H NMR (500 MHz, DMSO-d$_6$) δ [ppm] 8.58 (d, J=5.0, 1H), 8.19 (d, J=7.9, 2H), 7.78 (s, 1H), 7.75-7.74 (m, 2H), 7.71 (d, J=8.0, 2H), 7.62 (d, J=5.0, 1H), 7.32 (s, 2H), 4.12 (s, 2H), 3.92 (s, 6H), 3.74 (s, 3H).

N-{4-[2-(3,4,5-Trimethoxy-phenyl)-furo[3,2-b]pyridin-7-yl]-benzyl}-acetamide ("A54")

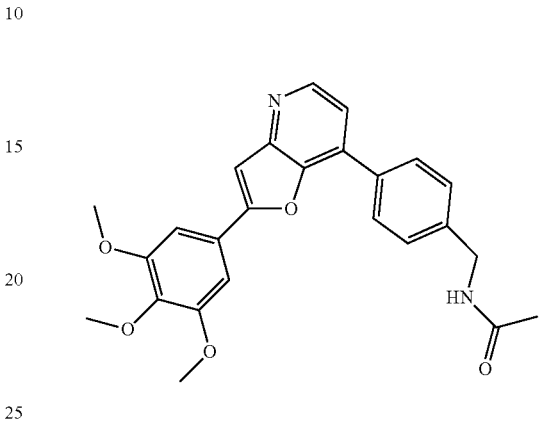

Starting from 4-[2-(3,4,5-Trimethoxy-phenyl)-furo[3,2-b]pyridin-7-yl]-benzylamine (0.063 mmol), the product is prepared analogously to "A52" and obtained as yellow solid in a yield of 23%. HPLC (method A): Rt 2.49 min (purity 98.6%); LCMS (ESI$^+$) (method E): Rt 1.817 min, M+H$^+$ 433.1 m/z; $^1$H NMR (400 MHz, DMSO-d$_6$) δ [ppm] 8.58 (d, J=5.2, 1H), 8.43 (d, J=5.8, 1H), 8.11 (d, J=8.3, 2H), 7.76 (s, 1H), 7.64 (d, J=5.3, 1H), 7.52 (d, J=8.4, 2H), 7.32 (s, 2H), 4.36 (d, J=6.0, 2H), 3.92 (s, 6H), 3.75 (s, 3H), 1.91 (s, 3H).

3-[2-(3,4,5-Trimethoxy-phenyl)-furo[3,2-b]pyridin-7-yl]-phenylamine ("A55")

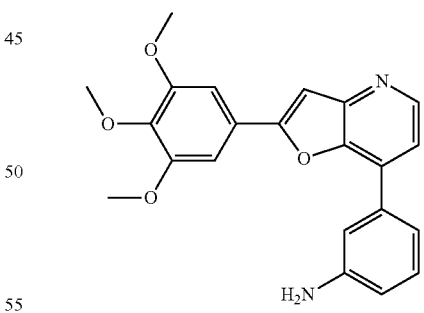

7-(3-Nitro-phenyl)-2-(3,4,5-trimethoxy-phenyl)-furo[3,2-b]pyridine (0.121 mmol) is dissolved in THF (10 ml) and Pd—C 5% (0.2 g) is added and the reaction is hydrogenated 16 h at RT. The mixture is filtered and the filtrate removed in vacuo. The precipitate is suspended in diethylether and filtrated. The product is obtained after reversed phase column chromatography as yellow solid in a yield of 27%. HPLC (method A): Rt 2.45 min (purity 99.2%); LCMS (ESI$^+$) (method E): Rt 1.89 min, M+H$^+$ 377.1 m/z; $^1$H NMR (400 MHz, DMSO-d$_6$) δ [ppm] 8.60 (d, J=5.3, 1H), 7.80 (s, 1H), 7.71-7.55 (m, 2H), 7.51-7.33 (m, 4H), 6.97 (d, J=6.9, 1H), 4.42 (s, br, 2H), 3.93 (s, 6H), 3.75 (s, 3H).

4-[2-(3,4,5-Trimethoxy-phenyl)-furo[3,2-b]pyridin-7-yl]-phenylamine ("A56")

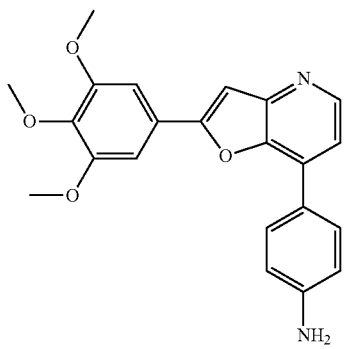 [SMILES: COc1cc(-c2cc3nccc(-c4ccc(N)cc4)c3o2)cc(OC)c1OC]

Starting from 7-(4-Nitro-phenyl)-2-(3,4,5-trimethoxy-phenyl)-furo[3,2-b]pyridine (0.064 mmol), the product is prepared analogously to "A55" and obtained as yellow solid in a yield of 66%. HPLC (method A): Rt 2.51 min (purity 98.6%); LCMS (ESI+) (method E): Rt 1.733 min, M+H+ 377.1 m/z; $^1$H NMR (400 MHz, DMSO-$d_6$) δ [ppm] 8.42 (d, J=5.2, 1H), 7.90 (d, J=8.7, 2H), 7.65 (s, 1H), 7.46 (d, J=5.2, 1H), 7.31 (s, 2H), 6.78 (d, J=8.7, 2H), 5.67 (br, 2H), 3.92 (s, 6H), 3.74 (s, 3H).

EXAMPLE 7

2-[4-[2-(3,4,5-trimethoxyphenyl)furo[3,2-b]pyridin-7-yl]pyrazol-1-yl]acetic acid ("A57")

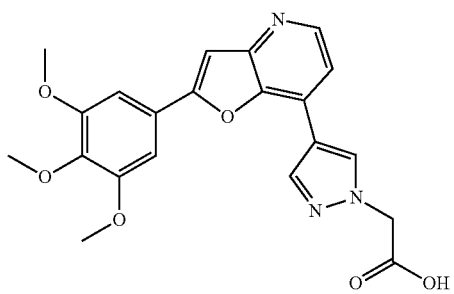 [SMILES: COc1cc(-c2cc3nccc(-c4cnn(CC(=O)O)c4)c3o2)cc(OC)c1OC]

Starting from ethyl 2-[4-[2-(3,4,5-trimethoxyphenyl)furo[3,2-b]pyridin-7-yl]pyrazol-1-yl]acetate (0.040 mmol), the product is prepared analogously to "A41" and obtained as yellow solid in quantitative yield. HPLC (method A): Rt 2.2.75 min (purity 100%); LCMS (ESI+) (method E): Rt 1.61 min, M+H+ 410.1 m/z.

2-[4-[2-(3,4,5-trimethoxyphenyl)furo[3,2-b]pyridin-7-yl]pyrazol-1-yl]acetamide ("A58")

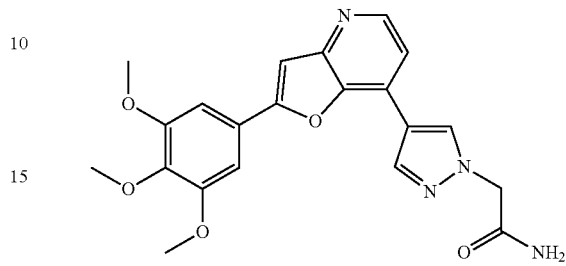

2-[4-[2-(3,4,5-trimethoxyphenyl)furo[3,2-b]pyridin-7-yl]pyrazol-1-yl]acetic acid (0.040 mmol) is dissolved in THF and thionylchloride (0.234 mmol) is added. The mixture is stirred 24 h at RT. Additional thionylchloride (0.234 mmol) is added and the reaction is stirred 24 h at RT. Additional Thionylchlorid (2.343 mmol) is added and the reaction is stirred 48 h. The solvent is removed in vacuo and ammonium hydroxide (32%, 1.205 mmol) is added. Water (3 ml) is added and the precipitate is filtered and resuspended in MeOH and filtered and dried at 50° C. in vacuo. The product is isolated as beige solid in a yield of 92%). HPLC (method A): Rt 2.40 min (purity 95%); LCMS (ESI+) (method E): Rt 1.49 min, M+H+ 409.1 m/z; $^1$H NMR (500 MHz, DMSO-$d_6$) δ [ppm] 8.67 (s, 1H), 8.45 (d, J=4.4, 1H), 8.32 (s, 1H), 7.75-7.51 (m, 3H), 7.47-7.26 (m, 3H), 4.93 (s, 2H), 3.95 (s, 6H), 3.74 (s, 3H).

3-[[2-(3,4,5-trimethoxyphenyl)furo[3,2-b]pyridin-7-yl]amino]benzoic acid ("A59")

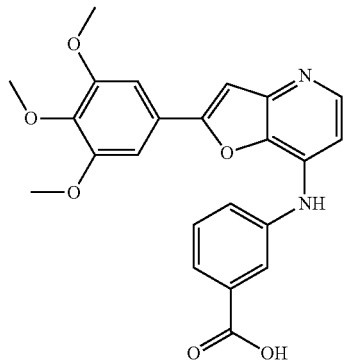 [SMILES: COc1cc(-c2cc3nccc(Nc4cccc(C(=O)O)c4)c3o2)cc(OC)c1OC]

7-Chloro-2-(3,4,5-trimethoxy-phenyl)-furo[3,2-b]pyridine (0.305 mmol), (3-amino-5-carboxylphenyl)boronic acid (0.460 mmol), palladium(II)-acetate (0.016 mmol), 2-dicyclohexylphosphino-2',6'-dimethoxybiphenyl (0.031 mmol) and $K_2CO_3$ (0.912 mmol) are suspended in 1,4-dioxane (1.00 ml) and water (100.00 μl). The suspension is heated to 150° C. in the microwave for 3 h. The solvent is removed in vacuo and the product purified over reversed phase column chromatography. The product isolated as yellow solid (yield 18%). HPLC (method A): Rt 2.69 min (purity 97.6%); LCMS (ESI+) (method E): Rt 1.64 min, M+H+ 421.1 m/z; $^1$H NMR (500 MHz, DMSO-$d_6$) δ [ppm] 13.25 (s, 1H), 10.65 (s, 1H), 8.32 (d, J=6.9, 1H), 7.97 (s, 1H), 7.92 (d, J=7.6, 1H), 7.81-7.71 (m, 2H), 7.68 (t, J=7.8, 1H), 7.20 (s, 2H), 7.04 (d, J=6.9, 1H), 3.85 (s, 6H), 3.73 (s, 3H).

Analogously to the examples given above the following compounds are prepared:
| Compound no. | |
|---|---|
| "A60" | 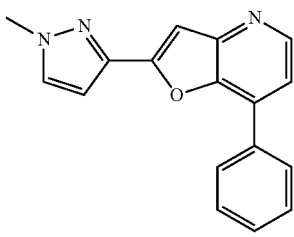 [SMILES: Cn1ccc(-c2cc3nccc(-c4ccccc4)c3o2)n1]
2-(1-Methyl-1H-pyrazol-3-yl)-7-phenyl-furo[3,2-b]pyridine |
| "A61" | 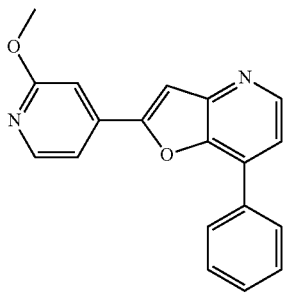 [SMILES: COc1cc(-c2cc3nccc(-c4ccccc4)c3o2)ccn1]
2-(2-Methoxy-pyridin-4-yl)-7-phenyl-furo[3,2-b]pyridine |
| "A62" | 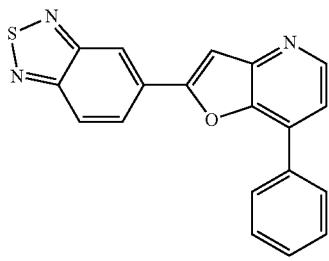 [SMILES: c1ccc(-c2ccnc3cc(-c4ccc5nsnc5c4)oc23)cc1]
5-(7-Phenyl-furo[3,2-b]pyridin-2-yl)-benzo[1,2,5]thiadiazole |
| "A63" | 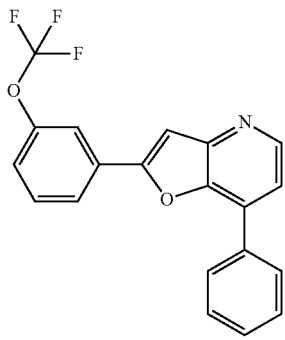 [SMILES: FC(F)(F)Oc1cccc(-c2cc3nccc(-c4ccccc4)c3o2)c1]
7-Phenyl-2-(3-trifluoromethoxy-phenyl)-furo[3,2-b]pyridine |
HPLC (Method A): Rt 3.27 min (purity 91.32%); LCMS (ESI+) (Method G): Rt 2.31 min, MH+ 356

-continued
| Compound no. | |
|---|---|
| "A64" | 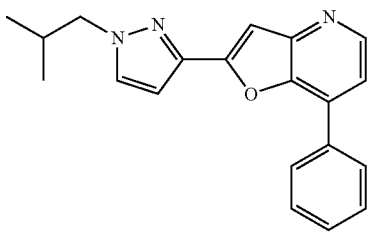 [SMILES: CC(C)Cn1ccc(-c2cc3nccc(-c4ccccc4)c3o2)n1] |
| | 2-(1-Isobutyl-1H-pyrazol-3-yl)-7-phenyl-furo[3,2-b]pyridine |
| "A65" | 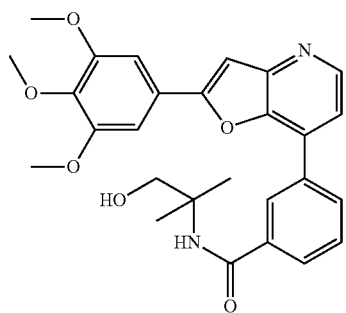 [SMILES: COc1cc(-c2cc3nccc(-c4cccc(C(=O)NC(C)(C)CO)c4)c3o2)cc(OC)c1OC] |
| | N-(2-Hydroxy-1,1-dimethyl-ethyl)-3-[2-(3,4,5-trimethoxy-phenyl)-furo[3,2-b]pyridin-7-yl]-benzamide |
| "A66" | 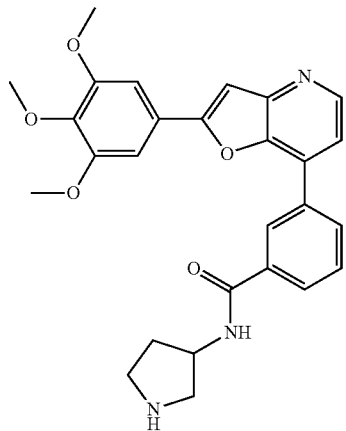 [SMILES: COc1cc(-c2cc3nccc(-c4cccc(C(=O)NC5CCNC5)c4)c3o2)cc(OC)c1OC] |
| | N-pyrrolidin-3-yl-3-[2-(3,4,5-trimethoxyphenyl)furo[3,2-b]pyridin-7-yl]benzamide |
| | HPLC (Method A): Rt 2.39 min (purity 100%); LCMS (ESI+)(Method G): Rt 1.549 min, MH+ 474.2; HCl Salt; $^1$H NMR(500 MHz, DMSO-$d_6$) δ [ppm] 9.16 (s, 1H), 8.99 (s, 1H), 8.92 (d, J = 6.3, 1H), 8.86 (t, J = 1.6, 1H), 8.65 (d, J = 5.2, 1H), 8.34 (d, J = 8.5, 1H), 8.11 (d, J = 7.9, 1H), 7.86-7.80 (m, 2H), 7.77 (t, J = 7.8, 1H), 7.39 (s, 2H), 4.63-4.52 (m, 1H), 3.94 (s, 6H), 3.74 (d, 3H), 3.52-3.34 (m, 2H), 3.34-3.18 (m, 2H), 2.30-2.18 (m, 1H), 2.12-1.99 (m, 1H) |

| Compound no. | |
|---|---|
| "A67" | 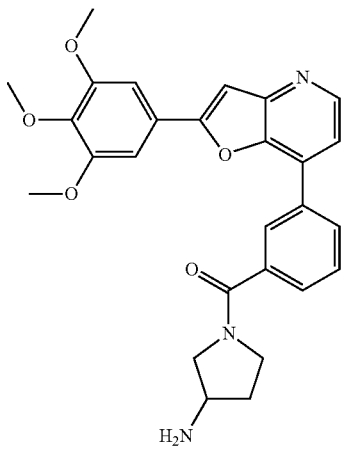 [SMILES: COc1cc(-c2cc3nccc(-c4cccc(C(=O)N5CCC(N)C5)c4)c3o2)cc(OC)c1OC] |

(3-aminopyrrolidin-1-yl)-[3-[2-(3,4,5-trimethoxyphenyl)furo[3,2-b]pyridin-7-yl]phenyl]methanone HPLC (Method A): Rt 2.36 min (purity 98.9%); LCMS (ESI+) (Method G): Rt 1.485 min, MH+ 474.2;

$^1$H NMR (500 MHz, DMSO-d$_6$, TFA exchange) δ [ppm] 8.92 (d, J = 6.3, 1H), 8.60 (s, 1H), 8.43-8.32 (m, 1H), 8.28-8.20 (m, 1H), 8.07 (s, 1H), 7.90 (t, J = 9.6, 1H), 7.83 (t, J = 7.8, 1H), 7.54 (s, 2H), 4.03-3.93 (m, 7H), 3.89-3.75 (m, 5H), 3.71-3.52 (m, 2H), 2.28 (dd, J = 13.8, 7.1, 1H), 2.10 (s, 1H)

| | |
|---|---|
| "A68" | 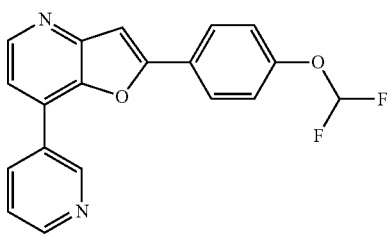 [SMILES: FC(F)Oc1ccc(-c2cc3nccc(-c4cccnc4)c3o2)cc1] |

2-(4-Difluoromethoxy-phenyl)-7-pyridin-3-yl-furo[3,2-b]pyridine

| | |
|---|---|
| "A69" | 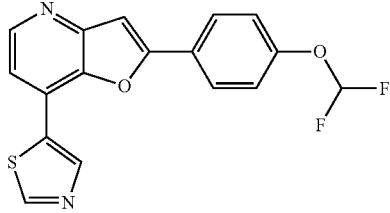 [SMILES: FC(F)Oc1ccc(-c2cc3nccc(-c4cncs4)c3o2)cc1] |

2-(4-Difluoromethoxy-phenyl)-7-thiazol-5-yl-furo[3,2-b]pyridine

| | |
|---|---|
| "A70" | 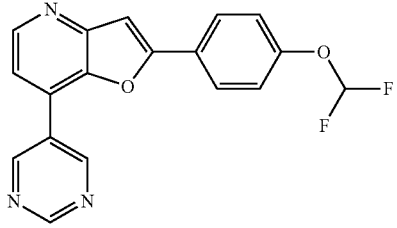 [SMILES: FC(F)Oc1ccc(-c2cc3nccc(-c4cncnc4)c3o2)cc1] |

2-(4-Difluoromethoxy-phenyl)-7-pyrimidin-5-yl-furo[3,2-b]pyridine

| Compound no. | | |
|---|---|---|
| "A71" | 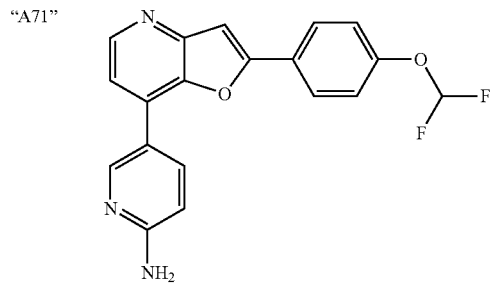 | |
| | 5-[2-(4-Difluoromethoxy-phenyl)-furo[3,2-b]pyridin-7-yl]-pyridin-2-ylamine | |
| "A72" | 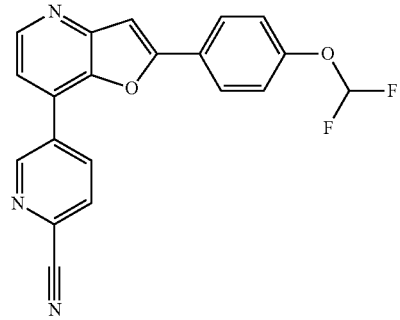 [SMILES: N#Cc1ccc(-c2ccnc3cc(-c4ccc(OC(F)F)cc4)oc23)cn1] | |
| | 5-[2-(4-Difluoromethoxy-phenyl)-furo[3,2-b]pyridin-7-yl]-pyridine-2-carbonitrile | |
| "A73" | 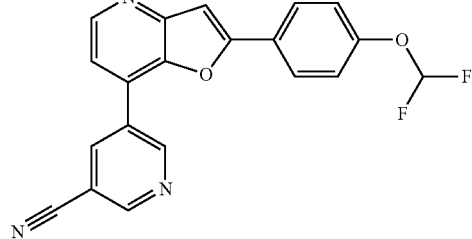 | |
| | 5-[2-(4-Difluoromethoxy-phenyl)-furo[3,2-b]pyridin-7-yl]-nicotinonitrile | |
| "A74" | 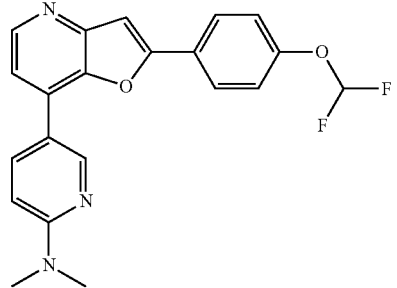 [SMILES: CN(C)c1ccc(-c2ccnc3cc(-c4ccc(OC(F)F)cc4)oc23)cn1] | |
| | {5-[2-(4-Difluoromethoxy-phenyl)-furo[3,2-b]pyridin-7-yl]-pyridin-2-yl}-dimethyl-amine | |

| Compound no. | |
|---|---|
| "A75" | 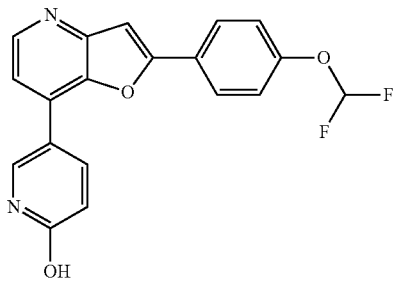 [SMILES: Oc1ccc(-c2ccnc3cc(-c4ccc(OC(F)F)cc4)oc23)cn1]<br>5-[2-(4-Difluoromethoxy-phenyl)-furo[3,2-b]pyridin-7-yl]-pyridin-2-ol |
| "A76" | 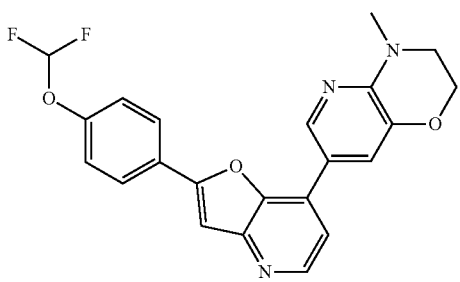 [SMILES: CN1CCOc2cc(-c3ccnc4cc(-c5ccc(OC(F)F)cc5)oc34)cnc21]<br>7-[2-(4-Difluoromethoxy-phenyl)-furo[3,2-b]pyridin-7-yl]-4-methyl-3,4-dihydro-2H-pyrido[3,2-b][1,4]oxazine |
| "A77" | 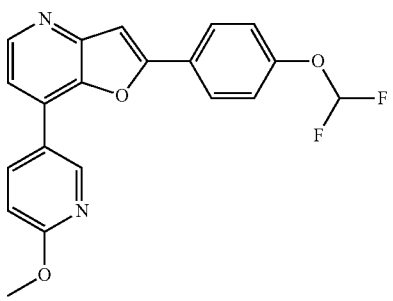 [SMILES: COc1ccc(-c2ccnc3cc(-c4ccc(OC(F)F)cc4)oc23)cn1]<br>2-(4-Difluoromethoxy-phenyl)-7-(6-methoxy-pyridin-3-yl)-furo[3,2-b]pyridine |
| "A78" | 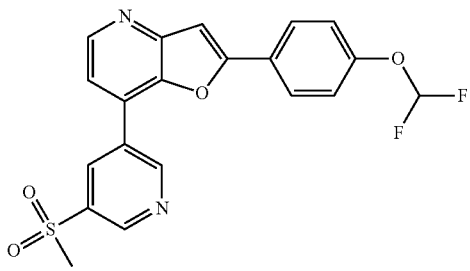 [SMILES: CS(=O)(=O)c1cncc(-c2ccnc3cc(-c4ccc(OC(F)F)cc4)oc23)c1]<br>2-(4-Difluoromethoxy-phenyl)-7-(5-methanesulfonyl-pyridin-3-yl)-furo[3,2-b]pyridine |

| Compound no. | |
|---|---|
| "A79" | 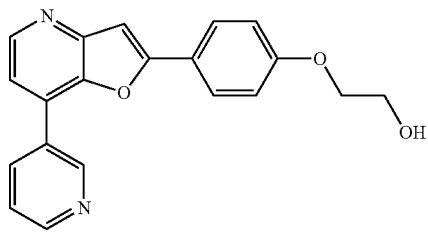 [SMILES: OCCOc1ccc(-c2cc3nccc(-c4cccnc4)c3o2)cc1]<br>2-[4-(7-Pyridin-3-yl-furo[3,2-b]pyridin-2-yl)-phenoxy]-ethanol |
| "A80" | 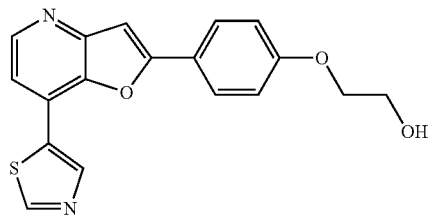 [SMILES: OCCOc1ccc(-c2cc3nccc(-c4cncs4)c3o2)cc1]<br>2-[4-(7-Thiazol-5-yl-furo[3,2-b]pyridin-2-yl)-phenoxy]-ethanol |
| "A81" | 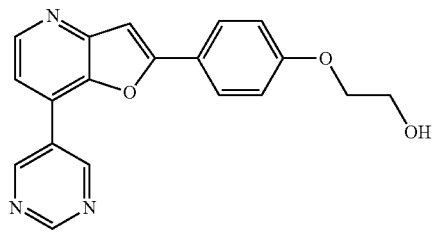 [SMILES: OCCOc1ccc(-c2cc3nccc(-c4cncnc4)c3o2)cc1]<br>2-[4-(7-Pyrimidin-5-yl-furo[3,2-b]pyridin-2-yl)-phenoxy]-ethanol |
| "A82" | 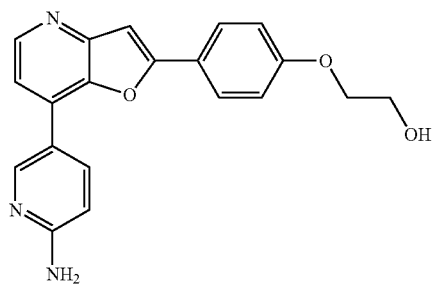 [SMILES: Nc1ccc(-c2ccnc3cc(-c4ccc(OCCO)cc4)oc23)cn1]<br>2-{4-[7-(6-Amino-pyridin-3-yl)-furo[3,2-b]pyridin-2-yl]-phenoxy}-ethanol |
| "A83" | 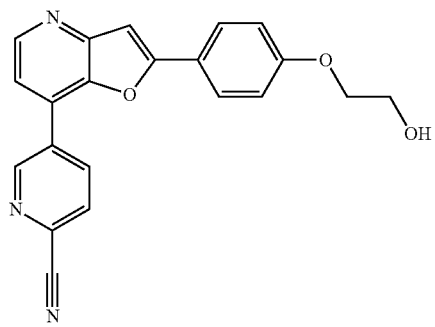 [SMILES: N#Cc1ccc(-c2ccnc3cc(-c4ccc(OCCO)cc4)oc23)cn1]<br>5-{2-[4-(2-Hydroxy-ethoxy)-phenyl]-furo[3,2-b]pyridin-7-yl}-pyridine-2-carbonitrile |

| Compound no. | |
|---|---|
| "A84" | 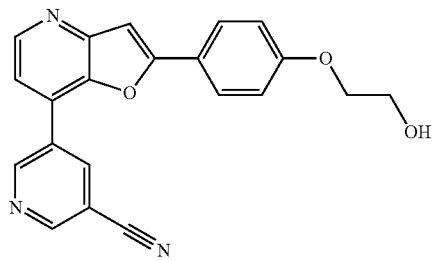 [SMILES: N#Cc1cncc(-c2ccnc3cc(-c4ccc(OCCO)cc4)oc23)c1]<br>5-{2-[4-(2-Hydroxy-ethoxy)-phenyl]-furo[3,2-b]pyridin-7-yl}-nicotinonitrile |
| "A85" | 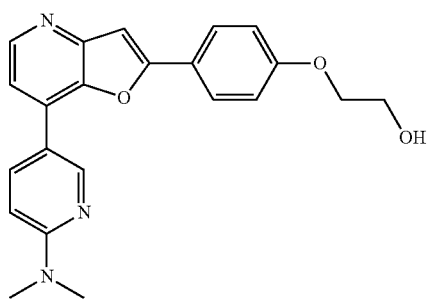<br>2-{4-[7-(6-Dimethylamino-pyridin-3-yl)-furo[3,2-b]pyridin-2-yl]-phenoxy}-ethanol |
| "A86" | 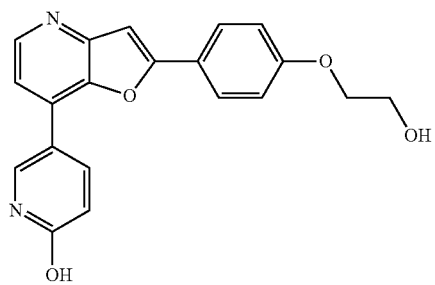 [SMILES: OCCOc1ccc(-c2cc3nccc(-c4ccc(O)nc4)c3o2)cc1]<br>5-{2-[4-(2-Hydroxy-ethoxy)-phenyl]-furo[3,2-b]pyridin-7-yl}-pyridin-2-ol |
| "A87" | 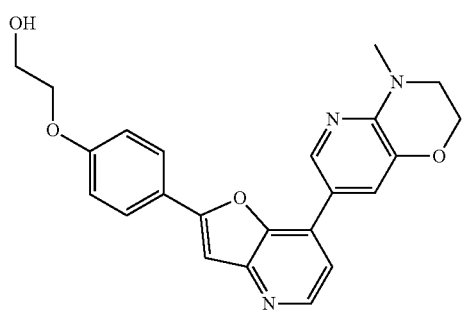 [SMILES: CN1CCOc2cc(-c3ccnc4cc(-c5ccc(OCCO)cc5)oc34)cnc21]<br>2-{4-[7-(4-Methyl-3,4-dihydro-2H-pyrido[3,2-b][1,4]oxazin-7-yl)-furo[3,2-b]pyridin-2-yl]-phenoxy}-ethanol |

| Compound no. | |
|---|---|
| "A88" | 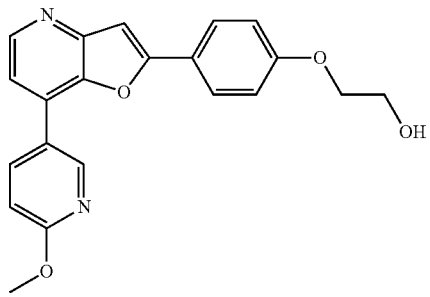 [SMILES: COc1ccc(-c2ccnc3cc(-c4ccc(OCCO)cc4)oc23)cn1]<br>2-{4-[7-(6-Methoxy-pyridin-3-yl)-furo[3,2-b]pyridin-2-yl]-phenoxy}-ethanol |
| "A89" | 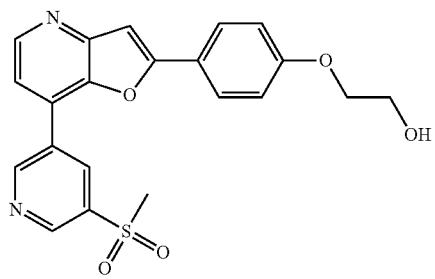 [SMILES: CS(=O)(=O)c1cncc(-c2ccnc3cc(-c4ccc(OCCO)cc4)oc23)c1]<br>2-{4-[7-(5-Methanesulfonyl-pyridin-3-yl)-furo[3,2-b]pyridin-2-yl]-phenoxy}-ethanol |
| "A90" | 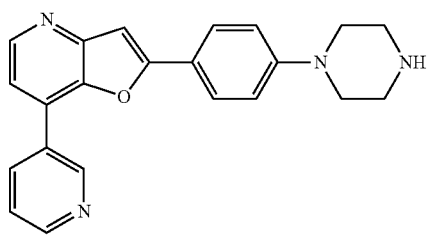 [SMILES: c1cncc(-c2ccnc3cc(-c4ccc(N5CCNCC5)cc4)oc23)c1]<br>2-(4-Piperazin-1-yl-phenyl)-7-pyridin-3-yl-furo[3,2-b]pyridine |
| "A91" | 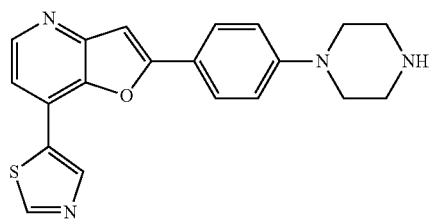 [SMILES: c1cc(-c2cncs2)c2oc(-c3ccc(N4CCNCC4)cc3)cc2n1]<br>2-(4-Piperazin-1-yl-phenyl)-7-thiazol-5-yl-furo[3,2-b]pyridine |
| "A92" | 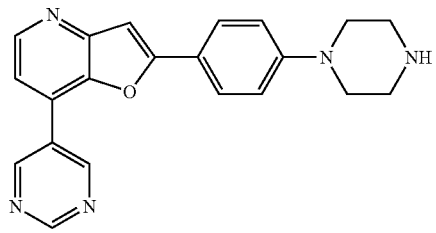 [SMILES: c1ncc(-c2ccnc3cc(-c4ccc(N5CCNCC5)cc4)oc23)cn1]<br>2-(4-Piperazin-1-yl-phenyl)-7-pyrimidin-5-yl-furo[3,2-b]pyridine |

| Compound no. | |
|---|---|
| "A93" | 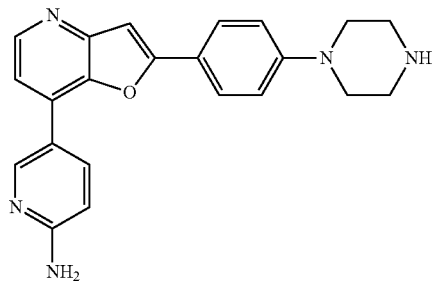 [SMILES: Nc1ccc(-c2ccnc3cc(-c4ccc(N5CCNCC5)cc4)oc23)cn1]<br>5-[2-(4-Piperazin-1-yl-phenyl)-furo[3,2-b]pyridin-7-yl]-pyridin-2-ylamine |
| "A94" | 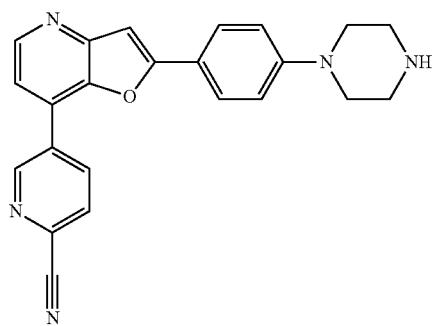 [SMILES: N#Cc1ccc(-c2ccnc3cc(-c4ccc(N5CCNCC5)cc4)oc23)cn1]<br>5-[2-(4-Piperazin-1-yl-phenyl)-furo[3,2-b]pyridin-7-yl]-pyridine-2-carbonitrile |
| "A95" | 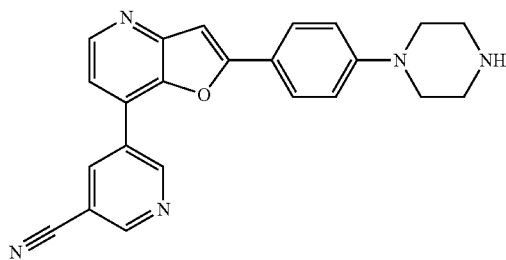 [SMILES: N#Cc1cncc(-c2ccnc3cc(-c4ccc(N5CCNCC5)cc4)oc23)c1]<br>5-[2-(4-Piperazin-1-yl-phenyl)-furo[3,2-b]pyridin-7-yl]-nicotinonitrile |
| "A96" | 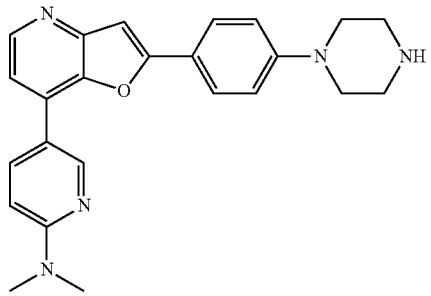<br>Dimethyl-{5-[2-(4-piperazin-1-yl-phenyl)-furo[3,2-b]pyridin-7-yl]-pyridin-2-yl}-amine |

| Compound no. | |
|---|---|
| "A97" | 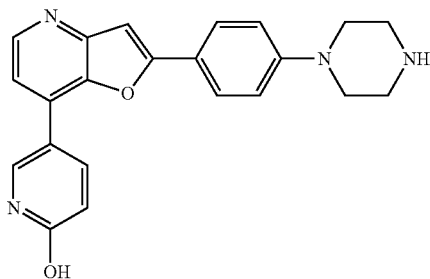 [SMILES: Oc1ccc(-c2ccnc3cc(-c4ccc(N5CCNCC5)cc4)oc23)cn1] |
| | 5-[2-(4-Piperazin-1-yl-phenyl)-furo[3,2-b]pyridin-7-yl]-pyridin-2-ol |
| "A98" | 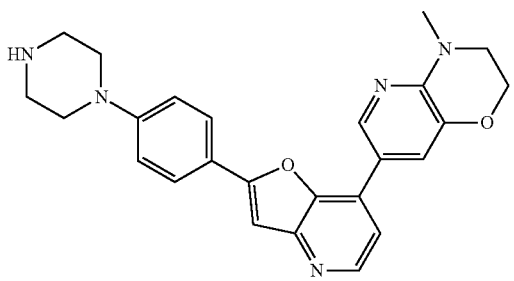 [SMILES: CN1CCOc2cc(-c3ccnc4cc(-c5ccc(N6CCNCC6)cc5)oc34)cnc21] |
| | 4-Methyl-7-[2-(4-piperazin-1-yl-phenyl)-furo[3,2-b]pyridin-7-yl]-3,4-dihydro-2H-pyrido[3,2-b][1,4]oxazine |
| "A99" | 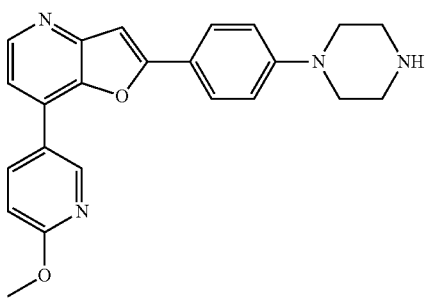 [SMILES: COc1ccc(-c2ccnc3cc(-c4ccc(N5CCNCC5)cc4)oc23)cn1] |
| | 7-(6-Methoxy-pyridin-3-yl)-2-(4-piperazin-1-yl-phenyl)-furo[3,2-b]pyridine |
| "A100" | 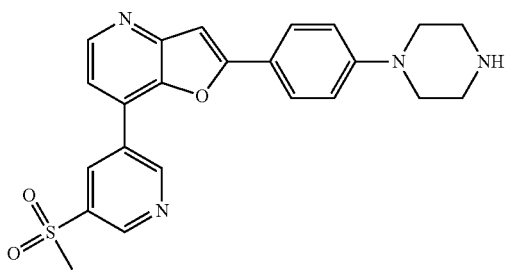 [SMILES: CS(=O)(=O)c1cncc(-c2ccnc3cc(-c4ccc(N5CCNCC5)cc4)oc23)c1] |
| | 7-(5-Methanesulfonyl-pyridin-3-yl)-2-(4-piperazin-1-yl-phenyl)-furo[3,2-b]pyridine |

| Compound no. | |
|---|---|
| "A101" | 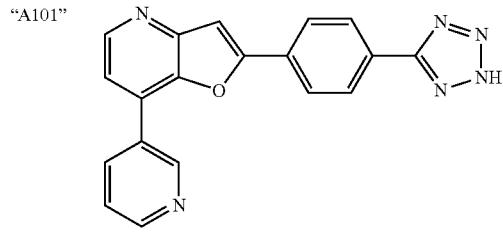<br>7-Pyridin-3-yl-2-[4-(2H-tetrazol-5-yl)-phenyl]-furo[3,2-b]pyridine |
| "A102" | 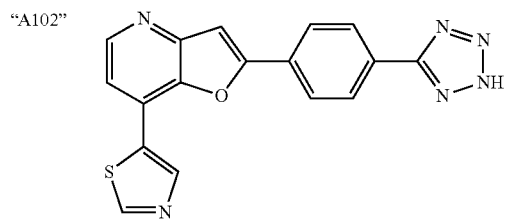<br>2-[4-(2H-Tetrazol-5-yl)-phenyl]-7-thiazol-5-yl-furo[3,2-b]pyridine |
| "A103" | 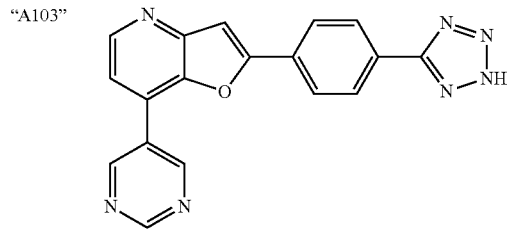<br>7-Pyrimidin-5-yl-2-[4-(2H-tetrazol-5-yl)-phenyl]-furo[3,2-b]pyridine |
| "A104" | 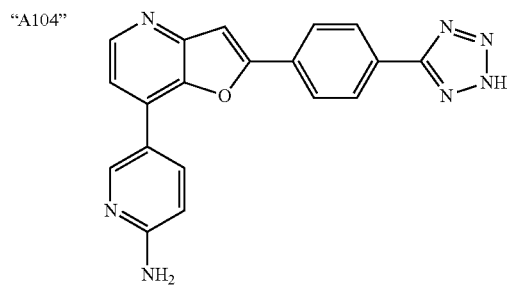<br>5-{2-[4-(2H-Tetrazol-5-yl)-phenyl]-furo[3,2-b]pyridin-7-yl}-pyridin-2-ylamine |
| "A105" | 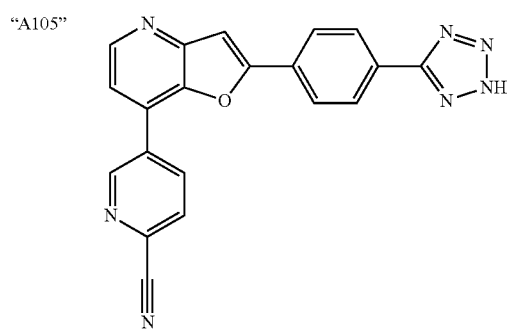<br>5-{2-[4-(2H-Tetrazol-5-yl)-phenyl]-furo[3,2-b]pyridin-7-yl}-pyridine-2-carbonitrile |

| Compound no. | | |
|---|---|---|
| "A106" | 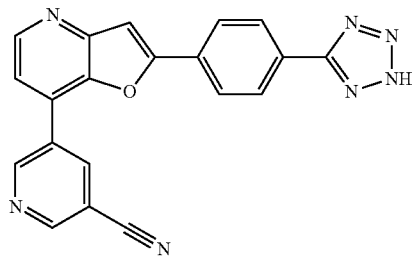 [SMILES: N#Cc1cncc(-c2ccnc3cc(-c4ccc(-c5nn[nH]n5)cc4)oc23)c1] | |
| | 5-{2-[4-(2H-Tetrazol-5-yl)-phenyl]-furo[3,2-b]pyridin-7-yl}-nicotinonitrile | |
| "A107" | 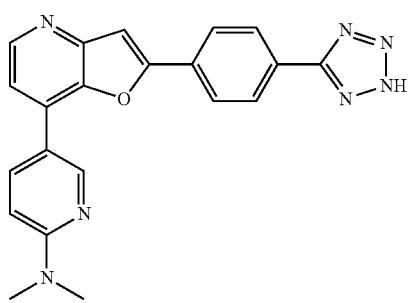 [SMILES: CN(C)c1ccc(-c2ccnc3cc(-c4ccc(-c5nn[nH]n5)cc4)oc23)cn1] | |
| | Dimethyl-(5-{2-[4-(2H-tetrazol-5-yl)-phenyl]-furo[3,2-b]pyridin-7-yl}-pyridin-2-yl)-amine | |
| "A108" | 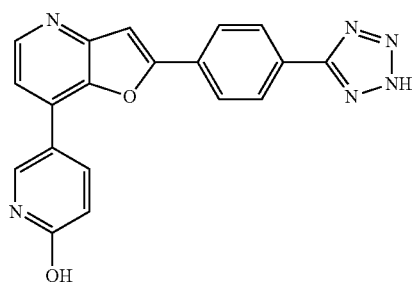 [SMILES: Oc1ccc(-c2ccnc3cc(-c4ccc(-c5nn[nH]n5)cc4)oc23)cn1] | |
| | 5-{2-[4-(2H-Tetrazol-5-yl)-phenyl]-furo[3,2-b]pyridin-7-yl}-pyridin-2-ol | |
| "A109" | 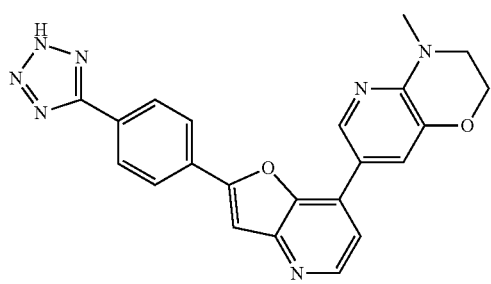 [SMILES: CN1CCOc2cc(-c3ccnc4cc(-c5ccc(-c6nn[nH]n6)cc5)oc34)cnc21] | |
| | 4-Methyl-7-{2-[4-(2H-tetrazol-5-yl)-phenyl]-furo[3,2-b]pyridin-7-yl}-3,4-dihydro-2H-pyrido[3,2-b][1,4]oxazine | |

| Compound no. | |
|---|---|
| "A110" | 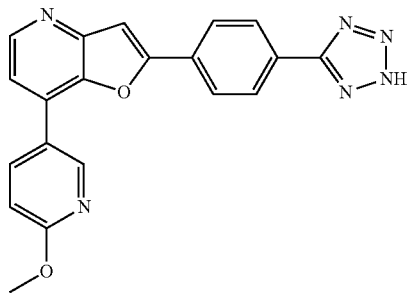 [SMILES: COc1ccc(-c2ccnc3cc(-c4ccc(-c5nn[nH]n5)cc4)oc23)cn1] |
| | 7-(6-Methoxy-pyridin-3-yl)-2-[4-(2H-tetrazol-5-yl)-phenyl]-furo[3,2-b]pyridine |
| "A111" | 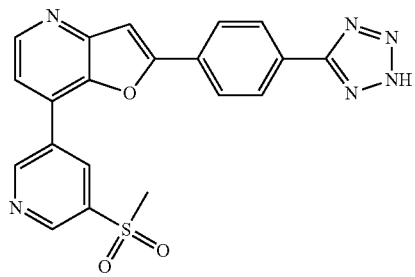 [SMILES: CS(=O)(=O)c1cncc(-c2ccnc3cc(-c4ccc(-c5nn[nH]n5)cc4)oc23)c1] |
| | 7-(5-Methanesulfonyl-pyridin-3-yl)-2-[4-(2H-tetrazol-5-yl)-phenyl]-furo[3,2-b]pyridine |
| "A112" | 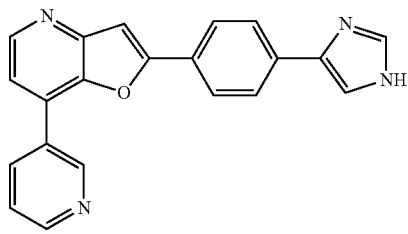 [SMILES: c1cncc(-c2ccnc3cc(-c4ccc(-c5c[nH]cn5)cc4)oc23)c1] |
| | 2-[4-(1H-Imidazol-4-yl)-phenyl]-7-pyridin-3-yl-furo[3,2-b]pyridine |
| "A113" | 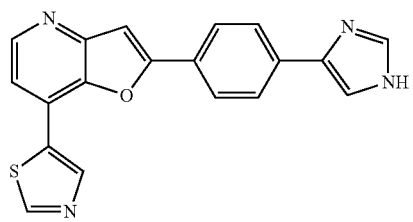 [SMILES: c1cc(-c2cncs2)c2oc(-c3ccc(-c4c[nH]cn4)cc3)cc2n1] |
| | 2-[4-(1H-Imidazol-4-yl)-phenyl]-7-thiazol-5-yl-furo[3,2-b]pyridine |
| "A114" | 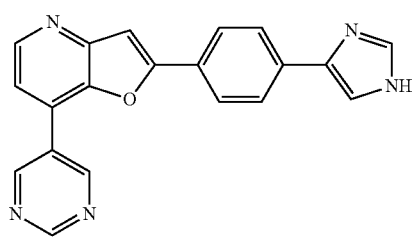 [SMILES: c1ncc(-c2ccnc3cc(-c4ccc(-c5c[nH]cn5)cc4)oc23)cn1] |
| | 2-[4-(1H-Imidazol-4-yl)-phenyl]-7-pyrimidin-5-yl-furo[3,2-b]pyridine |

| Compound no. | | |
|---|---|---|
| "A115" | 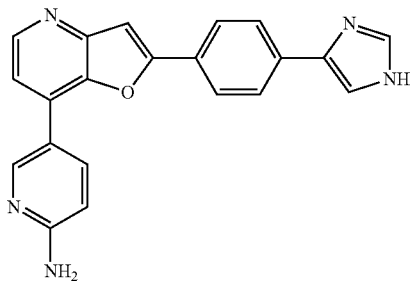 [SMILES: Nc1ccc(-c2ccnc3cc(-c4ccc(-c5c[nH]cn5)cc4)oc23)cn1] | |
5-{2-[4-(1H-Imidazol-4-yl)-phenyl]-furo[3,2-b]pyridin-7-yl}-pyridin-2-ylamine
| "A116" | 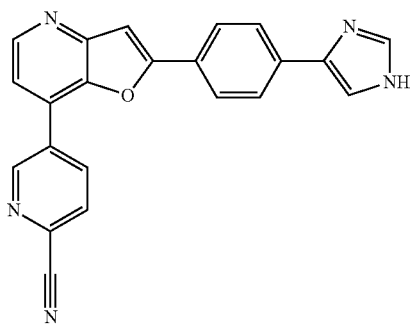 [SMILES: N#Cc1ccc(-c2ccnc3cc(-c4ccc(-c5c[nH]cn5)cc4)oc23)cn1] | |
5-{2-[4-(1H-Imidazol-4-yl)-phenyl]-furo[3,2-b]pyridin-7-yl}-pyridine-2-carbonitrile
| "A117" | 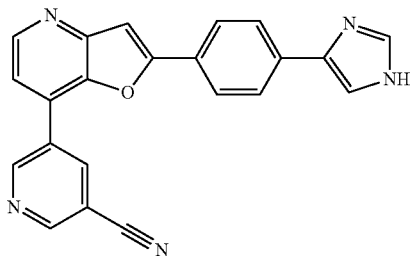 [SMILES: N#Cc1cncc(-c2ccnc3cc(-c4ccc(-c5c[nH]cn5)cc4)oc23)c1] | |
5-{2-[4-(1H-Imidazol-4-yl)-phenyl]-furo[3,2-b]pyridin-7-yl}-nicotinonitrile
| "A118" | 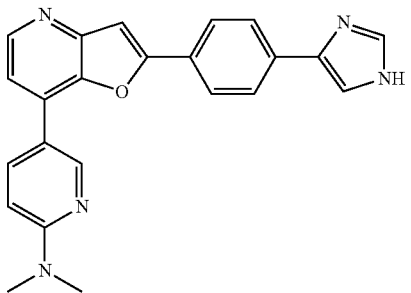 [SMILES: CN(C)c1ccc(-c2ccnc3cc(-c4ccc(-c5c[nH]cn5)cc4)oc23)cn1] | |
(5-{2-[4-(1H-Imidazol-4-yl)-phenyl]-furo[3,2-b]pyridin-7-yl}-pyridin-2-yl)-dimethyl-amine

| Compound no. | |
|---|---|
| "A119" | 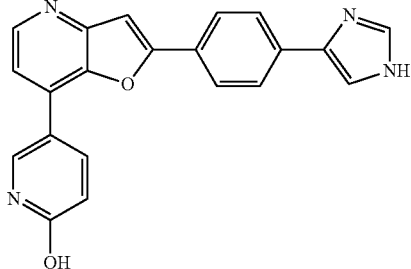 [SMILES: Oc1ccc(-c2ccnc3cc(-c4ccc(-c5c[nH]cn5)cc4)oc23)cn1]<br>5-{2-[4-(1H-Imidazol-4-yl)-phenyl]-furo[3,2-b]pyridin-7-yl}-pyridin-2-ol |
| "A120" | 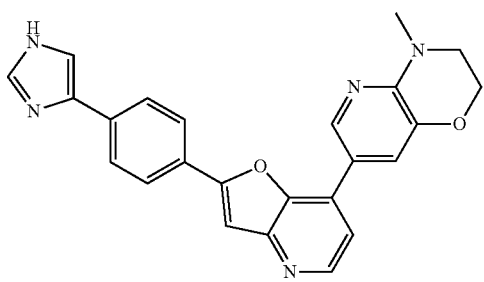 [SMILES: CN1CCOc2cc(-c3ccnc4cc(-c5ccc(-c6c[nH]cn6)cc5)oc34)cnc21]<br>7-{2-[4-(1H-Imidazol-4-yl)-phenyl]-furo[3,2-b]pyridin-7-yl}-4-methyl-3,4-dihydro-2H-pyrido[3,2-b][1,4]oxazine |
| "A121" | 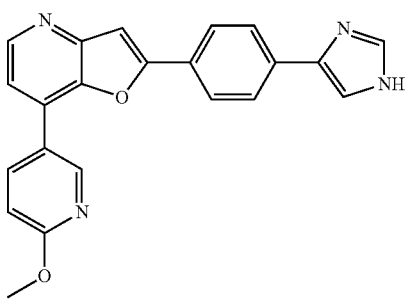 [SMILES: COc1ccc(-c2ccnc3cc(-c4ccc(-c5c[nH]cn5)cc4)oc23)cn1]<br>2-[4-(1H-Imidazol-4-yl)-phenyl]-7-(6-methoxy-pyridin-3-yl)-furo[3,2-b]pyridine |
| "A122" | 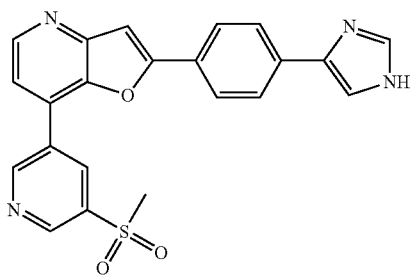 [SMILES: CS(=O)(=O)c1cncc(-c2ccnc3cc(-c4ccc(-c5c[nH]cn5)cc4)oc23)c1]<br>2-[4-(1H-Imidazol-4-yl)-phenyl]-7-(5-methanesulfonyl-pyridin-3-yl)-furo[3,2-b]pyridine |

| Compound no. | | |
|---|---|---|
| "A123" | 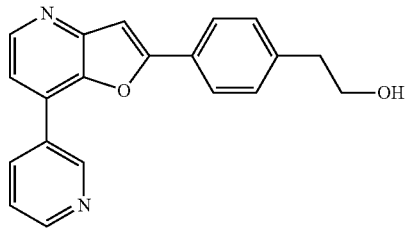 [SMILES: OCCc1ccc(-c2cc3nccc(-c4cccnc4)c3o2)cc1] 2-[4-(7-Pyridin-3-yl-furo[3,2-b]pyridin-2-yl)-phenyl]-ethanol | |
| "A124" | 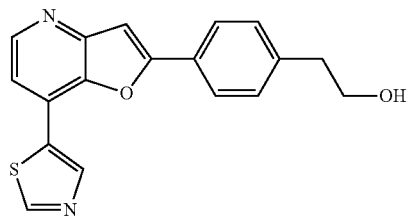 [SMILES: OCCc1ccc(-c2cc3nccc(-c4cncs4)c3o2)cc1] 2-[4-(7-Thiazol-5-yl-furo[3,2-b]pyridin-2-yl)-phenyl]-ethanol | |
| "A125" | 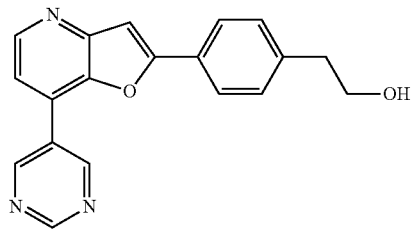 [SMILES: OCCc1ccc(-c2cc3nccc(-c4cncnc4)c3o2)cc1] 2-[4-(7-Pyrimidin-5-yl-furo[3,2-b]pyridin-2-yl)-phenyl]-ethanol | |
| "A126" | 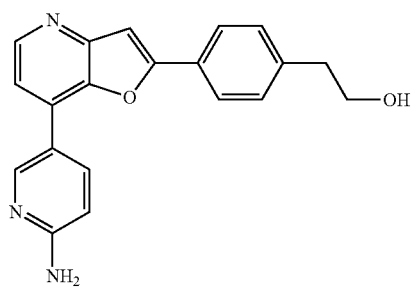 [SMILES: Nc1ccc(-c2ccnc3cc(-c4ccc(CCO)cc4)oc23)cn1] 2-{4-[7-(6-Amino-pyridin-3-yl)-furo[3,2-b]pyridin-2-yl]-phenyl}-ethanol | |
| "A127" | 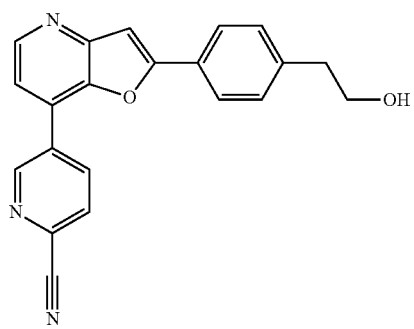 [SMILES: N#Cc1ccc(-c2ccnc3cc(-c4ccc(CCO)cc4)oc23)cn1] 5-{2-[4-(2-Hydroxy-ethyl)-phenyl]-furo[3,2-b]pyridin-7-yl}-pyridine-2-carbonitrile | |

| Compound no. | |
|---|---|
| "A128" | 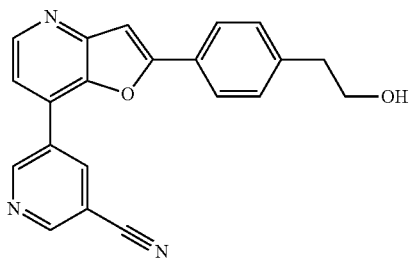 [SMILES: N#Cc1cncc(-c2ccnc3cc(-c4ccc(CCO)cc4)oc23)c1] |
5-{2-[4-(2-Hydroxy-ethyl)-phenyl]-furo[3,2-b]pyridin-7-yl}-nicotinonitrile
| "A129" | 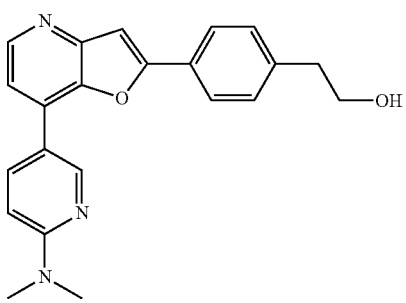 [SMILES: CN(C)c1ccc(-c2ccnc3cc(-c4ccc(CCO)cc4)oc23)cn1] |
|---|---|
2-{4-[7-(6-Dimethylamino-pyridin-3-yl)-furo[3,2-b]pyridin-2-yl]-phenyl}-ethanol
| "A130" | 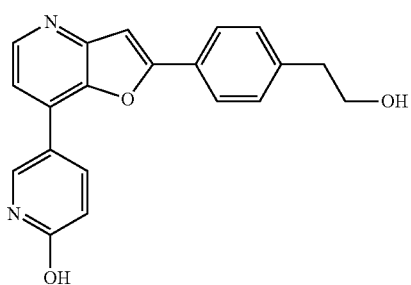 [SMILES: OCCc1ccc(-c2cc3nccc(-c4ccc(O)nc4)c3o2)cc1] |
|---|---|
5-{2-[4-(2-Hydroxy-ethyl)-phenyl]-furo[3,2-b]pyridin-7-yl}-pyridin-2-ol
| "A131" | 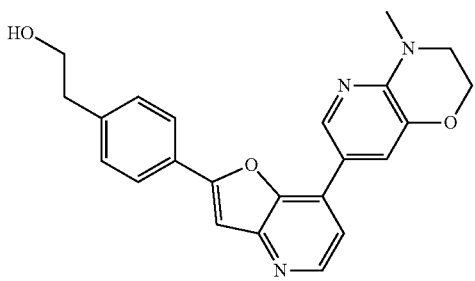 [SMILES: CN1CCOc2cc(-c3ccnc4cc(-c5ccc(CCO)cc5)oc34)cnc21] |
|---|---|
2-{4-[7-(4-Methyl-3,4-dihydro-2H-pyrido[3,2-b][1,4]oxazin-7-yl)-furo[3,2-b]pyridin-2-yl]-phenyl}-ethanol

| Compound no. | |
|---|---|
| "A132" | 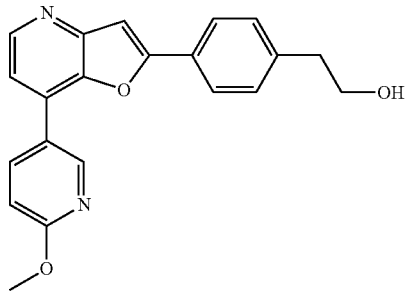 [SMILES: COc1ccc(-c2ccnc3cc(-c4ccc(CCO)cc4)oc23)cn1]<br>2-{4-[7-(6-Methoxy-pyridin-3-yl)-furo[3,2-b]pyridin-2-yl]-phenyl}-ethanol |
| "A133" | 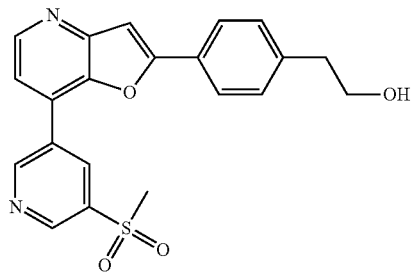 [SMILES: CS(=O)(=O)c1cncc(-c2ccnc3cc(-c4ccc(CCO)cc4)oc23)c1]<br>2-{4-[7-(5-Methanesulfonyl-pyridin-3-yl)-furo[3,2-b]pyridin-2-yl]-phenyl}-ethanol |
| "A134" | 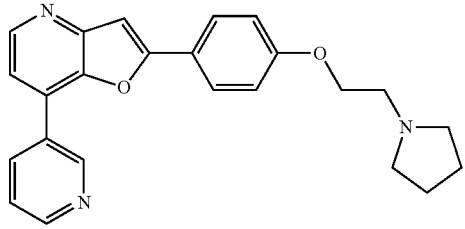 [SMILES: c1cncc(-c2ccnc3cc(-c4ccc(OCCN5CCCC5)cc4)oc23)c1]<br>7-Pyridin-3-yl-2-[4-(2-pyrrolidin-1-yl-ethoxy)-phenyl]-furo[3,2-b]pyridine |
| "A135" | 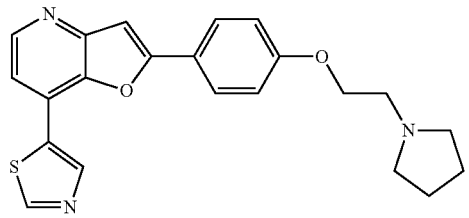 [SMILES: c1cc(-c2cncs2)c2oc(-c3ccc(OCCN4CCCC4)cc3)cc2n1]<br>2-[4-(2-Pyrrolidin-1-yl-ethoxy)-phenyl]-7-thiazol-5-yl-furo[3,2-b]pyridine |
| "A136" | 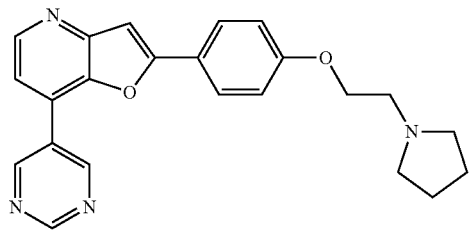 [SMILES: c1ncc(-c2ccnc3cc(-c4ccc(OCCN5CCCC5)cc4)oc23)cn1]<br>7-Pyrimidin-5-yl-2-[4-(2-pyrrolidin-1-yl-ethoxy)-phenyl]-furo[3,2-b]pyridine |

| Compound no. | |
|---|---|
| "A137" | 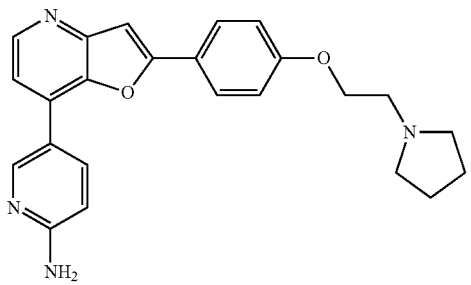 [SMILES: Nc1ccc(-c2ccnc3cc(-c4ccc(OCCN5CCCC5)cc4)oc23)cn1]<br>5-{2-[4-(2-Pyrrolidin-1-yl-ethoxy)-phenyl]-furo[3,2-b]pyridin-7-yl}-pyridin-2-ylamine |
| "A138" | 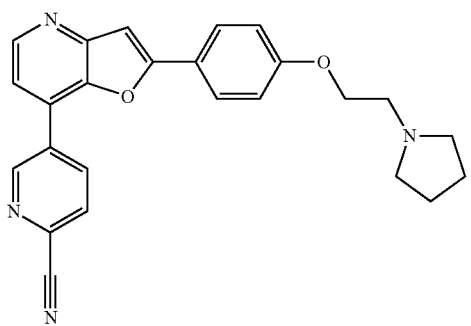 [SMILES: N#Cc1ccc(-c2ccnc3cc(-c4ccc(OCCN5CCCC5)cc4)oc23)cn1]<br>5-{2-[4-(2-Pyrrolidin-1-yl-ethoxy)-phenyl]-furo[3,2-b]pyridin-7-yl}-pyridine-2-carbonitrile |
| "A139" | 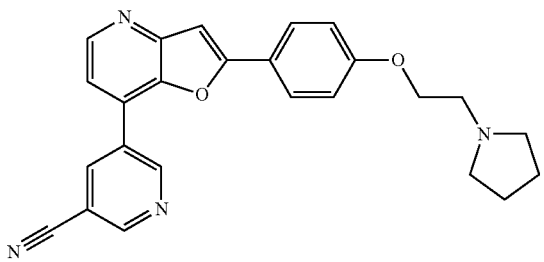 [SMILES: N#Cc1cncc(-c2ccnc3cc(-c4ccc(OCCN5CCCC5)cc4)oc23)c1]<br>5-{2-[4-(2-Pyrrolidin-1-yl-ethoxy)-phenyl]-furo[3,2-b]pyridin-7-yl}-nicotinonitrile |
| "A140" | 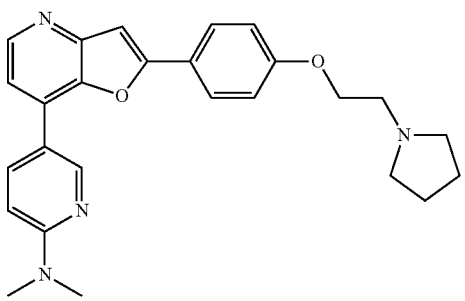 [SMILES: CN(C)c1ccc(-c2ccnc3cc(-c4ccc(OCCN5CCCC5)cc4)oc23)cn1]<br>Dimethyl-(5-{2-[4-(2-pyrrolidin-1-yl-ethoxy)-phenyl]-furo[3,2-b]pyridin-7-yl}-pyridin-2-yl)-amine |

| Compound no. | |
|---|---|
| "A141" | 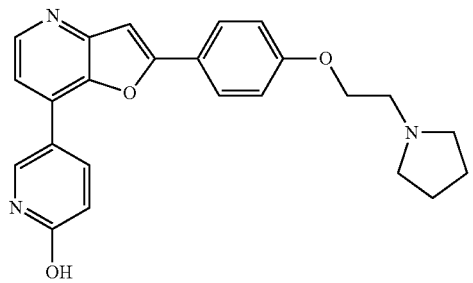 [SMILES: Oc1ccc(-c2ccnc3cc(-c4ccc(OCCN5CCCC5)cc4)oc23)cn1]<br>5-{2-[4-(2-Pyrrolidin-1-yl-ethoxy)-phenyl]-furo[3,2-b]pyridin-7-yl}-pyridin-2-ol |
| "A142" | 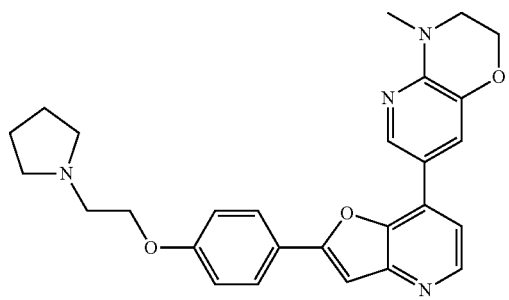 [SMILES: CN1CCOc2cc(-c3ccnc4cc(-c5ccc(OCCN6CCCC6)cc5)oc34)cnc21]<br>4-Methyl-7-{2-[4-(2-pyrrolidin-1-yl-ethoxy)-phenyl]-furo[3,2-b]pyridin-7-yl}-3,4-dihydro-2H-pyrido[3,2-b][1,4]oxazine |
| "A143" | 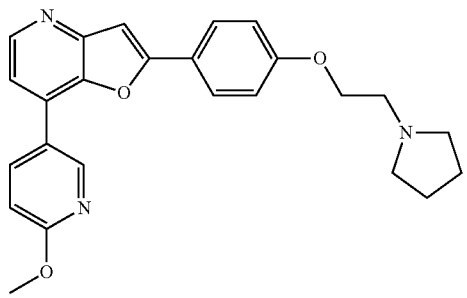 [SMILES: COc1ccc(-c2ccnc3cc(-c4ccc(OCCN5CCCC5)cc4)oc23)cn1]<br>7-(6-Methoxy-pyridin-3-yl)-2-[4-(2-pyrrolidin-1-yl-ethoxy)-phenyl]-furo[3,2-b]pyridine |
| "A144" | 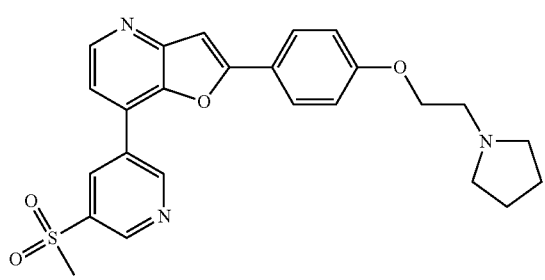 [SMILES: CS(=O)(=O)c1cncc(-c2ccnc3cc(-c4ccc(OCCN5CCCC5)cc4)oc23)c1]<br>7-(5-Methanesulfonyl-pyridin-3-yl)-2-[4-(2-pyrrolidin-1-yl-ethoxy)-phenyl]-furo[3,2-b]pyridine |

| Compound no. | |
|---|---|
| "A145" | 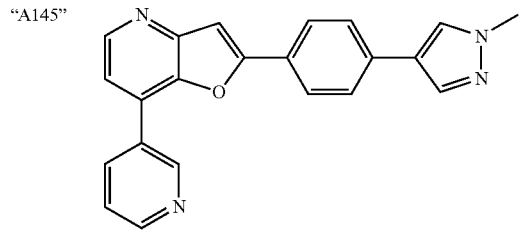 |
2-[4-(1-Methyl-1H-pyrazol-4-yl)-phenyl]-7-pyridin-3-yl-furo[3,2-b]pyridine
| "A146" | 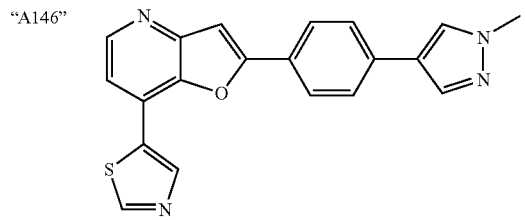 |
2-[4-(1-Methyl-1H-pyrazol-4-yl)-phenyl]-7-thiazol-5-yl-furo[3,2-b]pyridine
| "A147" | 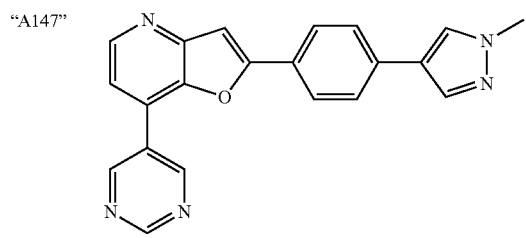 |
2-[4-(1-Methyl-1H-pyrazol-4-yl)-phenyl]-7-pyrimidin-5-yl-furo[3,2-b]pyridine
| "A148" | 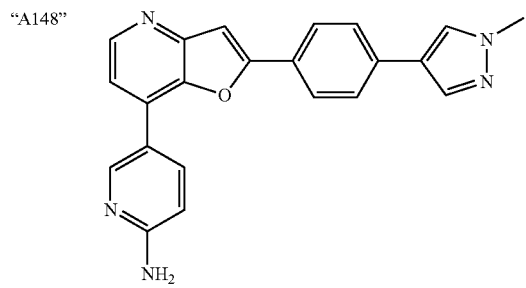 |
5-{2-[4-(1-Methyl-1H-pyrazol-4-yl)-phenyl]-furo[3,2-b]pyridin-7-yl}-pyridin-2-ylamine
| "A149" | 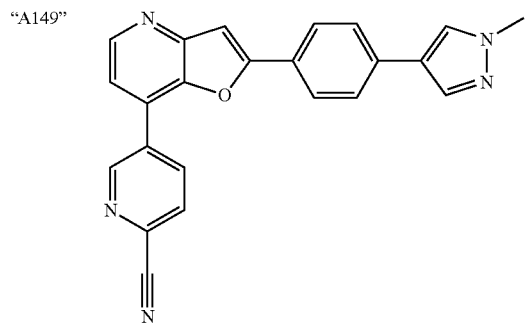 |

| Compound no. | |
|---|---|
| | 5-{2-[4-(1-Methyl-1H-pyrazol-4-yl)-phenyl]-furo[3,2-b]pyridin-7-yl}-pyridine-2-carbonitrile |
| "A150" | 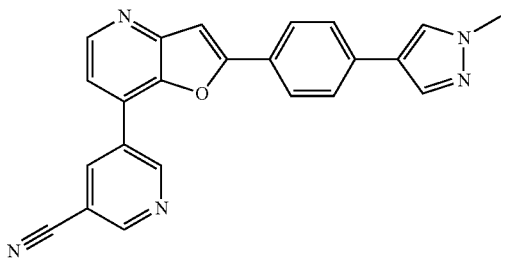 [SMILES: Cn1cc(-c2ccc(-c3cc4nccc(-c5cncc(C#N)c5)c4o3)cc2)cn1] |
| | 5-{2-[4-(1-Methyl-1H-pyrazol-4-yl)-phenyl]-furo[3,2-b]pyridin-7-yl}-nicotinonitrile |
| "A151" | 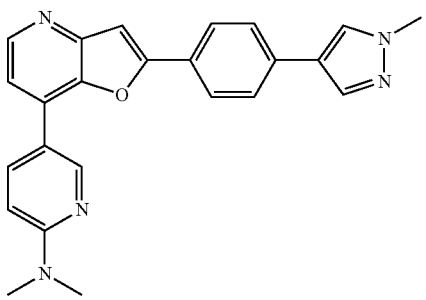 [SMILES: CN(C)c1ccc(-c2ccnc3cc(-c4ccc(-c5cnn(C)c5)cc4)oc23)cn1] |
| | Dimethyl-(5-{2-[4-(1-methyl-1H-pyrazol-4-yl)-phenyl]-furo[3,2-b]pyridin-7-yl}-pyridin-2-yl)-amine |
| "A152" | 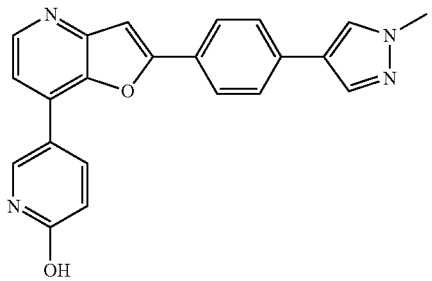 [SMILES: Cn1cc(-c2ccc(-c3cc4nccc(-c5ccc(O)nc5)c4o3)cc2)cn1] |
| | 5-{2-[4-(1-Methyl-1H-pyrazol-4-yl)-phenyl]-furo[3,2-b]pyridin-7-yl}-pyridin-2-ol |
| "A153" | 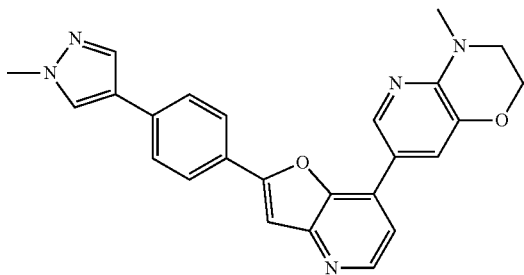 [SMILES: CN1CCOc2cc(-c3ccnc4cc(-c5ccc(-c6cnn(C)c6)cc5)oc34)cnc21] |
| | 4-Methyl-7-{2-[4-(1-methyl-1H-pyrazol-4-yl)-phenyl]-furo[3,2-b]pyridin-7-yl}-3,4-dihydro-2H-pyrido[3,2-b][1,4]oxazine |

| Compound no. | |
|---|---|
| "A154" | 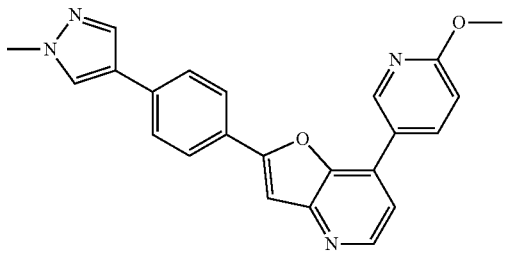<br>7-(6-Methoxy-pyridin-3-yl)-2-[4-(1-methyl-1H-pyrazol-4-yl)-phenyl]-furo[3,2-b]pyridine |
| "A155" | 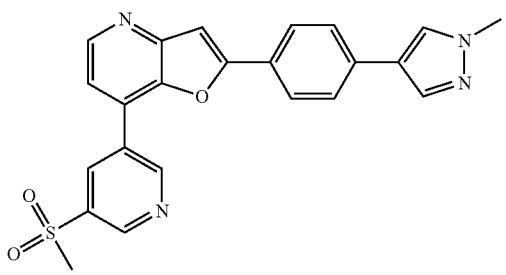 [SMILES: Cn1cc(-c2ccc(-c3cc4nccc(-c5cncc(S(C)(=O)=O)c5)c4o3)cc2)cn1]<br>7-(5-Methanesulfonyl-pyridin-3-yl)-2-[4-(1-methyl-1H-pyrazol-4-yl)-phenyl]-furo[3,2-b]pyridine |
| "A156" | 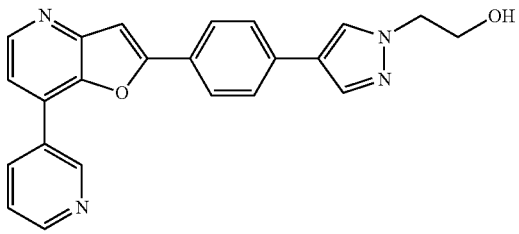 [SMILES: OCCn1cc(-c2ccc(-c3cc4nccc(-c5cccnc5)c4o3)cc2)cn1]<br>2-{4-[4-(7-Pyridin-3-yl-furo[3,2-b]pyridin-2-yl)-phenyl]-pyrazol-1-yl}-ethanol |
| "A157" | 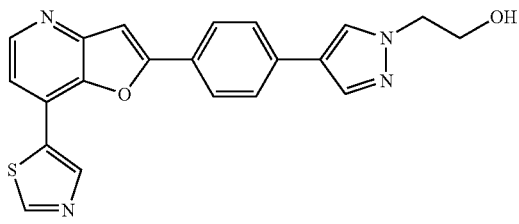 [SMILES: OCCn1cc(-c2ccc(-c3cc4nccc(-c5cncs5)c4o3)cc2)cn1]<br>2-{4-[4-(7-Thiazol-5-yl-furo[3,2-b]pyridin-2-yl)-phenyl]-pyrazol-1-yl}-ethanol |
| "A158" | 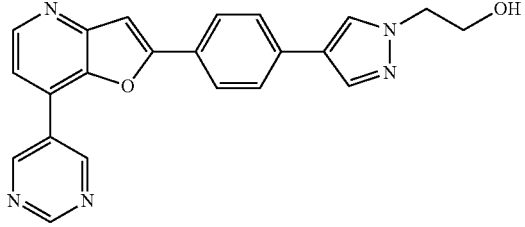 [SMILES: OCCn1cc(-c2ccc(-c3cc4nccc(-c5cncnc5)c4o3)cc2)cn1]<br>2-{4-[4-(7-Pyrimidin-5-yl-furo[3,2-b]pyridin-2-yl)-phenyl]-pyrazol-1-yl}-ethanol |

| Compound no. | |
|---|---|
| "A159" | 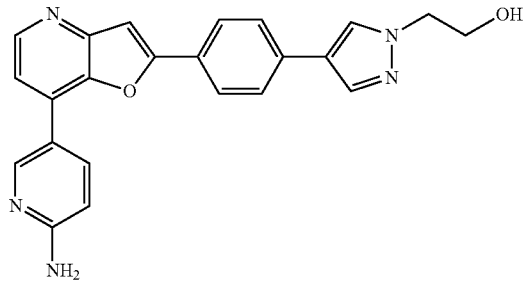 [SMILES: Nc1ccc(-c2ccnc3cc(-c4ccc(-c5cnn(CCO)c5)cc4)oc23)cn1]<br>2-(4-{4-[7-(6-Amino-pyridin-3-yl)-furo[3,2-b]pyridin-2-yl]-phenyl}-pyrazol-1-yl)-ethanol |
| "A160" | 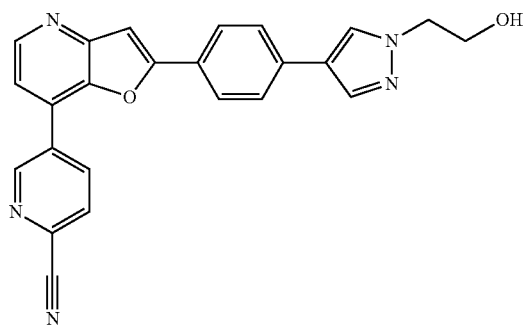 [SMILES: N#Cc1ccc(-c2ccnc3cc(-c4ccc(-c5cnn(CCO)c5)cc4)oc23)cn1]<br>5-(2-{4-[1-(2-Hydroxy-ethyl)-1H-pyrazol-4-yl]-phenyl}-furo[3,2-b]pyridin-7-yl)-pyridine-2-carbonitrile |
| "A161" | 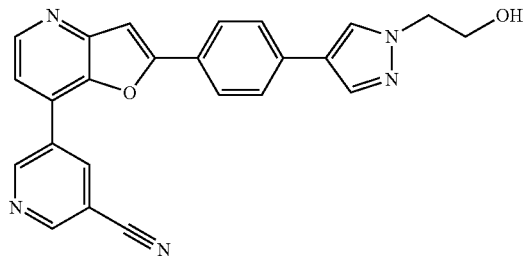 [SMILES: N#Cc1cncc(-c2ccnc3cc(-c4ccc(-c5cnn(CCO)c5)cc4)oc23)c1]<br>5-(2-{4-[1-(2-Hydroxy-ethyl)-1H-pyrazol-4-yl]-phenyl}-furo[3,2-b]pyridin-7-yl)-nicotinonitrile |
| "A162" | 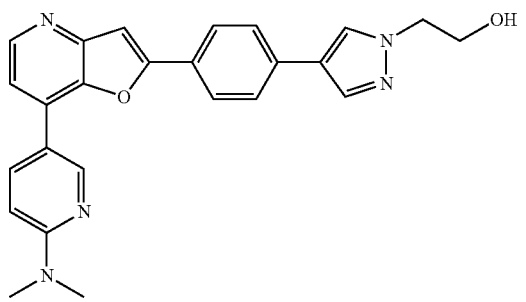 [SMILES: CN(C)c1ccc(-c2ccnc3cc(-c4ccc(-c5cnn(CCO)c5)cc4)oc23)cn1]<br>2-(4-{4-[7-(6-Dimethylamino-pyridin-3-yl)-furo[3,2-b]pyridin-2-yl]-phenyl}-pyrazol-1-yl)-ethanol |

| Compound no. | |
|---|---|
| "A163" | 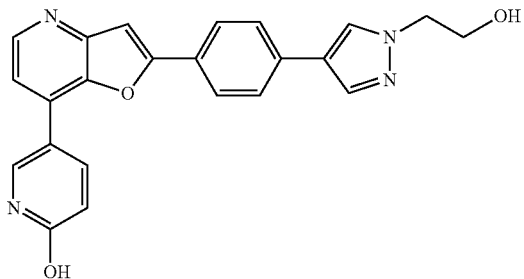 [SMILES: OCCn1cc(-c2ccc(-c3cc4nccc(-c5ccc(O)nc5)c4o3)cc2)cn1]<br>5-(2-{4-[1-(2-Hydroxy-ethyl)-1H-pyrazol-4-yl]-phenyl}-furo[3,2-b]pyridin-7-yl)-pyridin-2-ol |
| "A164" | 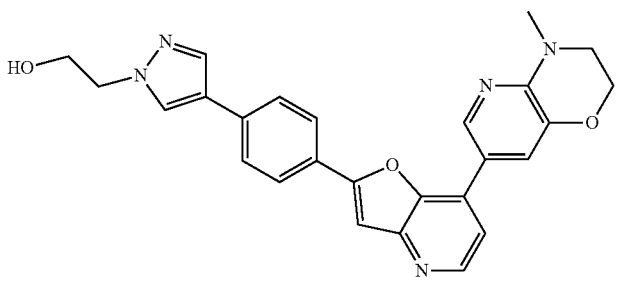 [SMILES: CN1CCOc2cc(-c3ccnc4cc(-c5ccc(-c6cnn(CCO)c6)cc5)oc34)cnc21]<br>2-(4-{4-[7-(4-Methyl-3,4-dihydro-2H-pyrido[3,2-b][1,4]oxazin-7-yl)-furo[3,2-b]pyridin-2-yl]-phenyl}-pyrazol-1-yl)-ethanol |
| "A165" | 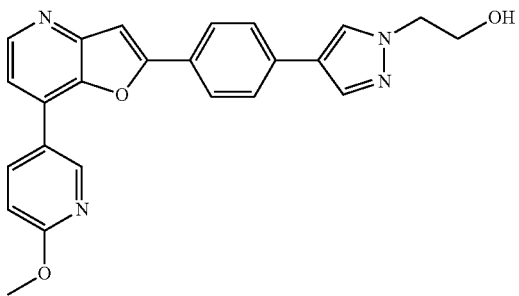 [SMILES: COc1ccc(-c2ccnc3cc(-c4ccc(-c5cnn(CCO)c5)cc4)oc23)cn1]<br>2-(4-{4-[7-(6-Methoxy-pyridin-3-yl)-furo[3,2-b]pyridin-2-yl]-phenyl}-pyrazol-1-yl)-ethanol |
| "A166" | 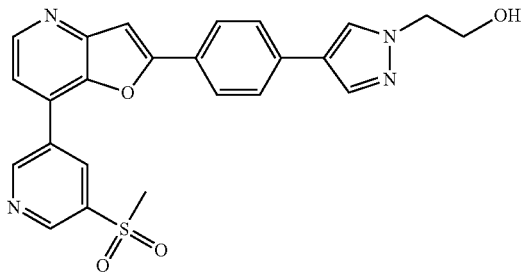 [SMILES: CS(=O)(=O)c1cncc(-c2ccnc3cc(-c4ccc(-c5cnn(CCO)c5)cc4)oc23)c1]<br>2-(4-{4-[7-(5-Methanesulfonyl-pyridin-3-yl)-furo[3,2-b]pyridin-2-yl]-phenyl}-pyrazol-1-yl)-ethanol |

Procedure A

2,7-Bis-(3,5-difluoro-phenyl)-furo[3,2-b]pyridine ("B1")

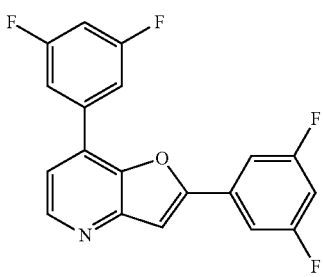 [SMILES: Fc1cc(F)cc(-c2cc3nccc(-c4cc(F)cc(F)c4)c3o2)c1]

To a 10 mL sealed tube with stirbar was added 7-chloro-2-iodo-furo[3,2-b]pyridine (300.00 mg; 1.07 mmol; 1.00 eq.), (3,5-difluorophenyl)boronic acid (177.99 mg; 1.13 mmol; 1.05 eq.), palladium(II) acetate (12.05 mg; 0.05 mmol; 0.05 eq.), 2-dicyclohexylphosphino-2',6'-dimethoxybiphenyl (44.07 mg; 0.11 mmol; 0.10 eq.), and potassium carbonate (445.09 mg; 3.22 mmol; 3.00 eq.). Reagents were suspended in dioxane (6.00 ml)/water (0.60 ml) under a $N_2$ atmosphere and stirred at 95° C. overnight. The reaction mixture was cooled to room temperature and concentrated on a rotary evaporator. The crude mixture was purified by Biotage chromatography (20-100% EtOAc/hex, 30 column vol.) to afford the title compound as a white solid (34 mg, 9%). (HPLC (method F): 95%); $^1$H NMR (400 MHz, DMSO-$d_6$) δ [ppm] 8.64 (d, J=5.1, 1H), 7.96 (s, 1H), 7.88 (dd, J=8.8, 2.2, 2H), 7.78-7.71 (m, 3H), 7.53-7.46 (m, 1H), 7.43 (ddd, J=9.3, 5.9, 2.3, 1H); MS (m/z) 344 [M+H]$^+$, RT: 4.4 min.

7-Chloro-2-phenyl-furo[3,2-b]pyridine

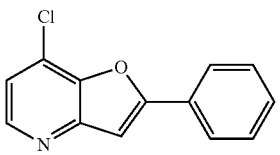 [SMILES: Clc1ccnc2cc(-c3ccccc3)oc12]

The title compound was prepared by procedure A using phenylboric acid (91.62 mg; 0.75 mmol; 1.05 eq.) instead of (3,5-difluorophenyl)boronic acid and was obtained as a white solid (140 mg, 85%). (HPLC (method F): 93%, RT: 7.02 min); $^1$H NMR (400 MHz, DMSO-$d_6$) δ [ppm] 8.48 (d, J=5.3, 1H), 8.06-8.00 (m, 2H), 7.81 (s, 1H), 7.60-7.49 (m, 4H); MS (m/z) 230 [M+H]$^+$, RT: 5.6 min.

7-Chloro-2-(3,5-difluoro-phenyl)-furo[3,2-b]pyridine

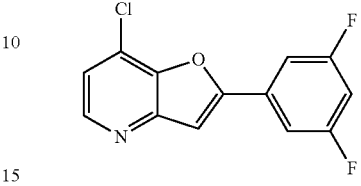

The title compound was prepared by procedure A and was obtained as a white solid (65 mg, 23%). (HPLC (method F): 88%); MS (m/z) 266 [M+H]$^+$, RT: 4.1 min.

Procedure F

4-(2-Phenyl-furo[3,2-b]pyridin-7-yloxy)-phenylamine ("B2")

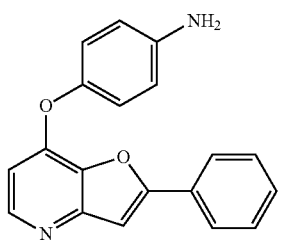 [SMILES: Nc1ccc(Oc2ccnc3cc(-c4ccccc4)oc23)cc1]

To a 10 mL sealed tube with stirbar was added 7-chloro-2-phenylfuro[3,2-b]pyridine (300.00 mg; 1.31 mmol; 1.00 eq.), 4-aminophenol (285.09 mg; 2.61 mmol; 2.00 eq.), and caesium carbonate (1 702.45 mg; 5.22 mmol; 4.00 eq.). The mixture was suspended in DMF (7.00 ml) and stirred at 125° C. overnight. The reaction mixture was cooled to room temperature and poured into 150 mL water. Filtered to collect precipitate, washing with water and hexane. The resulting crude material was purified by Biotage chromatography using a KP-NH column (10-50% EtOAc/Hex) to afford the title compound as a beige solid (216 mg, 55%). (HPLC (method F): 99%, RT: 4.73 min); $^1$H NMR (400 MHz, DMSO-$d_6$) δ [ppm] 8.29 (d, J=5.5, 1H), 7.96 (d, J=7.2, 2H), 7.66 (s, 1H), 7.54 (t, J=7.4, 3H), 7.47 (t, J=7.3, 1H), 6.99 (d, J=8.7, 2H), 6.67 (d, J=8.7, 2H), 6.56 (d, J=5.5, 1H), 5.20 (s, 2H); MS (m/z) 303 [M+H]+, RT: 2.6 min.

Procedure B (2H-Indazol-6-yl)-(2-phenyl-furo[3,2-b]pyridin-7-yl)-amine ("B3")

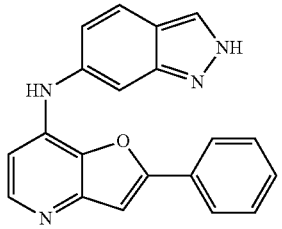 [SMILES: c1ccc(-c2cc3nccc(Nc4ccc5c[nH]nc5c4)c3o2)cc1]

To a 10 mL sealed tube with stirbar was added 7-chloro-2-phenylfuro[3,2-b]pyridine (50.00 mg; 0.22 mmol; 1.00 eq.), 6-aminoindazole (34.79 mg; 0.26 mmol; 1.20 eq.), palladium (II) acetate (2.44 mg; 0.01 mmol; 0.05 eq.), 2-(dicyclohexylphosphino)-2',4',6'-triisopropylbiphenyl (10.38 mg; 0.02 mmol; 0.10 eq.), and sodium tert. butoxide (62.77 mg; 0.65 mmol; 3.00 eq.). The reagents were suspended in dioxane (2.00 ml) under a $N_2$ atmosphere and stirred at 110° C. overnight. The reaction mixture was cooled to room temperature and concentrated on a rotary evaporator. The crude mixture was purified by Biotage chromatography (0-10% MeOH/$CH_2Cl_2$, 30 column vol) to afford the title compound as a brown solid (6.6 mg, 9%). (HPLC (method F): 97%, RT: 3.97 min); MS (m/z) 327 [M+H]+, RT: 2.6 min.

[3-Chloro-4-(1-methyl-1H-imidazol-2-ylsulfanyl)-phenyl]-(2-phenyl-furo[3,2-b]pyridin-7-yl)-amine ("B4")

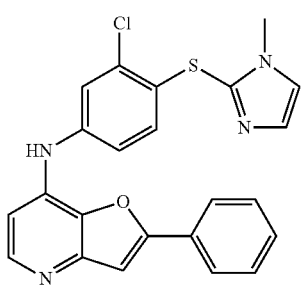 [SMILES: Cn1ccnc1Sc1ccc(Nc2ccnc3cc(-c4ccccc4)oc23)cc1Cl]

The title compound was prepared by procedure B using 3-chloro-4-(1-methyl-1H-imidazol-2-ylsulfanyl)-phenylamine (50.10 mg; 0.21 mmol; 1.20 eq.) instead of 6-aminoindazole and was obtained as a brown solid (5.7 mg, 8%). (HPLC (method F): 87%, RT: 3.93 min); 1H NMR (400 MHz, DMSO-$d_6$) δ [ppm] 9.26 (s, 1H), 8.20 (d, J=5.5, 1H), 8.00-7.93 (m, 2H), 7.58-7.50 (m, 4H), 7.48-7.41 (m, 2H), 7.22 (dd, J=8.7, 2.4, 1H), 7.15 (d, J=1.2, 1H), 6.96 (d, J=5.5, 1H), 6.68 (d, J=8.6, 1H), 3.68 (s, 3H); MS (m/z) 433 [M+H]+, RT: 2.5 min.

Procedure C

7-Chloro-2-(4-fluoro-phenyl)-furo[3,2-b]pyridine ("C1a")

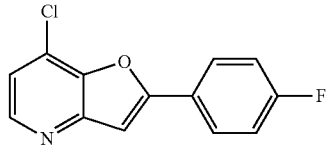 [SMILES: Fc1ccc(-c2cc3nccc(Cl)c3o2)cc1]

To a 30 mL microwave vial with stirbar was added 7-chloro-2-iodo-furo[3,2-b]pyridine (300.00 mg; 1.07 mmol; 1.00 eq.), 4-fluorophenylboronic acid (157.71 mg; 1.13 mmol; 1.05 eq.), palladium(II) acetate (12.05 mg; 0.05 mmol; 0.05 eq.), 2-dicyclohexylphosphino-2',6'-dimethoxybiphenyl (44.07 mg; 0.11 mmol; 0.10 eq.), and potassium carbonate (445.09 mg; 3.22 mmol; 3.00 eq.). Reagents were suspended in dioxane (6.00 ml)/water (0.60 ml) under $N_2$ and heated in microwave reactor at 150° C. for 15 min. The reaction mixture was cooled to room temperature and concentrated on a rotary evaporator. The crude mixture was purified by Biotage chromatography (20-100% EtOAc/hex 30 column vol.) to afford the title compound as a white solid (152 mg, 57%). (HPLC (method F): 95%, RT: 7.11 min); 1H NMR (400 MHz, DMSO-$d_6$) δ [ppm] 8.47 (d, J=5.2, 1H), 8.11-8.05 (m, 2H), 7.79 (s, 1H), 7.53 (d, J=5.3, 1H), 7.47-7.39 (m, 2H); MS (m/z) 248 [M+H]+, RT: 3.9 min.

(2-Benzyl-2H-indazol-6-yl)-(2-phenyl-furo[3,2-b]pyridin-7-yl)-amine ("B5")

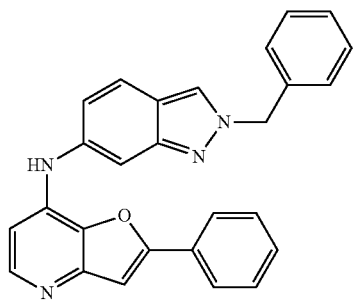 [SMILES: c1ccc(Cn2cc3ccc(Nc4ccnc5cc(-c6ccccc6)oc45)cc3n2)cc1]

The title compound was prepared by procedure B using 2-benzyl-2H-indazol-6-ylamine (58.33 mg; 0.26 mmol; 1.20 eq.) instead of 6-aminoindazole and was obtained as a brown waxy solid (87 mg, 96%). (HPLC (method F): 99%, RT: 4.69 min); 1H NMR (400 MHz, DMSO-$d_6$) δ [ppm] 9.09 (s, 1H), 8.48 (s, 1H), 8.15 (d, J=5.5, 1H), 8.00 (dd, J=8.3, 1.3, 2H), 7.74 (d, J=8.9, 1H), 7.53 (s, 1H), 7.46 (ddd, J=8.7, 8.0, 6.5, 5H), 7.38-7.30 (m, 5H), 7.09 (dd, J=8.9, 1.8, 1H), 6.96 (d, J=5.5, 1H), 5.62 (s, 2H); MS (m/z) 417 [M+H]+, RT: 2.9 min.

7-Chloro-2-(2-fluoro-phenyl)-furo[3,2-b]pyridine

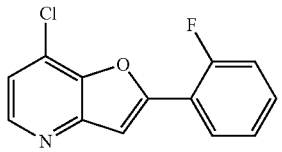 [SMILES: Fc1ccccc1-c1cc2nccc(Cl)c2o1]

The title compound was prepared by procedure C using 2-fluorophenylboronic acid (157.71 mg; 1.13 mmol; 1.05 eq.) instead of 4-fluorophenylboronic acid and was obtained as a white solid (102 mg, 39%). (HPLC (method F): 86%, RT: 7.17 min); MS (m/z) 248 [M+H]+, RT: 3.9 min.

2,7-Bis-(4-fluoro-phenyl)-furo[3,2-b]pyridine ("B6")

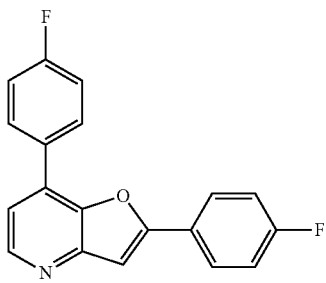 [SMILES: Fc1ccc(-c2cc3nccc(-c4ccc(F)cc4)c3o2)cc1]

The title compound was prepared by procedure C and was obtained as a white solid (47 mg, 14%). (HPLC (method F): 92%, RT: 7.27 min); $^1$H NMR (400 MHz, DMSO-$d_6$) δ 8.59-8.55 (m, 1H), 8.19 (dd, J=9.0, 5.4, 2H), 8.12-8.07 (m, 2H), 7.74 (s, 1H), 7.61 (d, J=5.1, 1H), 7.52-7.39 (m, 4H); MS (m/z) 308 [M+H]+, RT: 4.1 min.

7-Chloro-2-pyridin-3-yl-furo[3,2-b]pyridine

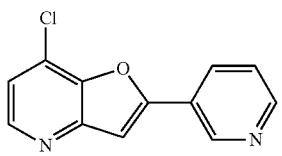 [SMILES: Clc1ccnc2cc(-c3cccnc3)oc12]

The title compound was prepared by procedure C using pyridine-3-boronic acid (138.55 mg; 1.13 mmol; 1.05 eq.) instead of 4-fluorophenylboronic acid and was obtained as a beige solid (36 mg, 15%). (HPLC (method F): 85%, RT: 7.11 min); MS (m/z) 231 [M+H]+, RT: 3.0 min.

Procedure D

N-Methyl-N-(3-{[2-(3,4,5-trimethoxy-phenyl)-furo[3,2-b]pyridin-7-ylamino]-methyl}-pyridin-2-yl)-methanesulfonamide ("B7")

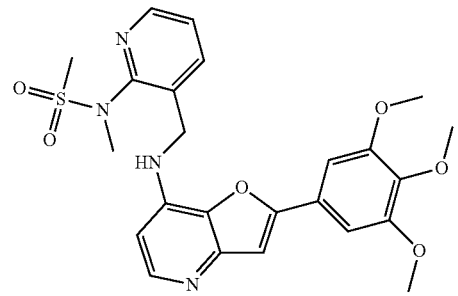 [SMILES: COc1cc(-c2cc3nccc(NCc4cccnc4N(C)S(C)(=O)=O)c3o2)cc(OC)c1OC]

To a dry 10 mL microwave vial with stirbar was added 7-chloro-2-(3,4,5-trimethoxyphenyl)furo[3,2-b]pyridine (50.00 mg; 0.16 mmol; 1.00 eq.), N-(3-aminomethyl-pyridin-2-yl)-N-methyl-methanesulfonamide (40.40 mg; 0.19 mmol; 1.20 eq.), chloro(2-dicyclohexylphosphino-2',4',6'-tri-i-propyl-1,1'-biphenyl)[2-(2-aminoethyl)phenyl]palladium(II) methyl-tert.-butyl ether adduct (2.59 mg; 0.003 mmol; 0.02 eq.), and potassium carbonate (30.26 mg; 0.22 mmol; 1.40 eq.). The vial was sealed and flushed with $N_2$. The reagents were suspended in tert.-BuOH (1.00 ml) and the reaction mixture was heated to 110° C. with stirring for 1 h. The reaction mixture was cooled to room temperature and concentrated on a rotary evaporator. The crude mixture was purified by Biotage chromatography (20-100% EtOAc/hex KP-NH SNAP column) to afford the title compound as a beige solid (27 mg, 34%). (HPLC (method F): 90%, RT: 4.62 min); MS (m/z) 499 [M+H]+, RT: 2.5 min.

N-Methyl-2-[2-(3,4,5-trimethoxy-phenyl)-furo[3,2-b]pyridin-7-ylamino]-benzamide ("B8")

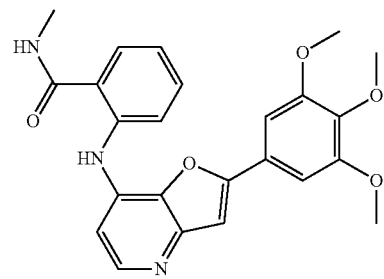 [SMILES: CNC(=O)c1ccccc1Nc1ccnc2cc(-c3cc(OC)c(OC)c(OC)c3)oc12]

The title compound was prepared by procedure D using 2-amino-N-methyl-benzamide (28.18 mg; 0.19 mmol; 1.20 eq.) instead of N-(3-aminomethyl-pyridin-2-yl)-N-methyl-methanesulfonamide and was obtained as a white solid (44 mg, 65%). (HPLC (method F): 98%, RT: 4.79 min); $^1$H NMR (400 MHz, DMSO-$d_6$) δ [ppm] 10.68 (s, 1H), 8.70 (d, J=4.6, 1H), 8.24 (d, J=5.5, 1H), 7.77-7.72 (m, 1H), 7.59 (s, 1H), 7.58-7.50 (m, 2H), 7.24 (s, 2H), 7.16 (d, J=5.5, 1H), 7.14-7.07

(m, 1H), 3.89 (s, 6H), 3.73 (s, 3H), 2.79 (d, J=4.6, 3H); MS (m/z) 434 [M+H]⁺, RT: 2.6 min.

3-Methanesulfonyl-benzyl)-[2-(3,4,5-trimethoxy-phenyl)-furo[3,2-b]pyridin-7-yl]-amine ("B9")

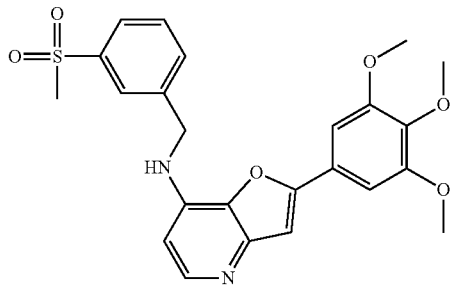 [SMILES: COc1cc(-c2cc3nccc(NCc4cccc(S(C)(=O)=O)c4)c3o2)cc(OC)c1OC]

The title compound was prepared by procedure D using 3-(methylsulfonyl)-benzylamine hydrochloride (41.60 mg; 0.19 mmol; 1.20 eq.) instead of N-(3-aminomethyl-pyridin-2-yl)-N-methyl-methanesulfonamide and was obtained as a white solid (47 mg, 65%). (HPLC (method F): 98%, RT: 4.43 min); ¹H NMR (400 MHz, DMSO-d₆) δ [ppm] 8.03-7.96 (m, 2H), 7.80 (dd, J=24.0, 7.9, 2H), 7.63 (dd, J=14.8, 7.1, 2H), 7.48 (s, 1H), 7.30 (s, 2H), 6.43 (d, J=5.6, 1H), 4.72 (d, J=6.3, 2H), 3.90 (s, 6H), 3.72 (s, 3H), 3.19 (s, 3H); MS (m/z) 469 [M+H]⁺, RT: 2.4 min.

Procedure E 2,2-Difluoro-6-[2-(3,4,5-trimethoxy-phenyl)-furo[3,2-b]pyridin-7-ylamino]-4H-benzo[1,4]oxazin-3-one ("B10")

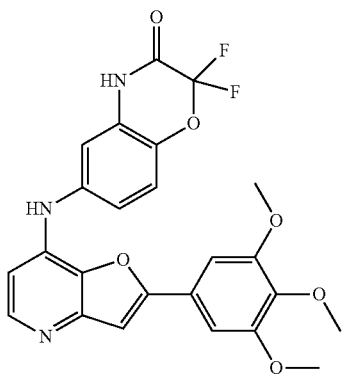 [SMILES: COc1cc(-c2cc3nccc(Nc4ccc5c(c4)NC(=O)C(F)(F)O5)c3o2)cc(OC)c1OC]

To a 10 mL microwave vial with stirbar was added 7-chloro-2-(3,4,5-trimethoxyphenyl)furo[3,2-b]pyridine (25.00 mg; 0.08 mmol; 1.00 eq.) and 6-amino-2,2-difluoro-4H-benzo[1,4]oxazin-3-one (16.43 mg; 0.08 mmol; 1.05 eq.). The vial was sealed and flushed with N₂ and the reagents were dissolved in NMP (1.00 ml). Hydrogen chloride in dioxane (0.02 ml; 4.00 M; 0.08 mmol; 1.05 eq.) was added and the reaction mixture was heated to 150° C. in a microwave reactor for 1 h. The reaction mixture was cooled to room temperature and quenched with NaOH(aq), extracted with EtOAc, dried (MgSO₄) and concentrated on a rotary evaporator. The crude mixture was purified by Biotage chromatography (2-10% MeOH/CH₂Cl₂ 15 column vol.; 10% MeOH/CH₂Cl₂ 5 column vol.) to afford the title compound as a beige solid (10 mg, 26%). (HPLC (method F): 90%, RT: 4.69 min); ¹H NMR (400 MHz, DMSO-d₆) δ [ppm] 11.99 (s, 1H), 9.14 (s, 1H), 8.17 (d, J=5.5, 1H), 7.57 (s, 1H), 7.35 (d, J=8.8, 1H), 7.22 (s, 2H), 7.08-7.00 (m, 2H), 6.88 (d, J=5.5, 1H), 3.85 (s, 6H), 3.72 (s, 3H); MS (m/z) 484 [M+H]⁺, RT: 2.9 min.

Procedure G 1-(2-Hydroxy-2-methyl-propyl)-5-methyl-3-oxo-2-phenyl-2,3-dihydro-1H-pyrazole-4-carboxylic acid [4-(2-phenyl-furo[3,2-b]pyridin-7-yloxy)-phenyl]-amide ("B11")

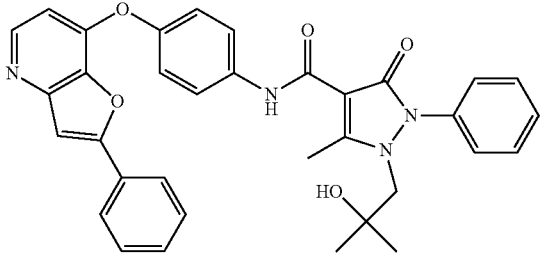 [SMILES: Cc1c(C(=O)Nc2ccc(Oc3ccnc4cc(-c5ccccc5)oc34)cc2)c(=O)n(-c2ccccc2)n1CC(C)(C)O]

To a 10 mL sealed tube with stirbar was added 1-(2-hydroxy-2-methyl-propyl)-5-methyl-3-oxo-2-phenyl-2,3-dihydro-1H-pyrazole-4-carboxylic acid (57.62 mg; 0.20 mmol; 1.20 eq.), and bis(2-oxo-3-oxazolidinyl)phosphinic chloride (63.15 mg; 0.25 mmol; 1.50 eq.). The tube was sealed and flushed with N₂. To this mixture was added dioxane (3.00 ml) and N,N-diisopropylethylamine (0.14 ml; 0.83 mmol; 4.00 eq.) and the mixture was stirred at room temperature for 1 h. To the reaction mixture was then added 4-[(2-phenylfuro[3,2-b]pyridin-7-yl)oxy]aniline (50.00 mg; 0.17 mmol; 1.00 eq.) and stirred at room temperature overnight. The reaction mixture was concentrated on a rotary evaporator. The crude mixture was purified by Biotage chromatography (50% EtOAc/hex 10 column vol.; 50-100% 10 column vol.) to afford a beige solid (14 mg, 15%). (HPLC (method F): 88%, RT: 6.27 min); ¹H NMR (400 MHz, DMSO-d₆) δ [ppm] 10.84 (s, 1H), 8.35 (d, J=5.6, 1H), 7.98-7.90 (m, 2H), 7.73 (d, J=9.0, 2H), 7.70 (s, 1H), 7.60-7.50 (m, 4H), 7.49-7.43 (m, 2H), 7.35 (d, J=7.4, 2H), 7.30 (d, J=9.0, 2H), 6.71 (d, J=5.5, 1H), 4.85 (s, 1H), 3.86 (s, 2H), 2.80 (s, 3H), 0.97 (s, 6H); MS (m/z) 575 [M+H]⁺, RT: 3.7 min.

1-(4-Fluoro-phenyl)-4-iodo-2-oxo-1,2-dihydro-pyridine-3-carboxylic acid [4-(2-phenyl-furo[3,2-b]pyridin-7-yloxy)-phenyl]-amide ("B12")

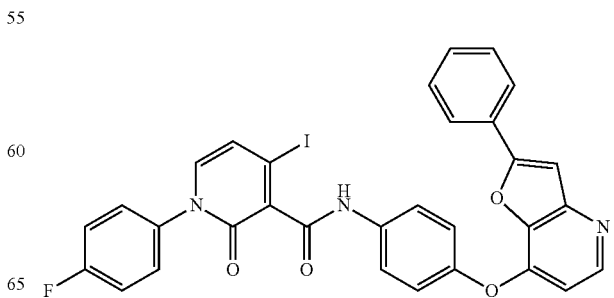

The title compound was prepared by procedure G using 1-(4-fluorophenyl)-4-iodo-2-oxo-1,2-dihydropyridine-3-carboxylic acid (71.27 mg; 0.20 mmol; 1.20 eq.) instead of 1-(2-hydroxy-2-methyl-propyl)-5-methyl-3-oxo-2-phenyl-2,3-dihydro-1H-pyrazole-4-carboxylic acid and was obtained as a white solid (64 mg, 60%). (HPLC (method F): 98%, RT: 6.00 min); $^1$H NMR (400 MHz, DMSO-$d_6$) δ [ppm] 10.66 (s, 1H), 8.34 (d, J=5.5, 1H), 7.96-7.91 (m, 2H), 7.82-7.75 (m, 2H), 7.70 (s, 1H), 7.57-7.44 (m, 6H), 7.40 (ddd, J=10.9, 6.3, 2.9, 2H), 7.37-7.32 (m, 2H), 6.86 (d, J=7.2, 1H), 6.73 (d, J=5.5, 1H); MS (m/z) 644 [M+H]$^+$, RT: 3.6 min.

1-(4-Fluoro-phenyl)-2-oxo-1,2-dihydro-pyridine-3-carboxylic acid [4-(2-phenyl-furo[3,2-b]pyridin-7-yloxy)-phenyl]-amide ("B13")

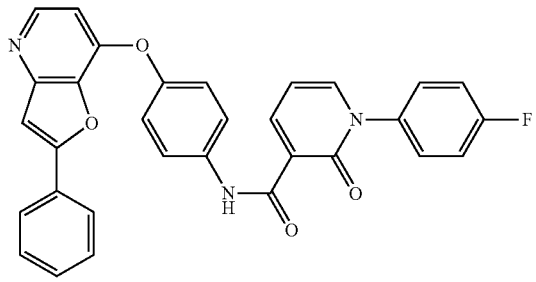 [SMILES: O=C(Nc1ccc(Oc2ccnc3cc(-c4ccccc4)oc23)cc1)c1cccn(-c2ccc(F)cc2)c1=O]

The title compound was prepared by procedure G using 1-(4-fluoro-phenyl)-2-oxo-1,2-dihydro-pyridine-3-carboxylic acid (46.28 mg; 0.20 mmol; 1.20 eq.) instead of 1-(2-hydroxy-2-methyl-propyl)-5-methyl-3-oxo-2-phenyl-2,3-dihydro-1H-pyrazole-4-carboxylic acid and was obtained as a yellow solid (56 mg, 65%). (HPLC (method F): 80%, RT: 6.73 min); $^1$H NMR (400 MHz, DMSO-$d_6$) δ [ppm] 12.02 (s, 1H), 8.60 (dd, J=7.3, 2.2, 1H), 8.36 (d, J=5.5, 1H), 8.13 (dd, J=6.6, 2.2, 1H), 7.95-7.89 (m, 2H), 7.88-7.81 (m, 2H), 7.70 (s, 1H), 7.67-7.58 (m, 2H), 7.57-7.39 (m, 5H), 7.39-7.29 (m, 2H), 6.78-6.69 (m, 2H); MS (m/z) 518 [M+H]$^+$, RT: 4.0 min.

Procedure H

4-Ethoxy-1-(4-fluoro-phenyl)-2-oxo-1,2-dihydro-pyridine-3-carboxylic acid [4-(2-phenyl-furo[3,2-b]pyridin-7-yloxy)-phenyl]-amide ("B14")

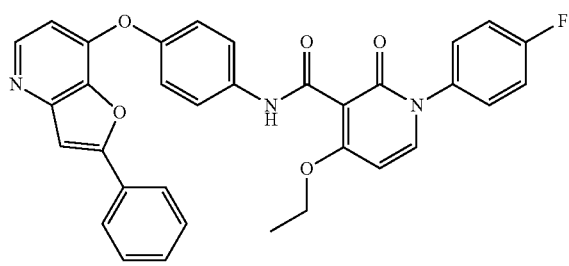 [SMILES: CCOc1ccn(-c2ccc(F)cc2)c(=O)c1C(=O)Nc1ccc(Oc2ccnc3cc(-c4ccccc4)oc23)cc1]

To a dry 5 mL sealed tube with stirbar was added 1-(4-fluorophenyl)-4-iodo-2-oxo-N-{4-[(2-phenylfuro[3,2-b]pyridin-7-yl)oxy]phenyl}-1,2-dihydropyridine-3-carboxamide (46.30 mg; 0.07 mmol; 1.00 eq.) and the vial was sealed and flushed with $N_2$. To the vial was added dry THF (1.00 ml) via syringe and then sodium ethoxide (0.04 ml; 0.09 mmol; 1.30 eq.) (21% solution in ethanol) was slowly added via syringe and the reaction mixture was stirred at room temperature for 1 h. The solution was concentrated, taken up in EtOAc and washed with sat. aq. NaHCO$_3$. The organic layer was collected, extracting aqueous layer with EtOAc (3×). Combined organic layers were dried (Na$_2$SO$_4$) and concentrated on rotary evaporator to afford the title compound as a beige solid (40 mg, 100%). (HPLC (method F): 99%, RT: 6.08 min); $^1$H NMR (400 MHz, DMSO-$d_6$) δ [ppm] 10.41 (s, 1H), 8.34 (d, J=5.5, 1H), 7.97-7.90 (m, 2H), 7.86 (d, J=7.8, 1H), 7.83-7.77 (m, 2H), 7.69 (s, 1H), 7.58-7.50 (m, 2H), 7.50-7.43 (m, 3H), 7.41-7.35 (m, 2H), 7.34-7.27 (m, 2H), 6.71 (d, J=5.5, 1H), 6.52 (d, J=7.9, 1H), 4.26 (q, J=7.0, 2H), 1.30 (t, J=7.0, 3H); MS (m/z) 562 [M+H]$^+$, RT: 3.5 min.

1H-Indazol-6-yl)-[2-(3,4,5-trimethoxy-phenyl)-furo[3,2-b]pyridin-7-yl]-amine ("B15"

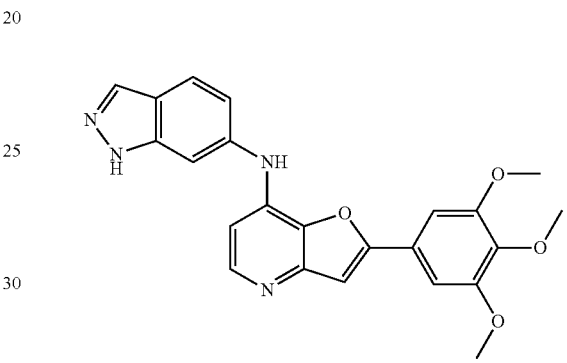

The title compound was prepared by procedure E using 6-aminoindazole (15.30 mg; 0.11 mmol; 1.05 eq.) instead of 6-amino-2,2-difluoro-4h-benzo[1,4]oxazin-3-one and was obtained as a beige solid (31 mg, 68%). (HPLC (method F): 94%, RT: 4.17 min); $^1$H NMR (400 MHz, DMSO-$d_6$) δ [ppm] 9.16 (s, 1H), 8.18 (d, J=5.5, 1H), 8.05-7.99 (m, 1H), 7.76 (d, J=8.6, 1H), 7.57 (s, 1H), 7.34 (s, 1H), 7.17 (s, 2H), 7.10 (dd, J=8.6, 1.8, 1H), 6.94 (d, J=5.5, 1H), 3.74 (s, 6H), 3.70 (s, 3H); MS (m/z) 417 [M+H]$^+$, RT: 2.5 min.

[3-Chloro-4-(1-methyl-1H-imidazol-2-ylsulfanyl)-phenyl]-[2-(3,4,5-trimethoxy-phenyl)-furo[3,2-b]pyridin-7-yl]-amine ("B16")

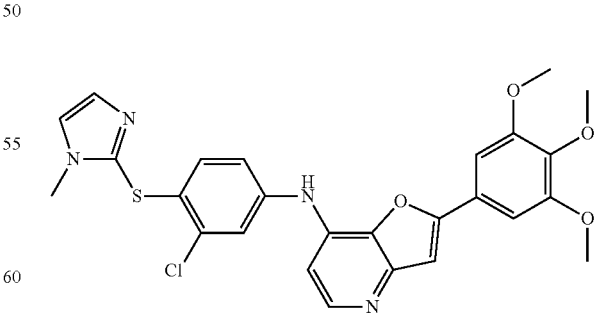

The title compound was prepared by procedure E using 3-chloro-4-(1-methyl-1H-imidazol-2-ylsulfanyl)-phenylamine (27.55 mg; 0.11 mmol; 1.05 eq.) instead of 6-amino-2,2-difluoro-4H-benzo[1,4]oxazin-3-one and was obtained as a brown oil (25 mg, 43%). (HPLC (method F): 95%, RT: 4.33 min); MS (m/z) 523 [M+H]⁺, RT: 2.6 min.

2,2-Difluoro-6-(2-phenyl-furo[3,2-b]pyridin-7-ylamino)-4H-benzo[1,4]oxazin-3-one ("B17")

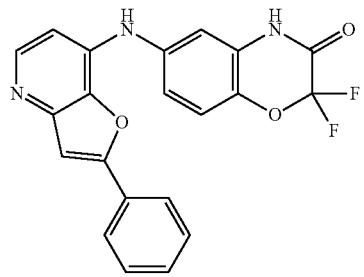 [SMILES: O=C1Nc2cc(Nc3ccnc4cc(-c5ccccc5)oc34)ccc2OC1(F)F]

The title compound was prepared by procedure E using 7-chloro-2-phenylfuro[3,2-b]pyridine (50.00 mg; 0.22 mmol; 1.00 eq.) instead of 7-chloro-2-(3,4,5-trimethoxyphenyl)furo[3,2-b]pyridine and was obtained as a yellow solid (57 mg, 73%). (HPLC (method F): 97%, RT: 4.58 min); ¹H NMR (400 MHz, DMSO-$d_6$) δ [ppm] 11.98 (s, 1H), 9.20 (s, 1H), 8.18 (d, J=5.5, 1H), 8.00-7.93 (m, 2H), 7.55 (s, 1H), 7.55-7.49 (m, 2H), 7.48-7.42 (m, 1H), 7.37-7.30 (m, 1H), 7.07 (dd, J=7.1, 2.4, 2H), 6.93 (d, J=5.5, 1H); MS (m/z) 394 [M+H]⁺, RT: 2.7 min.

N-Methyl-2-(2-phenyl-furo[3,2-b]pyridin-7-ylamino)-benzamide ("B18")

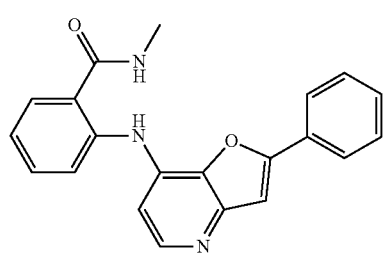 [SMILES: CNC(=O)c1ccccc1Nc1ccnc2cc(-c3ccccc3)oc12]

The title compound was prepared by procedure D using 7-chloro-2-phenylfuro[3,2-b]pyridine (50.00 mg; 0.22 mmol; 1.00 eq.) instead of 7-chloro-2-(3,4,5-trimethoxyphenyl)furo[3,2-b]pyridine, and using 2-amino-N-methylbenzamide (39.23 mg; 0.26 mmol; 1.20 eq.) instead of N-(3-aminomethyl-pyridin-2-yl)-N-methyl-methanesulfonamide and was obtained as a white solid (50 mg, 67%). (HPLC (method F): 92%, RT: 3.37 min); MS (m/z) 344 [M+H]⁺, RT: 2.5 min.

(3-Methanesulfonyl-benzyl)-(2-phenyl-furo[3,2-b]pyridin-7-yl)-amine ("B19")

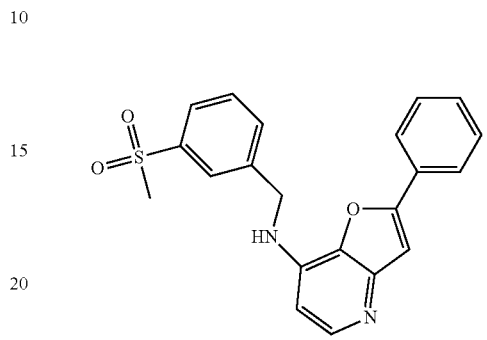

The title compound was prepared by procedure D using 7-chloro-2-phenyl-furo[3,2-b]pyridine (50.00 mg; 0.22 mmol; 1.00 eq.) instead of 7-chloro-2-(3,4,5-trimethoxyphenyl)furo[3,2-b]pyridine, and using 3-(methylsulfonyl)-benzylamine hydrochloride (57.92 mg; 0.26 mmol; 1.20 eq.) instead of N-(3-aminomethyl-pyridin-2-yl)-N-methyl-methanesulfonamide and was obtained as a waxy yellow solid (73 mg, 88%). (HPLC (method F): 98%, RT: 3.37 min); MS (m/z) 379 [M+H]⁺, RT: 2.2 min.

N-Methyl-N-{3-[(2-phenyl-furo[3,2-b]pyridin-7-ylamino)-methyl]-pyridin-2-yl}-methanesulfonamide ("B20")

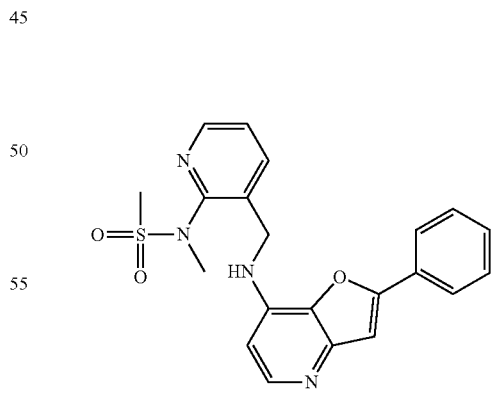

The title compound was prepared by procedure D using 7-chloro-2-phenylfuro[3,2-b]pyridine (50.00 mg; 0.22 mmol; 1.00 eq.) instead of 7-chloro-2-(3,4,5-trimethoxyphenyl)furo[3,2-b]pyridine and was obtained as a brown oil (89 mg, 94%). (HPLC (method F): 98%, RT: 3.40 min); MS (m/z) 409 [M+H]+, RT: 2.3 min.

(4-Methyl-1H-indol-5-yl)-(2-phenyl-furo[3,2-b]pyridin-7-yl)-amine ("B21")

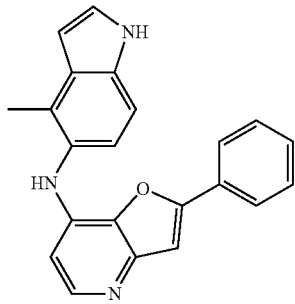 [SMILES: Cc1c(Nc2ccnc3cc(-c4ccccc4)oc23)ccc2[nH]ccc12]

The title compound was prepared by procedure E using 7-chloro-2-phenylfuro[3,2-b]pyridine (60.00 mg; 0.26 mmol; 1.00 eq.) instead of 7-chloro-2-(3,4,5-trimethoxyphenyl)furo[3,2-b]pyridine, and 4-methyl-1H-indol-5-ylamine (40.10 mg; 0.27 mmol; 1.05 eq.) instead of 6-amino-2,2-difluoro-4H-benzo[1,4]oxazin-3-one and was obtained as a brown oil (88 mg, 98%). (HPLC (method F): 96%, RT: 3.91 min); MS (m/z) 340 [M+H]+, RT: 2.7 min.

4-Methyl-1H-indol-5-yl)-[2-(3,4,5-trimethoxy-phenyl)-furo[3,2-b]pyridin-7-yl]-amine ("B22"

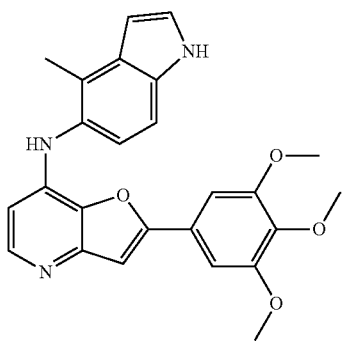 [SMILES: COc1cc(-c2cc3nccc(Nc4ccc5[nH]ccc5c4C)c3o2)cc(OC)c1OC]

The title compound was prepared by procedure E using 4-methyl-1H-indol-5-ylamine (33.61 mg; 0.23 mmol; 1.05 eq.) instead of 6-amino-2,2-difluoro-4H-benzo[1,4]oxazin-3-one and was obtained as a beige solid (36 mg, 38%). (HPLC (method F): 99%, RT: 3.81 min); $^1$H NMR (500 MHz, DMSO-d$_6$) δ [ppm] 11.13 (s, 1H), 8.53 (s, 1H), 7.96 (d, J=5.5, 1H), 7.44 (s, 1H), 7.39-7.35 (m, 1H), 7.31 (d, J=8.4, 1H), 7.15 (s, 2H), 7.02 (d, J=8.4, 1H), 6.52 (s, 1H), 6.18 (d, J=5.4, 1H), 3.78 (s, 6H), 3.70 (s, 3H), 2.37 (s, 3H); MS (m/z) 430 [M+H]+, RT: 3.8 min.

3-Fluoro-4-(2-phenyl-furo[3,2-b]pyridin-7-yloxy)-phenylamine ("B23")

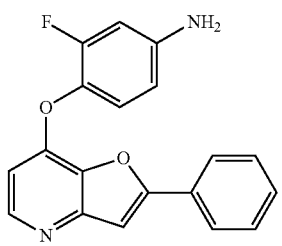 [SMILES: Nc1ccc(Oc2ccnc3cc(-c4ccccc4)oc23)c(F)c1]

The title compound was prepared by procedure F using 4-amino-2-fluorophenol (149.44 mg; 1.18 mmol; 1.80 eq.) instead of 4-aminophenol and was obtained as a brown solid (136 mg, 65%). (HPLC (method F): 97%, RT: 3.37 min); MS (m/z) 321 [M+H]+, RT: 3.1 min.

2,7-Bis-(3,4,5-trimethoxy-phenyl)-furo[3,2-b]pyridine ("B24")

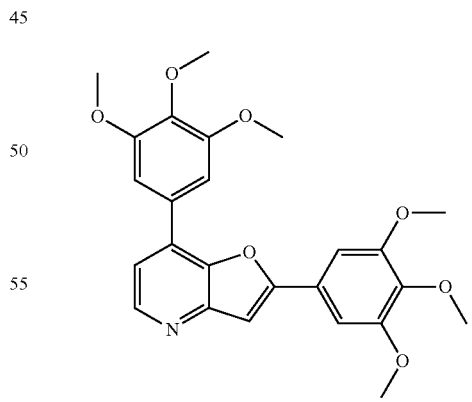

The title compound was prepared by procedure C using 3,4,5-trimethoxyphenylboronic acid (477.94 mg; 2.25 mmol; 1.05 eq.) instead of 4-fluoro-phenylboronic acid and was obtained as a yellow solid (115 mg, 12%). (HPLC (method F): 97%, RT: 3.81 min); $^1$H NMR (400 MHz, DMSO-d$_6$) δ [ppm] 8.54 (d, J=5.1, 1H), 7.75 (s, 1H), 7.67 (d, J=5.1, 1H), 7.45 (s, 2H), 7.30 (s, 2H), 3.95 (s, 6H), 3.89 (s, 6H), 3.77 (s, 3H), 3.73 (s, 3H); MS (m/z) 452 [M+H]$^+$, RT: 3.7 min.

1-(4-Fluoro-phenyl)-2-oxo-1,2-dihydro-pyridine-3-carboxylic acid [3-fluoro-4-(2-phenyl-furo[3,2-b]pyridin-7-yloxy)-phenyl]-amide ("B25")

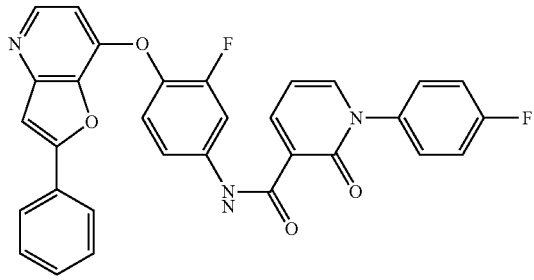

The title compound was prepared by procedure G using 1-(4-fluoro-phenyl)-2-oxo-1,2-dihydro-pyridine-3-carboxylic acid (26.21 mg; 0.11 mmol; 1.20 eq.) instead of 1-(2-hydroxy-2-methyl-propyl)-5-methyl-3-oxo-2-phenyl-2,3-dihydro-1H-pyrazole-4-carboxylic acid and using 3-fluoro-4-[(2-phenylfuro[3,2-b]pyridin-7-yl)oxy]aniline (30.00 mg; 0.09 mmol; 1.00 eq.) instead of 4-[(2-phenylfuro[3,2-b]pyridin-7-yl)oxy]aniline, and was obtained as a beige solid (36 mg, 72%). (HPLC (method F): 89%, RT: 4.63 min); MS (m/z) 536 [M+H]$^+$, RT: 4.2 min.

1-(4-Fluoro-phenyl)-4-iodo-2-oxo-1,2-dihydro-pyridine-3-carboxylic acid [3-fluoro-4-(2-phenyl-furo[3,2-b]pyridin-7-yloxy)-phenyl]-amide ("B26")

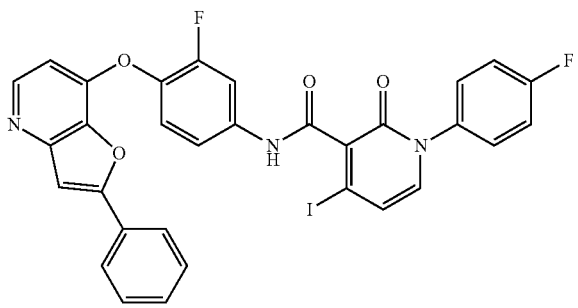 [SMILES: O=C(Nc1ccc(Oc2ccnc3cc(-c4ccccc4)oc23)c(F)c1)c1c(I)ccn(-c2ccc(F)cc2)c1=O]

The title compound was prepared by procedure G using 1-(4-fluorophenyl)-4-iodo-2-oxo-1,2-dihydropyridine-3-carboxylic acid (141.25 mg; 0.39 mmol; 1.20 eq.) instead of 1-(2-hydroxy-2-methyl-propyl)-5-methyl-3-oxo-2-phenyl-2,3-dihydro-1H-pyrazole-4-carboxylic acid and using 3-fluoro-4-[(2-phenylfuro[3,2-b]pyridin-7-yl)oxy]aniline (105.00 mg; 0.33 mmol; 1.00 eq.) instead of 4-[(2-phenylfuro[3,2-b]pyridin-7-yl)oxy]aniline, and was obtained as a brown solid (106 mg, 49%). (HPLC (method F): 94%, RT: 4.43 min); MS (m/z) 662 [M+H]$^+$, RT: 3.8 min.

4-Ethoxy-1-(4-fluoro-phenyl)-2-oxo-1,2-dihydro-pyridine-3-carboxylic acid [3-fluoro-4-(2-phenyl-furo[3,2-b]pyridin-7-yl)oxy)-phenyl]-amide ("B27")

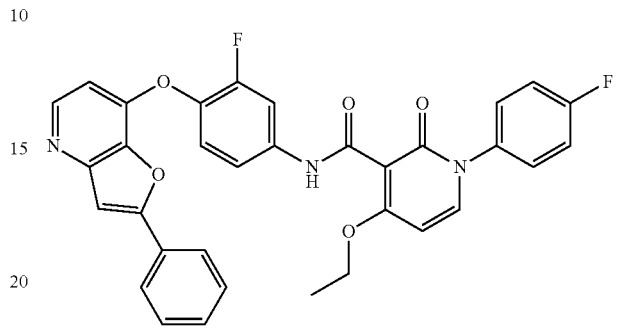

The title compound was prepared by procedure H using 1-(4-fluorophenyl)-N-{3-fluoro-4-[(2-phenylfuro[3,2-b]pyridin-7-yl)oxy]phenyl}-4-iodo-2-oxo-1,2-dihydropyridine-3-carboxamide (45.00 mg; 0.07 mmol; 1.00 eq.) and was obtained as a white solid (20 mg, 49%). (HPLC (method F): 98%, RT: 4.19 min); MS (m/z) 580 [M+H]$^+$, RT: 3.7 min.

1-(4-Fluoro-phenyl)-4-methylamino-2-oxo-1,2-dihydro-pyridine-3-carboxylic acid [3-fluoro-4-(2-phenyl-furo[3,2-b]pyridin-7-yloxy)-phenyl]-amide ("B28")

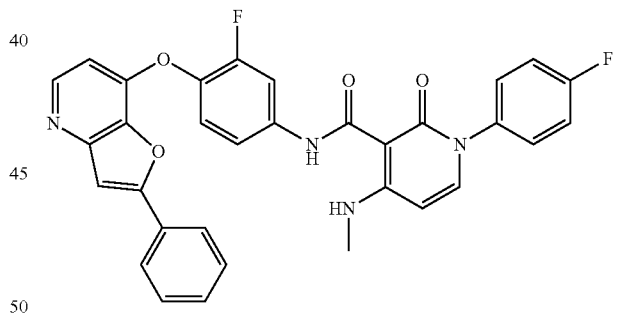

To a 2 mL microwave tube with stirbar was added 1-(4-fluoro-phenyl)-4-iodo-2-oxo-1,2-dihydro-pyridine-3-carboxylic acid [3-fluoro-4-(2-phenyl-furo[3,2-b]pyridin-7-yloxy)-phenyl]-amide (45.00 mg; 0.07 mmol; 1.00 eq.) and iPrOH (1.00 ml) and the vial was sealed and flushed with N$_2$. To the reaction mixture was added a solution of methylamine (0.05 ml; 0.54 mmol; 8.00 eq.) 40% in water. The reaction mixture was heated to 100° C. in a microwave reactor for 1 h. The reaction mixture was cooled to room temperature and the white precipitate was filtered, washed methanol, and dried under vacuo to afford the title compound as a white solid (19 mg, 49%). (HPLC (method F): 94%, RT: 4.96 min); $^1$H NMR (400 MHz, DMSO-d$_6$) δ [ppm] 10.46 (d, J=5.1, 1H), 8.36 (d, J=5.6, 1H), 8.02 (dd, J=13.3, 2.4, 1H), 7.96-7.89 (m, 2H), 7.75 (d, J=7.8, 1H), 7.71 (s, 1H), 7.56-7.44 (m, 6H), 7.42-7.32

(m, 3H), 6.74 (d, J=5.0, 1H), 6.27 (d, J=7.9, 1H), 3.03 (d, J=5.1, 3H); MS (m/z) 565 [M+H]+, RT: 4.3 min.

2,2-Dimethyl-6-[2-(3,4,5-trimethoxy-phenyl)-furo[3,2-b]pyridin-7-ylamino]-4H-pyrido[3,2-b][1,4]oxazin-3-one ("B29")

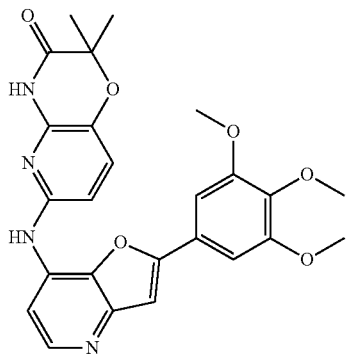 [SMILES: COc1cc(-c2cc3nccc(Nc4ccc5c(n4)NC(=O)C(C)(C)O5)c3o2)cc(OC)c1OC]

The title compound was prepared by procedure E using 6-amino-2,2-dimethyl-4H-pyrido[3,2-b][1,4]oxazin-3-one (25.38 mg; 0.13 mmol; 1.05 eq.) instead of 6-amino-2,2-difluoro-4H-benzo[1,4]oxazin-3-one and was obtained as a beige solid (18 mg, 30%). (HPLC (method F): 80%, RT: 3.77 min); $^1$H NMR (400 MHz, DMSO-$d_6$) δ [ppm] 11.20 (s, 1H), 9.46 (s, 1H), 8.23 (dd, J=12.1, 5.6, 2H), 7.58 (s, 1H), 7.45-7.35 (m, 3H), 6.86 (d, J=8.5, 1H), 3.92 (s, 6H), 3.73 (s, 3H), 1.43 (s, 6H); MS (m/z) 477 [M+H]+, RT: 2.9 min.

1H-indol-5-yl)-[2-(3,4,5-trimethoxy-phenyl)-furo[3,2-b]pyridin-7-yl]-amine ("B30")

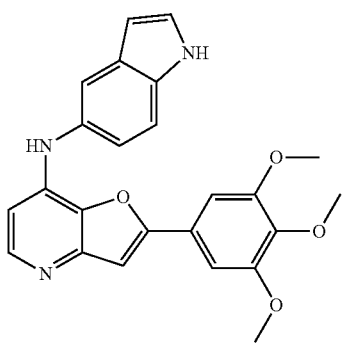 [SMILES: COc1cc(-c2cc3nccc(Nc4ccc5[nH]ccc5c4)c3o2)cc(OC)c1OC]

The title compound was prepared by procedure E using 5-aminoindole (30.38 mg; 0.23 mmol; 1.05 eq.) instead of 6-amino-2,2-difluoro-4H-benzo[1,4]-oxazin-3-one and was obtained as a pale yellow solid (54 mg, 59%). (HPLC (method F): 92%, RT: 3.71 min); $^1$H NMR (400 MHz, DMSO-$d_6$) δ [ppm] 11.16 (s, 1H), 8.78 (s, 1H), 8.03 (d, J=5.5, 1H), 7.51-7.42 (m, 3H), 7.41-7.35 (m, 1H), 7.20 (s, 2H), 7.08 (dd, J=8.5, 2.1, 1H), 6.62 (d, J=5.5, 1H), 6.43 (t, J=2.1, 1H), 3.80 (s, 6H), 3.70 (s, 3H); MS (m/z) 416 [M+H]+, RT: 2.7 min.

2,7-Di-p-tolyl-furo[3,2-b]pyridine ("B31")

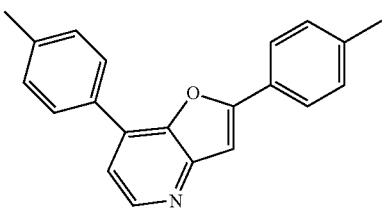

The title compound was prepared by procedure C using 4-tolylboronic acid (40.14 mg; 0.30 mmol; 1.10 eq.) instead of 4-fluorophenylboronic acid and was obtained as a beige solid (11 mg, 14%). (HPLC (method F): 97%, RT: 4.46 min); $^1$H NMR (400 MHz, DMSO-$d_6$) δ [ppm] 8.54 (d, J=5.1, 1H), 8.02 (d, J=8.2, 2H), 7.92 (d, J=8.2, 2H), 7.65 (s, 1H), 7.57 (d, J=5.1, 1H), 7.46 (d, J=8.3, 2H), 7.38 (d, J=8.4, 2H), 2.43 (s, 3H), 2.39 (s, 3H); MS (m/z) 300 [M+H]+, RT: 4.4 min.

2,7-Bis-(4-methoxy-3,5-dimethyl-phenyl)-furo[3,2-b]pyridine ("B32")

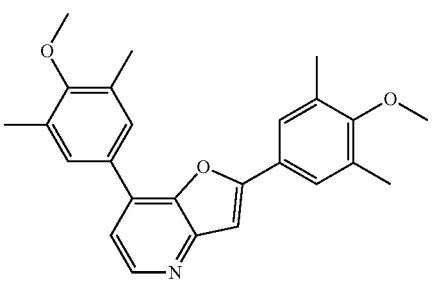

The title compound was prepared by procedure C using 3,5-dimethyl-4-methoxyphenylboronic acid (53.14 mg; 0.30 mmol; 1.10 eq.) instead of 4-fluorophenylboronic acid and was obtained as a beige solid (21 mg, 20%). (HPLC (method F): 72%, RT: 4.82 min); MS (m/z) 388 [M+H]+, RT: 4.5 min.

7-Chloro-2-(4-methoxy-3-methyl-phenyl)-furo[3,2-b]pyridine ("C2a")

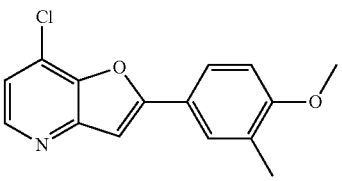 [SMILES: COc1ccc(-c2cc3nccc(Cl)c3o2)cc1C]

The title compound was prepared by procedure C using 4-methoxy-3-methylphenylboronic acid (49.00 mg; 0.30 mmol; 1.10 eq.) instead of 4-fluorophenylboronic acid and was obtained as a pale yellow solid (41 mg, 56%). (HPLC (method F): 98%, RT: 4.29 min); MS (m/z) 274 [M+H]+, RT: 4.2 min.

2,7-Bis-(4-methoxy-3-methyl-phenyl)-furo[3,2-b]pyridine ("B33")

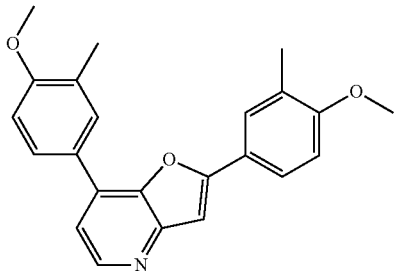 [SMILES: COc1ccc(-c2cc3nccc(-c4ccc(OC)c(C)c4)c3o2)cc1C]

The title compound was prepared by procedure C using 4-methoxy-3-methylphenylboronic acid (49.00 mg; 0.30 mmol; 1.10 eq.) instead of 4-fluorophenylboronic acid and was obtained as a brown solid (18 mg, 19%). (HPLC (method F): 89%, RT: 4.65 min); MS (m/z) 360 [M+H]+, RT: 4.2 min.

7-Chloro-2-m-tolyl-furo[3,2-b]pyridine

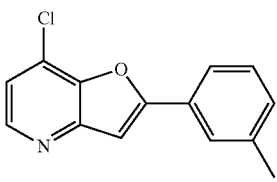 [SMILES: Cc1cccc(-c2cc3nccc(Cl)c3o2)c1]

The title compound was prepared by procedure C using m-tolylboronic acid (40.14 mg; 0.30 mmol; 1.10 eq.) instead of 4-fluorophenylboronic acid and was obtained as a pale yellow solid (39 mg, 60%). (HPLC (method F): 96%, RT: 4.48 min); MS (m/z) 244 [M+H]+, RT: 4.1 min.

7-Chloro-2-p-tolyl-furo[3,2-b]pyridine

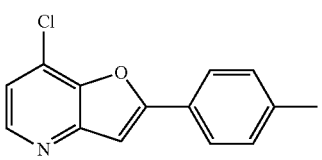 [SMILES: Cc1ccc(-c2cc3nccc(Cl)c3o2)cc1]

The title compound was prepared by procedure C using 4-tolylboronic acid (40.14 mg; 0.30 mmol; 1.10 eq.) instead of 4-fluorophenylboronic acid and was obtained as a pale yellow solid (42 mg, 63%). (HPLC (method F): 96%, RT: 4.38 min); MS (m/z) 244 [M+H]+, RT: 4.1 min.

7-Chloro-2-(4-methoxy-3,5-dimethyl-phenyl)-furo[3,2-b]pyridine

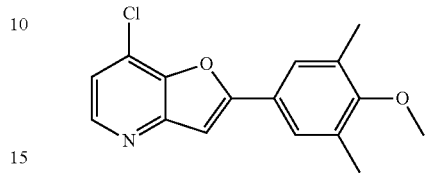

The title compound was prepared by procedure C using 3,5-dimethyl-4-methoxyphenylboronic acid (53.14 mg; 0.30 mmol; 1.10 eq.) instead of 4-fluorophenylboronic acid and was obtained as a pale yellow solid (44 mg, 57%). (HPLC (method F): 97%, RT: 4.59 min); MS (m/z) 288 [M+H]+, RT: 4.2 min.

2,7-Di-m-tolyl-furo[3,2-b]pyridine ("B34")

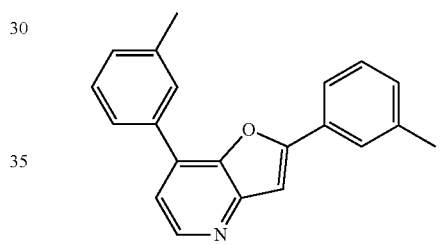

The title compound was prepared by procedure C using m-tolylboronic acid (40.14 mg; 0.30 mmol; 1.10 eq.) instead of 4-fluorophenylboronic acid and was obtained as a beige solid (19 mg, 24%). (HPLC (method F): 98%, RT: 4.48 min); 1H NMR (400 MHz, DMSO-$d_6$) δ [ppm] 8.60-8.53 (m, 1H), 7.92 (d, J=7.0, 2H), 7.89-7.77 (m, 2H), 7.71 (s, 1H), 7.59 (d, J=5.1, 1H), 7.54 (t, J=7.8, 1H), 7.46 (t, J=7.7, 1H), 7.38 (d, J=7.8, 1H), 7.31 (d, J=7.5, 1H), 2.47 (s, 3H), 2.42 (s, 3H); MS (m/z) 300 [M+H]+, RT: 4.4 min.

7-Chloro-2-(4-morpholin-4-yl-phenyl)-furo[3,2-b]pyridine

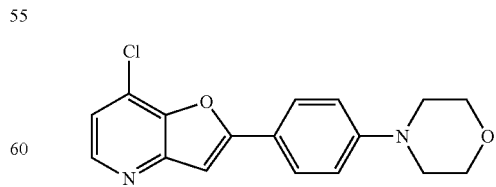

The title compound was prepared by procedure C using 4-[4-(4,4,5,5-tetramethyl-1,3,2-dioxaborolan-2-yl)phenyl]morpholine (85.37 mg; 0.30 mmol; 1.10 eq.) instead of 4-fluorophenylboronic acid and was obtained as a yellow solid (53 mg, 63%). (HPLC (method F): 67%, RT: 3.60 min); MS (m/z) 315 [M+H]+, RT: 3.8 min.

2,7-Bis-(4-methoxy-phenyl)-furo[3,2-b]pyridine ("B35")

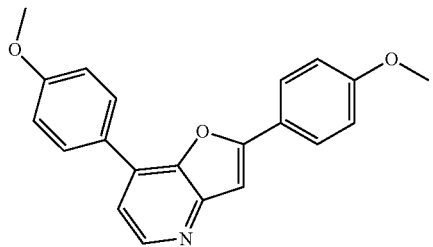 [SMILES: COc1ccc(-c2cc3nccc(-c4ccc(OC)cc4)c3o2)cc1]

The title compound was prepared by procedure C using 4-methoxyphenyl-boronic acid (44.86 mg; 0.30 mmol; 1.10 eq.) instead of 4-fluorophenylboronic acid and was obtained as a beige solid (13 mg, 15%). (HPLC (method F): 85%, RT: 4.01 min); $^1$H NMR (500 MHz, DMSO-$d_6$) δ [ppm] 8.58 (d, J=5.2, 1H), 8.11 (d, J=8.9, 2H), 8.00-7.91 (m, 3H), 7.66 (d, J=5.2, 1H), 7.20 (d, J=8.7, 2H), 7.13 (d, J=9.0, 2H), 3.87 (s, 3H), 3.85 (s, 3H); MS (m/z) 332 [M+H]+, RT: 3.8 min.

2-Benzo[1,3]dioxol-5-yl-7-chloro-furo[3,2-b]pyridine

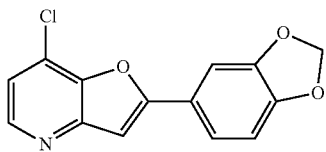 [SMILES: Clc1ccnc2cc(-c3ccc4c(c3)OCO4)oc12]

The title compound was prepared by procedure C using 3,4-(methylenedioxy)-phenylboronic acid (52.25 mg; 0.31 mmol; 1.10 eq.) instead of 4-fluoro-phenylboronic acid and was obtained as a white solid (49 mg, 63%). (HPLC (method F): 97%, RT: 3.88 min); MS (m/z) 274 [M+H]+, RT: 3.9 min.

2,7-Bis-benzo[1,3]dioxol-5-yl-furo[3,2-b]pyridine ("B36")

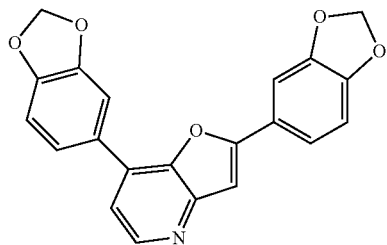 [SMILES: c1cc(-c2ccc3c(c2)OCO3)c2oc(-c3ccc4c(c3)OCO4)cc2n1]

The title compound was prepared by procedure C using 3,4-(methylenedioxy)-phenylboronic acid (52.25 mg; 0.31 mmol; 1.10 eq.) instead of 4-fluoro-phenylboronic acid and was obtained as a brown solid (16 mg, 16%). (HPLC (method F): 90%, RT: 3.86 min); $^1$H NMR (500 MHz, DMSO-$d_6$) δ [ppm] 8.48 (d, J=5.1, 1H), 7.70-7.64 (m, 2H), 7.59-7.50 (m, 4H), 7.18 (d, J=8.1, 1H), 7.12 (d, J=8.1, 1H), 6.14 (d, J=10.1, 4H); MS (m/z) 360 [M+H]+, RT: 3.8 min.

7-Chloro-2-(2,3-dihydro-benzo[1,4]dioxin-6-yl)-furo[3,2-b]pyridine

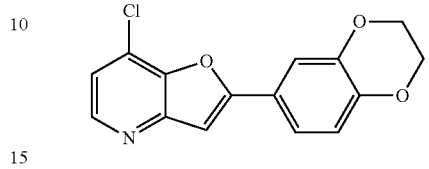

The title compound was prepared by procedure C using 1,4-benzodioxane-6-boronic acid (56.67 mg; 0.31 mmol; 1.10 eq.) instead of 4-fluorophenylboronic acid and was obtained as a beige solid (48 mg, 59%). (HPLC (method F): 98%, RT: 3.93 min); MS (m/z) 288 [M+H]+, RT: 3.9 min.

2,7-Bis-(2,3-dihydro-benzo[1,4]dioxin-6-yl)-furo[3,2-b]pyridine ("B37")

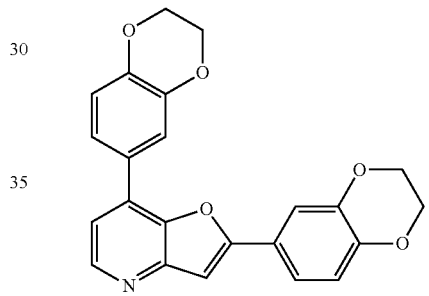

The title compound was prepared by procedure C using 1,4-benzodioxane-6-boronic acid (56.67 mg; 0.31 mmol; 1.10 eq.) instead of 4-fluorophenylboronic acid and was obtained as a brown solid (16 mg, 15%). (HPLC (method F): 95%, RT: 3.91 min); $^1$H NMR (500 MHz, DMSO-$d_6$) δ [ppm] 8.47 (d, J=5.2, 1H), 7.66-7.60 (m, 2H), 7.54 (s, 1H), 7.52-7.46 (m, 3H), 7.11 (d, J=8.3, 1H), 7.05 (d, J=8.6, 1H), 4.35 (s, 4H), 4.33 (s, 4H); MS (m/z) 388 [M+H]+, RT: 3.8 min.

7-Chloro-2-(3,5-dimethyl-phenyl)-furo[3,2-b]pyridine

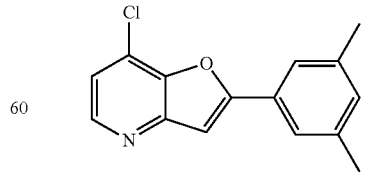

The title compound was prepared by procedure C using 3,5-dimethyl-phenylboronic acid (44.28 mg; 0.30 mmol; 1.10 eq.) instead of 4-fluorophenylboronic acid and was obtained as a beige solid (44 mg, 63%). (HPLC (method F): 85%, RT: 4.78 min; MS (m/z) 258 [M+H]+, RT: 4.4 min.

2,7-Bis-(3,5-dimethyl-phenyl)-furo[3,2-b]pyridine ("B38")

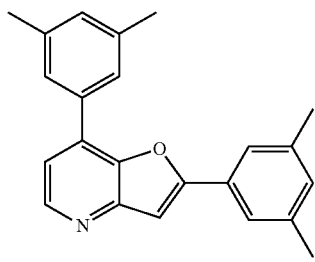

The title compound was prepared by procedure C using 3,5-dimethylphenyl-boronic acid (44.28 mg; 0.30 mmol; 1.10 eq.) instead of 4-fluorophenylboronic acid and was obtained as a beige solid (14 mg, 16%). (HPLC (method F): 98%, RT: 5.01 min); $^1$H NMR (500 MHz, DMSO-$d_6$) δ [ppm] 8.54 (d, J=5.0, 1H), 7.72 (s, 2H), 7.61-7.65 (m, 3H), 7.56 (d, J=5.1, 1H), 7.20 (s, 1H), 7.13 (s, 1H), 2.43 (s, 6H), 2.37 (s, 6H); MS (m/z) 328 [M+H]+, RT: 4.8 min.

7-Chloro-2-(3,4-dimethoxy-phenyl)-furo[3,2-b]pyridine ("C3a")

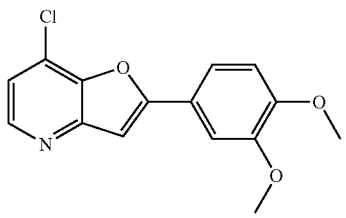 [SMILES: COc1ccc(-c2cc3nccc(Cl)c3o2)cc1OC]

The title compound was prepared by procedure C using 3,4-dimethoxyphenyl-boronic acid (53.72 mg; 0.30 mmol; 1.10 eq.) instead of 4-fluorophenylboronic acid and was obtained as a yellow solid (47 mg, 61%). (HPLC (method F): 95%, RT: 3.59 min); MS (m/z) 290 [M+H]+, RT: 3.7 min.

2,7-Bis-(3,4-dimethoxy-phenyl)-furo[3,2-b]pyridine ("B39")

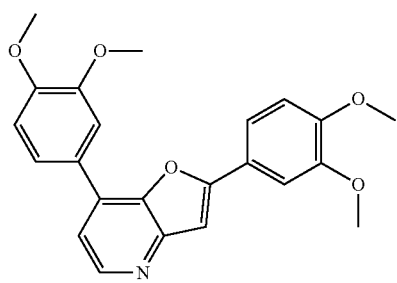 [SMILES: COc1ccc(-c2cc3nccc(-c4ccc(OC)c(OC)c4)c3o2)cc1OC]

The title compound was prepared by procedure C using 3,4-dimethoxyphenylboronic acid (53.72 mg; 0.30 mmol; 1.10 eq.) instead of 4-fluorophenylboronic acid and was obtained as a beige solid (20 mg, 19%). (HPLC (method F): 94%, RT: 3.60 min); $^1$H NMR (500 MHz, DMSO-$d_6$) δ [ppm] 8.48 (d, J=5.2, 1H), 7.73 (s, 1H), 7.71 (d, J=8.5, 1H), 7.61-7.53 (m, 4H), 7.20 (d, J=8.4, 1H), 7.13 (d, J=8.4, 1H), 3.92 (s, 3H), 3.87 (s, 3H), 3.86 (s, 3H), 3.83 (s, 3H); MS (m/z) 392 [M+H]+, RT: 3.3 min.

7-Chloro-2-(4-methoxy-phenyl)-furo[3,2-b]pyridine

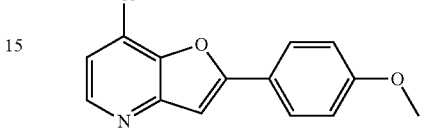

The title compound was prepared by procedure C using 4-methoxyphenylboronic acid (44.86 mg; 0.30 mmol; 1.10 eq.) instead of 4-fluorophenylboronic acid and was obtained as a pale yellow solid (47 mg, 65%). (HPLC (method F): 99%, RT: 3.90 min); MS (m/z) 260 [M+H]+, RT: 3.9 min.

2,7-Bis-(2,3,4-trimethoxy-phenyl)-furo[3,2-b]pyridine ("B40")

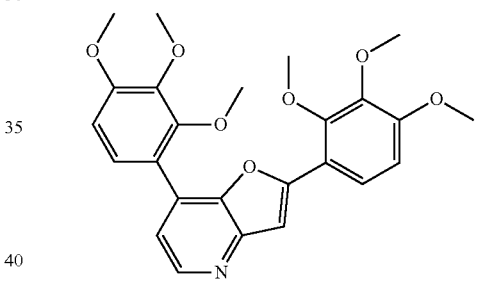

The title compound was prepared by procedure C using 2,3,4-trimethoxyphenylboronic acid (83.45 mg; 0.39 mmol; 1.10 eq.) instead of 4-fluorophenylboronic acid and was obtained as an orange waxy solid (28 mg, 17%). (HPLC (method F): 84%, RT: 4.09 min); $^1$H NMR (500 MHz, DMSO-$d_6$) δ [ppm] 8.49 (d, J=5.0, 1H), 7.55 (d, J=8.9, 1H), 7.37 (s, 1H), 7.35 (d, J=8.7, 1H), 7.30 (d, J=5.0, 1H), 7.01 (d, J=8.7, 1H), 6.98 (d, J=9.0, 1H), 3.94 (s, 3H), 3.90 (s, 3H), 3.86 (s, 3H), 3.84 (s, 3H), 3.82 (s, 3H), 3.72 (s, 3H); MS (m/z) 452 [M+H]+, RT: 3.5 min.

2,7-Bis-(3,5-dimethyl-isoxazol-4-yl)-furo[3,2-b]pyridine ("B41")

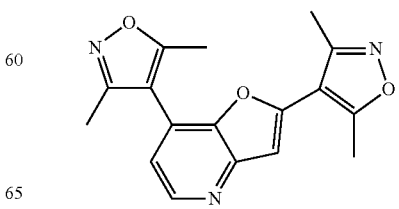

The title compound was prepared by procedure C using (3,5-dimethylisoxazol-4-yl)boronic acid (55.47 mg; 0.39 mmol; 1.10 eq.) instead of 4-fluorophenyl-boronic acid and was obtained as a brown solid (9 mg, 8%). (HPLC (method F): 95%, RT: 3.18 min); $^1$H NMR (500 MHz, DMSO-$d_6$) δ [ppm] 8.60 (d, J=4.9, 1H), 7.41-7.35 (m, 2H), 2.65 (s, 3H), 2.46 (s, 3H), 2.45 (s, 3H), 2.27 (s, 3H); MS (m/z) 310 [M+H]$^+$, RT: 3.0 min.

2,7-Bis-(2,3-dimethoxy-phenyl)-furo[3,2-b]pyridine ("B42")

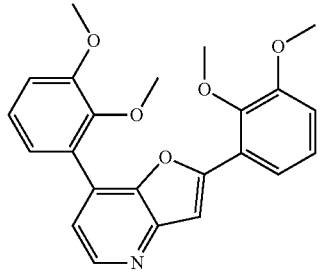 [SMILES: COc1cccc(-c2cc3nccc(-c4cccc(OC)c4OC)c3o2)c1OC]

The title compound was prepared by procedure C using 2,3-dimethoxyphenyl-boronic acid (57.30 mg; 0.31 mmol; 1.10 eq.) instead of 4-fluorophenylboronic acid and was obtained as a brown solid (14 mg, 12%). (HPLC (method F): 89%, RT: 4.10 min); $^1$H NMR (500 MHz, DMSO-$d_6$) δ [ppm] 8.55 (d, J=4.9, 1H), 7.53 (s, 1H), 7.38 (dd, J=7.6, 1.8, 1H), 7.34 (d, J=5.0, 1H), 7.28-7.23 (m, 2H), 7.21-7.13 (m, 3H), 3.90 (s, 3H), 3.87 (s, 6H), 3.64 (s, 3H); MS (m/z) 392 [M+H]$^+$, RT: 3.7 min.

2,7-Bis-(3-methoxy-phenyl)-furo[3,2-b]pyridine ("B43")

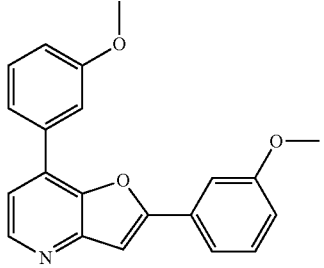 [SMILES: COc1cccc(-c2cc3nccc(-c4cccc(OC)c4)c3o2)c1]

The title compound was prepared by procedure C using 3-methoxyphenylboronic acid (59.81 mg; 0.39 mmol; 1.10 eq.) instead of 4-fluorophenylboronic acid and was obtained as a brown solid (7 mg, 6%). (HPLC (method F): 76%, RT: 4.16 min); MS (m/z) 332 [M+H]$^+$, RT: 4.1 min.

{4-[2-(4-Hydroxymethyl-phenyl)-furo[3,2-b]pyridin-7-yl]-phenyl}-methanol ("B44")

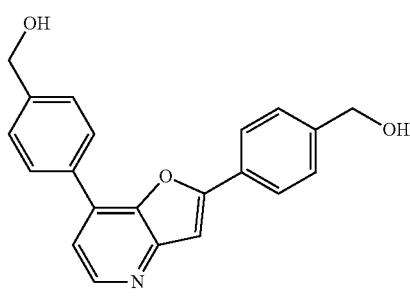 [SMILES: OCc1ccc(-c2cc3nccc(-c4ccc(CO)cc4)c3o2)cc1]

The title compound was prepared by procedure C using 4-(hydroxymethyl)-phenylboronic acid (59.81 mg; 0.39 mmol; 1.10 eq.) instead of 4-fluorophenylboronic acid and was obtained as a beige solid (7 mg, 6%). (HPLC (method F): 81%, RT: 3.05 min); $^1$H NMR (500 MHz, DMSO-$d_6$) δ [ppm] 8.55 (d, J=5.0, 1H), 8.08 (d, J=8.2, 2H), 7.99 (d, J=8.2, 2H), 7.67 (s, 1H), 7.61-7.56 (m, 3H), 7.50 (d, J=8.0, 2H), 5.31 (q, J=5.6, 2H), 4.62 (d, J=5.4, 2H), 4.58 (d, J=5.4, 2H); MS (m/z) 332 [M+H]$^+$, RT: 2.4 min.

2-(4-{2-[4-(1-Hydroxy-1-methyl-ethyl)-phenyl]-furo[3,2-b]pyridin-7-yl}-phenyl)-propan-2-ol ("B45")

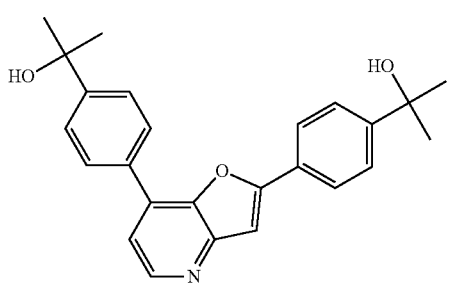 [SMILES: CC(C)(O)c1ccc(-c2cc3nccc(-c4ccc(C(C)(C)O)cc4)c3o2)cc1]

The title compound was prepared by procedure C using (4-(2-hydroxypropan-2-yl)phenyl)boronic acid (70.85 mg; 0.39 mmol; 1.10 eq.) instead of 4-fluorophenylboronic acid and was obtained as a beige solid (19 mg, 14%). (HPLC (method F): 88%, RT: 3.55 min); $^1$H NMR (500 MHz, DMSO-$d_6$) δ [ppm] 8.55 (d, J=5.0, 1H), 8.06 (d, J=8.3, 2H), 7.96 (d, J=8.3, 2H), 7.73 (d, J=8.3, 2H), 7.68-7.62 (m, 3H), 7.58 (d, J=5.1, 1H), 5.13 (s, 2H), 1.51 (s, 6H), 1.47 (s, 6H); MS (m/z) 388 [M+H]⁺, RT: 3.2 min.

(4-Methyl-1H-indol-5-yl)-(2-p-tolyl-furo[3,2-b]pyridin-7-yl)-amine ("B46")

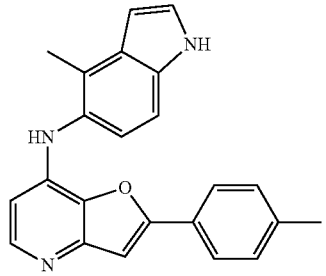 [SMILES: Cc1ccc(-c2cc3nccc(Nc4ccc5[nH]ccc5c4C)c3o2)cc1]

The title compound was prepared by procedure E using 7-chloro-2-(4-methylphenyl)furo[3,2-b]pyridine (27.00 mg; 0.11 mmol; 1.00 eq.) instead of 7-chloro-2-(3,4,5-trimethoxyphenyl)furo[3,2-b]pyridine, and 4-methyl-1H-indol-5-ylamine (17.01 mg; 0.12 mmol; 1.05 eq.) instead of 6-amino-2,2-difluoro-4H-benzo[1,4]oxazin-3-one, and was obtained as a beige solid (19 mg, 48%). (HPLC (method F): 95%, RT: 4.21 min); $^1$H NMR (500 MHz, DMSO-d$_6$) δ [ppm] 11.14 (s, 1H), 8.53 (s, 1H), 7.94 (d, J=5.5, 1H), 7.85 (d, J=8.1, 2H), 7.38 (t, J=2.7, 1H), 7.35 (s, 1H), 7.33-7.27 (m, 3H), 7.00 (d, J=8.4, 1H), 6.52 (s, 1H), 6.09 (d, J=5.5, 1H), 2.37 (s, 3H), 2.36 (s, 3H); MS (m/z) 354 [M+H]⁺, RT: 4.1 min.

{3-[4-(7-Chloro-furo[3,2-b]pyridin-2-yl)-phenoxy]-propyl}-dimethyl-amine ("C4a")

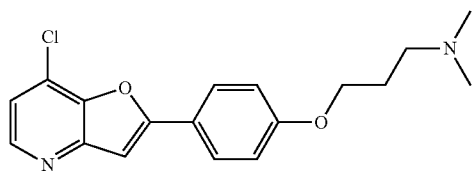 [SMILES: CN(C)CCCOc1ccc(-c2cc3nccc(Cl)c3o2)cc1]

The title compound was prepared by procedure C using 2-(4-[3-(dimethylamino)propoxy]phenyl)-4,4,5,5-tetramethyl-1,3,2-dioxaborolane (120.14 mg; 0.39 mmol; 1.10 eq.) instead of 4-fluorophenylboronic acid. Material was then purified by HCl salt formation. The residue was dissolved in 1 mL MeOH and 1N HCl in Et$_2$O (1 mL) was added with stirring. The mixture was stirred for 10 min. and Et$_2$O (5 mL) was added. The resulting yellow precipitate was collected by filtration to afford the title compound as a yellow solid (45 mg, 34%). (HPLC (method F): X %, RT: X min); $^1$H NMR (500 MHz, DMSO-d$_6$) δ[ppm] 10.22 (s, 1H), 8.44 (d, J=5.3, 1H), 7.97 (d, J=8.9, 2H), 7.63 (s, 1H), 7.49 (d, J=5.3, 1H), 7.14 (d, J=8.9, 2H), 4.16 (t, J=6.1, 2H), 3.23 (dd, J=15.7, 5.7, 2H), 2.79 (d, J=4.9, 6H), 2.21-2.13 (m, 2H); MS (m/z) 331 [M+H]⁺, RT: 2.7 min.

7-Chloro-2-(2,3-dimethoxy-phenyl)-furo[3,2-b]pyridine

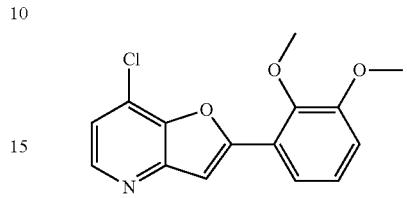

The title compound was prepared by procedure C using 2,3-dimethoxyphenylboronic acid (57.30 mg; 0.31 mmol; 1.10 eq.) instead of 4-fluorophenylboronic acid and was obtained as a beige solid (49 mg, 60%). (HPLC (method F): 92%, RT: 4.21 min); MS (m/z) 290 [M+H]⁺, RT: 3.9 min.

7-Chloro-2-(3-methoxy-phenyl)-furo[3,2-b]pyridine

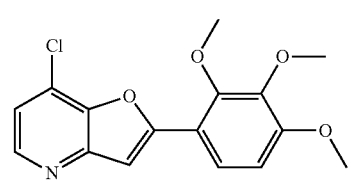 [SMILES: COc1ccc(-c2cc3nccc(Cl)c3o2)c(OC)c1OC]

The title compound was prepared by procedure C using 3-methoxyphenylboronic acid (59.81 mg; 0.39 mmol; 1.10 eq.) instead of 4-fluorophenylboronic acid and was obtained as a beige solid (69 mg, 74%). (HPLC (method F): 64%, RT: 4.26 min); MS (m/z) 260 [M+H]⁺, RT: 3.9 min.

7-Chloro-2-(2,3,4-trimethoxy-phenyl)-furo[3,2-b]pyridine

The title compound was prepared by procedure C using 2,3,4-trimethoxyphenylboronic acid (83.45 mg; 0.39 mmol; 1.10 eq.) instead of 4-fluorophenylboronic acid and was obtained as a pale yellow solid (68 mg, 59%). (HPLC (method F): 96%, RT: 3.94 min); MS (m/z) 320 [M+H]+, RT: 3.8 min.

[4-(7-Chloro-furo[3,2-b]pyridin-2-yl)-phenyl]-methanol

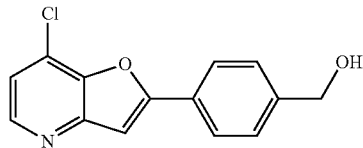 [SMILES: OCc1ccc(-c2cc3nccc(Cl)c3o2)cc1]

The title compound was prepared by procedure C using 4-(hydroxymethyl)-phenylboronic acid (59.81 mg; 0.39 mmol; 1.10 eq.) instead of 4-fluorophenylboronic acid and was obtained as a pale yellow solid (32 mg, 35%). (HPLC (method F): 81%, RT: 3.15 min); MS (m/z) 260 [M+H]+, RT: 2.9 min.

2-[4-(7-Chloro-furo[3,2-b]pyridin-2-yl)-phenyl]-propan-2-ol

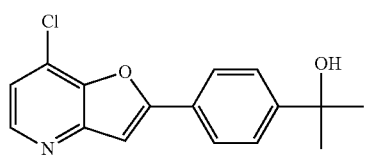 [SMILES: CC(C)(O)c1ccc(-c2cc3nccc(Cl)c3o2)cc1]

The title compound was prepared by procedure C using (4-(2-hydroxypropan-2-yl)phenyl)boronic acid (70.85 mg; 0.39 mmol; 1.10 eq.) instead of 4-fluorophenylboronic acid and was obtained as a pale yellow solid (54 mg, 52%). (HPLC (method F): 93%, RT: 3.66 min); MS (m/z) 288 [M+H]+, RT: 3.4 min.

7-Chloro-2-(3,5-dimethyl-isoxazol-4-yl)-furo[3,2-b]pyridine

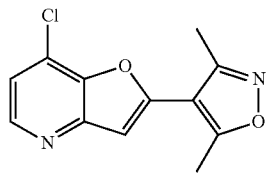 [SMILES: Cc1noc(C)c1-c1cc2nccc(Cl)c2o1]

The title compound was prepared by procedure C using (3,5-dimethylisoxazol-4-yl)boronic acid (55.47 mg; 0.39 mmol; 1.10 eq.) instead of 4-fluorophenylboronic acid and was obtained as a white solid (45 mg, 51%). (HPLC (method F): 73%, RT: 3.65 min); MS (m/z) 249 [M+H]+, RT: 3.4 min.

[2-(4-Methoxy-phenyl)-furo[3,2-b]pyridin-7-yl]-(4-methyl-1H-indol-5-yl)-amine ("B47")

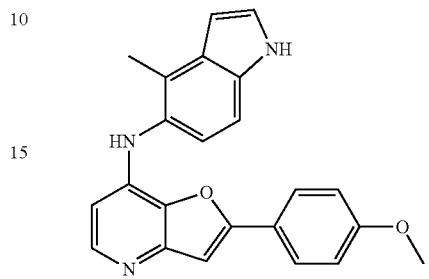

The title compound was prepared by procedure E using 7-chloro-2-(4-methoxyphenyl)furo[3,2-b]pyridine (30.10 mg; 0.12 mmol; 1.00 eq.) instead of 7-chloro-2-(3,4,5-trimethoxyphenyl)furo[3,2-b]pyridine, and 4-methyl-1H-indol-5-ylamine (17.79 mg; 0.12 mmol; 1.05 eq.) instead of 6-amino-2,2-difluoro-4H-benzo[1,4]oxazin-3-one, and was obtained as a beige solid (27 mg, 64%). (HPLC (method F): 93%, RT: 4.07 min); $^1$H NMR (500 MHz, DMSO-$d_6$) δ[ppm] 11.14 (s, 1H), 8.49 (s, 1H), 7.92 (d, J=5.5, 1H), 7.90 (d, J=8.8, 2H), 7.38 (t, J=2.7, 1H), 7.30 (d, J=8.4, 1H), 7.27 (s, 1H), 7.06 (d, J=8.9, 2H), 7.00 (d, J=8.5, 1H), 6.52 (s, 1H), 6.06 (d, J=5.5, 1H), 3.83 (s, 3H), 2.36 (s, 3H); MS (m/z) 370 [M+H]+, RT: 3.9 min.

2-Benzo[1,3]dioxol-5-yl-furo[3,2-b]pyridin-7-yl)-(4-methyl-1H-indol-5-yl)-amine ("B48"

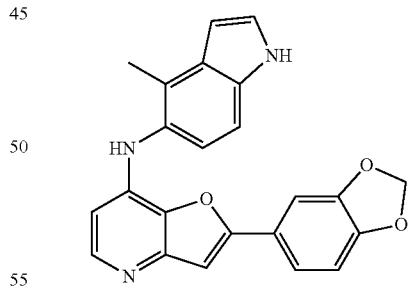

The title compound was prepared by procedure E using 2-(1,3-benzodioxol-5-yl)-7-chlorofuro[3,2-b]pyridine (32.50 mg; 0.12 mmol; 1.00 eq.) instead of 7-chloro-2-(3,4,5-trimethoxyphenyl)furo[3,2-b]pyridine, and 4-methyl-1H-indol-5-ylamine (18.23 mg; 0.12 mmol; 1.05 eq.) instead of 6-amino-2,2-difluoro-4H-benzo[1,4]oxazin-3-one, and was obtained as a beige solid (22 mg, 49%). (HPLC (method F): 99%, RT: 4.01 min); $^1$H NMR (500 MHz, DMSO-$d_6$) δ [ppm] 11.14 (s, 1H), 8.50 (s, 1H), 7.93 (d, J=5.5, 1H), 7.54 (s, 1H), 7.53-7.47 (m, 1H), 7.37 (t, J=2.6, 1H), 7.30 (t, J=4.0, 2H), 7.02 (dd, J=18.7, 8.3, 2H), 6.52 (s, 1H), 6.10 (s, 2H), 6.07 (d, J=5.5, 1H), 2.36 (s, 3H); MS (m/z) 384 [M+H]⁺, RT: 3.8 min.

[2-(4-Methoxy-3,5-dimethyl-phenyl)-furo[3,2-b]pyridin-7-yl]-(4-methyl-1H-indol-5-yl)-amine ("B49")

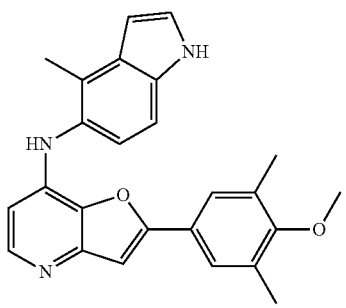 [SMILES: COc1c(C)cc(-c2cc3nccc(Nc4ccc5[nH]ccc5c4C)c3o2)cc1C]

The title compound was prepared by procedure E using 7-chloro-2-(4-methoxy-3,5-dimethylphenyl)furo[3,2-b]pyridine (28.90 mg; 0.10 mmol; 1.00 eq.) instead of 7-chloro-2-(3,4,5-trimethoxyphenyl)furo[3,2-b]pyridine, and 4-methyl-1H-indol-5-ylamine (15.42 mg; 0.11 mmol; 1.05 eq.) instead of 6-amino-2,2-difluoro-4H-benzo[1,4]oxazin-3-one, and was obtained as a white solid (22 mg, 56%). (HPLC (method F): 99%, RT: 4.37 min); ¹H NMR (500 MHz, DMSO-d₆) δ [ppm] 11.15 (s, 1H), 8.51 (s, 1H), 7.94 (d, J=5.5, 1H), 7.54 (s, 2H), 7.38 (t, J=2.7, 1H), 7.30 (d, J=8.3, 1H), 7.25 (s, 1H), 7.00 (d, J=8.4, 1H), 6.52 (s, 1H), 6.14 (d, J=5.5, 1H), 3.69 (s, 3H), 2.35 (s, 3H), 2.25 (s, 6H); MS (m/z) 398 [M+H]⁺, RT: 4.2 min.

[2-(4-Methoxy-3-methyl-phenyl)-furo[3,2-b]pyridin-7-yl]-(4-methyl-1H-indol-5-yl)-amine ("B50")

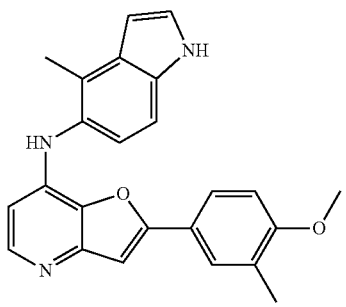

The title compound was prepared by procedure E using 7-chloro-2-(4-methoxy-3-methylphenyl)furo[3,2-b]pyridine (29.40 mg; 0.11 mmol; 1.00 eq.) instead of 7-chloro-2-(3,4,5-trimethoxyphenyl)furo[3,2-b]pyridine, and 4-methyl-1H-indol-5-ylamine (16.49 mg; 0.11 mmol; 1.05 eq.) instead of 6-amino-2,2-difluoro-4H-benzo[1,4]oxazin-3-one, and was obtained as a beige solid (30 mg, 73%). (HPLC (method F): 97%, RT: 4.34 min); ¹H NMR (500 MHz, DMSO-d₆) δ [ppm] 11.14 (s, 1H), 8.49 (s, 1H), 7.92 (d, J=5.5, 1H), 7.77 (d, J=8.6, 1H), 7.66 (s, 1H), 7.38 (s, 1H), 7.30 (d, J=8.4, 1H), 7.22 (s, 1H), 7.02 (dd, J=17.9, 8.5, 2H), 6.52 (s, 1H), 6.09 (d, J=5.5, 1H), 3.85 (s, 3H), 2.36 (s, 3H), 2.18 (s, 3H); MS (m/z) 384 [M+H]⁺, RT: 4.2 min.

(4-Methyl-1H-indol-5-yl)-(2-m-tolyl-furo[3,2-b]pyridin-7-yl)-amine ("B51")

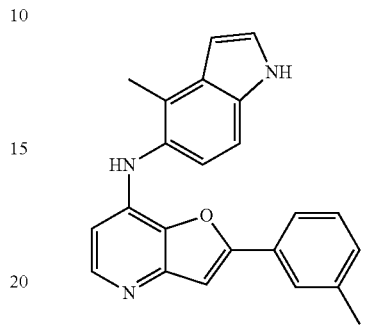

The title compound was prepared by procedure E using 7-chloro-2-(3-methylphenyl)furo[3,2-b]pyridine (23.00 mg; 0.09 mmol; 1.00 eq.) instead of 7-chloro-2-(3,4,5-trimethoxyphenyl)furo[3,2-b]pyridine, and 4-methyl-1H-indol-5-ylamine (14.49 mg; 0.10 mmol; 1.05 eq.) instead of 6-amino-2,2-difluoro-4H-benzo[1,4]oxazin-3-one, and was obtained as a beige solid (22 mg, 67%). (HPLC (method F): 99%, RT: 4.24 min); ¹H NMR (500 MHz, DMSO-d₆) δ [ppm] 11.15 (s, 1H), 8.55 (s, 1H), 7.96 (d, J=5.5, 1H), 7.75 (d, J=7.5, 1H), 7.69 (s, 1H), 7.44-7.34 (m, 3H), 7.31 (d, J=8.3, 1H), 7.22 (d, J=7.3, 1H), 7.01 (d, J=8.4, 1H), 6.52 (s, 1H), 6.13 (d, J=5.5, 1H), 2.36 (s, 3H), 2.35 (s, 3H); MS (m/z) 354 [M+H]⁺, RT: 4.1 min.

[2-(3,5-Dimethyl-phenyl)-furo[3,2-b]pyridin-7-yl]-(4-methyl-1H-indol-5-yl)-amine ("B52")

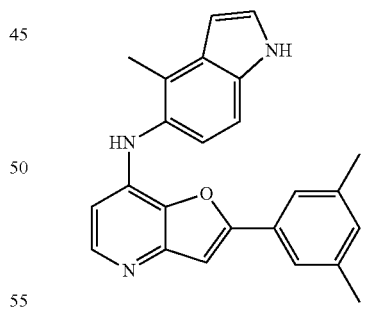

The title compound was prepared by procedure E using 7-chloro-2-(3,5-dimethylphenyl)furo[3,2-b]pyridine (26.00 mg; 0.10 mmol; 1.00 eq.) instead of 7-chloro-2-(3,4,5-trimethoxyphenyl)furo[3,2-b]pyridine, and 4-methyl-1H-indol-5-ylamine (15.49 mg; 0.11 mmol; 1.05 eq.) instead of 6-amino-2,2-difluoro-4H-benzo[1,4]oxazin-3-one, and was obtained as a beige solid (25 mg, 67%). (HPLC (method F): 96%, RT: 4.45 min); ¹H NMR (500 MHz, DMSO-d₆) δ [ppm] 11.15 (s, 1H), 8.54 (s, 1H), 7.95 (d, J=5.5, 1H), 7.50 (s, 2H), 7.38 (t, J=2.7, 1H), 7.33 (s, 1H), 7.31 (d, J=8.4, 1H), 7.08-6.95

(m, 2H), 6.52 (s, 1H), 6.14 (d, J=5.5, 1H), 2.36 (s, 3H), 2.30 (s, 6H); MS (m/z) 368 [M+H]+, RT: 4.3 min.

[2-(3,4-Dimethoxy-phenyl)-furo[3,2-b]pyridin-7-yl]-(4-methyl-1H-indol-5-yl)-amine ("B53")

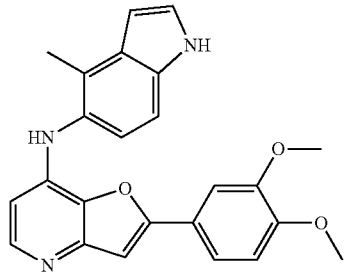 [SMILES: COc1ccc(-c2cc3nccc(Nc4ccc5[nH]ccc5c4C)c3o2)cc1OC]

The title compound was prepared by procedure E using 7-chloro-2-(3,4-dimethoxyphenyl)furo[3,2-b]pyridine (29.50 mg; 0.10 mmol; 1.00 eq.) instead of 7-chloro-2-(3,4,5-trimethoxyphenyl)furo[3,2-b]pyridine, and 4-methyl-1H-indol-5-ylamine (15.63 mg; 0.11 mmol; 1.05 eq.) instead of 6-amino-2,2-difluoro-4H-benzo[1,4]oxazin-3-one, and was obtained as a beige solid (23 mg, 57%). (HPLC (method F): 92%, RT: 3.82 min); $^1$H NMR (500 MHz, DMSO-$d_6$) δ [ppm] 11.13 (s, 1H), 8.50 (s, 1H), 7.94 (d, J=5.5, 1H), 7.52 (dd, J=8.4, 1.8, 1H), 7.38 (dd, J=10.5, 7.8, 2H), 7.31 (t, J=4.1, 2H), 7.06 (d, J=8.5, 1H), 7.01 (d, J=8.5, 1H), 6.52 (s, 1H), 6.12 (d, J=5.5, 1H), 3.82 (s, 3H), 3.76 (s, 3H), 2.37 (s, 3H); MS (m/z) 400 [M+H]+, RT: 3.6 min.

4-Methyl-1H-indol-5-yl)-[2-(4-morpholin-4-yl-phenyl)-furo[3,2-b]pyridin-7-yl]-amine ("B54"

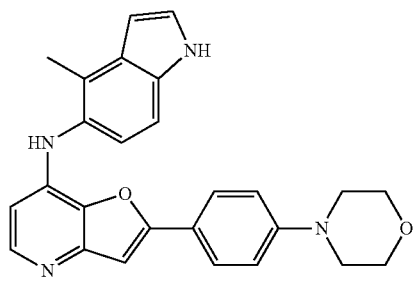 [SMILES: Cc1c(Nc2ccnc3cc(-c4ccc(N5CCOCC5)cc4)oc23)ccc2[nH]ccc12]

The title compound was prepared by procedure E using 7-chloro-2-(4-morpholin-4-ylphenyl)furo[3,2-b]pyridine (31.20 mg; 0.10 mmol; 1.00 eq.) instead of 7-chloro-2-(3,4,5-trimethoxyphenyl)furo[3,2-b]pyridine, and 4-methyl-1H-indol-5-ylamine (15.22 mg; 0.10 mmol; 1.05 eq.) instead of 6-amino-2,2-difluoro-4H-benzo[1,4]oxazin-3-one, and was obtained as a yellow solid (16 mg, 38%). (HPLC (method F): 94%, RT: 3.97 min); $^1$H NMR (500 MHz, DMSO-$d_6$) δ [ppm] 11.13 (s, 1H), 8.45 (s, 1H), 7.90 (d, J=5.4, 1H), 7.82 (d, J=8.9, 2H), 7.37 (s, 1H), 7.30 (d, J=8.3, 1H), 7.18 (s, 1H), 7.04 (d, J=9.0, 2H), 7.00 (d, J=8.4, 1H), 6.52 (s, 1H), 6.04 (d, J=5.5, 1H), 3.79-3.73 (m, 4H), 3.26-3.20 (m, 4H), 2.36 (s, 3H); MS (m/z) 425 [M+H]+, RT: 3.8 min.

2-(4-{2-[4-(Cyano-dimethyl-methyl)-phenyl]-furo[3,2-b]pyridin-7-yl}-phenyl)-2-methyl-propionitrile ("B55")

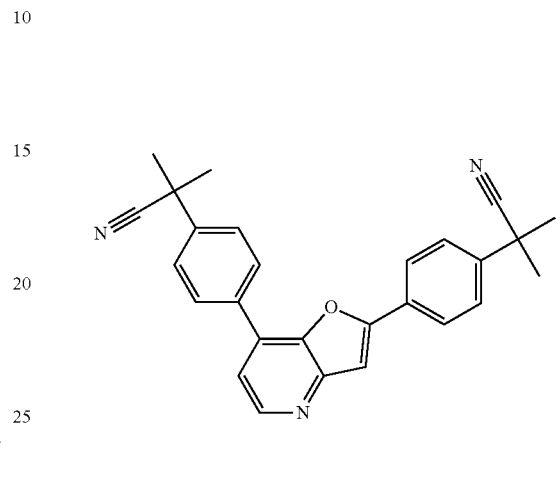

The title compound was prepared by procedure C using [4-(1-cyano-1-methylethyl)phenyl]boronic acid (148.80 mg; 0.79 mmol; 1.10 eq.) instead of 4-fluorophenylboronic acid and was obtained as a yellow oil (30 mg, 10%). (HPLC (method F): 76%, RT: 4.30 min); $^1$H NMR (500 MHz, DMSO-$d_6$) δ[ppm] 8.60 (d, J=5.1, 1H), 8.20 (d, J=8.4, 2H), 8.10 (d, J=8.5, 2H), 7.80 (d, J=8.5, 2H), 7.78 (s, 1H), 7.72 (d, J=8.5, 2H), 7.65 (d, J=5.1, 1H), 1.78 (s, 6H), 1.74 (s, 6H); MS (m/z) 406 [M+H]+, RT: 4.4 min.

2-[4-(7-Chloro-furo[3,2-b]pyridin-2-yl)-phenyl]-2-methyl-propionitrile

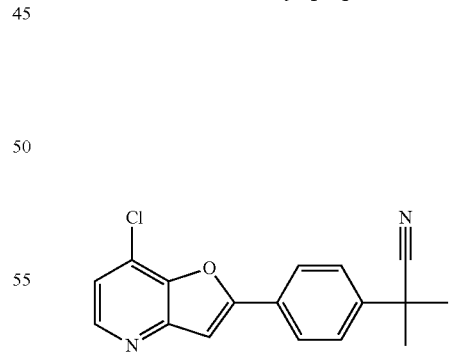

The title compound was prepared by procedure C using [4-(1-cyano-1-methylethyl)phenyl]boronic acid (148.80 mg; 0.79 mmol; 1.10 eq.) instead of 4-fluorophenylboronic acid and was obtained as a white solid (127 mg, 60%). (HPLC (method F): 72%, RT: 4.38 min); MS (m/z) 297 [M+H]+, RT: 4.4 min.

4-Methyl-1H-indol-5-yl)-[2-(2,3,4-trimethoxy-phenyl)-furo[3,2-b]pyridin-7-yl]-amine ("B56"

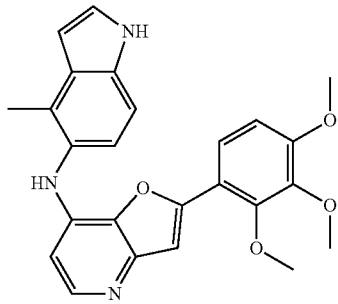

The title compound was prepared by procedure E using 7-chloro-2-(2,3,4-trimethoxyphenyl)furo[3,2-b]pyridine (34.40 mg; 0.11 mmol; 1.00 eq.) instead of 7-chloro-2-(3,4,5-trimethoxyphenyl)furo[3,2-b]pyridine, and 4-methyl-1H-indol-5-ylamine (16.51 mg; 0.11 mmol; 1.05 eq.) instead of 6-amino-2,2-difluoro-4H-benzo[1,4]oxazin-3-one, and was obtained as a beige solid (8 mg, 13%). (HPLC (method F): 97%, RT: 3.99 min); $^1$H NMR (500 MHz, CDCl$_3$) δ [ppm] 8.35 (s, 1H), 8.08 (d, J=5.5, 1H), 7.67 (d, J=8.8, 1H), 7.37 (s, 1H), 7.33-7.26 (m, 2H), 7.15 (d, J=8.5, 1H), 6.76 (d, J=8.9, 1H), 6.62 (s, 1H), 6.23 (d, J=5.6, 2H), 3.97 (s, 3H), 3.93 (s, 3H), 3.91 (s, 3H), 2.48 (s, 3H); MS (m/z) 430 [M+H]+, RT: 3.0 min.

[2-(3-Methoxy-phenyl)-furo[3,2-b]pyridin-7-yl]-(4-methyl-1H-indol-5-yl)-amine ("B57")

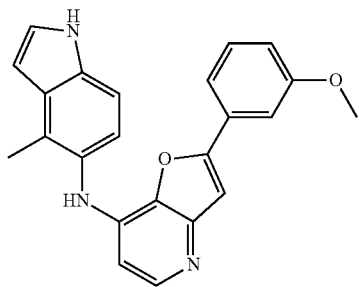

The title compound was prepared by procedure E using 7-chloro-2-(3-methoxyphenyl)furo[3,2-b]pyridine (29.70 mg; 0.11 mmol; 1.00 eq.) instead of 7-chloro-2-(3,4,5-trimethoxyphenyl)furo[3,2-b]pyridine, and 4-methyl-1H-indol-5-ylamine (17.56 mg; 0.12 mmol; 1.05 eq.) instead of 6-amino-2,2-difluoro-4H-benzo[1,4]oxazin-3-one, and was obtained as a beige solid (25 mg, 59%). (HPLC (method F): 98%, RT: 3.96 min); $^1$H NMR (500 MHz, DMSO-d$_6$) δ[ppm] 11.15 (s, 1H), 8.58 (s, 1H), 7.96 (d, J=5.4, 1H), 7.55 (d, J=7.6, 1H), 7.49 (s, 1H), 7.47 (s, 1H), 7.42-7.35 (m, 2H), 7.31 (d, J=8.4, 1H), 7.01 (d, J=8.5, 1H), 6.98 (d, J=8.0, 1H), 6.52 (s, 1H), 6.12 (d, J=5.4, 1H), 3.79 (s, 3H), 2.36 (s, 3H); MS (m/z) 370 [M+H]+, RT: 3.8 min.

{2-[4-(3-Dimethylamino-propoxy)-phenyl]-furo[3,2-b]pyridin-7-yl}-(4-methyl-1H-indo-5-yl)-amine ("B58")

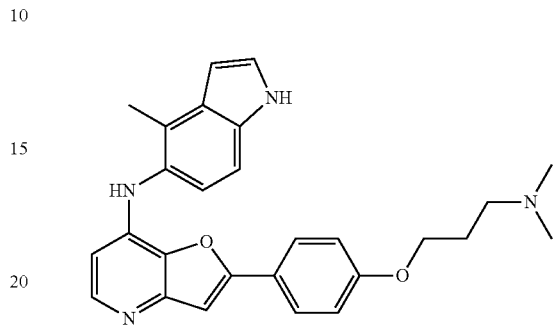

The title compound was prepared by procedure E using 3-[4-(7-chlorofuro[3,2-b]pyridin-2-yl)phenoxy]-N,N-dimethylpropan-1-amine (28.90 mg; 0.08 mmol; 1.00 eq.) instead of 7-chloro-2-(3,4,5-trimethoxyphenyl)furo[3,2-b]pyridine, and 4-methyl-1H-indol-5-ylamine (12.08 mg; 0.08 mmol; 1.05 eq.) instead of 6-amino-2,2-difluoro-4H-benzo[1,4]oxazin-3-one, and was obtained as a beige solid (11 mg, 33%). (HPLC (method F): 93%, RT: 3.08 min); $^1$H NMR (500 MHz, DMSO-d$_6$) δ [ppm] 11.15 (s, 1H), 8.51 (s, 1H), 7.92 (d, J=5.5, 1H), 7.89 (d, J=8.8, 2H), 7.38 (s, 1H), 7.30 (d, J=8.5, 1H), 7.26 (s, 1H), 7.04 (d, J=8.9, 2H), 7.00 (d, J=8.3, 1H), 6.52 (s, 1H), 6.05 (d, J=5.5, 1H), 4.07 (t, J=6.4, 2H), 2.40-2.33 (m, 5H), 2.15 (s, 6H), 1.90-1.84 (m, 2H); MS (m/z) 441 [M+H]+, RT: 2.4 min.

[2-(2,3-Dimethoxy-phenyl)-furo[3,2-b]pyridin-7-yl]-(4-methyl-1H-indol-5-yl)-amine ("B59")

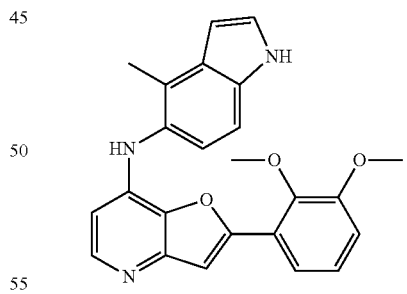

The title compound was prepared by procedure E using 7-chloro-2-(2,3-dimethoxyphenyl)furo[3,2-b]pyridine (30.00 mg; 0.10 mmol; 1.00 eq.) instead of 7-chloro-2-(3,4,5-trimethoxyphenyl)furo[3,2-b]pyridine, and 4-methyl-1H-indol-5-ylamine (15.89 mg; 0.11 mmol; 1.05 eq.) instead of 6-amino-2,2-difluoro-4H-benzo[1,4]oxazin-3-one, and was obtained as a beige solid (15 mg, 37%). (HPLC (method F): 99%, RT: 4.00 min); $^1$H NMR (500 MHz, DMSO-d$_6$) δ [ppm] 11.16 (s, 1H), 8.59 (s, 1H), 7.97 (d, J=5.5, 1H), 7.60 (d, J=7.6, 1H), 7.43-7.36 (m, 1H), 7.36-7.27 (m, 2H), 7.20-7.11 (m, 2H), 7.00 (d, J=8.5, 1H), 6.52 (s, 1H), 6.10 (d, J=5.5, 1H), 3.88 (s, 3H), 3.87 (s, 3H), 2.36 (s, 3H); MS (m/z) 400 [M+H]+, RT: 3.3 min.

[2-(2,3-Dihydro-benzo[1,4]dioxin-6-yl)-furo[3,2-b]pyridin-7-yl]-(4-methyl-1H-indol-5-yl)-amine ("B60")

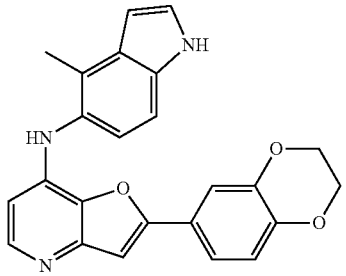 [SMILES: Cc1c(Nc2ccnc3cc(-c4ccc5c(c4)OCCO5)oc23)ccc2[nH]ccc12]

The title compound was prepared by procedure E using 7-chloro-2-(2,3-dihydro-1,4-benzodioxin-6-yl)furo[3,2-b]pyridine (28.50 mg; 0.10 mmol; 1.00 eq.) instead of 7-chloro-2-(3,4,5-trimethoxyphenyl)furo[3,2-b]pyridine, and 4-methyl-1H-indol-5-ylamine (15.21 mg; 0.10 mmol; 1.05 eq.) instead of 6-amino-2,2-difluoro-4H-benzo[1,4]oxazin-3-one, and was obtained as a beige solid (22 mg, 55%). (HPLC (method F): 96%, RT: 3.96 min); $^1$H NMR (500 MHz, DMSO-$d_6$) δ [ppm] 11.15 (s, 1H), 8.52 (s, 1H), 7.92 (d, J=5.5, 1H), 7.54 (d, J=1.8, 1H), 7.46 (d, J=8.5, 1H), 7.41-7.34 (m, 1H), 7.34-7.26 (m, 2H), 6.98 (dd, J=14.6, 8.5, 2H), 6.51 (s, 1H), 6.05 (d, J=5.4, 1H), 4.31 (s, 4H), 2.36 (s, 3H); MS (m/z) 398 [M+H]+, RT: 3.9 min.

3-(7-chlorofuro[3,2-b]pyridin-2-yl)quinoline

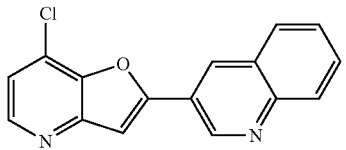 [SMILES: Clc1ccnc2cc(-c3cnc4ccccc4c3)oc12]

The title compound was prepared by procedure C using 3-(4,4,5,5-tetramethyl-1,3,2-dioxaborolan-2-yl)quinoline (150.63 mg; 0.59 mmol; 1.10 eq.) instead of 4-fluorophenylboronic acid and was obtained as an off-white solid (35 mg, 23%). (HPLC (method F): 94%, RT: 3.57 min); $^1$H NMR (500 MHz, DMSO-$d_6$) δ [ppm] 9.54 (s, 1H), 8.94 (s, 1H), 8.52 (s, 1H), 8.20 (m, 1H), 8.08 (s, 2H), 7.85 (m, 1H), 7.71 (m, 1H), 7.59 (m, 1H); MS (m/z) 281 [M+H]+, RT: 3.4 min.

{4-[7-(4-Methyl-1H-indol-5-ylamino)-furo[3,2-b]pyridin-2-yl]-phenyl}-methanol ("B61")

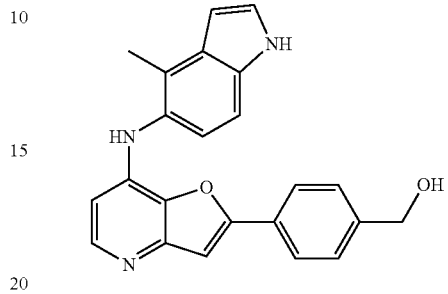

The title compound was prepared by procedure E using [4-(7-chlorofuro[3,2-b]pyridin-2-yl)phenyl]methanol (20.40 mg; 0.08 mmol; 1.00 eq.) instead of 7-chloro-2-(3,4,5-trimethoxyphenyl)furo[3,2-b]pyridine, and 4-methyl-1H-indol-5-ylamine (12.06 mg; 0.08 mmol; 1.05 eq.) instead of 6-amino-2,2-difluoro-4H-benzo[1,4]oxazin-3-one, and was obtained as a beige solid (8 mg, 28%). (HPLC (method F): 97%, RT: 3.30 min); $^1$H NMR (500 MHz, DMSO-$d_6$) δ [ppm] 11.14 (s, 1H), 8.54 (s, 1H), 7.94 (d, J=5.4, 1H), 7.91 (d, J=8.2, 2H), 7.42 (d, J=8.1, 2H), 7.40-7.35 (m, 2H), 7.30 (d, J=8.3, 1H), 7.00 (d, J=8.4, 1H), 6.52 (s, 1H), 6.09 (d, J=5.4, 1H), 5.26 (s, 1H), 4.55 (d, J=5.6, 2H), 2.36 (s, 3H); MS (m/z) 370 [M+H]+, RT: 3.2 min.

[2-(4-Isopropenyl-phenyl)-furo[3,2-b]pyridin-7-yl]-(4-methyl-1H-indol-5-yl)-amine ("B62")

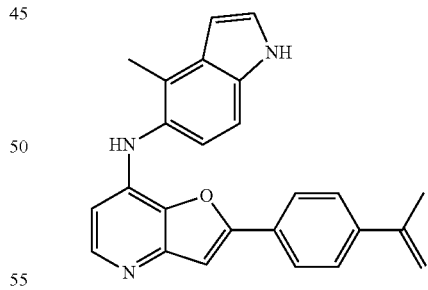

The title compound was prepared by procedure E using 2-[4-(7-chlorofuro[3,2-b]pyridin-2-yl)phenyl]propan-2-ol (29.50 mg; 0.10 mmol; 1.00 eq.) instead of 7-chloro-2-(3,4,5-trimethoxyphenyl)furo[3,2-b]pyridine, and 4-methyl-1H-indol-5-ylamine (15.74 mg; 0.11 mmol; 1.05 eq.) instead of 6-amino-2,2-difluoro-4H-benzo[1,4]oxazin-3-one, and was obtained as a beige solid (26 mg, 66%). (HPLC (method F): 93%, RT: 4.44 min); $^1$H NMR (500 MHz, DMSO-$d_6$) δ [ppm] 11.14 (s, 1H), 8.57 (s, 1H), 7.99-7.90 (m, 3H), 7.62 (d, J=8.5, 2H), 7.44 (s, 1H), 7.38 (t, J=2.7, 1H), 7.31 (d, J=8.4, 1H), 7.01

(d, J=8.4, 1H), 6.52 (s, 1H), 6.09 (d, J=5.5, 1H), 5.55 (s, 1H), 5.18 (s, 1H), 2.36 (s, 3H), 2.16 (s, 3H); MS (m/z) 380 [M+H]⁺, RT: 4.4 min.

[2-(3,5-Dimethyl-isoxazol-4-yl)-furo[3,2-b]pyridin-7-yl]-(4-methyl-1H-indol-5-yl)-amine ("B63")

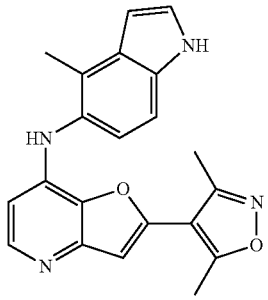 [SMILES: Cc1noc(C)c1-c1cc2nccc(Nc3ccc4[nH]ccc4c3C)c2o1]

The title compound was prepared by procedure E using 7-chloro-2-(3,5-dimethylisoxazol-4-yl)furo[3,2-b]pyridine (25.10 mg; 0.10 mmol; 1.00 eq.) instead of 7-chloro-2-(3,4,5-trimethoxyphenyl)furo[3,2-b]pyridine, and 4-methyl-1H-indol-5-ylamine (15.49 mg; 0.11 mmol; 1.05 eq.) instead of 6-amino-2,2-difluoro-4H-benzo[1,4]oxazin-3-one, and was obtained as a beige solid (19 mg, 52%). (HPLC (method F): 99%, RT: 3.49 min); ¹H NMR (500 MHz, DMSO-d₆) δ [ppm] 11.13 (s, 1H), 8.49 (s, 1H), 7.98 (d, J=5.5, 1H), 7.37 (t, J=2.7, 1H), 7.29 (d, J=8.5, 1H), 7.07 (s, 1H), 6.99 (d, J=8.4, 1H), 6.51 (s, 1H), 6.17 (d, J=5.5, 1H), 2.52 (s, 3H), 2.37 (s, 3H), 2.34 (s, 3H); MS (m/z) 359 [M+H]⁺, RT: 3.4 min.

N-(4-Fluoro-phenyl)-3-[2-(3,4,5-trimethoxy-phenyl)-furo[3,2-b]pyridin-7-yl]-benzamide ("B64")

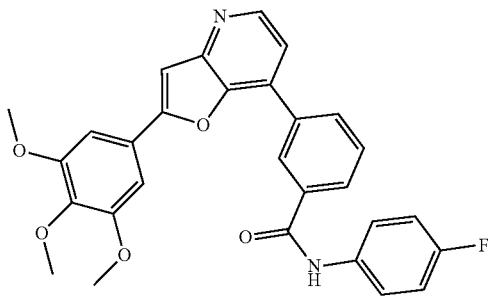 [SMILES: COc1cc(-c2cc3nccc(-c4cccc(C(=O)Nc5ccc(F)cc5)c4)c3o2)cc(OC)c1OC]

The title compound was prepared by procedure C using 7-chloro-2-(3,4,5-trimethoxyphenyl)furo[3,2-b]pyridine (45.00 mg; 0.14 mmol; 1.00 eq.) instead of 7-chloro-2-iodo-furo[3,2-b]pyridine, and 3-(4-fluorophenyl)aminocarbonylphenylboronic acid (40.10 mg; 0.15 mmol; 1.10 eq.) instead of 4-fluorophenylboronic acid and was obtained as a white solid (57 mg, 81%). (HPLC (method F): 87%, RT: 4.33 min); 1H NMR (500 MHz, DMSO-d₆) δ [ppm] 10.51 (s, 1H), 8.96 (s, 1H), 8.67-8.58 (m, 1H), 8.34 (d, J=7.4, 1H), 8.15 (d, J=7.4, 1H), 7.88-7.74 (m, 5H), 7.38 (s, 2H), 7.24 (t, J=7.8, 2H), 3.87 (s, 6H), 3.77-3.68 (m, 3H); MS (m/z) 499 [M+H]⁺, RT: 4.3 min.

N-{4-[2-(3,4,5-Trimethoxy-phenyl)-furo[3,2-b]pyridin-7-yl]-phenyl}-benzamide ("B65")

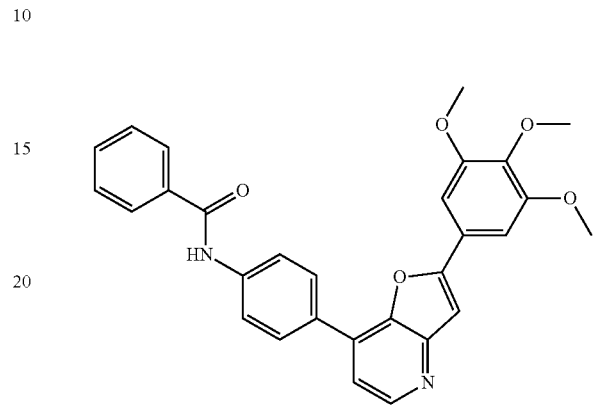

The title compound was prepared by procedure C using 7-chloro-2-(3,4,5-trimethoxyphenyl)furo[3,2-b]pyridine (45.00 mg; 0.14 mmol; 1.00 eq.) instead of 7-chloro-2-iodo-furo[3,2-b]pyridine, and 4-benzamidophenylboronic acid (37.32 mg; 0.15 mmol; 1.10 eq.) instead of 4-fluorophenylboronic acid and was obtained as a pale yellow solid (55 mg, 81%). (HPLC (method F): 94%, RT: 4.14 min); MS (m/z) 481 [M+H]⁺, RT: 4.1 min.

N-Phenyl-4-[2-(3,4,5-trimethoxy-phenyl)-furo[3,2-b]pyridin-7-yl]-benzamide ("B66")

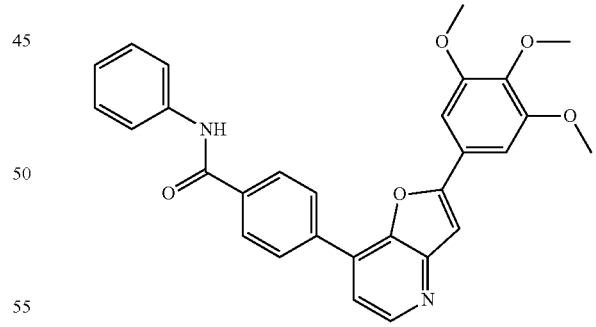

The title compound was prepared by procedure C using 7-chloro-2-(3,4,5-trimethoxyphenyl)furo[3,2-b]pyridine (45.00 mg; 0.14 mmol; 1.00 eq.) instead of 7-chloro-2-iodo-furo[3,2-b]pyridine, and 4-phenylaminocarbonylphenylboronic acid (37.32 mg; 0.15 mmol; 1.10 eq.) instead of 4-fluorophenylboronic acid and was obtained as a yellow solid (68 mg, 100%). (HPLC (method F): 77%, RT: 4.21 min); 1H NMR (500 MHz, DMSO-d₆) δ[ppm] 10.41 (s, 1H), 8.65-8.56 (m, 1H), 8.30 (d, J=7.9, 2H), 8.21 (d, J=8.5, 2H), 7.85-7.76 (m, 3H), 7.70 (dd, J=3.9, 1.2, 1H), 7.38 (t, J=7.6, 2H), 7.34 (s, 2H), 7.13 (t, J=7.4, 1H), 3.92 (s, 6H), 3.79-3.70 (m, 3H); MS (m/z) 481 [M+H]+, RT: 4.2 min.

4-Methyl-piperazin-1-yl)-{4-[2-(3,4,5-trimethoxy-phenyl)-furo[3,2-b]pyridin-7-yl]-phenyl}-methanone ("B67")

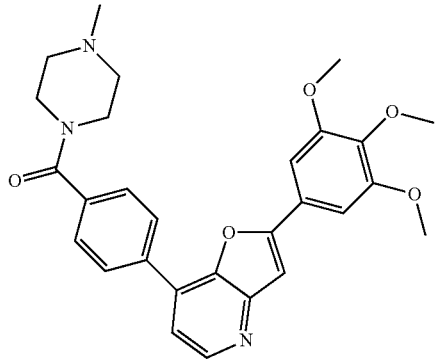 [SMILES: COc1cc(-c2cc3nccc(-c4ccc(C(=O)N5CCN(C)CC5)cc4)c3o2)cc(OC)c1OC]

The title compound was prepared by procedure C using 7-chloro-2-(3,4,5-trimethoxyphenyl)furo[3,2-b]pyridine (45.00 mg; 0.14 mmol; 1.00 eq.) instead of 7-chloro-2-iodo-furo[3,2-b]pyridine, and (4-methylpiperazine-1-yl)[4-(4,4,5,5-tetramethyl-1,3,2-dioxaborolan-2-yl)phenyl]methanone (51.12 mg; 0.15 mmol; 1.10 eq.) instead of 4-fluorophenyl-boronic acid and was obtained as a beige solid (57 mg, 84%). (HPLC (method F): 98%, RT: 2.70 min); $^1$H NMR (500 MHz, DMSO-$d_6$) δ [ppm] 8.59 (dd, J=5.1, 1.5, 1H), 8.25-8.16 (m, 2H), 7.77 (d, J=1.5, 1H), 7.69-7.61 (m, 3H), 7.32 (d, J=1.4, 2H), 3.91 (d, J=1.3, 6H), 3.74 (d, J=1.5, 3H), 3.71-3.57 (m, 2H), 3.46-3.35 (m, 2H), 2.43-2.26 (m, 4H), 2.21 (s, 3H); MS (m/z) 488 [M+H]+, RT: 2.7 min.

4-Methyl-piperazin-1-yl)-{3-[2-(3,4,5-trimethoxy-phenyl)-furo[3,2-b]pyridin-7-yl]-phenyl}-methanone ("B68")

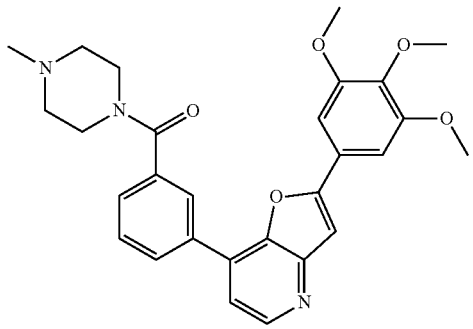

The title compound was prepared by procedure C using 7-chloro-2-(3,4,5-trimethoxyphenyl)furo[3,2-b]pyridine (45.00 mg; 0.14 mmol; 1.00 eq.) instead of 7-chloro-2-iodo-furo[3,2-b]pyridine, and 3-(4-methylpiperazine-1-carbonyl)-benzeneboronic acid pinacol ester (51.12 mg; 0.15 mmol; 1.10 eq.) instead of 4-fluorophenylboronic acid and was obtained as a beige solid (45 mg, 66%). (HPLC (method F): 95%, RT: 2.74 min); $^1$H NMR (500 MHz, DMSO-$d_6$) δ[ppm] 8.58 (dd, J=5.1, 0.7, 1H), 8.26 (s, 1H), 8.23-8.15 (m, 1H), 7.76 (d, J=0.7, 1H), 7.74-7.65 (m, 2H), 7.55 (d, J=7.6, 1H), 7.32 (s, 2H), 3.92 (s, 6H), 3.74 (d, J=0.7, 3H), 3.69-3.55 (m, 2H), 3.48-3.36 (m, 2H), 2.43-2.23 (m, 4H), 2.19 (s, 3H); MS (m/z) 488 [M+H]+, RT: 2.7 min.

2-Fluoro-N-(2-hydroxy-ethyl)-4-[2-(3,4,5-tri-methoxy-phenyl)-furo[3,2-b]pyridin-7-yl]-benza-mide ("B69")

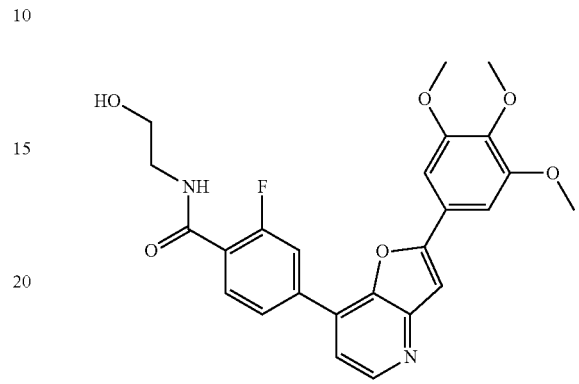

The title compound was prepared by procedure C using 7-chloro-2-(3,4,5-trimethoxyphenyl)furo[3,2-b]pyridine (45.00 mg; 0.14 mmol; 1.00 eq.) instead of 7-chloro-2-iodo-furo[3,2-b]pyridine, and 3-fluoro-4-[(2-hydroxyethyl)-car-bamoyl]benzeneboronic acid (35.14 mg; 0.15 mmol; 1.10 eq.) instead of 4-fluorophenylboronic acid and was obtained as a pale yellow solid (32 mg, 48%). (HPLC (method F): 99%, RT: 3.09 min); $^1$H NMR (500 MHz, DMSO-$d_6$) δ [ppm] 8.60 (dd, J=5.1, 1.8, 1H), 8.38 (s, 1H), 8.12-8.06 (m, 2H), 7.89 (t, J=7.9, 1H), 7.79 (d, J=1.8, 1H), 7.71 (dd, J=5.1, 1.8, 1H), 7.33 (d, J=1.7, 2H), 4.80-4.73 (m, 1H), 3.92 (d, J=1.7, 6H), 3.74 (d, J=1.8, 3H), 3.57-3.51 (m, 2H), 3.37 (dd, J=12.0, 6.1, 2H); MS (m/z) 467 [M+H]+, RT: 3.0 min.

1-{5-[2-(3,4,5-Trimethoxy-phenyl)-furo[3,2-b]pyri-din-7-yl]-thiophen-2-yl}-ethanone ("B70")

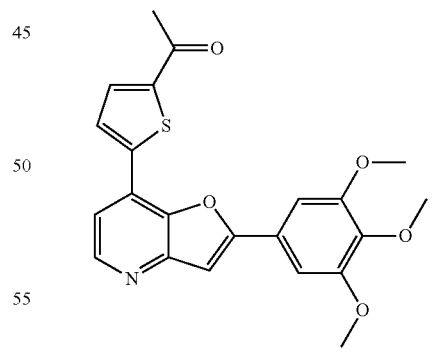

The title compound was prepared by procedure C using 7-chloro-2-(3,4,5-trimethoxyphenyl)furo[3,2-b]pyridine (45.00 mg; 0.14 mmol; 1.00 eq.) instead of 7-chloro-2-iodo-furo[3,2-b]pyridine, and 5-acetyl-2-thiopheneboronic acid (26.32 mg; 0.15 mmol; 1.10 eq.) instead of 4-fluorophenyl-boronic acid and was obtained as a yellow solid (15 mg, 26%). (HPLC (method F): 88%, RT: 3.84 min); $^1$H NMR (500 MHz, DMSO-$d_6$) δ [ppm] 8.56 (d, J=5.1, 1H), 8.22 (d, J=4.0, 1H), 8.12 (d, J=3.8, 1H), 7.79 (d, J=1.0, 1H), 7.78 (d, J=5.1, 1H), 7.40 (s, 2H), 3.94 (s, 6H), 3.76 (d, J=0.9, 3H), 2.63 (s, 3H); MS (m/z) 410 [M+H]⁺, RT: 2.5 min.

Procedure I 6-(2-(3,4,5-Trimethoxyphenyl)furo[3,2-b]pyridin-7-yl)indolin-2-one ("B71")

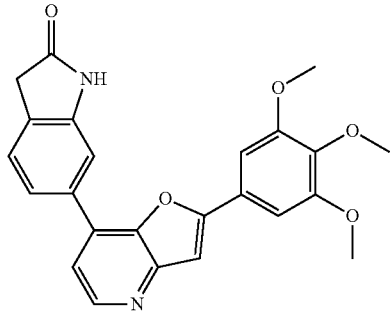 [SMILES: COc1cc(-c2cc3nccc(-c4ccc5c(c4)NC(=O)C5)c3o2)cc(OC)c1OC]

To a 5.0 mL sealed tube with stirbar was added 7-chloro-2-(3,4,5-trimethoxyphenyl)furo[3,2-b]pyridine (60.00 mg; 0.19 mmol; 1.00 eq.), palladium diacetate (4.21 mg; 0.02 mmol; 0.10 eq.), dicyclohexyl (2',6'-dimethoxybiphenyl-2-yl) phosphine (15.41 mg; 0.04 mmol; 0.20 eq.), cesium carbonate (0.05 ml; 0.56 mmol; 3.00 eq.) and 2-hydroxy-1,1,2-trimethylpropyl hydrogen (2-oxo-2,3-dihydro-1H-indol-6-yl) boronate (62.40 mg; 0.23 mmol; 1.20 eq.) in dioxane (2.00 ml) and water (0.25 ml). The mixture was stirred at 100° C. for 12 h before it was cooled to room temperature and was purified by Waters prep-HPLC to afford the title compound as a green solid (3.9 mg, 5%). (HPLC (method F): 99%); $^1$H NMR (400 MHz, DMSO-$d_6$) δ [ppm] 10.66 (s, 1H), 8.58 (d, J=5.5 Hz, 1H), 7.80 (s, 1H), 7.68 (dd, J=7.7, 1.5 Hz, 1H), 7.63 (d, J=5.1 Hz, 1H), 7.58 (d, J=1.1 Hz, 1H), 7.47 (d, J=8.0 Hz, 1H), 7.33 (s, 2H), 3.92 (s, 6H), 3.74 (s, 3H), 3.61 (s, 2H); MS (m/z) 417 [M+H]⁺, RT: 3.5 min.

N-(3-(2-(3,4,5-Trimethoxyphenyl)furo[3,2-b]pyridin-7-yl)phenyl)acetamide ("B72")

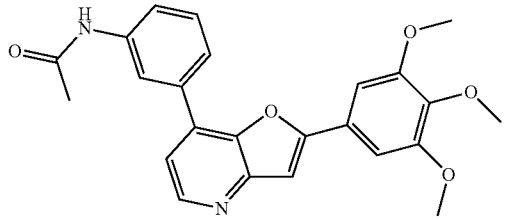 [SMILES: COc1cc(-c2cc3nccc(-c4cccc(NC(C)=O)c4)c3o2)cc(OC)c1OC]

The title compound was prepared by procedure I using [3-(acetylamino)-phenyl]boronic acid (40.30 mg; 0.23 mmol; 1.20 eq.) instead of 2-hydroxy-1,1,2-trimethylpropyl hydrogen (2-oxo-2,3-dihydro-1H-indol-6-yl) boronate and was obtained as a green yellow solid (39.1 mg, 49.3%). (HPLC (method F): 99%); $^1$H NMR (400 MHz, DMSO-$d_6$) δ [ppm] 10.27 (s, 1H), 9.00 (dd, J=1.8, 1.8 Hz, 1H), 8.62 (d, J=6.4 Hz, 1H), 7.85 (s, 1H), 7.74-7.71 (m, 2H), 7.58-7.50 (m, 2H), 7.45 (s, 2H), 7.33 (s, 2H), 3.97 (s, 6H), 3.76 (s, 3H), 2.09 (s, 3H); MS (m/z) 419 [M+H]⁺, RT: 3.6 min.

7-(4-Methoxy-3,5-dimethylphenyl)-2-(3,4,5-trimethoxyphenyl)furo[3,2-b]pyridine ("B73")

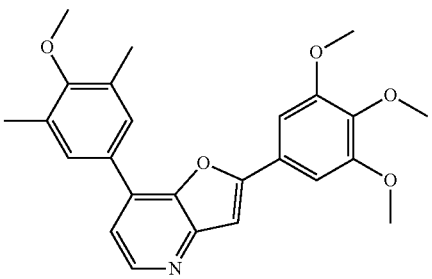

The title compound was prepared by procedure I using (4-methoxy-3,5-dimethylphenyl)boronic acid (34.45 mg; 0.19 mmol; 1.20 eq.) instead of 2-hydroxy-1,1,2-trimethylpropyl hydrogen (2-oxo-2,3-dihydro-1H-indol-6-yl) boronate and was obtained as a green yellow solid (35.0 mg, 51.8%). (HPLC (method F): 99%); $^1$H NMR (400 MHz, DMSO-$d_6$) δ [ppm] 8.62 (d, J=6.0 Hz, 1H), 7.96 (s, 2H), 7.83 (s, 1H), 7.78 (d, J=6.4 Hz, 1H), 7.40 (s, 2H), 3.93 (s, 6H), 3.75 (s, 3H), 2.37 (s, 6H); MS (m/z) 420 [M+H]⁺, RT: 4.6 min.

7-(1H-Indol-5-yl)-2-(3,4,5-trimethoxyphenyl)furo[3,2-b]pyridine ("B74")

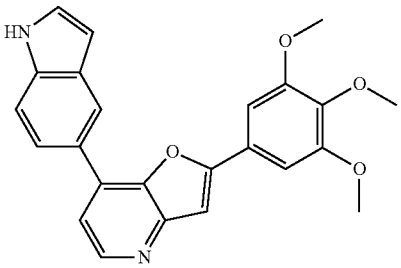 [SMILES: COc1cc(-c2cc3nccc(-c4ccc5[nH]ccc5c4)c3o2)cc(OC)c1OC]

The title compound was prepared by procedure I using 1H-indol-5-ylboronic acid (24.16 mg; 0.15 mmol; 1.20 eq.) instead of 2-hydroxy-1,1,2-trimethylpropyl hydrogen (2-oxo-2,3-dihydro-1H-indol-6-yl) boronate and was obtained as a green yellow solid (13.0 mg, 23.6%). (HPLC (method F): 99%); $^1$H NMR (400 MHz, DMSO-$d_6$) δ [ppm] 11.50 (s, 1H), 8.65 (d, J=1.8 Hz, 1H), 8.54 (s, 1H), 7.95 (dd, J=8.4, 1.8 Hz, 1H), 7.89 (d, J=6.0 Hz, 1H), 7.87 (s, 1H), 7.67 (d, J=8.4 Hz, 1H), 7.51 (dd, J=2.9, 2.9 Hz, 1H), 7.41 (s, 2H), 6.64 (m, 1H), 3.97 (s, 6H), 3.76 (s, 3H), 2.09 (s, 3H); MS (m/z) 401 [M+H]⁺, RT: 3.9 min.

N-Cyclopentyl-4-(2-(3,4,5-trimethoxyphenyl)furo[3,2-b]pyridin-7-yl)benzamide ("B75")

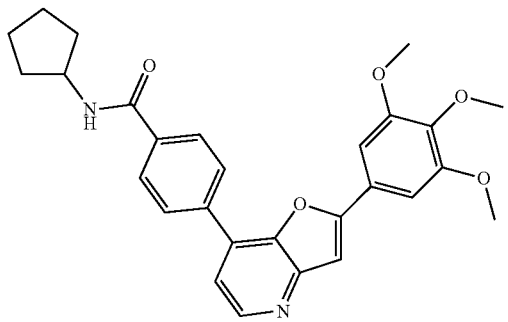 [SMILES: COc1cc(-c2cc3nccc(-c4ccc(C(=O)NC5CCCC5)cc4)c3o2)cc(OC)c1OC]

The title compound was prepared by procedure I using {4-[(cyclopentylamino)-arbonyl]phenyl}boronic acid (34.99 mg; 0.15 mmol; 1.20 eq.) instead of 2-hydroxy-1,1,2-trimethylpropyl hydrogen (2-oxo-2,3-dihydro-1H-indol-6-yl) boronate and was obtained as a green yellow solid (36.9 mg, 57.5%). (HPLC (method F): 99%); $^1$H NMR (400 MHz, DMSO-$d_6$) δ [ppm] 8.64 (d, J=6.0 Hz, 1H), 8.49 (d, J=7.2 Hz, 1H), 8.23 (dd, J=6.6, 1.8 Hz, 2H), 8.10 (dd, J=6.6, 1.8 Hz, 2H), 7.83 (s, 1H), 7.75 (d, J=5.2 Hz, 1H), 7.34 (s, 1H), 4.28 (m, 1H), 3.92 (s, 6H), 3.74 (s, 3H), 1.91 (m, 2H), 1.72 (m, 2H), 1.57 (m, 4H); MS (m/z) 473 [M+H]⁺, RT: 4.3 min.

7-(Benzo[d][1,3]dioxol-5-yl)-2-(3,4,5-trimethoxyphenyl)furo[3,2-b]pyridine ("B76")

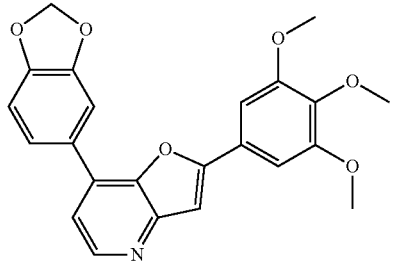 [SMILES: COc1cc(-c2cc3nccc(-c4ccc5c(c4)OCO5)c3o2)cc(OC)c1OC]

The title compound was prepared by procedure I using 1,3-benzodioxol-5-ylboronic acid (24.91 mg; 0.15 mmol; 1.20 eq.) instead of 2-hydroxy-1,1,2-trimethylpropyl hydrogen (2-oxo-2,3-dihydro-1H-indol-6-yl) boronate and was obtained as a green yellow solid (27.5 mg, 53.7%). (HPLC (method F): 99%); $^1$H NMR (400 MHz, DMSO-$d_6$) δ [ppm] 8.56 (d, J=5.2 Hz, 1H), 7.78-7.76 (m, 2H), 7.72 (d, J=1.8 Hz, 1H), 7.67 (d, J=6.4 Hz, 1H), 7.32 (s, 2H), 7.22 (d, J=8.0 Hz, 1H), 6.17 (s, 2H), 3.91 (s, 6H), 3.74 (s, 3H); MS (m/z) 406 [M+H]⁺, RT: 4.1 min.

7-(6-Methoxynaphthalen-2-yl)-2-(3,4,5-trimethoxyphenyl)furo[3,2-b]pyridine ("B77")

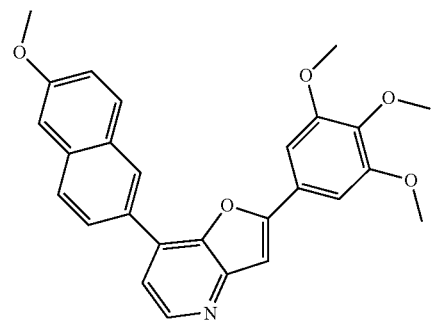 [SMILES: COc1ccc2cc(-c3ccnc4cc(-c5cc(OC)c(OC)c(OC)c5)oc34)ccc2c1]

The title compound was prepared by procedure I using (6-methoxy-2-naphthyl)boronic acid (30.33 mg; 0.15 mmol; 1.20 eq.) instead of 2-hydroxy-1,1,2-trimethylpropyl hydrogen (2-oxo-2,3-dihydro-1H-indol-6-yl) boronate and was obtained as a white solid (17.5 mg, 31.4%). (HPLC (method F): 99%); $^1$H NMR (400 MHz, DMSO-$d_6$) δ [ppm] 8.74 (s, 1H), 8.59 (d, J=5.2 Hz, 1H), 8.20 (dd, J=8.4, 1.6 Hz, 1H), 8.06 (d, J=7.7 Hz, 1H), 8.02 (d, J=8.8 Hz, 1H), 7.78 (s, 1H), 7.72 (d, J=5.1 Hz, 2H), 7.45 (d, J=2.5 Hz, 1H), 7.37 (s, 2H), 7.27 (dd, J=8.8, 2.6 Hz, 1H), 3.933 (s, 6H), 3.928 (s, 3H), 3.74 (s, 3H); MS (m/z) 442 [M+H]⁺, RT: 4.7 min.

7-(Benzo[b]thiophen-2-yl)-2-(3,4,5-trimethoxyphenyl)furo[3,2-b]pyridine ("B78")

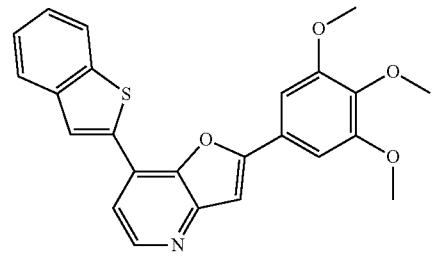 [SMILES: COc1cc(-c2cc3nccc(-c4cc5ccccc5s4)c3o2)cc(OC)c1OC]

The title compound was prepared by procedure I using 1-benzothien-2-ylboronic acid (26.72 mg; 0.15 mmol; 1.20 eq.) instead of 2-hydroxy-1,1,2-trimethylpropyl hydrogen (2-oxo-2,3-dihydro-1H-indol-6-yl) boronate and was obtained as a yellow solid (8.6 mg, 15.2%). (HPLC (method F): 99%); $^1$H NMR (400 MHz, DMSO-$d_6$) δ [ppm] 8.60 (d, J=5.2, 1H), 8.57 (s, 1H), 8.14 (m, 1H), 8.05 (m, 1H), 7.84 (s, 1H), 7.77 (d, J=5.2, 1H), 7.50 (m, 2H), 7.45 (s, 1H), 3.97 (s, 6H), 3.80 (s, 3H); MS (m/z) 418 [M+H]⁺, RT: 4.8 min.

Procedure K

3-[7-(4-Phenoxyphenoxy)furo[3,2-b]pyridin-2-yl]aniline ("B79")

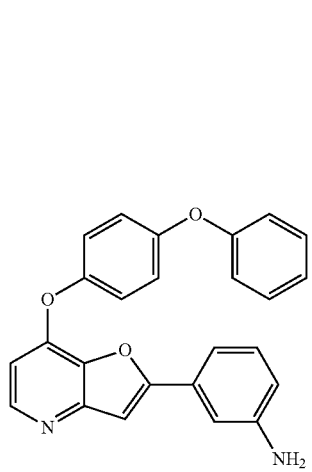 [SMILES: Nc1cccc(-c2cc3nccc(Oc4ccc(Oc5ccccc5)cc4)c3o2)c1]

3-(7-Chlorofuro[3,2-b]pyridin-2-yl)aniline

To a 20-mL microwave vial was added 7-chloro-2-iodofuro[3,2-b]pyridine (500.00 mg; 1.79 mmol), 3-(4,4,5,5-tetramethyl-1,3,2-dioxaborolan-2-yl)aniline (431.19 mg; 1.97 mmol), palladium(ii) acetate (20.08 mg; 0.09 mmol), 2-dicyclohexylphosphino-2',6'-dimethoxybiphenyl (73.45 mg; 0.18 mmol), and potassium carbonate (741.81 mg; 5.37 mmol). The reagents were suspended in dioxane (6.00 ml) and water (0.60 ml) and run in microwave reactor at 150° C. for 2 hours. The reaction mixture was cooled to room temperature, dried over Na₂SO₄, filtered and concentrated. The crude mixture was purified using Biotage column chromatography (50-100% EtOAc/Hexanes) to afford the title compound as a yellow solid (88.20 mg, 20%).

3-[7-(4-Phenoxyphenoxy)furo[3,2-b]pyridin-2-yl]aniline

To a 10-mL microwave vial was added 3-(7-chlorofuro[3,2-b]pyridin-2-yl)aniline (88.20 mg; 0.36 mmol), 4-phenoxyphenol (100.68 mg; 0.54 mmol), and cesium carbonate (352.35 mg, 1.08 mmol). The reagents were suspended in DMF (5.00 ml) and run in the microwave reactor at 160° C. for 2 hours. The reaction mixture was cooled to room temperature. Water and brine were added to the reaction mixture which was then extracted with EtOAc. The combined organic layers were dried over Na₂SO₄, filtered and concentrated. The crude mixture was purified using Biotage column chromatography (20-100% EtOAc/Hexanes) to afford the title compound as a white solid (111.70 mg, 79%). HPLC (method F): 91%, RT=3.949 min. MS: m/z=395 [M+H]⁺, RT=3.80 min.

N-{3-[7-(4-Phenoxyphenoxy)furo[3,2-b]pyridin-2-yl]phenyl}propanamide (2) ("B80")

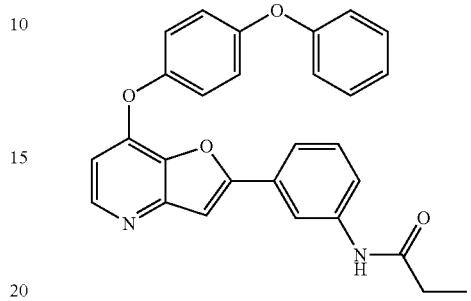

To a 20-mL glass vial was added 3-[7-(4-phenoxyphenoxy)furo[3,2-b]pyridin-2-yl]aniline (30.00 mg; 0.08 mmol) and pyridine (1.00 ml). The resulting mixture was cooled to 0° C. and stirred for 5 minutes. Then propanoyl chloride (0.01 ml; 0.08 mmol) was added. The ice bath was left to melt. The reaction mixture was stirred at room temperature overnight. Water was added to the mixture which was then extracted with EtOAc. The combined organic layers were dried over Na₂SO₄, filtered and concentrated. The crude mixture was purified using Biotage column chromatography (50-100% EtOAc/Hexanes) to afford the title compound as a white solid (28.00 mg, 82%). HPLC (method F): 92%, RT=4.530 min. ¹H NMR (DMSO-d₆) δ [ppm] 7.52 (d, 1H), 7.45 (d, 1H), 6.85-6.80 (dd, 2H), 6.70-6.64 (q, 1H), 6.60-6.49 (m, 6H), 6.36-6.34 (m, 3H), 6.26 (d, 2H), 6.01 (d, 1H), 1.63 (q, 2H), 0.42 (t, 3H). MS: m/z=451 [M+H]⁺, RT=4.08 min.

Procedure L

N-{3-[2-(3,4-Dimethoxyphenyl)furo[3,2-b]pyridin-7-yl]-2-methylphenyl}-3-(trifluoromethyl)benzamide ("B81")

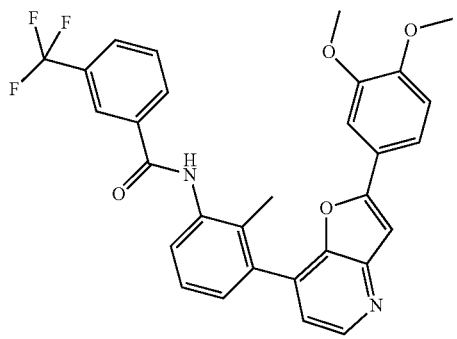 [SMILES: COc1ccc(-c2cc3nccc(-c4cccc(NC(=O)c5cccc(C(F)(F)F)c5)c4C)c3o2)cc1OC]

7-Chloro-2-(3,4-dimethoxyphenyl)furo[3,2-b]pyridine

The compound was synthesized according to the procedure K using (3,4-dimethoxyphenyl)boronic acid.

3-[2-(3,4-Dimethoxyphenyl)furo[3,2-b]pyridin-7-yl]-2-methylaniline

The compound was synthesized according to the procedure K using 7-chloro-2-(3,4-dimethoxyphenyl)furo[3,2-b]pyridine and 2-methyl-3-(4,4,5,5-tetramethyl-1,3,2-dioxaborolan-2-yl)aniline.

N-{3-[2-(3,4-Dimethoxyphenyl)furo[3,2-b]pyridin-7-yl]-2-methylphenyl}-3-(trifluoromethyl)benzamide To a 20-mL glass vial was added 3-[2-(3,4-dimethoxyphenyl)furo[3,2-b]pyridin-7-yl]-2-methylaniline (19.20 mg; 0.05 mmol), triethylamine (0.01 ml; 0.11 mmol) suspended in DCM (2.00 ml). 3-(trifluoromethyl)benzoyl chloride (16.67 mg; 0.08 mmol) was then added. The reaction mixture was stirred at room temperature overnight. Water was added to the reaction mixture which was then extracted with EtOAc. The combined organic layers were dried over $Na_2SO_4$, filtered and concentrated. The crude mixture was purified using Biotage column chromatography (20-100% EtOAc/Hexanes). Fractions containing the desired product were combined and concentrated. The mixture was then purified using preparative HPLC to afford the title compound as a yellow solid (3.80 mg, 13%). HPLC (method F): 100%, RT=4.531 min. $^1$H NMR ($CDCl_3$) δ [ppm] 8.58 (d, 1H), 8.19 (s, 1H), 8.12 (d, 1H), 7.96 (d, 1H), 7.88-7.84 (m, 2H), 7.71-7.68 (m, 2H), 7.60-7.47 (m, 3H), 7.39-7.38 (m, 2H), 7.00-6.97 (m, 1H), 4.01 (s, 3H), 3.96 (s, 3H), 2.27 (s, 3H). MS: m/z=533 [M+H]$^+$, RT=3.91 min.

N-{3-[7-(4-Phenoxyphenoxy)furo[3,2-b]pyridin-2-yl]phenyl}acrylamide ("B82")

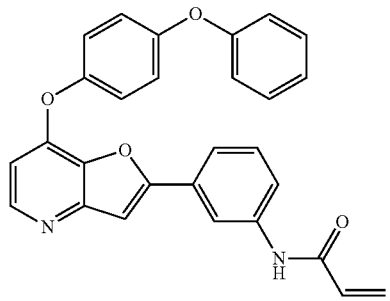 [SMILES: C=CC(=O)Nc1cccc(-c2cc3nccc(Oc4ccc(Oc5ccccc5)cc4)c3o2)c1]

To a 20-mL glass vial was added 3-[7-(4-phenoxyphenoxy)furo[3,2-b]pyridin-2-yl]aniline (30.00 mg; 0.08 mmol), N,N-diethylethanamine (0.02 ml; 0.15 mmol) suspended in 1-methylpyrrolidin-2-one (0.35 ml) and DCM (2.00 ml). The resulting mixture was cooled to 0° C. and stirred for 5 minutes. Acryloyl chloride (0.02 ml; 0.23 mmol) was added. The ice bath was left to melt. The reaction mixture was then stirred at room temperature overnight. The mixture was concentrated. The crude mixture was purified using Biotage column chromatography (0-40% MeOH/EtOAc) to afford the title compound as a white solid (5.00 mg, 15%). HPLC (method F): 100%, RT=4.538 min. $^1$H NMR (DMSO-$d_6$) δ [ppm] 10.29 (s, 1H), 8.31 (d, 1H), 8.22 (s, 1H), 7.74 (d, 1H), 7.63 (d, 1H), 7.55 (s, 1H), 7.43 (t, 1H), 7.35 (t, 2H), 7.31 (d, 2H), 7.09 (d, 3H), 7.02 (d, 2H), 6.66 (d, 1H), 6.41-6.36 (dd, 1H), 6.25 (d, 1H), 5.73 (d, 1H). MS: m/z=449 [M+H]$^+$, RT=4.08 min.

Procedure M

N-{3-[2-(3,4-Dimethoxyphenyl)furo[3,2-b]pyridin-7-yl]-2-methylphenyl}-4,5,6,7-tetrahydro-1-benzothiophene-2-carboxamide ("B83")

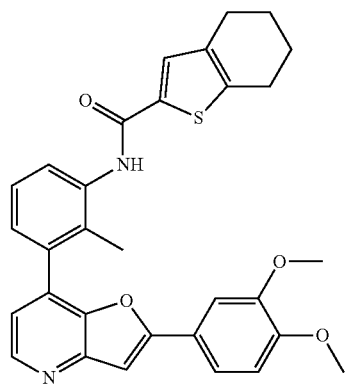 [SMILES: COc1ccc(-c2cc3nccc(-c4cccc(NC(=O)c5cc6c(s5)CCCC6)c4C)c3o2)cc1OC]

The compound was synthesized according to the procedure L with 3-[2-(3,4-dimethoxyphenyl)furo[3,2-b]pyridin-7-yl]-2-methylaniline (40.00 mg, 0.11 mmol) and 4,5,6,7-tetrahydro-1-benzothiophene-2-carbonyl chloride (24.5 mg, 0.12 mmol) and N-ethyl-N-isopropylpropan-2-amine (0.03 ml, 0.17 mmol). The title compound was obtained as a yellow solid (32 mg, 55%). HPLC (method F): 96%, RT=4.512 min. $^1$H NMR (DMSO-$d_6$) δ [ppm] 9.95 (s, 1H), 8.53 (d, 1H), 7.63 (d, 2H), 7.45-7.27 (m, 6H), 7.03 (d, 1H), 3.83 (s, 3H), 3.76 (s, 3H), 2.70 (s, 2H), 2.55 (m, 2H), 2.05 (s, 3H), 1.72-1.69 (m, 4H). MS: m/z=525 [M+H]$^+$, RT=4.50 min.

4-tert.-Butyl-N-{3-[2-(3,4-dimethoxyphenyl)furo[3,2-b]pyridin-7-yl]-2-methylphenyl}benzamide ("B84")

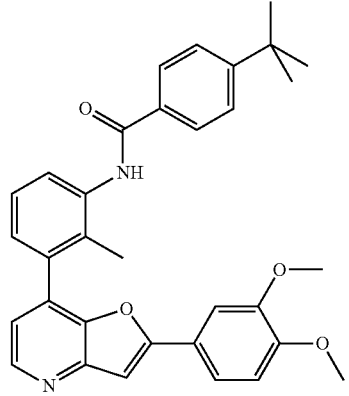 [SMILES: COc1ccc(-c2cc3nccc(-c4cccc(NC(=O)c5ccc(C(C)(C)C)cc5)c4C)c3o2)cc1OC]

The title compound was synthesized according to the procedure M using 4-tert.-butylbenzoyl chloride (24.01 mg, 0.12 mmol). The title compound was obtained as a yellow solid (35 mg, 61%). HPLC (method F): 95%, RT=4.709 min. $^1$H NMR (DMSO-$d_6$) δ [ppm] 10.06 (s, 1H), 8.60 (d, 1H), 7.95 (d, 2H), 7.67 (s, 1H), 7.56-750 (m, 5H), 7.44 (t, 1H), 7.40 (d, 1H), 7.36 (d, 1H), 7.09 (d, 1H), 3.89 (s, 3H), 3.81 (s, 3H), 2.13 (s, 3H), 1.32 (s, 9H). MS: m/z=521 [M+H]$^+$, RT=4.68 min.

Procedure N

N-{3-[7-(4-Phenoxyphenoxy)furo[3,2-b]pyridin-2-yl]phenyl}but-2-ynamide ("B85")

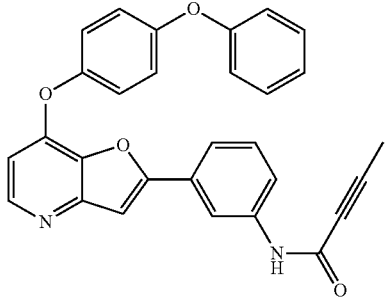 [SMILES: CC#CC(=O)Nc1cccc(-c2cc3nccc(Oc4ccc(Oc5ccccc5)cc4)c3o2)c1]

To a 20-mL glass vial was added but-2-ynoic acid (7.57 mg; 0.09 mmol), and bis(2-oxo-3-oxazolidinyl)phosphinic chloride (28.66 mg; 0.11 mmol), and N,N-diisopropylethylamine (0.05 ml; 0.30 mmol) suspended in dioxane (3.00 ml). The reaction mixture was stirred at room temperature for 1 hour. 3-[7-(4-phenoxyphenoxy)furo[3,2-b]pyridin-2-yl]aniline (29.60 mg; 0.08 mmol.) was added. The reaction mixture was then stirred at room temperature overnight. The mixture was purified using preparative HPLC to afford the title compound as a white solid (30.00 mg, 87%). HPLC (method F): 100%, RT=4.400 min. $^1$H NMR (DMSO-d$_6$) δ [ppm] 10.79 (s, 1H), 8.40 (d, 1H), 8.24 (s, 1H), 7.70 (d, 1H), 7.66 (d, 1H), 7.62 (s, 1H), 7.47 (t, 1H), 7.41 (t, 2H), 7.38 (d, 2H), 7.16 (m, 3H), 7.08 (d, 2H), 6.77 (d, 1H), 2.05 (s, 3H). MS: m/z=461 [M+H]$^+$, RT=4.52 min.

4-tert.-Butyl-N-(2-methyl-3-{2-[4-(pyrrolidin-1-ylcarbonyl)phenyl]furo[3,2-b]pyridin-7-yl}phenyl)benzamide ("B86")

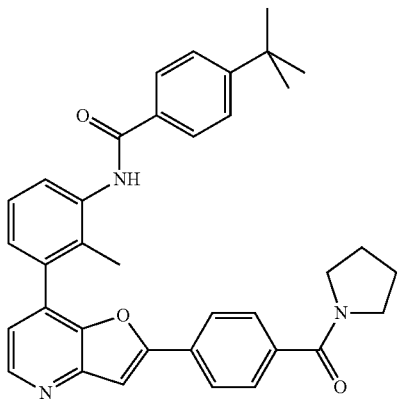 [SMILES: Cc1c(NC(=O)c2ccc(C(C)(C)C)cc2)cccc1-c1ccnc2cc(-c3ccc(C(=O)N4CCCC4)cc3)oc12]

7-Chloro-2-[4-(pyrrolidin-1-ylcarbonyl)phenyl]furo[3,2-b]pyridine

The compound was synthesized according to the procedure K using [4-(pyrrolidin-1-ylcarbonyl)phenyl]boronic acid.

2-Methyl-3-{2-[4-(pyrrolidin-1-ylcarbonyl)phenyl]furo[3,2-b]pyridin-7-yl}aniline The compound was synthesized according to the procedure K using 7-chloro-2-[4-(pyrrolidin-1-ylcarbonyl)phenyl]furo[3,2-b]pyridine and 2-methyl-3-(4,4,5,5-tetramethyl-1,3,2-dioxaborolan-2-yl)aniline.

4-tert.-Butyl-N-(2-methyl-3-{2-[4-(pyrrolidin-1-ylcarbonyl)phenyl]furo[3,2-b]pyridin-7-yl}phenyl)benzamide The compound was synthesized according to the procedure M using 2-methyl-3-{2-[4-(pyrrolidin-1-ylcarbonyl)phenyl]furo[3,2-b]pyridin-7-yl}aniline (50 mg, 0.13 mmol) and 4-tert-butylbenzoyl chloride (27.21 mg, 0.14 mmol). The title compound was obtained as white solid (6.00 mg, 9%). HPLC (method F): 100%, RT=4.714 min. MS: m/z=558 [M+H]$^+$, RT=4.85 min.

N-(2-Methyl-3-{2-[4-(pyrrolidin-1-ylcarbonyl)phenyl]furo[3,2-b]pyridin-7-yl}phenyl)-4,5,6,7-tetrahydro-1-benzothiophene-2-carboxamide ("B87")

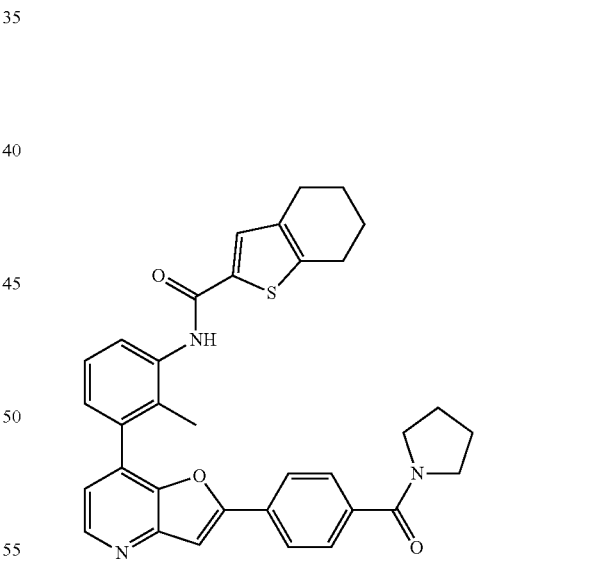

The compound was synthesized according to the procedure M using 2-methyl-3-{2-[4-(pyrrolidin-1-ylcarbonyl)phenyl]furo[3,2-b]pyridin-7-yl}aniline (40.00 mg, 0.10 mmol) and 4,5,6,7-tetrahydro-1-benzothiophene-2-carbonyl chloride (22.22 mg, 0.11 mmol). The title compound was obtained as a white solid (8.00 mg, 14%). HPLC (method F): 82%, RT=4.365. MS: m/z=562 [M+H]+, RT=4.33 min.

2E)-N-{3-[7-(4-phenoxyphenoxy)furo[3,2-b]pyridin-2-yl]phenyl}but-2-enamide ("B88")

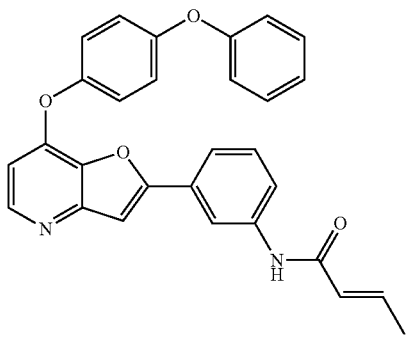 [SMILES: C/C=C/C(=O)Nc1cccc(-c2cc3nccc(Oc4ccc(Oc5ccccc5)cc4)c3o2)c1]

The compound was synthesized according to the procedure N using (2E)-but-2-enoic acid (7.86 mg, 0.09 mmol). The title compound was obtained as a white solid (18.00 mg, 51%). HPLC (method F): 96%, RT=4.566 min. $^1$H NMR (DMSO-$d_6$) δ [ppm] 10.14 (s, 1H), 8.38 (d, 1H), 8.25 (s, 1H), 7.72 (d, 1H), 7.64-7.61 (m, 2H), 7.43 (t, 1H), 7.37-7.33 (m, 4H), 7.12-7.10 (m, 3H), 7.03 (d, 2H), 6.80-6.75 (m, 2H), 6.08 (d, 1H), 1.82 (d, 3H). MS: m/z=463 [M+H]+, RT=4.55 min.

2E)-4-(Dimethylamino)-N-{3-[7-(4-phenoxyphenoxy)furo[3,2-b]pyridin-2-yl]phenyl}but-2-enamide ("B89")

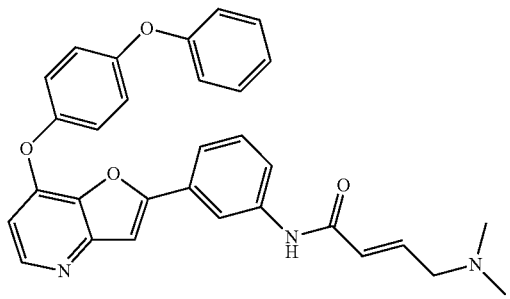

The compound was synthesized according to the procedure N using (2E)-4-(dimethylamino)but-2-enoic acid hydrochloride (15.12 mg, 0.09 mmol). The title compound was obtained as a yellow solid (11.00 mg, 23%). HPLC (method F): 97%, RT=3.678 min. $^1$H NMR (DMSO-$d_6$) δ [ppm] 10.57 (s, 1H), 8.39 (d, 1H), 8.28 (s, 1H), 7.81 (d, 1H), 7.73 (d, 1H), 7.66 (s, 1H), 7.51 (t, 1H), 7.42-7.37 (m, 4H), 7.16-7.14 (m, 3H), 7.08 (d, 2H), 6.79-6.73 (m, 2H), 6.47 (d, 1H), 3.96 (d, s, 2H), 2.79 (s, 6H). MS: m/z=506 [M+H]+, RT=3.65 min.

2-Methyl-N-{3-[7-(4-phenoxyphenoxy)furo[3,2-b]pyridin-2-yl]phenyl}acrylamide ("B90")

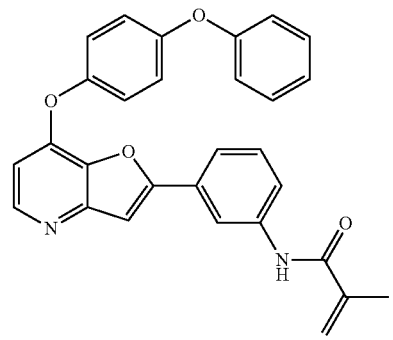 [SMILES: C=C(C)C(=O)Nc1cccc(-c2cc3nccc(Oc4ccc(Oc5ccccc5)cc4)c3o2)c1]

The compound was synthesized according to the procedure N using 2-methylacrylic acid (13.10 mg, 0.15 mmol). The title compound was obtained as a white solid (23.40 mg, 67%). HPLC (method F): 90%, RT=4.638 min. $^1$H NMR (DMSO-$d_6$) δ [ppm] 9.99 (s, 1H), 8.36 (d, 1H), 8.30 (s, 1H), 7.83 (d, 1H), 7.68 (d, 1H), 7.61 (s, 1H), 7.45 (t, 1H), 7.40-7.36 (m, 4H), 7.17-7.13 (m, 3H), 7.07 (d, 2H), 6.71 (d, 1H), 5.86 (s, 1H), 5.54 (s, 1H), 1.95 (s, 3H). MS: m/z=463 [M+H]+, RT=4.65 min.

Analogously to the examples given above the following compounds are prepared:

| Compound no. | |
|---|---|
| "C1" | 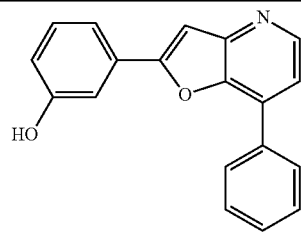 |

3-(7-Phenyl-furo[3,2-b]pyridin-2-yl)-phenol

HPLC (Method A): Rt 2.67 min (purity 100%); LCMS (ESI+) (Method G): Rt 1.781 min, MH+ 288.1;

| Compound no. | |
|---|---|
| "C2" | 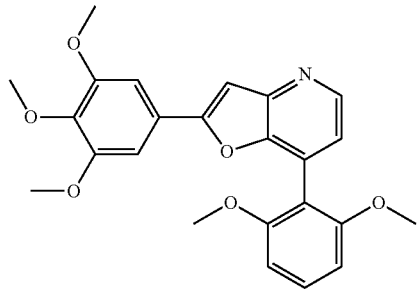 7-(2,6-Dimethoxy-phenyl)-2-(3,4,5-trimethoxy-phenyl)-furo[3,5-b]pyridine<br><br>HPLC (Method A): Rt 2.55 min (purity 99.3%); LCMS (ESI+) (Method G): Rt 1.965 min, MH+ 422.2;<br>$^1$H NMR (400 MHz, DMSO-d$_6$) δ [ppm] 8.46 (d, J = 5.0, 1H), 7.64 (s, 1H) 7.47 (t, J = 8.4, 1H), 7.21 (d, J = 5.0, 1H), 7.14 (s, 2H), 6.87 (d, J = 8.5, 2H), 3.84 (s, 6H), 3.73 (d, J = 10.6, 6H), 3.71 (s, 3H) |
| "C3" | 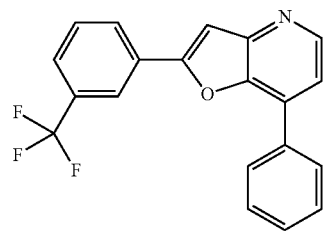 7-Phenyl-2-(3-trifluoromethyl-phenyl)-furo[3,2-b]pyridine<br><br>HPLC (Method A): Rt 3.11 min (purity 100%); LCMS (ESI+) (Method G): Rt 2.267 min, MH+ 340.1 |
| "C4" | 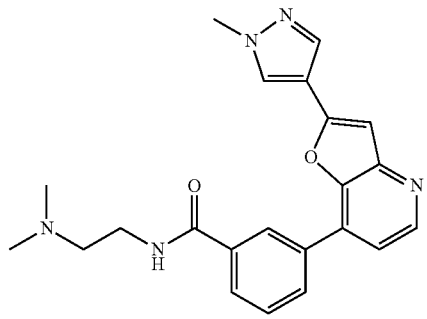 N-(2-Dimethylamino-ethyl)-3-[2-(1-methyl-1H-pyrazol-4-yl)-furo[3,2-b]pyridin-7-yl]-benzamide<br><br>HPLC (Method A): Rt 2.27 min (purity 99.3%); LCMS (ESI+) (Method G): Rt 1.286 min, MH+ 390.25;<br>$^1$H NMR (400 MHz, DMSO-d$_6$) δ [ppm] 9.34 (s, 1H), 8.88 (t, J = 5.7, 1H), 8.63-8.51 (m, 2H), 8.38 (s, 1H), 8.32 (dd, J = 6.7, 1.7, 1H), 8.10-8.00 (m, 2H), 7.77 (t, J = 7.8, 1H), 7.62 (d, J = 5.2, 1H), 7.28 (s, 1H), 3.95 (s, 3H), 3.69 (q, J = 5.9, 2H), 2.89 (d, J = 4.6, 7H) |

| Compound no. | |
|---|---|
| "C5" | 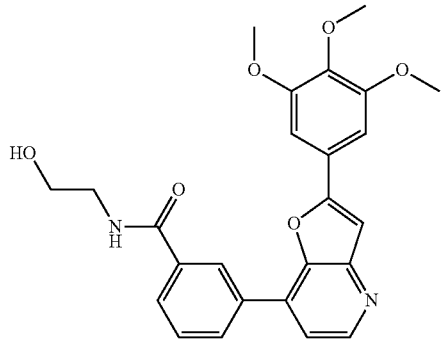 |

N-(2-Hydroxy-ethyl)-3-[2-(3,4,5-trimethoxy-phenyl)-furo[3,2-b]pyridin-7-yl]-benzamide HPLC (Method A): Rt 2.44 min (purity 99.9%); LCMS (ESI+) (Method G): Rt 1.632 min, MH+ 499.2;
$^1$H NMR (400 MHz, DMSO-$d_6$) δ [ppm] 8.82 (t, J = 1.6, 1H), 8.69-8.56 (m, 2H), 8.30-8.23 (m, 1H), 8.07-8.00 (m, 1H), 7.77-7.67 (m, 3H), 7.36 (s, 2H), 4.71 (br, 1H), 3.93 (s, 6H), 3.75 (s, 3H), 3.55 (t, J = 6.2, 2H), 3.38 (dd, J = 12.0, 6.1, 2H)

| "C6" | 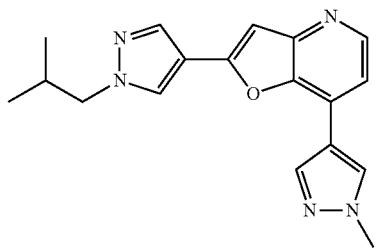 |
|---|---|

2-(1-Isobutyl-1H-pyrazol-4-yl)-7-(1-methyl-1H-pyrazol-4-yl)-furo[3,2-b]pyrdine

HPLC (Method A): Rt 2.61 min (purity 99.3%); LCMS (ESI+) (Method G): Rt 1.667 min, MH+ 322.15;
$^1$H NMR (500 MHz, DMSO-$d_6$) δ [ppm] 8.77 (s, 1H), 8.68 (s, 1H), 8.50 (d, J = 5.9, 1 H), 8.46 (s, 1H), 8.31 (d, J = 10.0, 1H), 7.77 (d, J = 5.8, 1H), 7.31 (s, 1H), 4.06-4.02 (m, 5H), 2.27-2.15 (m, 1H), 0.89 (dd, J = 15.7, 6.7, 6H)

| "C7" | 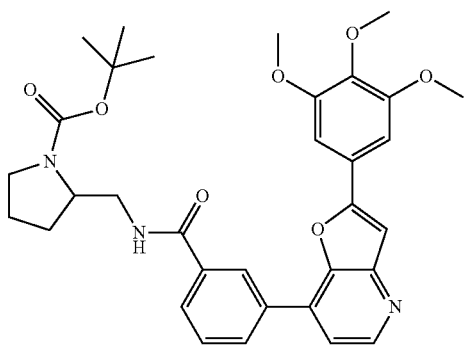 |
|---|---|

2-({3-[2-(3,4,5-Trimethoxy-phenyl)-furo[3,2-b]pyrdin-7-yl]-benzoylamino}-methyl)-pyrrolidine-1-carboxylic acid tert-butyl ester HPLC (Method A): Rt 2.83 min (purity 96.2%); LCMS (ESI+) (Method G): Rt 2.25 min, MH+ 588.3

| Compound no. | |
|---|---|
| "C8" | 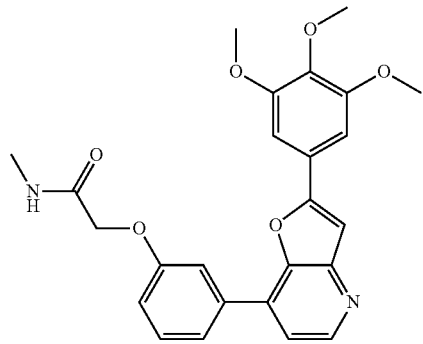 N-Methyl-2-{3-[2-(3,4,5-trimethoxy-phenyl)-furo[3,2-b]pyrdin-7-yl]-phenoxy}-acetamide HPLC (Method A): Rt 2.73 min (purity 97.9%); LCMS (ESI+) (Method G): Rt 1.824 min, MH+ 449.2;
$^1$H NMR (500 MHz, DMSO-$d_6$) δ [ppm] 8.57 (d, J = 5.1, 1H), 8.09 (d, J = 4.3, 1H), 7.80-7.66 (m, 3H), 7.63-7.51 (m, 2H), 7.33 (s, 2H), 7.20-7.14 (m, 1H), 4.61 (s, 2H), 3.91 (s, 6H), 3.74 (s, 3H), 2.67 (d, J = 4.7, 3H) |
| "C9" | 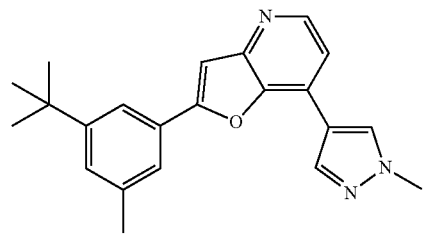 2-(3-tert.-Butyl-5-methyl-phenyl)-7-(1-methyl-1H-pyrazol-4-yl)-furo[3,2-b]pyridine LCMS (ESI+) (Method G): Rt 2.21 min, MH+ 346.2;
$^1$H NMR (500 MHz, DMSO-$d_6$) δ [ppm] 8.67 (s, 1H), 8.51 (d, J = 5.4, 1H), 8.37 (s, 1H), 7.89 (s, 1H), 7.79 (s, 1H), 7.73 (s, 1H), 7.69 (d, J = 5.4, 1H), 7.38 (s, 1H), 4.02 (s, 3H), 2.46 (s, 3H), 1.38 (s, 9H) |
| "C10" | 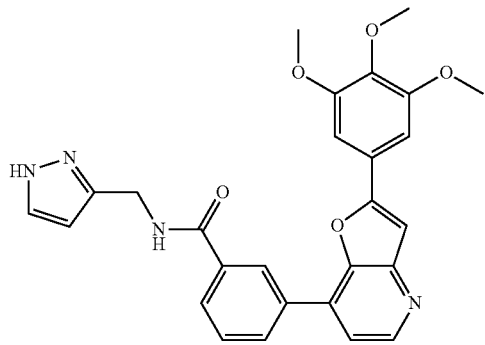 N-(1H-Pyrazol-3-ylmethyl)-3-[2-(3,4,5-trimethoxy-phenyl)-furo[3,2-b]pyridin-7-yl]-benzamide LCMS (ESI+) (Method G): Rt 1.73 min, MH+ 485.1;
$^1$H NMR (500 MHz, DMSO-$d_6$) δ [ppm] 12.57 (s, 1H), 9.09 (s, 1H), 8.86 (s, 1H), 8.59 (d, J = 5.1, 1H), 8.27 (d, J = 7.4, 1H), 8.07 (d, J = 7.9, 1H), 7.78-7.70 (m, 3H), 7.63 (s, 1H), 7.36 (s, 2H), 6.19 (s, 1H), 4.68-4.45 (m, 2H), 3.90 (s, 6H), 3.74 (s, 3H) |

| Compound no. | |
|---|---|
| "C11" | 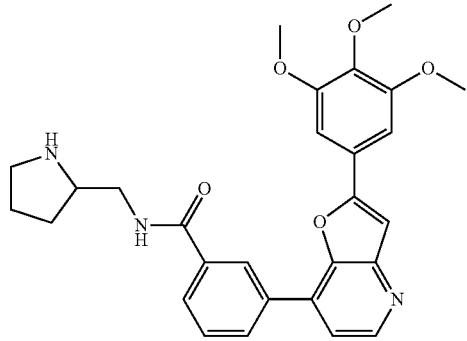<br>N-Pyrrolidin-2-ylmethyl-3-[2-(3,4,5-trimethoxy-phenyl)-furo[3,2-b]pyrdin-7-yl]-benzamide<br><br>HPLC (Method A): Rt 2.68 min (purity 98.5%); LCMS (ESI+) (Method G): Rt 1.631 min, MH+ 488.2;<br>$^1$H NMR (500 MHz, DMSO-$d_6$, TFA-$d_1$ exchange) δ [ppm] 9.04 (s, 1H), 8.94-8.86 (m, 1H), 8.46 (d, J = 7.9, 1 H), 8.30-8.22 (m, 2H), 8.06-7.99 (m, 1H), 7.91-7.82 (m, 1H), 7.55 (d, J = 1.6, 2H), 3.99 (d, J = 13.7, 6H), 3.85 (s, 3H), 3.83-3.75 (m, 1 H), 3.75-3.67 (m, 2H), 3.34 (dt, J = 11.6, 7.4, 1H), 3.24 (dd, J = 16.3, 9.9, 1H), 2.16 (dd, J = 12.5, 4.8, 1H), 2.08-1.93 (m, 2H), 1.82 (dq, J = 13.0, 8.6, 1H) |
| "C12" | 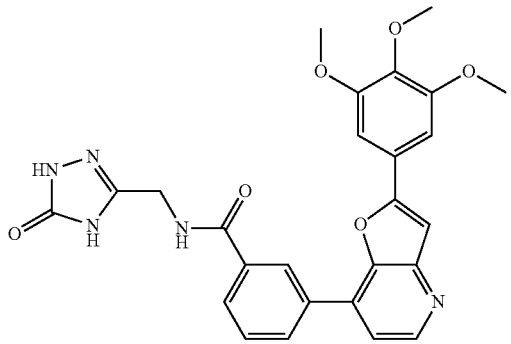<br>N-(5-Oxo-4,5-dihydro-1H-[1,2,4]triazol-3-ylmethyl)-3-[2-(3,4,5-trimethoxy-phenyl)-furo[3,2-b]pyrdin-7-yl]-benzamide<br><br>HPLC (Method A): Rt 2.73 min (purity 98.3%); LCMS (ESI+) (Method G): Rt 1.608 min, MH+ 502.1 |
| "C13" | 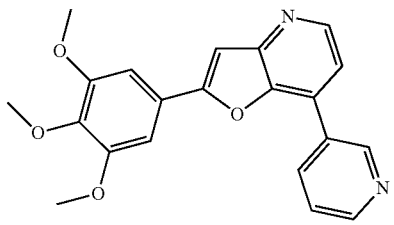<br>7-Pyridin-3-yl-2-(3,4,5-trimethoxy-phenyl)-furo[3,2-b]pyridine<br><br>HPLC (Method A): Rt 2.53 min (purity 100%); LCMS (ESI+) (Method G): Rt 1.611 min, MH+ 363.1;<br>$^1$H NMR (500 MHz, DMSO-$d_6$) δ [ppm] 9.36 (d, J = 1.7, 1H), 8.85-8.76 (m, 1H), 8.65 (d, J = 5.1, 1H), 8.63-8.60 (m, 1H), 7.80 (d, J = 5.2, 1H), 7.75 (dd, J = 6.8, 5.4, 2H), 7.34 (s, 2H), 3.92 (s, 6H), 3.76 (s, 3H). |

| Compound no. | |
|---|---|
| "C14" | 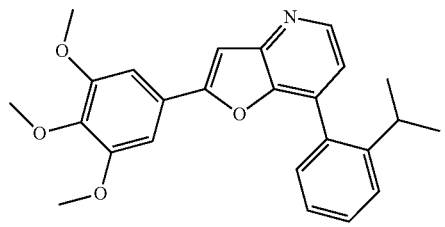<br>7-(2-Isopropyl-phenyl)-2-(3,4,5-trimethoxy-phenyl)-furo[3,2-b]pyridine<br><br>HPLC (Method A): Rt 2.92 min (purity 100%); LCMS (ESI+) (Method G): Rt 2.227 min, MH+ 404.1 |
| "C15" | 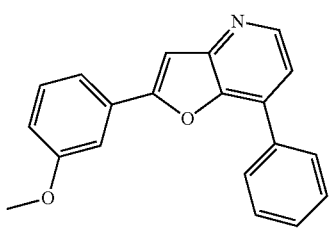<br>2-(3-Methoxy-phenyl)-7-phenyl-furo[3,2-b]pyridine<br><br>HPLC (Method A): Rt 2.57 min (purity 93.21%); LCMS (ESI+) (Method G): Rt 2.042 min, MH+ 302.1 |
| "C16" | 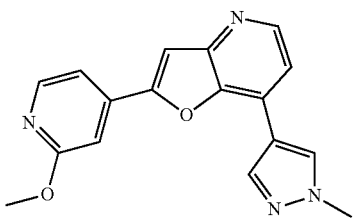<br>2-(2-Methoxy-pyridin-4-yl)-7-(1-methyl-1H-pyrazol-4-yl)-furo[3,2-b]pyridine<br><br>HPLC (Method A): Rt 2.49 min (purity 97.9%); LCMS (ESI+) (Method G): Rt 1.565 min, MH+ 307.1 |
| "C17" | 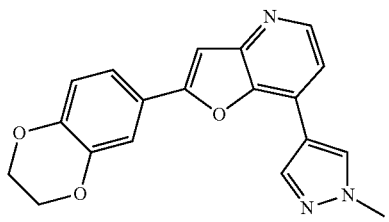<br>2-(2,3-Dihydro-benzo[1,4]dioxon-6-yl)-7-(1-methyl-1H-pyrazol-4-yl)-furo[3,2-b]pyridine<br><br>LCMS (ESI+) (Method G): Rt 1.67 min, MH+ 334 |

| Compound no. | |
|---|---|
| "C18" | 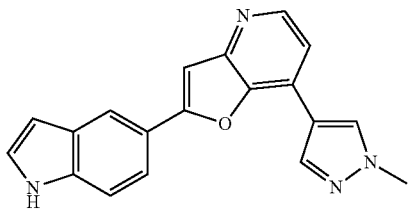<br>2-(1H-Indol-5-yl)-7-(1-methyl-1H-pyrazol-4-yl)-furo[3,2-b]pyridine<br><br>LCMS (ESI+) (Method G): Rt 1.65 min, MH+ 315; |
| "C19" | 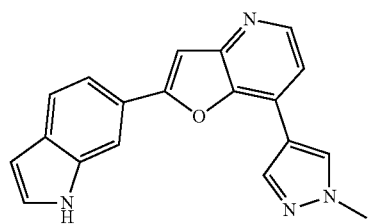<br>2-(1H-Indol-6-yl)-7-(1-methyl-1H-pyrazol-4-yl)-furo[3,2-b]pyridine<br><br>LCMS (ESI+) (Method G): Rt 1.72 min, MH+ 315 |
| "C20" | 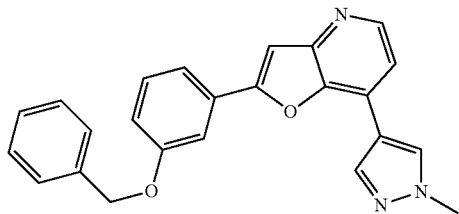<br>2-(3-Benzyloxy-phenyl)-7-(1-methyl-1H-pyrazol-4-yl)-furo[3,2-b]pyridine<br><br>HPLC (Method A): Rt 2.77 min (purity 98.3%); LCMS (ESI+) (Method G): Rt 2.079 min, MH+ 382.1 |
| "C22" | 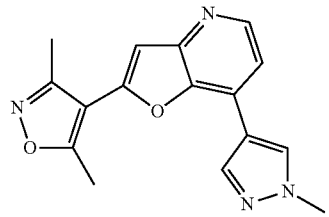<br>2-(3,5-Dimethyl-isoxazol-4-yl)-7-(1-methyl-1H-pyrazol-4-yl)-furo[3,2-b]pyridine<br><br>LCMS (ESI+) (Method G): Rt 1.47 min, MH+ 295.1 |

-continued

| Compound no. | |
|---|---|
| "C23" | 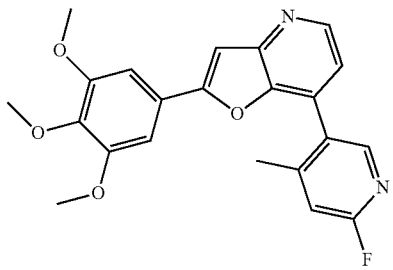
7-(6-Fluoro-4-methyl-pyridin-3-yl)-2-(3,4,5-trimethoxy-phenyl)-furo[3,2-b]pyridine LCMS (ESI+) (Method G): Rt 1.91 min, MH+ 395.1 |
| "C24" | 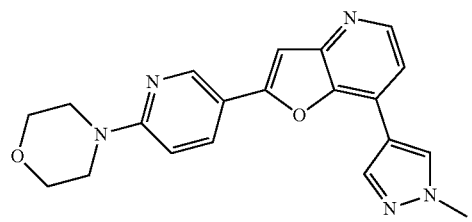
7-(1-Methyl-1H-pyrazol-4-yl)-2-(6-morpholin-4-yl-pyridin-3-yl)-furo[3,2-b]pyridine LCMS (ESI+) (Method G): Rt 1.49 min, MH+ 362.1 |
| "C25" | 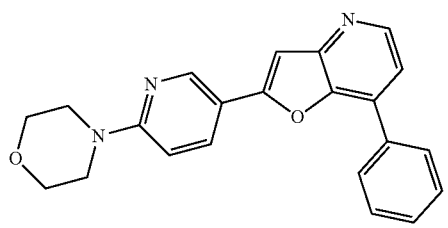
2-(6-Morpholin-4-yl-pyridin-3-yl)-7-phenyl-furo[3,2-b]pyridine LCMS (ESI+) (Method G): Rt 2.09 min, MH+ 358.1 |
| "C26" | 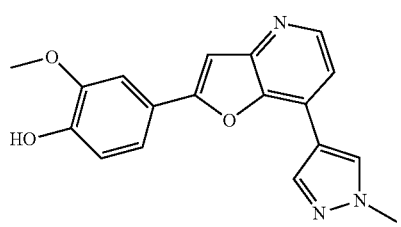
2-Methoxy-4-[7-(1-methyl-1H-pyrazol-4-yl)-furo[3,2-b]pyridin-2-yl]-phenol HPLC (Method A): Rt 2.49 min (purity 97.9%); LCMS (ESI+) (Method G): Rt 1.538 min, MH+ 322.1;
$^1$H NMR (500 MHz, DMSO-$d_6$) δ [ppm] 9.56 (s, 1H), 8.58 (s, 1H), 8.38 (d, J = 5.1, 1 H), 8.27 (s, 1 H), 7.64-7.56 (m, 2H), 7.52 (d, J = 6.9, 1 H), 7.46 (s, 1H), 6.96 (d, J = 8.1, 1H), 4.00 (s, 3H), 3.93 (s, 3H) |

| Compound no. | |
|---|---|
| "C27" | 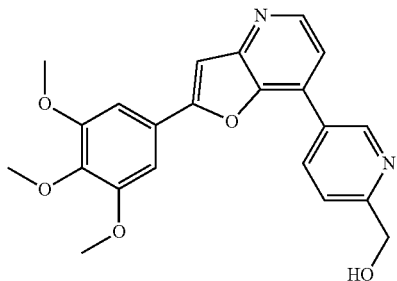<br>{5-[2-(3,4,5-Trimethoxy-phenyl)-furo[3,2-b]pyridin-7-yl]-pyridin-2-yl}-methanol<br><br>LCMS (ESI+) (Method G): Rt 1.52 min, MH+ 393.1 |
| "C28" | 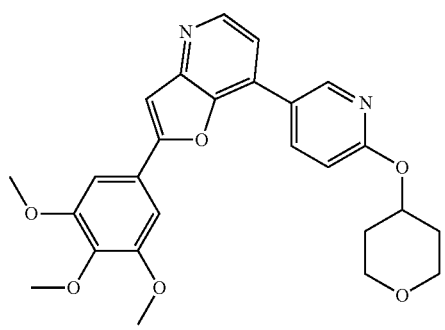<br>7-[6-(Tetrahydro-pyran-4-yloxy)-pyridin-3-yl]-2-(3,4,5-trimethoxy-phenyl)-furo[3,2-b]pyridine<br><br>LCMS (ESI+) (Method G): Rt 1.97 min, MH+ 463.2 |
| "C29" | 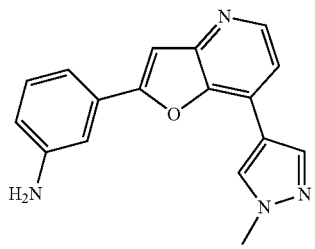<br>3-[7-(1-Methyl-1H-pyrazol-4-yl)-furo[3,2-b]pyridin-2-yl]-phenylamine<br><br>LCMS (ESI+) (Method G): Rt 1.53 min, MH+ 291.1 |
| "C30" | 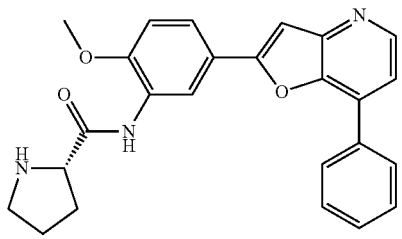<br>(S)-Pyrrolidine-2-carboxylic acid [2-methoxy-5-(7-phenyl-furo[3,2-b]pyridin-2-yl)-phenyl]-amide<br><br>LCMS (ESI+) (Method G): Rt 1.558 min, MH+ 414.1 |

| Compound no. | |
|---|---|
| "C31" | 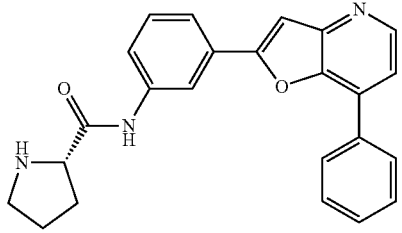<br>(S)-Pyrrolidine-2-carboxylic acid [3-(7-phenyl-furo[3,2-b]pyridin-2-yl)-phenyl]-amide<br><br>LCMS (ESI+) (Method G): Rt 1.71 min, MH+ 384.2 |
| "C32" | 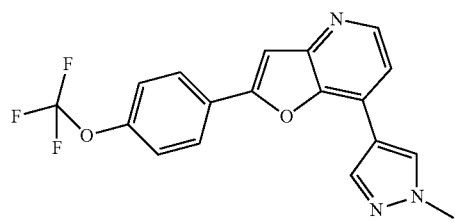<br>7-(1-Methyl-1H-pyrazol-4-yl)-2-(4-trifluoromethoxy-phenyl)-furo[3,2-b]pyridine<br><br>LCMS (ESI+) (Method G): Rt 1.92 min, MH+ 360 |
| "C33" | 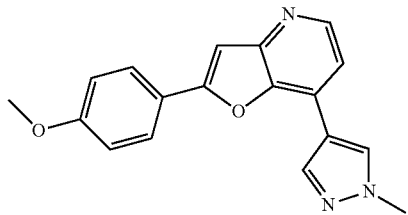<br>2-(4-Methoxy-phenyl)-7-(1-methyl-1H-pyrazol-4-yl)-furo[3,2-b]pyridine<br><br>LCMS (ESI+) (Method G): Rt 1.68 min, MH+ 306 |
| "C34" | 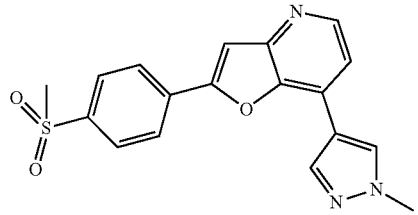<br>2-(4-Methanesulfonyl-phenyl)-7-(1-methyl-1H-pyrazol-4-yl)-furo[3,2-b]pyridine<br><br>LCMS (ESI+) (Method G): Rt 1.46 min, MH+ 354 |

| Compound no. | |
|---|---|
| "C35" | 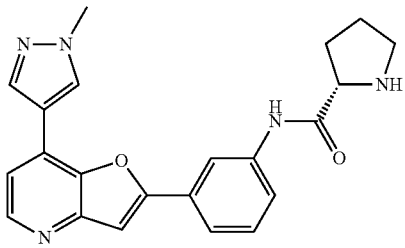

(S)-Pyrrolidine-2-carboxylic acid {3-[7-(1-methyl-1H-pyrazol-4-yl)-furo[3,2-b]pyridin-2-yl]-phenyl}-amide HPLC (Method A): Rt 1.83 min (purity 100%); LCMS (ESI+) (Method G): Rt 1.806 min, MH+ 388.2 m/z |
| "C36" | 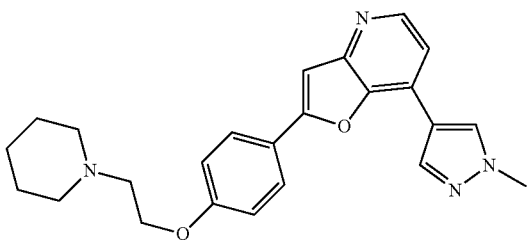

7-(1-Methyl-1H-pyrazol-4-yl)-2-[4-(2-piperidin-1-yl-ethoxy)-phenyl]-furo[3,2-b]pyridine LCMS (ESI+) (Method G): Rt 1.42 min, MH+ 403.1 |
| "C37" | 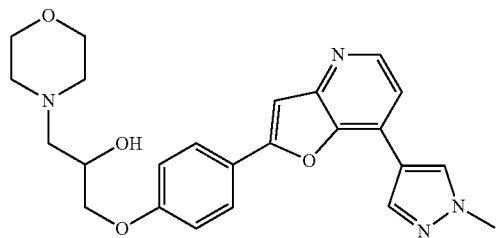

1-{4-[7-(1-Methyl-1H-pyrazol-4-yl)-furo[3,2-b]pyridin-2-yl]-phenoxy}-3-morpholin-4-yl-propan-2-ol LCMS (ESI+) (Method G): Rt 1.33 min, MH+ 435.1 |
| "C38" | 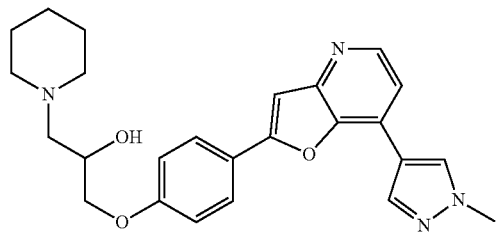

1-{4-[7-(1-Methyl-1H-pyrazol-4-yl)-furo[3,2-b]pyridin-2-yl]-phenoxy}-3-piperidin-1-yl-propan-2-ol LCMS (ESI+) (Method G): Rt 1.4 min, MH+ 433.1 |

| Compound no. | |
|---|---|
| "C39" | 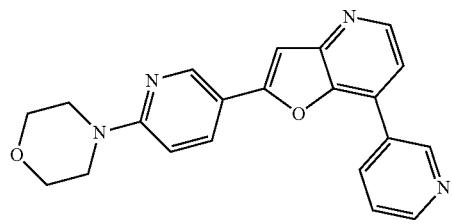 |

2-(6-Morpholin-4-yl-pyridin-3-yl)-7-
pyridin-3-yl-furo[3,2-b]pyridine

HPLC (Method A): Rt 1.76 min (purity 97%); LCMS (ESI+) (Method E):
Rt 1.312 min, MH+ 359.1 m/z

| "C40" | 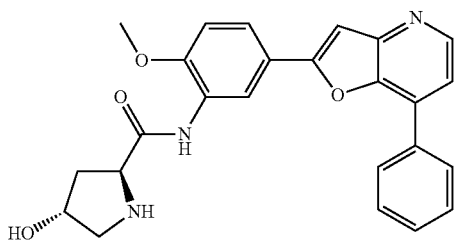 |
|---|---|

(2S,4R)-4-Hydroxy-pyrrolidine-2-carboxylic acid
[2-methoxy-5-(7-phenyl-furo[3,2-b]pyridin-
2-yl)-phenyl]-amide HPLC (Method A): Rt 2.01 min (purity 100%); LCMS (ESI+) (Method G):
Rt 2.014 min, MH+ 430.1 m/z

| "C41" | 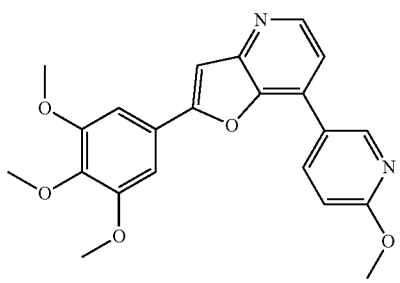 |
|---|---|

7-(6-Methoxy-pyridin-3-yl)-2-(3,4,5-
trimethoxy-phenyl)-furo[3,2-b]pyridine

LCMS (ESI+) (Method G): Rt 1.911 min, MH+ 393.1

| "C42" | 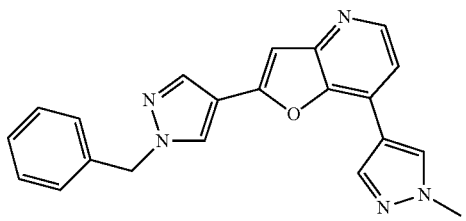 |
|---|---|

2-(1-Benzyl-1H-pyrazol-4-yl)-7-(1-methyl-
1H-pyrazol-4-yl)-furo[3,2-b]pyridine

HPLC (Method A): Rt 2.56 min (purity 98.9%); LCMS (ESI+) (Method G):
Rt 1.75 min, MH+ 356.1

| Compound no. | |
|---|---|
| "C43" | 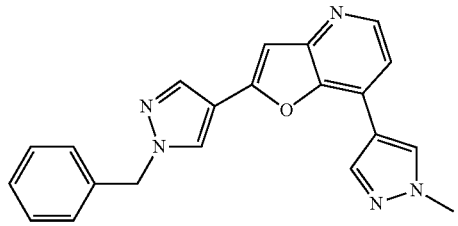 |

{3-[7-(1-Methyl-1H-pyrazol-4-yl)-furo
[3,2-b]pyridin-2-yl]-phenyl}-methanol

HPLC (Method A): Rt 2.45 min (purity 55.76%); LCMS (ESI+) (Method G):
Rt 1.482 min, MH+ 306.1

| "C44" | 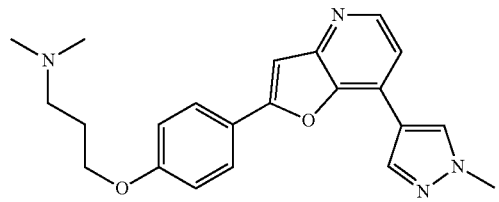 |
|---|---|

Dimethyl-(3-{4-[7-(1-methyl-1H-pyrazol-4-yl)-
furo[3,2-b]pyridin-2-yl]-phenoxy}-propyl)-amine LCMS (ESI+) (Method G): Rt 1.39 min, MH+ 377.2

| "C45" | 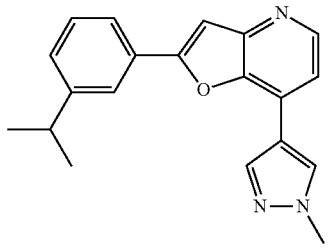 |
|---|---|

2-(3-Isopropyl-phenyl)-7-(1-methyl-
1H-pyrazol-4-yl)-furo[3,2-b]pyridine

HPLC (Method A): Rt 2.65 min (purity 74.18%); LCMS (ESI+) (Method G):
Rt 1.991 min, MH+ 318.1

| "C46" | 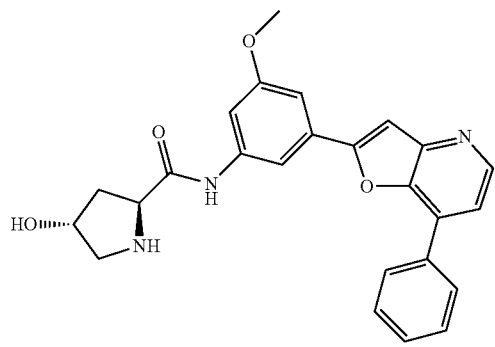 |
|---|---|

(2S,4R)-4-Hydroxy-pyrrolidine-2-carboxylic acid [3-methoxy-
5-(7-phenyl-furo[3,2-b]pyridin-2-yl)-phenyl]-amide HPLC (Method A): Rt 2.07 min (purity 100%); LCMS (ESI+) (Method E
TFA): Rt 2.07 min, MH+ 430.1 m/z

| Compound no. | |
|---|---|
| "C47" | 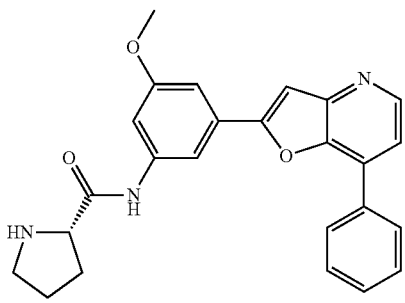 |

(S)-Pyrrolidine-2-carboxylic acid [3-methoxy-
5-(7-phenyl-furo[3,2-b]pyridin-2-yl)-
phenyl]-amide HPLC (Method A): Rt 2.13 min (purity 100%); LCMS (ESI+) (Method G):
Rt 2.133 min, MH+ 414.2 m/z

| "C48" | 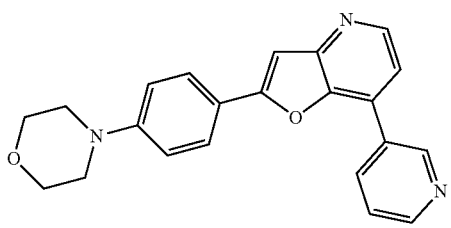 |
|---|---|

2-(4-Morpholin-4-yl-phenyl)-7-pyridin-3-yl-
furo[3,2-b]pyridine

HPLC (Method A): Rt 2.00 min (purity 100%); LCMS (ESI+) (Method G):
Rt 1.525 min, MH+ 358.2 m/z

| "C49" | 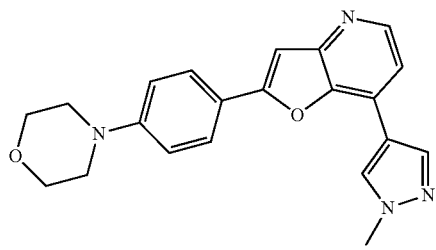 |
|---|---|

7-(1-Methyl-1H-pyrazol-4-yl)-2-(4-morpholin-4-yl-
phenyl)-furo[3,2-b]pyridine

HPLC (Method A): Rt 2.19 min (purity 100%); LCMS (ESI+) (Method G):
Rt 1.692 min, MH+ 361.1 m/z

| "C50" | 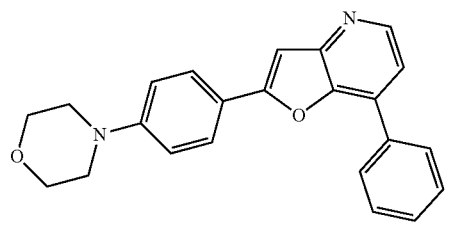 |
|---|---|

2-(4-Morpholin-4-yl-phenyl)-7-phenyl-furo[3,2-b]pyridine

HPLC (Method A): Rt 2.50 min (purity 100%); LCMS (ESI+) (Method G):
Rt 1.994 min, MH+ 357.1 m/z -continued

| Compound no. | |
|---|---|
| "C51" | 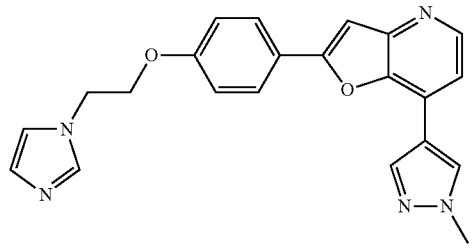 |

2-[4-(2-Imidazol-1-yl-ethoxy)-phenyl]-7-(1-methyl-
1H-pyrazol-4-yl)-furo[3,2-b]pyridine HPLC (Method A): Rt 1.93 min (purity 100%); LCMS (ESI+) (Method G):
Rt 1.380 min, MH+ 386.2 m/z

| "C52" | 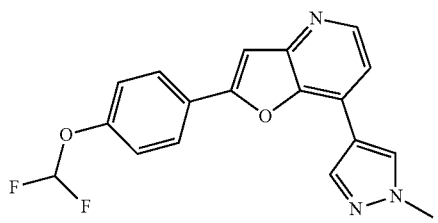 |
|---|---|

2-(4-Difluoromethoxy-phenyl)-7-(1-methyl-
1H-pyrazol-4-yl)-furo[3,2-b]pyridine

HPLC (Method A): Rt 2.54 min (purity 100%); LCMS (ESI+) (Method G):
Rt 1.797 min, MH+ 342.1 m/z

| "C53" | 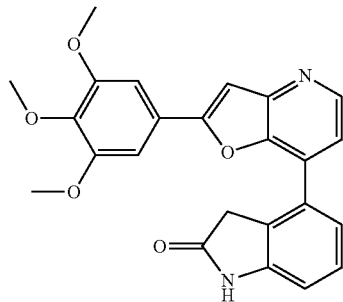 |
|---|---|

4-[2-(3,4,5-Trimethoxy-phenyl)-furo
[3,2-b]pyridin-7-yl]-1,3-dihydro-
indol-2-one HPLC (Method A): Rt 2.19 min (purity 90%); LCMS (ESI+) (Method G):
Rt 1.880 min, MH+ 417.1 m/z

| "C54" | 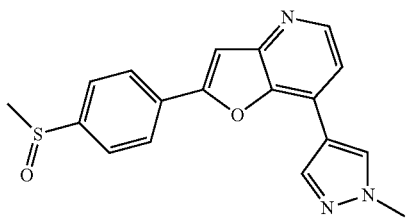 |
|---|---|

2-(4-Methanesulfinyl-phenyl)-7-(1-methyl-1H-
pyrazol-4-yl)-furo[3,2-b]pyridine

HPLC (Method A): Rt 2.10 min (purity 100%); LCMS (ESI+) (Method G):
Rt 1.392 min, MH+ 338.1 m/z

| Compound no. | |
|---|---|
| "C55" | 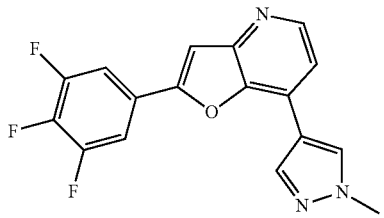

7-(1-Methyl-1H-pyrazol-4-yl)-2-(3,4,5-trifluoro-phenyl)-furo[3,2-b]pyridine

HPLC (Method A): Rt 2.77 min (purity 100%); LCMS (ESI+) (Method G): Rt 1.900 min, MH+ 330.1 m/z |
| "C56" | 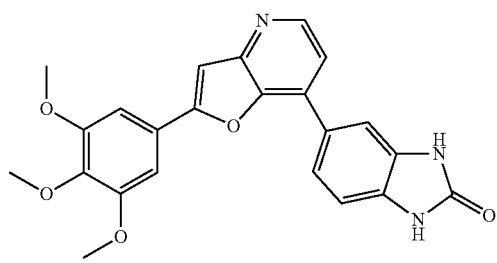

5-[2-(3,4,5-Trimethoxy-phenyl)-furo[3,2-b]pyridin-7-yl]-1,3-dihydro-benzoimidazol-2-one HPLC (Method A): Rt 2.14 min (purity 98%); LCMS (ESI+) (Method G): Rt 1.620 min, MH+ 418.1 m/z |
| "C57" | 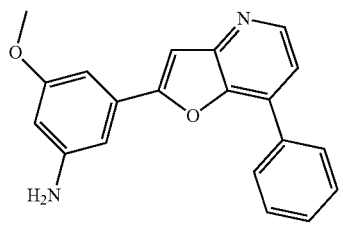

3-Methoxy-5-(7-phenyl-furo[3,2-b]pyridin-2-yl)-phenylamine

HPLC (Method A): Rt 2.13 min (purity 94%); LCMS (ESI+) (Method G): Rt 1.676 min, MH+ 317.1 m/z |
| "C58" | 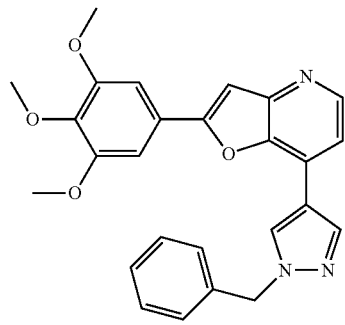

7-(1-Benzyl-1H-pyrazol-4-yl)-2-(3,4,5-trimethoxy-phenyl)-furo[3,2-b]pyridine

HPLC (Method A): Rt 2.67 min (purity 99.9%); LCMS (ESI+) (Method G): Rt 2.026 min, MH+ 442.1;
$^1$H NMR (400 MHz, DMSO-$d_6$) δ [ppm] 8.77 (s, 1H), 8.44 (d, J = 5.1, 1H), |

| Compound no. | |
|---|---|
| | 8.34 (s, 1H), 7.67 (s, 1H), 7.58 (d, J = 5.1, 1H), 7.42-7.27 (m, 7H), 5.49 (s, 2H), 3.93 (s, 6H), 3.74 (s, 3H) |
| "C59" | 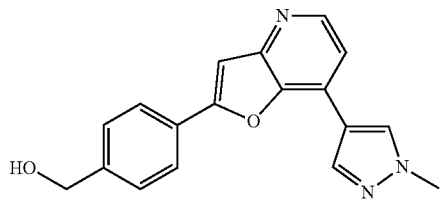<br>{4-[7-(1-Methyl-1H-pyrazol-4-yl)-furo[3,2-b]pyridin-2-yl]-phenyl}-methanol<br><br>LCMS (ESI+) (Method G): Rt 1.42 min, MH+ 306.1 |
| "C60" | 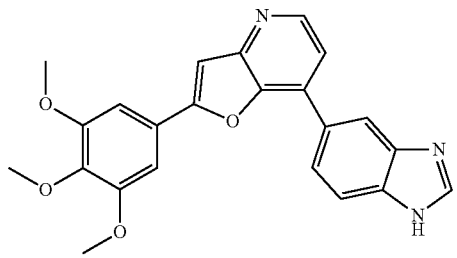<br>7-(1H-Benzoimidazol-5-yl)-2-(3,4,5-trimethoxy-phenyl)-furo[3,2-b]pyridine<br><br>HPLC (Method A): Rt 1.97 min (purity 100%); LCMS (ESI+) (Method G): Rt 1.488 min, MH+ 402.1 m/z;<br>$^1$H NMR (500 MHz, DMSO-d$_6$) δ [ppm] 9.27 (s, 1H), 8.65 (d, J = 5.2 Hz, 1H), 8.57 (d, J = 1.1 Hz, 1H), 8.22 (dd, J = 8.6, 1.5 Hz, 1H), 8.04 (d, J = 8.6 Hz, 1H), 7.82 (s, 1H), 7.76 (d, J = 5.2 Hz, 1 H), 7.36 (s, 2H), 3.93 (s, 6H), 3.76 (s, 3H) |
| "C61" | 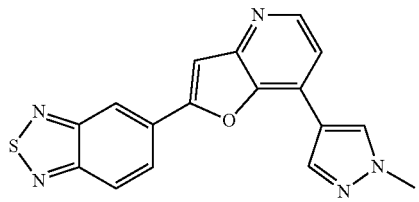<br>5-[7-(1-Methyl-1H-pyrazol-4-yl)-furo[3,2-b]pyridin-2-yl]-benzo[1,2,5]thiadiazole<br><br>HPLC (Method A): Rt 2.51 min (purity 100%); LCMS (ESI+) (Method G): Rt 1.691 min, MH+ 334.1 |
| "C62" | 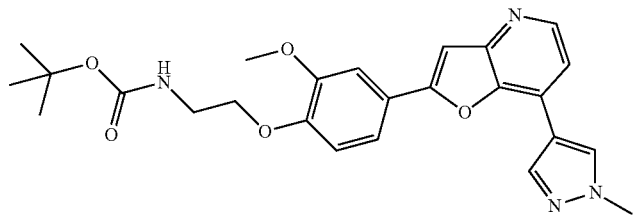<br>(2-{2-Methoxy-4-[7-(1-methyl-1H-pyrazol-4-yl)-furo[3,2-b]pyridin-2-yl]-phenoxy}-ethyl)-carbamic acid tert-butyl ester<br><br>HPLC (Method A): Rt 2.57 min (purity 97.1%); LCMS (ESI+) (Method G): Rt 1.907 min, MH+ 465.2 |

| Compound no. | |
|---|---|
| "C63" | 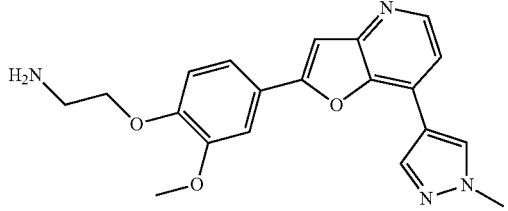

2-{2-Methoxy-4-[7-(1-methyl-1H-pyrazol-4-yl)-furo[3,2-b]pyridin-2-yl]-phenoxy}-ethylamine HPLC (Method A): Rt 2.35 min (purity 100%); LCMS (ESI+) (Method G): Rt 1.357 min, MH+ 365.1;
HCl salt: $^1$H NMR (500 MHz, DMSO-$d_6$) δ [ppm] 8.81 (s, 1H), 8.58 (d, J = 5.8, 1H), 8.46 (s, 1H), 8.15 (s, 3H), 7.89-7.83 (m, 2H), 7.80 (s, 1H), 7.77 (d, 1H), 7.24 (d, J = 8.5, 1H), 4.30 (t, J = 5.2, 2H), 4.04 (s, 3H), 3.97 (s, 3H), 3.32-3.22 (m, 2H) |
| "C64" | 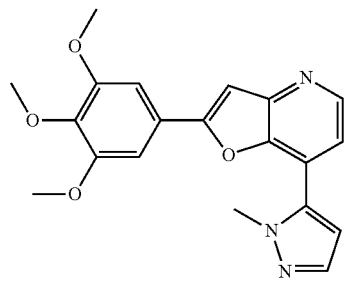

7-(2-Methyl-2H-pyrazol-3-yl)-2-(3,4,5-trimethoxy-phenyl)-furo[3,2-b]pyridine

HPLC (Method A): Rt 2.52 min (purity 97.8%); LCMS (ESI+) (Method G): Rt 1.764 min, MH+ 366.1 |
| "C65" | 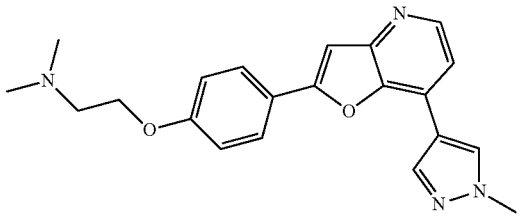

Dimethyl-(2-{4-[7-(1-methyl-1H-pyrazol-4-yl)-furo[3,2-b]pyridin-2-yl]-phenoxy}-ethyl)-amine LCMS (ESI+) (Method G): Rt 1.36 min, MH+ 363.2 |
| "C66" | 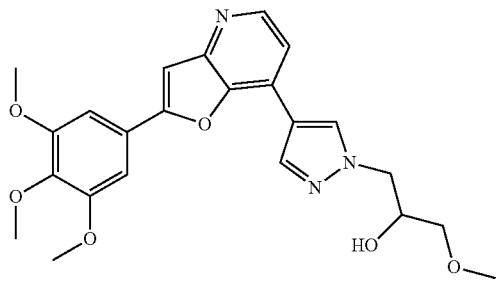

1-Methoxy-3-{4-[2-(3,4,5-trimethoxy-phenyl)-furo[3,2-b]pyridin-7-yl]-pyrazol-1-yl}-propan-2-ol HPLC (Method H): Rt 2.41 min (purity 100%); LCMS (ESI+) (Method G): Rt 1.652 min, MH+ 440.1 m/z |

| Compound no. | |
|---|---|
| "C67" | 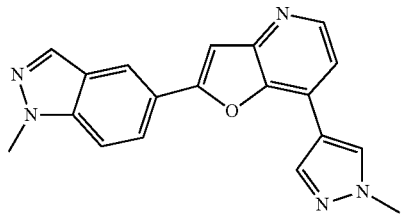<br>2-(1-Methyl-1H-indazol-5-yl)-7-(1-methyl-1H-pyrazol-4-yl)-furo[3,2-b]pyridine<br><br>HPLC (Method A): Rt 2.51 min (purity 90.6%); LCMS (ESI+) (Method G): Rt 1.63 min, MH+ 330.1;<br>$^1$H NMR (500 MHz, DMSO-$d_6$) δ [ppm] 8.67 (s, 1H), 8.57 (s, 1H), 8.42 (d, J = 5.1, 1H), 8.34 (s, 1H), 8.22 (d, J = 0.6, 1H), 8.14 (dd, J = 8.9, 1.6, 1H), 7.81 (d, J = 8.2, 1H), 7.62 (s, 1H), 7.55 (d, J = 5.1, 1H), 4.11 (s, 3H), 4.04 (d, 3H) |
| "C68" | 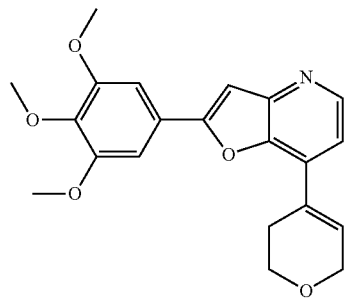<br>7-(3,6-Dihydro-2H-pyran-4-yl)-2-(3,4,5-trimethoxy-phenyl)-furo[3,2-b]pyridine<br><br>HPLC (Method H): Rt 2.24 min (purity 100%); LCMS (ESI+) (Method G): Rt 1.746 min, MH+ 369.1 m/z |
| "C69" | 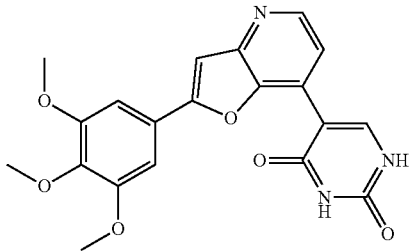<br>5-[2-(3,4,5-Trimethoxy-phenyl)-furo[3,2-b]pyridin-7-yl]-1H-pyrimidine-2,4-dione<br><br>HPLC (Method A): Rt 1.92 min (purity 100%); LCMS (ESI+) (Method G): Rt 1.450 min, MH+ 396.1 m/z |

-continued

| Compound no. | |
|---|---|
| "C70" | 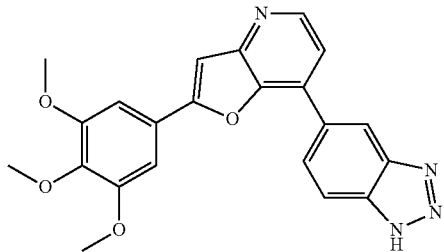<br>5-[2-(3,4,5-Trimethoxy-phenyl)-furo[3,2-b]pyridin-7-yl]-1H-benzotriazole<br><br>HPLC (Method A): Rt 2.20 min (purity 100%); LCMS (ESI+) (Method G): Rt 1.692 min, MH+ 403.1 m/z |
| "C71" | 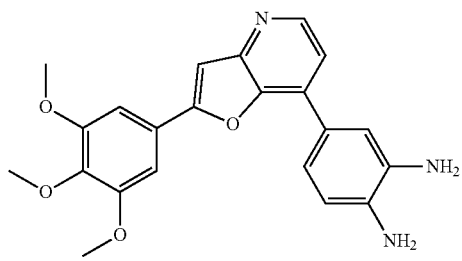<br>4-[2-(3,4,5-Trimethoxy-phenyl)-furo[3,2-b]pyridin-7-yl]-benzene-1,2-diamine<br><br>HPLC (Method A): Rt 1.97 min (purity 100%); LCMS (ESI+) (Method G): Rt 1.506 min, MH+ 392.1 m/z;<br>$^1$H NMR (TFA salt) (400 MHz, DMSO-$d_6$) δ [ppm] 8.54 (d, J = 5.8 Hz, 1H), 7.82 (d, J = 17.3 Hz, 2H), 7.64 (d, J = 5.7 Hz, 2H), 7.41 (s, 2H), 6.96 (d, J = 8.4 Hz, 1H), 3.95 (s, 6H), 3.76 (s, 3H) |
| "C72" | 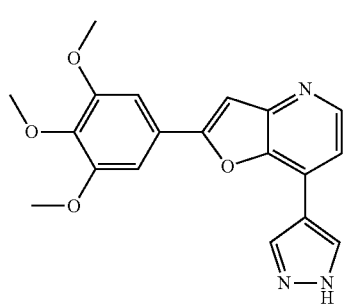<br>7-(1H-Pyrazol-4-yl)-2-(3,4,5-trimethoxy-phenyl)-furo[3,2-b]pyridine<br><br>HPLC (Method A): Rt 2.44 min (purity 100%); LCMS (ESI+) (Method G): Rt 1.605 min, MH+ 352.1 |
| "C73" | 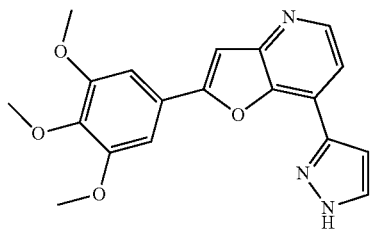<br>7-(1H-Pyrazol-3-yl)-2-(3,4,5-trimethoxy-phenyl)-furo[3,2-b]pyridine |

| Compound no. | |
|---|---|
| | HPLC (Method A): Rt 2.43 min (purity 97.3%); LCMS (ESI+) (Method G): Rt 1.646 min, MH+ 352.1 |
| "C74" | 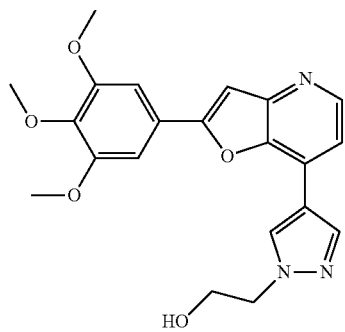<br>2-{4-[2-(3,4,5-Trimethoxy-phenyl)-furo[3,2-b]pyridin-7-yl]-pyrazol-1-yl}-ethanol<br><br>HPLC (Method A): Rt 2.4 min (purity 98.5%); LCMS (ESI+) (Method G): Rt 1.602 min, MH+ 396.2;<br>$^1$H NMR (400 MHz, DMSO-d$_6$) δ [ppm] 8.65 (s, 1H), 8.43 (d, J = 5.1, 1H), 8.31 (s, 1H), 7.67 (s, 1H), 7.57 (d, J = 5.1, 1H), 7.36 (s, 2H), 5.00 (t, J = 5.3, 1H), 4.30 (t, J = 5.4, 2H), 3.94 (s, 6H), 3.83 (dd, J = 10.2, 5.1, 2H), 3.75 (s, 3H) |
| "C75" | 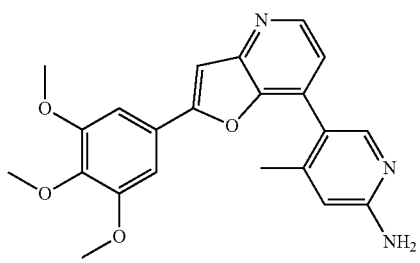<br>4-Methyl-5-[2-(3,4,5-trimethoxy-phenyl)-furo[3,2-b]pyridin-7-yl]-pyridin-2-ylamine<br><br>HPLC (Method A): Rt 2.36 min (purity 100%); LCMS (ESI+) (Method G): Rt 1.511 min, MH+ 392.2 |
| "C76" | 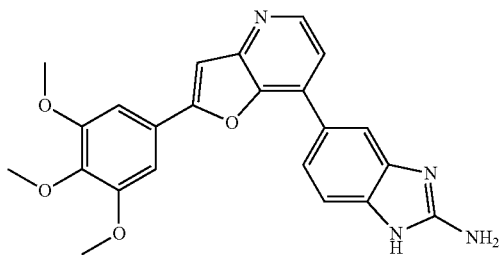<br>5-[2-(3,4,5-Trimethoxy-phenyl)-furo[3,2-b]pyridin-7-yl]-1H-benzoimidazol-2-ylamine<br><br>HPLC (Method A): Rt 2.01 min (purity 100%); LCMS (ESI+) (Method E TFA): Rt 1.537 min, MH+ 417.1 m/z;<br>$^1$H NMR (400 MHz, DMSO-d$_6$) δ [ppm] 8.48 (d, J = 5.1 Hz, 1H), 8.16 (s, 1H), 7.92 (d, J = 1.6 Hz, 1H), 7.70 (q, J = 2.1 Hz, 2H), 7.54 (d, J = 5.1 Hz, 1H), 7.31 (d, J = 8.8 Hz, 3H), 6.40 (s, 2H), 3.93 (s, 7H), 3.75 (s, 4H) |

| Compound no. | |
|---|---|
| "C77" | 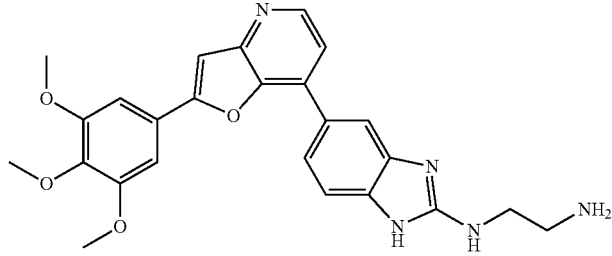 |

N1-{5-[2-(3,4,5-Trimethoxy-phenyl)-furo[3,2-b]pyridin-7-yl]-1H-benzoimidazol-2-yl}-ethane-1,2-diamine HPLC (Method A): Rt 1.90 min (purity 82%); LCMS (ESI+) (Method G): Rt 1.450 min, MH+ 460.2 m/z

| "C78" | 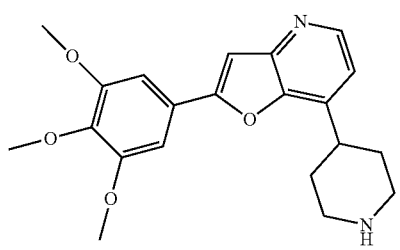 |

7-Piperidin-4-yl-2-(3,4,5-trimethoxy-phenyl)-furo[3,2-b]pyridine

HPLC (Method A): Rt 1.77 min (purity 98%); LCMS (ESI+) (Method G): Rt 1.339 min, MH+ 369.2 m/z

| "C79" | 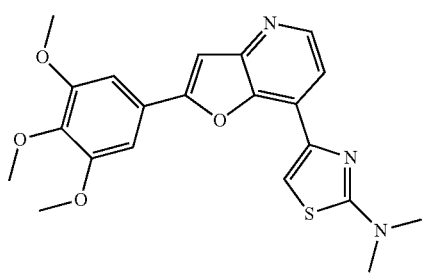 |

Dimethyl-{4-[2-(3,4,5-trimethoxy-phenyl)-furo[3,2-b]pyridin-7-yl]-thiazol-2-yl}-amine HPLC (Method H): Rt 3.06 min (purity 100%); LCMS (ESI+) (Method G): Rt 2.023 min, MH+ 412.1 m/z

| "C80" | 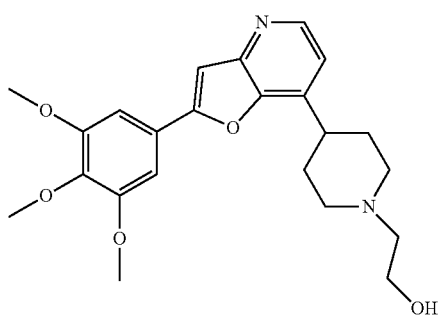 |

2-{4-[2-(3,4,5-Trimethoxy-phenyl)-furo[3,2-b]pyridin-7-yl]-piperidin-1-yl}-ethanol -continued

| Compound no. | |
|---|---|
| | HPLC (Method A): Rt 1.77 min (purity 100%); LCMS (ESI+) (Method G): Rt 1.341 min, MH+ 413.2 m/z |
| "C81" | 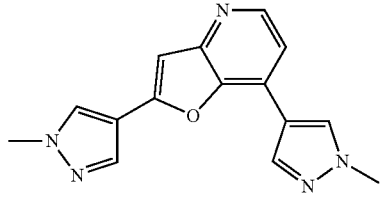

2,7-Bis-(1-methyl-1H-pyrazol-4-yl)-furo[3,2-b]pyridine |
| | HPLC (Method A): Rt 2.37 min (purity 32.15%); LCMS (ESI+) (Method G): Rt 1.401 min, MH+ 280.1 |
| "C82" | 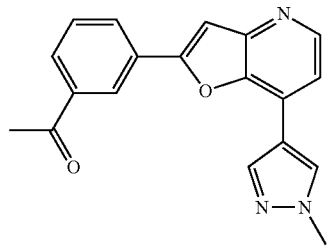

1-{3-[7-(1-Methyl-1H-pyrazol-4-yl)-furo[3,2-b]pyridin-2-yl]-phenyl}-ethanone |
| | HPLC (Method A): Rt 2.79 min (purity 96.5%); LCMS (ESI+) (Method G): Rt 1.627 min, MH+ 318.1 |
| "C83" | 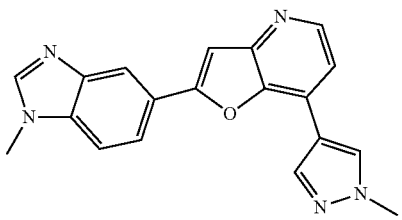

2-(1-Methyl-1H-benzoimidazol-5-yl)-7-(1-methyl-1H-pyrazol-4-yl)-furo[3,2-b]pyridine |
| | HPLC (Method A): Rt 2.53 min (purity 100%); LCMS (ESI+) (Method G): Rt 1.313 min, MH+ 330.1 |
| "C84" | 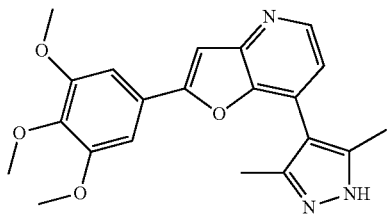

7-(3,5-Dimethyl-1H-pyrazol-4-yl)-2-(3,4,5-trimethoxy-phenyl)-furo[3,2-b]pyridine |
| | HPLC (Method H): Rt 2.37 min (purity 100%); LCMS (ESI+) (Method G): Rt 1.588 min, MH+ 380.1 m/z |

| Compound no. | |
|---|---|
| "C85" | 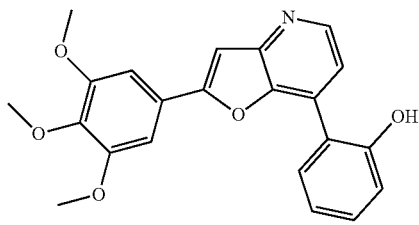

2-[2-(3,4,5-Trimethoxy-phenyl)-furo[3,2-b]pyridin-7-yl]-phenol

HPLC (Method A): Rt 2.93 min (purity 97.8%); LCMS (ESI+) (Method G): Rt 1.846 min, MH+ 378.1 |
| "C86" | 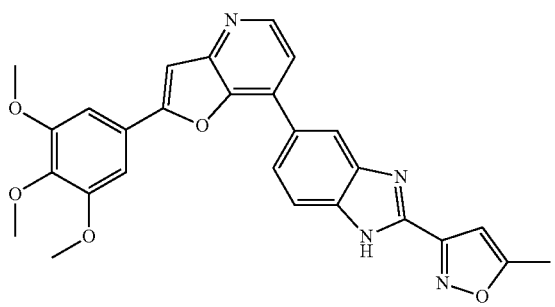

7-[2-(5-Methyl-isoxazol-3-yl)-1H-benzoimidazol-5-yl]-2-(3,4,5-trimethoxy-phenyl)-furo[3,2-b]pyridine HPLC (Method A): Rt 2.49 min (purity 100%); LCMS (ESI+) (Method G): Rt 1.916 min, MH+ 483.0 m/z |
| "C87" | 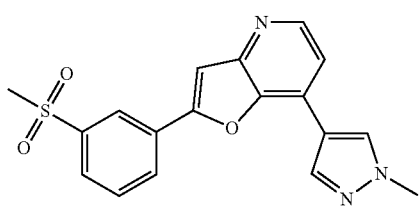

2-(3-Methanesulfonyl-phenyl)-7-(1-methyl-1H-pyrazol-4-yl)-furo[3,2-b]pyridine

HPLC (Method A): Rt 1.94 min (purity 100%); LCMS (ESI+) (Method G): Rt 1.472 min, MH+ 354.1 m/z |
| "C88" | 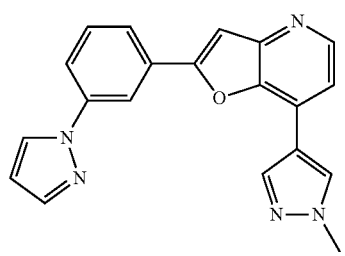

7-(1-Methyl-1H-pyrazol-4-yl)-2-(3-pyrazol-1-yl-phenyl)-furo[3,2-b]pyridine

HPLC (Method A): Rt 2.21 min (purity 94%); LCMS (ESI+) (Method G): Rt 1.701 min, MH+ 342.1 m/z |

-continued

| Compound no. | |
|---|---|
| "C89" | 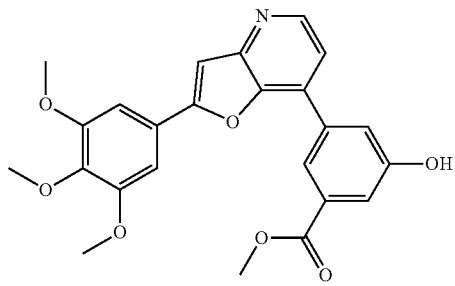 |

3-Hydroxy-5-[2-(3,4,5-trimethoxy-phenyl))-furo
[3,2-b]pyridin-7-yl]-benzoic acid methyl ester LCMS (ESI+) (Method G): Rt 1.921 min, MH+ 436.1

| "C90" | 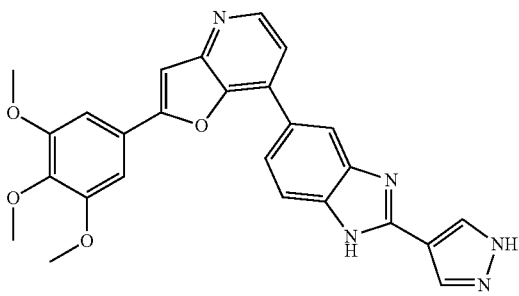 |
|---|---|

7-[2-(1H-Pyrazol-4-yl)-1H-benzoimidazol-5-yl]-2-(3,4,5-
trimethoxy-phenyl)-furo[3,2-b]pyridine HPLC (Method A): Rt 0.27 min (purity 100%); LCMS (ESI+) (Method G):
Rt 1.580 min, MH+ 468.0 m/z

| "C91" | 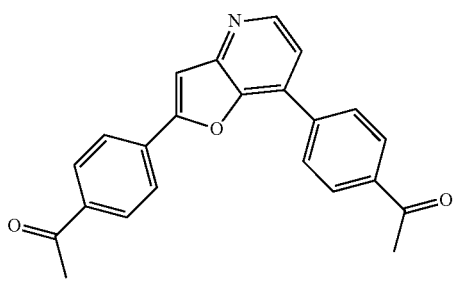 |
|---|---|

1-{4-[7-(4-Acetyl-phenyl)-furo[3,2-b]pyridin-
2-yl]-phenyl}-ethanone

HPLC (Method A): Rt 3.01 min (purity 100%); LCMS (ESI+) (Method G):
Rt 1.94 min, MH+ 356.2

| "C92" | 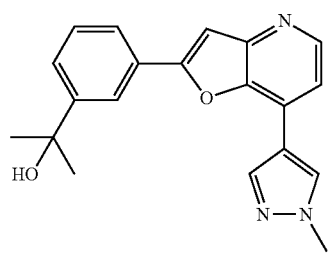 |
|---|---|

2-{3-[7-(1-Methyl-1H-pyrazol-4-yl)-furo
[3,2-b]pyridin-2-yl]-phenyl}-propan-2-ol

| Compound no. | |
|---|---|

HPLC (Method A): Rt 2.75 min (purity 100%); LCMS (ESI+) (Method G): Rt 1.627 min, MH+ 334.1;

¹H NMR (500 MHz, DMSO-d₆) δ [ppm] 8.61 (s, 1H), 8.45 (d, J = 5.1, 1H), 8.31 (s, 1H), 8.17-8.13 (m, 1H), 7.97 (d, J = 7.7, 1H), 7.63 (s, 1H), 7.61-7.54 (m, 2H), 7.53-7.48 (m, 1H), 5.18 (s, 1H), 4.01 (s, 3H), 1.52 (s, 6H)

"C93"

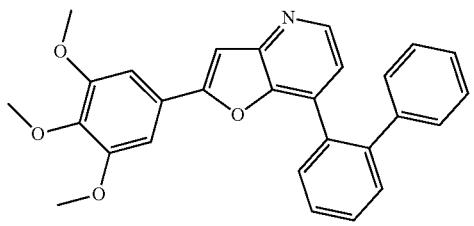

7-Biphenyl-2-yl-2-(3,4,5-trimethoxy-phenyl)-furo[3,2-b]pyridine

HPLC (Method A): Rt 3.17 min (purity 95.2%); LCMS (ESI+) (Method G): Rt 2.162 min, MH+ 438.2

"C94"

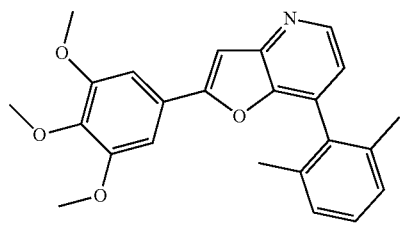

7-(2,6-Dimethyl-phenyl)-2-(3,4,5-trimethoxy-phenyl)-furo[3,2-b]pyridine

HPLC (Method A): Rt 3.09 min (purity 97.2%); LCMS (ESI+) (Method G): Rt 2.101 min, MH+ 390.2

"C95"

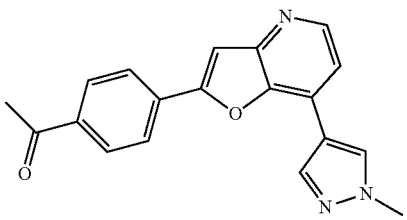

1-{4-[7-(1-Methyl-1H-pyrazol-4-yl)-furo[3,2-b]pyridin-2-yl]-phenyl}-ethanone

LCMS (ESI+) (Method G): Rt 1.625 min, MH+ 318.1

-continued

| Compound no. | |
|---|---|
| "C96" | 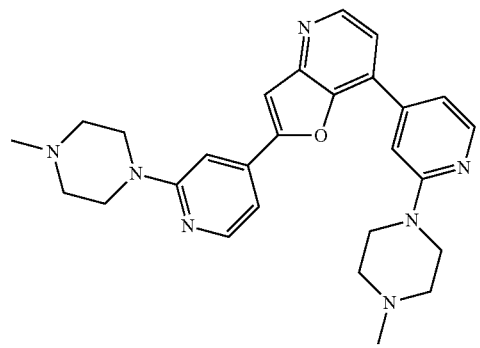<br>2,7-Bis-[2-(4-methyl-piperazin-1-yl)-pyridin-4-yl]-furo[3,2-b]pyridine<br><br>HPLC (Method A): Rt 1.70 min (purity 100%); LCMS (ESI+) (Method G): Rt 1.257 min, MH+ 470.2 m/z |
| "C97" | 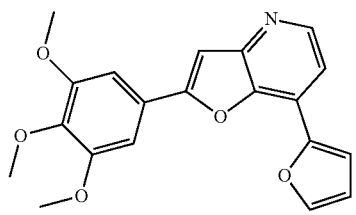<br>7-Furan-2-yl-2-(3,4,5-trimethoxy-phenyl)-furo[3,2-b]pyridine<br><br>HPLC (Method H): Rt 2.96 min (purity 100%); LCMS (ESI+) (Method G): Rt 1.862 min, MH+ 352 m/z |
| "C98" | 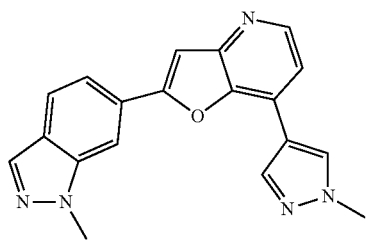<br>2-(1-Methyl-1H-indazol-6-yl)-7-(1-methyl-1H-pyrazol-4-yl)-furo[3,2-b]pyridine<br><br>HPLC (Method A): Rt 2.79 min (purity 97.83%); LCMS (ESI+) (Method G): Rt 1.652 min, MH+ 330.1;<br>$^1$H NMR (500 MHz, DMSO-$d_6$) δ [ppm] 8.71 (s, 1H), 8.46 (d, J = 5.1, 1H), 8.38 (S, 1H), 8.37 (s, 1H), 8.13 (d, J = 0.7, 1H), 7.93 (d, J = 8.4, 1H), 7.89 (dd, J = 8.5, 1.2, 1H), 7.77 (s, 1H), 7.60 (d, J = 5.1, 1H), 4.20 (s, 3H), 4.03 (s, 3H) |
| "C99" | 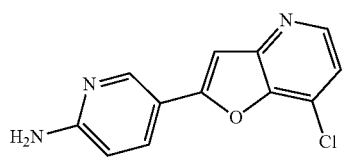<br>5-(7-Chloro-furo[3,2-b]pyridin-2-yl)-pyridin-2-ylamine<br><br>HPLC (Method A): Rt 2.36 min (purity 100%); LCMS (ESI+) (Method G): Rt 1.309 min, MH+ 246.1; |

| Compound no. | |
|---|---|
| "C100" | 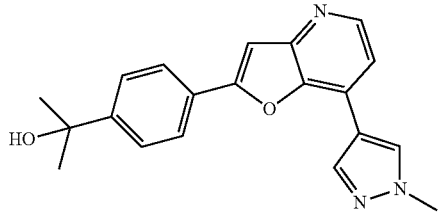<br>2-{4-[7-(1-Methyl-1H-pyrazol-4-yl)-furo[3,2-b]pyridin-2-yl]-phenyl}-propan-2-ol<br><br>HPLC (Method A): Rt 2.61 min (purity 100%); LCMS (ESI+) (Method G): Rt 1.598 min, MH+ 334.1;<br>$^1$H NMR (500 MHz, DMSO-d$_6$) δ [ppm] 8.63 (s, 1H), 8.43 (d, J = 5.1, 1H), 8.31 (t, J = 2.5, 1H), 8.06 (d, J = 8.5, 2H), 7.66 (d, J = 8.5, 2H), 7.57 (dd, J = 11.0, 5.9, 2H), 5.13 (d, J = 7.1, 1H), 4.01 (d, J = 8.5, 3H), 1.47 (d, J = 8.4, 6H) |
| "C101" | 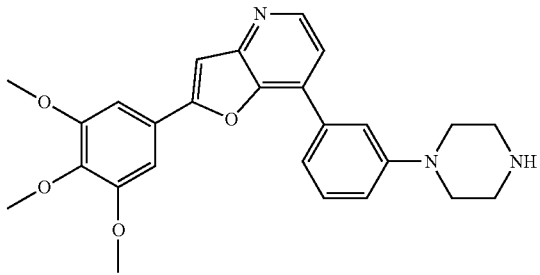<br>7-(3-Piperazin-1-yl-phenyl)-2-(3,4,5-trimethoxy-phenyl)-furo[3,2-b]pyridine<br><br>HPLC (Method A): Rt 2.09 min (purity 95%); LCMS (ESI+) (Method G): Rt 1.592 min, MH+ 446.2 m/z |
| "C102" | 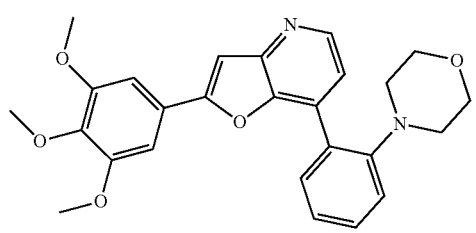<br>7-(2-Morpholin-4-yl-phenyl)-2-(3,4,5-trimethoxy-phenyl)-furo[3,2-b]pyridine<br><br>HPLC (Method A): Rt 2.85 min (purity 100%); LCMS (ESI+) (Method G): Rt 1.978 min, MH+ 447.1; |
| "C103" | 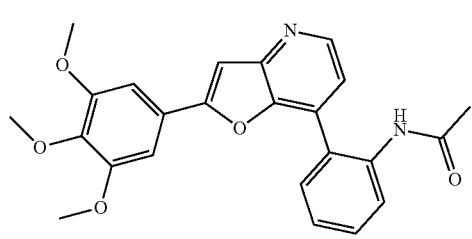<br>N-{2-[2-(3,4,5-Trimethoxy-phenyl)-furo[3,2-b]pyridin-7-yl]-phenyl}-acetamide<br><br>HPLC (Method A): Rt 2.64 min (purity 99.5%); LCMS (ESI+) (Method G): Rt 1.723 min, MH+ 419.1 |

| Compound no. | |
|---|---|
| "C104" | 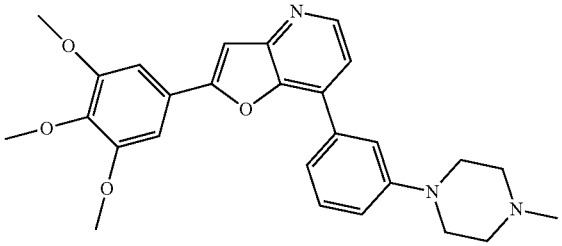 |

7-[3-(4-Methyl-piperazin-1-yl)-phenyl]-2-(3,4,5-trimethoxy-phenyl)-furo[3,2-b]pyridine HPLC (Method A): Rt ? min (purity 100%); LCMS (ESI+) (Method G): Rt 1.603 min, MH+ 460.2 m/z

| "C105" | 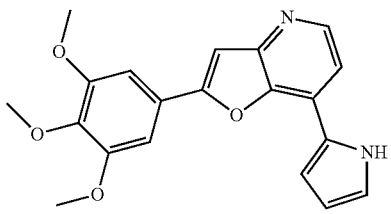 |
|---|---|

7-(1H-Pyrrol-2-yl)-2-(3,4,5-trimethoxy-phenyl)-furo[3,2-b]pyridine

HPLC (Method A): Rt 2.52 min (purity 100%); LCMS (ESI+) (Method G): Rt 1.839 min, MH+ 351.1 m/z

| "C106" | 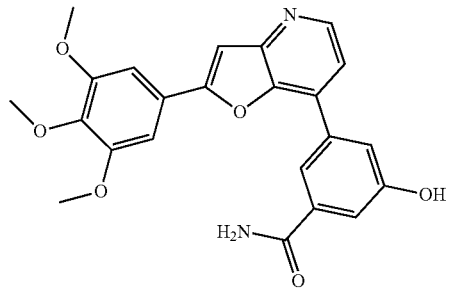 |
|---|---|

3-Hydroxy-5-[2-(3,4,5-trimethoxy-phenyl)-furo[3,2-b]pyridin-7-yl]-benzamide

LCMS (ESI+) (Method G): Rt 2.0785 min, MH+ 260.55

| "C107" | 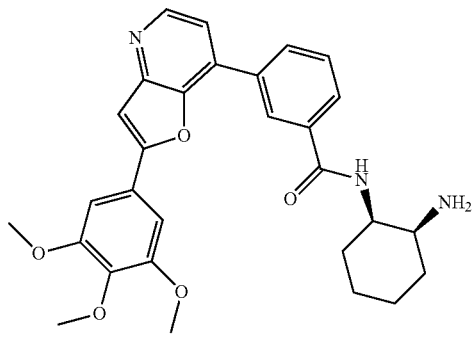 |
|---|---|

N-((1R,2S)-2-Amino-cyclohexyl)-3-[2-(3,4,5-trimethoxy-phenyl)-furo[3,2-b]pyridin-7-yl]-benzamide HPLC (Method A): Rt 2.36 min (purity 100%); LCMS (ESI+) (Method G): Rt 1.684 min, MH+ 502.2;

| Compound no. | |
|---|---|
| | ¹H NMR (400 MHz, DMSO-d₆) δ [ppm] 8.93 (s, 1H), 8.77 (d, J = 5.8, 1H), 8.56 (d, J = 7.4, 1H), 8.40 (d, J = 8.5, 1H), 8.31 (d, J = 7.9, 1H), 8.13 (d, J = 5.8, 1H), 7.99 (s, 1H), 7.79 (t, J = 7.8, 1H), 7.46 (s, 2H), 6.31 (br, 2H), 4.35-4.29 (m, 1H), 3.96 (s, 6H), 3.77 (s, 3H), 3.49 (s, 1 H), 2.06-1.82 (m, 2H), 1.82-1.58 (m, 4H), 1.49-1.36 (m, 2H) |
| "C108" | 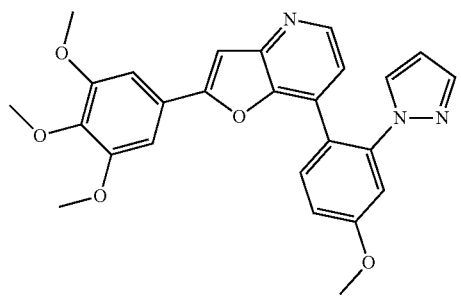

7-(4-Methoxy-2-pyrazol-1-yl-phenyl)-2-(3,4,5-trimethoxy-phenyl)-furo[3,2-b]pyridine HPLC (Method A): Rt 2.89 min (purity 100%); LCMS (ESI+) (Method G): Rt 1.946 min, MH+ 458.1 |
| "C109" | 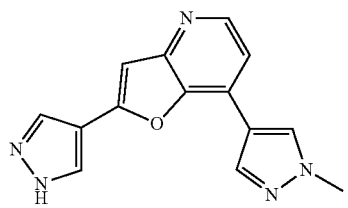

7-(1-Methyl-1H-pyrazol-4-yl)-2-(1H-pyrazol-4-yl)-furo[3,2-b]pyridine

HPLC (Method A): Rt 2.37 min (purity 90.2%); LCMS (ESI+) (Method G): Rt 1.325 min, MH+ 266.1 |
| "C110" | 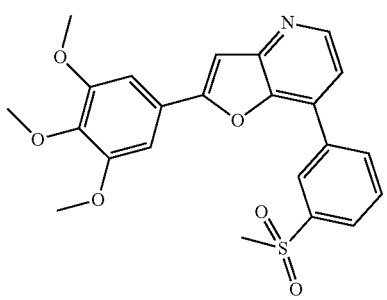

7-(3-Methanesulfonyl-phenyl)-2-(3,4,5-trimethoxy-phenyl)-furo[3,2-b]pyridine

HPLC (Method A): Rt 2.79 min (purity 98.4%); LCMS (ESI+) (Method G): Rt 1.836 min, MH+ 440.1;
¹H NMR (400 MHz, DMSO-d₆) δ [ppm] 8.91 (t, J = 1.8, 1H), 8.63 (d, J = 5.1, 1H), 8.44 (d, J = 8.2, 1H), 8.12 (d, J = 7.9, 1H), 7.92 (t, J = 7.8, 1H), 7.81 (s, 1H), 7.78 (d, J = 5.2, 1H), 7.37 (s, 2H), 3.93 (s, 6H), 3.74 (s, 3H), 3.33 (s, 3H) |

| Compound no. | |
|---|---|
| "C111" | 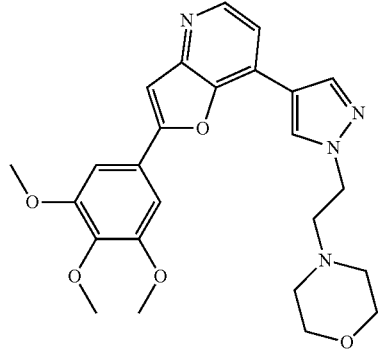<br>7-[1-(2-Morpholin-4-yl-ethyl)-1H-pyrazol-4-yl]-2-(3,4,5-trimethoxy-phenyl)-furo[3,2-b]pyridine<br><br>HPLC (Method A): Rt 2.10 min (purity 100%); LCMS (ESI+) (Method G): Rt 1.462 min, MH+ 465 m/z |
| "C112" | 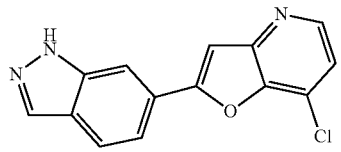<br>7-Chloro-2-(1H-indazol-6-yl)-furo[3,2-b]pyridine<br><br>HPLC (Method A): Rt 2.79 min (purity 95.2%); LCMS (ESI+) (Method G): Rt 1.818 min, MH+ 270 |
| "C113" | 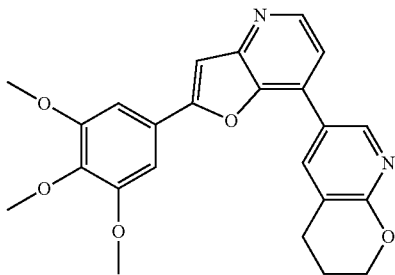<br>6-[2-(3,4,5-Trimethoxy-phenyl)-furo[3,2-b]pyridin-7-yl]-3,4-dihydro-2H-pyrano[2,3-b]pyridine<br><br>HPLC (Method A): Rt 2.31 min (purity 100%); LCMS (ESI+) (Method G): Rt 1.757 min, MH+ 419.1 m/z |
| "C114" | 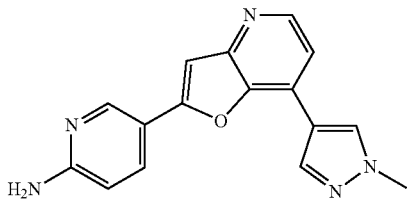<br>5-[7-(1-Methyl-1H-pyrazol-4-yl)-furo[3,2-b]pyridin-2-yl]-pyridin-2-ylamine<br><br>HPLC (Method A): Rt 2.29 min (purity 100%); LCMS (ESI+) (Method G): Rt 1.22 min, MH+ 292.1 |

-continued

| Compound no. | |
|---|---|
| "C115" | 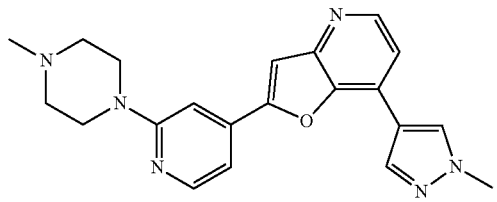<br>2-[2-(4-Methyl-piperazin-1-yl)-pyridin-4-yl]-7-(1-methyl-1H-pyrazol-4-yl)-furo[3,2-b]pyridine<br><br>HPLC (Method A): Rt 1.71 min (purity 96%); LCMS (ESI+) (Method G): Rt 1.718 min, MH+ 375.2 m/z |
| "C116" | 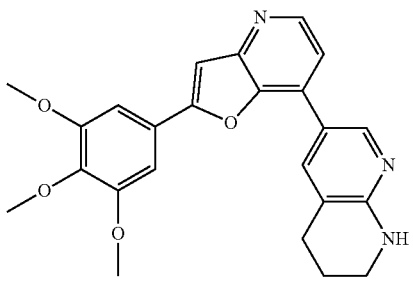<br>6-[2-(3,4,5-Trimethoxy-phenyl)-furo[3,2-b]pyridin-7-yl]-2,3,4-tetrahydro-[1,8]naphthyridine<br><br>HPLC (Method A): Rt 2.07 min (purity 93.4%); LCMS (ESI+) (Method G): Rt 1.563 min, MH+ 418.1 m/z;<br>$^1$H NMR (TFA exchange) (500 MHz, DMSO-$d_6$) δ [ppm] 8.96 (d, J = 2.1 Hz, 1H), 8.88 (d, J = 6.4 Hz, 1H), 8.58 (d, J = 1.8 Hz, 1H), 8.21 (d, J = 6.4 Hz, 1 H), 8.03 (s, 1H), 7.53 (s, 2H), 4.00 (s, 6H), 3.85 (s, 3H), 3.63-3.58 (m, 2H), 3.00 (t, J = 6.0 Hz, 2H), 2.01 (dd, J = 11.0, 5.8 Hz, 2H) |
| "C117" | 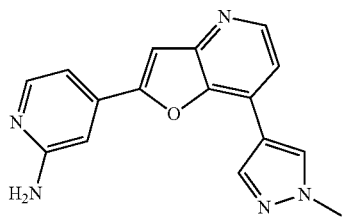<br>4-[7-(1-Methyl-1H-pyrazol-4-yl)-furo[3,2-b]pyridin-2-yl]-pyridin-2-ylamine<br><br>HPLC (Method A): Rt 2.27 min (purity 100%); LCMS (ESI+) (Method G): Rt 1.24 min, MH+ 292.1;<br>$^1$H NMR (400 MHz, DMSO-$d_6$) δ [ppm] 8.62 (s, 1H), 8.57 (d, J = 5.1, 1H), 8.36 (s, 1H), 8.16 (s, 1H), 8.14-8.01 (m, 3H), 7.72 (d, J = 5.0, 1H), 7.60 (s, 1H), 7.51 (dd, J = 6.7, 1.7, 1H), 4.01 (s, 3H) |
| "C118" | 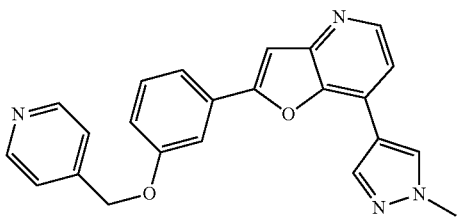<br>7-(1-Methyl-1H-pyrazol-4-yl)-2-[3-(pyridin-4-ylmethoxy)-phenyl]-furo[3,2-b]pyridine |

| Compound no. | |
|---|---|

HPLC (Method A): Rt 2.4 min (purity 95.5%); LCMS (ESI+) (Method G): Rt 1.478 min, MH+ 383.1;
$^{1}$H NMR (500 MHz, DMSO-$d_6$) δ [ppm] 8.64-8.59 (m, 3H), 8.44 (d, J = 6.2, 1H), 8.30 (d, J = 0.5, 1H), 7.77-7.74 (m, 1H), 7.73-7.72 (m, 1H), 7.71 (s, 1H), 7.58 (d, J = 5.1, 1H), 7.53-7.49 (m, 3H), 7.15 (dd, J = 8.2, 2.0, 1H), 5.35 (s, 2H), 4.05-3.99 (m, 3H)

"C119"

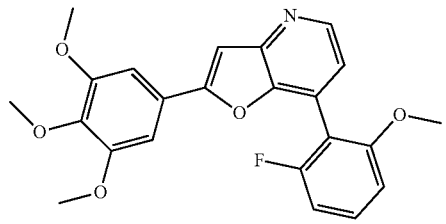

7-(2-Fluoro-6-methoxy-phenyl)-2-(3,4,5-trimethoxy-phenyl)-furo[3,2-b]pyridine

HPLC (Method A): Rt 2.87 min (purity 99.5%); LCMS (ESI+) (Method G): Rt 2.003 min, MH+ 410.1;
$^{1}$H NMR (400 MHz, DMSO-$d_6$) δ [ppm] 8.53 (d, J = 5.0, 1H), 7.70 (s, 1H), 7.57 (td, J = 8.4, 6.9, 1H), 7.31 (dd, J = 5.0, 1.0, 1H), 7.16 (s, 2H), 7.13 (d, J = 8.5, 1H), 7.04 (t, J = 8.7, 1H), 3.85 (s, 6H), 3.83 (s, 3H), 3.72 (s, 3H)

"C120"

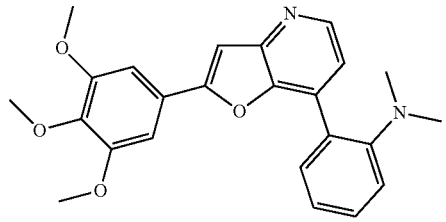

Dimethyl-{2-[2-(3,4,5-trimethoxy-phenyl)-furo[3,2-b]pyridin-7-yl]-phenyl}-amine

HPLC (Method A): Rt 2.85 min (purity 97.3%); LCMS (ESI+) (Method G): Rt 2.02 min, MH+ 405.1

"C121"

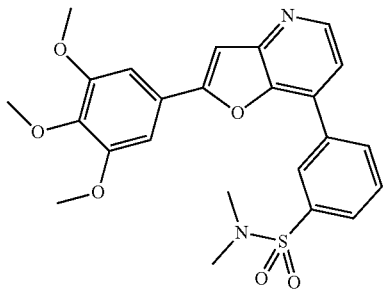

N,N-Dimethyl-3-[2-(3,4,5-trimethoxy-phenyl)-furo[3,2-b]pyridin-7-yl]-benzenesulfonamide HPLC (Method A): Rt 2.87 min (purity 100%); LCMS (ESI+) (Method G): Rt 1.998 min, MH+ 469.2

| Compound no. | |
|---|---|
| "C122" | 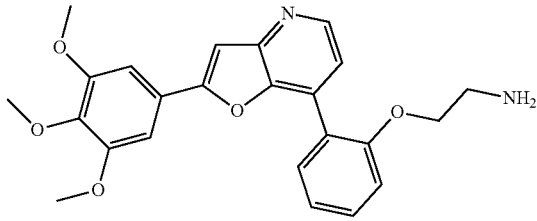 |

2-{2-[2-(3,4,5-Trimethoxy-phenyl)-furo
[3,2-b]pyridin-7-yl]-phenoxy}-ethylamine

HPLC (Method A): Rt 2.6 min (purity 93%); LCMS (ESI+) (Method G):
Rt 1.65 min, MH+ 421.1

| "C123" | 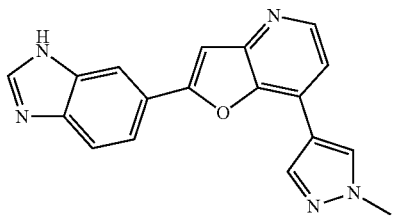 |
|---|---|

2-(3H-Benzoimidazol-5-yl)-7-(1-methyl-
1H-pyrazol-4-yl)-furo[3,2-b]pyridine

LCMS (ESI+) (Method G): Rt 1.297 min, MH+ 316.1

| "C124" | 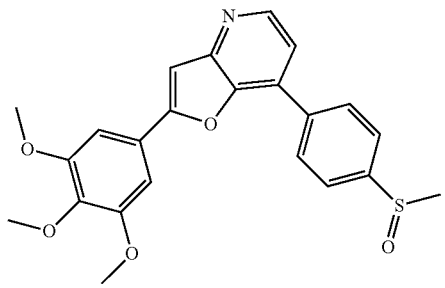 |
|---|---|

7-(4-Methanesulfinyl-phenyl)-2-(3,4,5-
trimethoxy-phenyl)-furo[3,2-b]pyridine

HPLC (Method A): Rt 2.56 min (purity 100%); LCMS (ESI+) (Method G):
Rt 1.715 min, MH+ 424.1;
$^1$H NMR (500 MHz, DMSO-$d_6$) δ [ppm] 8.62 (d, J = 5.2, 1 H), 8.38-8.32
(m, 2H), 7.98-7.93 (m, 2H), 7.79 (s, 1H), 7.71 (d, J = 5.2, 1H), 7.33 (s,
2H), 3.92 (s, 6H), 3.75 (s, 3H), 2.85 (s, 3H)

| "C125" | 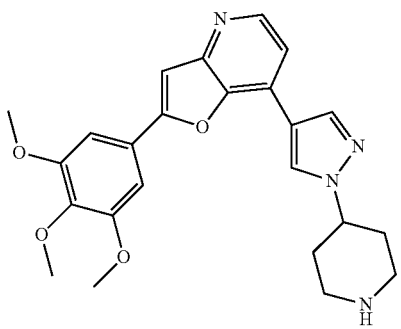 |
|---|---|

7-(1-Piperidin-4-yl-1H-pyrazol-4-yl)-2-(3,4,5-
trimethoxy-phenyl)-furo[3,2-b]pyridine

| Compound no. | |
|---|---|
| | HPLC (Method H): Rt 2.05 min (purity 100%); LCMS (ESI+) (Method G): Rt 1.457 min, MH+ 435.2 m/z |
| "C126" | 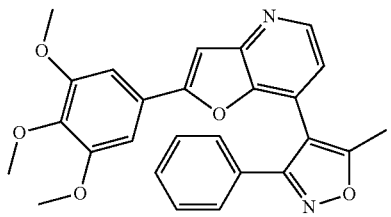<br>7-(5-Methyl-3-phenyl-isoxazol-4-yl)-2-(3,4,5-trimethoxy-phenyl)-furo[3,2-b]pyridine |
| | HPLC (Method H): Rt 3.19 min (purity 100%); LCMS (ESI+) (Method G): Rt 2.047 min, MH+ 443.2 m/z |
| "C127" | 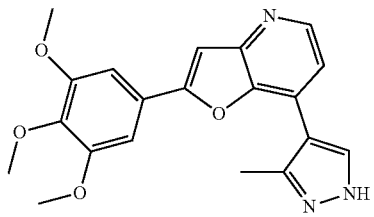<br>7-(3-Methyl-1H-pyrazol-4-yl)-2-(3,4,5-trimethoxy-phenyl)-furo[3,2-b]pyridine |
| | HPLC (Method H): Rt 2.23 min (purity 100%); LCMS (ESI+) (Method E TFA): Rt 1.616 min, MH+ 366 m/z |
| "C128" | 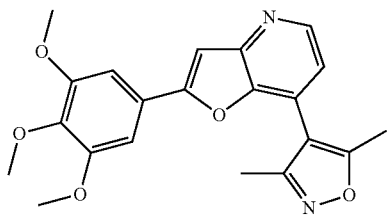<br>7-(3,5-Dimethyl-isoxazol-4-yl)-2-(3,4,5-trimethoxy-phenyl)-furo[3,2-b]pyridine |
| | HPLC (Method H): Rt 2.88 min (purity 100%); LCMS (ESI+) (Method G): Rt 1.929 min, MH+ 381.1 m/z |
| "C129" | 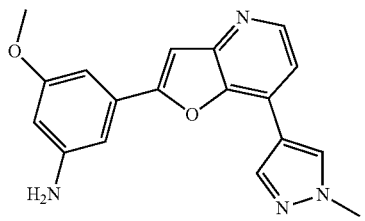<br>3-Methoxy-5-[7-(1-methyl-1H-pyrazol-4-yl)-furo[3,2-b]pyridin-2-yl]-phenylamine |
| | HPLC (Method A): Rt 1.350 min (purity 100%); LCMS (ESI+) (Method G): Rt 1.400 min, MH+ 321.1 m/z |

-continued

| Compound no. | |
|---|---|
| "C130" | 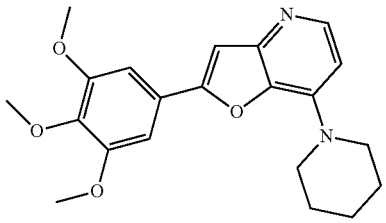<br>7-Piperidin-1-yl-2-(3,4,5-trimethoxy-phenyl)-furo[3,2-b]pyridine<br><br>HPLC (Method A): Rt 2.6 min (purity 100%); LCMS (ESI+) (Method G): Rt 1.963 min, MH+ 369.2 |
| "C131" | 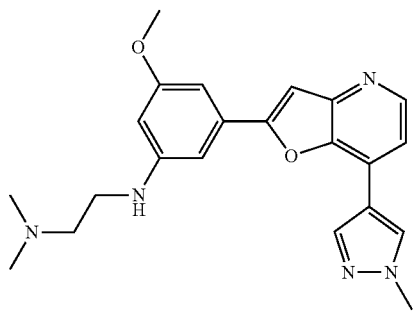<br>N'-{3-Methoxy-5-[7-(1-methyl-1H-pyrazol-4-yl)-furo[3,2-b]pyridin-2-yl]-phenyl}-N,N-dimethyl-ethane-1,2-diamine<br><br>LCMS (ESI+) (Method G): Rt 1.267 min, MH+ 392.1 m/z |
| "C132" | 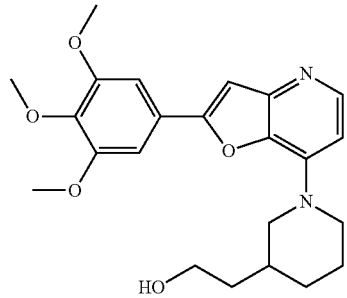<br>2-{1-[2-(3,4,5-Trimethoxy-phenyl)-furo[3,2-b]pyridin-7-yl]-piperidin-3-yl}-ethanol<br><br>HPLC (Method A): Rt 2.51 min (purity 97.3%); LCMS (ESI+) (Method G): Rt 1.796 min, MH+ 413.2;<br>$^1$HNMR (500 MHz, DMSO-$d_6$) δ [ppm] 8.10 (d, J = 5.6, 1H), 7.47 (s, 1H), 7.21 (s, 2H), 6.65 (d, J = 5.7, 1H), 4.41 (t, J = 5.2, 1H), 4.32 (d, J = 12.6, 1H), 4.06 (d, J = 12.7, 1H), 3.89 (s, 6H), 3.72 (s, 3H), 3.56-3.49 (m, 2H), 3.09-3.00 (m, 1 H), 2.86 (dd, J = 12.7, 10.4, 1H), 1.97-1.74 (m, 3H), 1.68-1.54 (m, 1H), 1.54-1.37 (m, 2H), 1.30-1.19 (m, 1H) |

| Compound no. | |
|---|---|
| "C133" | 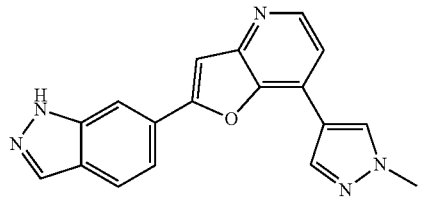

2-(1H-Indazol-6-yl)-7-(1-methyl-1H-pyrazol-4-yl)-furo[3,2-b]pyridine

HPLC (Method A): Rt 2.4 min (purity 96.75%); LCMS (ESI+) (Method G): Rt 1.556 min, MH+ 316.1;
$^1$H NMR (500 MHz, DMSO-d$_6$) δ [ppm] 13.30 (s, 1H), 8.67 (s, 1H), 8.46 (d, J = 5.1, 1H), 8.35 (s, 1H), 8.26 (s, 1H), 8.16 (s, 1 H), 7.94 (d, J = 8.4, 1H), 7.90-7.84 (m, 1H), 7.76 (s, 1H), 7.59 (d, J = 5.1, 1H), 4.03 (s, 3H) |
| "C134" | 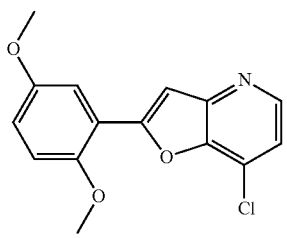

7-Chloro-2-(2,5-dimethoxy-phenyl)-furo[3,2-b]pyridine

HPLC (Method A): Rt 2.75 min (purity 97.14%); LCMS (ESI+) (Method G): RT 2.13 min, MH+ 290.1 |
| "C135" | 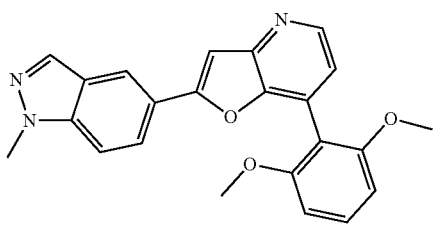

7-(2,6-Dimethoxy-phenyl)-2-(1-methyl-1H-indazol-5-yl)-furo[3,2-b]pyridine

HPLC (Method A): Rt 2.83 min (purity 94.89%); LCMS (ESI+) (Method G): Rt 1.907 min, MH+ 386.2;
$^1$H NMR (400 MHz, DMSO-d$_6$) δ [ppm] 8.45 (d, J = 4.9, 1H), 8.20 (s, 1H), 8.16 (d, J = 0.7, 1H), 7.94 (dd, J = 8.8, 1.6, 1H), 7.76 (d, J = 8.9, 1H), 7.59 (s, 1H), 7.49 (t, J = 8.4, 1H), 7.16 (d, J = 4.9, 1H), 6.88 (d, J = 8.4, 2H), 4.07 (s, 3H), 3.72 (s, 6H) |
| "C136" | 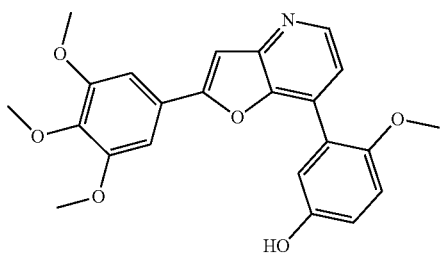

4-Methoxy-3-[2-(3,4,5-trimethoxy-phenyl)-furo[3,2-b]pyridin-7-yl]-phenol

LCMS (ESI+) (Method G): Rt 1.785 min, MH+ 408.1;
$^1$H NMR (500 MHz, DMSO-d$_6$) δ [ppm] 9.21 (s, 1 H), 8.49 (d, J = 5.0, 1H), |

| Compound no. | |
|---|---|
| | 7.68 (s, 1H), 7.34 (d, J = 5.0, 1H), 7.22 (s, 2H), 7.09 (d, J = 8.9, 1H), 7.03 (d, J = 3.0, 1H), 6.93-6.87 (m, 1H), 3.87 (s, 6H), 3.77 (s, 3H), 3.73 (s, 3H) |
| "C137" | 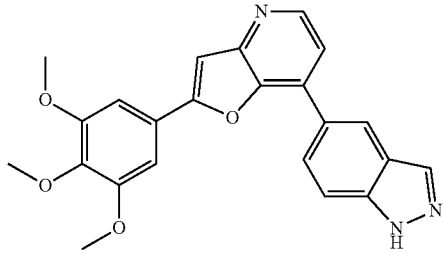 |

7-(1H-Indazol-5-yl)-2-(3,4,5-trimethoxy-phenyl)-furo[3,2-b]pyridine

HPLC (Method A): Rt 2.59 min (purity 100%); LCMS (ESI+) (Method G): Rt 1.784 min, MH+ 402.1;
$^1$H NMR (500 MHz, DMSO-d$_6$) δ [ppm] 13.28 (s, 1H), 8.62 (s, 1H), 8.55 (d, J = 5.1, 1H), 8.26 (s, 1 H), 8.11 (dd, J = 8.8, 1.6, 1H), 7.78 (d, J = 8.7, 1H), 7.73 (s, 1H), 7.64 (d, J = 5.1, 1H), 7.34 (s, 2H), 3.92 (s, 6H), 3.76 (d, J = 16.1, 3H)

"C138" 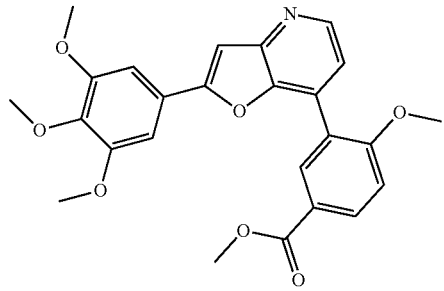

4-methoxy-3-[2-(3,4,5-trimethoxy-phenyl)-furo[3,2-b]pyridin-7-yl]-benzoic acid methyl ester HPLC (Method A): Rt 2.77 min (purity 99.8%); LCMS (ESI+) (Method G): Rt 2.008 min, MH+ 450.1

"C139" 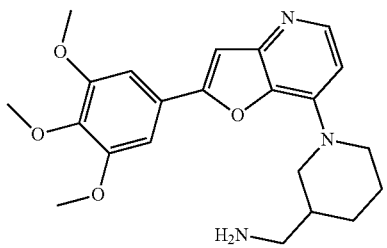

C-{1-[2-(3,4,5-Trimethoxy-phenyl)-furo[3,2-b]pyridin-7-yl]-piperidin-3-yl}-methylamine HPLC (Method A): Rt 2.41 min (purity 96.8%); LCMS (ESI+) (Method G): Rt 1.501 min, MH+ 398.2

| Compound no. | |
|---|---|
| "C140" | 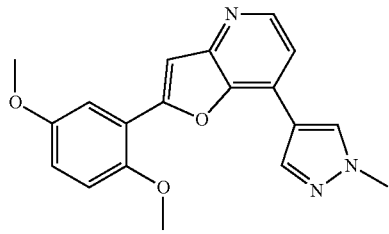<br>2-(2,5-Dimethoxy-phenyl)-7-(1-methyl-1H-pyrazol-4-yl)-furo[3,2-b]pyridine<br><br>HPLC (Method A): Rt 2.52 min (purity 98.31%); LCMS (ESI+) (Method G): Rt 1.774 min, MH+ 336.1;<br>$^1$H NMR (500 MHz, DMSO-$d_6$) δ [ppm] 8.60 (s, 1H), 8.44 (d, J = 5.1, 1H), 8.28 (s, br, 1H), 7.63 (d, J = 3.1, 1H), 7.56 (d, J = 5.1, 1H), 7.52 (s, 1H), 7.19 (d, J = 9.1, 1H), 7.08 (dd, J = 9.0, 3.1, 1H), 4.00 (s, 3H), 3.97 (s, 3H), 3.87 (s, 3H) |
| "C141" | 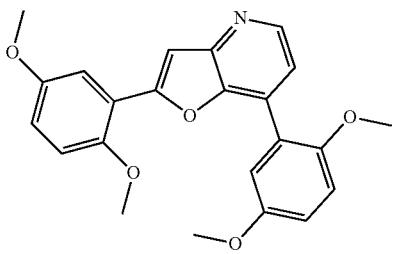<br>2,7-Bis-(2,5-dimethoxy-phenyl)-furo[3,2-b]pyridine<br><br>HPLC (Method A): Rt 2.96 min (purity 91.47%); LCMS (ESI+) (Method G): Rt 2.093 min, MH+ 392.1;<br>$^1$H NMR (500 MHz, DMSO-$d_6$) δ [ppm] 8.54 (d, J = 5.0, 1H), 7.54 (s, 1H), 7.41 (d, J = 5.0, 1H), 7.35 (d, J = 3.1, 1H), 7.25-7.17 (m, 3H), 7.11 (dd, J = 8.9, 3.2, 1H), 7.06 (dd, J = 9.0, 3.1, 1H), 3.97 (s, 3H), 3.80 (s, 3H), 3.79 (s, 3H), 3.76 (s, 3H) |
| "C142" | 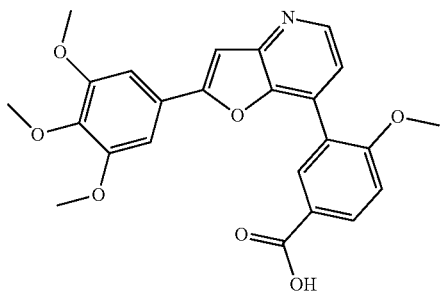<br>4-Methoxy-3-[2-(3,4,5-trimethoxy-phenyl)-furo[3,2-b]pyridin-7-yl]-benzoic acid<br><br>HPLC (Method A): Rt 2.52 min (purity 100%); LCMS (ESI+) (Method G): Rt 1.79 min, MH+ 436.1 |

| Compound no. | |
|---|---|
| "C143" | 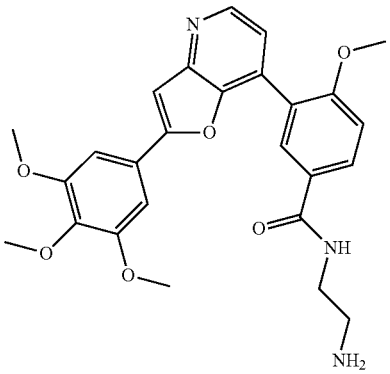<br>N-(2-Amino-ethyl)-4-methoxy-3-[2-(3,4,5-trimethoxy-phenyl)-furo[3,2-b]pyridin-7-yl]-benzamide<br><br>HPLC (Method A): Rt 2.37 min (purity 100%); LCMS (ESI+) (Method G): Rt 1.564 min, MH+ 478.2;<br>$^1$H NMR (500 MHz, DMSO-d$_6$) δ [ppm] 8.60 (t, J = 5.6, 1H), 8.57 (d, J = 5.0, 1H), 8.22 (d, J = 2.3, 1H), 8.07 (dd, J = 8.7, 2.3, 1H), 7.75 (br, 2H), 7.72 (s, 1H), 7.45 (d, J = 5.0, 1H), 7.38 (d, J = 8.8, 1H), 7.23 (s, 2H), 3.94 (s, 3H), 3.86 (s, 6H), 3.73 (s, 3H), 3.50 (dd, J = 12.0, 6.1, 2H), 3.02-2.93 (m, 2H) |
| "C144" | 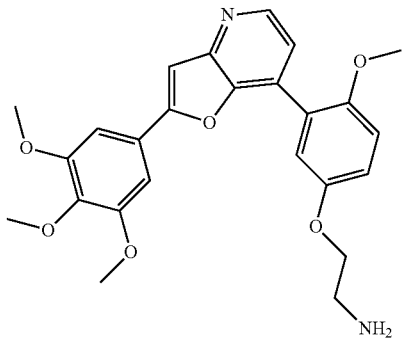<br>2-{4-Methoxy-3-[2-(3,4,5-trimethoxy-phenyl)-furo[3,2-b]pyridin-7-yl]-phenoxy}-ethylamine<br><br>HPLC (Method A): Rt 2.4 min (purity 96.3%); LCMS (ESI+) (Method G): Rt 1.594 min, MH+ 451.2;<br>HCl salt: $^1$H NMR (500 MHz, DMSO-d$_6$) δ [ppm] 8.58 (d, J = 5.2, 1H), 8.08 (s, 3H), 7.78 (s, 1H), 7.47 (d, J = 5.1, 1 H), 7.28 (d, J = 3.0, 1 H), 7.27-7.24 (m, 3H), 7.19 (dd, J = 9.0, 3.0, 1H), 4.22 (t, J = 5.1, 2H), 3.87 (s, 6H), 3.83 (s, 3H), 3.73 (s, 3H), 3.25-3.14 (m, 2H) |
| "C145" | 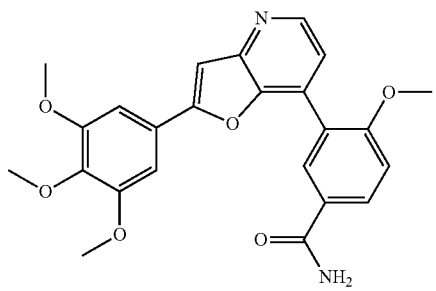<br>4-Methoxy-3-[2-(3,4,5-trimethoxy-phenyl)-furo[3,2-b]pyridin-7-yl]-benzamide |

| Compound no. | |
|---|---|

HPLC (Method A): Rt 2.171 min (purity 100%); LCMS (ESI+) (Method G): Rt 1.647 min, MH+ 435.1 m/z

"C146"

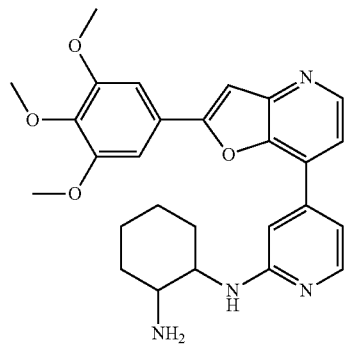

N-{4-[2-(3,4,5-Trimethoxy-phenyl)-furo[3,2-b]pyridin-7-yl]-pyridin-2-yl}-cyclohexane-1,2-diamine HPLC (Method A): Rt 2.41 min (purity 100%); LCMS (ESI+) (Method G): Rt 1.628 min, MH+ 475.2

"C147"

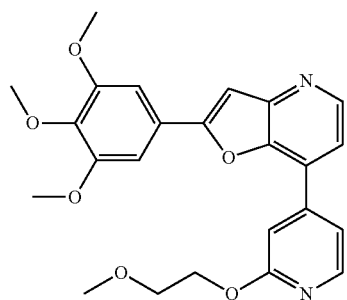

7-[2-(2-Methoxy-ethoxy)-pyridin-4-yl]-2-(3,4,5-trimethoxy-phenyl)-furo[3,2-b]pyridine HPLC (Method A): Rt 2.65 min (purity 100%); LCMS (ESI+) (Method G): Rt 1.971 min, MH+ 437.1

"C148"

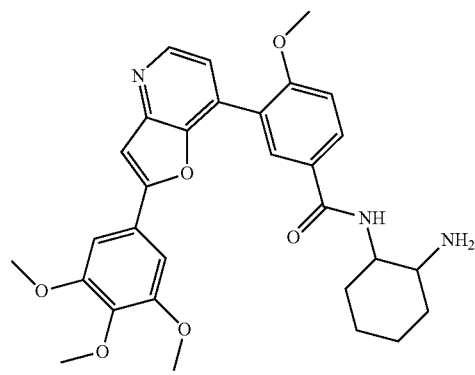

N-(2-Amino-cyclohexyl)-4-methoxy-3-[2-(3,4,5-trimethoxy-phenyl)-furo[3,2-b]pyridin-7-yl]-benzamide HPLC (Method A): Rt 2.47 min (purity 100%); LCMS (ESI+) (Method G): Rt 1.675 min, MH+ 532.2

| Compound no. | |
|---|---|
| "C149" | 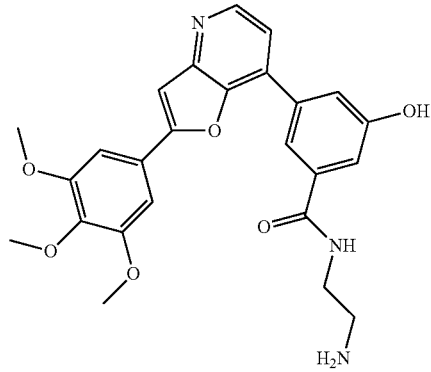<br>N-(2-Amino-ethyl)-3-hydroxy-5-[2-(3,4,5-trimethoxy-phenyl)-furo[3,2-b]pyridin-7-yl]-benzamide<br><br>HPLC (Method A): Rt 2.36 min (purity 100%); LCMS (ESI+) (Method G): Rt 1.49 min, MH+ 464.2 |
| "C150" | 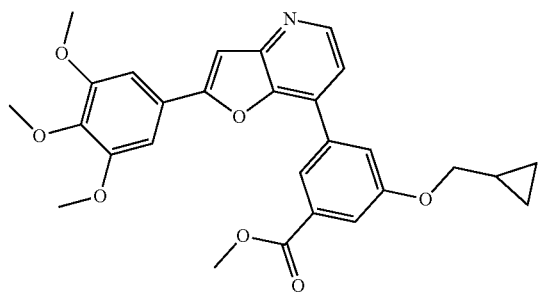<br>3-Cyclopropylmethoxy-5-[2-(3,4,5-trimethoxy-phenyl)-furo[3,2-b]pyridin-7-yl]-benzoic acid methyl ester<br><br>HPLC (Method A): Rt 2.83 min (purity 94.6%); LCMS (ESI+) (Method G): Rt 2.314 min, MH+ 490.2 |
| "C151" | 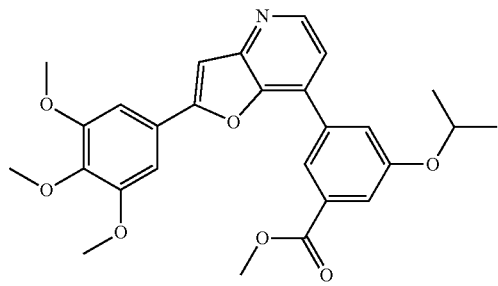<br>3-Isopropoxy-5-[2-(3,4,5-trimethoxy-phenyl)-furo[3,2-b]pyridin-7-yl]-benzoic acid methyl ester<br><br>HPLC (Method A): Rt 2.71 min (purity 95.9%); LCMS (ESI+) (Method G): Rt 2.285 min, MH+ 478.1 |

| Compound no. | |
|---|---|
| "C152" | 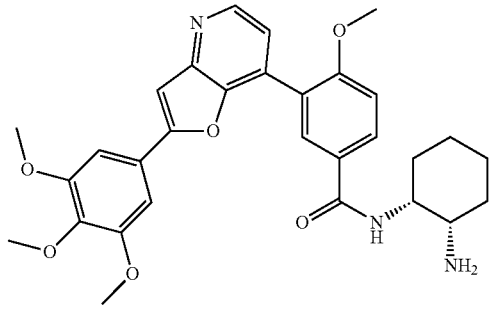 |

N-((1R,2S)-2-Amino-cyclohexyl)-4-methoxy-3-[2-(3,4,5-trimethoxy-phenyl)-furo[3,2-b]pyridin-7-yl]-benzamide HPLC (Method A): Rt 2.16 min (purity 100%); LCMS (ESI+) (Method E TFA): Rt 1.655 min, MH+ 532.3 m/z;

$^1$H NMR (HCl salt) (500 MHz, DMSO-$d_6$) δ [ppm] 8.68 (d, J = 5.4 Hz, 1H), 8.36 (d, J = 2.2 Hz, 1 H), 8.31-8.24 (m, 2H), 8.13 (s, 3H), 7.87 (s, 1H), 7.75 (d, J = 5.3 Hz, 1H), 7.38 (d, J = 8.8 Hz, 1H), 7.30 (s, 2H), 3.96 (s, 3H), 3.88 (s, 6H), 3.74 (s, 3H), 1.96-1.87 (m, 1H), 1.83 (dt, J = 15.0, 7.4 Hz, 1H), 1.68 (ddd, J = 32.0, 15.0, 6.1 Hz, 4H), 1.40 (d, J = 3.5 Hz, 2H)

| "C153" | 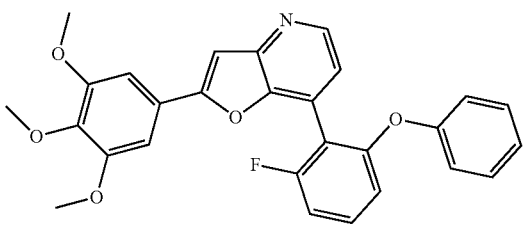 |
|---|---|

7-(2-Fluoro-6-phenoxy-phenyl)-2-(3,4,5-trimethoxy-phenyl)-furo[3,2-b]pyridine

HPLC (Method A): Rt 2.72 min (purity 99.5%); LCMS (ESI+) (Method G): Rt 2.223 min, MH+ 472.2

| "C154" | 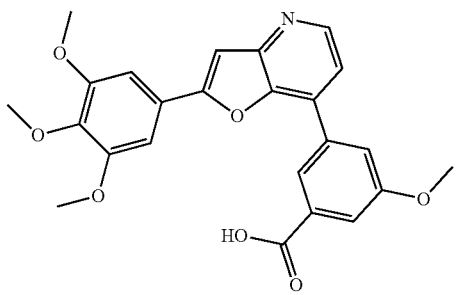 |
|---|---|

3-Methoxy-5-[2-(3,4,5-trimethoxy-phenyl)-furo[3,2-b]pyridin-7-yl]-benzoic acid

HPLC (Method A): Rt 2.55 min (purity 100%); LCMS (ESI+) (Method G): Rt 1.892 min, MH+ 436.1

| Compound no. | |
|---|---|
| "C155" | 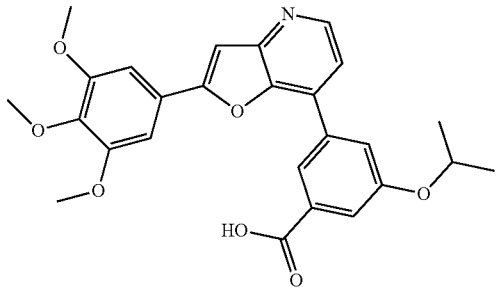
3-Isopropoxy-5-[2-(3,4,5-trimethoxy-phenyl)-furo[3,2-b]pyridin-7-yl]-benzoic acid LCMS (ESI+) (Method G): Rt 2.02 min, MH+ 464.2 |
| "C156" | 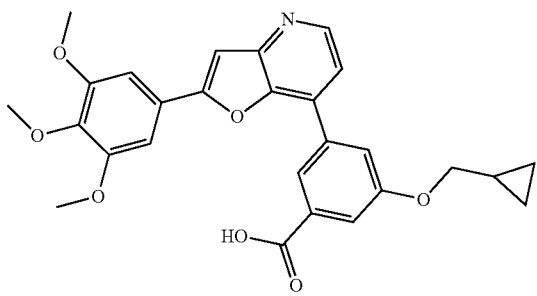
3-Cyclopropylmethoxy-5-[2-(3,4,5-trimethoxy-phenyl)-furo[3,2-b]pyridin-7-yl]-benzoic acid HPLC (Method A): Rt 2.65 min (purity 94.5%); LCMS (ESI+) (Method G): Rt 2.051 min, MH+ 476.2 |
| "C157" | 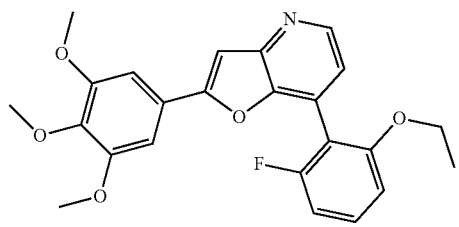
7-(2-Ethoxy-6-fluoro-phenyl)-2-(3,4,5-trimethoxy-phenyl)-furo[3,2-b]pyridine HPLC (Method A): Rt 2.57 min (purity 98.8%); LCMS (ESI+) (Method G): Rt 2.04 min, MH+ 424.2 |
| "C158" | 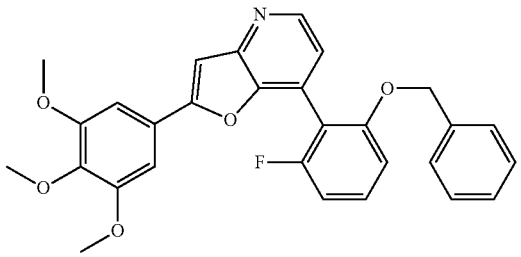
7-(2-Benzyloxy-6-fluoro-phenyl)-2-(3,4,5-trimethoxy-phenyl)-furo[3,2-b]pyridine HPLC (Method A): Rt 2.67 min (purity 100%); LCMS (ESI+) (Method G): RT 2.18 min, MH+ 486.2 |

| Compound no. | |
|---|---|
| "C159" | 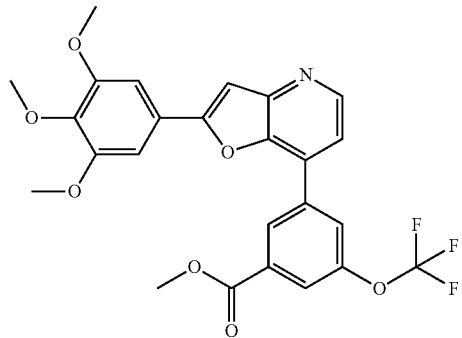<br>3-Trifluoromethoxy-5-[2-(3,4,5-trimethoxy-phenyl)-furo[3,2-b]pyridin-7-yl]-benzoic acid methyl ester<br><br>HPLC (Method A): Rt 2.83 min (purity 100%); LCMS (ESI+) (Method G):<br>Rt 2.361 min, MH+ 504.1 |
| "C160" | 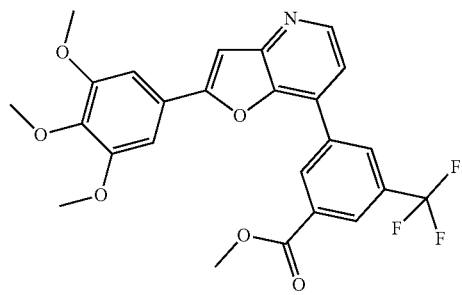<br>3-Trifluoromethyl-5-[2-(3,4,5-trimethoxy-phenyl)-furo[3,2-b]pyridin-7-yl]-benzoic acid methyl ester<br><br>HPLC (Method A): Rt 2.8 min (purity 100%); LCMS (ESI+) (Method G):<br>Rt 2.338 min, MH+ 488.1 |
| "C161" | 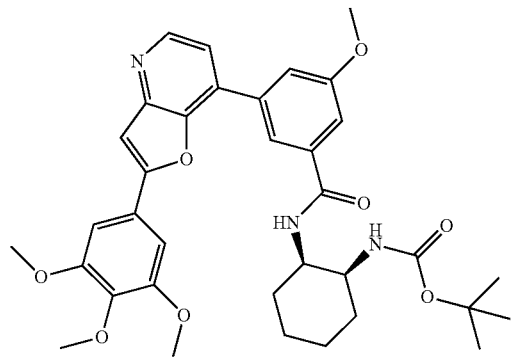<br>((1S,2R)-2-{3-Methoxy-5-[2-(3,4,5-trimethoxy-phenyl)-furo[3,2-b]pyridin-7-yl]-benzoylamino}-cyclohexyl)-carbamic acid tert-butyl ester<br><br>HPLC (Method A): Rt 2.92 min (purity 100%); LCMS (ESI+) (Method G):<br>Rt 2.21 min, MH+ 632.3 |

| Compound no. | |
|---|---|
| "C162" | 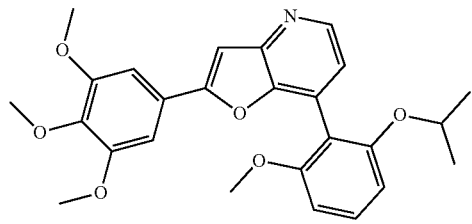<br>7-(2-Isopropoxy-6-methoxy-phenyl)-2-(3,4,5-trimethoxy-phenyl)-furo[3,2-b]pyridine<br><br>HPLC (Method A): Rt 2.6 min (purity 99%); LCMS (ESI+) (Method G): Rt 2.08 min, MH+ 450.2 |
| "C163" | 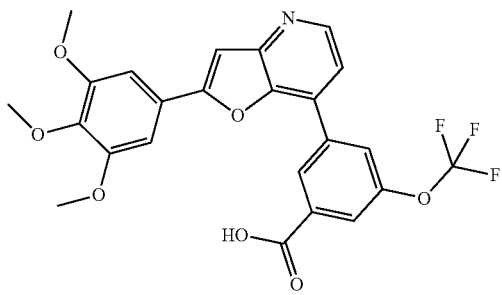<br>3-Trifluoromethoxy-5-[2-(3,4,5-trimethoxy-phenyl)-furo[3,2-b]pyridin-7-yl]-benzoic acid<br><br>HPLC (Method A): Rt 2.85 min (purity 98.5%); LCMS (ESI+) (Method G): Rt 2.098 min, MH+ 490.1 |
| "C164" | 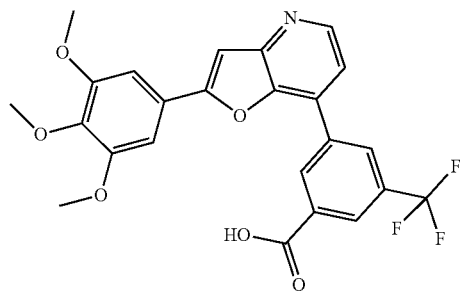<br>3-Trifluoromethyl-5-[2-(3,4,5-trimethoxy-phenyl)-furo[3,2-b]pyridin-7-yl]-benzoic acid<br><br>LCMS (ESI+) (Method G): Rt 2.066 min, MH+ 474.1 |
| "C165" | 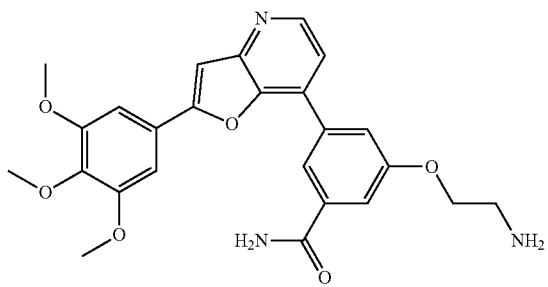<br>3-(2-Amino-ethoxy)-5-[2-(3,4,5-trimethoxy-phenyl)-furo[3,2-b]pyridin-7-yl]-benzamide |

| Compound no. | |
|---|---|

HPLC (Method A): Rt 2.33 min (purity 100%); LCMS (ESI+) (Method G): Rt 1.458 min, MH+ 464.2

"C166"

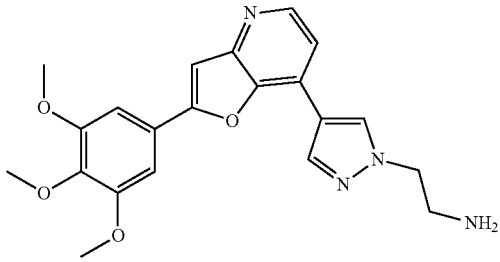

2-{4-[2-(3,4,5-Trimethoxy-phenyl)-furo[3,2-b]pyridin-7-yl]-pyrazol-1-yl}-ethylamine HPLC (Method A): Rt 2.32 min (purity 98.9%); LCMS (ESI+) (Method G): Rt 1.44 min, MH+ 395.2;
$^1$H NMR (500 MHz, DMSO-$d_6$) δ [ppm] 8.90 (s, 1H), 8.61 (d, J = 5.7, 1H), 8.55 (s, 1H), 8.16 (s, 3H), 7.89-7.83 (m, 2H), 7.47 (s, 2H), 4.58 (t, J = 6.1, 2H), 3.97 (s, 6H), 3.77 (s, 3H), 3.42-3.34 (m, 2H)

"C167"

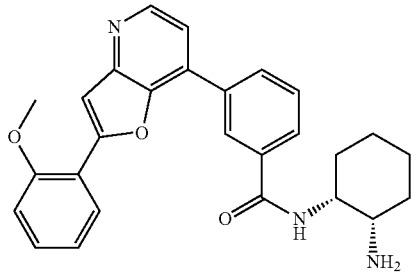

N-((1R,2S)-2-Amino-cyclohexyl)-3-[2-(2-methoxy-phenyl)-furo[3,2-b]pyridin-7-yl]-benzamide HPLC (Method A): Rt 2.15 min (purity 100%); LCMS (ESI+) (Method E TFA): Rt 1.637 min, MH+ 442.2 m/z;
$^1$H NMR (TFA-$d_1$ exchange) (500 MHz, DMSO-$d_6$) δ [ppm] 8.82 (d, J = 6.3 Hz, 1H), 8.75 (s, 1H), 8.36 (d, J = 7.9 Hz, 1H), 8.22 (d, J = 7.8 Hz, 1 H), 8.18-8.09 (m, 2H), 7.76 (t, J = 7.8 Hz, 1H), 7.72 (s, 1H), 7.54 (t, J = 7.4 Hz, 1H), 7.23 (d, J = 8.5 Hz, 1H), 7.13 (t, J = 7.6 Hz, 1H), 4.43 (d, J = 3.1 Hz, 1H), 4.02 (s, 3H), 3.51-3.37 (m, 1H), 1.88-1.77 (m, 2H), 1.77-1.60 (m, 4H), 1.46-1.32 (m, 2H)

"C168"

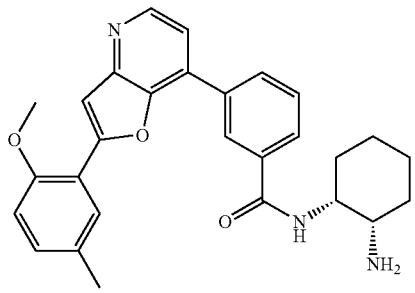

N-((1R,2S)-2-Amino-cyclohexyl)-3-[2-(2-methoxy-5-methyl-phenyl)-furo[3,2-b]pyridin-7-yl]-benzamide HPLC (Method A): Rt 2.31 min (purity 100%); LCMS (ESI+) (Method G): Rt 1.727 min, MH+ 456.2 m/z;
$^1$H NMR (TFA-$d_1$ exchange) (400 MHz, DMSO-$d_6$) δ [ppm] 8.93-8.81 (m, 2H), 8.43 (d, J = 8.5 Hz, 1H), 8.34 (d, J = 8.0 Hz, 1H), 8.21 (d, J = 6.4 Hz, 1 H), 8.02 (d, J = 1.7 Hz, 1 H), 7.84 (t, J = 7.8 Hz, 1H), 7.78 (s, 1H), 7.44 (dd, J = 8.7, 1.8 Hz, 1H), 7.19 (d, J = 8.6 Hz, 1H), 4.53 (d, J = 3.2 Hz, 1H),

| Compound no. | |
|---|---|
| | 4.07 (s, 3H), 3.62-3.48 (m, 1H), 2.42 (s, 3H), 1.95 (d, J = 9.1 Hz, 2H), 1.88-1.70 (m, 4H), 1.50 (s, 2H) |

"C169"

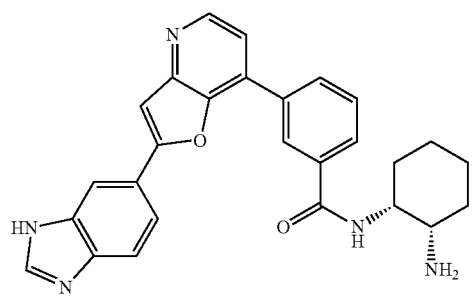

N-((1R,2S)-2-Amino-cyclohexyl)-3-[2-(3H-benzoimidazol-5-yl)-furo[3,2-b]pyridin-7-yl]-benzamide HPLC (Method A): Rt 1.80 min (purity 100%); LCMS (ESI+) (Method G): Rt 1.342 min, MH+ 452.2 m/z

"C170"

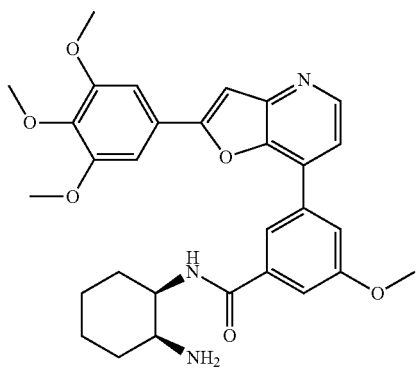

N-((1R,2S)-2-Amino-cyclohexyl)-3-methoxy-5-[2-(3,4,5-trimethoxy-phenyl)-furo[3,2-b]pyridin-7-yl]-benzamide HPLC (Method A): Rt 2.41 min (purity 100%); LCMS (ESI+) (Method G): Rt 1.76 min, MH+ 532.3

"C171"

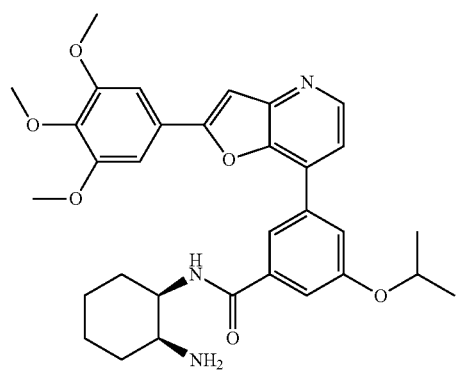

N-((1R,2S)-2-Amino-cyclohexyl)-3-isopropoxy-5-[2-(3,4,5-trimethoxy-phenyl)-furo[3,2-b]pyridin-7-yl)-benzamide HPLC (Method A): Rt 2.63 min (purity 98.8%); LCMS (ESI+) (Method G): Rt 1.885 min, MH+ 560.3

| Compound no. | |
|---|---|
| "C172" | 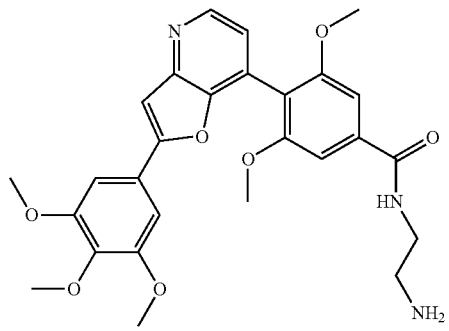 |

N-(2-Amino-ethyl)-3,5-dimethoxy-4-[2-(3,4,5-trimethoxy-phenyl)-furo[3,2-b]pyridin-7-yl]-benzamide HPLC (Method A): Rt 1.99 min (purity 94.5%); LCMS (ESI+) (Method E TFA): Rt 1.505 min, MH+ 508.2 m/z;
$^1$H NMR (TFA-$d_1$ exchange) (500 MHz, DMSO-$d_6$) δ [ppm] 8.76 (d, J = 6.2 Hz, 1H), 7.96 (s, 1H), 7.83 (d, J = 6.2 Hz, 1H), 7.42 (s, 2H), 7.30 (s, 2H), 3.85 (d, J = 2.8 Hz, 12H), 3.75 (s, 3H), 3.58 (t, J = 6.2 Hz, 2H), 3.05 (t, J = 6.1 Hz, 2H)

| "C173" | 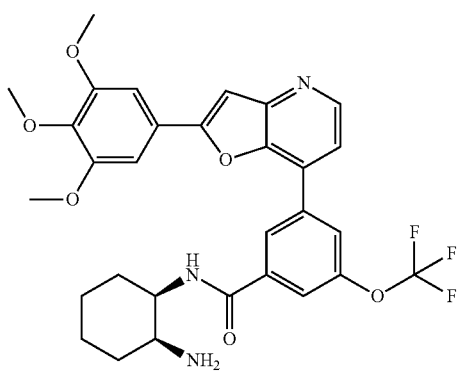 |
|---|---|

N-((1R,2S)-2-Amino-cyclohexyl)-3-trifluoromethoxy-5-[2-(3,4,5-trimethoxy-phenyl)-furo[3,2-b]pyridin-7-yl]-benzamide HPLC (Method A): Rt 2.48 min (purity 95.5%); LCMS (ESI+) (Method G): Rt 1.94 min, MH+ 586.2

| "C174" | 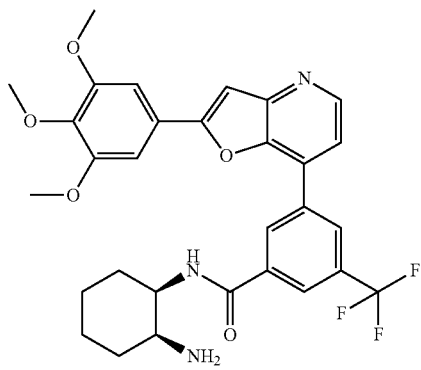 |
|---|---|

N-((1R,2S)-2-Amino-cyclohexyl)-3-trifluoromethyl-5-[2-(3,4,5-trimethoxy-phenyl)-furo[3,2-b]pyridin-7-yl)-benzamide

| Compound no. | |
|---|---|
| | HPLC (Method A): Rt 2.48 min (purity 96.8%); LCMS (ESI+) (Method G): Rt 1.915 min, MH+ 570.2 |
| "C175" | 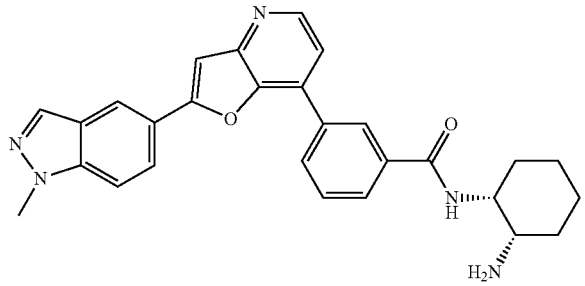 |
| | N-((1R,2S)-2-Amino-cyclohexyl)-3-[2-(1-methyl-1H-indazol-5-yl)-furo[3,2-b]pyridin-7-yl]-benzamide |
| | HPLC (Method A): Rt 2.08 min (purity 96.8%); LCMS (ESI+) (Method G): Rt 1.578 min, MH+ 466 m/z; <br> $^1$H NMR (TFA-d$_1$ exchange) (500 MHz, DMSO-d$_6$) δ [ppm] 8.89 (dd, J = 6.3, 1.3 Hz, 1 H), 8.86 (s, 1H), 8.74 (s, 1H), 8.47 (d, J = 7.8 Hz, 1H), 8.32 (d, J = 7.9 Hz, 1 H), 8.28-8.20 (m, 3H), 7.97 (d, J = 1.6 Hz, 1H), 7.91-7.81 (m, 2H), 4.53 (d, J = 3.1 Hz, 1H), 4.16 (s, 3H), 3.64-3.46 (m, 1H), 2.04-1.87 (m, 2H), 1.87-1.67 (m, 4H), 1.56-1.42 (m, 2H) |
| "C176" | 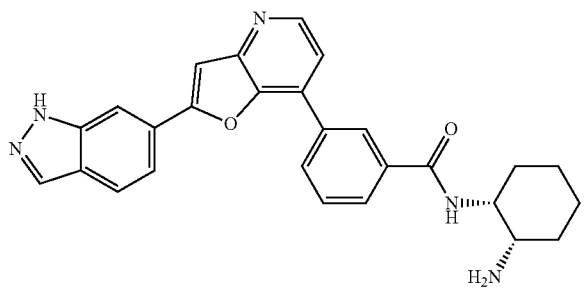 |
| | N-((1R,2S)-2-Amino-cyclohexyl)-3-[2-(1H-indazol-6-yl)-furo[3,2-b]pyridin-7-yl]-benzamide |
| | HPLC (Method H): Rt 2.03 min (purity 95.5%); LCMS (ESI+) (Method E TFA): Rt 1.532 min, MH+ 452 m/z; <br> $^1$H NMR (TFA-d$_1$ exchange) (500 MHz, DMSO-d$_6$) δ [ppm] 8.96 (d, J = 6.3 Hz, 1H), 8.82 (t, J = 1.5 Hz, 1 H), 8.53-8.44 (m, 2H), 8.30 (dd, J = 18.3, 7.1 Hz, 2H), 8.23 (s, 1H), 8.12 (d, J = 0.8 Hz, 1H), 7.99 (dt, J = 8.5, 4.8 Hz, 2H), 7.89 (t, J = 7.8 Hz, 1H), 4.51 (d, J = 3.3 Hz, 1 H), 3.63-3.48 (m, 1H), 1.83 (ddd, J = 26.4, 15.6, 8.8 Hz, 7H), 1.48 (s, 2H) |
| "C177" | 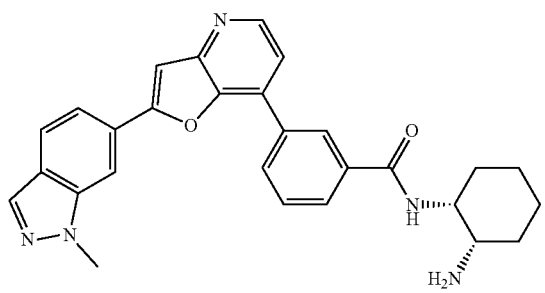 |
| | N-((1R,2S)-2-Amino-cyclohexyl)-3-[2-(1-methyl-1H-indazol-6-yl)-furo[3,2-b]pyridin-7-yl]benzamide |
| | HPLC (Method A): Rt 2.13 min (purity 100%); LCMS (ESI+) (Method G): Rt 1.618 min, MH+ 466 m/z; <br> $^1$H NMR (HCl salt) (500 MHz, DMSO-d$_6$) δ [ppm] 8.86 (s, 1H), 8.73 (d, J = 5.4 Hz, 1H), 8.47 (d, J = 7.5 Hz, 1 H), 8.41 (d, J = 9.1 Hz, 2H), 8.22 (d, J = |

| Compound no. | |
|---|---|
| | 7.9 Hz, 1H), 8.16 (d, J = 0.8 Hz, 1H), 8.09 (s, 3H), 7.98-7.92 (m, 3H), 7.87 (dd, J = 8.5, 1.3 Hz, 1H), 7.81 (t, J = 7.8 Hz, 1H), 4.39 (dd, J = 7.1, 3.7 Hz, 1H), 4.19 (s, 3H), 3.51 (d, J = 3.0 Hz, 1H), 1.97-1.84 (m, 2H), 1.79-1.62 (m, 4H), 1.48-1.37 (m, 2H) |
| "C178" | 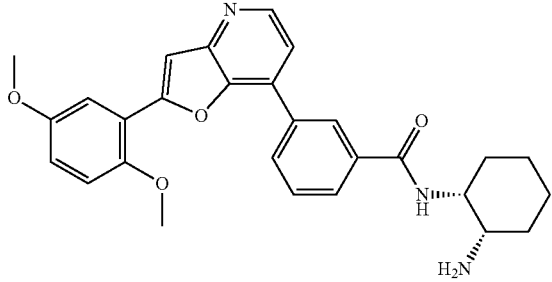<br>N-((1R,2S)-2-Amino-cyclohexyl)-3-[2-(2,5-dimethoxy-phenyl)-furo[3,2-b]pyridin-7-yl]-benzamide<br><br>HPLC (Method A): Rt 2.21 min (purity 100%); LCMS (ESI+) (Method E TFA): Rt 1.690 min, MH+ 472 m/z;<br>$^1$H NMR (TFA-d$_1$ exchange) (500 MHz, DMSO-d$_6$) δ [ppm] 8.96 (dd, J = 6.3, 0.9 Hz, 1H), 8.88 (s, 1H), 8.46 (d, J = 7.9 Hz, 1H), 8.32 (dd, J = 19.7, 7.1 Hz, 2H), 7.87 (t, J = 7.8 Hz, 1H), 7.81 (s, 1H), 7.67 (d, J = 3.0 Hz, 1H), 7.30-7.22 (m, 2H), 4.53-4.39 (m, 1H), 4.06 (s, 3H), 3.89 (s, 3H), 3.59-3.47 (m, 1H), 2.07-1.74 (m, 5H), 1.73 (s, 1H), 1.48 (s, 2H) |
| "C179" | 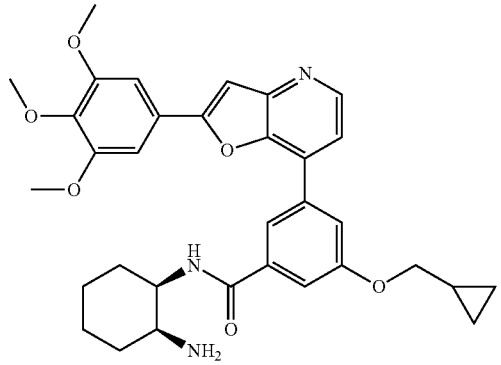<br>N-((1R,2S)-2-Amino-cyclohexyl)-3-cyclopropylmethoxy-5-[2-(3,4,5-trimethoxy-phenyl)-furo[3,2-b]pyridin-7-yl]-benzamide<br><br>HPLC (Method A): Rt 2.67 min (purity 83.3%); LCMS (ESI+) (Method G): Rt 1.9904 min, MH+ 572.3 |
| "C180" | 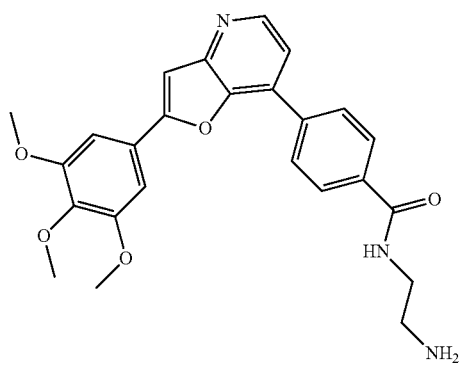<br>N-(2-Amino-ethyl)-4-[2-(3,4,5-trimethoxy-phenyl)-furo[3,2-b]pyridin-7-yl]benzamide |

-continued

| Compound no. | |
|---|---|
| | HPLC (Method A): Rt 1.98 min (purity 100%); LCMS (ESI+) (Method E TFA): Rt 1.487 min, MH+ 448 m/z;<br>¹H NMR (HCl salt) (400 MHz, DMSO-d₆) δ [ppm] 8.95 (t, J = 5.5 Hz, 1H) 8.69 (d, J = 5.4 Hz, 1 H), 8.30 (d, J = 8.6 Hz, 2H), 8.19 (d, J = 8.6 Hz, 2H), 8.05 (s, 3H), 7.89 (s, 1H), 7.84 (d, J = 5.5 Hz, 1H), 7.38 (s, 2H), 3.93 (s, 6H), 3.76 (s, 3H), 3.58 (dd, J = 11.8, 5.9 Hz, 3H), 3.04 (dd, J = 12.0, 6.0 Hz, 2H) |
| "C181" | 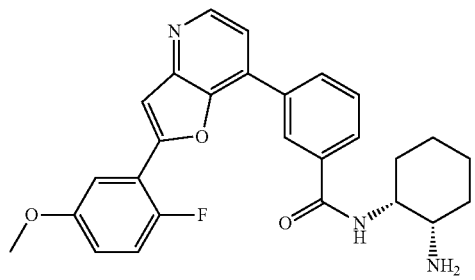<br>N-((1R,2S)-2-Amino-cyclohexyl)-3-[2-(2-fluoro-5-methoxy-phenyl)-furo[3,2-b]pyridin-7-yl]-benzamide |
| | HPLC (Method A): Rt 2.20 min (purity 100%); LCMS (ESI+) (Method G): Rt 1.671 min, MH+ 460.2 m/z |
| "C182" | 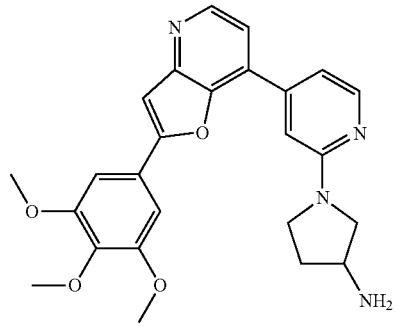<br>1-{4-[2-(3,4,5-Trimethoxy-phenyl)-furo[3,2-b] pyridin-7-yl]-pyridin-2-yl}-pyrrolidin-3-ylamine |
| | HPLC (Method A): Rt 2.32 min (purity 91.46%); LCMS (ESI+) (Method G): Rt 1.448 min, MH+ 447.2; HCl salt<br>¹H NMR (500 MHz, DMSO-d₆) δ [ppm] 8.65 (d, J = 5.1, 1H), 8.32 (d, J = 5.7, 1H), 8.21 (br, J = 20.8, 3H), 7.83 (s, 1H), 7.74 (d, J = 5.1, 1H), 7.42 (s, 1H), 7.38 (d, J = 4.9, 1H), 7.33 (s, 2H), 4.06-3.99 (m, 1H), 3.92 (s, 6H), 3.91-3.88 (m, 1H), 3.84 (dd, J = 11.9, 6.0, 1H), 3.81-3.76 (m, 1H), 3.75 (s, 3H), 3.74-3.66 (m, 1H), 2.45-2.33 (m, 1 H), 2.22-2.12 (m, 1H) |
| "C183" | 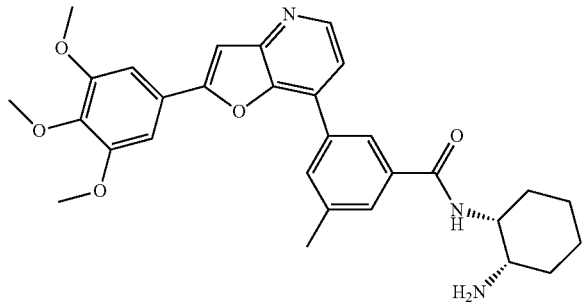<br>N-((1R,2S)-2-Amino-cyclohexyl)-3-methyl-5-[2-(3,4,5-trimethoxy-phenyl)-furo[3,2-b]pyridin-7-yl]-benzamide |
| | HPLC (Method A): Rt 2.44 min (purity 99%); LCMS (ESI+) (Method G): Rt 1.771 min, MH+ 516.2; HCl salt: |

| Compound no. | |
|---|---|
| | $^1$H NMR (500 MHz, DMSO-d$_6$) δ [ppm9 8.65 (d, J = 5.3, 1H), 8.60 (s, 1H), 8.31 (d, J = 7.5, 1H), 8.24 (s, 1H), 8.02 (s, 1H), 7.99 (s, br, 3H), 7.86 (d, J = 5.3, 1H), 7.82 (s, 1H), 7.39 (s, 2H), 4.36-4.31 (m, 1H), 3.94 (s, 6H), 3.75 (s, 3H), 3.51-3.45 (m, 1H), 2.54 (s, 3H), 1.95-1.60 (m, 6H), 1.50-1.38 (m, 2H) |
| "C184" | 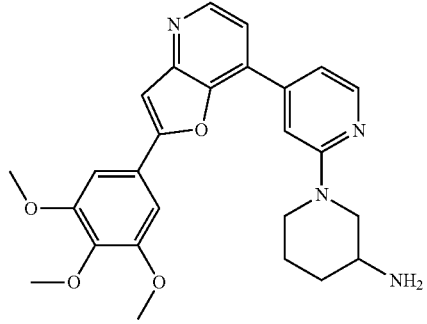

4'-[2-(3,4,5-Trimethoxy-phenyl)-furo[3,2-b]pyridin-7-yl]-3,4,5,6-tetrahydro-2H-[1,2'] bipyridinyl-3-ylamine HPLC (Method A): Rt 2.35 min (purity 94.38%); LCMS (ESI+) (Method G): Rt 1.334 min, MH+ 461.2; HCl salt:
$^1$H NMR (500 MHz, DMSO-d$_6$) δ [ppm] 8.62 (d, J = 5.1, 1H), 8.36 (d, J = 5.2, 1H), 7.98 (br, 3H), 7.80 (s, 1H), 7.67 (d, J = 5.1, 1H), 7.53 (s, 1H), 7.37-7.30 (m, 3H), 4.43 (d, J = 9.3, 1H), 4.01-3.87 (m, 7H), 3.75 (s, 3H), 3.27 (dd, J = 16.7, 8.8, 3H), 2.03 (d, J = 13.5, 1H), 1.82 (dd, J = 9.3, 3.9, 1H), 1.69-1.54 (m, 2H) |
| "C185" | 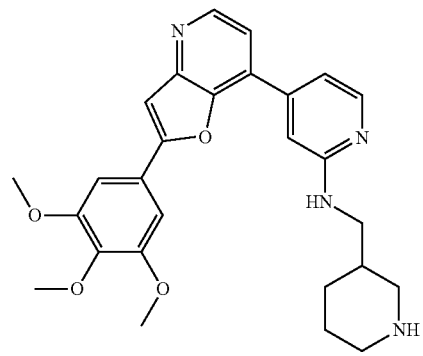

Piperidin-3-ylmethyl-{4-[2-(3,4,5-trimethoxy-phenyl)-furo[3,2-b]pyridin-7-yl]-pyridin-2-yl}-amine LCMS (ESI+) (Method G): Rt 1.523 min, MH+ 475.2 |
| "C186" | 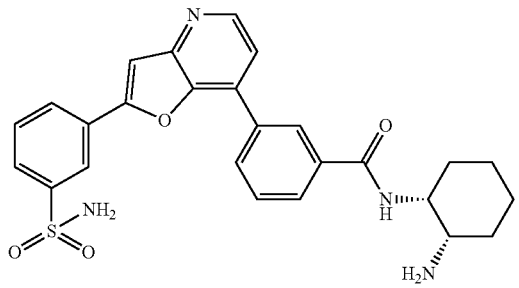

N-((1R,2S)-2-Amino-cyclohexyl)-3-[2-(3-sulfamoyl-phenyl)-furo[3,2-b]pyridin-7-yl]-benzamide HPLC (Method A): Rt 2.07 min (purity 97.8%); LCMS (ESI+) (Method G): Rt 1.435 min, MH+ 491.1 m/z; |

| Compound no. | |
|---|---|
| | $^1$H NMR (TFA-d$_1$ exchange) (400 MHz: DMSO-d$_6$) δ [ppm] 9.02 (d, J = 6.2 Hz, 1H), 8.86 (s, 1H), 8.69 (t, J = 1.6 Hz, 1 H), 8.47 (t, J = 6.9 Hz, 2H), 8.34 (t, J = 6.2 Hz, 2H), 8.19-8.10 (m, 2H), 7.92-7.80 (m, 2H), 4.49 (d, J = 3.5 Hz, 1H), 3.54-3.50 (m, 1H), 1.92 (d, J = 5.1 Hz, 2H), 1.86-1.67 (m, 5H), 1.49 (s, 2H) |
| "C187" | 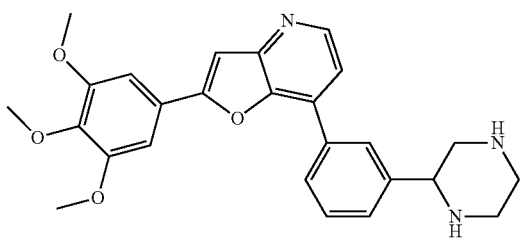<br>7-(3-Piperazin-2-yl-phenyl)-2-(3,4,5-trimethoxy-phenyl)-furo[3,2-b]pyridine<br><br>HPLC (Method A): Rt 2.32 min (purity 100%); LCMS (ESI+) (Method G): Rt 1.418 min, MH+ 446.2 |
| "C188" | 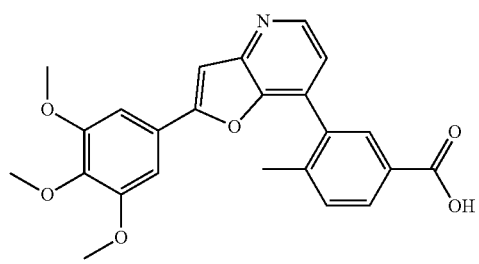<br>4-Methyl-3-[2-(3,4,5-trimethoxy-phenyl)-furo[3,2-b]pyridin-7-yl]-benzoic acid<br><br>HPLC (Method A): Rt 2.56 min (purity 99.7%); LCMS (ESI+) (Method G): Rt 1.8 min, MH+ 420.1 |
| "C189" | 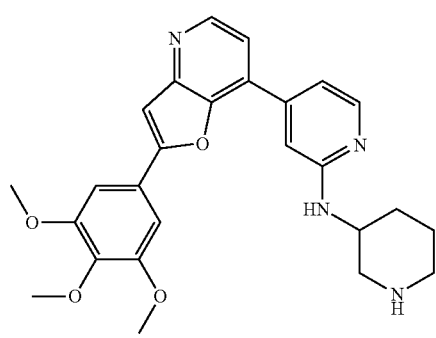<br>Piperidin-3-yl-{4-[2-(3,4,5-trimethoxy-phenyl)-furo[3,2-b]pyridin-7-yl]-pyridin-2-yl}-amine<br><br>HPLC (Method A): Rt 2.36 min (purity 97.8%); LCMS (ESI+) (Method G): Rt 1.527 min, MH+ 461.2 |

| Compound no. | |
|---|---|
| "C190" | 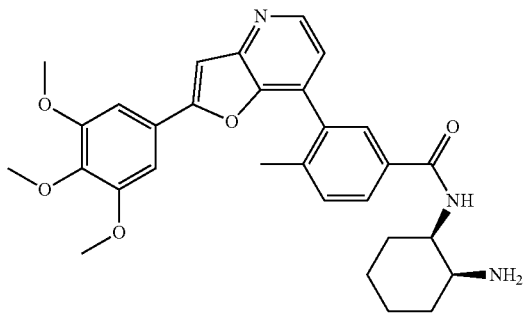<br>N-((1R,2S)-2-Amino-cyclohexyl)-4-methyl-3-[2-(3,4,5-trimethoxy-phenyl)-furo[3,2-b]pyridin-7-yl]-benzamide<br><br>HPLC (Method A): Rt 2.39 min (purity 97.8%); LCMS (ESI+) (Method G): Rt 1.674 min, MH+ 516.3; HCl salt:<br>$^1$H NMR (500 MHz, DMSO-$d_6$) δ [ppm] 8.66 (d, J = 5.1, 1H), 8.20 (d, J = 7.6, 1H), 8.09 (d, J = 1.7, 1H), 8.07-8.03 (m, 1H), 7.95 (s, 3H), 7.83 (s, 1H), 7.58 (t, J = 8.9, 1H), 7.45 (d, J = 5.1, 1H), 7.20 (s, 2H), 4.32 (dd, J = 7.0, 3.6, 1H), 3.84 (s, 6H), 3.72 (s, 3H), 3.46-3.41 (m, 1H), 2.34 (s, 3H), 1.89-1.75 (m, 2H), 1.75-1.57 (m, 4H), 1.45-1.34 (m, 2H) |
| "C191" | 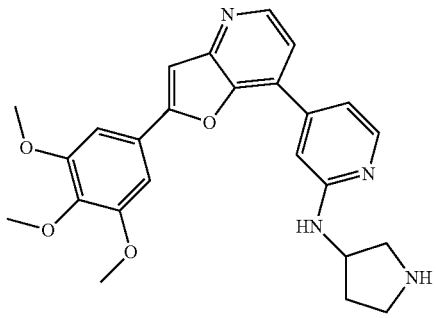<br>Pyrrolidin-3-yl-{4-[2-(3,4,5-trimethoxy-phenyl)-furo[3,2-b]pyridin-7-yl]-pyridin-2-yl}-amine<br><br>LCMS (ESI+) (Method G): Rt 1.45 min, MH+ 447.2 |
| "C192" | 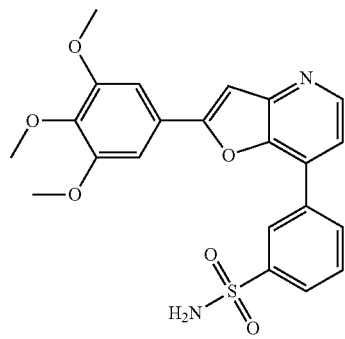<br>3-[2-(3,4,5-Trimethoxy-phenyl)-furo[3,2-b]pyridin-7-yl]-benzenesulfonamide<br><br>HPLC (Method A): Rt 2.22 min (purity 77%); LCMS (ESI+) (Method G): Rt 1.695 min, MH+ 441.1 m/z |

EXAMPLE 8

2-Chloro-N-{3-[7-(4-phenoxy-phenoxy)-furo[3,2-b]pyridin-2-yl]-phenyl}-acetamide ("D1")

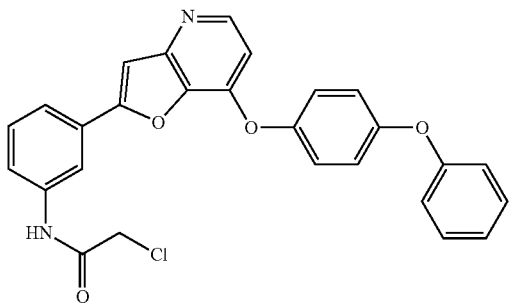 [SMILES: O=C(CCl)Nc1cccc(-c2cc3nccc(Oc4ccc(Oc5ccccc5)cc4)c3o2)c1]

8.1
3-(7-Chloro-furo[3,2-b]pyridin-2-yl)-phenylamine

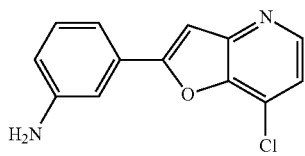 [SMILES: Nc1cccc(-c2cc3nccc(Cl)c3o2)c1]

To a solution of 7-chloro-2-iodo-furo[3,2-b]pyridine (1.0 g, 3.57 mmol) in 1,4-dioxane/water (9:1, 20 ml) 3-aminophenyl boronic acid (0.53 g, 3.93 mmol), 2-dicyclohexylphosphino-2',6' dimethoxybiphenyl (0.15 g, 0.26 mmol), palladium acetate (0.04 g, 0.18 mmol) and potassium carbonate (1.48 g, 10.71 mmol) are taken in a microwave tube, degassed briefly and irradiated to 150° C. for 1 hour. The reaction mixture is passed through celite, washed with dichloromethane/methanol (1:1, 25 ml), the filtrate is concentrated and purified by silica column using (230-400) mesh to get the product as yellow solid (0.35 g, 40.09%); TLC: chloroform/methanol (9/1) $R_f$—0.3. LCMS: (method C) 245.0 (M+H), Rt (min): 4.49;

$^1$H NMR: 400 MHz, DMSO-$d_6$: δ [ppm] 8.44 (d, J=5.24 Hz, 1H), 7.55 (d, J=5.20 Hz, 1H), 7.48 (d, J=5.28 Hz, 1H), 7.14-7.20 (m, 3H), 6.66-6.69 (m, 1H), 5.41 (br s, 2H).

8.2 3-[7-(4-Phenoxy-phenoxy)-furo[3,2-b]pyridin-2-yl]-phenylamine

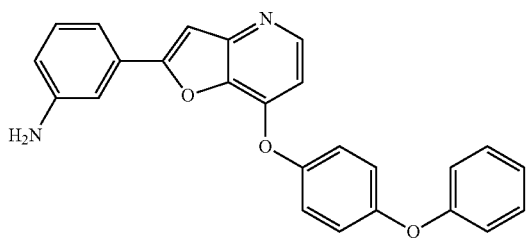 [SMILES: Nc1cccc(-c2cc3nccc(Oc4ccc(Oc5ccccc5)cc4)c3o2)c1]

To a solution of 3-(7-chloro-furo[3,2-b]pyridin-2-yl)-phenylamine (0.2 g, 0.81 mmol) in N,N-dimethylformamide (8 ml), 4-phenoxyphenol (0.23 g, 1.22 mmol) and cesium carbonate (0.8 g, 2.45 mmol) are added and irradiated in microwave at 150° C. for 2 hours. The reaction mixture is concentrated and the residue is taken in dichloromethane/methanol (1:1, ml) and passed through celite, the filtrate is concentrated and purified by silica column using (230-400) mesh to get the product as yellow solid (0.12 g, 38.83%); TLC: chloroform/methanol (9.8/0.2) $R_f$—0.3. LCMS: (method C) 395.2 (M+H), RT. 3.91 min;

$^1$H NMR: 400 MHz, DMSO-$d_6$: δ [ppm] 8.35 (d, J=5.56 Hz, 1H), 7.46 (s, 1H), 7.39-7.41 (m, 2H), 7.35 (dd, J=2.32, 6.70 Hz, 2H), 7.13-7.18 (m, 5H), 7.06-7.08 (m, 3H), 6.63-6.66 (m, 1H), 6.68-6.69 (m, 1H), 5.35 (br s, 2H).

8.3 To a solution of 3-[7-(4-phenoxy-phenoxy)-furo[3,2-b]pyridin-2-yl]-phenylamine (0.12 g, 0.30 mmol) in dry dichloromethane (4 ml), 2-chloroacetic acid (0.034 g, 0.36 mmol), triethylamine (0.91 g, 0.9 mmol) and 1-propanephosphonic acid anhydride (0.29 g, 0.9 mmol) are added and stirred for 12 hours. The reaction mixture is concentrated and the residue is taken in water, extracted with dichloromethane (15 ml), dried over MgSO$_4$ and concentrated. The crude product is purified by silica column using (230-400) mesh to get "D1" as white solid (0.085 g, 59.67%); HPLC: (method F) RT 4.54 min; LCMS: (method C) 471.0 (M+H), RT. 4.47 min;

$^1$H NMR: 400 MHz, DMSO-$d_6$: δ [ppm] 10.54 (s, 1H), 8.36 (d, J=5.56 Hz, 1H), 8.19 (d, J=1.68 Hz, 1H), 7.70-7.72 (m, 2H), 7.64 (s, 1H), 7.50 (t, J=7.96 Hz, 1H), 7.36-7.43 (m, 4H), 7.13-7.18 (m, 3H), 7.06-7.08 (m, 2H), 6.71 (d, J=5.52 Hz, 1H), 4.28 (s, 2H).

EXAMPLE 9

N-{2-[7-(4-Phenoxy-phenoxy)-furo[3,2-b]pyridin-2-yl]-phenyl}-acrylamide ("D2")

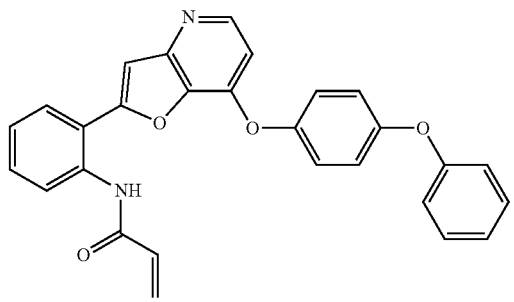 [SMILES: C=CC(=O)Nc1ccccc1-c1cc2nccc(Oc3ccc(Oc4ccccc4)cc3)c2o1]

9.1
2-(7-Chloro-furo[3,2-b]pyridin-2-yl)-phenylamine

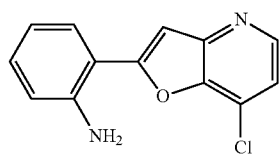 [SMILES: Nc1ccccc1-c1cc2nccc(Cl)c2o1]

To a solution of 7-chloro-2-iodo-furo[3,2-b]pyridine (0.75 g, 2.68 mmol) in 1,4-dioxane/water (9:1, 20 ml) 2-aminophenyl boronic acid (0.4 g, 2.95 mmol), 2-dicyclohexylphosphino-2',6' dimethoxybiphenyl (0.11 g, 0.26 mmol), palladium acetate (0.03 g, 0.13 mmol) and potassium carbonate (1.11 g, 8.05 mmol) are taken in a sealed tube, degassed briefly and heated to 85° C. for 12 hours. The reaction mixture is passed through celite, washed with dichloromethane/methanol (1:1, 25 ml), the filtrate is concentrated and purified by silica column using (230-400) mesh to get the product as yellow solid (0.3 g, 45.87%); TLC: chloroform/methanol (9.5/0.5) $R_f$—0.2;

$^1$H NMR: 400 MHz, DMSO-$d_6$: δ [ppm] 8.44 (d, J=5.24 Hz, 1H), 7.65 (dd, J=1.52, 7.90 Hz, 1H), 7.44-7.48 (m, 1H), 7.21 (s, 1H), 7.17-7.20 (m, 1H), 6.88 (dd, J=0.88, 8.24 Hz, 1H), 6.69-6.73 (m, 1H), 5.69 (br s, 2H).

9.2 2-[7-(4-Phenoxy-phenoxy)-furo[3,2-b]pyridin-2-yl]-phenylamine

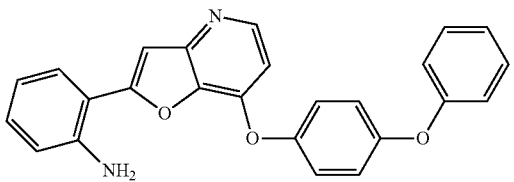 [SMILES: Nc1ccccc1-c1cc2nccc(Oc3ccc(Oc4ccccc4)cc3)c2o1]

To a solution of 2-(7-chloro-furo[3,2-b]pyridin-2-yl)-phenylamine (0.25 g, 1.04 mmol) in N,N-dimethylformamide (8 ml), 4-phenoxyphenol (0.29 g, 1.56 mmol) and cesium carbonate (1.01 g, 3.12 mmol) are added and irradiated in microwave at 150° C. for 2 hours. The reaction mixture is concentrated and the residue is taken in dichloromethane/methanol (1:1, 25 ml) and passed through celite, the filtrate is concentrated and purified by silica column using (230-400) mesh to get the product as yellow solid (0.2 g, 48.66%); TLC: chloroform/methanol (9.5/0.5) $R_f$—0.2. LCMS: (method C) 395.3 (M+H), Rt (min): 4.49.

9.3 To a solution of 2-[7-(4-phenoxy-phenoxy)-furo[3,2-b]pyridin-2-yl]-phenylamine (0.17 g, 0.43 mmol) in dry dichloromethane (4 ml), acrylic acid (0.034 g, 0.47 mmol), triethylamine (0.13 g, 1.29 mmol) and 1-propanephosphonic acid anhydride (0.41 g, 1.29 mmol) are added and stirred for 12 hours. The reaction mixture is concentrated and the residue is taken in water, extracted with dichloromethane (15 ml), dried over MgSO$_4$ and concentrated. The crude product is purified by silica column using (230-400) mesh to get "D2" as white solid (0.1 g, 54.87%); HPLC: (method F) RT 4.32 min; LCMS: (method C) 449.0 (M+H), RT. 4.35 min;

$^1$H NMR: 400 MHz, DMSO-$d_6$: δ [ppm] 10.00 (s, 1H), 8.37 (d, J=5.48 Hz, 1H), 7.79 (dd, J=1.36, 7.84 Hz, 1H), 7.64 (d, J=7.84 Hz, 1H), 7.48-7.52 (m, 1H), 7.37-7.42 (m, 3H), 7.32-7.36 (m, 3H), 7.12-7.15 (m, 3H), 7.04-7.06 (m, 2H), 6.78 (d, J=5.52 Hz, 1H), 6.47-6.51 (m, 1H), 6.24 (dd, J=1.88, 17.06 Hz, 1H), 5.77 (dd, J=1.76, 10.20 Hz, 1H).

EXAMPLE 10

The following compounds are obtained analogously to example 8:

2-Chloro-N-{2-[7-(4-phenoxy-phenoxy)-furo[3,2-b]pyridin-2-yl]-phenyl}-acetamide ("D3")

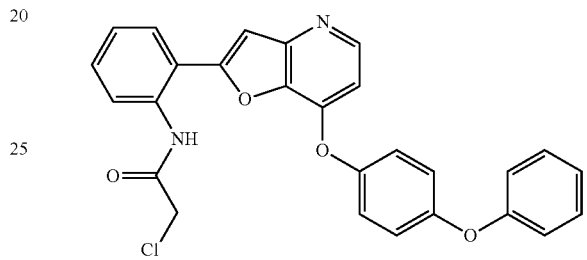

HPLC: (method F) RT 4.43 min; LCMS: (method C) 471.0 (M+H), RT. 4.39 min;

$^1$H NMR: 400 MHz, DMSO-$d_6$: δ [ppm] 10.15 (s, 1H), 8.38 (d, J=5.52 Hz, 1H), 7.82 (dd, J=1.40, 7.84 Hz, 1H), 7.61 (d, J=7.28 Hz, 1H), 7.49-7.53 (m, 1H), 7.47 (s, 1H), 7.38-7.43 (m, 3H), 7.31-7.35 (m, 2H), 7.12-7.17 (m, 3H), 7.05-7.07 (m, 2H), 6.77 (d, J=5.48 Hz, 1H), 4.34 (s, 2H);

2-Chloro-N-{3-[7-(4-phenoxy-phenoxy)-furo[3,2-b]pyridin-2-yl]-benzyl}-acetamide ("D5")

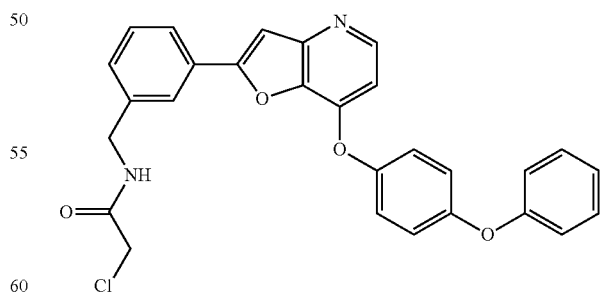

HPLC: (method F) RT 4.43 min; LCMS: (method C) 485.0 (M+H), RT. 4.45 min;

$^1$H NMR: 400 MHz, DMSO-$d_6$: δ [ppm] 8.83 (t, J=5.56 Hz, 1H), 8.60 (d, J=1.90 Hz, 1H), 7.82-7.86 (m, 2H), 7.67 (s, 1H), 7.49 (t, J=7.72 Hz, 1H), 7.35-7.43 (m, 5H), 7.13-7.18

(m, 3H), 7.07 (dd, J=0.92, 8.62 Hz, 2H), 6.73 (d, J=5.52 Hz, 1H), 4.39 (d, J=5.96 Hz, 2H), 4.15 (s, 2H);

2-Chloro-N-[3-(7-phenoxy-furo[3,2-b]pyridin-2-yl)-phenyl]-acetamide ("D7")

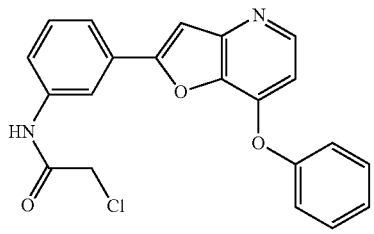 [SMILES: O=C(CCl)Nc1cccc(-c2cc3nccc(Oc4ccccc4)c3o2)c1]

HPLC: (method F) RT 3.60 min; LCMS: (method C) 379.0 (M+H), RT. 3.63 min;
¹H NMR: 400 MHz, DMSO-d₆: δ [ppm] 10.54 (s, 1H), 8.35 (d, J=5.56 Hz, 1H), 8.16 (s, 1H), 7.69-7.72 (m, 2H), 7.65 (s, 1H), 7.47-7.55 (m, 3H), 7.34 (t, J=8.56 Hz, 3H), 6.66 (d, J=5.52 Hz, 1H), 4.28 (s, 2H).

N-[3-(7-Phenoxy-furo[3,2-b]pyridin-2-yl)-phenyl]-propionamide ("D8")

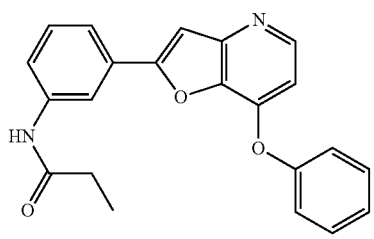 [SMILES: CCC(=O)Nc1cccc(-c2cc3nccc(Oc4ccccc4)c3o2)c1]

HPLC: (method F) RT 3.53 min; LCMS: (method C) 359.0 (M+H), RT. 3.48 min;
¹H NMR: 400 MHz, DMSO-d₆: δ [ppm] 10.13 (s, 1H), 8.41 (d, J=5.84 Hz, 1H), 8.24 (s, 1H), 7.71-7.73 (m, 1H), 7.65-7.67 (m, 2H), 7.53-7.57 (m, 2H), 7.46 (t, J=7.92 Hz, 1H), 7.36-7.39 (m, 3H), 6.74 (d, J=5.80 Hz, 1H), 2.32-2.37 (m, 2H), 1.09 (t, J=7.56 Hz, 3H);

2-Chloro-N-[3-(7-phenyl-furo[3,2-b]pyridin-2-yl)-phenyl]-acetamide ("D13")

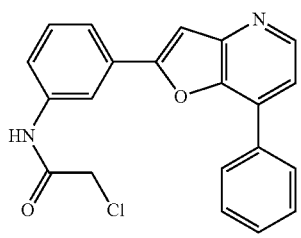 [SMILES: O=C(CCl)Nc1cccc(-c2cc3nccc(-c4ccccc4)c3o2)c1]

HPLC: (method F) RT 3.51 min; LCMS: (method C) 363.0 (M+H), RT. 3.47 min, 94.72% (Max), 94.17% (254 nm);
¹H NMR: 400 MHz, DMSO-d₆: δ [ppm] 10.53 (s, 1H), 8.58 (d, J=5.04 Hz, 1H), 8.19 (s, 1H), 8.09 (d, J=7.32 Hz, 2H), 7.78 (d, J=7.72 Hz, 1H), 7.72 (d, J=8.12 Hz, 1H), 7.50-7.67 (m, 6H), 4.30 (s, 2H);

N-[3-(7-Phenyl-furo[3,2-b]pyridin-2-yl)-phenyl]-propionamide ("D14")

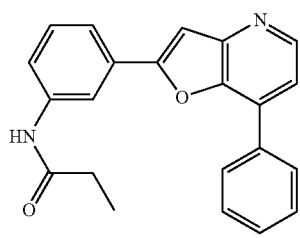

HPLC: (method F) RT 3.43 min; LCMS: (method C) 343.3 (M+H), RT. 3.41 min, 97.83% (Max), 97.45% (254 nm);
¹H NMR: 400 MHz, DMSO-d₆: δ [ppm] 10.09 (s, 1H), 8.58 (d, J=4.88 Hz, 1H), 8.20 (s, 1H), 8.10 (d, J=7.40 Hz, 2H), 7.57-7.74 (m, 7H), 7.47 (t, J=7.92 Hz, 1H), 2.33-2.39 (m, 2H), 1.10 (t, J=7.52 Hz, 3H);

2-Chloro-N-[3-(7-phenyl-furo[3,2-b]pyridin-2-yl)-benzyl]-acetamide ("D16")

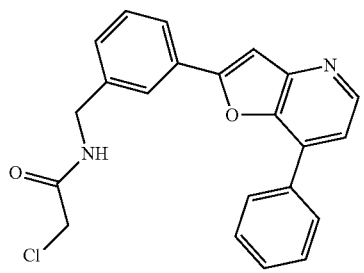 [SMILES: O=C(CCl)NCc1cccc(-c2cc3nccc(-c4ccccc4)c3o2)c1]

HPLC: (method F) RT 3.42 min; LCMS: (method C) 377.3 (M+H), RT. 3.37 min, 95.12% (Max), 93.53% (254 nm);
¹H NMR: 400 MHz, DMSO-d₆: δ [ppm] 8.85 (t, J=5.64 Hz, 1H), 8.58 (d, J=5.08 Hz, 1H), 8.11-8.13 (m, 2H), 7.91-

7.93 (m, 2H), 7.71 (s, 1H), 7.61-7.67 (m, 3H), 7.51-7.58 (m, 2H), 7.37-7.39 (m, 1H), 4.42 (d, J=5.92 Hz, 2H), 4.17 (s, 2H);

N-[3-(7-Phenyl-furo[3,2-b]pyridin-2-yl)-benzyl]-propionamide ("D17")

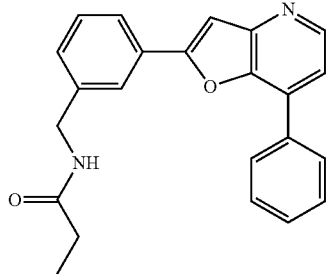 [SMILES: CCC(=O)NCc1cccc(-c2cc3nccc(-c4ccccc4)c3o2)c1]

HPLC: (method F) RT 3.25 min LCMS: (method C) 357.3 (M+H), RT. 3.31 min;
$^1$H NMR: 400 MHz, DMSO-d$_6$: δ [ppm] 8.57 (d, J=5.08 Hz, 1H), 8.38 (t, J=6.32 Hz, 1H), 8.10-8.11 (m, 2H), 7.88-7.89 (m, 2H), 7.70 (s, 1H), 7.49-7.66 (m, 5H), 7.34-7.36 (m, 1H), 4.36 (d, J=5.96 Hz, 2H), 2.19 (q, J=7.60 Hz, 2H), 1.04 (t, J=7.64 Hz, 3H);

2-Chloro-N-[3-(2-phenyl-furo[3,2-b]pyridin-7-yloxy)-phenyl]-acetamide ("D20")

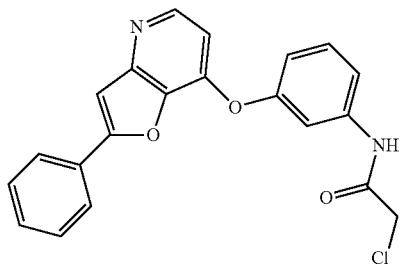 [SMILES: O=C(CCl)Nc1cccc(Oc2ccnc3cc(-c4ccccc4)oc23)c1]

HPLC: (method F) RT 3.64 min, LCMS: (method C) 379.0 (M+H), RT. 3.62 min;
$^1$H NMR: 400 MHz, DMSO-d$_6$: δ [ppm] 10.50 (s, 1H), 8.38 (d, J=5.48 Hz, 1H), 7.90-7.92 (m, 2H), 7.70 (s, 1H), 7.61 (t, J=1.72 Hz, 1H), 7.46-7.54 (m, 5H), 7.04-7.07 (m, 1H), 6.80 (d, J=5.48 Hz, 1H), 4.25 (s, 2H);

N-[3-(2-Phenyl-furo[3,2-b]pyridin-7-yloxy)-phenyl]-propionamide ("D21")

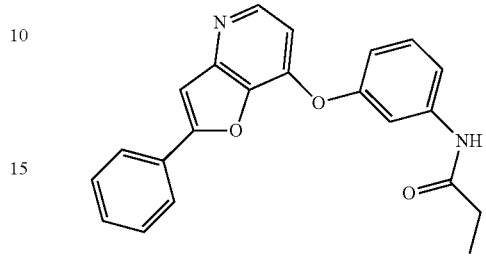

HPLC: (method F) RT 3.59 min, LCMS: (method C) 359.0 (M+H), RT. 3.58 min;
$^1$H NMR: 400 MHz, DMSO-d$_6$: δ [ppm] 10.07 (s, 1H), 8.37 (d, J=5.52 Hz, 1H), 7.92 (d, J=7.20 Hz, 2H), 7.70 (s, 1H), 7.64 (d, J=1.84 Hz, 1H), 7.40-7.54 (m, 5H), 6.97 (dd, J=1.20, 7.74 Hz, 1H), 6.77 (d, J=5.52 Hz, 1H), 2.28-2.33 (m, 2H), 1.04 (t, J=7.56 Hz, 3H);

2-Chloro-N-[4-(2-phenyl-furo[3,2-b]pyridin-7-yloxy)-phenyl]-acetamide ("D23")

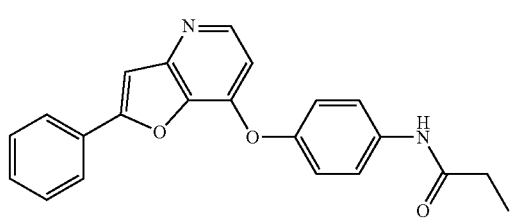

HPLC: (method F) RT 3.56 min LCMS: (method C) 379.0 (M+H), RT. 3.55 min;
$^1$H NMR: 400 MHz, CDCl$_3$: δ [ppm] 8.35 (d, J=5.52 Hz, 2H), 7.86-7.89 (m, 2H), 7.66 (dd, J=2.16, 6.82 Hz, 2H), 7.42-7.50 (m, 3H), 7.22-7.27 (m, 3H), 6.64 (d, J=5.56 Hz, 1H), 4.25 (s, 2H);

N-[4-(2-Phenyl-furo[3,2-b]pyridin-7-yloxy)-phenyl]-propionamide ("D24")

HPLC: (method F) RT 3.46 min; LCMS: (method C) 359.0 (M+H), RT. 3.50 min; $^1$H NMR: 400 MHz, DMSO-d$_6$: δ [ppm] 10.02 (s, 1H), 8.33 (d, J=5.52 Hz, 1H), 7.92 (d, J=8.44

Hz, 2H), 7.67-7.73 (m, 3H), 7.44-7.53 (m, 3H), 7.27 (d, J=8.96 Hz, 2H), 6.66 (d, J=5.52 Hz, 1H), 2.31-2.37 (m, 2H), 1.08-1.12 (m, 3H);

2-Chloro-N-[3-(2-methyl-furo[3,2-b]pyridin-7-yloxy)-phenyl]-acetamide ("D27")

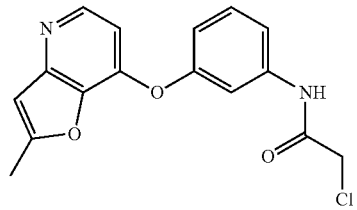 [SMILES: Cc1cc2nccc(Oc3cccc(NC(=O)CCl)c3)c2o1]

HPLC: (method F) RT 2.85 min, LCMS: (method C) 317.0 (M+H), RT. 2.78 min;
$^1$H NMR: 400 MHz, DMSO-d$_6$: δ [ppm] 10.48 (s, 1H), 8.29 (d, J=5.48 Hz, 1H), 7.51-7.52 (m, 1H), 7.42-7.45 (m, 2H), 6.94-6.96 (m, 1H), 6.80-6.80 (m, 1H), 6.68 (d, J=5.52 Hz, 1H), 4.24 (s, 2H), 2.49 (s, 3H);

N-[3-(2-Methyl-furo[3,2-b]pyridin-7-yloxy)-phenyl]-propionamide ("D28")

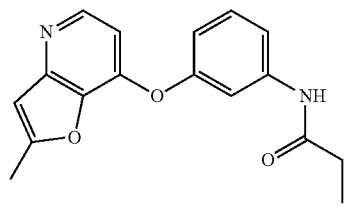 [SMILES: CCC(=O)Nc1cccc(Oc2ccnc3cc(C)oc23)c1]

HPLC: (Method F) RT 2.79 min; LCMS: (Method C) 297.0 (M+H), RT. 2.73 min;
$^1$H NMR: 400 MHz, DMSO-d$_6$: δ [ppm] 10.03 (s, 1H), 8.28 (d, J=5.52 Hz, 1H), 7.55 (t, J=2.00 Hz, 1H), 7.35-7.43 (m, 2H), 6.86-6.89 (m, 1H), 6.80 (d, J=0.96 Hz, 1H), 6.65 (d, J=5.52 Hz, 1H), 2.49 (s, 3H), 2.27-2.33 (m, 2H), 1.05 (t, J=7.56 Hz, 3H);

N-[3-(2-Methyl-furo[3,2-b]pyridin-7-yl)-phenyl]-propionamide ("D29")

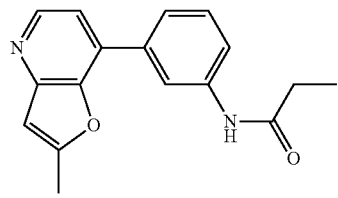

HPLC: (method F) RT 2.42 min; LCMS: (method C) 281.2 (M+H), RT. 2.47 min, 97.78% (Max), 97.70% (254 nm);
$^1$H NMR: 400 MHz, DMSO-d$_6$: δ [ppm] 10.06 (s, 1H), 8.48 (d, J=5.08 Hz, 1H), 8.21 (t, J=1.76 Hz, 1H), 7.72-7.74 (m, 1H), 7.61-7.63 (m, 1H), 7.49 (t, J=7.88 Hz, 1H), 7.39 (d, J=5.08 Hz, 1H), 6.83 (d, J=1.08 Hz, 1H), 2.54 (s, 3H), 2.36 (q, J=7.52 Hz, 2H), 1.10 (t, J=7.56 Hz, 3H).

EXAMPLE 11

The following compounds are obtained analogously to example 9:

N-{3-[7-(4-Phenoxy-phenoxy)-furo[3,2-b]pyridin-2-yl]-benzyl}-acrylamide ("D4")

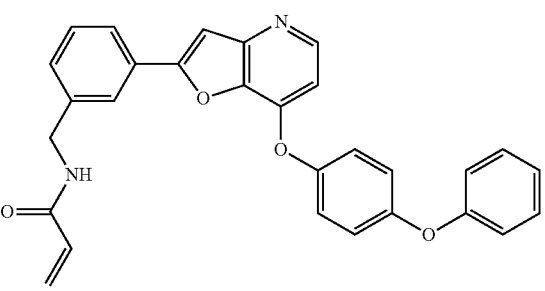 [SMILES: C=CC(=O)NCc1cccc(-c2cc3nccc(Oc4ccc(Oc5ccccc5)cc4)c3o2)c1]

HPLC: (method F) RT 4.31 min; LCMS: (method C) 463.0 (M+H), RT. 4.31 min;
$^1$H NMR: 400 MHz, DMSO-d$_6$: δ [ppm] 8.72 (t, J=5.76 Hz, 1H), 8.38 (d, J=5.60 Hz, 1H), 7.85 (t, J=7.84 Hz, 2H), 7.68 (s, 1H), 7.50 (t, J=7.72 Hz, 1H), 7.37-7.44 (m, 5H), 7.13-7.18 (m, 3H), 7.09 (d, J=1.04 Hz, 2H), 6.76 (d, J=5.64 Hz, 1H), 6.26-6.33 (m, 1H), 6.11-6.16 (m, 1H), 5.63 (dd, J=2.20, 10.14 Hz, 1H), 4.43 (d, J=5.92 Hz, 2H);

N-[3-(7-Phenoxy-furo[3,2-b]pyridin-2-yl)-phenyl]-acrylamide (D6")

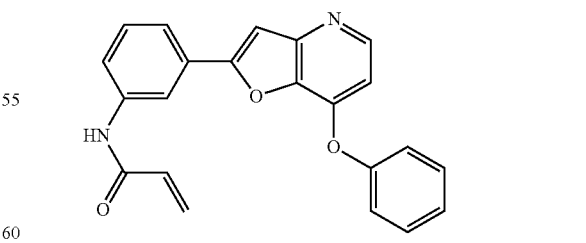

HPLC: (method F) RT 3.53 min; LCMS: (method C) 357.2 (M+H), RT. 3.56 min;
$^1$H NMR: 400 MHz, DMSO-d$_6$: δ [ppm] 10.38 (s, 1H), 8.35 (d, J=5.40 Hz, 1H), 8.26 (s, 1H), 7.80 (d, J=7.68 Hz, 1H), 7.64-7.69 (m, 2H), 7.46-7.55 (m, 3H), 7.34 (d, J=7.80 Hz, 3H), 6.65 (d, J=5.36 Hz, 1H), 6.41-6.48 (m, 1H), 6.29 (d, J=16.80 Hz, 1H), 5.79 (d, J=10.00 Hz, 1H);

N-{3-[7-(3-Chloro-phenoxy)-furo[3,2-b]pyridin-2-yl]-phenyl}-acrylamide ("D9")

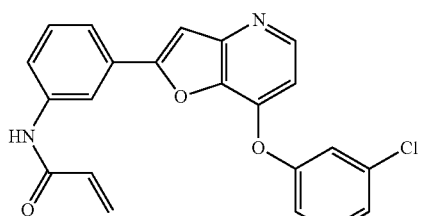

HPLC: (method F) RT 3.88 min; LCMS: (method C) 391.0 (M+H), RT. 3.89 min;

$^1$H NMR: 400 MHz, DMSO-d$_6$: δ [ppm] 10.40 (s, 1H), 8.44 (d, J=5.76 Hz, 1H), 8.30 (t, J=1.68 Hz, 1H), 7.80 (dd, J=1.16, 8.10 Hz, 1H), 7.70-7.72 (m, 2H), 7.54-7.58 (m, 2H), 7.50 (t, J=7.96 Hz, 1H), 7.43-7.45 (m, 1H), 7.36 (dd, J=0.76, 2.30 Hz, 1H), 6.84 (d, J=5.76 Hz, 1H), 6.41-6.48 (m, 1H), 6.30 (dd, J=2.04, 16.96 Hz, 1H), 5.79 (dd, J=2.04, 10.00 Hz, 1H);

N-{3-[7-(Quinolin-6-yloxy)-furo[3,2-b]pyridin-2-yl]-phenyl}-acrylamide ("D10")

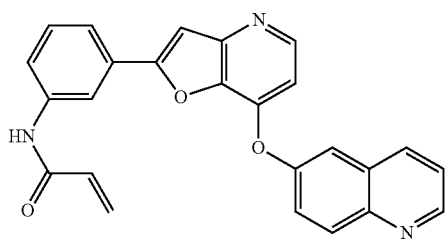 [SMILES: C=CC(=O)Nc1cccc(-c2cc3nccc(Oc4ccc5ncccc5c4)c3o2)c1]

HPLC: (method F) RT 2.40 min; LCMS: (method C) 408.3 (M+H), RT. 2.43 min;

$^1$H NMR: 400 MHz, DMSO-d$_6$: δ [ppm] 10.40 (s, 1H), 8.98 (dd, J=1.60, 4.30 Hz, 1H), 8.44-8.48 (m, 2H), 8.28 (s, 1H), 8.21 (d, J=9.12 Hz, 1H), 7.98 (d, J=2.68 Hz, 1H), 7.85 (dd, J=2.76, 9.12 Hz, 1H), 7.77-7.79 (m, 1H), 7.64-7.72 (m, 3H), 7.48 (t, J=7.92 Hz, 1H), 6.93 (d, J=5.72 Hz, 1H), 6.39-6.46 (m, 1H), 6.28 (dd, J=2.00, 16.94 Hz, 1H), 5.78 (dd, J=2.00, 10.06 Hz, 1H);

N-{3-[7-(4-Chloro-phenoxy)-furo[3,2-b]pyridin-2-yl]-phenyl}-acrylamide ("D11")

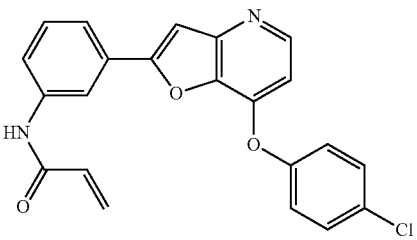 [SMILES: C=CC(=O)Nc1cccc(-c2cc3nccc(Oc4ccc(Cl)cc4)c3o2)c1]

HPLC: (method F) RT 3.88 min; LCMS: (method C) 391.0 (M+H), RT. 3.89 min;

$^1$H NMR: 400 MHz, DMSO-d$_6$: δ [ppm] 10.40 (s, 1H), 8.42 (d, J=5.00 Hz, 1H), 8.28 (s, 1H), 7.79 (dd, J=1.24, 8.12 Hz, 1H), 7.66-7.71 (m, 2H), 7.57-7.61 (m, 2H), 7.47-7.51 (m, 1H), 7.39-7.43 (m, 2H), 6.81 (d, J=5.64 Hz, 1H), 6.41-6.48 (m, 1H), 6.30 (dd, J=2.00, 16.96 Hz, 1H), 5.79 (dd, J=2.04, 10.00 Hz, 1H);

N-[3-(7-Phenyl-furo[3,2-b]pyridin-2-yl)-phenyl]-acrylamide ("D12")

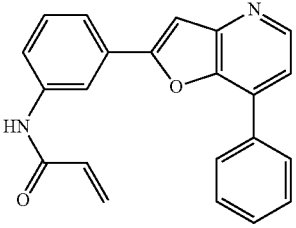 [SMILES: C=CC(=O)Nc1cccc(-c2cc3nccc(-c4ccccc4)c3o2)c1]

HPLC: (method F) RT 3.43 min, LCMS: (method C) 341.2 (M+H), RT. 3.48 min;

$^1$H NMR: 400 MHz, DMSO-d$_6$: δ [ppm] 10.37 (s, 1H), 8.58 (d, J=5.00 Hz, 1H), 8.26 (s, 1H), 8.10 (d, J=7.32 Hz, 2H), 7.75 (d, J=7.84 Hz, 1H), 7.81 (d, J=8.16 Hz, 1H), 7.49-7.67

(m, 6H), 6.43-6.50 (m, 1H), 6.30 (dd, J=1.84, 16.96 Hz, 1H), 5.80 (dd, J=1.88, 10.06 Hz, 1H);

N-{3-[7-(3,4,5-Trimethoxy-phenyl)-furo[3,2-b]pyridin-2-yl]-phenyl}-acrylamide ("D18")

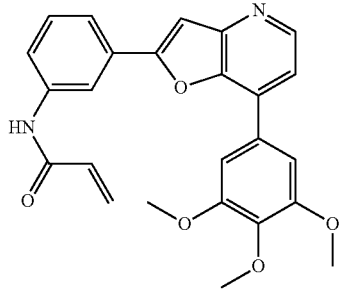 [SMILES: C=CC(=O)Nc1cccc(-c2cc3nccc(-c4cc(OC)c(OC)c(OC)c4)c3o2)c1]

HPLC: (method F) RT 3.47 min; LCMS: (method C) 431.3 (M+H), RT. 3.51 min, 91.19% (Max), 90.83% (254 nm);
$^1$H NMR: 400 MHz, DMSO-d$_6$: δ [ppm] 10.38 (s, 1H), 8.56 (d, J=5.08 Hz, 1H), 8.47 (s, 1H), 7.75-7.77 (m, 1H), 7.66-7.67 (m, 2H), 7.60 (d, J=8.96 Hz, 1H), 7.51 (t, J=7.92 Hz, 1H), 7.39 (s, 2H), 6.43-6.49 (m, 1H), 6.31 (dd, J=2.04, 16.94 Hz, 1H), 5.81 (dd, J=2.04, 10.00 Hz, 1H), 3.95 (s, 6H), 3.77 (s, 3H);

N-[3-(2-Phenyl-furo[3,2-b]pyridin-7-yloxy)-phenyl]-acrylamide ("D19")

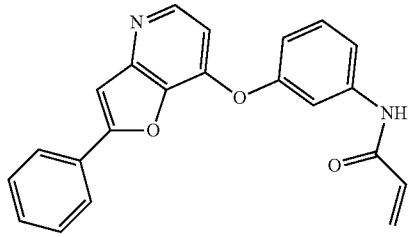 [SMILES: C=CC(=O)Nc1cccc(Oc2ccnc3cc(-c4ccccc4)oc23)c1]

HPLC: (method F) RT 3.56 min; LCMS: (method C) 357.0 (M+H), RT. 3.51 min;
$^1$H NMR: 400 MHz, DMSO-d$_6$: δ [ppm] 10.35 (s, 1H), 8.38 (d, J=5.52 Hz, 1H), 7.90-7.92 (m, 2H), 7.70-7.72 (m, 2H), 7.44-7.54 (m, 6H), 7.02-7.04 (m, 1H), 6.81 (d, J=5.52 Hz, 1H), 6.37-6.43 (m, 1H), 6.22-6.26 (m, 1H);

N-[4-(2-Phenyl-furo[3,2-b]pyridin-7-yloxy)-phenyl]-acrylamide ("D22")

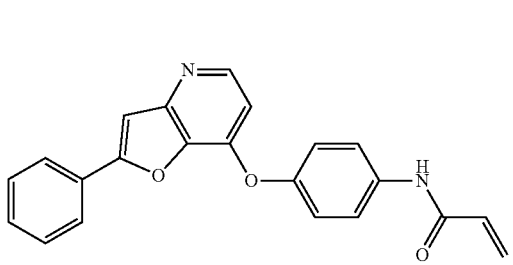 [SMILES: C=CC(=O)Nc1ccc(Oc2ccnc3cc(-c4ccccc4)oc23)cc1]

HPLC: (method F) RT 3.47 min; LCMS: (method C) 357.0 (M+H), RT. 3.47 min;
$^1$H NMR: 400 MHz, DMSO-d$_6$: δ [ppm] 8.35 (s, 1H), 7.88 (d, J=6.60 Hz, 2H), 7.69 (s, 2H), 7.47 (d, J=6.24 Hz, 4H), 7.23-7.27 (m, 3H), 6.64 (s, 1H), 6.48-6.52 (m, 1H), 6.30 (t, J=17.44 Hz, 1H), 5.83 (d, J=9.92 Hz, 1H);

N-[4-(2-Phenyl-furo[3,2-b]pyridin-7-yl)-phenyl]-acrylamide ("D26")

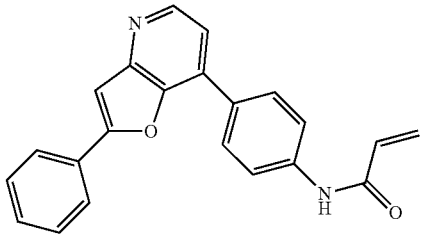 [SMILES: C=CC(=O)Nc1ccc(-c2ccnc3cc(-c4ccccc4)oc23)cc1]

HPLC: (method F) RT 3.56 min; LCMS: (method C) 341.3 (M+H), RT. 3.36 min, 97.84% (Max), 94.94% (254 nm);
$^1$H NMR: 400 MHz, DMSO-d$_6$: δ [ppm] 10.43 (s, 1H), 8.54 (d, J=5.12 Hz, 1H), 8.14 (d, J=8.76 Hz, 2H), 8.04-8.06 (m, 2H), 7.94 (d, J=8.76 Hz, 2H), 7.72 (s, 1H), 7.55-7.60 (m, 3H), 7.48 (t, J=7.28 Hz, 1H), 6.46-6.53 (m, 1H), 6.31 (dd, J=1.96, 16.96 Hz, 1H), 5.81 (dd, J=1.96, 10.08 Hz, 1H).

EXAMPLE 12

N-[3-(7-Phenyl-furo[3,2-b]pyridin-2-yl)-benzyl]-acrylamide ("D15")

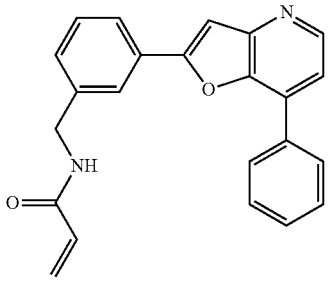 [SMILES: C=CC(=O)NCc1cccc(-c2cc3nccc(-c4ccccc4)c3o2)c1]

12.1
3-(7-Phenyl-furo[3,2-b]pyridin-2-yl)-benzylamine

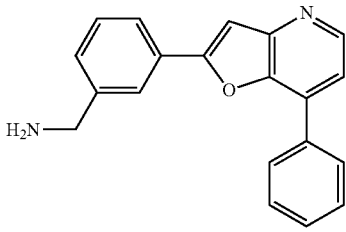 [SMILES: NCc1cccc(-c2cc3nccc(-c4ccccc4)c3o2)c1]

To a solution of 3-(7-chloro-furo[3,2-b]pyridin-2-yl)-benzylamine (0.43 g, 1.66 mmol) in 1,4-dioxane/water (9:1, 10 ml) phenyl boronic acid (0.23 g, 1.18 mmol), 2-dicyclohexylphosphino-2',6' dimethoxybiphenyl (0.07 g, 0.16 mmol), palladium acetate (0.02 g, 0.08 mmol) and potassium carbonate (0.69 g, 4.99 mmol) are taken in a microwave tube, degassed briefly and irradiated to 150° C. for 1 hour. The reaction mixture is passed through celite, washed with dichloromethane/methanol (1:1, 25 ml), the filtrate is concentrated and purified by silica column using (230-400) mesh to get the product as yellow solid (0.35 g, 70%); TLC: chloroform/methanol (9.5/0.5) $R_f$—0.3. LCMS: (method C) 301.2 (M+H), Rt (min): 2.45;

$^1$H NMR: 400 MHz, DMSO-$d_6$: δ [ppm] 8.57 (d, J=5.04 Hz, 1H), 8.11-8.13 (m, 2H), 8.06 (s, 1H), 7.92 (d, J=7.40 Hz, 1H), 7.70 (s, 1H), 7.49-7.67 (m, 6H), 5.26 (br s, 2H), 3.94 (s, 2H).

12.2 N-[3-(7-Phenyl-furo[3,2-b]pyridin-2-yl)-benzyl]-acrylamide ("D15")

"D15" is obtained analogously to example 9.
HPLC: (method F) RT 3.24 min; LCMS: (method C) 355.3 (M+H), RT. 3.26 min;
$^1$H NMR: 400 MHz, DMSO-$d_6$: δ [ppm] 8.74 (t, J=5.84 Hz, 1H), 8.63 (d, J=5.28 Hz, 1H), 8.12-8.14 (m, 2H), 7.94-7.96 (m, 2H), 7.75 (s, 1H), 7.72 (d, J=5.28 Hz, 1H), 7.64-7.68 (m, 2H), 7.59-7.61 (m, 1H), 7.54 (t, J=7.80 Hz, 1H), 7.40 (d, J=7.76 Hz, 1H), 6.30-6.36 (m, 1H), 6.16 (dd, J=2.20, 17.10 Hz, 1H), 5.66 (dd, J=2.20, 10.14 Hz, 1H), 4.47 (d, J=5.96 Hz, 2H).

EXAMPLE 13

N-[4-(2-Phenyl-furo[3,2-b]pyridin-7-yl)-benzyl]-acrylamide ("D25")

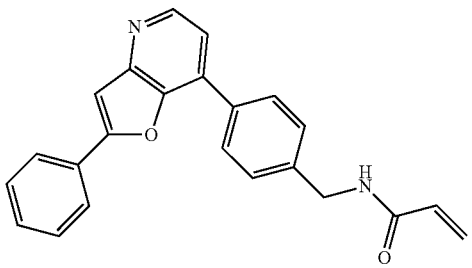 [SMILES: C=CC(=O)NCc1ccc(-c2ccnc3cc(-c4ccccc4)oc23)cc1]

13.1
4-(2-Phenyl-furo[3,2-b]pyridin-7-yl)-benzylamine

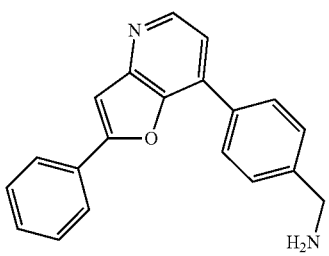 [SMILES: NCc1ccc(-c2ccnc3cc(-c4ccccc4)oc23)cc1]

To a solution of 7-chloro-2-phenyl-furo[3,2-b]pyridine (0.4 g, 1.74 mmol) in 1,4-dioxane/water (9:1, 10 ml) 4-aminomethylphenyl boronic acid hydrochloride (0.41 g, 2.26 mmol), 2-dicyclohexylphosphino-2',6' dimethoxybiphenyl (0.07 g, 0.17 mmol), palladium acetate (0.019 g, 0.08 mmol) and potassium carbonate (0.72 g, 5.22 mmol) are taken in a sealed tube, degassed briefly and heated to 100° C. for 12 hours. The reaction mixture is passed through celite, washed with dichloromethane/methanol (1:1, 25 ml), the filtrate is concentrated and purified by silica column using (230-400) mesh to get the product as brown solid (0.1 g, 19.15%); TLC: chloroform/methanol (9.5/0.5) $R_f$—0.2. LCMS: (method C) 355.0 (M+H), RT. 2.30 min;

$^1$H NMR: 400 MHz, DMSO-$d_6$: δ [ppm] 8.58 (d, J=5.04 Hz, 1H), 8.12 (d, J=8.32 Hz, 2H), 8.02 (d, J=7.32 Hz, 2H), 7.74 (s, 1H), 7.68 (d, J=8.20 Hz, 2H), 7.55-7.62 (m, 3H), 7.49 (t, J=7.36 Hz, 1H), 4.02 (s, 2H).

13.2 N-[4-(2-Phenyl-furo[3,2-b]pyridin-7-yl)-benzyl]-acrylamide ("D25")

"D25" is obtained analogously to example 9
HPLC: (method F) RT 3.12 min; LCMS: (method C) 355.0 (M+H), RT. 3.16 min;
$^1$H NMR: 400 MHz, DMSO-$d_6$: δ [ppm] 8.63 (d, J=5.84 Hz, 1H), 8.03 (d, J=8.32 Hz, 2H), 7.95-7.97 (m, 2H), 7.69 (s, 1H), 7.59-7.64 (m, 3H), 7.54-7.57 (m, 3H), 6.42 (dd, J=1.36, 16.96 Hz, 1H), 6.19-6.26 (m, 2H), 5.77 (dd, J=1.32, 10.26 Hz, 1H), 4.69 (d, J=6.12 Hz, 2H).

Pharmacological Data

TABLE 1

Syk, BTK, KDR, SRC, Zap70 inhibition of some representative compounds of the formula I

| Compound No. | $IC_{50}$ (BLNK cell assay) | $IC_{50}$ Syk (enzyme assay) | $IC_{50}$ BTK | $IC_{50}$ KDR | $IC_{50}$ SRC | $IC_{50}$ Zap70 |
|---|---|---|---|---|---|---|
| "B1" | | C | | | | |
| "B6" | | C | | | | |
| "B7" | | C | | | | |
| "B8" | | B | B | | B | |
| "B9" | | C | | | | |
| "B10" | | B | | A | | |
| "B13" | | B | | | | |
| "B14" | | B | | | | |
| "B15" | | B | C | B | C | C |
| "B16" | | C | | C | C | |
| "B20" | | C | | | | |
| "B21" | | B | | B | A | |
| "B22" | C | A | B | A | A | |
| "B24" | | A | | C | C | |
| "B29" | | B | | | | |
| "B30" | C | A | B | A | A | |
| "B79" | | C | B | | | |
| "B71" | C | A | | C | | C |
| "B72" | | B | | | C | |
| "B73" | | B | | | | |
| "B74" | B | B | C | | | |
| "B75" | | C | | | | |
| "B76" | | A | | | | B |
| "B32" | | C | | | | |
| "B34" | | C | | | | |
| "B35" | | C | | | | |
| "B37" | | C | | | | |
| "B39" | | B | | | | |
| "B40" | | B | | B | C | |
| "B41" | | C | | C | C | |
| "B42" | | C | | | | |
| "B43" | | C | | C | | |

TABLE 1-continued

Syk, BTK, KDR, SRC, Zap70 inhibition of some representative compounds of the formula I

| Compound No. | IC$_{50}$ (BLNK cell assay) | IC$_{50}$ BTK | IC$_{50}$ KDR | IC$_{50}$ SRC | IC$_{50}$ Zap70 |
|---|---|---|---|---|---|
| "A5" | C | A | | | |
| "A7" | | A | | | |
| "B44" | | B | C | A | |
| | | IC$_{50}$ (enzyme assay) | | | |
| "B45" | | B | B | | |
| "B46" | | C | B | A | |
| "A36" | | A | C | | |
| "A8" | | A | | | |
| "B47" | | C | B | B | |
| "B48" | | B | B | A | |
| "B49" | | B | B | A | |
| "B50" | | B | B | B | |
| "B51" | | C | B | B | |
| "B52" | | B | B | B | |
| "B53" | | A | A | A | |
| "B54" | | B | B | A | |
| "A38" | | A | B | C | |
| "A11" | | B | | | |
| "A12" | | C | | | |
| "A13" | | A | B | | |
| "B55" | | B | | | |
| "B56" | | B | A | A | |
| "B57" | | B | A | A | |
| "B58" | | B | A | A | |
| "B59" | | B | A | A | |
| "B60" | | B | B | A | |
| "A51" | | A | B | C | |
| "A55" | | A | C | | B |
| "A53" | | A | B | | |
| "A56" | | A | B | | B |
| "A52" | | A | C | C | |
| "A42" | | A | C | C | B |
| "B61" | | B | A | | A |
| "B62" | | C | | | |
| "B63" | | B | A | A | |
| "A17" | | A | B | | C |
| "A18" | | B | | | |
| "A19" | | C | C | | |
| "A45" | | A | C | B | C |
| "A20" | | A | C | B | |
| "A21" | | A | | | |
| "A54" | | B | | | |
| "A22" | | B | | | |
| "A23" | | A | | | |
| "A24" | | B | | | |
| "A25" | | B | C | C | C |
| "A26" | | B | | | |
| "A43" | | A | | | |
| "A27" | | A | | | |
| "A28" | | A | B | | |
| "A29" | | A | B | | |
| "A31" | | C | | | |
| "A32" | | B | | | |
| "A33" | | A | | | |
| "A34" | | A | | | |
| "A66" | | A | | B | |
| "A67" | | B | | B | |
| "C1" | | B | | | |
| "C2" | | A | C | B | C |
| "C5" | | A | | | |
| "C6" | | B | | | |
| "C7" | | B | | | |
| "C8" | | A | | | |
| "C9" | | B | | | |
| "C10" | | A | | | |
| "C11" | | A | | C | |
| "C12" | | A | B | | C |
| "C13" | | A | | | |
| "C14" | | B | | | |
| "C15" | | B | | | |
| "C16" | | B | | | |
| "C17" | | B | B | | |
| "C18" | | B | B | | |
| "C19" | | A | C | | |
| "C20" | | C | | | |
| "C22" | | B | | | |
| "C23" | | A | | | |
| "C24" | | B | B | | |
| "C25" | | B | | | |
| "C26" | | A | B | B | B |
| "C27" | | A | C | | C |
| "C28" | | B | | | |
| "C29" | | A | B | C | C |
| "C30" | | B | B | | C |
| "C31" | | B | B | | |
| "C32" | | B | | | |
| "C33" | | B | B | | |
| "C34" | | B | C | | |
| "C36" | | B | | | |
| "C37" | | B | B | | |
| "C38" | | B | | | |
| "C39" | | C | | | |
| "C40" | | B | B | C | |
| "C45" | | B | C | | |
| "C46" | | A | C | | C |
| "C49" | | B | B | | |
| "C50" | | B | | | |
| "C54" | | B | | | |
| "C56" | | A | | | |
| "C58" | | A | | | A |
| "C59" | | B | B | | |
| "C60" | | A | B | C | C |
| "C62" | | B | B | | |
| "C64" | | B | | | C |
| "C66" | | B | B | | C |
| "C68" | | B | A | | |
| "C70" | | A | B | | B |
| "C72" | | A | C | A | B | C |
| "C73" | | A | C | A | B | B |
| "C75" | | B | | | |
| "C79" | | B | | | |
| "C85" | | A | | | |
| "C90" | | A | | | |
| "C95" | | B | | | |
| "C96" | | C | | | |
| "C98" | | A | C | | |
| "C100" | | A | | | |
| "C105" | | B | | | |
| "C110" | | A | B | | |
| "C113" | | A | B | B | |
| "C119" | | A | | C | |
| "C123" | | A | C | B | |
| "C127" | | A | B | B | |
| "C133" | | A | | | |
| "C136" | | A | B | B | |
| "C140" | | A | | B | |
| "C149" | | A | | B | |
| "C155" | | A | B | B | |
| "C163" | | A | B | B | |
| "C170" | | A | A | | |
| "C175" | | A | | | |
| "C178" | | A | B | A | |
| "C185" | | A | A | | C |
| "D8" | | | C | | |
| "D19" | | | B | | |
| "D20" | | | A | | |
| "D21" | | | C | | |
| "D22" | | | B | | |
| "D23" | | | A | | |
| "D24" | | | C | | |
| "D16" | | | B | | |

TABLE 1-continued

Syk, BTK, KDR, SRC, Zap70 inhibition
of some representative compounds of the formula I

| Compound No. | $IC_{50}$ (BLNK cell assay) | $IC_{50}$ BTK | $IC_{50}$ KDR | $IC_{50}$ SRC | $IC_{50}$ Zap70 |
|---|---|---|---|---|---|
| "D14" | | C | | | |
| "D4" | | A | | | |
| "D9" | | C | | | |
| "D10" | | C | | | |
| "D11" | | B | | | |
| "D27" | | A | | | |
| "D28" | | C | | | |
| "D15" | | B | | | |
| "D29" | | C | | | |
| "D25" | | B | | | |

$IC_{50}$:
<0.3 μM = A
0.3-3 μM = B
3-50 μM = C

The compounds shown in Table 1 are particularly preferred compounds according to the invention.

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound selected from the following group:

| No. | Name and/or structure |
|---|---|
| "A5" | 7-Phenyl-2-(3,4,5-trimethoxy-phenyl)-furo[3,2-b]pyridine |
| "A6" | 7-Phenyl-2-(3,4,5-trimethoxy-phenyl)-furo[3,2-b]pyridine |
| "A7" | N-Methyl-3-[2-(3,4,5-trimethoxy-phenyl)-furo[3,2-b]pyridin-7-yl]-benzamide |
| "A8" | N-(2-Dimethylamino-ethyl)-3-[2-(3,4,5-trimethoxy-phenyl)-furo[3,2-b]pyridin-7-yl]-benzamide |
| "A9" | 3-[2-(3,4,5-Trimethoxy-phenyl)-furo[3,2-b]pyridin-7-yl]-benzonitrile |
| "A10" | 7-(3-Nitro-phenyl)-2-(3,4,5-trimethoxy-phenyl)-furo[3,2-b]pyridine |
| "A11" | 3-[2-(3,4,5-Trimethoxy-phenyl)-furo[3,2-b]pyridin-7-yl]-benzoic acid methyl ester |
| "A12" | 4-[2-(3,4,5-Trimethoxy-phenyl)-furo[3,2-b]pyridin-7-yl]-benzonitrile |
| "A13" | N-Methyl-4-[2-(3,4,5-trimethoxy-phenyl)-furo[3,2-b]pyridin-7-yl]-benzamide |
| "A14" | 7-(4-Nitro-phenyl)-2-(3,4,5-trimethoxy-phenyl)-furo[3,2-b]pyridine |
| "A15" | 4-[2-(3,4,5-Trimethoxy-phenyl)-furo[3,2-b]pyridin-7-yl]-benzoic acid methyl ester |
| "A16" | 7-(4-Methyl-naphthalen-1-yl)-2-(3,4,5-trimethoxy-phenyl)-furo[3,2-b]pyridine |
| "A17" | 7-(1H-Indazol-4-yl)-2-(3,4,5-trimethoxy-phenyl)-furo[3,2-b]pyridine |
| "A18" | 5-[2-(3,4,5-Trimethoxy-phenyl)-furo[3,2-b]pyridin-7-yl]-quinoline |
| "A19" | 3-(7-Phenyl-furo[3,2-b]pyridin-2-yl)-benzoic acid methyl ester |
| "A20" | 7-(1H-Indol-4-yl)-2-(3,4,5-trimethoxy-phenyl)-furo[3,2-b]pyridine |
| "A21" | 7-o-Tolyl-2-(3,4,5-trimethoxy-phenyl)-furo[3,2-b]pyridine |
| "A22" | 7-Naphthalene-1-yl-2-(3,4,5-trimethoxy-phenyl)-furo[3,2-b]pyridine |
| "A23" | 6-[2-(3,4,5-Trimethoxy-phenyl)-furo[3,2-b]pyridin-7-yl]-quinoline |
| "A24" | 4-[2-(3,4,5-Trimethoxy-phenyl)-furo[3,2-b]pyridin-7-yl]-quinoline |
| "A25" | 7-(1H-Indol-3-yl)-2-(3,4,5-trimethoxy-phenyl)-furo[3,2-b]pyridine |
| "A26" | 8-Methyl-5-[2-(3,4,5-trimethoxy-phenyl)-furo[3,2-b]pyridin-7-yl]-quinoline |
| "A27" | 7-(1H-Indol-6-yl)-2-(3,4,5-trimethoxy-phenyl)-furo[3,2-b]pyridine |
| "A28" | 7-(2,4-Dimethoxy-phenyl)-2-(3,4,5-trimethoxy-phenyl)-furo[3,2-b]pyridine |
| "A29" | 7-(2-Methoxy-pyridin-4-yl)-2-(3,4,5-trimethoxy-phenyl)-furo[3,2-b]pyridine |

-continued

| No. | Name and/or structure |
|---|---|
| "A30" | 5-[2-(3,4,5-Trimethoxy-phenyl)-furo[3,2-b]pyridin-7-yl]-nicotinonitrile |
| "A31" | 7-(3-Benzyloxy-phenyl)-2-(3,4,5-trimethoxy-phenyl)-furo[3,2-b]pyridine |
| "A32" | 7-(2,4-Dimethyl-phenyl)-2-(3,4,5-trimethoxy-phenyl)-furo[3,2-b]pyridine |
| "A33" | {4-[2-(3,4,5-Trimethoxy-phenyl)-furo[3,2-b]pyridin-7-yl]-pyrazol-1-yl}-acetic acid ethyl ester |
| "A34" | 7-(1-Methyl-1H-pyrazol-4-yl)-2-(3,4,5-trimethoxy-phenyl)-furo[3,2-b]pyridine |
| "A35" | 3-(7-Phenyl-furo[3,2-b]pyridin-2-yl)-phenol |
| "A36" | 3-[2-(3,4,5-Trimethoxy-phenyl)-furo[3,2-b]pyridin-7-yl]-phenol |
| "A37" | (2-{3-[2-(3,4,5-Trimethoxy-phenyl)-furo[3,2-b]pyridin-7-yl]-phenoxy}-ethyl)-carbamic acid tert.-butyl ester |
| "A38" | 2-{3-[2-(3,4,5-Trimethoxy-phenyl)-furo[3,2-b]pyridin-7-yl]-phenoxy}-ethylamine |
| "A39" | 3-Methyl-5-(7-phenyl-furo[3,2-b]pyridin-2-yl)-benzoic acid |
| "A40" | 2,3-dimethoxy-5-(7-phenylfuro[3,2-b]pyridin-2-yl)benzoic acid |
| "A41" | 3-[2-(3,4,5-Trimethoxy-phenyl)-furo[3,2-b]pyridin-7-yl]-benzoic acid |
| "A42" | 4-[2-(3,4,5-Trimethoxy-phenyl)-furo[3,2-b]pyridin-7-yl]-benzoic acid |
| "A43" | N-(2-Hydroxy-1,1-dimethyl-ethyl)-3-methyl-5-(7-phenyl-furo[3,2-b]pyridin-2-yl)-benzamide |
| "A44" | N-(2-hydroxy-1,1-dimethyl-ethyl)-2,3-dimethoxy-5-(7-phenylfuro[3,2-b]pyridin-2-yl)benzamide |
| "A45" | N-(2-Amino-cyclohexyl)-3-[2-(3,4,5-trimethoxy-phenyl)-furo[3,2-b]pyridin-7-yl]-benzamide |
| "A46" | (1-{3-[2-(3,4,5-Trimethoxy-phenyl)-furo[3,2-b]pyridin-7-yl]-benzoyl}-pyrrolidin-3-yl)-carbamic acid tert-butyl ester |
| "A47" | tert.-Butyl 3-[[3-[2-(3,4,5-trimethoxyphenyl)furo[3,2-b]pyridin-7-yl]benzoyl]amino]pyrrolidine-1-carboxylate |
| "A48" | N-(2-methoxyethyl)-3-[2-(3,4,5-trimethoxyphenyl)furo[3,2-b]pyridin-7-yl]benzamide |
| "A49" | N-(3-dimethylaminopropyl)-3-[2-(3,4,5-trimethoxyphenyl)furo[3,2-b]pyridin-7-yl]benzamide |
| "A50" | Morpholino-[3-[2-(3,4,5-trimethoxyphenyl)furo[3,2-b]pyridin-7-yl]phenyl]methanone |
| "A51" | 3-[2-(3,4,5-Trimethoxy-phenyl)-furo[3,2-b]pyridin-7-yl]-benzylamine |
| "A52" | N-[[3-[2-(3,4,5-trimethoxyphenyl)furo[3,2-b]pyridin-7-yl]phenyl]methyl]acetamide |
| "A53" | 4-[2-(3,4,5-Trimethoxy-phenyl)-furo[3,2-b]pyridin-7-yl]-benzylamine |
| "A54" | N-{4-[2-(3,4,5-Trimethoxy-phenyl)-furo[3,2-b]pyridin-7-yl]-benzyl}-acetamide |
| "A55" | 3-[2-(3,4,5-Trimethoxy-phenyl)-furo[3,2-b]pyridin-7-yl]-phenylamine |
| "A56" | 4-[2-(3,4,5-Trimethoxy-phenyl)-furo[3,2-b]pyridin-7-yl]-phenylamine |
| "A57" | 2-[4-[2-(3,4,5-trimethoxyphenyl)furo[3,2-b]pyridin-7-yl]pyrazol-1-yl]acetic acid |
| "A58" | 2-[4-[2-(3,4,5-trimethoxyphenyl)furo[3,2-b]pyridin-7-yl]pyrazol-1-yl]acetamide |
| "A59" | 3-[[2-(3,4,5-trimethoxyphenyl)furo[3,2-b]pyridin-7-yl]amino]benzoic acid |
| "A60" | 2-(1-Methyl-1H-pyrazol-3-yl)-7-phenyl-furo[3,2-b]pyridine |
| "A61" | 2-(2-Methoxy-pyridin-4-yl)-7-phenyl-furo[3,2-b]pyridine |
| "A62" | 5-(7-Phenyl-furo[3,2-b]pyridin-2-yl)-benzo[1,2,5]thiadiazole |
| "A63" | 7-Phenyl-2-(3-trifluoromethoxy-phenyl)-furo[3,2-b]pyridine |
| "A64" | 2-(1-Isobutyl-1H-pyrazol-3-yl)-7-phenyl-furo[3,2-b]pyridine |
| "A65" | N-(2-Hydroxy-1,1-dimethyl-ethyl)-3-[2-(3,4,5-trimethoxy-phenyl)-furo[3,2-b]pyridin-7-yl]-benzamide |
| "A66" | N-pyrrolidin-3-yl-3-[2-(3,4,5-trimethoxyphenyl)furo[3,2-b]pyridin-7-yl]benzamide |
| "A67" | (3-aminopyrrolidin-1-yl)-[3-[2-(3,4,5-trimethoxyphenyl)furo[3,2-b]pyridin-7-yl]phenyl]methanone |
| "A68" | 2-(4-Difluoromethoxy-phenyl)-7-pyridin-3-yl-furo[3,2-b]pyridine |
| "A69" | 2-(4-Difluoromethoxy-phenyl)-7-thiazol-5-yl-furo[3,2-b]pyridine |
| "A70" | 2-(4-Difluoromethoxy-phenyl)-7-pyrimidin-5-yl-furo[3,2-b]pyridine |
| "A71" | 5-[2-(4-Difluoromethoxy-phenyl)-furo[3,2-b]pyridin-7-yl]-pyridin-2-ylamine |
| "A72" | 5-[2-(4-Difluoromethoxy-phenyl)-furo[3,2-b]pyridin-7-yl]-pyridine-2-carbonitrile |
| "A73" | 5-[2-(4-Difluoromethoxy-phenyl)-furo[3,2-b]pyridin-7-yl]-nicotinonitrile |
| "A74" | {5-[2-(4-Difluoromethoxy-phenyl)-furo[3,2-b]pyridin-7-yl]-pyridin-2-yl}-dimethyl-amine |
| "A75" | 5-[2-(4-Difluoromethoxy-phenyl)-furo[3,2-b]pyridin-7-yl]-pyridin-2-ol |
| "A76" | 7-[2-(4-Difluoromethoxy-phenyl)-furo[3,2-b]pyridin-7-yl]-4-methyl-3,4-dihydro-2H-pyrido[3,2-b][1,4]oxazine |
| "A77" | 2-(4-Difluoromethoxy-phenyl)-7-(6-methoxy-pyridin-3-yl)-furo[3,2-b]pyridine |
| "A78" | 2-(4-Difluoromethoxy-phenyl)-7-(5-methanesulfonyl-pyridin-3-yl)-furo[3,2-b]pyridine |
| "A79" | 2-[4-(7-Pyridin-3-yl-furo[3,2-b]pyridin-2-yl)-phenoxy]-ethanol |
| "A80" | 2-[4-(7-Thiazol-5-yl-furo[3,2-b]pyridin-2-yl)-phenoxy]-ethanol |
| "A81" | 2-[4-(7-Pyrimidin-5-yl-furo[3,2-b]pyridin-2-yl)-phenoxy]-ethanol |
| "A82" | 2-{4-[7-(6-Amino-pyridin-3-yl)-furo[3,2-b]pyridin-2-yl]-phenoxy}-ethanol |
| "A83" | 5-{2-[4-(2-Hydroxy-ethoxy)-phenyl]-furo[3,2-b]pyridin-7-yl}-pyridine-2-carbonitrile |
| "A84" | 5-{2-[4-(2-Hydroxy-ethoxy)-phenyl]-furo[3,2-b]pyridin-7-yl}-nicotinonitrile |
| "A85" | 2-{4-[7-(6-Dimethylamino-pyridin-3-yl)-furo[3,2-b]pyridin-2-yl]-phenoxy}-ethanol |
| "A86" | 5-{2-[4-(2-Hydroxy-ethoxy)-phenyl]-furo[3,2-b]pyridin-7-yl}-pyridin-2-ol |
| "A87" | 2-{4-[7-(4-Methyl-3,4-dihydro-2H-pyrido[3,2-b][1,4]oxazin-7-yl)-furo[3,2-b]pyridin-2-yl]-phenoxy}-ethanol |
| "A88" | 2-{4-[7-(6-Methoxy-pyridin-3-yl)-furo[3,2-b]pyridin-2-yl]-phenoxy}-ethanol |
| "A89" | 2-{4-[7-(5-Methanesulfonyl-pyridin-3-yl)-furo[3,2-b]pyridin-2-yl]-phenoxy}-ethanol |
| "A90" | 2-(4-Piperazin-1-yl-phenyl)-7-pyridin-3-yl-furo[3,2-b]pyridine |
| "A91" | 2-(4-Piperazin-1-yl-phenyl)-7-thiazol-5-yl-furo[3,2-b]pyridine |
| "A92" | 2-(4-Piperazin-1-yl-phenyl)-7-pyrimidin-5-yl-furo[3,2-b]pyridine |
| "A93" | 5-[2-(4-Piperazin-1-yl-phenyl)-furo[3,2-b]pyridin-7-yl]-pyridin-2-ylamine |
| "A94" | 5-[2-(4-Piperazin-1-yl-phenyl)-furo[3,2-b]pyridin-7-yl]-pyridine-2-carbonitrile |
| "A95" | 5-[2-(4-Piperazin-1-yl-phenyl)-furo[3,2-b]pyridin-7-yl]-nicotinonitrile |
| "A96" | Dimethyl-{5-[2-(4-piperazin-1-yl-phenyl)-furo[3,2-b]pyridin-7-yl]-pyridin-2-yl}-amine |
| "A97" | 5-[2-(4-Piperazin-1-yl-phenyl)-furo[3,2-b]pyridin-7-yl]-pyridin-2-ol |
| "A98" | 4-Methyl-7-[2-(4-piperazin-1-yl-phenyl)-furo[3,2-b]pyridin-7-yl]-3,4-dihydro-2H-pyrido[3,2-b][1,4]oxazine |
| "A99" | 7-(6-Methoxy-pyridin-3-yl)-2-(4-piperazin-1-yl-phenyl)-furo[3,2-b]pyridine |
| "A100" | 7-(5-Methanesulfonyl-pyridin-3-yl)-2-(4-piperazin-1-yl-phenyl)-furo[3,2-b]pyridine |
| "A101" | 2-Pyridin-3-yl-2-[4-(2H-tetrazol-5-yl)-phenyl]-furo[3,2-b]pyridine |
| "A102" | 2-[4-(2H-Tetrazol-5-yl)-phenyl]-7-thiazol-5-yl-furo[3,2-b]pyridine |
| "A103" | 7-Pyrimidin-5-yl-2-[4-(2H-tetrazol-5-yl)-phenyl]-furo[3,2-b]pyridine |
| "A104" | 5-{2-[4-(2H-Tetrazol-5-yl)-phenyl]-furo[3,2-b]pyridin-7-yl}-pyridin-2-ylamine |
| "A105" | 5-{2-[4-(2H-Tetrazol-5-yl)-phenyl]-furo[3,2-b]pyridin-7-yl}-pyridine-2-carbonitrile |
| "A106" | 5-{2-[4-(2H-Tetrazol-5-yl)-phenyl]-furo[3,2-b]pyridin-7-yl}-nicotinonitrile |
| "A107" | Dimethyl-(5-{2-[4-(2H-tetrazol-5-yl)-phenyl]-furo[3,2-b]pyridin-7-yl}-pyridin-2-yl)-amine |
| "A108" | 5-{2-[4-(2H-Tetrazol-5-yl)-phenyl]-furo[3,2-b]pyridin-7-yl}-pyridin-2-ol |
| "A109" | 4-Methyl-7-{2-[4-(2H-tetrazol-5-yl)-phenyl]-furo[3,2-b]pyridin-7-yl}-3,4-dihydro-2H-pyrido[3,2-b][1,4]oxazine |
| "A110" | 7-(6-Methoxy-pyridin-3-yl)-2-[4-(2H-tetrazol-5-yl)-phenyl]-furo[3,2-b]pyridine |
| "A111" | 7-(5-Methanesulfonyl-pyridin-3-yl)-2-[4-(2H-tetrazol-5-yl)-phenyl]-furo[3,2-b]pyridine |
| "A112" | 2-[4-(1H-Imidazol-4-yl)-phenyl]-7-pyridin-3-yl-furo[3,2-b]pyridine |
| "A113" | 2-[4-(1H-Imidazol-4-yl)-phenyl]-7-thiazol-5-yl-furo[3,2-b]pyridine |
| "A114" | 2-[4-(1H-Imidazol-4-yl)-phenyl]-7-pyrimidin-5-yl-furo[3,2-b]pyridine |
| "A115" | 5-{2-[4-(1H-Imidazol-4-yl)-phenyl]-furo[3,2-b]pyridin-7-yl}-pyridin-2-ylamine |

| No. | Name and/or structure |
|---|---|
| "A116" | 5-{2-[4-(1H-Imidazol-4-yl)-phenyl]-furo[3,2-b]pyridin-7-yl}-pyridine-2-carbonitrile |
| "A117" | 5-{2-[4-(1H-Imidazol-4-yl)-phenyl]-furo[3,2-b]pyridin-7-yl}-nicotinonitrile |
| "A118" | (5-{2-[4-(1H-Imidazol-4-yl)-phenyl]-furo[3,2-b]pyridin-7-yl}-pyridin-2-yl)-dimethyl-amine |
| "A119" | 5-{2-[4-(1H-Imidazol-4-yl)-phenyl]-furo[3,2-b]pyridin-7-yl}-pyridin-2-ol |
| "A120" | 7-{2-[4-(1H-Imidazol-4-yl)-phenyl]-furo[3,2-b]pyridin-7-yl}-4-methyl-3,4-dihydro-2H-pyrido[3,2-b][1,4]oxazine |
| "A121" | 2-[4-(1H-Imidazol-4-yl)-phenyl]-7-(6-methoxy-pyridin-3-yl)-furo[3,2-b]pyridine |
| "A122" | 2-[4-(1H-Imidazol-4-yl)-phenyl]-7-(5-methanesulfonyl-pyridin-3-yl)-furo[3,2-b]pyridine |
| "A123" | 2-{4-(7-Pyridin-3-yl-furo[3,2-b]pyridin-2-yl)-phenyl}-ethanol |
| "A124" | 2-{4-(7-Thiazol-5-yl-furo[3,2-b]pyridin-2-yl)-phenyl}-ethanol |
| "A125" | 2-{4-(7-Pyrimidin-5-yl-furo[3,2-b]pyridin-2-yl)-phenyl}-ethanol |
| "A126" | 2-{4-[7-(6-Amino-pyridin-3-yl)-furo[3,2-b]pyridin-2-yl]-phenyl}-ethanol |
| "A127" | 5-{2-[4-(2-Hydroxy-ethyl)-phenyl]-furo[3,2-b]pyridin-7-yl}-pyridine-2-carbonitrile |
| "A128" | 5-{2-[4-(2-Hydroxy-ethyl)-phenyl]-furo[3,2-b]pyridin-7-yl}-nicotinonitrile |
| "A129" | 2-{4-[7-(6-Dimethylamino-pyridin-3-yl)-furo[3,2-b]pyridin-2-yl]-phenyl}-ethanol |
| "A130" | 5-{2-[4-(2-Hydroxy-ethyl)-phenyl]-furo[3,2-b]pyridin-7-yl}-pyridin-2-ol |
| "A131" | 2-{4-[7-(4-Methyl-3,4-dihydro-2H-pyrido[3,2-b][1,4]oxazin-7-yl)-furo[3,2-b]pyridin-2-yl]-phenyl}-ethanol |
| "A132" | 2-{4-[7-(6-Methoxy-pyridin-3-yl)-furo[3,2-b]pyridin-2-yl]-phenyl}-ethanol |
| "A133" | 2-{4-[7-(5-Methanesulfonyl-pyridin-3-yl)-furo[3,2-b]pyridin-2-yl]-phenyl}-ethanol |
| "A134" | 7-Pyridin-3-yl-2-[4-(2-pyrrolidin-1-yl-ethoxy)-phenyl]-furo[3,2-b]pyridine |
| "A135" | 2-[4-(2-Pyrrolidin-1-yl-ethoxy)-phenyl]-7-thiazol-5-yl-furo[3,2-b]pyridine |
| "A136" | 7-Pyrimidin-5-yl-2-[4-(2-pyrrolidin-1-yl-ethoxy)-phenyl]-furo[3,2-b]pyridine |
| "A137" | 5-{2-[4-(2-Pyrrolidin-1-yl-ethoxy)-phenyl]-furo[3,2-b]pyridin-7-yl}-pyridin-2-ylamine |
| "A138" | 5-{2-[4-(2-Pyrrolidin-1-yl-ethoxy)-phenyl]-furo[3,2-b]pyridin-7-yl}-pyridine-2-carbonitrile |
| "A139" | 5-{2-[4-(2-Pyrrolidin-1-yl-ethoxy)-phenyl]-furo[3,2-b]pyridin-7-yl}-nicotinonitrile |
| "A140" | Dimethyl-(5-{2-[4-(2-pyrrolidin-1-yl-ethoxy)-phenyl]-furo[3,2-b]pyridin-7-yl}-pyridin-2-yl)-amine |
| "A141" | 5-{2-[4-(2-Pyrrolidin-1-yl-ethoxy)-phenyl]-furo[3,2-b]pyridin-7-yl}-pyridin-2-ol |
| "A142" | 4-Methyl-7-{2-[4-(2-pyrrolidin-1-yl-ethoxy)-phenyl]-furo[3,2-b]pyridin-7-yl}-3,4-dihydro-2H-pyrido[3,2-b][1,4]oxazine |
| "A143" | 7-(6-Methoxy-pyridin-3-yl)-2-[4-(2-pyrrolidin-1-yl-ethoxy)-phenyl]-furo[3,2-b]pyridine |
| "A144" | 7-(5-Methanesulfonyl-pyridin-3-yl)-2-[4-(2-pyrrolidin-1-yl-ethoxy)-phenyl]-furo[3,2-b]pyridine |
| "A145" | 2-[4-(1-Methyl-1H-pyrazol-4-yl)-phenyl]-7-pyridin-3-yl-furo[3,2-b]pyridine |
| "A146" | 2-[4-(1-Methyl-1H-pyrazol-4-yl)-phenyl]-7-thiazol-5-yl-furo[3,2-b]pyridine |
| "A147" | 2-[4-(1-Methyl-1H-pyrazol-4-yl)-phenyl]-7-pyrimidin-5-yl-furo[3,2-b]pyridine |
| "A148" | 5-{2-[4-(1-Methyl-1H-pyrazol-4-yl)-phenyl]-furo[3,2-b]pyridin-7-yl}-pyridin-2-ylamine |
| "A149" | 5-{2-[4-(1-Methyl-1H-pyrazol-4-yl)-phenyl]-furo[3,2-b]pyridin-7-yl}-pyridine-2-carbonitrile |
| "A150" | 5-{2-[4-(1-Methyl-1H-pyrazol-4-yl)-phenyl]-furo[3,2-b]pyridin-7-yl}-nicotinonitrile |
| "A151" | Dimethyl-(5-{2-[4-(1-methyl-1H-pyrazol-4-yl)-phenyl]-furo[3,2-b]pyridin-7-yl}-pyridin-2-yl)-amine |
| "A152" | 5-{2-[4-(1-Methyl-1H-pyrazol-4-yl)-phenyl]-furo[3,2-b]pyridin-7-yl}-pyridin-2-ol |
| "A153" | 4-Methyl-7-{2-[4-(1-methyl-1H-pyrazol-4-yl)-phenyl]-furo[3,2-b]pyridin-7-yl}-3,4-dihydro-2H-pyrido[3,2-b][1,4]oxazine |
| "A154" | 7-(6-Methoxy-pyridin-3-yl)-2-[4-(1-methyl-1H-pyrazol-4-yl)-phenyl]-furo[3,2-b]pyridine |
| "A155" | 7-(5-Methanesulfonyl-pyridin-3-yl)-2-[4-(1-methyl-1H-pyrazol-4-yl)-phenyl]-furo[3,2-b]pyridine |
| "A156" | 2-{4-[4-(7-Pyridin-3-yl-furo[3,2-b]pyridin-2-yl)-phenyl]-pyrazol-1-yl}-ethanol |
| "A157" | 2-{4-[4-(7-Thiazol-5-yl-furo[3,2-b]pyridin-2-yl)-phenyl]-pyrazol-1-yl}-ethanol |
| "A158" | 2-{4-[4-(7-Pyrimidin-5-yl-furo[3,2-b]pyridin-2-yl)-phenyl]-pyrazol-1-yl}-ethanol |
| "A159" | 2-{4-{4-[7-(6-Amino-pyridin-3-yl)-furo[3,2-b]pyridin-2-yl]-phenyl}-pyrazol-1-yl)-ethanol |
| "A160" | 5-(2-{4-[1-(2-Hydroxy-ethyl)-1H-pyrazol-4-yl]-phenyl}-furo[3,2-b]pyridin-7-yl)-pyridine-2-carbonitrile |
| "A161" | 5-(2-{4-[1-(2-Hydroxy-ethyl)-1H-pyrazol-4-yl]-phenyl}-furo[3,2-b]pyridin-7-yl)-nicotinonitrile |
| "A162" | 2-(4-{4-[7-(6-Dimethylamino-pyridin-3-yl)-furo[3,2-b]pyridin-2-yl]-phenyl}-pyrazol-1-yl)-ethanol |
| "A163" | 5-(2-{4-[1-(2-Hydroxy-ethyl)-1H-pyrazol-4-yl]-phenyl}-furo[3,2-b]pyridin-7-yl)-pyridin-2-ol |
| "A164" | 2-(4-{4-[7-(4-Methyl-3,4-dihydro-2H-pyrido[3,2-b][1,4]oxazin-7-yl)-furo[3,2-b]pyridin-2-yl]-phenyl}-pyrazol-1-yl)-ethanol |
| "A165" | 2-(4-{4-[7-(6-Methoxy-pyridin-3-yl)-furo[3,2-b]pyridin-2-yl]-phenyl}-pyrazol-1-yl)-ethanol |
| "A166" | 2-(4-{4-[7-(5-Methanesulfonyl-pyridin-3-yl)-furo[3,2-b]pyridin-2-yl]-phenyl}-pyrazol-1-yl)-ethanol |
| "B1" | 2,7-Bis-(3,5-difluoro-phenyl)-furo[3,2-b]pyridine |
| "B2" | 4-(2-Phenyl-furo[3,2-b]pyridin-7-yloxy)-phenylamine |
| "B3" | (2H-Indazol-6-yl)-(2-phenyl-furo[3,2-b]pyridin-7-yl)-amine |
| "B4" | [3-Chloro-4-(1-methyl-1H-imidazol-2-ylsulfanyl)-phenyl]-(2-phenyl-furo[3,2-b]pyridin-7-yl)-amine |
| "B5" | (2-Benzyl-2H-indazol-6-yl)-(2-phenyl-furo[3,2-b]pyridin-7-yl)-amine |
| "B6" | 2,7-Bis-(4-fluoro-phenyl)-furo[3,2-b]pyridine |
| "B7" | N-Methyl-N-(3-{[2-(3,4,5-trimethoxy-phenyl)-furo[3,2-b]pyridin-7-ylamino]-methyl}-pyridin-2-yl)-methanesulfonamide |
| "B8" | N-Methyl-2-[2-(3,4,5-trimethoxy-phenyl)-furo[3,2-b]pyridin-7-ylamino]-benzamide |
| "B9" | (3-Methanesulfonyl-benzyl)-[2-(3,4,5-trimethoxy-phenyl)-furo[3,2-b]pyridin-7-yl]-amine |
| "B10" | 2,2-Difluoro-6-[2-(3,4,5-trimethoxy-phenyl)-furo[3,2-b]pyridin-7-ylamino]-4H-benzo[1,4]oxazin-3-one |
| "B11" | 1-(2-Hydroxy-2-methyl-propyl)-5-methyl-3-oxo-2-phenyl-2,3-dihydro-1H-pyrazole-4-carboxylic acid [4-(2-phenyl-furo[3,2-b]pyridin-7-yloxy)-phenyl]-amide |
| "B12" | 1-(4-Fluoro-phenyl)-4-iodo-2-oxo-1,2-dihydro-pyridine-3-carboxylic acid [4-(2-phenyl-furo[3,2-b]pyridin-7-yloxy)-phenyl]-amide |
| "B13" | 1-(4-Fluoro-phenyl)-2-oxo-1,2-dihydro-pyridine-3-carboxylic acid [4-(2-phenyl-furo[3,2-b]pyridin-7-yloxy)-phenyl]-amide |
| "B14" | 4-Ethoxy-1-(4-fluoro-phenyl)-2-oxo-1,2-dihydro-pyridine-3-carboxylic acid [4-(2-phenyl-furo[3,2-b]pyridin-7-yloxy)-phenyl]-amide |
| "B15" | (1H-Indazol-6-yl)-[2-(3,4,5-trimethoxy-phenyl)-furo[3,2-b]pyridin-7-yl]-amine |
| "B16" | [3-Chloro-4-(1-methyl-1H-imidazol-2-ylsulfanyl)-phenyl]-[2-(3,4,5-trimethoxy-phenyl)-furo[3,2-b]pyridin-7-yl]-amine |
| "B17" | 2,2-Difluoro-6-(2-phenyl-furo[3,2-b]pyridin-7-ylamino)-4H-benzo[1,4]oxazin-3-one |
| "B18" | N-Methyl-2-(2-phenyl-furo[3,2-b]pyridin-7-ylamino)-benzamide |
| "B19" | (3-Methanesulfonyl-benzyl)-(2-phenyl-furo[3,2-b]pyridin-7-yl)-amine |
| "B20" | N-Methyl-N-{3-[(2-phenyl-furo[3,2-b]pyridin-7-ylamino)-methyl]-pyridin-2-yl}-methanesulfonamide |
| "B21" | (4-Methyl-1H-indol-5-yl)-(2-phenyl-furo[3,2-b]pyridin-7-yl)-amine |
| "B22" | (4-Methyl-1H-indol-5-yl)-[2-(3,4,5-trimethoxy-phenyl)-furo[3,2-b]pyridin-7-yl]-amine |
| "B23" | 3-Fluoro-4-(2-phenyl-furo[3,2-b]pyridin-7-yloxy)-phenylamine |
| "B24" | 2,7-Bis-(3,4,5-trimethoxy-phenyl)-furo[3,2-b]pyridine |
| "B25" | 1-(4-Fluoro-phenyl)-2-oxo-1,2-dihydro-pyridine-3-carboxylic acid [3-fluoro-4-(2-phenyl-furo[3,2-b]pyridin-7-yloxy)-phenyl]-amide |
| "B26" | 1-(4-Fluoro-phenyl)-4-iodo-2-oxo-1,2-dihydro-pyridine-3-carboxylic acid [3-fluoro-4-(2-phenyl-furo[3,2-b]pyridin-7-yloxy)-phenyl]-amide |
| "B27" | 4-Ethoxy-1-(4-fluoro-phenyl)-2-oxo-1,2-dihydro-pyridine-3-carboxylic acid [3-fluoro-4-(2-phenyl-furo[3,2-b]pyridin-7-yloxy)-phenyl]-amide |
| "B28" | 1-(4-Fluoro-phenyl)-4-methylamino-2-oxo-1,2-dihydro-pyridine-3-carboxylic acid [3-fluoro-4-(2-phenyl-furo[3,2-b]pyridin-7-yloxy)-phenyl]-amide |

-continued

| No. | Name and/or structure |
|---|---|
| "B29" | 2,2-Dimethyl-6-[2-(3,4,5-trimethoxy-phenyl)-furo[3,2-b]pyridin-7-ylamino]-4H-pyrido[3,2-b][1,4]oxazin-3-one |
| "B30" | (1H-Indol-5-yl)-[2-(3,4,5-trimethoxy-phenyl)-furo[3,2-b]pyridin-7-yl]-amine |
| "B31" | 2,7-Di-p-tolyl-furo[3,2-b]pyridine |
| "B32" | 2,7-Bis-(4-methoxy-3,5-dimethyl-phenyl)-furo[3,2-b]pyridine |
| "B33" | 2,7-Bis-(4-methoxy-3-methyl-phenyl)-furo[3,2-b]pyridine |
| "B34" | 2,7-Di-m-tolyl-furo[3,2-b]pyridine |
| "B35" | 2,7-Bis-(4-methoxy-phenyl)-furo[3,2-b]pyridine |
| "B36" | 2,7-Bis-benzo[1,3]dioxol-5-yl-furo[3,2-b]pyridine |
| "B37" | 2,7-Bis-(2,3-dihydro-benzo[1,4]dioxin-6-yl)-furo[3,2-b]pyridine |
| "B38" | 2,7-Bis-(3,5-dimethyl-phenyl)-furo[3,2-b]pyridine |
| "B39" | 2,7-Bis-(3,4-dimethoxy-phenyl)-furo[3,2-b]pyridine |
| "B40" | 2,7-Bis-(2,3,4-trimethoxy-phenyl)-furo[3,2-b]pyridine |
| "B41" | 2,7-Bis-(3,5-dimethyl-isoxazol-4-yl)-furo[3,2-b]pyridine |
| "B42" | 2,7-Bis-(2,3-dimethoxy-phenyl)-furo[3,2-b]pyridine |
| "B43" | 2,7-Bis-(3-methoxy-phenyl)-furo[3,2-b]pyridine |
| "B44" | {4-[2-(4-Hydroxymethyl-phenyl)-furo[3,2-b]pyridin-7-yl]-phenyl}-methanol |
| "B45" | 2-(4-{2-[4-(1-Hydroxy-1-methyl-ethyl)-phenyl]-furo[3,2-b]pyridin-7-yl}-phenyl)-propan-2-ol |
| "B46" | (4-Methyl-1H-indol-5-yl)-(2-p-tolyl-furo[3,2-b]pyridin-7-yl)-amine |
| "B47" | [2-(4-Methoxy-phenyl)-furo[3,2-b]pyridin-7-yl]-(4-methyl-1H-indol-5-yl)-amine |
| "B48" | (2-Benzo[1,3]dioxol-5-yl-furo[3,2-b]pyridin-7-yl)-(4-methyl-1H-indol-5-yl)-amine |
| "B49" | [2-(4-Methoxy-3,5-dimethyl-phenyl)-furo[3,2-b]pyridin-7-yl]-(4-methyl-1H-indol-5-yl)-amine |
| "B50" | [2-(4-Methoxy-3-methyl-phenyl)-furo[3,2-b]pyridin-7-yl]-(4-methyl-1H-indol-5-yl)-amine |
| "B51" | (4-Methyl-1H-indol-5-yl)-(2-m-tolyl-furo[3,2-b]pyridin-7-yl)-amine |
| "B52" | [2-(3,5-Dimethyl-phenyl)-furo[3,2-b]pyridin-7-yl]-(4-methyl-1H-indol-5-yl)-amine |
| "B53" | [2-(3,4-Dimethoxy-phenyl)-furo[3,2-b]pyridin-7-yl]-(4-methyl-1H-indol-5-yl)-amine |
| "B54" | (4-Methyl-1H-indol-5-yl)-[2-(4-morpholin-4-yl-phenyl)-furo[3,2-b]pyridin-7-yl]-amine |
| "B55" | 2-(4-{2-[4-(Cyano-dimethyl-methyl)-phenyl]-furo[3,2-b]pyridin-7-yl}-phenyl)-2-methyl-propionitrile |
| "B56" | (4-Methyl-1H-indol-5-yl)-[2-(2,3,4-trimethoxy-phenyl)-furo[3,2-b]pyridin-7-yl]-amine |
| "B57" | [2-(3-Methoxy-phenyl)-furo[3,2-b]pyridin-7-yl]-(4-methyl-1H-indol-5-yl)-amine |
| "B58" | {2-[4-(3-Dimethylamino-propoxy)-phenyl]-furo[3,2-b]pyridin-7-yl}-(4-methyl-1H-indol-5-yl)-amine |
| "B59" | [2-(2,3-Dimethoxy-phenyl)-furo[3,2-b]pyridin-7-yl]-(4-methyl-1H-indol-5-yl)-amine |
| "B60" | [2-(2,3-Dihydro-benzo[1,4]dioxin-6-yl)-furo[3,2-b]pyridin-7-yl]-(4-methyl-1H-indol-5-yl)-amine |
| "B61" | {4-[7-(4-Methyl-1H-indol-5-ylamino)-furo[3,2-b]pyridin-2-yl]-phenyl}-methanol |
| "B62" | [2-(4-Isopropenyl-phenyl)-furo[3,2-b]pyridin-7-yl]-(4-methyl-1H-indol-5-yl)-amine |
| "B63" | [2-(3,5-Dimethyl-isoxazol-4-yl)-furo[3,2-b]pyridin-7-yl]-(4-methyl-1H-indol-5-yl)-amine |
| "B64" | N-(4-Fluoro-phenyl)-3-[2-(3,4,5-trimethoxy-phenyl)-furo[3,2-b]pyridin-7-yl]-benzamide |
| "B65" | N-{4-[2-(3,4,5-Trimethoxy-phenyl)-furo[3,2-b]pyridin-7-yl]-phenyl}-benzamide |
| "B66" | N-Phenyl-4-[2-(3,4,5-trimethoxy-phenyl)-furo[3,2-b]pyridin-7-yl]-benzamide |
| "B67" | (4-Methyl-piperazin-1-yl)-{4-[2-(3,4,5-trimethoxy-phenyl)-furo[3,2-b]pyridin-7-yl]-phenyl}-methanone |
| "B68" | (4-Methyl-piperazin-1-yl)-{3-[2-(3,4,5-trimethoxy-phenyl)-furo[3,2-b]pyridin-7-yl]-phenyl}-methanone |
| "B69" | 2-Fluoro-N-(2-hydroxy-ethyl)-4-[2-(3,4,5-trimethoxy-phenyl)-furo[3,2-b]pyridin-7-yl]-benzamide |
| "B70" | 1-{5-[2-(3,4,5-Trimethoxy-phenyl)-furo[3,2-b]pyridin-7-yl]-thiophen-2-yl}-ethanone |
| "B71" | 6-(2-(3,4,5-Trimethoxyphenyl)furo[3,2-b]pyridin-7-yl)indolin-2-one |
| "B72" | N-(3-(2-(3,4,5-Trimethoxyphenyl)furo[3,2-b]pyridin-7-yl)phenyl)acetamide |
| "B73" | 7-(4-Methoxy-3,5-dimethylphenyl)-2-(3,4,5-trimethoxyphenyl)furo[3,2-b]pyridine |
| "B74" | 7-(1H-Indol-5-yl)-2-(3,4,5-trimethoxyphenyl)furo[3,2-b]pyridine |
| "B75" | N-Cyclopentyl-4-(2-(3,4,5-trimethoxyphenyl)furo[3,2-b]pyridin-7-yl)benzamide |
| "B76" | 7-(Benzo[d][1,3]dioxol-5-yl)-2-(3,4,5-trimethoxyphenyl)furo[3,2-b]pyridin |
| "B77" | 7-(6-Methoxynaphthalen-2-yl)-2-(3,4,5-trimethoxyphenyl)furo[3,2-b]pyridine |
| "B78" | 7-(Benzo[b]thiophen-2-yl)-2-(3,4,5-trimethoxyphenyl)furo[3,2-b]pyridine |
| "B79" | 3-[7-(4-Phenoxyphenoxy)furo[3,2-b]pyridin-2-yl]aniline |
| "B80" | N-{3-[7-(4-Phenoxyphenoxy)furo[3,2-b]pyridin-2-yl]phenyl}propanamide |
| "B81" | N-{3-[2-(3,4-Dimethoxyphenyl)furo[3,2-b]pyridin-7-yl]-2-methylphenyl}-3-(trifluoromethyl)benzamide |
| "B82" | N-{3-[7-(4-Phenoxyphenoxy)furo[3,2-b]pyridin-2-yl]phenyl}acrylamide |
| "B83" | N-{3-[2-(3,4-Dimethoxyphenyl)furo[3,2-b]pyridin-7-yl]-2-methylphenyl}-4,5,6,7-tetrahydro-1-benzothiophene-2-carboxamide |
| "B84" | 4-tert.-Butyl-N-{3-[2-(3,4-dimethoxyphenyl)furo[3,2-b]pyridin-7-yl]-2-methylphenyl}benzamide |
| "B85" | N-{3-[7-(4-Phenoxyphenoxy)furo[3,2-b]pyridin-2-yl]phenyl}but-2-ynamide |
| "B86" | 4-tert.-Butyl-N-{2-methyl-3-{2-[4-(pyrrolidin-1-ylcarbonyl)phenyl]furo[3,2-b]pyridin-7-yl}phenyl}benzamide |
| "B87" | N-(2-Methyl-3-{2-[4-(pyrrolidin-1-ylcarbonyl)phenyl]furo[3,2-b]pyridin-7-yl}phenyl)-4,5,6,7-tetrahydro-1-benzothiophene-2-carboxamide |
| "B88" | (2E)-N-{3-[7-(4-phenoxyphenoxy)furo[3,2-b]pyridin-2-yl]phenyl}but-2-enamide |
| "B89" | (2E)-4-(Dimethylamino)-N-{3-[7-(4-phenoxyphenoxy)furo[3,2-b]pyridin-2-yl]phenyl}but-2-enamide |
| "B90" | 2-Methyl-N-{3-[7-(4-phenoxyphenoxy)furo[3,2-b]pyridin-2-yl]phenyl}acrylamide |
| "C1" | 3-(7-Phenyl-furo[3,2-b]pyridin-2-yl)-phenol |
| "C2" | 7-(2,6-Dimethoxy-phenyl)-2-(3,4,5-trimethoxy-phenyl)-furo[3,2-b]pyridine |
| "C3" | 7-Phenyl-2-(3-trifluoromethyl-phenyl)-furo[3,2-b]pyridine |
| "C4" | N-(2-Dimethylamino-ethyl)-3-[2-(1-methyl-1H-pyrazol-4-yl)-furo[3,2-b]pyridin-7-yl]-benzamide |
| "C5" | N-(2-Hydroxy-ethyl)-3-[2-(3,4,5-trimethoxy-phenyl)-furo[3,2-b]pyridin-7-yl]-benzamide |
| "C6" | 2-(1-Isobutyl-1H-pyrazol-4-yl)-7-(1-methyl-1H-pyrazol-4-yl)-furo[3,2-b]pyridine |
| "C7" | 2-({3-[2-(3,4,5-Trimethoxy-phenyl)-furo[3,2-b]pyridin-7-yl]-benzoylamino}-methyl)-pyrrolidine-1-carboxylic acid tert-butyl ester |
| "C8" | N-Methyl-2-{3-[2-(3,4,5-trimethoxy-phenyl)-furo[3,2-b]pyridin-7-yl]-phenoxy}-acetamide |
| "C9" | 2-(3-tert.-Butyl-5-methyl-phenyl)-7-(1-methyl-1H-pyrazol-4-yl)-furo[3,2-b]pyridine |
| "C10" | N-(1H-Pyrazol-3-ylmethyl)-3-[2-(3,4,5-trimethoxy-phenyl)-furo[3,2-b]pyridin-7-yl]-benzamide |
| "C11" | N-Pyrrolidin-2-ylmethyl-3-[2-(3,4,5-trimethoxy-phenyl)-furo[3,2-b]pyridin-7-yl]-benzamide |
| "C12" | N-(5-Oxo-4,5-dihydro-1H-[1,2,4]triazol-3-ylmethyl)-3-[2-(3,4,5-trimethoxy-phenyl)-furo[3,2-b]pyridin-7-yl]-benzamide |
| "C13" | 7-Pyridin-3-yl-2-(3,4,5-trimethoxy-phenyl)-furo[3,2-b]pyridine |
| "C14" | 7-(2-Isopropyl-phenyl)-2-(3,4,5-trimethoxy-phenyl)-furo[3,2-b]pyridine |
| "C15" | 2-(3-Methoxy-phenyl)-7-phenyl-furo[3,2-b]pyridine |
| "C16" | 2-(2-Methoxy-pyridin-4-yl)-7-(1-methyl-1H-pyrazol-4-yl)-furo[3,2-b]pyridine |
| "C17" | 2-(2,3-Dihydro-Benzo[1,4]dioxin-6-yl)-7-(1-methyl-1H-pyrazol-4-yl)-furo[3,2-b]pyridine |
| "C18" | 2-(1H-Indol-5-yl)-7-(1-methyl-1H-pyrazol-4-yl)-furo[3,2-b]pyridine |
| "C19" | 2-(1H-Indol-6-yl)-7-(1-methyl-1H-pyrazol-4-yl)-furo[3,2-b]pyridine |
| "C20" | 2-(3-Benzyloxy-phenyl)-7-(1-methyl-1H-pyrazol-4-yl)-furo[3,2-b]pyridine |
| "C22" | 2-(3,5-Dimethyl-isoxazol-4-yl)-7-(1-methyl-1H-pyrazol-4-yl)-furo[3,2-b]pyridine |
| "C23" | 7-(6-Fluoro-4-methyl-pyridin-3-yl)-2-(3,4,5-trimethoxy-phenyl)-furo[3,2-b]pyridine |
| "C24" | 7-(1-Methyl-1H-pyrazol-4-yl)-2-(6-morpholin-4-yl-pyridin-3-yl)-furo[3,2-b]pyridine |

| No. | Name and/or structure |
|---|---|
| "C25" | 2-(6-Morpholin-4-yl-pyridin-3-yl)-7-phenyl-furo[3,2-b]pyridine |
| "C26" | 2-Methoxy-4-[7-(1-methyl-1H-pyrazol-4-yl)-furo[3,2-b]pyridin-2-yl]-phenol |
| "C27" | {5-[2-(3,4,5-Trimethoxy-phenyl)-furo[3,2-b]pyridin-7-yl]-pyridin-2-yl}-methanol |
| "C28" | 7-[6-(Tetrahydro-pyran-4-yloxy)-pyridin-3-yl]-2-(3,4,5-trimethoxy-phenyl)-furo[3,2-b]pyridine |
| "C29" | 3-[7-(1-Methyl-1H-pyrazol-4-yl)-furo[3,2-b]pyridin-2-yl]-phenylamine |
| "C30" | (S)-Pyrrolidine-2-carboxylic acid [2-methoxy-5-(7-phenyl-furo[3,2-b]pyridin-2-yl)-phenyl]-amide |
| "C31" | (S)-Pyrrolidine-2-carboxylic acid [3-(7-phenyl-furo[3,2-b]pyridin-2-yl)-phenyl]-amide |
| "C32" | 7-(1-Methyl-1H-pyrazol-4-yl)-2-(4-trifluoromethoxy-phenyl)-furo[3,2-b]pyridine |
| "C33" | 2-(4-Methoxy-phenyl)-7-(1-methyl-1H-pyrazol-4-yl)-furo[3,2-b]pyridine |
| "C34" | 2-(4-Methanesulfonyl-phenyl)-7-(1-methyl-1H-pyrazol-4-yl)-furo[3,2-b]pyridine |
| "C35" | (S)-Pyrrolidine-2-carboxylic acid {3-[7-(1-methyl-1H-pyrazol-4-yl)-furo[3,2-b]pyridin-2-yl]-phenyl}-amide |
| "C36" | 7-(1-Methyl-1H-pyrazol-4-yl)-2-[4-(2-piperidin-1-yl-ethoxy)-phenyl]-furo[3,2-b]pyridine |
| "C37" | 1-{4-[7-(1-Methyl-1H-pyrazol-4-yl)-furo[3,2-b]pyridin-2-yl]-phenoxy}-3-morpholin-4-yl-propan-2-ol |
| "C38" | 1-{4-[7-(1-Methyl-1H-pyrazol-4-yl)-furo[3,2-b]pyridin-2-yl]-phenoxy}-3-piperidin-1-yl-propan-2-ol |
| "C39" | 2-(6-Morpholin-4-yl-pyridin-3-yl)-7-pyridin-3-yl-furo[3,2-b]pyridine |
| "C40" | (2S,4R)-4-Hydroxy-pyrrolidine-2-carboxylic acid [2-methoxy-5-(7-phenyl-furo[3,2-b]pyridin-2-yl)-phenyl]-amide |
| "C41" | 7-(6-Methoxy-pyridin-3-yl)-2-(3,4,5-trimethoxy-phenyl)-furo[3,2-b]pyridine |
| "C42" | 2-(1-Benzyl-1H-pyrazol-4-yl)-7-(1-methyl-1H-pyrazol-4-yl)-furo[3,2-b]pyridine |
| "C43" | {3-[7-(1-Methyl-1H-pyrazol-4-yl)-furo[3,2-b]pyridin-2-yl]-phenyl}-methanol |
| "C44" | Dimethyl-(3-{4-[7-(1-methyl-1H-pyrazol-4-yl)-furo[3,2-b]pyridin-2-yl]-phenoxy}-propyl)-amine |
| "C45" | 2-(3-Isopropyl-phenyl)-7-(1-methyl-1H-pyrazol-4-yl)-furo[3,2-b]pyridine |
| "C46" | (2S,4R)-4-Hydroxy-pyrrolidine-2-carboxylic acid [3-methoxy-5-(7-phenyl-furo[3,2-b]pyridin-2-yl)-phenyl]-amide |
| "C47" | (S)-Pyrrolidine-2-carboxylic acid [3-methoxy-5-(7-phenyl-furo[3,2-b]pyridin-2-yl)-phenyl]-amide |
| "C48" | 2-(4-Morpholin-4-yl-phenyl)-7-pyridin-3-yl-furo[3,2-b]pyridine |
| "C49" | 7-(1-Methyl-1H-pyrazol-4-yl)-2-(4-morpholin-4-yl-phenyl)-furo[3,2-b]pyridine |
| "C50" | 2-(4-Morpholin-4-yl-phenyl)-7-phenyl-furo[3,2-b]pyridine |
| "C51" | 2-[4-(2-Imidazol-1-yl-ethoxy)-phenyl]-7-(1-methyl-1H-pyrazol-4-yl)-furo[3,2-b]pyridine |
| "C52" | 2-(4-Difluoromethoxy-phenyl)-7-(1-methyl-1H-pyrazol-4-yl)-furo[3,2-b]pyridine |
| "C53" | 4-[2-(3,4,5-Trimethoxy-phenyl)-furo[3,2-b]pyridin-7-yl]-1,3-dihydro-indol-2-one |
| "C54" | 2-(4-Methanesulfinyl-phenyl)-7-(1-methyl-1H-pyrazol-4-yl)-furo[3,2-b]pyridine |
| "C55" | 7-(1-Methyl-1H-pyrazol-4-yl)-2-(3,4,5-trifluoro-phenyl)-furo[3,2-b]pyridine |
| "C56" | 5-[2-(3,4,5-Trimethoxy-phenyl)-furo[3,2-b]pyridin-7-yl]-1,3-dihydro-benzoimidazol-2-one |
| "C57" | 3-Methoxy-5-(7-phenyl-furo[3,2-b]pyridin-2-yl)-phenylamine |
| "C58" | 7-(1-Benzyl-1H-pyrazol-4-yl)-2-(3,4,5-trimethoxy-phenyl)-furo[3,2-b]pyridine |
| "C59" | {4-[7-(1-Methyl-1H-pyrazol-4-yl)-furo[3,2-b]pyridin-2-yl]-phenyl}-methanol |
| "C60" | 7-(1H-Benzoimidazol-5-yl)-2-(3,4,5-trimethoxy-phenyl)-furo[3,2-b]pyridine |
| "C61" | 5-[7-(1-Methyl-1H-pyrazol-4-yl)-furo[3,2-b]pyridin-2-yl]-benzo[1,2,5]thiadiazole |
| "C62" | (2-{2-Methoxy-4-[7-(1-methyl-1H-pyrazol-4-yl)-furo[3,2-b]pyridin-2-yl]-phenoxy}-ethyl)-carbamic acid tert-butyl ester |
| "C63" | 2-{2-Methoxy-4-[7-(1-methyl-1H-pyrazol-4-yl)-furo[3,2-b]pyridin-2-yl]-phenoxy}-ethylamine |
| "C64" | 7-(2-Methyl-2H-pyrazol-3-yl)-2-(3,4,5-trimethoxy-phenyl)-furo[3,2-b]pyridine |
| "C65" | Dimethyl-(2-{4-[7-(1-methyl-1H-pyrazol-4-yl)-furo[3,2-b]pyridin-2-yl]-phenoxy}-ethyl)-amine |
| "C66" | 1-Methoxy-3-{4-[2-(3,4,5-trimethoxy-phenyl)-furo[3,2-b]pyridin-7-yl]-pyrazol-1-yl}-propan-2-ol |
| "C67" | 2-(1-Methyl-1H-indazol-5-yl)-7-(1-methyl-1H-pyrazol-4-yl)-furo[3,2-b]pyridine |
| "C68" | 7-(3,6-Dihydro-2H-pyran-4-yl)-2-(3,4,5-trimethoxy-phenyl)-furo[3,2-b]pyridine |
| "C69" | 5-[2-(3,4,5-Trimethoxy-phenyl)-furo[3,2-b]pyridin-7-yl]-1H-pyrimidine-2,4-dione |
| "C70" | 5-[2-(3,4,5-Trimethoxy-phenyl)-furo[3,2-b]pyridin-7-yl]-1H-benzotriazole |
| "C71" | 4-[2-(3,4,5-Trimethoxy-phenyl)-furo[3,2-b]pyridin-7-yl]-benzene-1,2-diamine |
| "C72" | 7-(1H-Pyrazol-4-yl)-2-(3,4,5-trimethoxy-phenyl)-furo[3,2-b]pyridine |
| "C73" | 7-(1H-Pyrazol-3-yl)-2-(3,4,5-trimethoxy-phenyl)-furo[3,2-b]pyridine |
| "C74" | 2-{4-[2-(3,4,5-Trimethoxy-phenyl)-furo[3,2-b]pyridin-7-yl]-pyrazol-1-yl}-ethanol |
| "C75" | 4-Methyl-5-[2-(3,4,5-trimethoxy-phenyl)-furo[3,2-b]pyridin-7-yl]-pyridin-2-ylamine |
| "C76" | 5-[2-(3,4,5-Trimethoxy-phenyl)-furo[3,2-b]pyridin-7-yl]-1H-benzoimidazol-2-ylamine |
| "C77" | N1-{5-[2-(3,4,5-Trimethoxy-phenyl)-furo[3,2-b]pyridin-7-yl]-1H-benzoimidazol-2-yl}-ethane-1,2-diamine |
| "C78" | 7-Piperidin-4-yl-2-(3,4,5-trimethoxy-phenyl)-furo[3,2-b]pyridine |
| "C79" | Dimethyl-{4-[2-(3,4,5-trimethoxy-phenyl)-furo[3,2-b]pyridin-7-yl]-thiazol-2-yl}-amine |
| "C80" | 2-{4-[2-(3,4,5-Trimethoxy-phenyl)-furo[3,2-b]pyridin-7-yl]-piperidin-1-yl}-ethanol |
| "C81" | 2,7-Bis-(1-methyl-1H-pyrazol-4-yl)-furo[3,2-b]pyridine |
| "C82" | 1-{3-[7-(1-Methyl-1H-pyrazol-4-yl)-furo[3,2-b]pyridin-2-yl]-phenyl}-ethanone |
| "C83" | 2-(1-Methyl-1H-benzoimidazol-5-yl)-7-(1-methyl-1H-pyrazol-4-yl)-furo[3,2-b]pyridine |
| "C84" | 7-(3,5-Dimethyl-1H-pyrazol-4-yl)-2-(3,4,5-trimethoxy-phenyl)-furo[3,2-b]pyridine |
| "C85" | 2-[2-(3,4,5-Trimethoxy-phenyl)-furo[3,2-b]pyridin-7-yl]-phenol |
| "C86" | 7-[2-(5-Methyl-isoxazol-3-yl)-1H-benzoimidazol-5-yl]-2-(3,4,5-trimethoxy-phenyl)-furo[3,2-b]pyridine |
| "C87" | 2-(3-Methanesulfonyl-phenyl)-7-(1-methyl-1H-pyrazol-4-yl)-furo[3,2-b]pyridine |
| "C88" | 7-(1-Methyl-1H-pyrazol-4-yl)-2-(3-pyrazol-1-yl-phenyl)-furo[3,2-b]pyridine |
| "C89" | 3-Hydroxy-5-[2-(3,4,5-trimethoxy-phenyl)-furo[3,2-b]pyridin-7-yl]-benzoic acid methyl ester |
| "C90" | 7-[2-(1H-Pyrazol-4-yl)-1H-benzoimidazol-5-yl]-2-(3,4,5-trimethoxy-phenyl)-furo[3,2-b]pyridine |
| "C91" | 1-{4-[7-(4-Acetyl-phenyl)-furo[3,2-b]pyridin-2-yl]-phenyl}-ethanone |
| "C92" | 2-{3-[7-(1-Methyl-1H-pyrazol-4-yl)-furo[3,2-b]pyridin-2-yl]-phenyl}-propan-2-ol |
| "C93" | 7-Biphenyl-2-yl-2-(3,4,5-trimethoxy-phenyl)-furo[3,2-b]pyridine |
| "C94" | 7-(2,6-Dimethyl-phenyl)-2-(3,4,5-trimethoxy-phenyl)-furo[3,2-b]pyridine |
| "C95" | 1-{4-[7-(1-Methyl-1H-pyrazol-4-yl)-furo[3,2-b]pyridin-2-yl]-phenyl}-ethanone |
| "C96" | 2,7-Bis-[2-(4-methyl-piperazin-1-yl)-pyridin-4-yl]-furo[3,2-b]pyridine |
| "C97" | 7-Furan-2-yl-2-(3,4,5-trimethoxy-phenyl)-furo[3,2-b]pyridine |
| "C98" | 2-(1-Methyl-1H-indazol-6-yl)-7-(1-methyl-1H-pyrazol-4-yl)-furo[3,2-b]pyridine |
| "C100" | 2-{4-[7-(1-Methyl-1H-pyrazol-4-yl)-furo[3,2-b]pyridin-2-yl]-phenyl}-propan-2-ol |
| "C101" | 7-(3-Piperazin-1-yl-phenyl)-2-(3,4,5-trimethoxy-phenyl)-furo[3,2-b]pyridine |
| "C102" | 7-(2-Morpholin-4-yl-phenyl)-2-(3,4,5-trimethoxy-phenyl)-furo[3,2-b]pyridine |
| "C103" | N-{2-[2-(3,4,5-Trimethoxy-phenyl)-furo[3,2-b]pyridin-7-yl]-phenyl}-acetamide |
| "C104" | 7-[3-(4-Methyl-piperazin-1-yl)-phenyl]-2-(3,4,5-trimethoxy-phenyl)-furo[3,2-b]pyridine |
| "C105" | 7-(1H-Pyrrol-2-yl)-2-(3,4,5-trimethoxy-phenyl)-furo[3,2-b]pyridine |
| "C106" | 3-Hydroxy-5-[2-(3,4,5-trimethoxy-phenyl)-furo[3,2-b]pyridin-7-yl]-benzamide |

| No. | Name and/or structure |
|---|---|
| "C107" | N-((1R,2S)-2-Amino-cyclohexyl)-3-[2-(3,4,5-trimethoxy-phenyl)-furo[3,2-b]pyridin-7-yl]-benzamide |
| "C108" | 7-(4-Methoxy-2-pyrazol-1-yl-phenyl)-2-(3,4,5-trimethoxy-phenyl)-furo[3,2-b]pyridine |
| "C109" | 7-(1-Methyl-1H-pyrazol-4-yl)-2-(1H-pyrazol-4-yl)-furo[3,2-b]pyridine |
| "C110" | 7-(3-Methanesulfonyl-phenyl)-2-(3,4,5-trimethoxy-phenyl)-furo[3,2-b]pyridine |
| "C111" | 7-[1-(2-Morpholin-4-yl-ethyl)-1H-pyrazol-4-yl]-2-(3,4,5-trimethoxy-phenyl)-furo[3,2-b]pyridine |
| "C112" | 7-Chloro-2-(1H-indazol-6-yl)-furo[3,2-b]pyridine |
| "C113" | 6-[2-(3,4,5-Trimethoxy-phenyl)-furo[3,2-b]pyridin-7-yl]-3,4-dihydro-2H-pyrano[2,3-b]pyridine |
| "C114" | 5-[7-(1-Methyl-1H-pyrazol-4-yl)-furo[3,2-b]pyridin-2-yl]-pyridin-2-ylamine |
| "C115" | 2-[2-(4-Methyl-piperazin-1-yl)-pyridin-4-yl]-7-(1-methyl-1H-pyrazol-4-yl)-furo[3,2-b]pyridine |
| "C116" | 6-[2-(3,4,5-Trimethoxy-phenyl)-furo[3,2-b]pyridin-7-yl]-1,2,3,4-tetrahydro-[1,8]naphthyridine |
| "C117" | 4-[7-(1-Methyl-1H-pyrazol-4-yl)-furo[3,2-b]pyridin-2-yl]-pyridin-2-ylamine |
| "C118" | 7-(1-Methyl-1H-pyrazol-4-yl)-2-[3-(pyridin-4-ylmethoxy)-phenyl]-furo[3,2-b]pyridine |
| "C119" | 7-(2-Fluoro-6-methoxy-phenyl)-2-(3,4,5-trimethoxy-phenyl)-furo[3,2-b]pyridine |
| "C120" | Dimethyl-{2-[2-(3,4,5-trimethoxy-phenyl)-furo[3,2-b]pyridin-7-yl]-phenyl}-amine |
| "C121" | N,N-Dimethyl-3-[2-(3,4,5-trimethoxy-phenyl)-furo[3,2-b]pyridin-7-yl]-benzenesulfonamide |
| "C122" | 2-{2-[2-(3,4,5-Trimethoxy-phenyl)-furo[3,2-b]pyridin-7-yl]-phenoxy}-ethylamine |
| "C123" | 2-(3H-Benzoimidazol-5-yl)-7-(1-methyl-1H-pyrazol-4-yl)-furo[3,2-b]pyridine |
| "C124" | 7-(4-Methanesulfinyl-phenyl)-2-(3,4,5-trimethoxy-phenyl)-furo[3,2-b]pyridine |
| "C125" | 7-(1-Piperidin-4-yl-1H-pyrazol-4-yl)-2-(3,4,5-trimethoxy-phenyl)-furo[3,2-b]pyridine |
| "C126" | 7-(5-Methyl-3-phenyl-isoxazol-4-yl)-2-(3,4,5-trimethoxy-phenyl)-furo[3,2-b]pyridine |
| "C127" | 7-(3-Methyl-1H-pyrazol-4-yl)-2-(3,4,5-trimethoxy-phenyl)-furo[3,2-b]pyridine |
| "C128" | 7-(3,5-Dimethyl-isoxazol-4-yl)-2-(3,4,5-trimethoxy-phenyl)-furo[3,2-b]pyridine |
| "C129" | 3-Methoxy-5-[7-(1-methyl-1H-pyrazol-4-yl)-furo[3,2-b]pyridin-2-yl]-phenylamine |
| "C130" | 7-Piperidin-1-yl-2-(3,4,5-trimethoxy-phenyl)-furo[3,2-b]pyridine |
| "C131" | N'-{3-Methoxy-5-[7-(1-methyl-1H-pyrazol-4-yl)-furo[3,2-b]pyridin-2-yl]-phenyl}-N,N-dimethyl-ethane-1,2-diamine |
| "C132" | 2-{1-[2-(3,4,5-Trimethoxy-phenyl)-furo[3,2-b]pyridin-7-yl]-piperidin-3-yl}-ethanol |
| "C133" | 2-(1H-Indazol-6-yl)-7-(1-methyl-1H-pyrazol-4-yl)-furo[3,2-b]pyridine |
| "C135" | 7-(2,6-Dimethoxy-phenyl)-2-(1-methyl-1H-indazol-5-yl)-furo[3,2-b]pyridine |
| "C136" | 4-Methoxy-3-[2-(3,4,5-trimethoxy-phenyl)-furo[3,2-b]pyridin-7-yl]-phenol |
| "C137" | 7-(1H-Indazol-5-yl)-2-(3,4,5-trimethoxy-phenyl)-furo[3,2-b]pyridine |
| "C138" | 4-Methoxy-3-[2-(3,4,5-trimethoxy-phenyl)-furo[3,2-b]pyridin-7-yl]-benzoic acid methyl ester |
| "C139" | C-{1-[2-(3,4,5-Trimethoxy-phenyl)-furo[3,2-b]pyridin-7-yl]-piperidin-3-yl}-methylamine |
| "C140" | 2-(2,5-Dimethoxy-phenyl)-7-(1-methyl-1H-pyrazol-4-yl)-furo[3,2-b]pyridine |
| "C141" | 2,7-Bis-(2,5-dimethoxy-phenyl)-furo[3,2-b]pyridine |
| "C142" | 4-Methoxy-3-[2-(3,4,5-trimethoxy-phenyl)-furo[3,2-b]pyridin-7-yl]-benzoic acid |
| "C143" | N-(2-Amino-ethyl)-4-methoxy-3-[2-(3,4,5-trimethoxy-phenyl)-furo[3,2-b]pyridin-7-yl]-benzamide |
| "C144" | 2-{4-Methoxy-3-[2-(3,4,5-trimethoxy-phenyl)-furo[3,2-b]pyridin-7-yl]-phenoxy}-ethylamine |
| "C145" | 4-Methoxy-3-[2-(3,4,5-trimethoxy-phenyl)-furo[3,2-b]pyridin-7-yl]-benzamide |
| "C146" | N-{4-[2-(3,4,5-Trimethoxy-phenyl)-furo[3,2-b]pyridin-7-yl]-pyridin-2-yl}-cyclohexane-1,2-diamine |
| "C147" | 7-[2-(2-Methoxy-ethoxy)-pyridin-4-yl]-2-(3,4,5-trimethoxy-phenyl)-furo[3,2-b]pyridine |
| "C148" | N-(2-Amino-cyclohexyl)-4-methoxy-3-[2-(3,4,5-trimethoxy-phenyl)-furo[3,2-b]pyridin-7-yl]-benzamide |
| "C149" | N-(2-Amino-ethyl)-3-hydroxy-5-[2-(3,4,5-trimethoxy-phenyl)-furo[3,2-b]pyridin-7-yl]-benzamide |
| "C150" | 3-Cyclopropylmethoxy-5-[2-(3,4,5-trimethoxy-phenyl)-furo[3,2-b]pyridin-7-yl]-benzoic acid methyl ester |
| "C151" | 3-Isopropoxy-5-[2-(3,4,5-trimethoxy-phenyl)-furo[3,2-b]pyridin-7-yl]-benzoic acid methyl ester |
| "C152" | N-((1R,2S)-2-Amino-cyclohexyl)-4-methoxy-3-[2-(3,4,5-trimethoxy-phenyl)-furo[3,2-b]pyridin-7-yl]-benzamide |
| "C153" | 7-(2-Fluoro-6-phenoxy-phenyl)-2-(3,4,5-trimethoxy-phenyl)-furo[3,2-b]pyridine |
| "C154" | 3-Methoxy-5-[2-(3,4,5-trimethoxy-phenyl)-furo[3,2-b]pyridin-7-yl]-benzoic acid |
| "C155" | 3-Isopropoxy-5-[2-(3,4,5-trimethoxy-phenyl)-furo[3,2-b]pyridin-7-yl]-benzoic acid |
| "C156" | 3-Cyclopropylmethoxy-5-[2-(3,4,5-trimethoxy-phenyl)-furo[3,2-b]pyridin-7-yl]-benzoic acid |
| "C157" | 7-(2-Ethoxy-6-fluoro-phenyl)-2-(3,4,5-trimethoxy-phenyl)-furo[3,2-b]pyridine |
| "C158" | 7-(2-Benzyloxy-6-fluoro-phenyl)-2-(3,4,5-trimethoxy-phenyl)-furo[3,2-b]pyridine |
| "C159" | 3-Trifluoromethoxy-5-[2-(3,4,5-trimethoxy-phenyl)-furo[3,2-b]pyridin-7-yl]-benzoic acid methyl ester |
| "C160" | 3-Trifluoromethyl-5-[2-(3,4,5-trimethoxy-phenyl)-furo[3,2-b]pyridin-7-yl]-benzoic acid methyl ester |
| "C161" | ((1S,2R)-2-{3-Methoxy-5-[2-(3,4,5-trimethoxy-phenyl)-furo[3,2-b]pyridin-7-yl]-benzoylamino}-cyclohexyl)-carbamic acid tert-butyl ester |
| "C162" | 7-(2-Isopropoxy-6-methoxy-phenyl)-2-(3,4,5-trimethoxy-phenyl)-furo[3,2-b]pyridine |
| "C163" | 3-Trifluoromethoxy-5-[2-(3,4,5-trimethoxy-phenyl)-furo[3,2-b]pyridin-7-yl]-benzoic acid |
| "C164" | 3-Trifluoromethyl-5-[2-(3,4,5-trimethoxy-phenyl)-furo[3,2-b]pyridin-7-yl]-benzoic acid |
| "C165" | 3-(2-Amino-ethoxy)-5-[2-(3,4,5-trimethoxy-phenyl)-furo[3,2-b]pyridin-7-yl]-benzamide |
| "C166" | 2-{4-[2-(3,4,5-Trimethoxy-phenyl)-furo[3,2-b]pyridin-7-yl]-pyrazol-1-yl}-ethylamine |
| "C167" | N-((1R,2S)-2-Amino-cyclohexyl)-3-[2-(2-methoxy-phenyl)-furo[3,2-b]pyridin-7-yl]-benzamide |
| "C168" | N-((1R,2S)-2-Amino-cyclohexyl)-3-[2-(2-methoxy-5-methyl-phenyl)-furo[3,2-b]pyridin-7-yl]-benzamide |
| "C169" | N-((1R,2S)-2-Amino-cyclohexyl)-3-[2-(3H-benzoimidazol-5-yl)-furo[3,2-b]pyridin-7-yl]-benzamide |
| "C170" | N-((1R,2S)-2-Amino-cyclohexyl)-3-methoxy-5-[2-(3,4,5-trimethoxy-phenyl)-furo[3,2-b]pyridin-7-yl]-benzamide |
| "C171" | N-((1R,2S)-2-Amino-cyclohexyl)-3-isopropoxy-5-[2-(3,4,5-trimethoxy-phenyl)-furo[3,2-b]pyridin-7-yl]-benzamide |
| "C172" | N-(2-Amino-ethyl)-3,5-dimethoxy-4-[2-(3,4,5-trimethoxy-phenyl)-furo[3,2-b]pyridin-7-yl]-benzamide |
| "C173" | N-((1R,2S)-2-Amino-cyclohexyl)-3-trifluoromethoxy-5-[2-(3,4,5-trimethoxy-phenyl)-furo[3,2-b]pyridin-7-yl]-benzamide |
| "C174" | N-((1R,2S)-2-Amino-cyclohexyl)-3-trifluoromethyl-5-[2-(3,4,5-trimethoxy-phenyl)-furo[3,2-b]pyridin-7-yl]-benzamide |
| "C175" | N-((1R,2S)-2-Amino-cyclohexyl)-3-[2-(1-methyl-1H-indazol-5-yl)-furo[3,2-b]pyridin-7-yl]-benzamide |
| "C176" | N-((1R,2S)-2-Amino-cyclohexyl)-3-[2-(1H-indazol-6-yl)-furo[3,2-b]pyridin-7-yl]-benzamide |
| "C177" | N-((1R,2S)-2-Amino-cyclohexyl)-3-[2-(1-methyl-1H-indazol-6-yl)-furo[3,2-b]pyridin-7-yl]-benzamide |
| "C178" | N-((1R,2S)-2-Amino-cyclohexyl)-3-[2-(2,5-dimethoxy-phenyl)-furo[3,2-b]pyridin-7-yl]-benzamide |
| "C179" | N-((1R,2S)-2-Amino-cyclohexyl)-3-cyclopropylmethoxy-5-[2-(3,4,5-trimethoxy-phenyl)-furo[3,2-b]pyridin-7-yl]-benzamide |
| "C180" | N-(2-Amino-ethyl)-4-[2-(3,4,5-trimethoxy-phenyl)-furo[3,2-b]pyridin-7-yl]-benzamide |
| "C181" | N-((1R,2S)-2-Amino-cyclohexyl)-3-[2-(2-fluoro-5-methoxy-phenyl)-furo[3,2-b]pyridin-7-yl]-benzamide |
| "C182" | 1-{4-[2-(3,4,5-Trimethoxy-phenyl)-furo[3,2-b]pyridin-7-yl]-pyridin-2-yl}-pyrrolidin-3-ylamine |
| "C183" | N-((1R,2S)-2-Amino-cyclohexyl)-3-methyl-5-[2-(3,4,5-trimethoxy-phenyl)-furo[3,2-b]pyridin-7-yl]-benzamide |
| "C184" | 4'-[2-(3,4,5-Trimethoxy-phenyl)-furo[3,2-b]pyridin-7-yl]-3,4,5,6-tetrahydro-2H-[1,2']bipyridinyl-3-ylamine |
| "C185" | Piperidin-3-ylmethyl-{4-[2-(3,4,5-trimethoxy-phenyl)-furo[3,2-b]pyridin-7-yl]-pyridin-2-yl}-amine |

-continued

| No. | Name and/or structure |
|---|---|
| "C186" | N-((1R,2S)-2-Amino-cyclohexyl)-3-[2-(3-sulfamoyl-phenyl)-furo[3,2-b]pyridin-7-yl]-benzamide |
| "C187" | 7-(3-Piperazin-2-yl-phenyl)-2-(3,4,5-trimethoxy-phenyl)-furo[3,2-b]pyridine |
| "C188" | 4-Methyl-3-[2-(3,4,5-trimethoxy-phenyl)-furo[3,2-b]pyridin-7-yl]-benzoic acid |
| "C189" | Piperidin-3-yl-{4-[2-(3,4,5-trimethoxy-phenyl)-furo[3,2-b]pyridin-7-yl]-pyridin-2-yl}-amine |
| "C190" | N-((1R,2S)-2-Amino-cyclohexyl)-4-methyl-3-[2-(3,4,5-trimethoxy-phenyl)-furo[3,2-b]pyridin-7-yl]-benzamide |
| "C191" | Pyrrolidin-3-yl-{4-[2-(3,4,5-trimethoxy-phenyl)-furo[3,2-b]pyridin-7-yl]-pyridin-2-yl}-amine |
| "C192" | 3-[2-(3,4,5-Trimethoxy-phenyl)-furo[3,2-b]pyridin-7-yl]-benzenesulfonamide |
| "D1" | 2-Chloro-N-{3-[7-(4-phenoxy-phenoxy)-furo[3,2-b]pyridin-2-yl]-phenyl}-acetamide |
| "D2" | N-{2-[7-(4-Phenoxy-phenoxy)-furo[3,2-b]pyridin-2-yl]-phenyl}-acrylamide |
| "D3" | 2-Chloro-N-{2-[7-(4-phenoxy-phenoxy)-furo[3,2-b]pyridin-2-yl]-phenyl}-acetamide |
| "D4" | N-{3-[7-(4-Phenoxy-phenoxy)-furo[3,2-b]pyridin-2-yl]-benzyl}-acrylamide |
| "D5" | 2-Chloro-N-{3-[7-(4-phenoxy-phenoxy)-furo[3,2-b]pyridin-2-yl]-benzyl}-acetamide |
| "D6" | N-[3-(7-Phenoxy-furo[3,2-b]pyridin-2-yl)-phenyl]-acrylamide |
| "D7" | 2-Chloro-N-[3-(7-phenoxy-furo[3,2-b]pyridin-2-yl)-phenyl]-acetamide |
| "D8" | N-[3-(7-Phenoxy-furo[3,2-b]pyridin-2-yl)-phenyl]-propionamide |
| "D9" | N-{3-[7-(3-Chloro-phenoxy)-furo[3,2-b]pyridin-2-yl]-phenyl}-acrylamide |
| "D10" | N-{3-[7-(Quinolin-6-yloxy)-furo[3,2-b]pyridin-2-yl]-phenyl}-acrylamide |
| "D11" | N-{3-[7-(4-Chloro-phenoxy)-furo[3,2-b]pyridin-2-yl]-phenyl}-acrylamide |
| "D12" | N-[3-(7-Phenyl-furo[3,2-b]pyridin-2-yl)-phenyl]-acrylamide |
| "D13" | 2-Chloro-N-[3-(7-phenyl-furo[3,2-b]pyridin-2-yl)-phenyl]-acetamide |
| "D14" | N-[3-(7-Phenyl-furo[3,2-b]pyridin-2-yl)-phenyl]-propionamide |
| "D15" | N-[3-(7-Phenyl-furo[3,2-b]pyridin-2-yl)-benzyl]-acrylamide |
| "D16" | 2-Chloro-N-[3-(7-phenyl-furo[3,2-b]pyridin-2-yl)-benzyl]-acetamide |
| "D17" | N-[3-(7-Phenyl-furo[3,2-b]pyridin-2-yl)-benzyl]-propionamide |
| "D18" | N-{3-[7-(3,4,5-Trimethoxy-phenyl)-furo[3,2-b]pyridin-2-yl]-phenyl}-acrylamide |
| "D19" | N-[3-(2-Phenyl-furo[3,2-b]pyridin-7-yloxy)-phenyl]-acrylamide |
| "D20" | 2-Chloro-N-[3-(2-phenyl-furo[3,2-b]pyridin-7-yloxy)-phenyl]-acetamide |
| "D21" | N-[3-(2-Phenyl-furo[3,2-b]pyridin-7-yloxy)-phenyl]-propionamide |
| "D22" | N-[4-(2-Phenyl-furo[3,2-b]pyridin-7-yloxy)-phenyl]-acrylamide |
| "D23" | 2-Chloro-N-[4-(2-phenyl-furo[3,2-b]pyridin-7-yloxy)-phenyl]-acetamide |
| "D24" | N-[4-(2-Phenyl-furo[3,2-b]pyridin-7-yloxy)-phenyl]-propionamide |
| "D25" | N-[4-(2-Phenyl-furo[3,2-b]pyridin-7-yloxy)-benzyl]-acrylamide |
| "D26" | N-[4-(2-Phenyl-furo[3,2-b]pyridin-7-yl)-phenyl]-acrylamide |
| "D27" | 2-Chloro-N-[3-(2-methyl-furo[3,2-b]pyridin-7-yloxy)-phenyl]-acetamide |
| "D28" | N-[3-(2-Methyl-furo[3,2-b]pyridin-7-yloxy)-phenyl]-propionamide |
| "D29" | N-[3-(2-Methyl-furo[3,2-b]pyridin-7-yl)-phenyl]-propionamide | and pharmaceutically acceptable solvates, salts, tautomers and stereoisomers thereof, including mixtures thereof in all ratios.

2. A pharmaceutical composition comprising at least one compound according to claim 1, and a pharmaceutically acceptable carrier, excipient or vehicle.

3. A method for inhibiting Syk comprising administering to a subject a compound according to claim 1.

4. A pharmaceutical composition comprising at least one compound according to claim 1, and at least one further medicament active ingredient.

5. A kit consisting of separate packs of
(a) an effective amount of a compound according to claim 1, and
(b) an effective amount of a further medicament active ingredient.

6. A compound according to claim 1, wherein said compound is selected from the following group:

| No. | Name and/or structure |
|---|---|
| "A5" | 7-Phenyl-2-(3,4,5-trimethoxy-phenyl)-furo[3,2-b]pyridine |
| "A6" | 7-Phenyl-2-(3,4,5-trimethoxy-phenyl)-furo[3,2-b]pyridine |
| "A7" | N-Methyl-3-[2-(3,4,5-trimethoxy-phenyl)-furo[3,2-b]pyridin-7-yl]-benzamide |
| "A8" | N-(2-Dimethylamino-ethyl)-3-[2-(3,4,5-trimethoxy-phenyl)-furo[3,2-b]pyridin-7-yl]-benzamide |
| "A9" | 3-[2-(3,4,5-Trimethoxy-phenyl)-furo[3,2-b]pyridin-7-yl]-benzonitrile |
| "A10" | 7-(3-Nitro-phenyl)-2-(3,4,5-trimethoxy-phenyl)-furo[3,2-b]pyridine |
| "A11" | 3-[2-(3,4,5-Trimethoxy-phenyl)-furo[3,2-b]pyridin-7-yl]-benzoic acid methyl ester |
| "A12" | 4-[2-(3,4,5-Trimethoxy-phenyl)-furo[3,2-b]pyridin-7-yl]-benzonitrile |
| "A13" | N-Methyl-4-[2-(3,4,5-trimethoxy-phenyl)-furo[3,2-b]pyridin-7-yl]-benzamide |
| "A14" | 7-(4-Nitro-phenyl)-2-(3,4,5-trimethoxy-phenyl)-furo[3,2-b]pyridine |
| "A15" | 4-[2-(3,4,5-Trimethoxy-phenyl)-furo[3,2-b]pyridin-7-yl]-benzoic acid methyl ester |
| "A16" | 7-(4-Methyl-naphthalen-1-yl)-2-(3,4,5-trimethoxy-phenyl)-furo[3,2-b]pyridine |
| "A17" | 7-(1H-Indazol-4-yl)-2-(3,4,5-trimethoxy-phenyl)-furo[3,2-b]pyridine |
| "A18" | 5-[2-(3,4,5-Trimethoxy-phenyl)-furo[3,2-b]pyridin-7-yl]-quinoline |
| "A19" | 3-(7-Phenyl-furo[3,2-b]pyridin-2-yl)-benzoic acid methyl ester |
| "A20" | 7-(1H-Indol-4-yl)-2-(3,4,5-trimethoxy-phenyl)-furo[3,2-b]pyridine |
| "A21" | 7-o-Tolyl-2-(3,4,5-trimethoxy-phenyl)-furo[3,2-b]pyridine |
| "A22" | 7-Naphthalene-1-yl-2-(3,4,5-trimethoxy-phenyl)-furo[3,2-b]pyridine |
| "A23" | 6-[2-(3,4,5-Trimethoxy-phenyl)-furo[3,2-b]pyridin-7-yl]-quinoline |
| "A24" | 4-[2-(3,4,5-Trimethoxy-phenyl)-furo[3,2-b]pyridin-7-yl]-quinoline |
| "A25" | 7-(1H-Indol-3-yl)-2-(3,4,5-trimethoxy-phenyl)-furo[3,2-b]pyridine |
| "A26" | 8-Methyl-5-[2-(3,4,5-trimethoxy-phenyl)-furo[3,2-b]pyridin-7-yl]-quinoline |
| "A27" | 7-(1H-Indol-6-yl)-2-(3,4,5-trimethoxy-phenyl)-furo[3,2-b]pyridine |
| "A28" | 7-(2,4-Dimethoxy-phenyl)-2-(3,4,5-trimethoxy-phenyl)-furo[3,2-b]pyridine |
| "A29" | 7-(2-Methoxy-pyridin-4-yl)-2-(3,4,5-trimethoxy-phenyl)-furo[3,2-b]pyridine |
| "A30" | 5-[2-(3,4,5-Trimethoxy-phenyl)-furo[3,2-b]pyridin-7-yl]-nicotinonitrile |
| "A31" | 7-(3-Benzyloxy-phenyl)-2-(3,4,5-trimethoxy-phenyl)-furo[3,2-b]pyridine |
| "A32" | 7-(2,4-Dimethyl-phenyl)-2-(3,4,5-trimethoxy-phenyl)-furo[3,2-b]pyridine |
| "A33" | {4-[2-(3,4,5-Trimethoxy-phenyl)-furo[3,2-b]pyridin-7-yl]-pyrazol-1-yl}-acetic acid ethyl ester |
| "A34" | 7-(1-Methyl-1H-pyrazol-4-yl)-2-(3,4,5-trimethoxy-phenyl)-furo[3,2-b]pyridine |
| "A35" | 3-(7-Phenyl-furo[3,2-b]pyridin-2-yl)-phenol |
| "A36" | 3-[2-(3,4,5-Trimethoxy-phenyl)-furo[3,2-b]pyridin-7-yl]-phenol |
| "A37" | (2-{3-[2-(3,4,5-Trimethoxy-phenyl)-furo[3,2-b]pyridin-7-yl]-phenoxy}-ethyl)-carbamic acid tert-butyl ester |
| "A38" | 2-{3-[2-(3,4,5-Trimethoxy-phenyl)-furo[3,2-b]pyridin-7-yl]-phenoxy}-ethylamine |
| "A39" | 3-Methyl-5-(7-phenyl-furo[3,2-b]pyridin-2-yl)-benzoic acid |
| "A40" | 2,3-dimethoxy-5-(7-phenylfuro[3,2-b]pyridin-2-yl)benzoic acid |
| "A41" | 3-[2-(3,4,5-Trimethoxy-phenyl)-furo[3,2-b]pyridin-7-yl]-benzoic acid |
| "A42" | 4-[2-(3,4,5-Trimethoxy-phenyl)-furo[3,2-b]pyridin-7-yl]-benzoic acid |
| "A43" | N-(2-Hydroxy-1,1-dimethyl-ethyl)-3-methyl-5-(7-phenyl-furo[3,2-b]pyridin-2-yl)-benzamide |
| "A44" | N-(2-hydroxy-1,1-dimethyl-ethyl)-2,3-dimethoxy-5-(7-phenylfuro[3,2-b]pyridin-2-yl)benzamide |
| "A45" | N-(2-Amino-cyclohexyl)-3-[2-(3,4,5-trimethoxy-phenyl)-furo[3,2-b]pyridin-7-yl]-benzamide |
| "A46" | (1-{3-[2-(3,4,5-Trimethoxy-phenyl)-furo[3,2-b]pyridin-7-yl]-benzoyl}-pyrrolidin-3-yl)-carbamic acid tert-butyl ester |
| "A47" | tert.-Butyl 3-[[3-[2-(3,4,5-trimethoxyphenyl)furo[3,2-b]pyridin-7-yl]benzoyl]amino]pyrrolidine-1-carboxylate |
| "A48" | N-(2-methoxyethyl)-3-[2-(3,4,5-trimethoxyphenyl)furo[3,2-b]pyridin-7-yl]benzamide |

-continued

| No. | Name and/or structure |
|---|---|
| "A49" | N-(3-dimethylaminopropyl)-3-[2-(3,4,5-trimethoxyphenyl)furo[3,2-b]pyridin-7-yl]benzamide |
| "A50" | Morpholino-[3-[2-(3,4,5-trimethoxyphenyl)furo[3,2-b]pyridin-7-yl]phenyl]methanone |
| "A51" | 3-[2-(3,4,5-Trimethoxy-phenyl)-furo[3,2-b]pyridin-7-yl]-benzylamine |
| "A52" | N-[[3-[2-(3,4,5-trimethoxyphenyl)furo[3,2-b]pyridin-7-yl]phenyl]methyl]acetamide |
| "A53" | 4-[2-(3,4,5-Trimethoxy-phenyl)-furo[3,2-b]pyridin-7-yl]-benzylamine |
| "A54" | N-{4-[2-(3,4,5-Trimethoxy-phenyl)-furo[3,2-b]pyridin-7-yl]-benzyl}-acetamide |
| "A55" | 3-[2-(3,4,5-Trimethoxy-phenyl)-furo[3,2-b]pyridin-7-yl]-phenylamine |
| "A56" | 4-[2-(3,4,5-Trimethoxy-phenyl)-furo[3,2-b]pyridin-7-yl]-phenylamine |
| "A57" | 2-[4-[2-(3,4,5-trimethoxyphenyl)furo[3,2-b]pyridin-7-yl]pyrazol-1-yl]acetic acid |
| "A58" | 2-[4-[2-(3,4,5-trimethoxyphenyl)furo[3,2-b]pyridin-7-yl]pyrazol-1-yl]acetamide |
| "A59" | 3-[[2-(3,4,5-trimethoxyphenyl)furo[3,2-b]pyridin-7-yl]amino]benzoic acid |
| "A63" | 7-Phenyl-2-(3-trifluoromethoxy-phenyl)-furo[3,2-b]pyridine |
| "A65" | N-(2-Hydroxy-1,1-dimethyl-ethyl)-3-[2-(3,4,5-trimethoxy-phenyl)-furo[3,2-b]pyridin-7-yl]-benzamide |
| "A66" | N-pyrrolidin-3-yl-3-[2-(3,4,5-trimethoxyphenyl)furo[3,2-b]pyridin-7-yl]benzamide |
| "A67" | (3-aminopyrrolidin-1-yl)-[3-[2-(3,4,5-trimethoxyphenyl)furo[3,2-b]pyridin-7-yl]phenyl]methanone |
| "A68" | 2-(4-Difluoromethoxy-phenyl)-7-pyridin-3-yl-furo[3,2-b]pyridine |
| "A69" | 2-(4-Difluoromethoxy-phenyl)-7-thiazol-5-yl-furo[3,2-b]pyridine |
| "A70" | 2-(4-Difluoromethoxy-phenyl)-7-pyrimidin-5-yl-furo[3,2-b]pyridine |
| "A71" | 5-[2-(4-Difluoromethoxy-phenyl)-furo[3,2-b]pyridin-7-yl]-pyridin-2-ylamine |
| "A72" | 5-[2-(4-Difluoromethoxy-phenyl)-furo[3,2-b]pyridin-7-yl]-pyridine-2-carbonitrile |
| "A73" | 5-[2-(4-Difluoromethoxy-phenyl)-furo[3,2-b]pyridin-7-yl]-nicotinonitrile |
| "A74" | {5-[2-(4-Difluoromethoxy-phenyl)-furo[3,2-b]pyridin-7-yl]-pyridin-2-yl}-dimethyl-amine |
| "A75" | 5-[2-(4-Difluoromethoxy-phenyl)-furo[3,2-b]pyridin-7-yl]-pyridin-2-ol |
| "A76" | 7-[2-(4-Difluoromethoxy-phenyl)-furo[3,2-b]pyridin-7-yl]-4-methyl-3,4-dihydro-2H-pyrido[3,2-b][1,4]oxazine |
| "A77" | 2-(4-Difluoromethoxy-phenyl)-7-(6-methoxy-pyridin-3-yl)-furo[3,2-b]pyridine |
| "A78" | 2-(4-Difluoromethoxy-phenyl)-7-(5-methanesulfonyl-pyridin-3-yl)-furo[3,2-b]pyridine |
| "A79" | 2-[4-(7-Pyridin-3-yl-furo[3,2-b]pyridin-2-yl)-phenoxy]-ethanol |
| "A80" | 2-[4-(7-Thiazol-5-yl-furo[3,2-b]pyridin-2-yl)-phenoxy]-ethanol |
| "A81" | 2-[4-(7-Pyrimidin-5-yl-furo[3,2-b]pyridin-2-yl)-phenoxy]-ethanol |
| "A82" | 2-{4-[7-(6-Amino-pyridin-3-yl)-furo[3,2-b]pyridin-2-yl]-phenoxy}-ethanol |
| "A83" | 5-{2[4-(2-Hydroxy-ethoxy)-phenyl]-furo[3,2-b]pyridin-7-yl}-pyridine-2-carbonitrile |
| "A84" | 5-{2[4-(2-Hydroxy-ethoxy)-phenyl]-furo[3,2-b]pyridin-7-yl}-nicotinonitrile |
| "A85" | 2-{4-[7-(6-Dimethylamino-pyridin-3-yl)-furo[3,2-b]pyridin-2-yl]-phenoxy}-ethanol |
| "A86" | 5-{2[4-(2-Hydroxy-ethoxy)-phenyl]-furo[3,2-b]pyridin-7-yl}-pyridin-2-ol |
| "A87" | 2-{4-[7-(4-Methyl-3,4-dihydro-2H-pyrido[3,2-b][1,4]oxazin-7-yl)-furo[3,2-b]pyridin-2-yl]-phenoxy}-ethanol |
| "A88" | 2-{4-[7-(6-Methoxy-pyridin-3-yl)-furo[3,2-b]pyridin-2-yl]-phenoxy}-ethanol |
| "A89" | 2-{4-[7-(5-Methanesulfonyl-pyridin-3-yl)-furo[3,2-b]pyridin-2-yl]-phenoxy}-ethanol |
| "A90" | 2-(4-Piperazin-1-yl-phenyl)-7-pyridin-3-yl-furo[3,2-b]pyridine |
| "A91" | 2-(4-Piperazin-1-yl-phenyl)-7-thiazol-5-yl-furo[3,2-b]pyridine |
| "A92" | 2-(4-Piperazin-1-yl-phenyl)-7-pyrimidin-5-yl-furo[3,2-b]pyridine |
| "A93" | 5-[2-(4-Piperazin-1-yl-phenyl)-furo[3,2-b]pyridin-7-yl]-pyridin-2-ylamine |
| "A94" | 5-[2-(4-Piperazin-1-yl-phenyl)-furo[3,2-b]pyridin-7-yl]-pyridine-2-carbonitrile |
| "A95" | 5-[2-(4-Piperazin-1-yl-phenyl)-furo[3,2-b]pyridin-7-yl]-nicotinonitrile |
| "A96" | Dimethyl-{5-[2-(4-piperazin-1-yl-phenyl)-furo[3,2-b]pyridin-7-yl]-pyridin-2-yl}-amine |
| "A97" | 5-[2-(4-Piperazin-1-yl-phenyl)-furo[3,2-b]pyridin-7-yl]-pyridin-2-ol |
| "A98" | 4-Methyl-7-[2-(4-piperazin-1-yl-phenyl)-furo[3,2-b]pyridin-7-yl]-3,4-dihydro-2H-pyrido[3,2-b][1,4]oxazine |
| "A99" | 7-(6-Methoxy-pyridin-3-yl)-2-(4-piperazin-1-yl-phenyl)-furo[3,2-b]pyridine |
| "A100" | 7-(5-Methanesulfonyl-pyridin-3-yl)-2-(4-piperazin-1-yl-phenyl)-furo[3,2-b]pyridine |
| "A101" | 7-Pyridin-3-yl-2-[4-(2H-tetrazol-5-yl)-phenyl]-furo[3,2-b]pyridine |
| "A102" | 2-[4-(2H-Tetrazol-5-yl)-phenyl]-7-thiazol-5-yl-furo[3,2-b]pyridine |
| "A103" | 7-Pyrimidin-5-yl-2-[4-(2H-tetrazol-5-yl)-phenyl]-furo[3,2-b]pyridine |
| "A104" | 5-{2[4-(2H-Tetrazol-5-yl)-phenyl]-furo[3,2-b]pyridin-7-yl}-pyridin-2-ylamine |
| "A105" | 5-{2[4-(2H-Tetrazol-5-yl)-phenyl]-furo[3,2-b]pyridin-7-yl}-pyridine-2-carbonitrile |
| "A106" | 5-{2[4-(2H-Tetrazol-5-yl)-phenyl]-furo[3,2-b]pyridin-7-yl}-nicotinonitrile |
| "A107" | Dimethyl-(5-{2[4-(2H-tetrazol-5-yl)-phenyl]-furo[3,2-b]pyridin-7-yl}-pyridin-2-yl)-amine |
| "A108" | 5-{2[4-(2H-Tetrazol-5-yl)-phenyl]-furo[3,2-b]pyridin-7-yl}-pyridin-2-ol |
| "A109" | 4-Methyl-7-{2[4-(2H-tetrazol-5-yl)-phenyl]-furo[3,2-b]pyridin-7-yl}-3,4-dihydro-2H-pyrido[3,2-b][1,4]oxazine |
| "A110" | 7-(6-Methoxy-pyridin-3-yl)-2-[4-(2H-tetrazol-5-yl)-phenyl]-furo[3,2-b]pyridine |
| "A111" | 7-(5-Methanesulfonyl-pyridin-3-yl)-2-[4-(2H-tetrazol-5-yl)-phenyl]-furo[3,2-b]pyridine |
| "A112" | 2-[4-(1H-Imidazol-4-yl)-phenyl]-7-pyridin-3-yl-furo[3,2-b]pyridine |
| "A113" | 2-[4-(1H-Imidazol-4-yl)-phenyl]-7-thiazol-5-yl-furo[3,2-b]pyridine |
| "A114" | 2-[4-(1H-Imidazol-4-yl)-phenyl]-7-pyrimidin-5-yl-furo[3,2-b]pyridine |
| "A115" | 5-{2[4-(1H-Imidazol-4-yl)-phenyl]-furo[3,2-b]pyridin-7-yl}-pyridin-2-ylamine |
| "A116" | 5-{2[4-(1H-Imidazol-4-yl)-phenyl]-furo[3,2-b]pyridin-7-yl}-pyridine-2-carbonitrile |
| "A117" | 5-{2[4-(1H-Imidazol-4-yl)-phenyl]-furo[3,2-b]pyridin-7-yl}-nicotinonitrile |
| "A118" | (5-{2[4-(1H-Imidazol-4-yl)-phenyl]-furo[3,2-b]pyridin-7-yl}-pyridin-2-yl)-dimethyl-amine |
| "A119" | 5-{2[4-(1H-Imidazol-4-yl)-phenyl]-furo[3,2-b]pyridin-7-yl}-pyridin-2-ol |
| "A120" | 7-{2[4-(1H-Imidazol-4-yl)-phenyl]-furo[3,2-b]pyridin-7-yl}-4-methyl-3,4-dihydro-2H-pyrido[3,2-b][1,4]oxazine |
| "A121" | 2-[4-(1H-Imidazol-4-yl)-phenyl]-7-(6-methoxy-pyridin-3-yl)-furo[3,2-b]pyridine |
| "A122" | 2-[4-(1H-Imidazol-4-yl)-phenyl]-7-(5-methanesulfonyl-pyridin-3-yl)-furo[3,2-b]pyridine |
| "A123" | 2-[4-(7-Pyridin-3-yl-furo[3,2-b]pyridin-2-yl)-phenyl]-ethanol |
| "A124" | 2-[4-(7-Thiazol-5-yl-furo[3,2-b]pyridin-2-yl)-phenyl]-ethanol |
| "A125" | 2-[4-(7-Pyrimidin-5-yl-furo[3,2-b]pyridin-2-yl)-phenyl]-ethanol |
| "A126" | 2-{4-[7-(6-Amino-pyridin-3-yl)-furo[3,2-b]pyridin-2-yl]-phenyl}-ethanol |
| "A127" | 5-{2[4-(2-Hydroxy-ethyl)-phenyl]-furo[3,2-b]pyridin-7-yl}-pyridine-2-carbonitrile |
| "A128" | 5-{2[4-(2-Hydroxy-ethyl)-phenyl]-furo[3,2-b]pyridin-7-yl}-nicotinonitrile |
| "A129" | 2-{4-[7-(6-Dimethylamino-pyridin-3-yl)-furo[3,2-b]pyridin-2-yl]-phenyl}-ethanol |
| "A130" | 5-{2[4-(2-Hydroxy-ethyl)-phenyl]-furo[3,2-b]pyridin-7-yl}-pyridin-2-ol |
| "A131" | 2-{4-[7-(4-Methyl-3,4-dihydro-2H-pyrido[3,2-b][1,4]oxazin-7-yl)-furo[3,2-b]pyridin-2-yl]-phenyl}-ethanol |
| "A132" | 2-{4-[7-(6-Methoxy-pyridin-3-yl)-furo[3,2-b]pyridin-2-yl]-phenyl}-ethanol |
| "A133" | 2-{4-[7-(5-Methanesulfonyl-pyridin-3-yl)-furo[3,2-b]pyridin-2-yl]-phenyl}-ethanol |
| "A134" | 7-Pyridin-3-yl-2-[4-(2-pyrrolidin-1-yl-ethoxy)-phenyl]-furo[3,2-b]pyridine |
| "A135" | 2-[4-(2-Pyrrolidin-1-yl-ethoxy)-phenyl]-7-thiazol-5-yl-furo[3,2-b]pyridine |
| "A136" | 7-Pyrimidin-5-yl-2-[4-(2-pyrrolidin-1-yl-ethoxy)-phenyl]-furo[3,2-b]pyridine |

| No. | Name and/or structure |
|---|---|
| "A137" | 5-{2[4-(2-Pyrrolidin-1-yl-ethoxy)-phenyl]-furo[3,2-b]pyridin-7-yl}-pyridin-2-ylamine |
| "A138" | 5-{2[4-(2-Pyrrolidin-1-yl-ethoxy)-phenyl]-furo[3,2-b]pyridin-7-yl}-pyridine-2-carbonitrile |
| "A139" | 5-{2[4-(2-Pyrrolidin-1-yl-ethoxy)-phenyl]-furo[3,2-b]pyridin-7-yl}-nicotinonitrile |
| "A140" | Dimethyl-(5-{2[4-(2-pyrrolidin-1-yl-ethoxy)-phenyl]-furo[3,2-b]pyridin-7-yl}-pyridin-2-yl)-amine |
| "A141" | 5-{2[4-(2-Pyrrolidin-1-yl-ethoxy)-phenyl]-furo[3,2-b]pyridin-7-yl}-pyridin-2-ol |
| "A142" | 4-Methyl-7-{2-[4-(2-pyrrolidin-1-yl-ethoxy)-phenyl]-furo[3,2-b]pyridin-7-yl}-3,4-dihydro-2H-pyrido[3,2-b][1,4]oxazine |
| "A143" | 7-(6-Methoxy-pyridin-3-yl)-2-[4-(2-pyrrolidin-1-yl-ethoxy)-phenyl]-furo[3,2-b]pyridine |
| "A144" | 7-(5-Methanesulfonyl-pyridin-3-yl)-2-[4-(2-pyrrolidin-1-yl-ethoxy)-phenyl]-furo[3,2-b]pyridine |
| "A145" | 2-[4-(1-Methyl-1H-pyrazol-4-yl)-phenyl]-7-pyridin-3-yl-furo[3,2-b]pyridine |
| "A146" | 2-[4-(1-Methyl-1H-pyrazol-4-yl)-phenyl]-7-thiazol-5-yl-furo[3,2-b]pyridine |
| "A147" | 2-[4-(1-Methyl-1H-pyrazol-4-yl)-phenyl]-7-pyrimidin-5-yl-furo[3,2-b]pyridine |
| "A148" | 5-{2[4-(1-Methyl-1H-pyrazol-4-yl)-phenyl]-furo[3,2-b]pyridin-7-yl}-pyridin-2-ylamine |
| "A149" | 5-{2[4-(1-Methyl-1H-pyrazol-4-yl)-phenyl]-furo[3,2-b]pyridin-7-yl}-pyridine-2-carbonitrile |
| "A150" | 5-{2[4-(1-Methyl-1H-pyrazol-4-yl)-phenyl]-furo[3,2-b]pyridin-7-yl}-nicotinonitrile |
| "A151" | Dimethyl-(5-{2[4-(1-methyl-1H-pyrazol-4-yl)-phenyl]-furo[3,2-b]pyridin-7-yl}-pyridin-2-yl)-amine |
| "A152" | 5-{2[4-(1-Methyl-1H-pyrazol-4-yl)-phenyl]-furo[3,2-b]pyridin-7-yl}-pyridin-2-ol |
| "A153" | 4-Methyl-7-{2-[4-(1-methyl-1H-pyrazol-4-yl)-phenyl]-furo[3,2-b]pyridin-7-yl}-3,4-dihydro-2H-pyrido[3,2-b][1,4]oxazine |
| "A154" | 7-(6-Methoxy-pyridin-3-yl)-2-[4-(1-methyl-1H-pyrazol-4-yl)-phenyl]-furo[3,2-b]pyridine |
| "A155" | 7-(5-Methanesulfonyl-pyridin-3-yl)-2-[4-(1-methyl-1H-pyrazol-4-yl)-phenyl]-furo[3,2-b]pyridine |
| "A156" | 2-{4-[2-(7-Pyridin-3-yl-furo[3,2-b]pyridin-2-yl)-phenyl]-pyrazol-1-yl}-ethanol |
| "A157" | 2-{4-[2-(7-Thiazol-5-yl-furo[3,2-b]pyridin-2-yl)-phenyl]-pyrazol-1-yl}-ethanol |
| "A158" | 2-{4-[2-(7-Pyrimidin-5-yl-furo[3,2-b]pyridin-2-yl)-phenyl]-pyrazol-1-yl}-ethanol |
| "A159" | 2-(4-{4-[7-(6-Amino-pyridin-3-yl)-furo[3,2-b]pyridin-2-yl]-phenyl}-pyrazol-1-yl)-ethanol |
| "A160" | 5-(2-{4-[1-(2-Hydroxy-ethyl)-1H-pyrazol-4-yl]-phenyl}-furo[3,2-b]pyridin-7-yl)-pyridine-2-carbonitrile |
| "A161" | 5-(2-{4-[1-(2-Hydroxy-ethyl)-1H-pyrazol-4-yl]-phenyl}-furo[3,2-b]pyridin-7-yl)-nicotinonitrile |
| "A162" | 2-(4-{4-[7-(6-Dimethylamino-pyridin-3-yl)-furo[3,2-b]pyridin-2-yl]-phenyl}-pyrazol-1-yl)-ethanol |
| "A163" | 5-(2-{4-[1-(2-Hydroxy-ethyl)-1H-pyrazol-4-yl]-phenyl}-furo[3,2-b]pyridin-7-yl)-pyridin-2-ol |
| "A164" | 2-(4-{4-[7-(4-Methyl-3,4-dihydro-2H-pyrido[3,2-b][1,4]oxazin-7-yl)-furo[3,2-b]pyridin-2-yl]-phenyl}-pyrazol-1-yl)-ethanol |
| "A165" | 2-(4{4-[7-(6-Methoxy-pyridin-3-yl)-furo[3,2-b]pyridin-2-yl]-phenyl}-pyrazol-1-yl)-ethanol |
| "A166" | 2-(4-{4-[7-(5-Methanesulfonyl-pyridin-3-yl)-furo[3,2-b]pyridin-2-yl]-phenyl}-pyrazol-1-yl)-ethanol |
| "B1" | 2,7-Bis-(3,5-difluoro-phenyl)-furo[3,2-b]pyridine |
| "B2" | 4-(2-Phenyl-furo[3,2-b]pyridin-7-yloxy)-phenylamine |
| "B3" | (2H-Indazol-6-yl)-(2-phenyl-furo[3,2-b]pyridin-7-yl)-amine |
| "B4" | [3-Chloro-4-(1-methyl-1H-imidazol-2-ylsulfanyl)-phenyl]-(2-phenyl-furo[3,2-b]pyridin-7-yl)-amine |
| "B5" | (2-Benzyl-2H-indazol-6-yl)-(2-phenyl-furo[3,2-b]pyridin-7-yl)-amine |
| "B6" | 2,7-Bis-(4-fluoro-phenyl)-furo[3,2-b]pyridine |
| "B7" | N-Methyl-N-(3-{[2-(3,4,5-trimethoxy-phenyl)-furo[3,2-b]pyridin-7-ylamino]-methyl}-pyridin-2-yl)-methanesulfonamide |
| "B8" | N-Methyl-2-[2-(3,4,5-trimethoxy-phenyl)-furo[3,2-b]pyridin-7-ylamino]-benzamide |
| "B9" | (3-Methanesulfonyl-benzyl)-[2-(3,4,5-trimethoxy-phenyl)-furo[3,2-b]pyridin-7-yl]-amine |
| "B10" | 2,2-Difluoro-6-[2-(3,4,5-trimethoxy-phenyl)-furo[3,2-b]pyridin-7-ylamino]-4H-benzo[1,4]oxazin-3-one |
| "B11" | 1-(2-Hydroxy-2-methyl-propyl)-5-methyl-3-oxo-2-phenyl-2,3-dihydro-1H-pyrazole-4-carboxylic acid [4-(2-phenyl-furo[3,2-b]pyridin-7-yloxy)-phenyl]-amide |
| "B12" | 1-(4-Fluoro-phenyl)-4-iodo-2-oxo-1,2-dihydro-pyridine-3-carboxylic acid [4-(2-phenyl-furo[3,2-b]pyridin-7-yloxy)-phenyl]-amide |
| "B13" | 1-(4-Fluoro-phenyl)-2-oxo-1,2-dihydro-pyridine-3-carboxylic acid [4-(2-phenyl-furo[3,2-b]pyridin-7-yloxy)-phenyl]-amide |
| "B14" | 4-Ethoxy-1-(4-fluoro-phenyl)-2-oxo-1,2-dihydro-pyridine-3-carboxylic acid [4-(2-phenyl-furo[3,2-b]pyridin-7-yloxy)-phenyl]-amide |
| "B15" | (1H-Indazol-6-yl)-[2-(3,4,5-trimethoxy-phenyl)-furo[3,2-b]pyridin-7-yl]-amine |
| "B16" | [3-Chloro-4-(1-methyl-1H-imidazol-2-ylsulfanyl)-phenyl]-[2-(3,4,5-trimethoxy-phenyl)-furo[3,2-b]pyridin-7-yl]-amine |
| "B17" | 2,2-Difluoro-6-(2-phenyl-furo[3,2-b]pyridin-7-ylamino)-4H-benzo[1,4]oxazin-3-one |
| "B18" | N-Methyl-2-(2-phenyl-furo[3,2-b]pyridin-7-ylamino)-benzamide |
| "B19" | (3-Methanesulfonyl-benzyl)-(2-phenyl-furo[3,2-b]pyridin-7-yl)-amine |
| "B20" | N-Methyl-N-{3-[(2-phenyl-furo[3,2-b]pyridin-7-ylamino)-methyl]-pyridin-2-yl}-methanesulfonamide |
| "B21" | (4-Methyl-1H-indol-5-yl)-(2-phenyl-furo[3,2-b]pyridin-7-yl)-amine |
| "B22" | (4-Methyl-1H-indol-5-yl)-[2-(3,4,5-trimethoxy-phenyl)-furo[3,2-b]pyridin-7-yl]-amine |
| "B23" | 3-Fluoro-4-(2-phenyl-furo[3,2-b]pyridin-7-yloxy)-phenylamine |
| "B24" | 2,7-Bis-(3,4,5-trimethoxy-phenyl)-furo[3,2-b]pyridine |
| "B25" | 1-(4-Fluoro-phenyl)-2-oxo-1,2-dihydro-pyridine-3-carboxylic acid [3-fluoro-4-(2-phenyl-furo[3,2-b]pyridin-7-yloxy)-phenyl]-amide |
| "B26" | 1-(4-Fluoro-phenyl)-4-iodo-2-oxo-1,2-dihydro-pyridine-3-carboxylic acid [3-fluoro-4-(2-phenyl-furo[3,2-b]pyridin-7-yloxy)-phenyl]-amide |
| "B27" | 4-Ethoxy-1-(4-fluoro-phenyl)-2-oxo-1,2-dihydro-pyridine-3-carboxylic acid [3-fluoro-4-(2-phenyl-furo[3,2-b]pyridin-7-yloxy)-phenyl]-amide |
| "B28" | 1-(4-Fluoro-phenyl)-4-methylamino-2-oxo-1,2-dihydro-pyridine-3-carboxylic acid [3-fluoro-4-(2-phenyl-furo[3,2-b]pyridin-7-yloxy)-phenyl]-amide |
| "B29" | 2,2-Dimethyl-6-[2-(3,4,5-trimethoxy-phenyl)-furo[3,2-b]pyridin-7-ylamino]-4H-pyrido[3,2-b][1,4]oxazin-3-one |
| "B30" | (1H-Indol-5-yl)-[2-(3,4,5-trimethoxy-phenyl)-furo[3,2-b]pyridin-7-yl]-amine |
| "B31" | 2,7-Di-p-tolyl-furo[3,2-b]pyridine |
| "B32" | 2,7-Bis-(4-methoxy-3,5-dimethyl-phenyl)-furo[3,2-b]pyridine |
| "B33" | 2,7-Bis-(4-methoxy-3-methyl-phenyl)-furo[3,2-b]pyridine |
| "B34" | 2,7-Di-m-tolyl-furo[3,2-b]pyridine |
| "B35" | 2,7-Bis-(4-methoxy-phenyl)-furo[3,2-b]pyridine |
| "B38" | 2,7-Bis-(3,5-dimethyl-phenyl)-furo[3,2-b]pyridine |
| "B39" | 2,7-Bis-(3,4-dimethoxy-phenyl)-furo[3,2-b]pyridine |
| "B40" | 2,7-Bis-(2,3,4-trimethoxy-phenyl)-furo[3,2-b]pyridine |
| "B42" | 2,7-Bis-(2,3-dimethoxy-phenyl)-furo[3,2-b]pyridine |
| "B43" | 2,7-Bis-(3-methoxy-phenyl)-furo[3,2-b]pyridine |
| "B44" | {4-[2-(4-Hydroxymethyl-phenyl)-furo[3,2-b]pyridin-7-yl]-phenyl}-methanol |
| "B45" | 2-(4-{2-[4-(1-Hydroxy-1-methyl-ethyl)-phenyl]-furo[3,2-b]pyridin-7-yl}-phenyl)-propan-2-ol |
| "B46" | (4-Methyl-1H-indol-5-yl)-(2-p-tolyl-furo[3,2-b]pyridin-7-yl)-amine |
| "B47" | [2-(4-Methoxy-phenyl)-furo[3,2-b]pyridin-7-yl]-(4-methyl-1H-indol-5-yl)-amine |
| "B49" | [2-(4-Methoxy-3,5-dimethyl-phenyl)-furo[3,2-b]pyridin-7-yl]-(4-methyl-1H-indol-5-yl)-amine |
| "B50" | [2-(4-Methoxy-3-methyl-phenyl)-furo[3,2-b]pyridin-7-yl]-(4-methyl-1H-indol-5-yl)-amine |
| "B51" | (4-Methyl-1H-indol-5-yl)-(2-m-tolyl-furo[3,2-b]pyridin-7-yl)-amine |
| "B52" | [2-(3,5-Dimethyl-phenyl)-furo[3,2-b]pyridin-7-yl]-(4-methyl-1H-indol-5-yl)-amine |
| "B53" | [2-(3,4-Dimethoxy-phenyl)-furo[3,2-b]pyridin-7-yl]-(4-methyl-1H-indol-5-yl)-amine |
| "B54" | (4-Methyl-1H-indol-5-yl)-[2-(4-morpholin-4-yl-phenyl)-furo[3,2-b]pyridin-7-yl]-amine |
| "B55" | 2-(4-{2-[4-(Cyano-dimethyl-methyl)-phenyl]-furo[3,2-b]pyridin-7-yl}-phenyl)-2-methyl-propionitrile |
| "B56" | (4-Methyl-1H-indol-5-yl)-[2-(2,3,4-trimethoxy-phenyl)-furo[3,2-b]pyridin-7-yl]-amine |

| No. | Name and/or structure |
|---|---|
| "B57" | [2-(3-Methoxy-phenyl)-furo[3,2-b]pyridin-7-yl]-(4-methyl-1H-indol-5-yl)-amine |
| "B58" | {2-[4-(3-Dimethylamino-propoxy)-phenyl]-furo[3,2-b]pyridin-7-yl}-(4-methyl-1H-indol-5-yl)-amine |
| "B59" | [2-(2,3-Dimethoxy-phenyl)-furo[3,2-b]pyridin-7-yl]-(4-methyl-1H-indol-5-yl)-amine |
| "B61" | {4-[7-(4-Methyl-1H-indol-5-ylamino)-furo[3,2-b]pyridin-2-yl]-phenyl}-methanol |
| "B62" | [2-(4-Isopropenyl-phenyl)-furo[3,2-b]pyridin-7-yl]-(4-methyl-1H-indol-5-yl)-amine |
| "B64" | N-(4-Fluoro-phenyl)-3-[2-(3,4,5-trimethoxy-phenyl)-furo[3,2-b]pyridin-7-yl]-benzamide |
| "B65" | N-{4-[2-(3,4,5-Trimethoxy-phenyl)-furo[3,2-b]pyridin-7-yl]-phenyl}-benzamide |
| "B66" | N-Phenyl-4-[2-(3,4,5-trimethoxy-phenyl)-furo[3,2-b]pyridin-7-yl]-benzamide |
| "B67" | (4-Methyl-piperazin-1-yl)-{4-[2-(3,4,5-trimethoxy-phenyl)-furo[3,2-b]pyridin-7-yl]-phenyl}-methanone |
| "B68" | (4-Methyl-piperazin-1-yl)-{3-[2-(3,4,5-trimethoxy-phenyl)-furo[3,2-b]pyridin-7-yl]-phenyl}-methanone |
| "B69" | 2-Fluoro-N-(2-hydroxy-ethyl)-4-[2-(3,4,5-trimethoxy-phenyl)-furo[3,2-b]pyridin-7-yl]-benzamide |
| "B70" | 1-{5-[2-(3,4,5-Trimethoxy-phenyl)-furo[3,2-b]pyridin-7-yl]-thiophen-2-yl}-ethanone |
| "B71" | 6-(2-(3,4,5-Trimethoxyphenyl)furo[3,2-b]pyridin-7-yl)indolin-2-one |
| "B72" | N-(3-(2-(3,4,5-Trimethoxyphenyl)furo[3,2-b]pyridin-7-yl)phenyl)acetamide |
| "B73" | 7-(4-Methoxy-3,5-dimethylphenyl)-2-(3,4,5-trimethoxyphenyl)furo[3,2-b]pyridine |
| "B74" | 7-(1H-Indol-5-yl)-2-(3,4,5-trimethoxyphenyl)furo[3,2-b]pyridine |
| "B75" | N-Cyclopentyl-4-(2-(3,4,5-trimethoxyphenyl)furo[3,2-b]pyridin-7-yl)benzamide |
| "B76" | 7-(Benzo[d][1,3]dioxol-5-yl)-2-(3,4,5-trimethoxyphenyl)furo[3,2-b]pyridin |
| "B77" | 7-(6-Methoxynaphthalen-2-yl)-2-(3,4,5-trimethoxyphenyl)furo[3,2-b]pyridine |
| "B78" | 7-(Benzo[b]thiophen-2-yl)-2-(3,4,5-trimethoxyphenyl)furo[3,2-b]pyridine |
| "B79" | 3-[7-(4-Phenoxyphenoxy)furo[3,2-b]pyridin-2-yl]aniline |
| "B80" | N-{3-[7-(4-Phenoxyphenoxy)furo[3,2-b]pyridin-2-yl]phenyl}propanamide |
| "B81" | N-{3-[2-(3,4-Dimethoxyphenyl)furo[3,2-b]pyridin-7-yl]-2-methylphenyl}-3-(trifluoromethyl)benzamide |
| "B82" | N-{3-[7-(4-Phenoxyphenoxy)furo[3,2-b]pyridin-2-yl]phenyl}acrylamide |
| "B83" | N-{3-[2-(3,4-Dimethoxyphenyl)furo[3,2-b]pyridin-7-yl]-2-methylphenyl}-4,5,6,7-tetrahydro-1-benzothiophene-2-carboxamide |
| "B84" | 4-tert.-Butyl-N-{3-[2-(3,4-dimethoxyphenyl)furo[3,2-b]pyridin-7-yl]-2-methylphenyl}benzamide |
| "B85" | N-{3-[7-(4-Phenoxyphenoxy)furo[3,2-b]pyridin-2-yl]phenyl}but-2-ynamide |
| "B86" | 4-tert.-Butyl-N-(2-methyl-3-{2-[4-(pyrrolidin-1-ylcarbonyl)phenyl]furo[3,2-b]pyridin-7-yl}phenyl)benzamide |
| "B87" | N-(2-Methyl-3-{2-[4-(pyrrolidin-1-ylcarbonyl)phenyl]furo[3,2-b]pyridin-7-yl}phenyl)-4,5,6,7-tetrahydro-1-benzothiophene-2-carboxamide |
| "B88" | (2E)-N-{3-[7-(4-phenoxyphenoxy)furo[3,2-b]pyridin-2-yl]phenyl}but-2-enamide |
| "B89" | (2E)-4-(Dimethylamino)-N-{3-[7-(4-phenoxyphenoxy)furo[3,2-b]pyridin-2-yl]phenyl}but-2-enamide |
| "B90" | 2-Methyl-N-{3-[7-(4-phenoxyphenoxy)furo[3,2-b]pyridin-2-yl]phenyl}acrylamide |
| "C1" | 3-(7-Phenyl-furo[3,2-b]pyridin-2-yl)-phenol |
| "C2" | 7-(2,6-Dimethoxy-phenyl)-2-(3,4,5-trimethoxy-phenyl)-furo[3,2-b]pyridine |
| "C3" | 7-Phenyl-2-(3-trifluoromethyl-phenyl)-furo[3,2-b]pyridine |
| "C5" | N-(2-Hydroxy-ethyl)-3-[2-(3,4,5-trimethoxy-phenyl)-furo[3,2-b]pyridin-7-yl]-benzamide |
| "C7" | 2-({3-[2-(3,4,5-Trimethoxy-phenyl)-furo[3,2-b]pyridin-7-yl]-benzoylamino}-methyl)-pyrrolidine-1-carboxylic acid tert-butyl ester |
| "C8" | N-Methyl-2-{3-[2-(3,4,5-trimethoxy-phenyl)-furo[3,2-b]pyridin-7-yl]-phenoxy}-acetamide |
| "C9" | 2-(3-tert.-Butyl-5-methyl-phenyl)-7-(1-methyl-1H-pyrazol-4-yl)-furo[3,2-b]pyridine |
| "C10" | N-(1H-Pyrazol-3-ylmethyl)-3-[2-(3,4,5-trimethoxy-phenyl)-furo[3,2-b]pyridin-7-yl]-benzamide |
| "C11" | N-Pyrrolidin-2-ylmethyl-3-[2-(3,4,5-trimethoxy-phenyl)-furo[3,2-b]pyridin-7-yl]-benzamide |
| "C12" | N-(5-Oxo-4,5-dihydro-1H-[1,2,4]triazol-3-ylmethyl)-3-[2-(3,4,5-trimethoxy-phenyl)-furo[3,2-b]pyridin-7-yl]-benzamide |
| "C13" | 7-Pyridin-3-yl-2-(3,4,5-trimethoxy-phenyl)-furo[3,2-b]pyridine |
| "C14" | 7-(2-Isopropyl-phenyl)-2-(3,4,5-trimethoxy-phenyl)-furo[3,2-b]pyridine |
| "C15" | 2-(3-Methoxy-phenyl)-7-phenyl-furo[3,2-b]pyridine |
| "C20" | 2-(3-Benzyloxy-phenyl)-7-(1-methyl-1H-pyrazol-4-yl)-furo[3,2-b]pyridine |
| "C23" | 7-(6-Fluoro-4-methyl-pyridin-3-yl)-2-(3,4,5-trimethoxy-phenyl)-furo[3,2-b]pyridine |
| "C26" | 2-Methoxy-4-[7-(1-methyl-1H-pyrazol-4-yl)-furo[3,2-b]pyridin-2-yl]-phenol |
| "C27" | {5-[2-(3,4,5-Trimethoxy-phenyl)-furo[3,2-b]pyridin-7-yl]-pyridin-2-yl}-methanol |
| "C28" | 7-[6-(Tetrahydro-pyran-4-yloxy)-pyridin-3-yl]-2-(3,4,5-trimethoxy-phenyl)-furo[3,2-b]pyridine |
| "C29" | 3-[7-(1-Methyl-1H-pyrazol-4-yl)-furo[3,2-b]pyridin-2-yl]-phenylamine |
| "C30" | (S)-Pyrrolidine-2-carboxylic acid [2-methoxy-5-(7-phenyl-furo[3,2-b]pyridin-2-yl)-phenyl]-amide |
| "C31" | (S)-Pyrrolidine-2-carboxylic acid [3-(7-phenyl-furo[3,2-b]pyridin-2-yl)-phenyl]-amide |
| "C32" | 7-(1-Methyl-1H-pyrazol-4-yl)-2-(4-trifluoromethoxy-phenyl)-furo[3,2-b]pyridine |
| "C33" | 2-(4-Methoxy-phenyl)-7-(1-methyl-1H-pyrazol-4-yl)-furo[3,2-b]pyridine |
| "C34" | 2-(4-Methanesulfonyl-phenyl)-7-(1-methyl-1H-pyrazol-4-yl)-furo[3,2-b]pyridine |
| "C35" | (S)-Pyrrolidine-2-carboxylic acid {3-[7-(1-methyl-1H-pyrazol-4-yl)-furo[3,2-b]pyridin-2-yl]-phenyl}-amide |
| "C36" | 7-(1-Methyl-1H-pyrazol-4-yl)-2-[4-(2-piperidin-1-yl-ethoxy)-phenyl]-furo[3,2-b]pyridine |
| "C37" | 1-{4-[7-(1-Methyl-1H-pyrazol-4-yl)-furo[3,2-b]pyridin-2-yl]-phenoxy}-3-morpholin-4-yl-propan-2-ol |
| "C38" | 1-{4-[7-(1-Methyl-1H-pyrazol-4-yl)-furo[3,2-b]pyridin-2-yl]-phenoxy}-3-piperidin-1-yl-propan-2-ol |
| "C40" | (2S,4R)-4-Hydroxy-pyrrolidine-2-carboxylic acid [2-methoxy-5-(7-phenyl-furo[3,2-b]pyridin-2-yl)-phenyl]-amide |
| "C41" | 7-(6-Methoxy-pyridin-3-yl)-2-(3,4,5-trimethoxy-phenyl)-furo[3,2-b]pyridine |
| "C44" | Dimethyl-(3-{4-[7-(1-methyl-1H-pyrazol-4-yl)-furo[3,2-b]pyridin-2-yl]-phenoxy}-propyl)-amine |
| "C45" | 2-(3-Isopropyl-phenyl)-7-(1-methyl-1H-pyrazol-4-yl)-furo[3,2-b]pyridine |
| "C46" | (2S,4R)-4-Hydroxy-pyrrolidine-2-carboxylic acid [3-methoxy-5-(7-phenyl-furo[3,2-b]pyridin-2-yl)-phenyl]-amide |
| "C47" | (S)-Pyrrolidine-2-carboxylic acid [3-methoxy-5-(7-phenyl-furo[3,2-b]pyridin-2-yl)-phenyl]-amide |
| "C48" | 2-(4-Morpholin-4-yl-phenyl)-7-pyridin-3-yl-furo[3,2-b]pyridine |
| "C49" | 7-(1-Methyl-1H-pyrazol-4-yl)-2-(4-morpholin-4-yl-phenyl)-furo[3,2-b]pyridine |
| "C50" | 2-(4-Morpholin-4-yl-phenyl)-7-phenyl-furo[3,2-b]pyridine |
| "C51" | 2-[4-(2-Imidazol-1-yl-ethoxy)-phenyl]-7-(1-methyl-1H-pyrazol-4-yl)-furo[3,2-b]pyridine |
| "C52" | 2-(4-Difluoromethoxy-phenyl)-7-(1-methyl-1H-pyrazol-4-yl)-furo[3,2-b]pyridine |
| "C53" | 4-[2-(3,4,5-Trimethoxy-phenyl)-furo[3,2-b]pyridin-7-yl]-1,3-dihydro-indol-2-one |
| "C54" | 2-(4-Methanesulfinyl-phenyl)-7-(1-methyl-1H-pyrazol-4-yl)-furo[3,2-b]pyridine |
| "C55" | 7-(1-Methyl-1H-pyrazol-4-yl)-2-(3,4,5-trifluoro-phenyl)-furo[3,2-b]pyridine |
| "C56" | 5-[2-(3,4,5-Trimethoxy-phenyl)-furo[3,2-b]pyridin-7-yl]-1,3-dihydro-benzoimidazol-2-one |
| "C57" | 3-Methoxy-5-(7-phenyl-furo[3,2-b]pyridin-2-yl)-phenylamine |
| "C58" | 7-(1-Benzyl-1H-pyrazol-4-yl)-2-(3,4,5-trimethoxy-phenyl)-furo[3,2-b]pyridine |
| "C59" | {4-[7-(1-Methyl-1H-pyrazol-4-yl)-furo[3,2-b]pyridin-2-yl]-phenyl}-methanol |
| "C60" | 7-(1H-Benzoimidazol-5-yl)-2-(3,4,5-trimethoxy-phenyl)-furo[3,2-b]pyridine |
| "C62" | (2-{2-Methoxy-4-[7-(1-methyl-1H-pyrazol-4-yl)-furo[3,2-b]pyridin-2-yl]-phenoxy}-ethyl)-carbamic acid tert-butyl ester |

| No. | Name and/or structure |
|---|---|
| "C63" | 2-{2-Methoxy-4-[7-(1-methyl-1H-pyrazol-4-yl)-furo[3,2-b]pyridin-2-yl]-phenoxy}-ethylamine |
| "C64" | 7-(2-Methyl-2H-pyrazol-3-yl)-2-(3,4,5-trimethoxy-phenyl)-furo[3,2-b]pyridine |
| "C65" | Dimethyl-(2-{4-[7-(1-methyl-1H-pyrazol-4-yl)-furo[3,2-b]pyridin-2-yl]-phenoxy}-ethyl)-amine |
| "C66" | 1-Methoxy-3-{4-[2-(3,4,5-trimethoxy-phenyl)-furo[3,2-b]pyridin-7-yl]-pyrazol-1-yl}-propan-2-ol |
| "C68" | 7-(3,6-Dihydro-2H-pyran-4-yl)-2-(3,4,5-trimethoxy-phenyl)-furo[3,2-b]pyridine |
| "C69" | 5-[2-(3,4,5-Trimethoxy-phenyl)-furo[3,2-b]pyridin-7-yl]-1H-pyrimidine-2,4-dione |
| "C70" | 5-[2-(3,4,5-Trimethoxy-phenyl)-furo[3,2-b]pyridin-7-yl]-1H-benzotriazole |
| "C71" | 4-[2-(3,4,5-Trimethoxy-phenyl)-furo[3,2-b]pyridin-7-yl]-benzene-1,2-diamine |
| "C72" | 7-(1H-Pyrazol-4-yl)-2-(3,4,5-trimethoxy-phenyl)-furo[3,2-b]pyridine |
| "C73" | 7-(1H-Pyrazol-3-yl)-2-(3,4,5-trimethoxy-phenyl)-furo[3,2-b]pyridine |
| "C74" | 2-{4-[2-(3,4,5-Trimethoxy-phenyl)-furo[3,2-b]pyridin-7-yl]-pyrazol-1-yl}-ethanol |
| "C75" | 4-Methyl-5-[2-(3,4,5-trimethoxy-phenyl)-furo[3,2-b]pyridin-7-yl]-pyridin-2-ylamine |
| "C76" | 5-[2-(3,4,5-Trimethoxy-phenyl)-furo[3,2-b]pyridin-7-yl]-1H-benzoimidazol-2-ylamine |
| "C77" | N1-{5-[2-(3,4,5-Trimethoxy-phenyl)-furo[3,2-b]pyridin-7-yl]-1H-benzoimidazol-2-yl}-ethane-1,2-diamine |
| "C78" | 7-Piperidin-4-yl-2-(3,4,5-trimethoxy-phenyl)-furo[3,2-b]pyridine |
| "C79" | Dimethyl-{4-[2-(3,4,5-trimethoxy-phenyl)-furo[3,2-b]pyridin-7-yl]-thiazol-2-yl}-amine |
| "C80" | 2-{4-[2-(3,4,5-Trimethoxy-phenyl)-furo[3,2-b]pyridin-7-yl]-piperidin-1-yl}-ethanol |
| "C82" | 1-{3-[7-(1-Methyl-1H-pyrazol-4-yl)-furo[3,2-b]pyridin-2-yl]-phenyl}-ethanone |
| "C84" | 7-(3,5-Dimethyl-1H-pyrazol-4-yl)-2-(3,4,5-trimethoxy-phenyl)-furo[3,2-b]pyridine |
| "C85" | 2-[2-(3,4,5-Trimethoxy-phenyl)-furo[3,2-b]pyridin-7-yl]-phenol |
| "C86" | 7-[2-(5-Methyl-isoxazol-3-yl)-1H-benzoimidazol-5-yl]-2-(3,4,5-trimethoxy-phenyl)-furo[3,2-b]pyridine |
| "C87" | 2-(3-Methanesulfonyl-phenyl)-7-(1-methyl-1H-pyrazol-4-yl)-furo[3,2-b]pyridine |
| "C88" | 7-(1-Methyl-1H-pyrazol-4-yl)-2-(3-pyrazol-1-yl-phenyl)-furo[3,2-b]pyridine |
| "C89" | 3-Hydroxy-5-[2-(3,4,5-trimethoxy-phenyl)-furo[3,2-b]pyridin-7-yl]-benzoic acid methyl ester |
| "C90" | 7-[2-(1H-Pyrazol-4-yl)-1H-benzoimidazol-5-yl]-2-43,4,5-trimethoxy-phenyl)-furo[3,2-b]pyridine |
| "C91" | 1-{4-[7-(4-Acetyl-phenyl)-furo[3,2-b]pyridin-2-yl]-phenyl}-ethanone |
| "C92" | 2-{3-[7-(1-Methyl-1H-pyrazol-4-yl)-furo[3,2-b]pyridin-2-yl]-phenyl}-propan-2-ol |
| "C93" | 7-Biphenyl-2-yl-2-(3,4,5-trimethoxy-phenyl)-furo[3,2-b]pyridine |
| "C94" | 7-(2,6-Dimethyl-phenyl)-2-(3,4,5-trimethoxy-phenyl)-furo[3,2-b]pyridine |
| "C95" | 1-{4-[7-(1-Methyl-1H-pyrazol-4-yl)-furo[3,2-b]pyridin-2-yl]-phenyl}-ethanone |
| "C97" | 7-Furan-2-yl-2-(3,4,5-trimethoxy-phenyl)-furo[3,2-b]pyridine |
| "C100" | 2-{4[7-(1-Methyl-1H-pyrazol-4-yl)-furo[3,2-b]pyridin-2-yl]-phenyl}-propan-2-ol |
| "C101" | 7-(3-Piperazin-1-yl-phenyl)-2-(3,4,5-trimethoxy-phenyl)-furo[3,2-b]pyridine |
| "C102" | 7-(2-Morpholin-4-yl-phenyl)-2-(3,4,5-trimethoxy-phenyl)-furo[3,2-b]pyridine |
| "C103" | N-{2-[2-(3,4,5-Trimethoxy-phenyl)-furo[3,2-b]pyridin-7-yl]-phenyl}-acetamide |
| "C104" | 7-[3-(4-Methyl-piperazin-1-yl)-phenyl]-2-(3,4,5-trimethoxy-phenyl)-furo[3,2-b]pyridine |
| "C105" | 7-(1H-Pyrrol-2-yl)-2-(3,4,5-trimethoxy-phenyl)-furo[3,2-b]pyridine |
| "C106" | 3-Hydroxy-5-[2-(3,4,5-trimethoxy-phenyl)-furo[3,2-b]pyridin-7-yl]-benzamide |
| "C107" | N-((1R,2S)-2-Amino-cyclohexyl)-3-[2-(3,4,5-trimethoxy-phenyl)-furo[3,2-b]pyridin-7-yl]-benzamide |
| "C108" | 7-(4-Methoxy-2-pyrazol-1-yl-phenyl)-2-(3,4,5-trimethoxy-phenyl)-furo[3,2-b]pyridine |
| "C110" | 7-(3-Methanesulfonyl-phenyl)-2-(3,4,5-trimethoxy-phenyl)-furo[3,2-b]pyridine |
| "C111" | 7-[1-(2-Morpholin-4-yl-ethyl)-1H-pyrazol-4-yl]-2-(3,4,5-trimethoxy-phenyl)-furo[3,2-b]pyridine |
| "C113" | 6-[2-(3,4,5-Trimethoxy-phenyl)-furo[3,2-b]pyridin-7-yl]-3,4-dihydro-2H-pyrano[2,3-b]pyridine |
| "C116" | 6-[2-(3,4,5-Trimethoxy-phenyl)-furo[3,2-b]pyridin-7-yl]-1,2,3,4-tetrahydro-[1,8]naphthyridine |
| "C118" | 7-(1-Methyl-1H-pyrazol-4-yl)-2-[3-(pyridin-4-ylmethoxy)-phenyl]-furo[3,2-b]pyridine |
| "C119" | 7-(2-Fluoro-6-methoxy-phenyl)-2-(3,4,5-trimethoxy-phenyl)-furo[3,2-b]pyridine |
| "C120" | Dimethyl-{2-[2-(3,4,5-trimethoxy-phenyl)-furo[3,2-b]pyridin-7-yl]-phenyl}-amine |
| "C121" | N,N-Dimethyl-3-[2-(3,4,5-trimethoxy-phenyl)-furo[3,2-b]pyridin-7-yl]-benzenesulfonamide |
| "C122" | 2-{2-[2-(3,4,5-Trimethoxy-phenyl)-furo[3,2-b]pyridin-7-yl]-phenoxy}-ethylamine |
| "C124" | 7-(4-Methanesulfinyl-phenyl)-2-(3,4,5-trimethoxy-phenyl)-furo[3,2-b]pyridine |
| "C125" | 7-(1-Piperidin-4-yl-1H-pyrazol-4-yl)-2-(3,4,5-trimethoxy-phenyl)-furo[3,2-b]pyridine |
| "C126" | 7-(5-Methyl-3-phenyl-isoxazol-4-yl)-2-(3,4,5-trimethoxy-phenyl)-furo[3,2-b]pyridine |
| "C127" | 7-(3-Methyl-1H-pyrazol-4-yl)-2-(3,4,5-trimethoxy-phenyl)-furo[3,2-b]pyridine |
| "C128" | 7-(3,5-Dimethyl-isoxazol-4-yl)-2-(3,4,5-trimethoxy-phenyl)-furo[3,2-b]pyridine |
| "C129" | 3-Methoxy-5-[7-(1-methyl-1H-pyrazol-4-yl)-furo[3,2-b]pyridin-2-yl]-phenylamine |
| "C130" | 7-Piperidin-1-yl-2-(3,4,5-trimethoxy-phenyl)-furo[3,2-b]pyridine |
| "C131" | N'-{3-Methoxy-5-[7-(1-methyl-1H-pyrazol-4-yl)-furo[3,2-b]pyridin-2-yl]-phenyl}-N,N-dimethyl-ethane-1,2-diamine |
| "C132" | 2-{1-[2-(3,4,5-Trimethoxy-phenyl)-furo[3,2-b]pyridin-7-yl]-piperidin-3-yl}-ethanol |
| "C136" | 4-Methoxy-3-[2-(3,4,5-trimethoxy-phenyl)-furo[3,2-b]pyridin-7-yl]-phenol |
| "C137" | 7-(1H-Indazol-5-yl)-2-(3,4,5-trimethoxy-phenyl)-furo[3,2-b]pyridine |
| "C138" | 4-Methoxy-3-[2-(3,4,5-trimethoxy-phenyl)-furo[3,2-b]pyridin-7-yl]-benzoic acid methyl ester |
| "C139" | C-{1-[2-(3,4,5-Trimethoxy-phenyl)-furo[3,2-b]pyridin-7-yl]-piperidin-3-yl}-methylamine |
| "C140" | 2-(2,5-Dimethoxy-phenyl)-7-(1-methyl-1H-pyrazol-4-yl)-furo[3,2-b]pyridine |
| "C141" | 2,7-Bis-(2,5-dimethoxy-phenyl)-furo[3,2-b]pyridine |
| "C142" | 4-Methoxy-3-[2-(3,4,5-trimethoxy-phenyl)-furo[3,2-b]pyridin-7-yl]-benzoic acid |
| "C143" | N-(2-Amino-ethyl)-4-methoxy-3-[2-(3,4,5-trimethoxy-phenyl)-furo[3,2-b]pyridin-7-yl]-benzamide |
| "C144" | 2-{4-Methoxy-3-[2-(3,4,5-trimethoxy-phenyl)-furo[3,2-b]pyridin-7-yl]-phenoxy}-ethylamine |
| "C145" | 4-Methoxy-3-[2-(3,4,5-trimethoxy-phenyl)-furo[3,2-b]pyridin-7-yl]-benzamide |
| "C146" | N-{4-[2-(3,4,5-Trimethoxy-phenyl)-furo[3,2-b]pyridin-7-yl]-pyridin-2-yl}-cyclohexane-1,2-diamine |
| "C147" | 7-[2-(2-Methoxy-ethoxy)-pyridin-4-yl]-2-(3,4,5-trimethoxy-phenyl)-furo[3,2-b]pyridine |
| "C148" | N-(2-Amino-cyclohexyl)-4-methoxy-3-[2-(3,4,5-trimethoxy-phenyl)-furo[3,2-b]pyridin-7-yl]-benzamide |
| "C149" | N-(2-Amino-ethyl)-3-hydroxy-5-[2-(3,4,5-trimethoxy-phenyl)-furo[3,2-b]pyridin-7-yl]-benzamide |
| "C150" | 3-Cyclopropylmethoxy-5-[2-(3,4,5-trimethoxy-phenyl)-furo[3,2-b]pyridin-7-yl]-benzoic acid methyl ester |
| "C151" | 3-Isopropoxy-5-[2-(3,4,5-trimethoxy-phenyl)-furo[3,2-b]pyridin-7-yl]-benzoic acid methyl ester |
| "C152" | N-((1R,2S)-2-Amino-cyclohexyl)-4-methoxy-3-[2-(3,4,5-trimethoxy-phenyl)-furo[3,2-b]pyridin-7-yl]-benzamide |
| "C153" | 7-(2-Fluoro-6-phenoxy-phenyl)-2-(3,4,5-trimethoxy-phenyl)-furo[3,2-b]pyridine |
| "C154" | 3-Methoxy-5-[2-(3,4,5-trimethoxy-phenyl)-furo[3,2-b]pyridin-7-yl]-benzoic acid |
| "C155" | 3-Isopropoxy-5-[2-(3,4,5-trimethoxy-phenyl)-furo[3,2-b]pyridin-7-yl]-benzoic acid |
| "C156" | 3-Cyclopropylmethoxy-5-[2-(3,4,5-trimethoxy-phenyl)-furo[3,2-b]pyridin-7-yl]-benzoic acid |

| No. | Name and/or structure |
|---|---|
| "C157" | 7-(2-Ethoxy-6-fluoro-phenyl)-2-(3,4,5-trimethoxy-phenyl)-furo[3,2-b]pyridine |
| "C158" | 7-(2-Benzyloxy-6-fluoro-phenyl)-2-(3,4,5-trimethoxy-phenyl)-furo[3,2-b]pyridine |
| "C159" | 3-Trifluoromethoxy-5-[2-(3,4,5-trimethoxy-phenyl)-furo[3,2-b]pyridin-7-yl]-benzoic acid methyl ester |
| "C160" | 3-Trifluoromethyl-5-[2-(3,4,5-trimethoxy-phenyl)-furo[3,2-b]pyridin-7-yl]-benzoic acid methyl ester |
| "C161" | ((1S,2R)-2-{3-Methoxy-5-[2-(3,4,5-trimethoxy-phenyl)-furo[3,2-b]pyridin-7-yl]-benzoylamino}-cyclohexyl)-carbamic acid tert-butyl ester |
| "C162" | 7-(2-Isopropoxy-6-methoxy-phenyl)-2-(3,4,5-trimethoxy-phenyl)-furo[3,2-b]pyridine |
| "C163" | 3-Trifluoromethoxy-5-[2-(3,4,5-trimethoxy-phenyl)-furo[3,2-b]pyridin-7-yl]-benzoic acid |
| "C164" | 3-Trifluoromethyl-5-[2-(3,4,5-trimethoxy-phenyl)-furo[3,2-b]pyridin-7-yl]-benzoic acid |
| "C165" | 3-(2-Amino-ethoxy)-5-[2-(3,4,5-trimethoxy-phenyl)-furo[3,2-b]pyridin-7-yl]-benzamide |
| "C166" | 2-{4-[2-(3,4,5-Trimethoxy-phenyl)-furo[3,2-b]pyridin-7-yl]-pyrazol-1-yl}-ethylamine |
| "C167" | N-((1R,2S)-2-Amino-cyclohexyl)-3-[2-(2-methoxy-phenyl)-furo[3,2-b]pyridin-7-yl]-benzamide |
| "C168" | N-((1R,2S)-2-Amino-cyclohexyl)-3-[2-(2-methoxy-5-methyl-phenyl)-furo[3,2-b]pyridin-7-yl]-benzamide |
| "C170" | N-((1R,2S)-2-Amino-cyclohexyl)-3-methoxy-5-[2-(3,4,5-trimethoxy-phenyl)-furo[3,2-b]pyridin-7-yl]-benzamide |
| "C171" | N-((1R,2S)-2-Amino-cyclohexyl)-3-isopropoxy-5-[2-(3,4,5-trimethoxy-phenyl)-furo[3,2-b]pyridin-7-yl]-benzamide |
| "C172" | N-(2-Amino-ethyl)-3,5-dimethoxy-4-[2-(3,4,5-trimethoxy-phenyl)-furo[3,2-b]pyridin-7-yl]-benzamide |
| "C173" | N-((1R,2S)-2-Amino-cyclohexyl)-3-trifluoromethoxy-5-[2-(3,4,5-trimethoxy-phenyl)-furo[3,2-b]pyridin-7-yl]-benzamide |
| "C174" | N-((1R,2S)-2-Amino-cyclohexyl)-3-trifluoromethyl-5-[2-(3,4,5-trimethoxy-phenyl)-furo[3,2-b]pyridin-7-yl]-benzamide |
| "C178" | N-((1R,2S)-2-Amino-cyclohexyl)-3-[2-(2,5-dimethoxy-phenyl)-furo[3,2-b]pyridin-7-yl]-benzamide |
| "C179" | N-((1R,2S)-2-Amino-cyclohexyl)-3-cyclopropylmethoxy-5-[2-(3,4,5-trimethoxy-phenyl)-furo[3,2-b]pyridin-7-yl]-benzamide |
| "C180" | N-(2-Amino-ethyl)-4-[2-(3,4,5-trimethoxy-phenyl)-furo[3,2-b]pyridin-7-yl]-benzamide |
| "C181" | N-((1R,2S)-2-Amino-cyclohexyl)-3-[2-(2-fluoro-5-methoxy-phenyl)-furo[3,2-b]pyridin-7-yl]-benzamide |
| "C182" | 1-{4-[2-(3,4,5-Trimethoxy-phenyl)-furo[3,2-b]pyridin-7-yl]-pyridin-2-yl}-pyrrolidin-3-ylamine |
| "C183" | N-((1R,2S)-2-Amino-cyclohexyl)-3-methyl-5-[2-(3,4,5-trimethoxy-phenyl)-furo[3,2-b]pyridin-7-yl]-benzamide |
| "C184" | 4'-[2-(3,4,5-Trimethoxy-phenyl)-furo[3,2-b]pyridin-7-yl]-3,4,5,6-tetrahydro-2H-[1,2']bipyridinyl-3-ylamine |
| "C185" | Piperidin-3-ylmethyl-{4-[2-(3,4,5-trimethoxy-phenyl)-furo[3,2-b]pyridin-7-yl]-pyridin-2-yl}-amine |
| "C186" | N-((1R,2S)-2-Amino-cyclohexyl)-3-[2-(3-sulfamoyl-phenyl)-furo[3,2-b]pyridin-7-yl]-benzamide |
| "C187" | 7-(3-Piperazin-2-yl-phenyl)-2-(3,4,5-trimethoxy-phenyl)-furo[3,2-b]pyridine |
| "C188" | 4-Methyl-3-[2-(3,4,5-trimethoxy-phenyl)-furo[3,2-b]pyridin-7-yl]-benzoic acid |
| "C189" | Piperidin-3-yl-{4-[2-(3,4,5-trimethoxy-phenyl)-furo[3,2-b]pyridin-7-yl]-pyridin-2-yl}-amine |
| "C190" | N-((1R,2S)-2-Amino-cyclohexyl)-4-methyl-3-[2-(3,4,5-trimethoxy-phenyl)-furo[3,2-b]pyridin-7-yl]-benzamide |
| "C191" | Pyrrolidin-3-yl-{4-[2-(3,4,5-trimethoxy-phenyl)-furo[3,2-b]pyridin-7-yl]-pyridin-2-yl}-amine |
| "C192" | 3-[2-(3,4,5-Trimethoxy-phenyl)-furo[3,2-b]pyridin-7-yl]-benzenesulfonamide |
| "D1" | 2-Chloro-N-{3-[7-(4-phenoxy-phenoxy)-furo[3,2-b]pyridin-2-yl]-phenyl}-acetamide |
| "D2" | N-{2-[7-(4-Phenoxy-phenoxy)-furo[3,2-b]pyridin-2-yl]-phenyl}-acrylamide |
| "D3" | 2-Chloro-N-{2-[7-(4-phenoxy-phenoxy)-furo[3,2-b]pyridin-2-yl]-phenyl}-acetamide |
| "D4" | N-{3-[7-(4-Phenoxy-phenoxy)-furo[3,2-b]pyridin-2-yl]-benzyl}-acrylamide |
| "D5" | 2-Chloro-N-{3-[7-(4-phenoxy-phenoxy)-furo[3,2-b]pyridin-2-yl]-benzyl}-acetamide |
| "D6" | N-[3-(7-Phenoxy-furo[3,2-b]pyridin-2-yl)-phenyl]-acrylamide |
| "D7" | 2-Chloro-N-[3-(7-phenoxy-furo[3,2-b]pyridin-2-yl)-phenyl]-acetamide |
| "D8" | N-[3-(7-Phenoxy-furo[3,2-b]pyridin-2-yl)-phenyl]-propionamide |
| "D9" | N-{3-[7-(3-Chloro-phenoxy)-furo[3,2-b]pyridin-2-yl]-phenyl}-acrylamide |
| "D10" | N-{3-[7-(Quinolin-6-yloxy)-furo[3,2-b]pyridin-2-yl]-phenyl}-acrylamide |
| "D11" | N-{3-[7-(4-Chloro-phenoxy)-furo[3,2-b]pyridin-2-yl]-phenyl}-acrylamide |
| "D12" | N-[3-(7-Phenyl-furo[3,2-b]pyridin-2-yl)-phenyl]-acrylamide |
| "D13" | 2-Chloro-N-[3-(7-phenyl-furo[3,2-b]pyridin-2-yl)-phenyl]-acetamide |
| "D14" | N-[3-(7-Phenyl-furo[3,2-b]pyridin-2-yl)-phenyl]-propionamide |
| "D15" | N-[3-(7-Phenyl-furo[3,2-b]pyridin-2-yl)-benzyl]-acrylamide |
| "D16" | 2-Chloro-N-[3-(7-phenyl-furo[3,2-b]pyridin-2-yl)-benzyl]-acetamide |
| "D17" | N-[3-(7-Phenyl-furo[3,2-b]pyridin-2-yl)-benzyl]-propionamide |
| "D18" | N-{3-[7-(3,4,5-Trimethoxy-phenyl)-furo[3,2-b]pyridin-2-yl]-phenyl}-acrylamide |
| "D19" | N-[3-(2-Phenyl-furo[3,2-b]pyridin-7-yloxy)-phenyl]-acrylamide |
| "D20" | 2-Chloro-N-[3-(2-phenyl-furo[3,2-b]pyridin-7-yloxy)-phenyl]-acetamide |
| "D21" | N-[3-(2-Phenyl-furo[3,2-b]pyridin-7-yloxy)-phenyl]-propionamide |
| "D22" | N-[4-(2-Phenyl-furo[3,2-b]pyridin-7-yloxy)-phenyl]-acrylamide |
| "D23" | 2-Chloro-N-[4-(2-phenyl-furo[3,2-b]pyridin-7-yloxy)-phenyl]-acetamide |
| "D24" | N-[4-(2-Phenyl-furo[3,2-b]pyridin-7-yloxy)-phenyl]-propionamide |
| "D25" | N-[4-(2-Phenyl-furo[3,2-b]pyridin-7-yl)-benzyl]-acrylamide |
| "D26" | N-[4-(2-Phenyl-furo[3,2-b]pyridin-7-yl)-phenyl]-acrylamide | and pharmaceutically acceptable solvates, salts, tautomers and stereoisomers thereof, including mixtures thereof in all ratios.

7. A compound according to claim 6, wherein said compound is selected from the following group:

| No. | Name and/or structure |
|---|---|
| "A5" | 7-Phenyl-2-(3,4,5-trimethoxy-phenyl)-furo[3,2-b]pyridine |
| "A6" | 7-Phenyl-2-(3,4,5-trimethoxy-phenyl)-furo[3,2-b]pyridine |
| "A7" | N-Methyl-3-[2-(3,4,5-trimethoxy-phenyl)-furo[3,2-b]pyridin-7-yl]-benzamide |
| "A8" | N-(2-Dimethylamino-ethyl)-3-[2-(3,4,5-trimethoxy-phenyl)-furo[3,2-b]pyridin-7-yl]-benzamide |
| "A9" | 3-[2-(3,4,5-Trimethoxy-phenyl)-furo[3,2-b]pyridin-7-yl]-benzonitrile |
| "A10" | 7-(3-Nitro-phenyl)-2-(3,4,5-trimethoxy-phenyl)-furo[3,2-b]pyridine |
| "A11" | 3-[2-(3,4,5-Trimethoxy-phenyl)-furo[3,2-b]pyridin-7-yl]-benzoic acid methyl ester |
| "A12" | 4-[2-(3,4,5-Trimethoxy-phenyl)-furo[3,2-b]pyridin-7-yl]-benzonitrile |
| "A13" | N-Methyl-4-[2-(3,4,5-trimethoxy-phenyl)-furo[3,2-b]pyridin-7-yl]-benzamide |
| "A14" | 7-(4-Nitro-phenyl)-2-(3,4,5-trimethoxy-phenyl)-furo[3,2-b]pyridine |
| "A15" | 4-[2-(3,4,5-Trimethoxy-phenyl)-furo[3,2-b]pyridin-7-yl]-benzoic acid methyl ester |
| "A16" | 7-(4-Methyl-naphthalen-1-yl)-2-(3,4,5-trimethoxy-phenyl)-furo[3,2-b]pyridine |
| "A17" | 7-(1H-Indazol-4-yl)-2-(3,4,5-trimethoxy-phenyl)-furo[3,2-b]pyridine |
| "A18" | 5-[2-(3,4,5-Trimethoxy-phenyl)-furo[3,2-b]pyridin-7-yl]-quinoline |
| "A20" | 7-(1H-Indol-4-yl)-2-(3,4,5-trimethoxy-phenyl)-furo[3,2-b]pyridine |
| "A21" | 7-o-Tolyl-2-(3,4,5-trimethoxy-phenyl)-furo[3,2-b]pyridine |
| "A22" | 7-Naphthalene-1-yl-2-(3,4,5-trimethoxy-phenyl)-furo[3,2-b]pyridine |
| "A23" | 6-[2-(3,4,5-Trimethoxy-phenyl)-furo[3,2-b]pyridin-7-yl]-quinoline |
| "A24" | 4-[2-(3,4,5-Trimethoxy-phenyl)-furo[3,2-b]pyridin-7-yl]-quinoline |
| "A25" | 7-(1H-Indol-3-yl)-2-(3,4,5-trimethoxy-phenyl)-furo[3,2-b]pyridine |
| "A26" | 8-Methyl-5-[2-(3,4,5-trimethoxy-phenyl)-furo[3,2-b]pyridin-7-yl]-quinoline |

| No. | Name and/or structure |
|---|---|
| "A27" | 7-(1H-Indol-6-yl)-2-(3,4,5-trimethoxy-phenyl)-furo[3,2-b]pyridine |
| "A28" | 7-(2,4-Dimethoxy-phenyl)-2-(3,4,5-trimethoxy-phenyl)-furo[3,2-b]pyridine |
| "A29" | 7-(2-Methoxy-pyridin-4-yl)-2-(3,4,5-trimethoxy-phenyl)-furo[3,2-b]pyridine |
| "A30" | 5-[2-(3,4,5-Trimethoxy-phenyl)-furo[3,2-b]pyridin-7-yl]-nicotinonitrile |
| "A31" | 7-(3-Benzyloxy-phenyl)-2-(3,4,5-trimethoxy-phenyl)-furo[3,2-b]pyridine |
| "A32" | 7-(2,4-Dimethyl-phenyl)-2-(3,4,5-trimethoxy-phenyl)-furo[3,2-b]pyridine |
| "A33" | {4-[2-(3,4,5-Trimethoxy-phenyl)-furo[3,2-b]pyridin-7-yl]-pyrazol-1-yl}-acetic acid ethyl ester |
| "A34" | 7-(1-Methyl-1H-pyrazol-4-yl)-2-(3,4,5-trimethoxy-phenyl)-furo[3,2-b]pyridine |
| "A36" | 3-[2-(3,4,5-Trimethoxy-phenyl)-furo[3,2-b]pyridin-7-yl]-phenol |
| "A37" | (2-{3-[2-(3,4,5-Trimethoxy-phenyl)-furo[3,2-b]pyridin-7-yl]-phenoxy}-ethyl)-carbamic acid tert.-butyl ester |
| "A38" | 2-{3-[2-(3,4,5-Trimethoxy-phenyl)-furo[3,2-b]pyridin-7-yl]-phenoxy}-ethylamine |
| "A41" | 3-[2-(3,4,5-Trimethoxy-phenyl)-furo[3,2-b]pyridin-7-yl]benzoic acid |
| "A42" | 4-[2-(3,4,5-Trimethoxy-phenyl)-furo[3,2-b]pyridin-7-yl-benzoic acid |
| "A45" | N-(2-Amino-cyclohexyl)-3-[2-(3,4,5-trimethoxy-phenyl)-furo[3,2-b]pyridin-7-yl]-benzamide |
| "A46" | (1-{3-[2-(3,4,5-Trimethoxy-phenyl)-furo[3,2-b]pyridin-7-yl]-benzoyl}-pyrrolidin-3-yl)-carbamic acid tert-butyl ester |
| "A47" | tert.-Butyl 3-[[3-[2-(3,4,5-trimethoxyphenyl)furo[3,2-b]pyridin-7-yl]benzoyl]amino]pyrrolidine-1-carboxylate |
| "A48" | N-(2-methoxyethyl)-3-[2-(3,4,5-trimethoxyphenyl)furo[3,2-b]pyridin-7-yl]benzamide |
| "A49" | N-(3-dimethylaminopropyl)-3-[2-(3,4,5-trimethoxyphenyl)furo[3,2-b]pyridin-7-yl]benzamide |
| "A50" | Morpholino-[3-[2-(3,4,5-trimethoxyphenyl)furo[3,2-b]pyridin-7-yl]phenyl]methanone |
| "A51" | 3-[2-(3,4,5-Trimethoxy-phenyl)-furo[3,2-b]pyridin-7-yl]-benzylamine |
| "A52" | N-[[3-[2-(3,4,5-trimethoxyphenyl)furo[3,2-b]pyridin-7-yl phenyl]methyl]acetamide |
| "A53" | 4-[2-(3,4,5-Trimethoxy-phenyl)-furo[3,2-b]pyridin-7-yl]-benzylamine |
| "A54" | N-{4-[2-(3,4,5-Trimethoxy-phenyl)-furo[3,2-b]pyridin-7-yl]-benzyl}-acetamide |
| "A55" | 3-[2-(3,4,5-Trimethoxy-phenyl)-furo[3,2-b]pyridin-7-yl]-phenylamine |
| "A56" | 4-[2(3,4,5-Trimethoxy-phenyl)-furo[3,2-b]pyridin-7-yl]-phenylamine |
| "A57" | 2-[4-[2-(3,4,5-trimethoxyphenyl)furo[3,2-b]pyridin-7-yl]pyrazol-1-yl]acetic acid |
| "A58" | 2-[4-[2-(3,4,5-trimethoxyphenyl)furo[3,2-b]pyridin-7-yl]pyrazol-1-yl]acetamide |
| "A59" | 3-[[2-(3,4,5-trimethoxyphenyl)furo[3,2-b]pyridin-7-yl]amino]benzoic acid |
| "A65" | N-(2-Hydroxy-1,1-dimethyl-ethyl)-3-[2-(3,4,5-trimethoxy-phenyl)-furo[3,2-b]pyridin-7-yl]-benzamide |
| "A66" | N-pyrrolidin-3-yl-3-[2-(3,4,5-trimethoxyphenyl)furo[3,2-b]pyridin-7-yl]benzamide |
| "A67" | (3-aminopyrrolidin-1-yl)-[3-[2-(3,4,5-trimethoxyphenyl)furo[3,2-b]pyridin-7-yl]phenyl]methanone |
| "B7" | N-Methyl-N-(3-{[2-(3,4,5-trimethoxy-phenyl)-furo[3,2-b]pyridin-7-ylamino]-methyl}-pyridin-2-yl)-methanesulfonamide |
| "B8" | N-Methyl-2-[2-(3,4,5-trimethoxy-phenyl)-furo[3,2-b]pyridin-7-ylamino]-benzamide |
| "B9" | (3-Methanesulfonyl-benzyl)-[2-(3,4,5-trimethoxy-phenyl)-furo[3,2-b]pyridin-7-yl]-amine |
| "B15" | (1H-Indazol-6-yl)-[2-(3,4,5-trimethoxy-phenyl)-furo[3,2-b]pyridin-7-yl]-amine |
| "B16" | [3-Chloro-4-(1-methyl-1H-imidazol-2-ylsulfanyl)-phenyl]-[2-(3,4,5-trimethoxy-phenyl)-furo[3,2-b]pyridin-7-yl]-amine |
| "B22" | (4-Methyl-1H-indol-5-yl)-[2-(3,4,5-trimethoxy-phenyl)-furo[3,2-b]pyridin-7-yl]-amine |
| "B24" | 2,7-Bis-(3,4,5-trimethoxy-phenyl)-furo[3,2-b]pyridine |
| "B29" | 2,2-Dimethyl-6-[2-(3,4,5-trimethoxy-phenyl)-furo[3,2-b]pyridin-7-ylamino]-4H-pyrido[3,2-b] |
| "B30" | (1H-Indol-5-yl)-[2-(3,4,5-trimethoxy-phenyl)-furo[3,2-b]pyridin-7-yl]-amine |
| "B56" | (4-Methyl-1H-indol-5-yl)-[2-(2,3,4-trimethoxy-phenyl)-furo[3,2-b]pyridin-7-yl]-amine |
| "B64" | N-(4-Fluoro-phenyl)-3-[2-(3,4,5-trimethoxy-phenyl)-furo[3,2-b]pyridin-7-yl]-benzamide |
| "B65" | N-{4-[2-(3,4,5-Trimethoxy-phenyl)-[3,2-b]pyridin-7-yl]-phenyl}-benzamide |
| "B66" | N-Phenyl-4-[2-(3,4,5-trimethoxy-phenyl)-furo[3,2-b]pyridin-7-yl]-benzamide |
| "B67" | (4-Methyl-piperazin-1-yl)-{4-[2-(3,4,5-trimethoxy-phenyl)-furo[3,2-b]pyridin-7-yl]-phenyl}-methanone |
| "B68" | (4-Methyl-piperazin-1-yl)-{3-[2-(3,4,5-trimethoxy-phenyl)-furo[3,2-b]pyridin-7-yl]-phenyl}-methanone |
| "B69" | 2-Fluoro-N-(2-hydroxy-ethyl)-4-[2-(3,4,5-trimethoxy-phenyl)-furo[3,2-b]pyridin-7-yl]-benzamide |
| "B70" | 1-{5-[2-(3,4,5-Trimethoxy-phenyl)-furo[3,2-b]pyridin-7-yl]-thiophen-2-yl}-ethanone |
| "B71" | 6-(2-(3,4,5-Trimethoxyphenyl)furo[3,2-b]pyridin-7-yl)indolin-2-one |
| "B72" | N-(3-(2-(3,4,5-Trimethoxyphenyl)furo[3,2-b]pyridin-7-yl)phenyl)acetamide |
| "B73" | 7-(4-Methoxy-3,5-dimethylphenyl)-2-(3,4,5-trimethoxyphenyl)furo[3,2-b]pyridine |
| "B74" | 7-(1H-Indol-5-yl)-2-(3,4,5-trimethoxyphenyl)furo[3,2-b]pyridine |
| "B75" | N-Cyclopentyl-4-(2-(3,4,5-trimethoxyphenyl)furo[3,2-b]pyridin-7-yl)benzamide |
| "B76" | 7-(Benzo[d][1,3]dioxol-5-yl)-2-(3,4,5-trimethoxyphenyl)furo[3,2-b]pyridin |
| "B77" | 7-(6-Methoxynaphthalen-2-yl)-2-(3,4,5-trimethoxyphenyl)furo[3,2-b]pyridine |
| "B78" | 7-(Benzo[b]thiophen-2-yl)-2-(3,2,5-trimethoxyphenyl)furo[3,2-b]pyridine |
| "C2" | 7-(2,6-Dimethoxy-phenyl)-2-(3,4,5-trimethoxy-phenyl)-furo[3,2-b]pyridine |
| "C7" | 2-({3-[2-(3,4,5-Trimethoxy-phenyl)-furo[3,2-b]pyridin-7-yl]-benzoylamino}-methyl)-pyrrolidine-1-carboxylic acid tert-butyl ester |
| "C8" | N-Methyl-2-{3-[2-(3,4,5-trimethoxy-phenyl)-furo[3,2-b]pyridin-7-yl]-phenoxy}-acetamide |
| "C10" | N-(1H-Pyrazol-3-ylmethyl)-3-[2-(3,4,5-trimethoxy-phenyl)-furo[3,2-b]pyridin-7-yl]-benzamide |
| "C11" | N-Pyrrolidin-2-ylmethyl-3-[2-(3,4,5-trimethoxy-phenyl)-furo[3,2-b]pyridin-7-yl]-benzamide |
| "C12" | N-(5-Oxo-4,5-dihydro-1H-[1,2,4]triazol-3-ylmethyl)-3-[2-(3,4,5-trimethoxy-phenyl)-furo[3,2-b]pyridin-7-yl]-benzamide |
| "C13" | 7-Pyridin-3-yl-2-(3,4,5-Trimethoxy-phenyl)-furo[3,2-b]pyridine |
| "C14" | 7-(2-Isopropyl-phenyl)-2-(3,4,5-trimethoxy-phenyl)-furo[3,2-b]pyridine |
| "C23" | 7-(6-Fluoro-4-methyl-pyridin-3-yl)-2-(3,4,5-trimethoxy-phenyl)-furo[3,2-b]pyridine |
| "C27" | {5-[2-(3,4,5-Trimethoxy-phenyl)-furo[3,2-b]pyridin-7-yl]-pyridin-2-yl}-methanol |
| "C28" | 7-[6-(Tetrahydro-pyran-4-yloxy)-pyridin-3-yl]-2-(3,4,5-trimethoxy-phenyl)-furo[3,2-b]pyridine |
| "C41" | 7-(6-Methoxy-pyridin-3-yl)-2-(3,4,5-trimethoxy-phenyl)-furo[3,2-b]pyridine |
| "C53" | 4-[2-(3,4,5-Trimethoxy-phenyl)-furo[3,2-b]pyridin-7-yl]-1,3-dihydro-indol-2-one |
| "C56" | 5-[2-(3,4,5-Trimethoxy-phenyl)-furo[3,2-b]pyridin-7-yl]-1,3-dihydro-benzoimidazol-2-one |
| "C58" | 7-(1-Benzyl-1H-pyrazol-4-yl)-2-(3,4,5-trimethoxy-phenyl)-furo[3,2-b]pyridine |
| "C60" | 7-(1H-Benzoimidazol-5-yl)-2-(3,4,5-trimethoxy-phenyl)-furo[3,2-b]pyridine |
| "C64" | 7-(2-Methyl-2H-pyrazol-3-yl)-2-(3,4,5-trimethoxy-phenyl)-furo[3,2-b]pyridine |
| "C66" | 1-Methoxy-3-{4-[2-(3,4,5-trimethoxy-phenyl)-furo[3,2-b]pyridin-7-yl]-pyrazol-1-yl}-propan-2-ol |
| "C68" | 7-(3,6-Dihydro-2H-pyran-4-yl)-2-(3,4,5-trimethoxy-phenyl)-furo[3,2-b]pyridine |
| "C69" | 5-[2-(3,4,5-Trimethoxy-phenyl)-furo[3,2-b]pyridin-7-yl]-1H-pyrimidine-2,4-dione |
| "C70" | 5-[2-(3,4,5-Trimethoxy-phenyl)-furo[3,2-b]pyridin-7-yl]-1H-benzotriazole |
| "C71" | 4-[2-(3,4,5-Trimethoxy-phenyl)-furo[3,2-b]pyridin-7-yl]-benzene-1,2-diamine |
| "C72" | 7-(1H-Pyrazol-4-yl)-2-(3,4,5-trimethoxy-phenyl)-furo[3,2-b]pyridine |

| No. | Name and/or structure |
|---|---|
| "C73" | 7-(1H-Pyrazol-3-yl)-2-(3,4,5-trimethoxy-phenyl)-furo[3,2-b]pyridine |
| "C74" | 2-{4-[2-(3,4,5-Trimethoxy-phenyl)-furo[3,2-b]pyridin-7-yl]-pyrazol-1-yl}-ethanol |
| "C75" | 4-Methyl-5-[2-(3,4,5-trimethoxy-phenyl)-furo[3,2-b]pyridin-7-yl]-pyridin-2-ylamine |
| "C76" | 5-[2-(3,4,5-Trimethoxy-phenyl)-furo[3,2-b]pyridin-7-yl]-1H-benzoimidazol-2-ylamine |
| "C77" | N1-{5-[2-(3,4,5-Trimethoxy-phenyl)-furo[3,2-b]pyridin-7-yl]-1H-benzoimidazol-2-yl}-ethane-1,2-diamine |
| "C78" | 7-Piperidin-4-yl-2-(3,4,5-trimethoxy-phenyl)-furo[3,2-b]pyridine |
| "C79" | Dimethyl-{4-[2-(3,4,5-trimethoxy-phenyl)-furo[3,2-b]pyridin-7-yl]-thiazol-2-yl}-amine |
| "C80" | 2-{4-[2-(3,4,5-Trimethoxy-phenyl)-furo[3,2-b]pyridin-7-yl]-piperidin-1-yl}-ethanol |
| "C84" | 7-(3,5-Dimethyl-1H-pyrazol-4-yl)-2-(3,4,5-trimethoxy-phenyl)-furo[3,2-b]pyridine |
| "C85" | 2-[2-(3,4,5-Trimethoxy-phenyl)-furo[3,2-b]pyridin-7-yl]-phenol |
| "C86" | 7-[2-(5-Methyl-isoxazol-3-yl)-1H-benzoimidazol-5-yl]-2-(3,4,5-trimethoxy-phenyl)-furo[3,2-b]pyridine |
| "C89" | 3-Hydroxy-5-[2-(3,4,5-trimethoxy-phenyl)-furo[3,2-b]pyridin-7-yl]-benzoic acid methyl ester |
| "C90" | 7-[2-(1H-Pyrazol-4-yl)-1H-benzoimidazol-5-yl]-2-[3,4,5-trimethoxy-phenyl)-furo[3,2-b]pyridine |
| "C93" | 7-Biphenyl-2-yl-2-(3,4,5-trimethoxy-phenyl)-furo[3,2-b]pyridine |
| "C94" | 7-(2,6-Dimethyl-phenyl)-2-(3,4,5-trimethoxy-phenyl)-furo[3,2-b]pyridine |
| "C97" | 7-Furan-2-yl-2-(3,4,5-trimethoxy-phenyl)-furo[3,2-b]pyridine |
| "C101" | 7-(3-Piperazin-1-yl-phenyl)-2-(3,4,5-trimethoxy-phenyl)-furo[3,2-b]pyridine |
| "C102" | 7-(2-Morpholin-4-yl-phenyl)-2-(3,4,5-trimethoxy-phenyl)-furo[3,2-b]pyridine |
| "C103" | N-{2-[2-(3,4,5-Trimethoxy-phenyl)-furo[3,2-b]pyridin-7-yl]-phenyl}-acetamide |
| "C104" | 7-[3-(4-Methyl-piperazin-1-yl)-phenyl]-2-(3,4,5-trimethoxy-phenyl)-furo[3,2-b]pyridine |
| "C105" | 7-(1H-Pyrrol-2-yl)-2-(3,4,5-trimethoxy-phenyl)-furo[3,2-b]pyridine |
| "C106" | 3-Hydroxy-5-[2-(3,4,5-Trimethoxy-phenyl)-furo[3,2-b]pyridin-7-yl]-benzamide |
| "C107" | N-((1R,2S)-2-Amino-cyclohexyl)-3-[2-(3,4,5-trimethoxy-phenyl)-furo[3,2-b]pyridin-7-yl]-benzamide |
| "C108" | 7-(4-Methoxy-2-pyrazol-1-yl-phenyl)-2-(3,4,5-trimethoxy-phenyl)-furo[3,2-b]pyridine |
| "C110" | 7-(3-Methanesulfonyl-phenyl)-2-(3,4,5-trimethoxy-phenyl)-furo[3,2-b]pyridine |
| "C111" | 7-[1-(2-Morpholin-4-yl-ethyl)-1H-pyrazol-4-yl]-2-(3,4,5-trimethoxy-phenyl)-furo[3,2-b]pyridine |
| "C113" | 6-[2-(3,4,5-Trimethoxy-phenyl)-furo[3,2-b]pyridin-7-yl]-3,4-dihydro-2H-pyrano[2,3-b]pyridine |
| "C116" | 6-[2-(3,4,5-Trimethoxy-phenyl)-furo[3,2-b]pyridin-7-yl]-1,2,3,4-tetrahydro-[1,8]naphthyridine |
| "C119" | 7-(2-Fluoro-6-methoxy-phenyl)-2-(3,4,5-trimethoxy-phenyl)-furo[3,2-b]pyridine |
| "C120" | Dimethyl-{2-[2-(3,4,5-trimethoxy-phenyl)-furo[3,2-b]pyridin-7-yl]-phenyl}-amine |
| "C121" | N,N-Dimethyl-3-[2-(3,4,5-trimethoxy-phenyl)-furo[3,2-b]pyridin-7-yl]-benzene sulfonamide |
| "C122" | 2-{2-[2-(3,4,5-Trimethoxy-phenyl)-furo[3,2-b]pyridin-7-yl]-phenoxy}-ethylamine |
| "C124" | 7-(4-Methanesulfinyl-phenyl)-2-(3,4,5-trimethoxy-phenyl)-furo[3,2-b]pyridine |
| "C125" | 7-(1-Piperidin-4-yl-1H-pyrazol-4-yl)-2-(3,4,5-trimethoxy-phenyl)-furo[3,2-b]pyridine |
| "C126" | 7-(5-Methyl-3-phenyl-isoxazol-4-yl)-2-(3,4,5-trimethoxy-phenyl)-furo[3,2-b]pyridine |
| "C127" | 7-(3-Methyl-1H-pyrazol-4-yl)-2-(3,4,5-trimethoxy-phenyl)-furo[3,2-b]pyridine |
| "C128" | 7-(3,5-Dimethyl-isoxazol-4-yl)-2-(3,4,5-trimethoxy-phenyl)-furo[3,2-b]pyridine |
| "C130" | 7-Piperidin-1-yl-2-(3,4,5-trimethoxy-phenyl)-furo[3,2-b]pyridine |
| "C132" | 2-{1-[2-(3,4,5-Trimethoxy-phenyl)-furo[3,2-b]pyridin-7-yl]-piperidin-3-yl}-ethanol |
| "C136" | 4-Methoxy-3-[2-(3,4,5-trimethoxy-phenyl)-furo[3,2-b]pyridin-7-yl]-phenol |
| "C137" | 7-(1H-Indazol-5-yl)-2-(3,4,5-trimethoxy-phenyl)-furo[3,2-b]pyridine |
| "C138" | 4-Methoxy-3-[2-(3,4,5-trimethoxy-phenyl)-furo[3,2-b]pyridin-7-yl]-benzoic acid methyl ester |
| "C139" | C-{1-[2-(3,4,5-Trimethoxy-phenyl)-furo[3,2-b]pyridin-7-yl]-piperidin-3-yl}-methylamine |
| "C142" | 4-Methoxy-3-[2-(3,4,5-trimethoxy-phenyl)-furo[3,2-b]pyridin-7-yl]-benzoic acid |
| "C143" | N-(2-Amino-ethyl)-4-methoxy-3-[2-(3,4,5-trimethoxy-phenyl)-furo[3,2-b]pyridin-7-yl]-benzamide |
| "C144" | 2-{4-Methoxy-3-[2-(3,4,5-trimethoxy-phenyl)-furo[3,2-b]pyridin-7-yl]-phenoxy}-ethylamine |
| "C145" | 4-Methoxy-3-[2-(3,4,5-trimethoxy-phenyl)-furo[3,2-b]pyridin-7-yl]-benzamide |
| "C146" | N-{4-[2-(3,4,5-Trimethoxy-phenyl)-furo[3,2-b]pyridin-7-yl]-pyridin-2-yl}-cyclohexane-1,2-diamine |
| "C147" | 7-[2-(2-Methoxy-ethoxy)-pyridin-4-yl]-2-(3,4,5-trimethoxy-phenyl)-furo[3,2-b]pyridine |
| "C148" | N-(2-Amino-cyclohexyl)-4-methoxy-3-[2-(3,4,5-trimethoxy-phenyl)-furo[3,2-b]pyridin-7-yl]-benzamide |
| "C149" | N-(2-Amino-ethyl)-3-hydroxy-5-[2-(3,4,5-trimethoxy-phenyl)-furo[3,2-b]pyridin-7-yl]-benzamide |
| "C150" | 3-Cyclopropylmethoxy-5-[2-(3,4,5-trimethoxy-phenyl)-furo[3,2-b]pyridin-7-yl]-benzoic acid methyl ester |
| "C151" | 3-Isopropoxy-5-[2-(3,4,5-trimethoxy-phenyl)-furo[3,2-b]pyridin-7-yl]-benzoic acid methyl ester |
| "C152" | N-((1R,2S)-2-Amino-cyclohexyl)-4-methoxy-3-[2-(3,4,5-trimethoxy-phenyl)-furo[3,2-b]pyridin-7-yl]-benzamide |
| "C153" | 7-(2-Fluoro-6-phenoxy-phenyl)-2-(3,4,5-trimethoxy-phenyl)-furo[3,2-b]pyridine |
| "C154" | 3-Methoxy-5-[2-(3,4,5-trimethoxy-phenyl)-furo[3,2-b]pyridin-7-yl]-benzoic acid |
| "C155" | 3-Isopropoxy-5-[2-(3,4,5-trimethoxy-phenyl)-furo[3,2-b]pyridin-7-yl]-benzoic acid |
| "C156" | 3-Cyclopropylmethoxy-5-[2-(3,4,5-trimethoxy-phenyl)-furo[3,2-b]pyridin-7-yl]-benzoic acid |
| "C157" | 7-(2-Ethoxy-6-fluoro-phenyl)-2-(3,4,5-trimethoxy-phenyl)-furo[3,2-b]pyridine |
| "C158" | 7-(2-Benzyloxy-6-fluoro-phenyl)-2-(3,4,5-trimethoxy-phenyl)-furo[3,2-b]pyridine |
| "C159" | 3-Trifluoromethoxy-5-[2-(3,4,5-trimethoxy-phenyl)-furo[3,2-b]pyridin-7-yl]-benzoic acid methyl ester |
| "C160" | 3-Trifluoromethyl-5-[2-(3,4,5-trimethoxy-phenyl)-furo[3,2-b]pyridin-7-yl]-benzoic acid methyl ester |
| "C161" | ((1S,2R)-2-{3-Methoxy-5-[2-(3,4,5-trimethoxy-phenyl)-furo[3,2-b]pyridin-7-yl]-benzoylamino}-cyclohexyl)-carbamic acid tert-butyl ester |
| "C162" | 7-(2-Isopropoxy-6-methoxy-phenyl)-2-(3,4,5-trimethoxy-phenyl)-furo[3,2-b]pyridine |
| "C163" | 3-Trifluoromethoxy-5-[2-(3,4,5-trimethoxy-phenyl)-furo[3,2-b]pyridin-7-yl]-benzoic acid |
| "C164" | 3-Trifluoromethyl-5-[2-(3,4,5-trimethoxy-phenyl)-furo[3,2-b]pyridin-7-yl]-benzoic acid |
| "C165" | 3-(2-Amino-ethoxy)-5-[2-(3,4,5-trimethoxy-phenyl)-furo[3,2-b]pyridin-7-yl]-benzamide |
| "C166" | 2-{4-[2-(3,4,5-Trimethoxy-phenyl)-furo[3,2-b]pyridin-7-yl]-pyrazol-1-yl}-ethylamine |
| "C170" | N-((1R,2S)-2-Amino-cyclohexyl)-3-methoxy-5-[2-(3,4,5-trimethoxy-phenyl)-furo[3,2-b]pyridin-7-yl]-benzamide |
| "C171" | N-((1R,2S)-2-Amino-cyclohexyl)-3-isopropoxy-5-[2-(3,4,5-trimethoxy-phenyl)-furo[3,2-b]pyridin-7-yl]-benzamide |
| "C172" | N-(2-Amino-ethyl)-3,5-dimethoxy-4-[2-(3,4,5-trimethoxy-phenyl)-furo[3,2-b]pyridin-7-yl]-benzamide |
| "C173" | N-((1R,2S)-2-Amino-cyclohexyl)-3-trifluoromethoxy-5-[2-(3,4,5-trimethoxy-phenyl)-furo[3,2-b]pyridin-7-yl]-benzamide |
| "C174" | N-((1R,2S)-2-Amino-cyclohexyl)-3-trifluoromethyl-5-[2-(3,4,5-trimethoxy-phenyl)-furo[3,2-b]pyridin-7-yl]-benzamide |
| "C179" | N-((1R,2S)-2-Amino-cyclohexyl)-3-cyclopropylmethoxy-5-[2-(3,4,5-trimethoxy-phenyl)-furo[3,2-b]pyridin-7-yl]-benzamide |
| "C182" | 1-{4-[2-(3,4,5-Trimethoxy-phenyl)-furo[3,2-b]pyridin-7-yl]-pyridin-2-yl}-pyrrolidin-3-ylamine |
| "C183" | N-((1R,2S)-2-Amino-cyclohexyl)-3-methyl-5-[2-(3,4,5-trimethoxy-phenyl)-furo[3,2-b]pyridin-7-yl]-benzamide |
| "C184" | 4'-[2-(3,4,5-Trimethoxy-phenyl)-furo[3,2-b]pyridin-7-yl]-3,4,5,6-tetrahydro-2H-[1,2']bipyrodonyl |
| "C185" | Piperidin-3-ylmethyl-{4-[2-(3,4,5-trimethoxy-phenyl)-furo[3,2-b]pyridin-7-yl]-pyridin-2-yl}-amine |
| "C187" | 7-(3-Piperazin-2-yl-phenyl)-2-(3,4,5-trimethoxy-phenyl)-furo[3,2-b]pyridine |

-continued

| No. | Name and/or structure |
|---|---|
| "C188" | 4-Methyl-3-[2-(3,4,5-trimethoxy-phenyl)-furo[3,2-b]pyridin-7-yl]-benzoic acid |
| "C189" | Piperidin-3-yl-{4-[3-(3,4,5-trimethoxy-phenyl)-furo[3,2-b]pyridin-7-yl]-pyridin-2-yl}-amine |
| "C190" | N-((1R,2S)-2-Amino-cyclohexyl)-4-methyl-3-[2-(3,4,5-trimethoxy-phenyl)-furo[3,2-b]pyridin-7-yl]-benzamide |
| "C191" | Pyrrolidin-3-yl-{4-[2-(3,4,5-trimethoxy-phenyl)-furo[3,2-b]pyridin-7-yl]-pyridin-2-yl}-amine |
| "C192" | 3-[2-(3,4,5-Trimethoxy-phenyl)-furo[3,2-bpyridin-7-yl]-benzenesulfonamide |
| "D18" | N-{3-[7-(3,4,5-Trimethoxy-phenyl)-furo[3,2-b]pyridin-2-yl]-phenyl}-acrylamide | and pharmaceutically acceptable solvates, salts, tautomers and stereoisomers thereof, including mixtures thereof in all ratios.

8. A compound according to claim 1, wherein said compound is selected from the following group:

| No. | Name and/or structure |
|---|---|
| "A5" | 7-Phenyl-2-(3,4,5-trimethoxy-phenyl)-furo[3,2-b]pyridine |
| "A6" | 7-Phenyl-2-(3,4,5-trimethoxy-phenyl)-furo[3,2-b]pyridine |
| "A7" | N-Methyl-3-[2-(3,4,5-trimethoxy-phenyl)-furo[3,2-b]pyridin-7-yl]-benzamide |
| "A8" | N-(2-Dimethylamino-ethyl)-3-[2-(3,4,5-trimethoxy-phenyl)-furo[3,2-b]pyridin-7-yl]-benzamide |
| "A9" | 3-[2-(3,4,5-Trimethoxy-phenyl)-furo[3,2-b]pyridin-7-yl]-benzonitrile |
| "A10" | 7-(3-Nitro-phenyl)-2-(3,4,5-trimethoxy-phenyl)-furo[3,2-b]pyridine |
| "A11" | 3-[2-(3,4,5-Trimethoxy-phenyl)-furo[3,2-b]pyridin-7-yl]-benzoic acid methyl ester |
| "A12" | 4-[2-(3,4,5-Trimethoxy-phenyl)-furo[3,2-b]pyridin-7-yl]-benzonitrile |
| "A13" | N-Methyl-4-[2-(3,4,5-trimethoxy-phenyl)-furo[3,2-b]pyridin-7-yl]-benzamide |
| "A14" | 7-(4-Nitro-phenyl)-2-(3,4,5-trimethoxy-phenyl)-furo[3,2-b]pyridine |
| "A15" | 4-[2-(3,4,5-Trimethoxy-phenyl)-furo[3,2-b]pyridin-7-yl]-benzoic acid methyl ester |
| "A16" | 7-(4-Methyl-naphthalen-1-yl)-2-(3,4,5-trimethoxy-phenyl)-furo[3,2-b]pyridine |
| "A17" | 7-(1H-Indazol-4-yl)-2-(3,4,5-trimethoxy-phenyl)-furo[3,2-b]pyridine |
| "A18" | 5-[2-(3,4,5-Trimethoxy-phenyl)-furo[3,2-b]pyridin-7-yl]-quinoline |
| "A19" | 3-(7-Phenyl-furo[3,2-b]pyridin-2-yl)-benzoic acid methyl ester |
| "A20" | 7-(1H-Indol-4-yl)-2-(3,4,5-trimethoxy-phenyl)-furo[3,2-b]pyridine |
| "A21" | 7-o-Tolyl-2-(3,4,5-trimethoxy-phenyl)-furo[3,2-b]pyridine |
| "A22" | 7-Naphthalene-1-yl-2-(3,4,5-trimethoxy-phenyl)-furo[3,2-b]pyridine |
| "A23" | 6-[2-(3,4,5-Trimethoxy-phenyl)-furo[3,2-b]pyridin-7-yl]-quinoline |
| "A24" | 4-[2-(3,4,5-Trimethoxy-phenyl)-furo[3,2-b]pyridin-7-yl]-quinoline |
| "A25" | 7-(1H-Indol-3-yl)-2-(3,4,5-trimethoxy-phenyl)-furo[3,2-b]pyridine |
| "A26" | 8-Methyl-5-[2-(3,4,5-trimethoxy-phenyl)-furo[3,2-b]pyridin-7-yl]-quinoline |
| "A27" | 7-(1H-Indol-6-yl)-2-(3,4,5-trimethoxy-phenyl)-furo[3,2-b]pyridine |
| "A28" | 7-(2,4-Dimethoxy-phenyl)-2-(3,4,5-trimethoxy-phenyl)-furo[3,2-b]pyridine |
| "A29" | 7-(2-Methoxy-pyridin-4-yl)-2-(3,4,5-trimethoxy-phenyl)-furo[3,2-b]pyridine |
| "A30" | 5-[2-(3,4,5-Trimethoxy-phenyl)-furo[3,2-b]pyridin-7-yl]-nicotinonitrile |
| "A31" | 7-(3-Benzyloxy-phenyl)-2-(3,4,5-trimethoxy-phenyl)-furo[3,2-b]pyridine |
| "A32" | 7-(2,4-Dimethyl-phenyl)-2-(3,4,5-trimethoxy-phenyl)-furo[3,2-b]pyridine |
| "A33" | {4-[2-(3,4,5-Trimethoxy-phenyl)-furo[3,2-b]pyridin-7-yl]-pyrazol-1-yl}-acetic acid ethyl ester |
| "A34" | 7-(1-Methyl-1H-pyrazol-4-yl)-2-(3,4,5-trimethoxy-phenyl)-furo[3,2-b]pyridine | and pharmaceutically acceptable solvates, salts, tautomers and stereoisomers thereof, including mixtures thereof in all ratios.

9. A compound according to claim 1, wherein said compound is selected from the following group:

| No. | Name and/or structure |
|---|---|
| "A35" | 3-(7-Phenyl-furo[3,2-b]pyridin-2-yl)-phenol |
| "A36" | 3-(3,4,5-Trimethoxy-phenyl)-furo[3,2-b]pyridin-7-yl]-phenol |
| "A37" | (2-{3-[2-(3,4,5-Trimethoxy-phenyl)-furo[3,2-b]pyridin-7-yl]-phenoxy}-ethyl)-carbamic acid tert.-butyl ester |
| "A38" | 2-{3-[2-(3,4,5-Trimethoxy-phenyl)-furo[3,2-b]pyridin-7-yl]-phenoxy}-ethylamine |
| "A39" | 3-Methyl-5-(7-phenyl-furo[3,2-b]pyridin-2-yl)-benzoic acid |
| "A40" | 2,3-dimethoxy-5-(7-phenylfuro[3,2-b]pyridin-2-yl)benzoic acid |
| "A41" | 3-[2-(3,4,5-Trimethoxy-phenyl)-furo[3,2-b]pyridin-7-yl]-benzoic acid |
| "A42" | 4-[2-(3,4,5-Trimethoxy-phenyl)-furo[3,2-b]pyridin-7-yl]-benzoic acid |
| "A43" | N-(2-Hydroxy-1,1-dimethyl-ethyl)-3-methyl-5-(7-phenyl-furo[3,2-b]pyridin-2-yl)-benzamide |
| "A44" | N-(2-hydroxy-1,1-dimethyl-ethyl)-2,3-dimethoxy-5-(7-phenylfuro[3,2-b]pyridin-2-yl)benzamide |
| "A45" | N-(2-Amino-cyclohexyl)-3-[2-(3,4,5-trimethoxy-phenyl)-furo[3,2-b]pyridin-7-yl]-benzamide |
| "A46" | (1-{3-[2-(3,4,5-Trimethoxy-phenyl)-furo[3,2-b]pyridin-7-yl]-benzoyl}-pyrrolidin-3-yl)-carbamic acid tert-butyl ester |
| "A47" | tert.-Butyl 3-[[3-[2-(3,4,5-trimethoxyphenyl)furo[3,2-b]pyridin-7-yl]benzoyl]amino]pyrrolidine-1-carboxylate |
| "A48" | N-(2-methoxyethyl)-3-[2-(3,4,5-trimethoxyphenyl)furo[3,2-b]pyridin-7-yl]benzamide |
| "A49" | N-(3-dimethylaminopropyl)-3-[2-(3,4,5-trimethoxyphenyl)furo[3,2-b]pyridin-7-yl]benzamide |
| "A50" | Morpholino-[3-[2-(3,4,5-trimethoxyphenyl)furo[3,2-b]pyridin-7-yl]phenyl]methanone |
| "A51" | 3-[2-(3,4,5-Trimethoxy-phenyl)-furo[3,2-b]pyridin-7-yl]-benzylamine |
| "A52" | N-[[3-[2-(3,4,5-trimethoxyphenyl)furo[3,2-b]pyridin-7-yl]phenyl]methyl]acetamide |
| "A53" | 4-[2-(3,4,5-Trimethoxy-phenyl)-furo[3,2-b]pyridin-7-yl]-benzylamine |
| "A54" | N-{4-[2-(3,4,5-Trimethoxy-phenyl)-furo[3,2-b]pyridin-7-yl]-benzyl}-acetamide |
| "A55" | 3-[2-(3,4,5-Trimethoxy-phenyl)-furo[3,2-b]pyridin-7-yl]-phenylamine |
| "A56" | 4-[2-(3,4,5-Trimethoxy-phenyl)-furo[3,2-b]pyridin-7-yl]-phenylamine |
| "A57" | 2-[4-[2-(3,4,5-trimethoxyphenyl)furo[3,2-b]pyridin-7-yl]pyrazol-1-yl]acetic acid |
| "A58" | 2-[4-[2-(3,4,5-trimethoxyphenyl)furo[3,2-b]pyridin-7-yl]pyrazol-1-yl]acetamide |
| "A59" | 3-[[2-(3,4,5-trimethoxyphenyl)furo[3,2-b]pyridin-7-yl]amino]benzoic acid |
| "A60" | 2-(1-Methyl-1H-pyrazol-3-yl)-7-phenyl-furo[3,2-b]pyridine |
| "A61" | 2-(2-Methoxy-pyridin-4-yl)-7-phenyl-furo[3,2-b]pyridine |
| "A62" | 5-(7-Phenyl-furo[3,2-b]pyridin-2-yl)-benzo[1,2,5]thiadiazole |
| "A63" | 7-Phenyl-2-(3-trifluoromethoxy-phenyl)-furo[3,2-b]pyridine |
| "A64" | 2-(1-Isobutyl-1H-pyrazol-3-yl)-7-phenyl-furo[3,2-b]pyridine | and pharmaceutically acceptable solvates, salts, tautomers and stereoisomers thereof, including mixtures thereof in all ratios.

10. A compound according to claim 1, wherein said compound is selected from the following group:

| No. | Name and/or structure |
|---|---|
| "A65" | N-(2-Hydroxy-1,1-dimethyl-ethyl)-3-[2-(3,4,5-trimethoxy-phenyl)-furo[3,2-b]pyridin-7-yl]-benzamide |
| "A66" | N-pyrrolidin-3-yl-3-[2-(3,4,5-trimethoxyphenyl)furo[3,2-b]pyridin-7-yl]benzamide |
| "A67" | (3-aminopyrrolidin-1-yl)-[3-[2-(3,4,5-trimethoxyphenyl)furo[3,2-b]pyridin-7-yl]phenyl]methanone |
| "A68" | 2-(4-Difluoromethoxy-phenyl)-7-pyridin-3-yl-furo[3,2-b]pyridine |
| "A69" | 2-(4-Difluoromethoxy-phenyl)-7-thiazol-5-yl-furo[3,2-b]pyridine |

| No. | Name and/or structure |
|---|---|
| "A70" | 2-(4-Difluoromethoxy-phenyl)-7-pyrimidin-5-yl-furo[3,2-b]pyridine |
| "A71" | 5-[2-(4-Difluoromethoxy-phenyl)-furo[3,2-b]pyridin-7-yl]-pyridin-2-ylamine |
| "A72" | 5-[2-(4-Difluoromethoxy-phenyl)-furo[3,2-b]pyridin-7-yl]-pyridine-2-carbonitrile |
| "A73" | 5-[2-(4-Difluoromethoxy-phenyl)-furo[3,2-b]pyridin-7-yl]-nicotinonitrile |
| "A74" | 15-[2-(4-Difluoromethoxy-phenyl)-furo[3,2-b]pyridin-7-yl]-pyridin-2-yl}-dimethyl-amine |
| "A75" | 5-[2-(4-Difluoromethoxy-phenyl)-furo[3,2-b]pyridin-7-yl]-pyridin-2-ol |
| "A76" | 7-[2-(4-Difluoromethoxy-phenyl)-furo[3,2-b]pyridin-7-yl]-4-methyl-3,4-dihydro-2H-pyrido[3,2-b][1,4]oxazine |
| "A77" | 2-(4-Difluoromethoxy-phenyl)-7-(6-methoxy-pyridin-3-yl)-furo[3,2-b]pyridine |
| "A78" | 2-(4-Difluoromethoxy-phenyl)-7-(5-methanesulfonyl-pyridin-3-yl)-furo[3,2-b]pyridine |
| "A79" | 2-[4-(7-Pyridin-3-yl-furo[3,2-b]pyridin-2-yl)-phenoxy]-ethanol |
| "A80" | 2-[4-(7-Thiazol-5-yl-furo[3,2-b]pyridin-2-yl)-phenoxy]-ethanol |
| "A81" | 2-[4-(7-Pyrimidin-5-yl-furo[3,2-b]pyridin-2-yl)-phenoxy]-ethanol |
| "A82" | 2-{4-[7-(6-Amino-pyridin-3-yl)-furo[3,2-b]pyridin-2-yl]-phenoxy}-ethanol |
| "A83" | 5-{2-[4-(2-Hydroxy-ethoxy)-phenyl]-furo[3,2-b]pyridin-7-yl}-pyridine-2-carbonitrile |
| "A84" | 5-{2-[4-(2-Hydroxy-ethoxy)-phenyl]-furo[3,2-b]pyridin-7-yl}-nicotinonitrile |
| "A85" | 2-{4-[7-(6-Dimethylamino-pyridin-3-yl)-furo[3,2-b]pyridin-2-yl]-phenoxy}-ethanol |
| "A86" | 5-{2-[4-(2-Hydroxy-ethoxy)-phenyl]-furo[3,2-b]pyridin-7-yl}-pyridin-2-ol |
| "A87" | 2-{4-[7-(4-Methyl-3,4-dihydro-2H-pyrido[3,2-b][1,4]oxazin-7-yl)-furo[3,2-b]pyridin-2-yl]-phenoxy}-ethanol |
| "A88" | 2-{4-[7-(6-Methoxy-pyridin-3-yl)-furo[3,2-b]pyridin-2-yl]-phenoxy}-ethanol |
| "A89" | 2-{4-[7-(5-Methanesulfonyl-pyridin-3-yl)-furo[3,2-b]pyridin-2-yl]-phenoxy}-ethanol |
| "A90" | 2-(4-Piperazin-1-yl-phenyl)-7-pyridin-3-yl-furo[3,2-b]pyridine |
| "A91" | 2-(4-Piperazin-1-yl-phenyl)-7-thiazol-5-yl-furo[3,2-b]pyridine |
| "A92" | 2-(4-Piperazin-1-yl-phenyl)-7-pyrimidin-5-yl-furo[3,2-b]pyridine |
| "A93" | 5-[2-(4-Piperazin-1-yl-phenyl)-furo[3,2-b]pyridin-7-yl]-pyridin-2-ylamine |
| "A94" | 5-[2-(4-Piperazin-1-yl-phenyl)-furo[3,2-b]pyridin-7-yl]-pyridine-2-carbonitrile | and pharmaceutically acceptable solvates, salts, tautomers and stereoisomers thereof, including mixtures thereof in all ratios.

11. A compound according to claim 1, wherein said compound is selected from the following group:

| No. | Name and/or structure |
|---|---|
| "A95" | 5-[2-(4-Piperazin-1-yl-phenyl)-furo[3,2-b]pyridin-7-yl]-nicotinonitrile |
| "A96" | Dimethyl-{5-[2-(4-piperazin-1-yl-phenyl)-furo[3,2-b]pyridin-7-yl]-pyridin-2-yl}-amine |
| "A97" | 5-[2-(4-Piperazin-1-yl-phenyl)-furo[3,2-b]pyridin-7-yl]-pyridin-2-ol |
| "A98" | 4-Methyl-7-[2-(4-piperazin-1-yl-phenyl)-furo[3,2-b]pyridin-7-yl]-3,4-dihydro-2H-pyrido[3,2-b][1,4]oxazine |
| "A99" | 7-(6-Methoxy-pyridin-3-yl)-2-(4-piperazin-1-yl-phenyl)-furo[3,2-b]pyridine |
| "A100" | 7-(5-Methanesulfonyl-pyridin-3-yl)-2-(4-piperazin-1-yl-phenyl)-furo[3,2-b]pyridine |
| "A101" | 7-Pyridin-3-yl-2-[4-(2H-tetrazol-5-yl)-phenyl]-furo[3,2-b]pyridine |
| "A102" | 2-[4-(2H-Tetrazol-5-yl)-phenyl]-7-thiazol-5-yl-furo[3,2-b]pyridine |
| "A103" | 7-Pyrimidin-5-yl-2-[4-(2H-tetrazol-5-yl)-phenyl]-furo[3,2-b]pyridine |
| "A104" | 5-{2-[4-(2H-Tetrazol-5-yl)-phenyl]-furo[3,2-b]pyridin-7-yl}-pyridin-2-ylamine |
| "A105" | 5-{2-[4-(2H-Tetrazol-5-yl)-phenyl]-furo[3,2-b]pyridin-7-yl}-pyridine-2-carbonitrile |
| "A106" | 5-{2-[4-(2H-Tetrazol-5-yl)-phenyl]-furo[3,2-b]pyridin-7-yl}-nicotinonitrile |
| "A107" | Dimethyl-(5-{2-[4-(2H-tetrazol-5-yl)-phenyl]-furo[3,2-b]pyridin-7-yl}-pyridin-2-yl)-amine |
| "A108" | 5-{2-[4-(2H-Tetrazol-5-yl)-phenyl]-furo[3,2-b]pyridin-7-yl}-pyridin-2-ol |
| "A109" | 4-Methyl-7-{2-[4-(2H-tetrazol-5-yl)-phenyl]-furo[3,2-b]pyridin-7-yl}-3,4-dihydro-2H-pyrido[3,2-b][1,4]oxazine |
| "A110" | 7-(6-Methoxy-pyridin-3-yl)-2-[4-(2H-tetrazol-5-yl)-phenyl]-furo[3,2-b]pyridine |
| "A111" | 7-(5-Methanesulfonyl-pyridin-3-yl)-2-[4-(2H-tetrazol-5-yl)-phenyl]-furo[3,2-b]pyridine |
| "A112" | 2-[4-(1H-Imidazol-4-yl)-phenyl]-7-pyridin-3-yl-furo[3,2-b]pyridine |
| "A113" | 2-[4-(1H-Imidazol-4-yl)-phenyl]-7-thiazol-5-yl-furo[3,2-b]pyridine |
| "A114" | 2-[4-(1H-Imidazol-4-yl)-phenyl]-7-pyrimidin-5-yl-furo[3,2-b]pyridine |
| "A115" | 5-{2-[4-(1H-Imidazol-4-yl)-phenyl]-furo[3,2-b]pyridin-7-yl}-pyridin-2-ylamine |
| "A116" | 5-{2-[4-(1H-Imidazol-4-yl)-phenyl]-furo[3,2-b]pyridin-7-yl}-pyridine-2-carbonitrile |
| "A117" | 5-{2-[4-(1H-Imidazol-4-yl)-phenyl]-furo[3,2-b]pyridin-7-yl}-nicotinonitrile |
| "A118" | (5-{2-[4-(1H-Imidazol-4-yl)-phenyl]-furo[3,2-b]pyridin-7-yl}-pyridin-2-yl)-dimethyl-amine |
| "A119" | 5-{2-[4-(1H-Imidazol-4-yl)-phenyl]-furo[3,2-b]pyridin-7-yl}-pyridin-2-ol |
| "A120" | 7-{2-[4-(1H-Imidazol-4-yl)-phenyl]-furo[3,2-b]pyridin-7-yl}-4-methyl-3,4-dihydro-2H-pyrido[3,2-b][1,4]oxazine |
| "A121" | 2-[4-(1H-Imidazol-4-yl)-phenyl]-7-(6-methoxy-pyridin-3-yl)-furo[3,2-b]pyridine |
| "A122" | 2-[4-(1H-Imidazol-4-yl)-phenyl]-7-(5-methanesulfonyl-pyridin-3-yl)-furo[3,2-b]pyridine |
| "A123" | 2-[4-(7-Pyridin-3-yl-furo[3,2-b]pyridin-2-yl)-phenyl]-ethanol |
| "A124" | 2-[4-(7-Thiazol-5-yl-furo[3,2-b]pyridin-2-yl)-phenyl]-ethanol | and pharmaceutically acceptable solvates, salts, tautomers and stereoisomers thereof, including mixtures thereof in all ratios.

12. A compound according to claim 1, wherein said compound is selected from the following group:

| No. | Name and/or structure |
|---|---|
| "A125" | 2-[4-(7-Pyrimidin-5-yl-furo[3,2-b]pyridin-2-yl)-phenyl]-ethanol |
| "A126" | 2-{4-[7-(6-Amino-pyridin-3-yl)-furo[3,2-b]pyridin-2-yl]-phenyl}-ethanol |
| "A127" | 5-{2-[4-(2-Hydroxy-ethyl)-phenyl]-furo[3,2-b]pyridin-7-yl}-pyridine-2-carbonitrile |
| "A128" | 5-{2-[4-(2-Hydroxy-ethyl)-phenyl]-furo[3,2-b]pyridin-7-yl}-nicotinonitrile |
| "A129" | 2-{4-[7-(6-Dimethylamino-pyridin-3-yl)-furo[3,2-b]pyridin-2-yl]-phenyl}-ethanol |
| "A130" | 5-{2-[4-(2-Hydroxy-ethyl)-phenyl]-furo[3,2-b]pyridin-7-yl}-pyridin-2-ol |
| "A131" | 2-{4-[7-(4-Methyl-3,4-dihydro-2H-pyrido[3,2-b][1,4]oxazin-7-yl)-furo[3,2-b]pyridin-2-yl]-phenyl}-ethanol |
| "A132" | 2-{4-[7-(6-Methoxy-pyridin-3-yl)-furo[3,2-b]pyridin-2-yl]-phenyl}-ethanol |
| "A133" | 2-{4-[7-(5-Methanesulfonyl-pyridin-3-yl)-furo[3,2-b]pyridin-2-yl]-phenyl}-ethanol |
| "A134" | 7-Pyridin-3-yl-2-[4-(2-pyrrolidin-1-yl-ethoxy)-phenyl]-furo[3,2-b]pyridine |
| "A135" | 2-[4-(2-Pyrrolidin-1-yl-ethoxy)-phenyl]-7-thiazol-5-yl-furo[3,2-b]pyridine |
| "A136" | 7-Pyrimidin-5-yl-2-[4-(2-pyrrolidin-1-yl-ethoxy)-phenyl]-furo[3,2-b]pyridine |
| "A137" | 5-{2-[4-(2-Pyrrolidin-1-yl-ethoxy)-phenyl]-furo[3,2-b]pyridin-7-yl}-pyridin-2-ylamine |
| "A138" | 5-{2-[4-(2-Pyrrolidin-1-yl-ethoxy)-phenyl]-furo[3,2-b]pyridin-7-yl}-pyridine-2-carbonitrile |
| "A139" | 5-{2-[4-(2-Pyrrolidin-1-yl-ethoxy)-phenyl]-furo[3,2-b]pyridin-7-yl}-nicotinonitrile |

-continued

| No. | Name and/or structure |
|---|---|
| "A140" | Dimethyl-(5-{2-[4-(2-pyrrolidin-1-yl-ethoxy)-phenyl]-furo[3,2-b]pyridin-7-yl}-pyridin-2-yl)-amine |
| "A141" | 5-{2-[4-(2-Pyrrolidin-1-yl-ethoxy)-phenyl]-furo[3,2-b]pyridin-7-yl}-pyridin-2-ol |
| "A142" | 4-Methyl-7-{2-[4-(2-pyrrolidin-1-yl-ethoxy)-phenyl]-furo[3,2-b]pyridin-7-yl}-3,4-dihydro-2H-pyrido[3,2-b][1,4]oxazine |
| "A143" | 7-(6-Methoxy-pyridin-3-yl)-2-[4-(2-pyrrolidin-1-yl-ethoxy)-phenyl]-furo[3,2-b]pyridine |
| "A144" | 7-(5-Methanesulfonyl-pyridin-3-yl)-2-[4-(2-pyrrolidin-1-yl-ethoxy)-phenyl]-furo[3,2-b]pyridine |
| "A145" | 2-[4-(1-Methyl-1H-pyrazol-4-yl)-phenyl]-7-pyridin-3-yl-furo[3,2-b]pyridine |
| "A146" | 2-[4-(1-Methyl-1H-pyrazol-4-yl)-phenyl]-7-thiazol-5-yl-furo[3,2-b]pyridine |
| "A147" | 2-[4-(1-Methyl-1H-pyrazol-4-yl)-phenyl]-7-pyrimidin-5-yl-furo[3,2-b]pyridine |
| "A148" | 5-{2-[4-(1-Methyl-1H-pyrazol-4-yl)-phenyl]-furo[3,2-b]pyridin-7-yl}-pyridin-2-ylamine |
| "A149" | 5-{2-[4-(1-Methyl-1H-pyrazol-4-yl)-phenyl]-furo[3,2-b]pyridin-7-yl}-pyridine-2-carbonitrile |
| "A150" | 5-{2-[4-(1-Methyl-1H-pyrazol-4-yl)-phenyl]-furo[3,2-b]pyridin-7-yl}-nicotinonitrile |
| "A151" | Dimethyl-(5-{2-[4-(1-methyl-1H-pyrazol-4-yl)-phenyl]-furo[3,2-b]pyridin-7-yl}-pyridin-2-yl)-amine |
| "A152" | 5-{2-[4-(1-Methyl-1H-pyrazol-4-yl)-phenyl]-furo[3,2-b]pyridin-7-yl}-pyridin-2-ol |
| "A153" | 4-Methyl-7-{2-[4-(1-methyl-1H-pyrazol-4-yl)-phenyl]-furo[3,2-b]pyridin-7-yl1-3,4-dihydro-2H-pyrido[3,2-b][1,4]oxazine |
| "A154" | 7-(6-Methoxy-pyridin-3-yl)-244-(1-methyl-1H-pyrazol-4-yl)-phenyl]-furo[3,2-b]pyridine | and pharmaceutically acceptable solvates, salts, tautomers and stereoisomers thereof, including mixtures thereof in all ratios.

13. A compound according to claim 1, wherein said compound is selected from the following group:

| No. | Name and/or structure |
|---|---|
| "A155" | 7-(5-Methanesulfonyl-pyridin-3-yl)-2-[4-(1-methyl-1H-pyrazol-4-yl)-phenyl]-furo[3,2-b]pyridine |
| "A156" | 2-{4-[4-(7-Pyridin-3-yl-furo[3,2-b]pyridin-2-yl)-phenyl]-pyrazol-1-yl}-ethanol |
| "A157" | 2-{4-[4-(7-Thiazol-5-yl-furo[3,2-b]pyridin-2-yl)-phenyl]-pyrazol-1-yl}-ethanol |
| "A158" | 2-{4-[4-(7-Pyrimidin-5-yl-furo[3,2-b]pyridin-2-yl)-phenyl]-pyrazol-1-yl}-ethanol |
| "A159" | 2-(4-{4-[7-(6-Amino-pyridin-3-yl)-furo[3,2-b]pyridin-2-yl]-phenyl}-pyrazol-1-yl)-ethanol |
| "A160" | 5-(2-{4-[1-(2-Hydroxy-ethyl)-1H-pyrazol-4-yl]-phenyl}-furo[3,2-b]pyridin-7-yl)-pyridine-2-carbonitrile |
| "A161" | 5-(2-{4-[1-(2-Hydroxy-ethyl)-1H-pyrazol-4-yl]-phenyl}-furo[3,2-b]pyridin-7-yl)-nicotinonitrile |
| "A162" | 2-(4-{4-[7-(6-Dimethylamino-pyridin-3-yl)-furo[3,2-b]pyridin-2-yl]-phenyl}-pyrazol-1-yl)-ethanol |
| "A163" | 5-(2-{4-[1-(2-Hydroxy-ethyl)-1H-pyrazol-4-yl]-phenyl}-furo[3,2-b]pyridin-7-yl)-pyridin-2-ol |
| "A164" | 2-(4-{4-[7-(4-Methyl-3,4-dihydro-2H-pyrido[3,2-b][1,4]oxazin-7-yl)-furo[3,2-b]pyridin-2-yl]-phenyl}-pyrazol-1-yl)-ethanol |
| "A165" | 2-(4-{4-[7-(6-Methoxy-pyridin-3-yl)-furo[3,2-b]pyridin-2-yl]-phenyl}-pyrazol-1-yl)-ethanol |
| "A166" | 2-(4-{4-[7-(5-Methanesulfonyl-pyridin-3-yl)-furo[3,2-b]pyridin-2-yl]-phenyl}-pyrazol-1-yl)-ethanol |
| "B1" | 2,7-Bis-(3,5-difluoro-phenyl)-furo[3,2-b]pyridine |
| "B2" | 4-(2-Phenyl-furo[3,2-b]pyridin-7-yloxy)-phenylamine |
| "B3" | (2H-Indazol-6-yl)-(2-phenyl-furo[3,2-b]pyridin-7-yl)-amine |
| "B4" | [3-Chloro-4-(1-methyl-1H-imidazol-2-ylsulfanyl)-phenyl]-(2-phenyl-furo[3,2-b]pyridin-7-yl)-amine |
| "B5" | (2-Benzyl-2H-indazol-6-yl)-(2-phenyl-furo[3,2-b]pyridin-7-yl)-amine |
| "B6" | 2,7-Bis-(4-fluoro-phenyl)-furo[3,2-b]pyridine |
| "B7" | N-Methyl-N-(3-{[2-(3,4,5-trimethoxy-phenyl)-furo[3,2-b]pyridin-7-ylamino]-methyl}-pyridin-2-yl)-methanesulfonamide |
| "B8" | N-Methyl-2-[2-(3,4,5-trimethoxy-phenyl)-furo[3,2-b]pyridin-7-ylamino]-benzamide |
| "B9" | (3-Methanesulfonyl-benzyl)-[2-(3,4,5-trimethoxy-phenyl)-furo[3,2-b]pyridin-7-yl]-amine |
| "B10" | 2,2-Difluoro-6-[2-(3,4,5-trimethoxy-phenyl)-furo[3,2-b]pyridin-7-ylamino]-4H-benzo[1,4]oxazin-3-one |
| "B11" | 1-(2-Hydroxy-2-methyl-propyl)-5-methyl-3-oxo-2-phenyl-2,3-dihydro-1H-pyrazole-4-carboxylic acid [4-(2-phenyl-furo[3,2-b]pyridin-7-yloxy)-phenyl]-amide |
| "B12" | 1-(4-Fluoro-phenyl)-4-iodo-2-oxo-1,2-dihydro-pyridine-3-carboxylic acid [4-(2-phenyl-furo[3,2-b]pyridin-7-yloxy)-phenyl]-amide |
| "B13" | 1-(4-Fluoro-phenyl)-2-oxo-1,2-dihydro-pyridine-3-carboxylic acid [4-(2-phenyl-furo[3,2-b]pyridin-7-yloxy)-phenyl]-amide |
| "B14" | 4-Ethoxy-1-(4-fluoro-phenyl)-2-oxo-1,2-dihydro-pyridine-3-carboxylic acid [4-(2-phenyl-furo[3,2-b]pyridin-7-yloxy)-phenyl]-amide |
| "B15" | (1H-Indazol-6-yl)-[2-(3,4,5-trimethoxy-phenyl)-furo[3,2-b]pyridin-7-yl]-amine |
| "B16" | [3-Chloro-4-(1-methyl-1H-imidazol-2-ylsulfanyl)-phenyl]-[2-(3,4,5-trimethoxy-phenyl)-furo[3,2-b]pyridin-7-yl]-amine |
| "B17" | 2,2-Difluoro-6-(2-phenyl-furo[3,2-b]pyridin-7-ylamino)-4H-benzo[1,4]oxazin-3-one |
| "B18" | N-Methyl-2-(2-phenyl-furo[3,2-b]pyridin-7-ylamino)-benzamide | and pharmaceutically acceptable solvates, salts, tautomers and stereoisomers thereof, including mixtures thereof in all ratios.

14. A compound according to claim 1, wherein said compound is selected from the following group:

| No. | Name and/or structure |
|---|---|
| "B19" | (3-Methane sulfonyl-benzyl)-(2-phenyl-furo[3,2-b]pyridin-7-yl)-amine |
| "B20" | N-Methyl-N-{3-[(2-phenyl-furo[3,2-b]pyridin-7-ylamino)-methyl]-pyridin-2-yl}-methane sulfonamide |
| "B21" | (4-Methyl-1H-indol-5-yl)-(2-phenyl-furo[3,2-b]pyridin-7-yl)-amine |
| "B22" | (4-Methyl-1H-indol-5-yl)-[2-(3,4,5-trimethoxy-phenyl)-furo[3,2-b]pyridin-7-yl]-amine |
| "B23" | 3-Fluoro-4-(2-phenyl-furo[3,2-b]pyridin-7-yloxy)-phenylamine |
| "B24" | 2,7-Bis-(3,4,5-trimethoxy-phenyl)-furo[3,2-b]pyridine |
| "B25" | 1-(4-Fluoro-phenyl)-2-oxo-1,2-dihydro-pyridine-3-carboxylic acid [3-fluoro-4-(2-phenyl-furo[3,2-b]pyridin-7-yloxy)-phenyl]-amide |
| "B26" | 1-(4-Fluoro-phenyl)-4-iodo-2-oxo-1,2-dihydro-pyridine-3-carboxylic acid [3-fluoro-4-(2-phenyl-furo[3,2-b]pyridin-7-yloxy)-phenyl]-amide |
| "B27" | 4-Ethoxy-1-(4-fluoro-phenyl)-2-oxo-1,2-dihydro-pyridine-3-carboxylic acid [3-fluoro-4-(2-phenyl-furo[3,2-b]pyridin-7-yloxy)-phenyl]-amide |
| "B28" | 1-(4-Fluoro-phenyl)-4-methylamino-2-oxo-1,2-dihydro-pyridine-3-carboxylic acid [3-fluoro-4-(2-phenyl-furo[3,2-b]pyridin-7-yloxy)-phenyl]-amide |
| "B29" | 2,2-Dimethyl-6-[2-(3,4,5-trimethoxy-phenyl)-furo[3,2-b]pyridin-7-ylamino]-4H-pyrido[3,2-b][1,4]oxazin-3-one |
| "B30" | (1H-Indol-5-yl)-[2-(3,4,5-trimethoxy-phenyl)-furo[3,2-b]pyridin-7-yl]-amine |
| "B31" | 2,7-Di-p-tolyl-furo[3,2-b]pyridine |
| "B32" | 2,7-Bis-(4-methoxy-3,5-dimethyl-phenyl)-furo[3,2-b]pyridine |
| "B33" | 2,7-Bis-(4-methoxy-3-methyl-phenyl)-furo[3,2-b]pyridine |
| "B34" | 2,7-Di-m-tolyl-furo[3,2-b]pyridine |
| "B35" | 2,7-Bis-(4-methoxy-phenyl)-furo[3,2-b]pyridine |
| "B36" | 2,7-Bis-benzo[1,3]dioxol-5-yl-furo[3,2-b]pyridine |
| "B37" | 2,7-Bis-(2,3-dihydro-benzo[1,4]dioxin-6-yl)-furo[3,2-b]pyridine |
| "B38" | 2,7-Bis-(3,5-dimethyl-phenyl)-furo[3,2-b]pyridine |
| "B39" | 2,7-Bis-(3,4-dimethoxy-phenyl)-furo[3,2-b]pyridine |
| "B40" | 2,7-Bis-(2,3,4-trimethoxy-phenyl)-furo[3,2-b]pyridine |
| "B41" | 2,7-Bis-(3,5-dimethyl-isoxazol-4-yl)-furo[3,2-b]pyridine |
| "B42" | 2,7-Bis-(2,3-dimethoxy-phenyl)-furo[3,2-b]pyridine |
| "B43" | 2,7-Bis-(3-methoxy-phenyl)-furo[3,2-b]pyridine |
| "B44" | {4-[2-(4-Hydroxymethyl-phenyl)-furo[3,2-b]pyridin-7-yl]-phenyl}-methanol |

15. A compound according to claim 1, wherein said compound is selected from the following group:

| No. | Name and/or structure |
|---|---|
| "B45" | 2-(4-{2-[4-(1-Hydroxy-1-methyl-ethyl)-phenyl]-furo[3,2-b]pyridin-7-yl}-phenyl)-propan-2-ol |
| "B46" | (4-Methyl-1H-indol-5-yl)-(2-p-tolyl-furo[3,2-b]pyridin-7-yl)-amine |
| "B47" | [2-(4-Methoxy-phenyl)-furo[3,2-b]pyridin-7-yl]-(4-methyl-1H-indol-5-yl)-amine |
| "B48" | (2-Benzo[1,3]dioxol-5-yl-furo[3,2-b]pyridin-7-yl)-(4-methyl-1H-indol-5-yl)-amine |
| "B49" | [2-(4-Methoxy-3,5-dimethyl-phenyl)-furo[3,2-b]pyridin-7-yl]-(4-methyl-1H-indol-5-yl)-amine |
| "B50" | [2-(4-Methoxy-3-methyl-phenyl)-furo[3,2-b]pyridin-7-yl]-(4-methyl-1H-indol-5-yl)-amine |
| "B51" | (4-Methyl-1H-indol-5-yl)-(2-m-tolyl-furo[3,2-b]pyridin-7-yl)-amine |
| "B52" | [2-(3,5-Dimethyl-phenyl)-furo[3,2-b]pyridin-7-yl]-(4-methyl-1H-indol-5-yl)-amine |
| "B53" | [2-(3,4-Dimethoxy-phenyl)-furo[3,2-b]pyridin-7-yl]-(4-methyl-1H-indol-5-yl)-amine |
| "B54" | (4-Methyl-1H-indol-5-yl)-[2-(4-morpholin-4-yl-phenyl)-furo[3,2-b]pyridin-7-yl]-amine |
| "B55" | 2-(4-{2-[4-(Cyano-dimethyl-methyl)-phenyl]-furo[3,2-b]pyridin-7-yl}-phenyl)-2-methyl-propionitrile |
| "B56" | (4-Methyl-1H-indol-5-yl)-[2-(2,3,4-trimethoxy-phenyl)-furo[3,2-b]pyridin-7-yl]-amine |
| "B57" | [2-(3-Methoxy-phenyl)-furo[3,2-b]pyridin-7-yl]-(4-methyl-1H-indol-5-yl)-amine |
| "B58" | 12-[4-(3-Dimethylamino-propoxy)-phenyl]-furo[3,2-b]pyridin-7-yl}-(4-methyl-1H-indol-5-yl)-amine |
| "B59" | [2-(2,3-Dimethoxy-phenyl)-furo[3,2-b]pyridin-7-yl]-(4-methyl-1H-indol-5-yl)-amine |
| "B60" | [2-(2,3-Dihydro-benzo[1,4]dioxin-6-yl)-furo[3,2-b]pyridin-7-yl]-(4-methyl-1H-indol-5-yl)-amine |
| "B61" | {4-[7-(4-Methyl-1H-indol-5-ylamino)-furo[3,2-b]pyridin-2-yl]-phenyl}-methanol |
| "B62" | [2-(4-Isopropenyl-phenyl)-furo[3,2-b]pyridin-7-yl]-(4-methyl-1H-indol-5-yl)-amine |
| "B63" | [2-(3,5-Dimethyl-isoxazol-4-yl)-furo[3,2-b]pyridin-7-yl]-(4-methyl-1H-indol-5-yl)-amine |
| "B64" | N-(4-Fluoro-phenyl)-3-[2-(3,4,5-trimethoxy-phenyl)-furo[3,2-b]pyridin-7-yl]-benzamide |
| "B65" | N-{4-[2-(3,4,5-Trimethoxy-phenyl)-furo[3,2-b]pyridin-7-yl]-phenyl}-benzamide |
| "B66" | N-Phenyl-4-[2-(3,4,5-trimethoxy-phenyl)-furo[3,2-b]pyridin-7-yl]-benzamide |
| "B67" | (4-Methyl-piperazin-1-yl)-14-[2-(3,4,5-trimethoxy-phenyl)-furo[3,2-b]pyridin-7-yl]-phenyl}-methanone |
| "B68" | (4-Methyl-piperazin-1-yl)-13-[2-(3,4,5-trimethoxy-phenyl)-furo[3,2-b]pyridin-7-yl]-phenyl}-methanone |
| "B69" | 2-Fluoro-N-(2-hydroxy-ethyl)-4-[2-(3,4,5-trimethoxy-phenyl)-furo[3,2-b]pyridin-7-yl]-benzamide |
| "B70" | 1-{5-[2-(3,4,5-Trimethoxy-phenyl)-furo[3,2-b]pyridin-7-yl]-thiophen-2-yl}-ethanone |
| "B71" | 6-(2-(3,4,5-Trimethoxyphenyl)furo[3,2-b]pyridin-7-yl)indolin-2-one |
| "B72" | N-(3-(2-(3,4,5-Trimethoxyphenyl)furo[3,2-b]pyridin-7-yl)phenyl)acetamide |
| "B73" | 7-(4-Methoxy-3,5-dimethylphenyl)-2-(3,4,5-trimethoxyphenyl)furo[3,2-b]pyridine |
| "B74" | 7-(1H-Indol-5-yl)-2-(3,4,5-trimethoxyphenyl)furo[3,2-b]pyridine |
| "B75" | N-Cyclopentyl-4-(2-(3,4,5-trimethoxyphenyl)furo[3,2-b]pyridin-7-yl)benzamide |
| "B76" | 7-(Benzo[d][1,3]dioxol-5-yl)-2-(3,4,5-trimethoxyphenyl)furo[3,2-b]pyridin |
| "B77" | 7-(6-Methoxynaphthalen-2-yl)-2-(3,4,5-trimethoxyphenyl)furo[3,2-b]pyridine |
| "B78" | 7-(Benzo[b]thiophen-2-yl)-2-(3,4,5-trimethoxyphenyl)furo[3,2-b]pyridine | and pharmaceutically acceptable solvates, salts, tautomers and stereoisomers thereof, including mixtures thereof in all ratios.

16. A compound according to claim 1, wherein said compound is selected from the following group:

| No. | Name and/or structure |
|---|---|
| "B79" | 3-[7-(4-Phenoxyphenoxy)furo[3,2-b]pyridin-2-yl]aniline |
| "B80" | N-{3-[7-(4-Phenoxyphenoxy)furo[3,2-b]pyridin-2-yl]phenyl}propanamide |
| "B81" | N-{3-[2-(3,4-Dimethoxyphenyl)furo[3,2-b]pyridin-7-yl]-2-methylphenyl}-3-(trifluoromethyl)benzamide |
| "B82" | N-{3-[7-(4-Phenoxyphenoxy)furo[3,2-b]pyridin-2-yl]phenyl}acrylamide |
| "B83" | N-{3-[2-(3,4-Dimethoxyphenyl)furo[3,2-b]pyridin-7-yl]-2-methylphenyl}-4,5,6,7-tetrahydro-1-benzothiophene-2-carboxamide |
| "B84" | 4-tert.-Butyl-N-13-[2-(3,4-dimethoxyphenyl)furo[3,2-b]pyridin-7-yl]-2-methylphenyl}benzamide |
| "B85" | N-{3-[7-(4-Phenoxyphenoxy)furo[3,2-b]pyridin-2-yl]phenyl}but-2-ynamide |
| "B86" | 4-tert.-Butyl-N-(2-methyl-3-{2-[4-(pyrrolidin-1-ylcarbonyl)phenyl]furo[3,2-b]pyridin-7-yl}phenyl)benzamide |
| "B87" | N-(2-Methyl-3-{2-[4-(pyrrolidin-1-ylcarbonyl)phenyl]furo[3,2-b]pyridin-7-yl}phenyl)-4,5,6,7-tetrahydro-1-benzothiophene-2-carboxamide |
| "B88" | (2E)-N-{3-[7-(4-phenoxyphenoxy)furo[3,2-b]pyridin-2-yl]phenyl}but-2-enamide |
| "B89" | (2E)-4-(Dimethylamino)-N-{3-[7-(4-phenoxyphenoxy)furo[3,2-b]pyridin-2-yl]phenyl}but-2-enamide |
| "B90" | 2-Methyl-N-{3-[7-(4-phenoxyphenoxy)furo[3,2-b]pyridin-2-yl]phenyl}acrylamide |
| "C1" | 3-(7-Phenyl-furo[3,2-b]pyridin-2-yl)-phenol |
| "C2" | 7-(2,6-Dimethoxy-phenyl)-2-(3,4,5-trimethoxy-phenyl)-furo[3,2-b]pyridine |
| "C3" | 7-Phenyl-2-(3-trifluoromethyl-phenyl)-furo[3,2-b]pyridine |
| "C4" | N-(2-Dimethylamino-ethyl)-3-[2-(1-methyl-1H-pyrazol-4-yl)-furo[3,2-b]pyridin-7-yl]-benzamide |
| "C5" | N-(2-Hydroxy-ethyl)-3-[2-(3,4,5-trimethoxy-phenyl)-furo[3,2-b]pyridin-7-yl]-benzamide |
| "C6" | 2-(1-Isobutyl-1H-pyrazol-4-yl)-7-(1-methyl-1H-pyrazol-4-yl)-furo[3,2-b]pyridine |
| "C7" | 2-({3-[2-(3,4,5-Trimethoxy-phenyl)-furo[3,2-b]pyridin-7-yl]-benzoylamino}-methyl)-pyrrolidine-1-carboxylic acid tert-butyl ester |
| "C8" | N-Methyl-2-{3-[2-(3,4,5-trimethoxy-phenyl)-furo[3,2-b]pyridin-7yll-phenoxy}-acetamide |
| "C9" | 2-(3-tert.-Butyl-5-methyl-phenyl)-7-(1-methyl-1H-pyrazol-4-yl)-furo[3,2-b]pyridine |
| "C10" | N-(1H-Pyrazol-3-ylmethyl)-3-[2-(3,4,5-trimethoxy-phenyl)-furo[3,2-b]pyridin-7-yl]-benzamide |
| "C11" | N-Pyrrolidin-2-ylmethyl-3-[2-(3,4,5-trimethoxy-phenyl)-furo[3,2-b]pyridin-7-yl]-benzamide |
| "C12" | N-(5-Oxo-4,5-dihydro-1H-[1,2,4]triazol-3-ylmethyl)-3-[2-(3,4,5-trimethoxy-phenyl)-furo[3,2-b]pyridin-7-yl]-benzamide |
| "C13" | 7-Pyridin-3-yl-2-(3,4,5-trimethoxy-phenyl)-furo[3,2-b]pyridine |
| "C14" | 7-(2-Isopropyl-phenyl)-2-(3,4,5-trimethoxy-phenyl)-furo[3,2-b]pyridine |
| "C15" | 2-(3-Methoxy-phenyl)-7-phenyl-furo[3,2-b]pyridine |
| "C16" | 2-(2-Methoxy-pyridin-4-yl)-7-(1-methyl-1H-pyrazol-4-yl)-furo[3,2-b]pyridine |
| "C17" | 2-(2,3-Dihydro-benzo[1,4]dioxin-6-yl)-7-(1-methyl-1H-pyrazol-4-yl)-furo[3,2-b]pyridine |
| "C18" | 2-(1H-Indol-5-yl)-7-(1-methyl-1H-pyrazol-4-yl)-furo[3,2-b]pyridine | and pharmaceutically acceptable solvates, salts, tautomers and stereoisomers thereof, including mixtures thereof in all ratios.

17. A compound according to claim 1, wherein said compound is selected from the following group:

| No. | Name and/or structure |
|---|---|
| "C19" | 2-(1H-Indol-6-yl)-7-(1-methyl-1H-pyrazol-4-yl)-furo[3,2-b]pyridine |
| "C20" | 2-(3-Benzyloxy-phenyl)-7-(1-methyl-1H-pyrazol-4-yl)-furo[3,2-b]pyridine |
| "C22" | 2-(3,5-Dimethyl-isoxazol-4-yl)-7-(1-methyl-1H-pyrazol-4-yl)-furo[3,2-b]pyridine |
| "C23" | 7-(6-Fluoro-4-methyl-pyridin-3-yl)-2-(3,4,5-trimethoxy-phenyl)-furo[3,2-b]pyridine |
| "C24" | 7-(1-Methyl-1H-pyrazol-4-yl)-2-(6-morpholin-4-yl-pyridin-3-yl)-furo[3,2-b]pyridine |
| "C25" | 2-(6-Morpholin-4-yl-pyridin-3-yl)-7-phenyl-furo[3,2-b]pyridine |
| "C26" | 2-Methoxy-4-(7-(1-methyl-1H-pyrazol-4-yl)-furo[3,2-b]pyridin-2-yl]-phenol |
| "C27" | {5-[2-(3,4,5-Trimethoxy-phenyl)-furo[3,2-b]pyridin-7-yl]-pyridin-2-yl}-methanol |
| "C28" | 7-[6-(Tetrahydro-pyran-4-yloxy)-pyridin-3-yl]-2-(3,4,5-trimethoxy-phenyl)-furo[3,2-b]pyridine |
| "C29" | 3-[7-(1-Methyl-1H-pyrazol-4-yl)-furo[3,2-b]pyridin-2-yl]-phenylamine |
| "C30" | (S)-Pyrrolidine-2-carboxylic acid[2-methoxy-5-(7-phenyl-furo[3,2-b]pyridin-2-yl)-phenyl]-amide |
| "C31" | (S)-Pyrrolidine-2-carboxylic acid[3-(7-phenyl-furo[3,2-b]pyridin-2-yl)-phenyl]-amide |
| "C32" | 7-(1-Methyl-1H-pyrazol-4-yl)-2-(4-trifluoromethoxy-phenyl)-furo[3,2-b]pyridine |
| "C33" | 2-(4-Methoxy-phenyl)-7-(1-methyl-1H-pyrazol-4-yl)-furo[3,2-b]pyridine |
| "C34" | 2-(4-Methanesulfonyl-phenyl)-7-(1-methyl-1H-pyrazol-4-yl)-furo[3,2-b]pyridine |
| "C35" | (S)-Pyrrolidine-2-carboxylic acid{3-[7-(1-methyl-1H-pyrazol-4-yl)-furo[3,2-b]pyridin-2-yl]-phenyl}-amide |
| "C36" | 7-(1-Methyl-1H-pyrazol-4-yl)-2-[4-(2-piperidin-1-yl-ethoxy)-phenyl]-furo[3,2-b]pyridine |
| "C37" | 1-{4-[7-(1-Methyl-1H-pyrazol-4-yl)-furo[3,2-b]pyridin-2-yl]-phenoxy}-3-morpholin-4-yl-propan-2-ol |
| "C38" | 1-{4-[7-(1-Methyl-1H-pyrazol-4-yl)-furo[3,2-b]pyridin-2-yl]-phenoxy}-3-piperidin-1-yl-propan-2-ol |
| "C39" | 2-(6-Morpholin-4-yl-pyridin-3-yl)-7-pyridin-3-yl-furo[3,2-b]pyridine |
| "C40" | (2S,4R)-4-Hydroxy-pyrrolidine-2-carboxylic acid[2-methoxy-5-(7-phenyl-furo[3,2-b]pyridin-2-yl)-phenyl]-amide |
| "C41" | 7-(6-Methoxy-pyridin-3-yl)-2-(3,4,5-trimethoxy-phenyl)-furo[3,2-b]pyridine |
| "C42" | 2-(1-Benzyl-1H-pyrazol-4-yl)-7-(1-methyl-1H-pyrazol-4-yl)-furo[3,2-b]pyridine |
| "C43" | {3-[7-(1-Methyl-1H-pyrazol-4-yl)-furo[3,2-b]pyridin-2-yl]phenyl}-methanol |
| "C44" | Dimethyl-(3-{4-[7-(1-methyl-1H-pyrazol-4-yl)-furo[3,2-b]pyridin-2-yl]-phenoxy}-propyl)-amine |
| "C45" | 2-(3-Isopropyl-phenyl)-7-(1-methyl-1H-pyrazol-4-yl)-furo[3,2-b]pyridine |
| "C46" | (2S,4R)-4-Hydroxy-pyrrolidine-2-carboxylic acid[3-methoxy-5-(7-phenyl-furo[3,2-b]pyridin-2-yl)-phenyl]-amide |
| "C47" | (S)-Pyrrolidine-2-carboxylic acid[3-methoxy-5-(7-phenyl-furo[3,2-b]pyridin-2-yl)-phenyl]-amide |
| "C48" | 2-(4-Morpholin-4-yl-phenyl)-7-pyridin-3-yl-furo[3,2-b]pyridine |
| "C49" | 7-(1-Methyl-1H-pyrazol-4-yl)-2-(4-morpholin-4-yl-phenyl)-furo[3,2-b]pyridine | and pharmaceutically acceptable solvates, salts, tautomers and stereoisomers thereof, including mixtures thereof in all ratios.

18. A compound according to claim 1, wherein said compound is selected from the following group:

| No. | Name and/or structure |
|---|---|
| "C50" | 2-(4-Morpholin-4-yl-phenyl)-7-phenyl-furo[3,2-b]pyridine |
| "C51" | 2-[4-(2-Imidazol-1-yl-ethoxy)-phenyl]-7-(1-methyl-1H-pyrazol-4-yl)-furo[3,2-b]pyridine |
| "C52" | 2-(4-Difluoromethoxy-phenyl)-7-(1-methyl-1H-pyrazol-4-yl)-furo[3,2-b]pyridine |
| "C53" | 4-[2-(3,4,5-Trimethoxy-phenyl)-furo[3,2-b]pyridin-7-yl]-1,3-dihydro-indol-2-one |
| "C54" | 2-(4-Methanesulfinyl-phenyl)-7-(1-methyl-1H-pyrazol-4-yl)-furo[3,2-b]pyridine |
| "C55" | 7-(1-Methyl-1H-pyrazol-4-yl)-2-(3,4,5-trifluoro-phenyl)-furo[3,2-b]pyridine |
| "C56" | 5-[2-(3,4,5-Trimethoxy-phenyl)-furo[3,2-b]pyridin-7-yl]-1,3-dihydro-benzoimidazol-2-one |
| "C57" | 3-Methoxy-5-(7-phenyl-furo[3,2-b]pyridin-2-yl)-phenylamine |
| "C58" | 7-(1-Benzyl-1H-pyrazol-4-yl)-2-(3,4,5-trimethoxy-phenyl)-furo[3,2-b]pyridine |
| "C59" | {4-[7-(1-Methyl-1H-pryzol-4-yl)-furo[3,2-b]pyridin-2-yl]-phenyl}-methanol |
| "C60" | 7-(1H-Benzoimidazol-5-yl)-2-(3,4,5-trimethoxy-phenyl)-furo[3,2-b]pyridine |
| "C61" | 5-[7-(1-Methyl-1H-pyrazol-4-yl)-furo[3,2-b]pyridin-2-yl]-benzo[1,2,5]thiadiazole |
| "C62" | (2-{Methoxy-4-[7-(1-methyl-1H-pyrazol-4-yl)-furo[3,2-b]pyridin-2-yl]-phenoxy}-ethyl)-carbamic acid tert-butyl ester |
| "C63" | 2-{2-Methoxy-4-[7-(1-methyl-1H-pyrazol-4-yl)-furo[3,2-b]pyridin-2-yl]-phenoxy}-ethylamine |
| "C64" | 7-(2-Methyl-2H-pyrazol-3-yl)-2-(3,4,5-trimethoxy-phenyl)-furo[3,2-b]pyridine |
| "C65" | Dimethyl-(2-{4-[7-(1-methyl-1H-pyrazol-4-yl)-furo[3,2-b]pyridin 2-yl]-phenoxy}-ethyl)-amine |
| "C66" | 1-Methoxy-3-{4-[2-(3,4,5-trimethoxy-phenyl)-furo[3,2-b]pyridin-7-yl]-pyrazol-1-yl}-propan-2-ol |
| "C67" | 2-(1-Methyl-1H-indazol-5-yl)-7-(1-methyl-1H-pyrazol-4-yl)-furo[3,2-b]pyridine |
| "C68" | 7-(3,6-Dihydro-2H-pyran-4-yl)-2-(3,4,5-trimethoxy-phenyl)-furo[3,2-b]pyridine |
| "C69" | 5-[2-(3,4,5-Trimethoxy-phenyl)-furo[3,2-b]pyridin-7-yl]-1H-pyrimidine-2,4-dione |
| "C70" | 5-[2-(3,4,5-Trimethoxy-phenyl)-furo[3,2-b]pyridin-7-yl]-1H-benzotriazole |
| "C71" | 4-[2-(3,4,5-Trimethoxy-phenyl)-furo[3,2-b]pyridin-7-yl]-benzene-1,2-diamine |
| "C72" | 7-(1H-Pyrazol-4-yl)-2-(3,4,5-trimethoxy-phenyl)-furo[3,2-b]pyridine |
| "C73" | 7-(1H-Pyrazol-3-yl)-2-(3,4,5-trimethoxy-phenyl)-furo[3,2-b]pyridine |
| "C74" | 2-{4-[2-(3,4,5-Trimethoxy-phenyl)-furo[3,2-b]pyridin-7-yl]-pyrazol-1-yl}-ethanol |
| "C75" | 4-Methyl-5-[2-(3,4,5-trimethoxy-phenyl)-furo[3,2-b]pyridin-7-yl]-pyridin-2-ylamine |
| "C76" | 5-[2-(3,4,5-Trimethoxy-phenyl)-furo[3,2-b]pyridin-7-yl]-benzoimidazol-2-ylamine |
| "C77" | N1-{5-[2-(3,4,5-Trimethoxy-phenyl)-furo[3,2-b]pyridin-7-yl]-1H-benzoimidazol-2-yl}-ethane-1,2-diamine |
| "C78" | 7-Piperidin-4-yl-2-(3,4,5-trimethoxy-phenyl)-furo[3,2-b]pyridine |
| "C79" | Dimethyl-{4-[2-(3,4,5-trimethoxy-phenyl)-furo[3,2-b]pyridin-7-yl]-thiazol-2-yl}-amine | and pharmaceutically acceptable solvates, salts, tautomers and stereoisomers thereof, including mixtures thereof in all ratios.

19. A compound according to claim 1, wherein said compound is selected from the following group:

| No. | Name and/or structure |
|---|---|
| "C80" | 2-{4-[2-(3,4,5-Trimethoxy-phenyl)-furo[3,2-b]pyridin-7-yl]-piperidin-1-yl}-ethanol |
| "C81" | 2,7-Bis-(1-methyl-1H-pyrazol-4-yl)-furo[3,2-b]pyridine |
| "C82" | 1-{3-[7-(1-Methyl-1H-pyrazol-4-yl)-furo[3,2-b]pyridin-2-yl]-phenyl}-ethanone |
| "C83" | 2-(1-Methyl-1H-benzoimidazol-5-yl)-7-(1-methyl-1H-pyrazol-4-yl)-furo[3,2-b]pyridine |
| "C84" | 7-(3,5-Dimethyl-1H-pyrazol-4-yl)-2-(3,4,5-trimethoxy-phenyl)-furo[3,2-b]pyridine |
| "C85" | 2-[2-(3,4,5-Trimethoxy-phenyl)-furo[3,2-b]pyridin-7-yl]-phenol |
| "C86" | 7-[2-(5-Methyl-isoxazol-3-yl)-1H-benzoimidazol-5-yl]-2-(3,4,5-trimethoxy-phenyl)-furo[3,2-b]pyridine |

| No. | Name and/or structure |
|---|---|
| "C87" | 2-(3-Methanesulfonyl-phenyl)-7-(1-methyl-1H-pyrazol-4-yl)-furo[3,2-b]pyridine |
| "C88" | 7-(1-Methyl-1H-pyrazol-4-yl)-2-(3-pyrazol-1-yl-phenyl)-furo[3,2-b]pyridine |
| "C89" | 3-Hydroxy-5-[2-(3,4,5-trimethoxy-phenyl)-furo[3,2-b]pyridin-7-yl]-benzoic acid methyl ester |
| "C90" | 7-[2-(1H-Pyrazol-4-yl)-1H-benzoimidazol-5-yl]-2-(3,4,5-trimethoxy-phenyl)-furo[3,2-b]pyridine |
| "C91" | 1-{4-[7-(4-Acetyl-phenyl)-furo[3,2-b]pyridin-2-yl]-phenyl}-ethanone |
| "C92" | 2-{3-[7-(1-Methyl-1H-pyrazol-4-yl)-furo[3,2-b]pyridin-2-yl]-phenyl}-propan-2-ol |
| "C93" | 7-Biphenyl-2-yl-2-(3,4,5-trimethoxy-phenyl)-furo[3,2-b]pyridine |
| "C94" | 7-(2,6-Dimethyl-phenyl)-2-(3,4,5-trimethoxy-phenyl)-furo[3,2-b]pyridine |
| "C95" | 1-{4-[7-(1-Methyl-1H-pyrazol-4-yl)-furo[3,2-b]pyridin-2-yl]-phenyl}-ethanone |
| "C96" | 2,7-Bis-[2-(4-methyl-piperazin-1-yl)-pyridin-4-yl]-furo[3,2-b]pyridine |
| "C97" | 7-Furan-2-yl-2-(3,4,5-trimethoxy-phenyl)-furo[3,2-b]pyridine |
| "C98" | 2-(1-Methyl-1H-indazol-6-yl)-7-(1-methyl-1H-pyrazol-4-yl)-furo[3,2-b]pyridine |
| "C100" | 2-{4-[7-(1-Methyl-1H-pyrazol-4-yl)-furo[3,2-b]pyridin-2-yl]-phenyl}-propan-2-ol |
| "C101" | 7-(3-Piperazin-1-yl-phenyl)-2-(3,4,5-trimethoxy-phenyl)-furo[3,2-b]pyridine |
| "C102" | 7-(2-Morpholin-4-yl-phenyl)-2-(3,4,5-trimethoxy-phenyl)-furo[3,2-b]pyridine |
| "C103" | N-{2-[2-(3,4,5-Trimethoxy-phenyl)-furo[3,2-b]pyridin-7-yl]-phenyl}-acetamide |
| "C104" | 7-[3-(4-Methyl-piperazin-1-yl)-phenyl]-2-(3,4,5-trimethoxy-phenyl)-furo[3,2-b]pyridine |
| "C105" | 7-(1H-Pyrrol-2-yl)-2-(3,4,5-trimethoxy-phenyl)-furo[3,2-b]pyridine |
| "C106" | 3-Hydroxy-5-[2-(3,4,5-trimethoxy-phenyl)-furo[3,2-b]pyridin-7-yl]-benzamide |
| "C107" | N-((1R,2S)-2-Amino-cyclohexyl)-3-[2-(3,4,5-trimethoxy-phenyl)-furo[3,2-b]pyridin-7-yl]-benzamide |
| "C108" | 7-(4-Methoxy-2-pyrazol-1-yl-phenyl)-2-(3,4,5-trimethoxy-phenyl)-furo[3,2-b]pyridine |
| "C109" | 7-(1-Methyl-1H-pyrazol-4-yl)-2-(1H-pyrazol-4-yl)-furo[3,2-b]pyridine |
| "C110" | 7-(3-Methanesulfonyl-phenyl)-2-(3,4,5-trimethoxy-phenyl)-furo[3,2-b]pyridine | and pharmaceutically acceptable solvates, salts, tautomers and stereoisomers thereof, including mixtures thereof in all ratios.

20. A compound according to claim 1, wherein said compound is selected from the following group:

| No. | Name and/or structure |
|---|---|
| "C111" | 7-[1-(2-Morpholin-4-yl-ethyl)-1H-pyrazol-4-yl]-2-(3,4,5-trimethoxy-phenyl)-furo[3,2-b]pyridine |
| "C112" | 7-Chloro-2-(1H-indazol-6-yl)-furo[3,2-b]pyridine |
| "C113" | 6-[2-(3,4,5-Trimethoxy-phenyl)-furo[3,2-b]pyridin-7-yl]-3,4-dihydro-2H-pyrano[2,3-b]pyridine |
| "C114" | 5-[7-(1-Methyl-1H-pyrazol-4-yl)-furo[3,2-b]pyridin-2-yl]-pyridin-2-ylamine |
| "C115" | 2-[2-(4-Methyl-piperazin-1-yl)-pyridin-4-yl]-7-(1-methyl-1H-pyrazol-4-yl)-furo[3,2-b]pyridine |
| "C116" | 6-[2-(3,4,5-Trimethoxy-phenyl)furo[3,2-b]pyridin-7-yl]-1,2,3,4-tetrahydro-[1,8]naphthuridine |
| "C117" | 4-[7-(1-Methyl-1H-pyrazol-4-yl)-furo[3,2-b]pyridin-2-yl]-pyridin-2-ylamine |
| "C118" | 7-(1-Methyl-1H-pyrazol-4-yl)-2-[3-(pyridin-4-ylmethoxy)-phenyl]-furo[3,2-b]pyridine |
| "C119" | 7-(2-Fluoro-6-methoxy-phenyl)-2-(3,4,5-trimethoxy-phenyl)-furo[3,2-b]pyridine |
| "C120" | Dimethyl-{2-[2-(3,4,5-trimethoxy-phenyl)-furo[3,2-b]pyridin-7-yl]-phenyl}-amine |
| "C121" | N,N-Dimethyl-3-[2-(3,4,5-trimethoxy-phenyl)-furo[3,2-b]pyridin-7-yl]-benzenesulfonamide |
| "C122" | 2-{2-[2-(3,4,5-Trimethoxy-phenyl)-furo[3,2-b]pyridin-7-yl]-phenoxy}-ethylamine |
| "C123" | 2-(3H-Benzoimidazol-5-yl)-7-(1-methyl-1H-pyrazol-4-yl)-furo[3,2-b]pyridine |
| "C124" | 7-(4-Methanesulfinyl-phenyl)-2-(3,4,5-trimethoxy-phenyl)-furo[3,2-b]pyridine |
| "C125" | 7-(1-Piperidin-4-yl-1H-pyrazol-4-yl)-2-(3,4,5-trimethoxy-phenyl)-furo[3,2-b]pyridine |
| "C126" | 7-(5-Methyl-3-phenyl-isoxazol-4-yl)-2-(3,4,5-trimethoxy-phenyl)-furo[3,2-b]pyridine |
| "C127" | 7-(3-Methyl-1H-pyrazol-4-yl)-2-(3,4,5-trimethoxy-phenyl)-furo[3,2-b]pyridine |
| "C128" | 7-(3,5-Dimethyl-isoxazol-4-yl)-2-(3,4,5-trimethoxy-phenyl)-furo[3,2-b]pyridine |
| "C129" | 3-Methoxy-5-[7-(1-methyl-1H-pyrazol-4-yl)-furo[3,2-b]pyridin-2-yl]-phenylamine |
| "C130" | 7-Piperidin-1-yl-2-(3,4,5-trimethoxy-phenyl)-furo[3,2-b]pyridine |
| "C131" | N'-{3-Methoxy-5-[7-(1-methyl-1H-pyrazol-4-yl)-furo[3,2-b]pyridin-2-yl]-phenyl}-N,N-dimethyl-ethane-1,2-diamine |
| "C132" | 2-{1-[2-(3,4,5-Trimethoxy-phenyl)-furo[3,2-b]pyridin-7-yl]-piperidin-3-yl}-ethanol |
| "C133" | 2-(1H-Indazol-6-yl)-7-(1-methyl-1H-pyrazol-4-yl)-furo[3,2-b]pyridine |
| "C135" | 7-(2,6-Dimethoxy-phenyl)-2-(1-methyl-1H-indazol-5-yl)-furo[3,2-b]pyridine |
| "C136" | 4-Methoxy-3-[2-(3,4,5-trimethoxy-phenyl)-furo[3,2-b]pyridin-7-yl]-phenol |
| "C137" | 7-(1H-Indazol-5-yl)-2-(3,4,5-trimethoxy-phenyl)-furo[3,2-b]pyridine |
| "C138" | 4-Methoxy-3-[2-(3,4,5-trimethoxy-phenyl)-furo[3,2-b]pyridin-7-yl]-benzoic acid methyl ester |
| "C139" | C-{1-[2-(3,4,5-Trimethoxy-phenyl)-furo[3,2-b]pyridin-7-yl]piperidin-3-yl}-methylamine |
| "C140" | 2-(2,5-Dimethoxy-phenyl)-7-(1-methyl-1H-pyrazol-4-yl)-furo[3,2-b]pyridine |
| "C141" | 2,7-Bis-(2,5-dimethoxy-phenyl)-furo[3,2-b]pyridine | and pharmaceutically acceptable solvates, salts, tautomers and stereoisomers thereof, including mixtures thereof in all ratios.

21. A compound according to claim 1, wherein said compound is selected from the following group:

| No. | Name and/or structure |
|---|---|
| "C142" | 4-Methoxy-3-[2-(3,4,5-trimethoxy-phenyl)-furo[3,2-b]pyridin-7-yl]-benzoic acid |
| "C143" | N-(2-Amino-ethyl)-4-methoxy-3-[2-(3,4,5-trimethoxy-phenyl)-furo[3,2-b]pyridin-7-yl]-benzamide |
| "C144" | 2-{4-Methoxy-3-[3-(3,4,5-trimethoxy-phenyl)-furo[3,2-b]pyridin-7-yl]-phenoxy}-ethylamine |
| "C145" | 4-Methoxy-3-[2-(3,4,5-trimethoxy-phenyl)-furo[3,2-b]pyridin-7-yl]-benzamide |
| "C146" | N-{4-[2-(3,4,5-Trimethoxy-phenyl)-furo[3,2-b]pyridin-2-yl]-cyclohexane-1,2-diamine |
| "C147" | 7-[2-(2-Methoxy-ethoxy)-pyridin-4-yl]-2-(3,4,5-trimethoxy-phenyl)-furo[3,2-b]pyridine |
| "C148" | N-(2-Amino-cyclohexyl)-4-methoxy-3-[2-(3,4,5-trimethoxy-phenyl)-furo[3,2-b]pyridin-7-yl]-benzamide |
| "C149" | N-(2-Amino-ethyl)-3-hydroxy-5-[2-(3,4,5-trimethoxy-phenyl)-furo[3,2-b]pyridin-7-yl]-benzamide |
| "C150" | 3-Cyclopropylmethoxy-5-[2-(3,4,5-trimethoxy-phenyl)-furo[3,2-b]pyridin-7-yl]-benzoic acid methyl ester |
| "C151" | 3-Isopropoxy-5-[2-(3,4,5-trimethoxy-phenyl)-furo[3,2-b]pyridin-7-yl]-benzoic acid methyl ester |
| "C152" | N-((1R,2S)-2-Amino-cyclohexyl)-4-methoxy-3-[2-(3,4,5-trimethoxy-phenyl)-furo[3,2-b]pyridin-7-yl]-benzamide |
| "C153" | 7-(2-Fluoro-6-phenoxy-phenyl)-2-(3,4,5-trimethoxy-phenyl)-furo[3,2-b]pyridine |
| "C154" | 3-Methoxy-5-[2-(3,4,5-trimethoxy-phenyl)-furo[3,2-b]pyridin-7-yl]-benzoic acid |

| No. | Name and/or structure |
|---|---|
| "C155" | 3-Isopropoxy-5-[2-(3,4,5-trimethoxy-phenyl)-furo[3,2-b]pyridin-7-yl]-benzoic acid |
| "C156" | 3-Cyclopropylmethoxy-5-[2-(3,4,5-trimethoxy-phenyl)-furo[3,2-b]pyridin-7-yl]-benzoic acid |
| "C157" | 7-(2-Ethoxy-6-fluoro-phenyl)-2-(3,4,5-trimethoxy-phenyl)-furo[3,2-b]pyridine |
| "C158" | 7-(2-Benzyloxy-6-fluoro-phenyl)-2-(3,4,5-trimethoxy-phenyl)-furo[3,2-b]pyridine |
| "C159" | 3-Trifluoromethoxy-5-[2-(3,4,5-trimethoxy-phenyl)-furo[3,2-b]pyridin-7-yl]-benzoic acid methyl ester |
| "C160" | 3-Trifluoromethyl-5-[2-(3,4,5-trimethoxy-phenyl)-furo[3,2-b]pyridin-7-yl]-benzoic acid methyl ester |
| "C161" | ((1S,2R)-2-{3-Methoxy-5-[2-(3,4,5-trimethoxy-phenyl)-furo[3,2-b]pyridin-7-yl]-benzoylamino}-cyclohexyl)-carbamic acid tert-butyl ester |
| "C162" | 7-(2-Isopropoxy-6-methoxy-phenyl)-2-(3,4,5-trimethoxy-phenyl)-furo[3,2-b]pyridine |
| "C163" | 3-Trifluoromethoxy-5-[2-(3,4,5-trimethoxy-phenyl)-furo[3,2-b]pyridin-7-yl]-benzoic acid |
| "C164" | 3-Trifluoromethyl-5-[2-(3,4,5-trimethoxy-phenyl)-furo[3,2-b]pyridin-7-yl]-benzoic acid |
| "C165" | 3-(2-Amino-ethoxy)-5-[2-(3,4,5-trimethoxy-phenyl)-furo[3,2-b]pyridin-7-yl]-benzamide |
| "C166" | 2-{4-[2-(3,4,5-Trimethoxy-phenyl)-furo[3,2-b]pyridin-7-yl]-pyrazol-1-yl}-ethylamine |
| "C167" | N-((1R,2S)-2-Amino-cyclohexyl)-3-[2-(2-methoxy-phenyl)-furo[3,2-b]pyridin-7-yl]-benzamide |
| "C168" | N-((1R,2S)-2-Amino-cyclohexyl)-3-[2-(2-methoxy-5-methyl-phenyl)-furo[3,2-b]pyridin-7-yl]-benzamide |
| "C169" | N-((1R,2S)-2-Amino-cyclohexyl)-3-[2-(3H-benzoimidazol-5-yl)-furo[3,2-b]pyridin-7-yl]-benzamide |
| "C170" | N-((1R,2S)-2-Amino-cyclohexyl)-3-methoxy-5-[2-(3,4,5-trimethoxy-phenyl)-furo[3,2-b]pyridin-7-yl]-benzamide |
| "C171" | N-((1R,2S)-2-Amino-cyclohexyl)-3-isopropoxy-5-[2-(3,4,5-trimethoxy-phenyl)-furo[3,2-b]pyridin-7-yl]-benzamide | and pharmaceutically acceptable solvates, salts, tautomers and stereoisomers thereof, including mixtures thereof in all ratios.

22. A compound according to claim 1, wherein said compound is selected from the following group:

| No. | Name and/or structure |
|---|---|
| "C172" | N-(2-Amino-ethyl)-3,5-dimethoxy-4-[2-(3,4,5-trimethoxy-phenyl)-furo[3,2-b]pyridin-7-yl]-benzamide |
| "C173" | N-((1R,2S)-2-Amino-cyclohexyl)-3-trifluoromethoxy-5-[2-(3,4,5-trimethoxy-phenyl)-furo[3,2-b]pyridin-7-yl]-benzamide |
| "C174" | N-((1R,2S)-2-Amino-cyclohexyl)-3-trifluoromethyl-5-[2-(3,4,5-trimethoxy-phenyl)-furo[3,2-b]pyridin-7-yl]-benzamide |
| "C175" | N-((1R,2S)-2-Amino-cyclohexyl)-3-[2-(1-methyl-1H-indazol-5-yl)-furo[3,2-b]pyridin-7-yl]-benzamide |
| "C176" | N-((1R,2S)-2-Amino-cyclohexyl)-3-[2-(1H-indazol-6-yl)-furo[3,2-b]pyridin-7-yl]-benzamide |
| "C177" | N-((1R,2S)-2-Amino-cyclohexyl)-3-[2-(1-methyl-1H-indazol-6-yl)-furo[3,2-b]pyridin-7-yl]-benzamide |
| "C178" | N-((1R,2S)-2-Amino-cyclohexyl)-3-[2-(2,5-dimethoxy-phenyl)-furo[3,2-b]pyridin-7-yl]-benzamide |
| "C179" | N-((1R,2S)-2-Amino-cyclohexyl)-3-cyclopropylmethoxy-5-[2-(3,4,5-trimethoxy-phenyl)-furo[3,2-b]pyridin-7-yl]-benzamide |
| "C180" | N-(2-Amino-ethyl)-4-[2-(3,4,5-trimethoxy-phenyl)-furo[3,2-b]pyridin-7-yl]-benzamide |
| "C181" | N-((1R,2S)-2-Amino-cyclohexyl)-3-[2-(2-fluoro-5-methoxy-phenyl)-furo[3,2-b]pyridin-7-yl]-benzamide |
| "C182" | 1-{4-[2-(3,4,5-Trimethoxy-phenyl)-furo[3,2-b]pyridin-7-yl]-pyridin-2-yl}-pyrrolidin-3-ylamine |
| "C183" | N-((1R,2S)-2-Amino-cyclohexyl)-3-methyl-5-[2-(3,4,5-trimethoxy-phenyl)-furo[3,2-b]pyridin-7-yl]-benzamide |
| "C184" | 4'-[2-(3,4,5-Trimethoxy-phenyl)-furo[3,2-b]pyridin-7-yl]-3,4,5,6-tetrahydro-2H-[1,2']bipyridinyl-3-ylamine |
| "C185" | Piperidin-3-ylmethyl-{4-[2-(3,4,5-trimethoxy-phenyl)-furo[3,2-b]pyridin-7-yl]-pyridin-2-yl}-amine |
| "C186" | N-((1R,2S)-2-Amino-cyclohexyl)-3-[2-(3-sulfamoyl-phenyl)-furo[3,2-b]pyridin-7-yl]-benzamide |
| "C187" | 7-(3-Piperazin-2-yl-phenyl)-2-(3,4,5-trimethoxy-phenyl)-furo[3,2-b]pyridine |
| "C188" | 4-Methyl-3-[2-(3,4,5-trimethoxy-phenyl)-furo[3,2-b]pyridin-7-yl]-benzoic acid |
| "C189" | Piperidin-3-yl-{4-[2-(3,4,5-trimethoxy-phenyl)-furo[3,2-b]pyridin-7-yl]-pyridin-2-yl}-amine |
| "C190" | N-((1R,2S)-2-Amino-cyclohexyl)-4-methyl-3-[2-(3,4,5-trimethoxy-phenyl)-furo[3,2-b]pyridin-7-yl]-benzamide |
| "C191" | Pyrrolidin-3-yl-{4-[2-(3,4,5-trimethoxy-phenyl)-furo[3,2-b]pyridin-7-yl]-pyridin-2-yl}-amine |
| "C192" | 3-[2-(3,4,2-Trimethoxy-phenyl)-furo[3,2-b]pyridin-7-yl]benzenesulfonamide |
| "D1" | 2-Chloro-N-{3-[7-(4-phenoxy-phenoxy)-furo[3,2-b]pyridin-2-yl]-phenyl}-acetamide |
| "D2" | N-{2-[7-(4-Phenoxy-phenoxy)-furo[3,2-b]pyridin-2-yl]-phenyl}-acrylamide |
| "D3" | 2-Chloro-N-{2-[7-(4-phenoxy-phenoxy)-furo[3,2-b]pyridin-2-yl]-phenyl}-acetamide |
| "D4" | N-{3-[7-(4-Phenoxy-phenoxy)-furo[3,2-b]pyridin-2-yl]-benzyl}-acrylamide |
| "D5" | 2-Chloro-N-{3-[7-(4-phenoxy-phenoxy)-furo[3,2-b]pyridin-2-yl]-benzyl}-acetamide |
| "D6" | N-[3-(7-Phenoxy-furo[3,2-b]pyridin-2-yl)-phenyl]-acrylamide |
| "D7" | 2-Chloro-N-[3-(7-phenoxy-furo[3,2-b]pyridin-2-yl)-phenyl]-acetamide |
| "D8" | N-[3-(7-Phenoxy-furo[3,2-b]pyridin-2-yl)-phenyl]-propionamide |
| "D9" | N-{3-[7-(3-Chloro-phenoxy)-furo[3,2-b]pyridin-2-yl]-phenyl}-acrylamide | and pharmaceutically acceptable solvates, salts, tautomers and stereoisomers thereof, including mixtures thereof in all ratios.

23. A compound according to claim 1, wherein said compound is selected from the following group:

| No. | Name and/or structure |
|---|---|
| "D10" | N-{3-[7-(Quinolin-6-yloxy)-furo[3,2-b]pyridin-2-yl]-phenyl}-acrylamide |
| "D11" | N-{3-[7-(4-Chloro-phenoxy)-furo[3,2-b]pyridin-2-yl]-phenyl}-acrylamide |
| "D12" | N-[3-(7-Phenyl-furo[3,2-b]pyridin-2-yl)-phenyl]-acrylamide |
| "D13" | 2-Chloro-N-[3-(7-phenyl-furo[3,2-b]pyridin-2-yl)-phenyl]-acetamide |
| "D14" | N-[3-(7-Phenyl-furo[3,2-b]pyridin-2-yl)-phenyl]-propionamide |
| "D15" | N-[3-(7-Phenyl-furo[3,2-b]pyridin-2-yl)-benzyl]-acrylamide |
| "D16" | 2-Chloro-N-[3-(7-phenyl-furo[3,2-b]pyridin-2-yl)-benzyl]-acetamide |
| "D17" | N-[3-(7-Phenyl-furo[3,2-b]pyridin-2-yl)-benzyl]-propionamide |
| "D18" | N-{3-[7-(3,4,5-Trimethoxy-phenyl)-furo[3,2-b]pyridin-2-yl]-phenyl}-acrylamide |
| "D19" | N-[3-(2-Phenyl-furo[3,2-b]pyridin-7-yloxy)-phenyl]-acrylamide |
| "D20" | 2-Chloro-N-[3-(2-phenyl-furo[3,2-b]pyridin-7-yloxy)-phenyl]-acetamide |
| "D21" | N-[3-(2-Phenyl-furo[3,2-b]pyridin-7-yloxy)-phenyl]-propionamide |
| "D22" | N-[4-(2-Phenyl-furo[3,2-b]pyridin-7-yloxy)-phenyl]-acrylamide |
| "D23" | 2-Chloro-N-[4-(2-phenyl-furo[3,2-b]pyridin-7-yloxy)-phenyl]-acetamide |
| "D24" | N-[4-(2-Phenyl-furo[3,2-b]pyridin-7-yloxy)-phenyl]-propionamide |
| "D25" | N-[4-(2-Phenyl-furo[3,2-b]pyridin-7-yl)-benzyl]-acrylamide |
| "D26" | N-[4-(2-Phenyl-furo[3,2-b]pyridin-7-yl)-phenyl]-acrylamide |
| "D27" | 2-Chloro-N-[3-(2-methyl-furo[3,2-b]pyridin-7-yloxy)-phenyl]-acetamide |
| "D28" | N-[3-(2-Methyl-furo[3,2-b]pyridin-7-yloxy)-phenyl]-propionamide |
| "D29" | N-[3-(2-Methyl-furo[3,2-b]pyridin-7-yl)-phenyl]-propionamide | and pharmaceutically acceptable solvates, salts, tautomers and stereoisomers thereof, including mixtures thereof in all ratios.

* * * * *